United States Patent
Li et al.

(10) Patent No.: US 12,286,435 B2
(45) Date of Patent: Apr. 29, 2025

(54) COMPOUND HAVING BENZO SEVEN-MEMBERED RING STRUCTURE, PREPARATION METHOD THEREFOR, AND USE THEREOF

(71) Applicant: BIONNA (BEIJING) MEDICAL TECHNOLOGY CO., LTD., Beijing (CN)

(72) Inventors: Hao Li, Beijing (CN); Jin Long Bai, Beijing (CN); Hai Rui Ren, Beijing (CN); Bao Li Cai, Beijing (CN); Kiew Ching Lee, Beijing (CN); Kun Yin, Beijing (CN)

(73) Assignee: Bionna (Beijing) Medical Technology Co., Ltd., Beijing (CN)

( * ) Notice: Subject to any disclaimer, the term of this patent is extended or adjusted under 35 U.S.C. 154(b) by 871 days.

(21) Appl. No.: 17/391,241

(22) Filed: Aug. 2, 2021

(65) Prior Publication Data
US 2021/0380592 A1      Dec. 9, 2021

Related U.S. Application Data

(63) Continuation-in-part of application No. PCT/CN2020/073380, filed on Jan. 21, 2020.

(30) Foreign Application Priority Data

Feb. 2, 2019    (CN) .......................... 201910107535.1

(51) Int. Cl.
| | |
|---|---|
| *C07D 487/04* | (2006.01) |
| *A61P 3/10* | (2006.01) |
| *A61P 35/00* | (2006.01) |
| *C07D 261/20* | (2006.01) |
| *C07D 413/04* | (2006.01) |
| *C07D 519/00* | (2006.01) |

(52) U.S. Cl.
CPC .............. *C07D 487/04* (2013.01); *A61P 3/10* (2018.01); *A61P 35/00* (2018.01); *C07D 261/20* (2013.01); *C07D 413/04* (2013.01); *C07D 519/00* (2013.01)

(58) Field of Classification Search
CPC .. C07D 261/20; C07D 413/04; C07D 487/04; C07D 519/00; A61P 3/10; A61P 35/00
See application file for complete search history.

(56) References Cited

FOREIGN PATENT DOCUMENTS

| | | |
|---|---|---|
| CN | 108727380 A | 11/2018 |
| WO | 2013033268 A2 | 3/2013 |
| WO | 2013184878 A1 | 12/2013 |
| WO | 2018188660 A1 | 10/2018 |

OTHER PUBLICATIONS

Extended European Search Report issued on Sep. 2, 2022, in EP20749201.5. 8 pages.
International Search Report and Written Opinion issued for Application No. PCT/CN2020/073380, dated Apr. 15, 2020.
Chen, Deheng, et al. "Discovery, structural insight, and bioactivities of BY27 as a selective inhibitor of the second promodomains of BET proteins." European Journal of Medicinal Chemistry 182 (2019): 111633.
Chung, Chun-wa, et al. "Discovery and characterization of small molecule inhibitors of the BET family bromodomains." Journal of medicinal chemistry 54.11 (2011): 3827-3838.

*Primary Examiner* — Sarah Pihonak
(74) *Attorney, Agent, or Firm* — Meunier Carlin & Curfman LLC

(57) ABSTRACT

The present invention relates to a compound having a benzo seven-membered ring structure, and a preparation method therefor, and use thereof. The compound has a structure as represented by formula (I). Provided is use of the compound having the structure and prepared with the preparation method of the present invention, enantiomers, diastereomers, racemates and mixtures thereof of the compound, as well as chemically acceptable salts, crystalline hydrates and solvent mixtures of the compound and the enantiomers, diastereomers, racemates and mixtures thereof of the compound in the preparation of drugs for treating BET Bromodomain BRD4 activity or expression level related diseases.

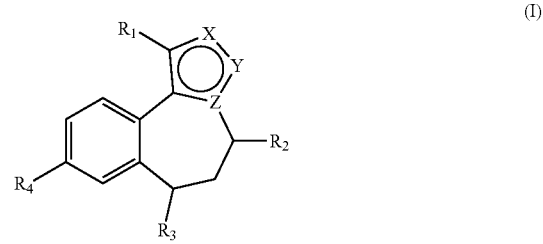

(I)

11 Claims, No Drawings

COMPOUND HAVING BENZO SEVEN-MEMBERED RING STRUCTURE, PREPARATION METHOD THEREFOR, AND USE THEREOF

This application is a continuation in part of PCT/CN2020/073380 filed on Jan. 21, 2020, which claims the priority to Chinese application No. 201910107535.1 with the title of "Compound having benzo seven-membered ring structure, preparation method and use thereof" filed with CNIPA on Feb. 2, 2019, parts of the disclosure of which both are incorporated herein by reference in their entireties.

TECHNICAL FIELD

The present invention relates to the field of BRD4 protein-inhibiting compounds, in particular to a compound having a benzo seven-membered ring structure, the preparation method and use thereof.

BACKGROUND

Bromodomain (BRD) is a class of conserved protein domains that can specifically recognize acetylated lysines in histones. By binding with acetylated lysines, it promotes the enrichment of the related proteins such as chromatin remodeling factors and transcription factors on specific transcription sites, changes the activity of RNA polymerase II and regulates the transcription and expression of genes. BRD4 protein can directly cause phosphorylation of the C-terminal of RNA topoisomerase II, affecting RNA polymerase-mediated gene transcription. It has been confirmed through studies that BRD4 protein is closely related to the occurrence of many diseases in human.

In 2010, a class of benzodiazepine compounds was reported, such as I-BET762 (2010, Nature, v468, 1119-1123). This class of compounds has high binding potency with BD1 and BD2 domains of BET Bromodomain BRD4. In animal models, I-BET762 can regulate the transcription of related genes and has the potential for the treatment of inflammatory diseases and tumor diseases (2011, Nature, v478, 529-533). RVX-208, which is a compound in phase III clinical trial, can increase high-density lipoprotein (HDL) in human, and is mainly developed as a therapeutic drug for heart diseases associated with coronary artery lesion in clinic. Studies have shown that RVX-208 also has the function of binding to the BD1 and BD2 domains of BET Bromodomain BRD4 (2013, Proceedings of National Academy of Sciences, USA, v110, 19754-19759).

OTX-015 is a novel anti-tumor drug acquired and clinically developed by Merck & Co. OTX-015 has a good binding ability with the BD1 and BD2 domains of BET Bromodomain BRD4. In animal models, OTX-015 has good anti-tumor efficacy (2013, Cancer Cell, v24, 777-790).

Therefore, it is important in drug development to study inhibitors of the BD1 domain and BD2 domain of BET Bromodomain BRD4, which have prospects in the development of potential drugs for the treatment of diabetes, inflammatory diseases, cancer and heart diseases, and male contraceptives. (2012, Nature Review Cancer, v12, 465-477; 2012, Cell, v150, 673-684; 2013, Cell, v154, 569-582).

However, most of the BET inhibitors in the current literatures and patents are not related to compounds with a benzo seven-membered ring structure, and it is difficult to predict the application prospects of these compounds in treatment of diseases related to BET Bromodomain BRD4 activity.

SUMMARY OF THE INVENTION

In view of the above problems, the present invention provides a compound having a benzo seven-membered ring structure, the preparation method and use thereof.

The compound having a benzo seven-membered ring structure has the structure of formula (I):

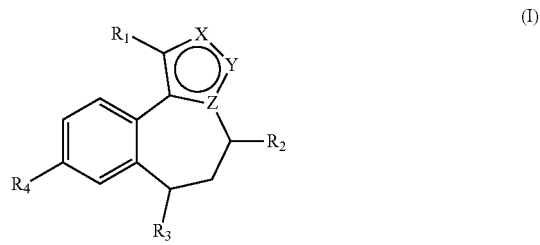

wherein, X, Y and Z each independently represent CH, N and O, and X, Y and Z form a five-membered heterocyclic ring or a five-membered heteroaromatic ring structure together with the other two carbon atoms;

$R_1$ represents H, C1-C6 alkyl, C3-C6 cycloalkyl, halogen, hydroxyl, cyano, deuterium, C1-C6 alkyl substituted by C1-C4 alkoxyl, or C3-C6 cycloalkyl substituted by halogen, hydroxyl, cyano, deuterium or C1-C4 alkoxyl;

$R_2$ represents H, deuterium, halogen, hydroxyl, amino, cyano, ester group, trifluoromethyl, aminocarbonyl, aminocarbonylamino, carbamoyloxyl, C1-C6 alkyl, C3-C6 cycloalkyl, C1-C6 alkyl substituted by halogen, hydroxyl, amino, cyano, deuterium, C1-C4 alkoxyl or C1-C4 alkylamino, C3-C6 cycloalkyl substituted by halogen, hydroxyl, amino, cyano, deuterium, C1-C4 alkoxyl or C1-C4 alkylamino, C1-C6 alkyl substituted by (C1-C6 alkoxyl) carbonyl, C1-C6 alkyl substituted by (C1-C6 alkylamino)carbonyl, C1-C6 alkyl substituted by (C1-C6 alkoxyl)carbonylamino, C1-C6 alkyl substituted by carboxyl;

$R_3$ represents —OAr, —NR$_5$Ar or —NHR$_6$;

Ar represents benzene ring, substituted benzene ring, 5-12 membered monocyclic or fused heterocyclic ring containing 1-4 heteroatoms selected from the group consisting of S, O and N, 5-12 membered monocyclic or fused heteroaromatic ring containing 1-4 heteroatoms selected from the group consisting of S, O and N, 5-12 membered monocyclic or fused heterocyclic ring containing 1-4 heteroatoms selected from the group consisting of S, O and N and substituted by 1-3 substituents, 5-12 membered monocyclic or fused heteroaromatic ring containing 1-4 heteroatoms selected from the group consisting of S, O and N and substituted by 1-3 substituents;

the substituents on Ar may each independently represent a substituent selected from the group consisting of deuterium, halogen, hydroxyl, amino, cyano, ester group, trifluoromethyl, aminocarbonyl, aminocarbonylamino, carbamoyloxyl, C1-C6 alkyl, C3-C6 cycloalkyl, C1-C6 alkyl substituted by halogen, hydroxyl, amino, cyano, deuterium, C1-C4 alkoxyl, C1-C4 alkylamino or di(C1-C4 alkyl)amino, C1-C6 alkyl substituted by 3-7 membered saturated heterocyclic ring, C3-C6 cycloalkyl substituted by halogen, hydroxyl, amino, cyano, deuterium, C1-C4 alkoxyl, C1-C4 alkylamino, C1-C4 alkyl-substituted sulfonyl or di(C1-C4 alkyl)amino, C3-C6 cycloalkyl substituted by 3-7 membered saturated heterocyclic ring, C1-C6 alkyl substituted by (C1-C6 alkoxyl)carbonyl, C1-C6 alkyl substituted by (C1-C6 alkylamino)carbonyl, C1-C6 alkyl substituted by (C1-C6 alkoxy)carbonylamino, C1-C6 alkyl substituted by (C1-C6 alkylamino)carbonylamino, C1-C6 alkyl substituted by carboxyl, aminocarbonyl substituted by C1-C6 alkyl, aminocarbonylamino substituted by C1-C6 alkyl, aminocarbonylhydroxyl substituted by C1-C6 alkyl, and the like;

$R_5$ represents H, deuterium, C1-C5 alkyl, C1-C5 alkylcarbonyl, or formyl;

$R_6$ represents substituted or unsubstituted C4-C8 aliphatic ring;

$R_4$ represents H, OMe, Cl, Br, benzene ring, benzene ring substituted by 1-3 substituents, 5-12 membered monocyclic or fused heterocyclic ring containing 1-4 heteroatoms selected from the group consisting of S, O and N, 5-12 membered monocyclic or fused heteroaromatic ring containing 1-4 heteroatoms selected from the group consisting of S, O and N, saturated or partially saturated 5-12 membered monocyclic or fused heterocyclic ring containing 1-4 heteroatoms selected from the group consisting of S, O and N, 5-12 membered monocyclic or fused heterocyclic ring containing 1-4 heteroatoms selected from the group consisting of S, O and N and substituted by 1-3 substituents, 5-12 membered monocyclic or fused heteroaromatic ring containing 1-4 heteroatoms selected from the group consisting of S, O and N and substituted by 1-3 substituents, saturated or partially saturated 5-12 membered monocyclic or fused heterocyclic ring containing 1-4 heteroatoms selected from the group consisting of S, O and N and substituted by 1-3 substituents; the above-mentioned substituents may each independently represent a substituent selected from the group consisting of deuterium, halogen, hydroxyl, amino, cyano, ester group, carboxyl, trifluoromethyl, C1-C6 alkyl, C3-C6 cycloalkyl, C1-C6 alkyl substituted by halogen, hydroxyl, amino, cyano, deuterium, ester group, carboxyl, C1-C4 alkoxyl, C1-C4 alkylamino, C1-C4 alkylaminocarbonyl, C1-C4 alkylaminocarbonylamino, C1-C4 alkyloxycarbonylamino or C1-C4 alkylcarbamoyloxyl, C1-C6 alkyl substituted by (C1-C6 alkylamino)carbonyl, C3-C6 cycloalkyl substituted by halogen, hydroxyl, amino, cyano, deuterium, ester group, carboxyl, C1-C4 alkoxyl, C1-C4 alkylamino, C1-C5 acyl, C1-C4 alkylaminocarbonyl, C1-C4 alkylaminocarbonylamino, C1-C4 alkyloxycarbonylamino or C1-C4 alkylcarbamoyloxyl, or C1-C6 alkyl substituted by (C1-C6 alkoxyl)carbonyl, and the like.

Further, the compound has a structure represented by the following formula (I-1) and/or (I-2) and/or (I-3):

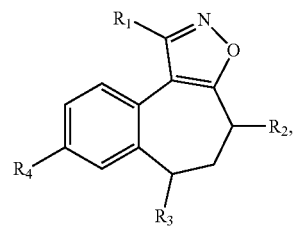

(I-2)

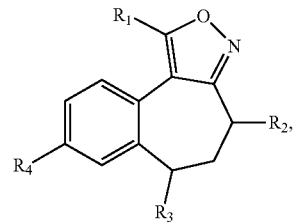

(I-3)

wherein, in each formula, $R_1$, $R_2$, $R_3$, and $R_4$ have the same definition as those in formula (I).

Further, the compound also has a structure represented by the following formula (I-4) and/or (I-5):

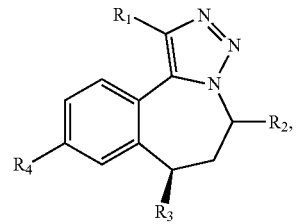

(I-4)

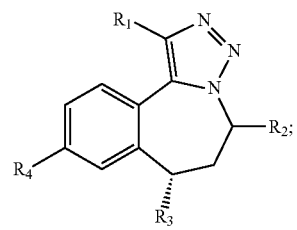

(I-5)

wherein, in each formula, $R_1$, $R_2$, $R_3$, and $R_4$ have the same definition as those in formula (I).

Further, the compound also has a structure represented by the following formula (I-6) and/or (I-7):

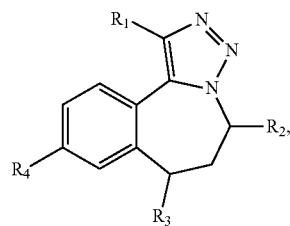

(I-1)

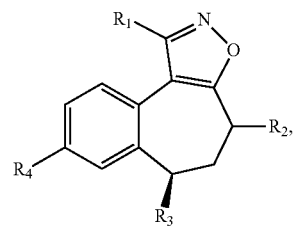

(I-6)

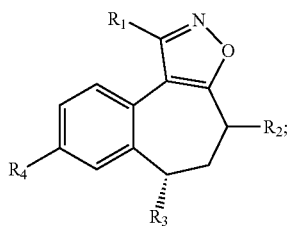
(I-7)
wherein, in each formula, $R_1$, $R_2$, $R_3$, and $R_4$ have the same definition as those in formula
Further, the compound also has a structure represented by the following formula (I-8) and/or (I-9):
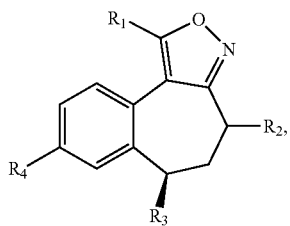
(I-8)
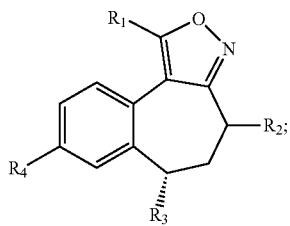
(I-9)
wherein, in each formula, $R_1$, $R_2$, $R_3$, and $R_4$ have the same definition as those in formula (I).
Further, the compound is selected from the following group:
| No. | Code | Structure |
|---|---|---|
| 1 | FA01 | 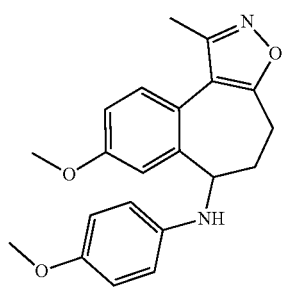 [SMILES: COc1ccc(NC2CCc3onc(C)c3-c3ccc(OC)cc32)cc1] |
| 2 | FA02 | 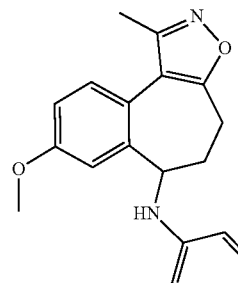 |
| 3 | FA03 | 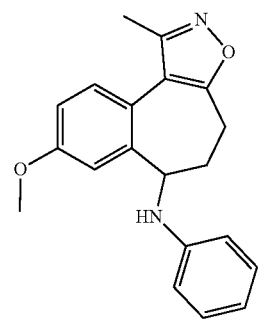 [SMILES: COc1ccc2c(c1)C(Nc1ccccc1)CCc1onc(C)c1-2] |
| 4 | FA05 | 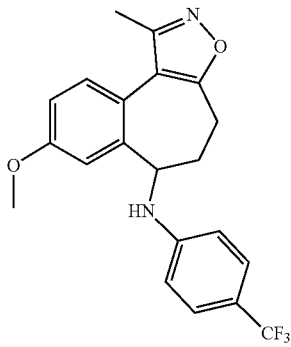 [SMILES: COc1ccc2c(c1)C(Nc1ccc(C(F)(F)F)cc1)CCc1onc(C)c1-2] |
| 5 | FA06 | 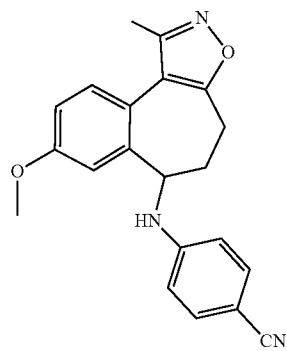 [SMILES: COc1ccc2c(c1)C(Nc1ccc(C#N)cc1)CCc1onc(C)c1-2] |

| No. | Code | Structure |
|---|---|---|
| 6 | BB188 | 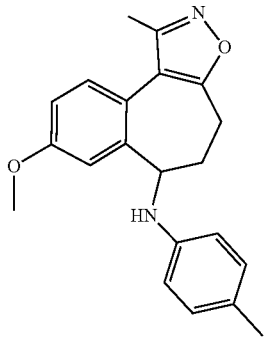 |
| 7 | BB189 | 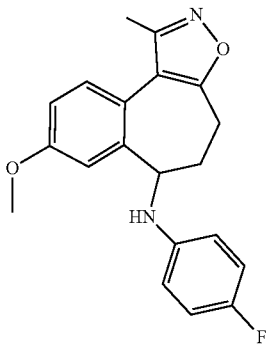 [SMILES: COc1ccc2c(c1)C(Nc1ccc(F)cc1)CCc1onc(C)c1-2] |
| 8 | BE02 | 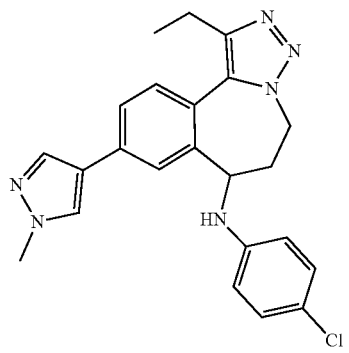 [SMILES: CCc1nnn2c1-c1ccc(-c3cnn(C)c3)cc1C(Nc1ccc(Cl)cc1)CC2] |
| 9 | BE25 | 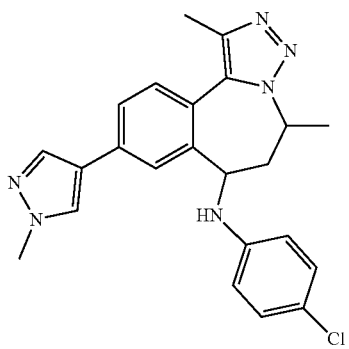 [SMILES: Cc1nnn2c1-c1ccc(-c3cnn(C)c3)cc1C(Nc1ccc(Cl)cc1)CC2C] |
| No. | Code | Structure |
|---|---|---|
| 10 | BE44 | 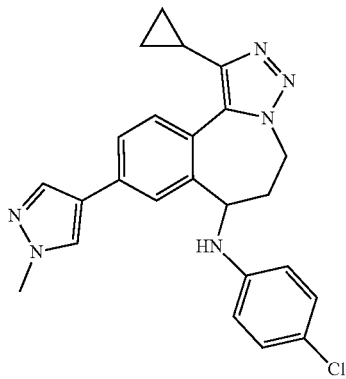 [SMILES: Cn1cc(-c2ccc3c(c2)C(Nc2ccc(Cl)cc2)CCn2nnc(C4CC4)c2-3)cn1] |
| 11 | BE95 | 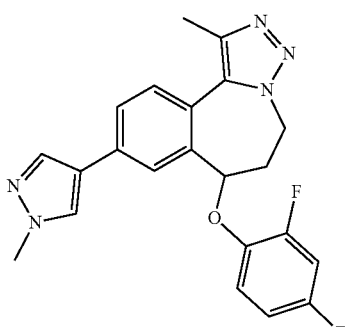 |
| 12 | LA55 | 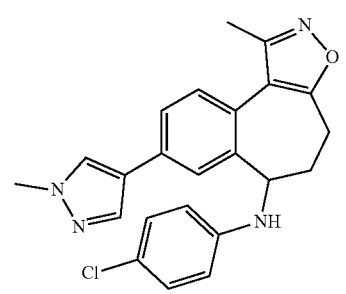 [SMILES: Cc1noc2c1-c1ccc(-c3cnn(C)c3)cc1C(Nc1ccc(Cl)cc1)CC2] |
| 13 | LA93 | 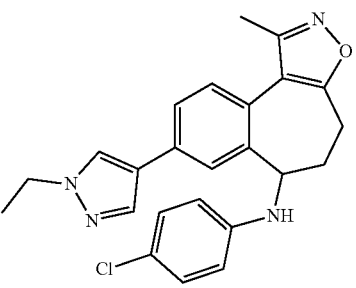 [SMILES: CCn1cc(-c2ccc3c(c2)C(Nc2ccc(Cl)cc2)CCc2onc(C)c2-3)cn1] |
| 14 | LA108 | 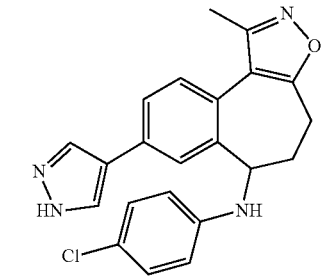 [SMILES: Cc1noc2c1-c1ccc(-c3cn[nH]c3)cc1C(Nc1ccc(Cl)cc1)CC2] |

| No. | Code | Structure |
|---|---|---|
| 15 | LA198 | 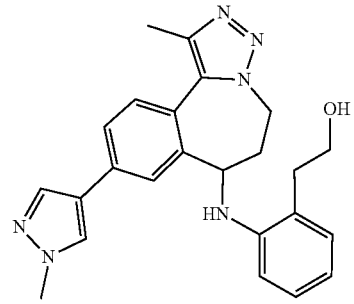 [SMILES: Cc1nnn2c1-c1ccc(-c3cnn(C)c3)cc1C(Nc1ccccc1CCO)CC2] |
| 16 | LB01 | 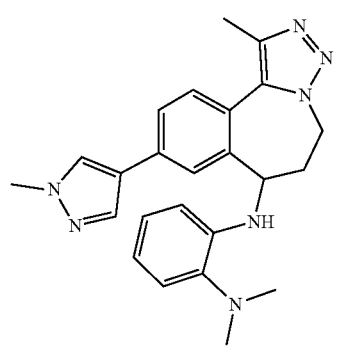 [SMILES: Cc1nnn2c1-c1ccc(-c3cnn(C)c3)cc1C(Nc1ccccc1N(C)C)CC2] |
| 17 | LB17 | 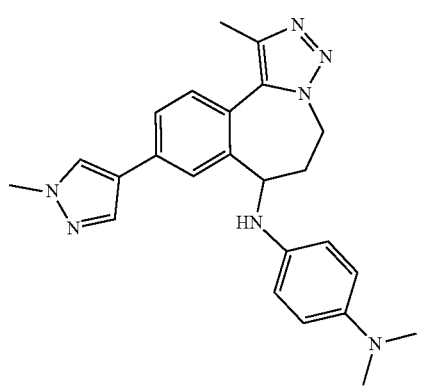 |
| 18 | LB20 | 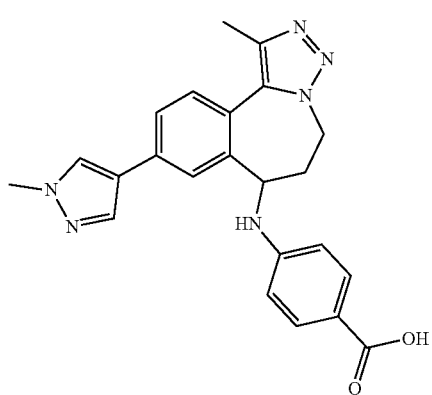 [SMILES: Cc1nnn2c1-c1ccc(-c3cnn(C)c3)cc1C(Nc1ccc(C(=O)O)cc1)CC2] |
| 19 | LB24 | 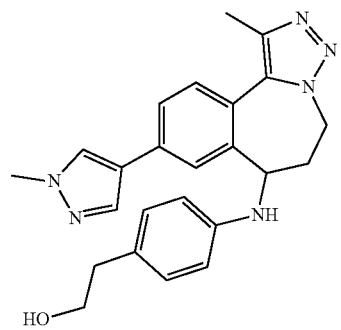 [SMILES: Cc1nnn2c1-c1ccc(-c3cnn(C)c3)cc1C(Nc1ccc(CCO)cc1)CC2] |
| 20 | LB32 | 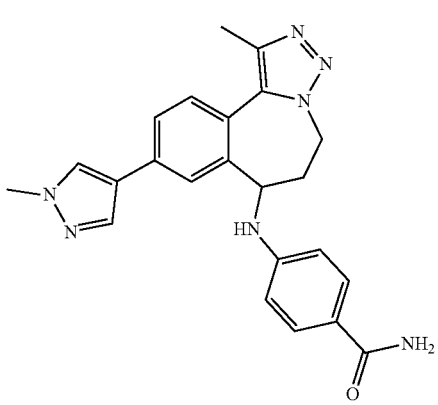 [SMILES: Cc1nnn2c1-c1ccc(-c3cnn(C)c3)cc1C(Nc1ccc(C(N)=O)cc1)CC2] |
| 21 | LB35 | 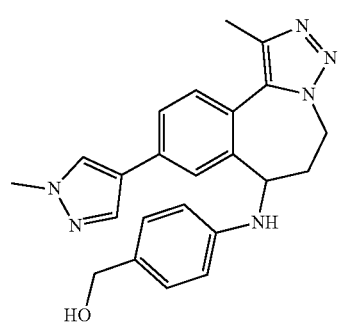 [SMILES: Cc1nnn2c1-c1ccc(-c3cnn(C)c3)cc1C(Nc1ccc(CO)cc1)CC2] |
| 22 | LB36 | 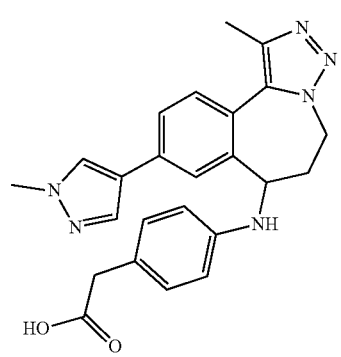 [SMILES: Cc1nnn2c1-c1ccc(-c3cnn(C)c3)cc1C(Nc1ccc(CC(=O)O)cc1)CC2] |

| No. | Code | Structure |
|---|---|---|
| 23 | LB37 | 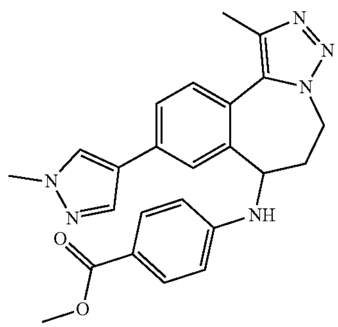 [SMILES: COC(=O)c1ccc(NC2CCn3nnc(C)c3-c3ccc(-c4cnn(C)c4)cc32)cc1] |
| 24 | LB38 | 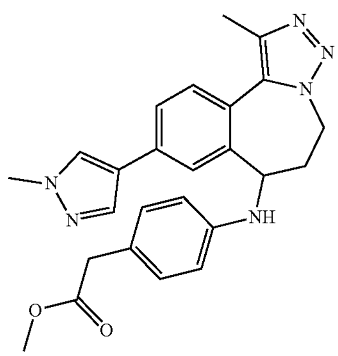 [SMILES: COC(=O)Cc1ccc(NC2CCn3nnc(C)c3-c3ccc(-c4cnn(C)c4)cc32)cc1] |
| 25 | RA180 | 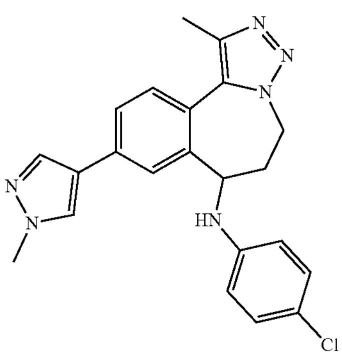 [SMILES: Cc1nnn2c1-c1ccc(-c3cnn(C)c3)cc1C(Nc1ccc(Cl)cc1)CC2] |
| 26 | RA188 | 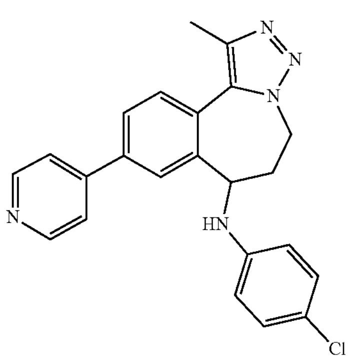 [SMILES: Cc1nnn2c1-c1ccc(-c3ccncc3)cc1C(Nc1ccc(Cl)cc1)CC2] |
| 27 | RA193 | |
| 28 | RA194 | |
| 29 | RB03 | |
| 30 | RB05 | |

| No. | Code | Structure |
|---|---|---|
| 31 | RB06 | 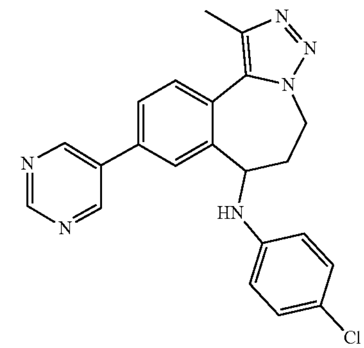 [SMILES: Cc1nnn2c1-c1ccc(-c3cncnc3)cc1C(Nc1ccc(Cl)cc1)CC2] |
| 32 | RB07 | 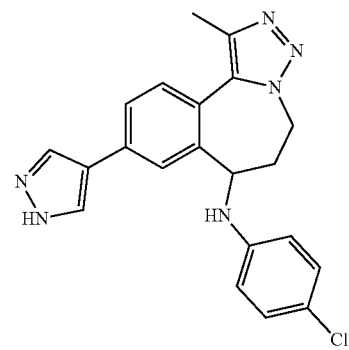 [SMILES: Cc1nnn2c1-c1ccc(-c3cn[nH]c3)cc1C(Nc1ccc(Cl)cc1)CC2] |
| 33 | RB11 | 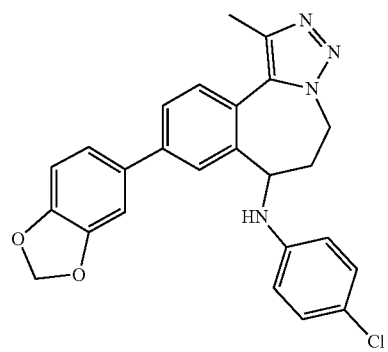 [SMILES: Cc1nnn2c1-c1ccc(-c3ccc4c(c3)OCO4)cc1C(Nc1ccc(Cl)cc1)CC2] |
| 34 | RB31 | 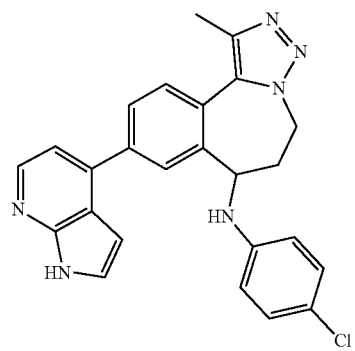 [SMILES: Cc1nnn2c1-c1ccc(-c3ccnc4[nH]ccc34)cc1C(Nc1ccc(Cl)cc1)CC2] |
| 35 | RB42 | 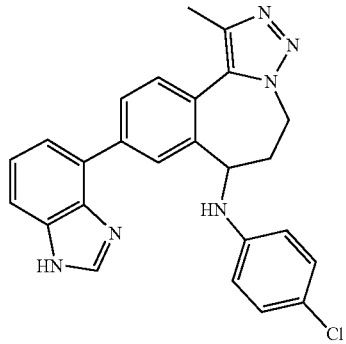 [SMILES: Cc1nnn2c1-c1ccc(-c3cccc4[nH]cnc34)cc1C(Nc1ccc(Cl)cc1)CC2] |
| 36 | RB43 | 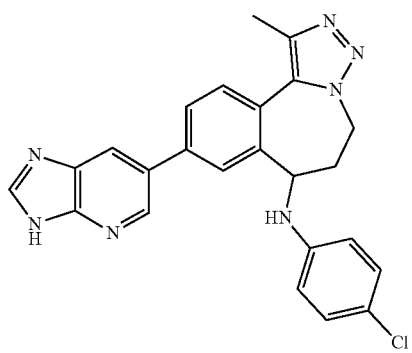 [SMILES: Cc1nnn2c1-c1ccc(-c3cnc4[nH]cnc4c3)cc1C(Nc1ccc(Cl)cc1)CC2] |
| 37 | RB48 | 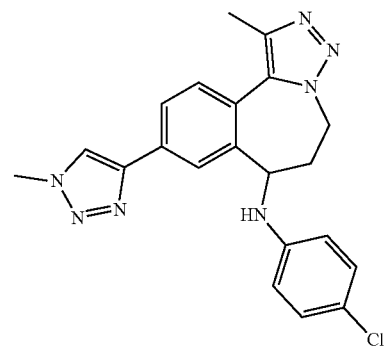 [SMILES: Cc1nnn2c1-c1ccc(-c3cn(C)nn3)cc1C(Nc1ccc(Cl)cc1)CC2] |
| 38 | RB66 | 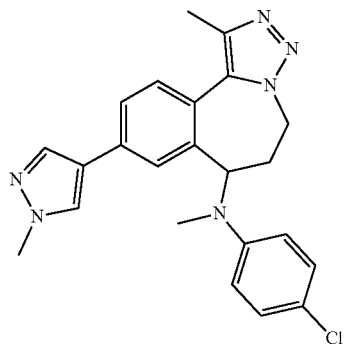 [SMILES: Cc1nnn2c1-c1ccc(-c3cnn(C)c3)cc1C(N(C)c1ccc(Cl)cc1)CC2] |

| No. | Code | Structure |
|---|---|---|
| 39 | BE114 | 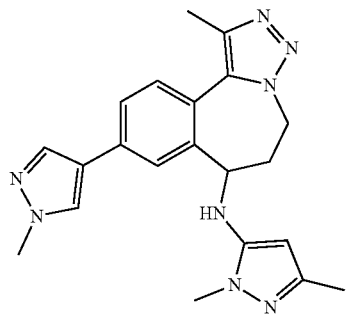 [SMILES: Cc1cc(NC2CCn3nnc(C)c3-c3ccc(-c4cnn(C)c4)cc32)n(C)n1] |
| 40 | BE118 | 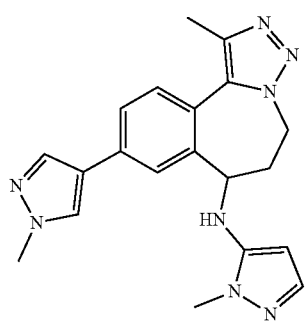 [SMILES: Cc1nnn2c1-c1ccc(-c3cnn(C)c3)cc1C(Nc1ccnn1C)CC2] |
| 41 | BE128 | 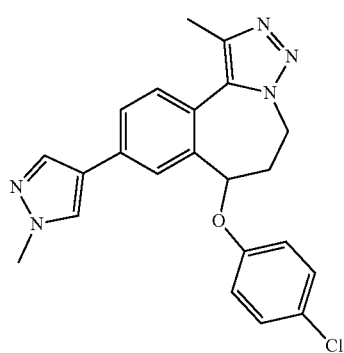 [SMILES: Cc1nnn2c1-c1ccc(-c3cnn(C)c3)cc1C(Oc1ccc(Cl)cc1)CC2] |
| 42 | BE130 | 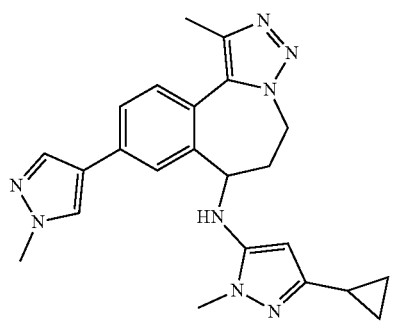 [SMILES: Cc1nnn2c1-c1ccc(-c3cnn(C)c3)cc1C(Nc1cc(C3CC3)nn1C)CC2] |
| 43 | LB42 | 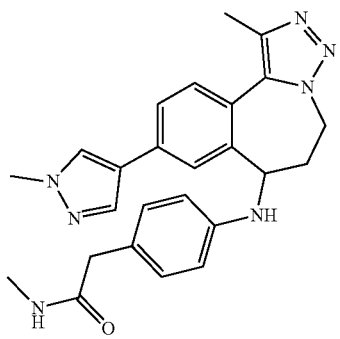 [SMILES: CNC(=O)Cc1ccc(NC2CCn3nnc(C)c3-c3ccc(-c4cnn(C)c4)cc32)cc1] |
| 44 | LB62 | 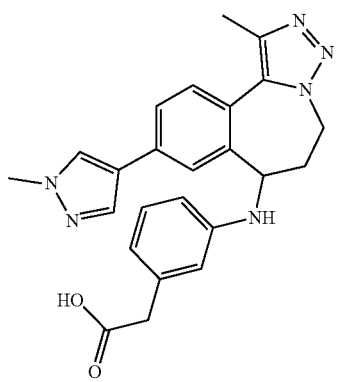 [SMILES: Cc1nnn2c1-c1ccc(-c3cnn(C)c3)cc1C(Nc1cccc(CC(=O)O)c1)CC2] |
| 45 | LB63 | 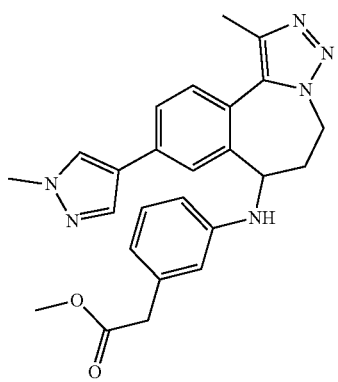 [SMILES: COC(=O)Cc1cccc(NC2CCn3nnc(C)c3-c3ccc(-c4cnn(C)c4)cc32)c1] |
| 46 | LB68 | 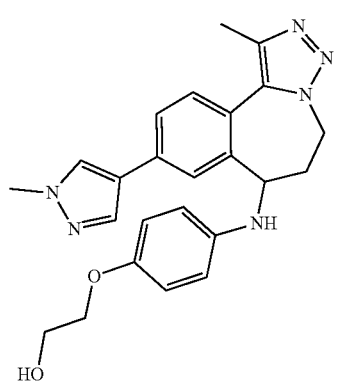 [SMILES: Cc1nnn2c1-c1ccc(-c3cnn(C)c3)cc1C(Nc1ccc(OCCO)cc1)CC2] |

| No. | Code | Structure |
|---|---|---|
| 47 | LB71 | 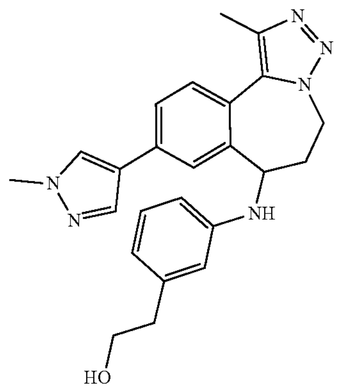 [SMILES: Cc1nnn2c1-c1ccc(-c3cnn(C)c3)cc1C(Nc1cccc(CCO)c1)CC2] |
| 48 | LB77 | 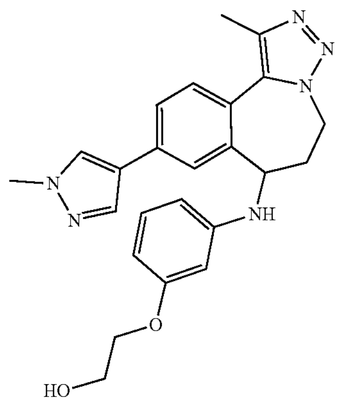 [SMILES: Cc1nnn2c1-c1ccc(-c3cnn(C)c3)cc1C(Nc1cccc(OCCO)c1)CC2] |
| 49 | LB83 | 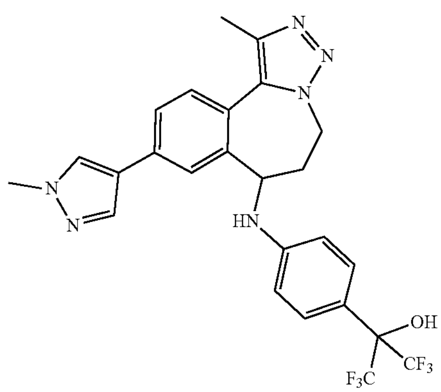 [SMILES: Cc1nnn2c1-c1ccc(-c3cnn(C)c3)cc1C(Nc1ccc(C(O)(C(F)(F)F)C(F)(F)F)cc1)CC2] |
| 50 | LB86 | 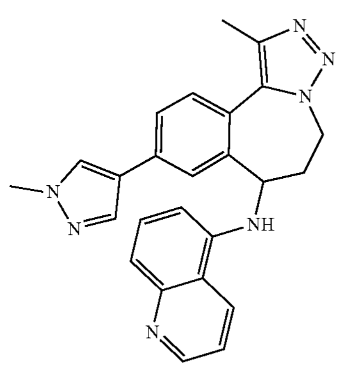 [SMILES: Cc1nnn2c1-c1ccc(-c3cnn(C)c3)cc1C(Nc1cccc3ncccc13)CC2] |
| 51 | LB88 | |
| 52 | LB89 | |
| 53 | LB90 | |
| 54 | LB91 | |

| No. | Code | Structure |
|---|---|---|
| 55 | LB92 | (structure) |
| 56 | LB97 | (structure) |
| 57 | LB98 | (structure) |
| 58 | LB103 | (structure) |
| 59 | LB113 | (structure) |
| 60 | LB114 | (structure) |
| 61 | LB128 | (structure) |
| 62 | LB138 | (structure) |

| No. | Code | Structure |
|-----|------|-----------|
| 63 | LB139 | 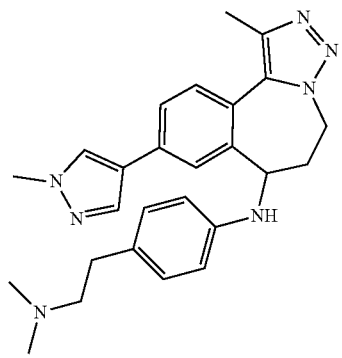 [SMILES: Cc1nnn2c1-c1ccc(-c3cnn(C)c3)cc1C(Nc1ccc(CCN(C)C)cc1)CC2] |
| 64 | LB142 | 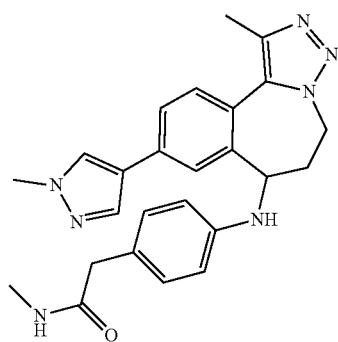 [SMILES: CNC(=O)Cc1ccc(NC2CCn3nnc(C)c3-c3ccc(-c4cnn(C)c4)cc32)cc1] |
| 65 | LB143 | 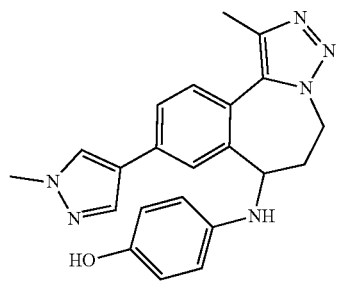 [SMILES: Cc1nnn2c1-c1ccc(-c3cnn(C)c3)cc1C(Nc1ccc(O)cc1)CC2] |
| 66 | RB90 | 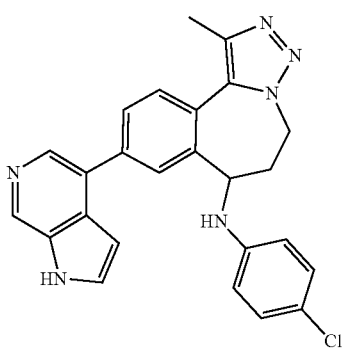 [SMILES: Cc1nnn2c1-c1ccc(-c3cncc4[nH]ccc34)cc1C(Nc1ccc(Cl)cc1)CC2] |
| No. | Code | Structure |
|-----|------|-----------|
| 67 | RB99 | 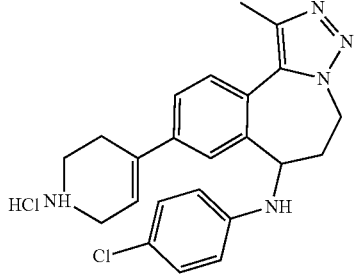 [SMILES: Cl ; Cc1nnn2c1-c1ccc(C3=CCNCC3)cc1C(Nc1ccc(Cl)cc1)CC2] |
| 68 | LB152 | 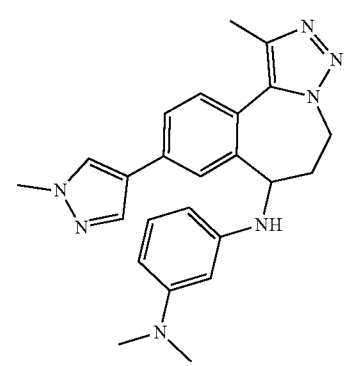 [SMILES: Cc1nnn2c1-c1ccc(-c3cnn(C)c3)cc1C(Nc1cccc(N(C)C)c1)CC2] |
| 69 | LB160 | 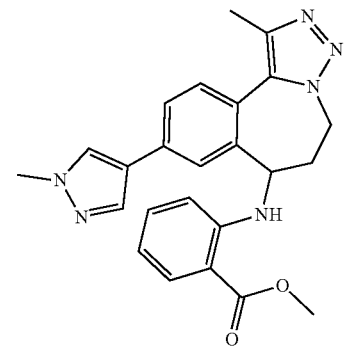 [SMILES: COC(=O)c1ccccc1NC1CCn2nnc(C)c2-c2ccc(-c3cnn(C)c3)cc21] |
| 70 | LB164 | 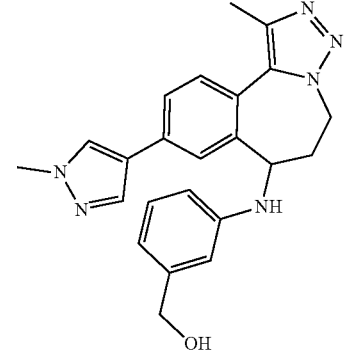 [SMILES: Cc1nnn2c1-c1ccc(-c3cnn(C)c3)cc1C(Nc1cccc(CO)c1)CC2] |

| No. | Code | Structure |
|-----|------|-----------|
| 71 | LB170 | 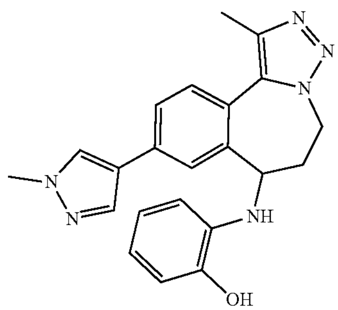 [SMILES: Cc1nnn2c1-c1ccc(-c3cnn(C)c3)cc1C(Nc1ccccc1O)CC2] |
| 72 | LB171 | 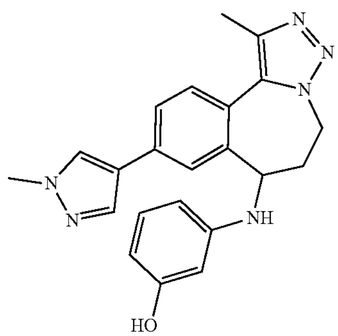 |
| 73 | LB173 | 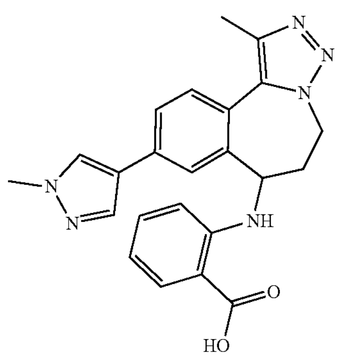 [SMILES: Cc1nnn2c1-c1ccc(-c3cnn(C)c3)cc1C(Nc1ccccc1C(=O)O)CC2] |
| 74 | LB175 | 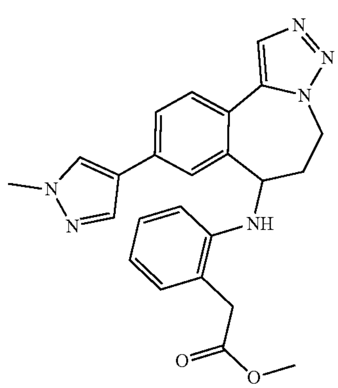 [SMILES: COC(=O)Cc1ccccc1NC1CCn2nncc2-c2ccc(-c3cnn(C)c3)cc21] |
| 75 | LB181 | |
| 76 | LB185 | |
| 77 | LB186 | |
| 78 | LB192 | |

| No. | Code | Structure |
|---|---|---|
| 79 | LC01 | 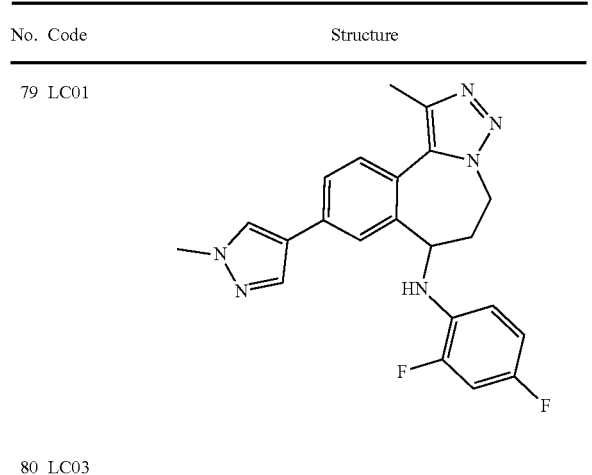 |
| 80 | LC03 | 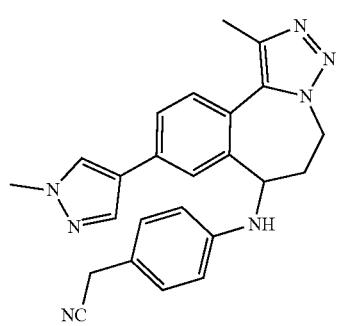 [SMILES: Cc1nnn2c1-c1ccc(-c3cnn(C)c3)cc1C(Nc1ccc(CC#N)cc1)CC2] |
| 81 | LC07 | 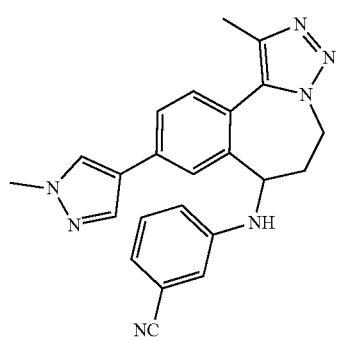 [SMILES: Cc1nnn2c1-c1ccc(-c3cnn(C)c3)cc1C(Nc1cccc(C#N)c1)CC2] |
| 82 | LC09 | 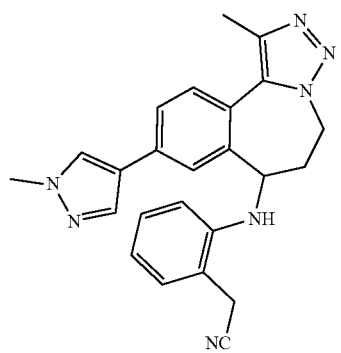 [SMILES: Cc1nnn2c1-c1ccc(-c3cnn(C)c3)cc1C(Nc1ccccc1CC#N)CC2] |
| 83 | LC10 | 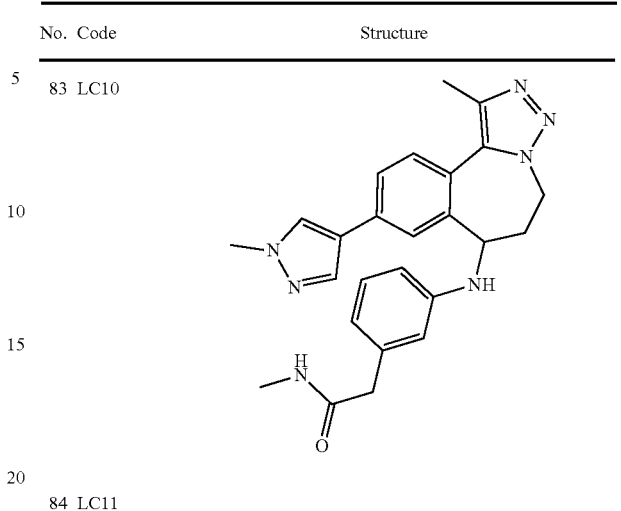 |
| 84 | LC11 | 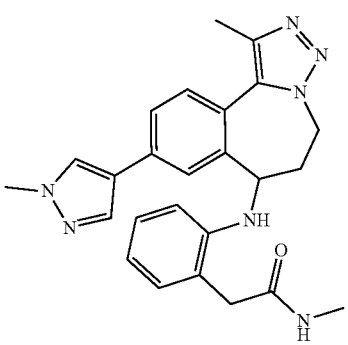 |
| 85 | LC18 | 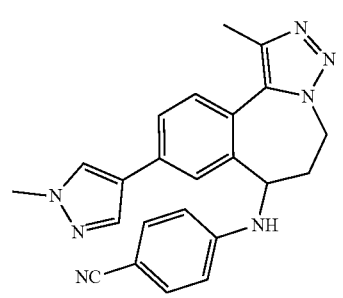 [SMILES: Cc1nnn2c1-c1ccc(-c3cnn(C)c3)cc1C(Nc1ccc(C#N)cc1)CC2] |
| 86 | LC20 | 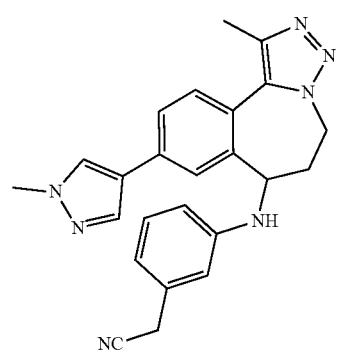 [SMILES: Cc1nnn2c1-c1ccc(-c3cnn(C)c3)cc1C(Nc1cccc(CC#N)c1)CC2] |

| No. | Code | Structure |
|---|---|---|
| 87 | LC29 | 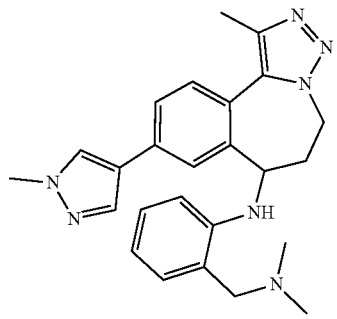 [SMILES: Cc1nnn2c1-c1ccc(-c3cnn(C)c3)cc1C(Nc1ccccc1CN(C)C)CC2] |
| 88 | LC31 | 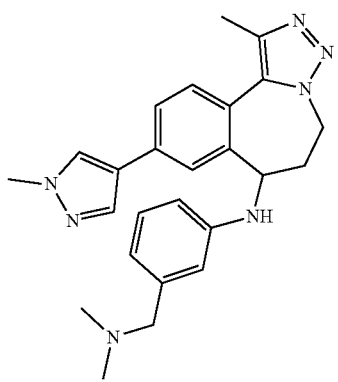 [SMILES: Cc1nnn2c1-c1ccc(-c3cnn(C)c3)cc1C(Nc1cccc(CN(C)C)c1)CC2] |
| 89 | LC56 | 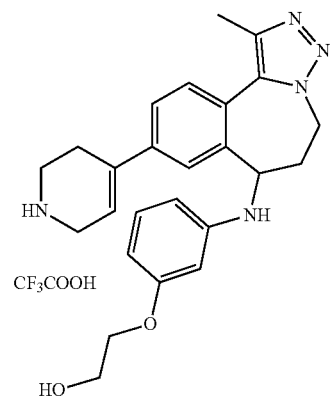 [SMILES: "CF3COOH" ; Cc1nnn2c1-c1ccc(C3=CCNCC3)cc1C(Nc1cccc(OCCO)c1)CC2] |
| 90 | LC75 | 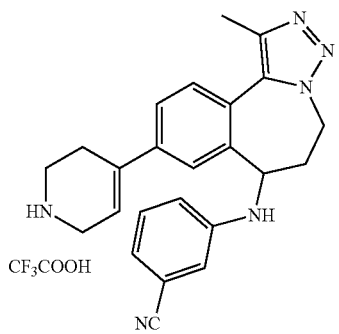 [SMILES: "CF3COOH" ; Cc1nnn2c1-c1ccc(C3=CCNCC3)cc1C(Nc1cccc(C#N)c1)CC2] |
| 91 | LC79 | 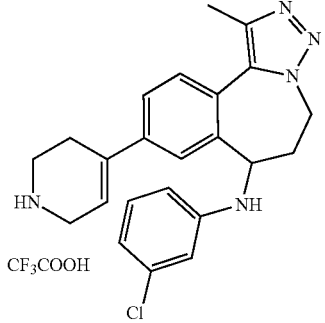 [SMILES: "CF3COOH" ; Cc1nnn2c1-c1ccc(C3=CCNCC3)cc1C(Nc1cccc(Cl)c1)CC2] |
| 92 | LC84 | 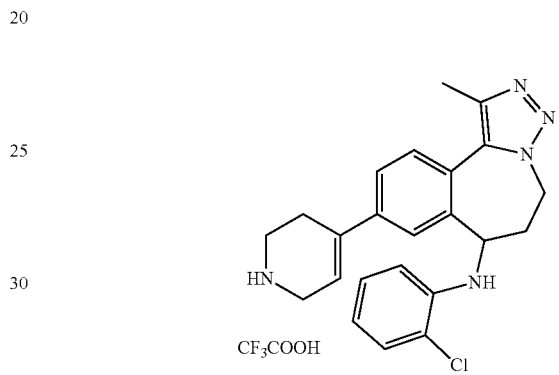 |
| 93 | LC87 | 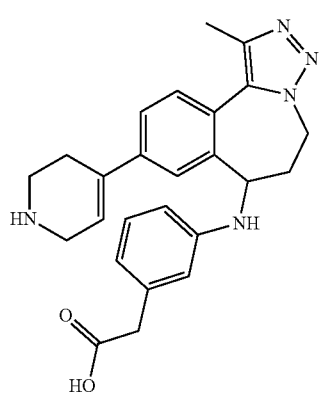 [SMILES: Cc1nnn2c1-c1ccc(C3=CCNCC3)cc1C(Nc1cccc(CC(=O)O)c1)CC2] |
| 94 | LC97 | 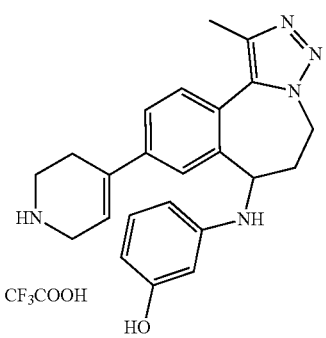 [SMILES: "CF3COOH" ; Cc1nnn2c1-c1ccc(C3=CCNCC3)cc1C(Nc1cccc(O)c1)CC2] |

-continued
| No. Code | Structure |
|---|---|
| 95 LC99 | 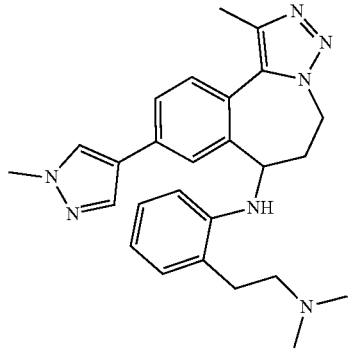 |
| 96 LC101 | 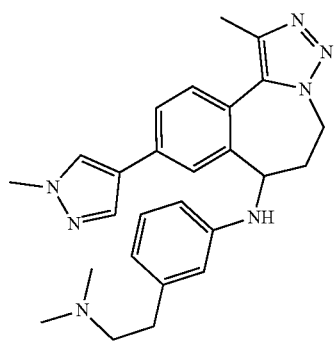 [SMILES: Cc1nnn2c1-c1ccc(-c3cnn(C)c3)cc1C(Nc1cccc(CCN(C)C)c1)CC2] |
| 97 LC117 | 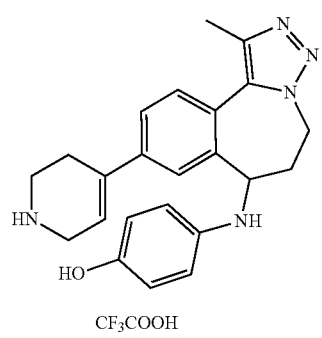 [SMILES: Cc1nnn2c1-c1ccc(C3=CCNCC3)cc1C(Nc1ccc(O)cc1)CC2 ; "CF3COOH"]<br>CF₃COOH |
| 98 LC127 | 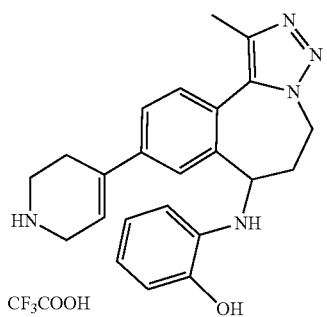 [SMILES: "CF3COOH" ; Cc1nnn2c1-c1ccc(C3=CCNCC3)cc1C(Nc1ccccc1O)CC2]<br>CF₃COOH |
-continued
| No. Code | Structure |
|---|---|
| 99 LC128 | 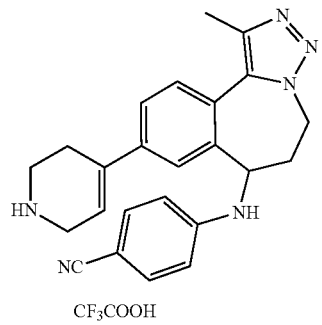 [SMILES: "CF3COOH" ; Cc1nnn2c1-c1ccc(C3=CCNCC3)cc1C(Nc1ccc(C#N)cc1)CC2]<br>CF₃COOH |
| 100 LC131 | 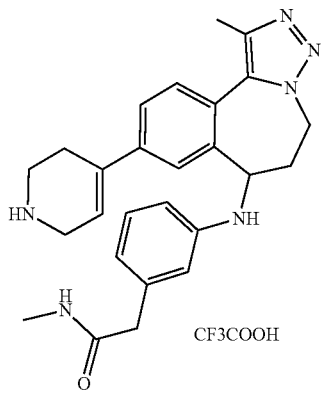<br>CF3COOH |
| 101 LC132 | 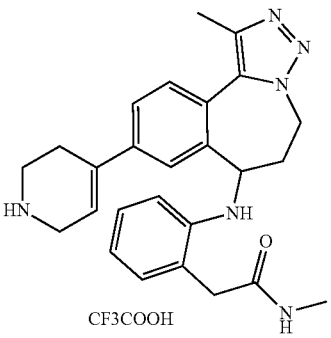 [SMILES: CNC(=O)Cc1ccccc1NC1CCn2nnc(C)c2-c2ccc(C3=CCNCC3)cc21 ; "CF3COOH"]<br>CF3COOH |
| 102 LC133 | 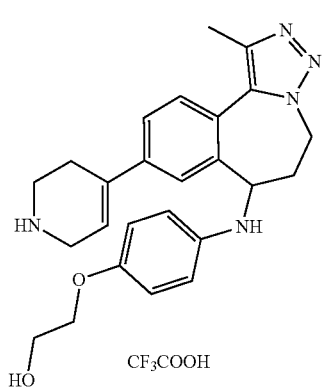 [SMILES: Cc1nnn2c1-c1ccc(C3=CCNCC3)cc1C(Nc1ccc(OCCO)cc1)CC2 ; "CF3COOH"]<br>CF₃COOH |

-continued

| No. | Code | Structure |
|-----|------|-----------|
| 103 | LC136 | 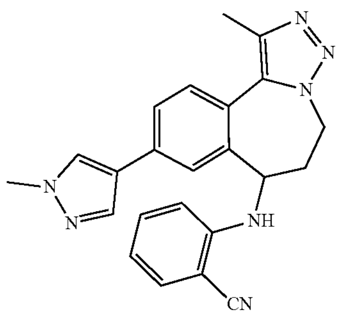 [SMILES: Cc1nnn2c1-c1ccc(-c3cnn(C)c3)cc1C(Nc1ccccc1C#N)CC2] |
| 104 | LC158 | CF₃COOH |
| 105 | LC159 | CF₃COOH |
| 106 | LC160 | CF₃COOH |

-continued

| No. | Code | Structure |
|-----|------|-----------|
| 107 | LC174 | 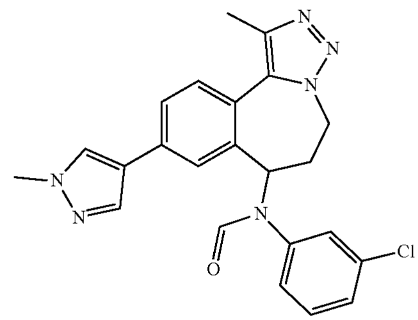 [SMILES: Cc1nnn2c1-c1ccc(-c3cnn(C)c3)cc1C(N(C=O)c1cccc(Cl)c1)CC2] |
| 108 | LC185 | 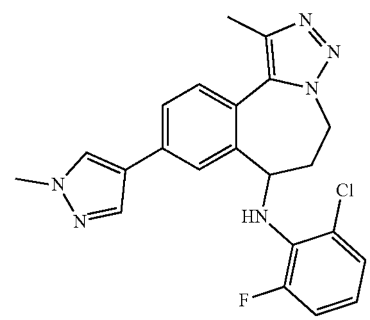 [SMILES: Cc1nnn2c1-c1ccc(-c3cnn(C)c3)cc1C(Nc1c(F)cccc1Cl)CC2] |
| 109 | LC186 | 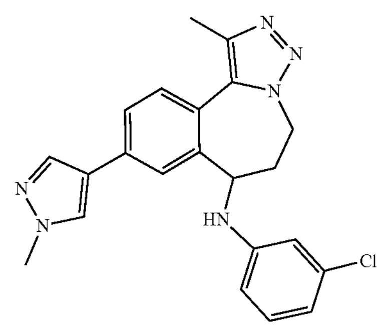 [SMILES: Cc1nnn2c1-c1ccc(-c3cnn(C)c3)cc1C(Nc1cccc(Cl)c1)CC2] |
| 110 | LC190 | CF₃COOH |
| 111 | LC191 | 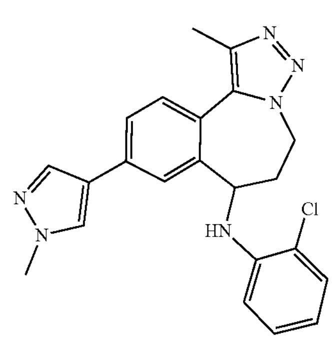 [SMILES: Cc1nnn2c1-c1ccc(-c3cnn(C)c3)cc1C(Nc1ccccc1Cl)CC2] |

-continued

| No. | Code | Structure |
|---|---|---|
| 112 | LC192 | (structure with CF₃COOH) |
| 113 | LC193 | (structure with CF₃COOH) |
| 114 | LC198 | (structure with CF₃COOH) |
| 115 | LD07 | (structure with CF₃COOH) |

-continued

| No. | Code | Structure |
|---|---|---|
| 116 | LD08 | (structure with CF₃COOH) |
| 117 | LD13 | (structure) |
| 118 | LD14 | (structure) |
| 119 | LD17 | (structure with CF₃COOH) |
| 120 | LD19 | (structure) |

| No. | Code | Structure |
|---|---|---|
| 121 | LD23 | 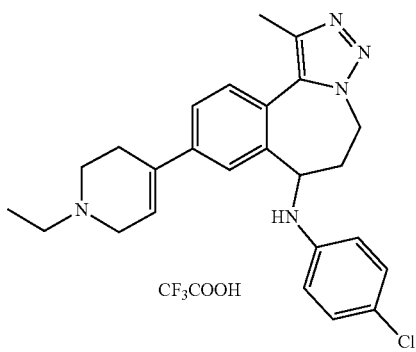 [SMILES: CCN1CC=C(c2ccc3c(c2)C(Nc2ccc(Cl)cc2)CCn2nnc(C)c2-3)CC1 ; "CF3COOH"] |
| 122 | LD24 | 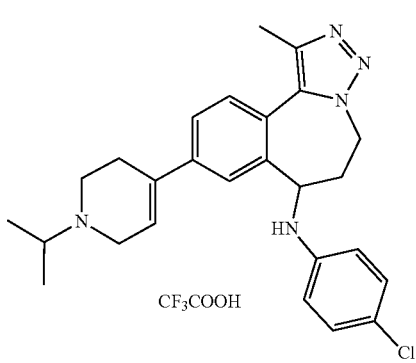 [SMILES: Cc1nnn2c1-c1ccc(C3=CCN(C(C)C)CC3)cc1C(Nc1ccc(Cl)cc1)CC2 ; "CF3COOH"] |
| 123 | LD31 | 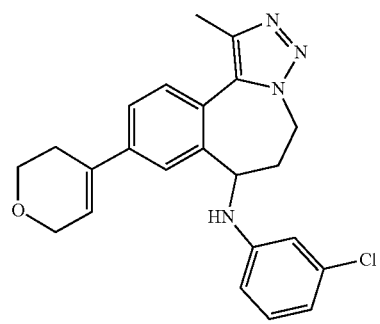 [SMILES: Cc1nnn2c1-c1ccc(C3=CCOCC3)cc1C(Nc1cccc(Cl)c1)CC2] |
| 124 | LD76 | 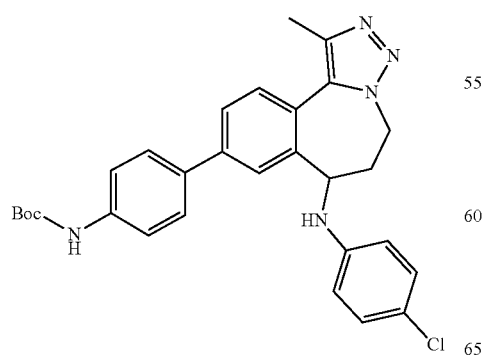 |
| 125 | LD77 | 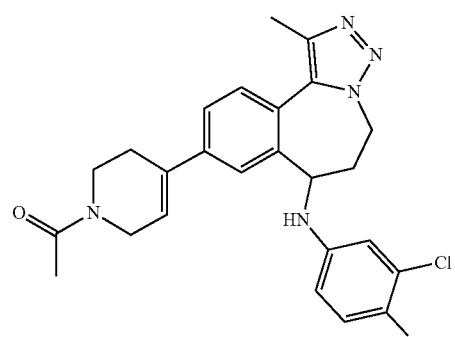 |
| 126 | BF169 | 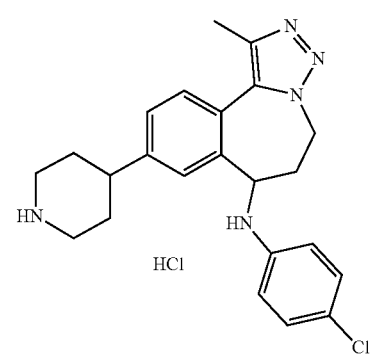 [SMILES: Cc1nnn2c1-c1ccc(C3CCNCC3)cc1C(Nc1ccc(Cl)cc1)CC2 ; Cl] |
| 127 | BF178 | 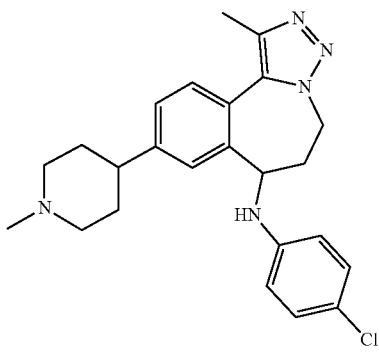 [SMILES: Cc1nnn2c1-c1ccc(C3CCN(C)CC3)cc1C(Nc1ccc(Cl)cc1)CC2] |
| 128 | BJ28 | 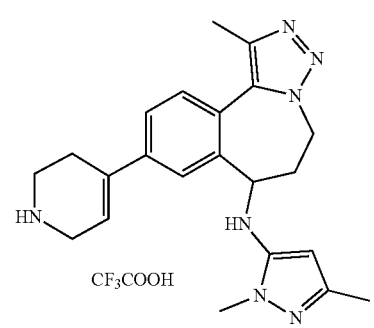 [SMILES: Cc1cc(NC2CCn3nnc(C)c3-c3ccc(C4=CCNCC4)cc32)n(C)n1 ; "CF3COOH"] |

| No. | Code | Structure |
|-----|------|-----------|
| 129 | BJ122 | (structure with CF₃COOH) |
| 130 | BJ123 | (structure with HCl) |
| 131 | BJ126 | (structure with HCl) |
| 132 | BJ179 | (structure with CF₃COOH) |
| 133 | BJ183 | (structure with CF₃COOH) |
| 134 | BJ193 | (structure) |
| 135 | BH06 | (structure with CF₃COOH) |
| 136 | BH23 | (structure with CF₃COOH) |
| 137 | BH27 | (structure) |

| No. | Code | Structure |
|---|---|---|
| 138 | BH29 | 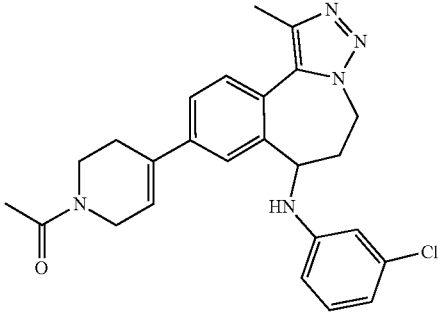 [SMILES: CC(=O)N1CC=C(c2ccc3c(c2)C(Nc2cccc(Cl)c2)CCn2nnc(C)c2-3)CC1] |
| 139 | BH32 | 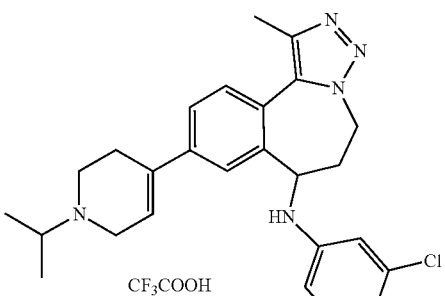 CF₃COOH |
| 140 | BH33 | 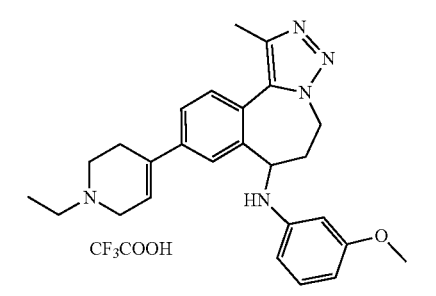 [SMILES: CCN1CC=C(c2ccc3c(c2)C(Nc2cccc(OC)c2)CCn2nnc(C)c2-3)CC1 ; "CF3COOH"] CF₃COOH |
| 141 | BH36 | 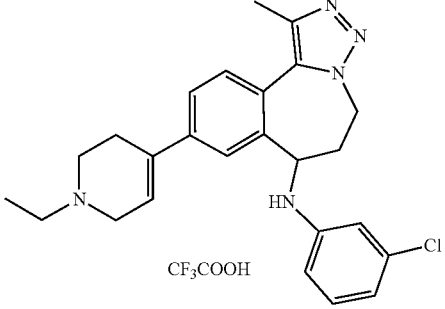 CF₃COOH |
| 142 | BH37 | 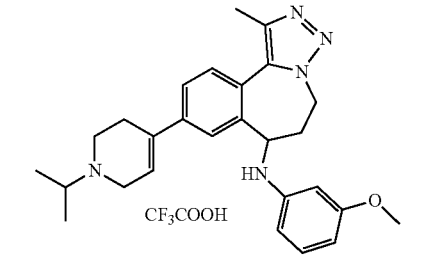 CF₃COOH |
| 143 | BH43 | 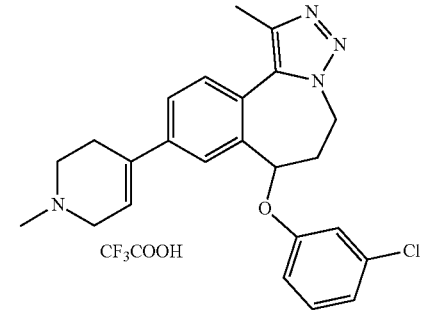 [SMILES: Cc1nnn2c1-c1ccc(C3=CCN(C)CC3)cc1C(Oc1cccc(Cl)c1)CC2 ; "CF3COOH"] CF₃COOH |
| 144 | BH46 | 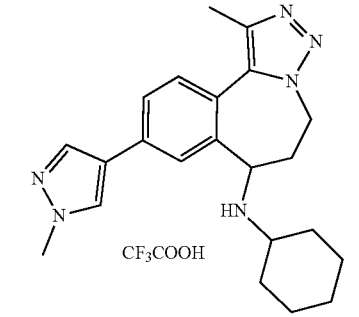 CF₃COOH |
| 145 | BH57 | 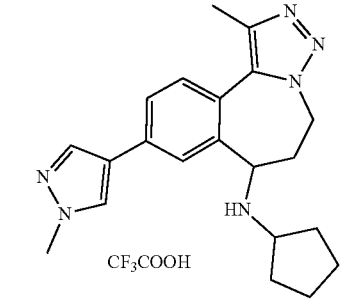 [SMILES: Cc1nnn2c1-c1ccc(-c3cnn(C)c3)cc1C(NC1CCCC1)CC2 ; "CF3COOH"] CF₃COOH |
| 146 | BH81 | 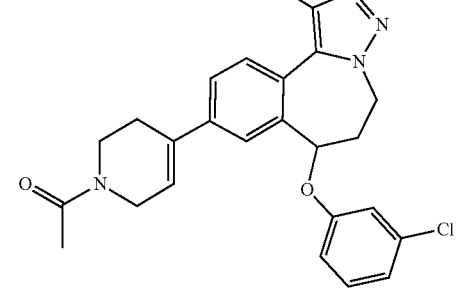 |
| 147 | BH86 | 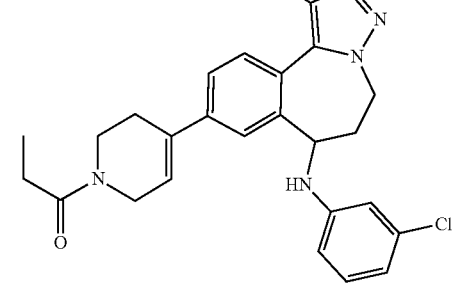 |

| No. | Code | Structure |
|---|---|---|
| 148 | BH87 | (sec-butyl piperidine variant; CF₃COOH; 3-Cl anilino) |
| 149 | BH104 | (cyclohexyl piperidine variant; CF₃COOH; 3-Cl anilino) |
| 150 | BH107 | (cyclopentyl piperidine variant; CF₃COOH; 3-Cl anilino) |
| 151 | BH108 | (n-butyl piperidine variant; CF₃COOH; 3-Cl anilino) |
| 152 | BH120 | (n-propyl piperidine variant; CF₃COOH; 3-Cl anilino) |
| 153 | BH123 | (cyclopropanecarbonyl piperidine variant; 3-Cl anilino) |
| 154 | BH159 | (cyclobutyl piperidine variant; CF₃COOH; 3-Cl anilino) |
| 155 | BH187 | (cyclohexyl piperidine variant; CF₃COOH; 2-F,5-Cl anilino) |
| 156 | BH190 | (cyclopentyl piperidine variant; CF₃COOH; 2-F,5-Cl anilino) |
| 157 | BH192 | (acetyl piperidine variant; 2-F,5-Cl anilino) |

| No. | Code | Structure |
|---|---|---|
| 158 | BI23 | 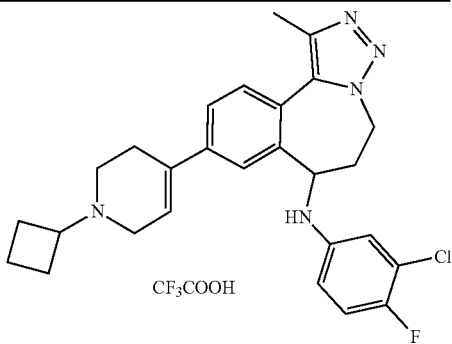 CF₃COOH |
| 159 | BI24 | 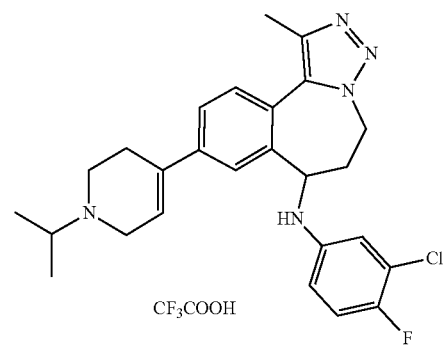 [SMILES: Cc1nnn2c1-c1ccc(C3=CCN(C(C)C)CC3)cc1C(Nc1ccc(F)c(Cl)c1)CC2 ; "CF3COOH"] CF₃COOH |
| 160 | BI26 | 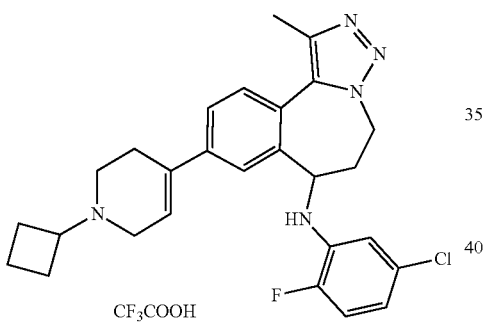 CF₃COOH |
| 161 | BI29 | 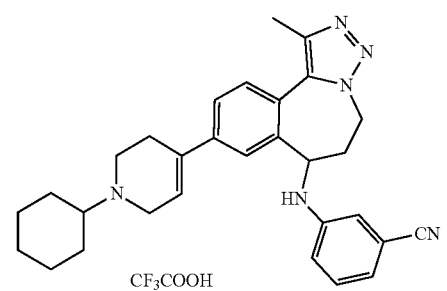 [SMILES: Cc1nnn2c1-c1ccc(C3=CCN(C4CCCCC4)CC3)cc1C(Nc1cccc(C#N)c1)CC2 ; "CF3COOH"] CF₃COOH |
| 162 | BI31 | 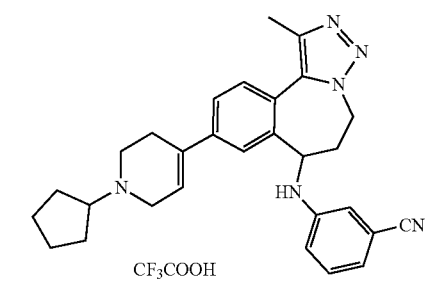 [SMILES: Cc1nnn2c1-c1ccc(C3=CCN(C4CCCC4)CC3)cc1C(Nc1cccc(C#N)c1)CC2 ; "CF3COOH"] CF₃COOH |
| 163 | BI34 | 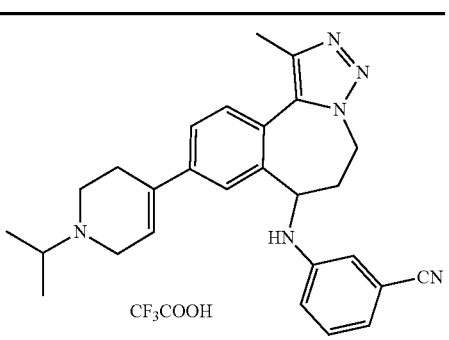 CF₃COOH |
| 164 | BI36 | 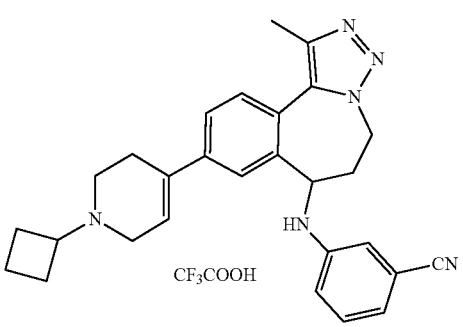 CF₃COOH |
| 165 | BI37 | 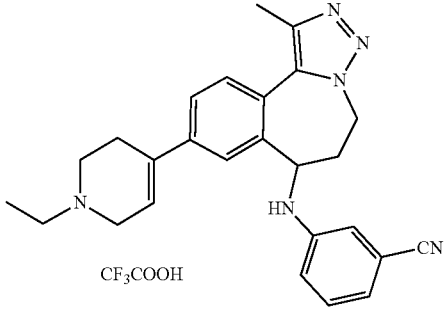 [SMILES: CCN1CC=C(c2ccc3c(c2)C(Nc2cccc(C#N)c2)CCn2nnc(C)c2-3)CC1 ; "CF3COOH"] CF₃COOH |
| 166 | BI55 | 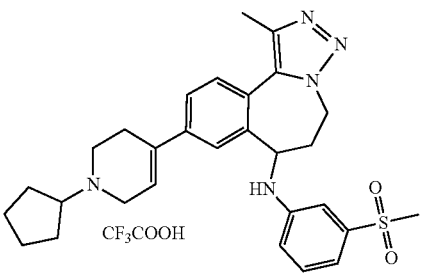 [SMILES: Cc1nnn2c1-c1ccc(C3=CCN(C4CCCC4)CC3)cc1C(Nc1cccc(S(C)(=O)=O)c1)CC2 ; "CF3COOH"] CF₃COOH |
| 167 | BI57 | 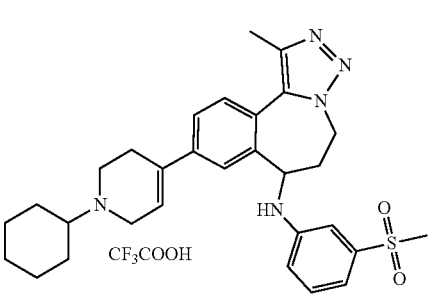 [SMILES: Cc1nnn2c1-c1ccc(C3=CCN(C4CCCCC4)CC3)cc1C(Nc1cccc(S(C)(=O)=O)c1)CC2 ; "CF3COOH"] CF₃COOH |

| No. | Code | Structure |
|---|---|---|
| 168 | BI60 | (structure with isopropyl-piperidine, triazole-benzazepine, methylsulfonyl-aniline, CF₃COOH) |
| 169 | BI61 | (structure with cyclobutyl-piperidine, triazole-benzazepine, methylsulfonyl-aniline, CF₃COOH) |
| 170 | BI68 | (structure with isopropyl-piperidine, triazole-benzazepine, 5-chloro-2-fluoroaniline, CF₃COOH) |
| 171 | WYA10 | (structure with cyclopentyl-piperidine, triazole-benzazepine, 3-chloro-4-fluoroaniline, CF₃COOH) |
| 172 | WA78 | (structure with tetrahydropyridine, triazole-benzazepine, indol-4-ylamino, CF₃COOH) |
| 173 | WA82 | (structure with tetrahydropyridine, triazole-benzazepine, indol-aminyl, CF3COOH) |
| 174 | WA83 | (structure with tetrahydropyridine, triazole-benzazepine, indol-aminyl, CF3COOH) |
| 175 | RC71 | (structure with tetrahydropyridine, triazole-benzazepine, 3-(cyanomethyl)aniline, CF₃COOH) |
| 176 | RC73 | (structure with tetrahydropyridine, triazole-benzazepine, 4-(cyanomethyl)aniline, CF₃COOH) |

| No. | Code | Structure |
|-----|------|-----------|
| 177 | RC82 | (structure) CF₃COOH |
| 178 | RC116 | (structure) CF₃COOH |
| 179 | RD06 | (structure) CF₃COOH |
| 180 | RD21 | (structure) CF₃COOH |

| No. | Code | Structure |
|-----|------|-----------|
| 181 | RD41 | (structure) CF₃COOH |
| 182 | RD115 | (structure) CF₃COOH |
| 183 | RD121 | (structure) CF₃COOH |
| 184 | RD123 | (structure) CF₃COOH |

-continued
| No. | Code | Structure |
|---|---|---|
| 185 | RD142 | 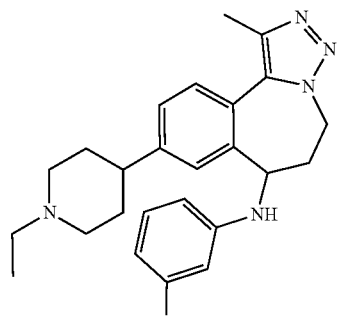<br>CF₃COOH |
| 186 | RD178 | 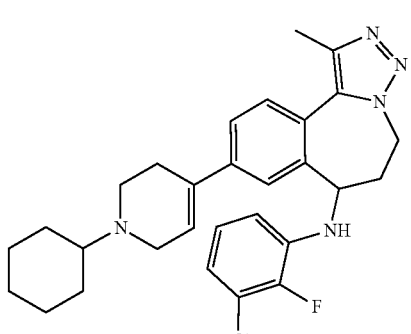<br>CF₃COOH |
| 187 | RD179 | 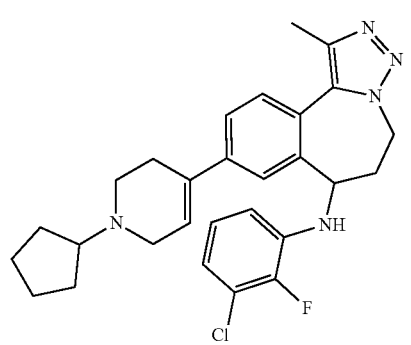<br>CF₃COOH |
| 188 | RD180 | 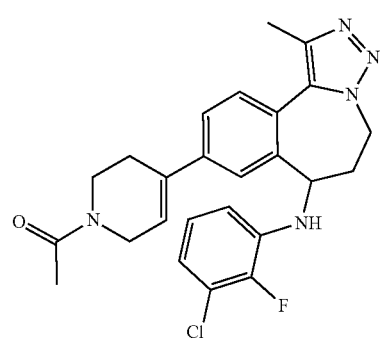<br>CF₃COOH |
-continued
| No. | Code | Structure |
|---|---|---|
| 189 | RE10(S) | 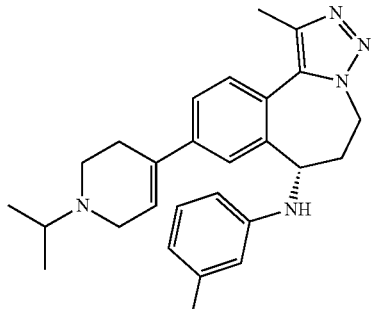<br>CF₃COOH |
| 190 | RE13(R) | 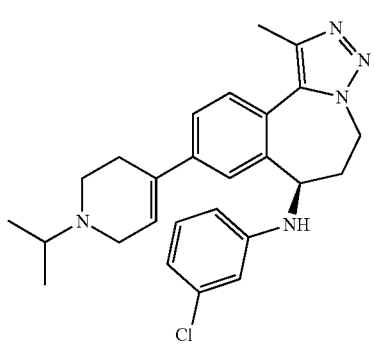<br>CF₃COOH |
| 191 | RE29 | 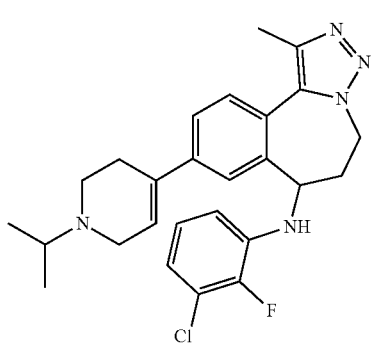<br>CF₃COOH |
| 192 | RE30 | 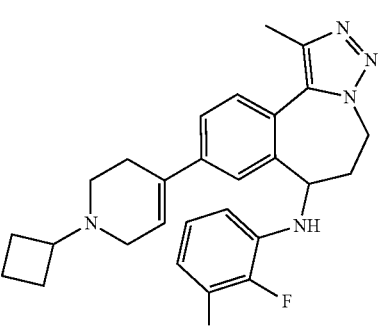<br>CF₃COOH |

-continued
| No. | Code | Structure |
|---|---|---|
| 193 | RE124 | 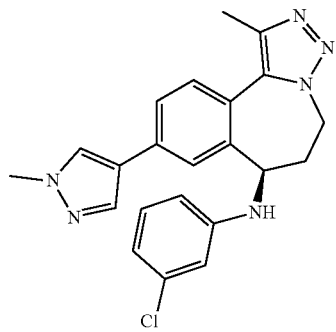 [SMILES: Cc1nnn2c1-c1ccc(-c3cnn(C)c3)cc1[C@H](Nc1cccc(Cl)c1)CC2] |
| 194 | RE127 | 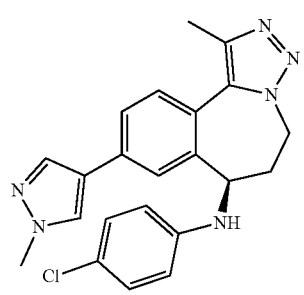 [SMILES: Cc1nnn2c1-c1ccc(-c3cnn(C)c3)cc1[C@H](Nc1ccc(Cl)cc1)CC2] |
| 195 | RE136 | 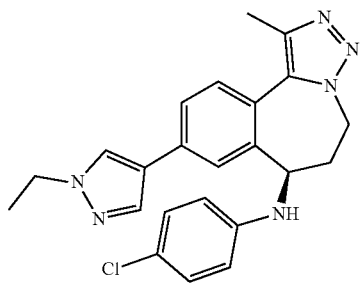 |
Further, the preparation method comprises the following steps of:
(1) preparing the compound of formula Ib with the compound of formula Ia,
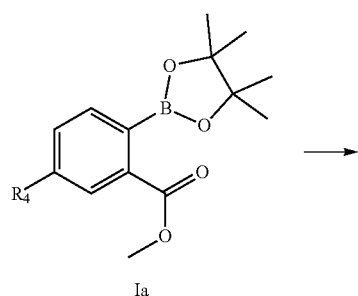
Ia
(2) preparing the compound of formula Ic with the compound of formula Ib,
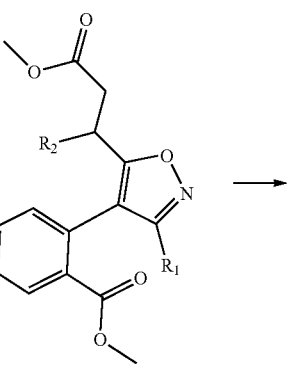
Ib
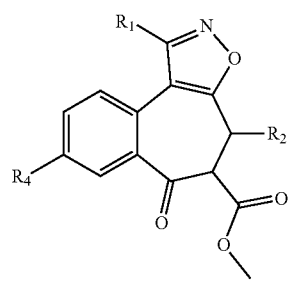
Ic
(3) preparing the compound of formula Id with the compound of formula Ic,
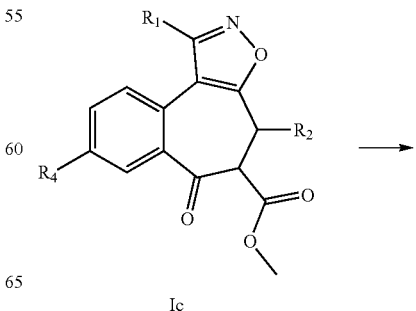
Ic

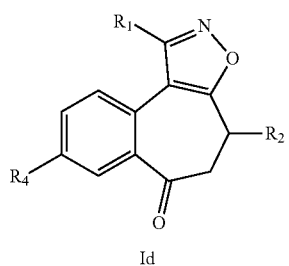
Id
(4) preparing the compound of formula (I-2) with the compound of formula Id,
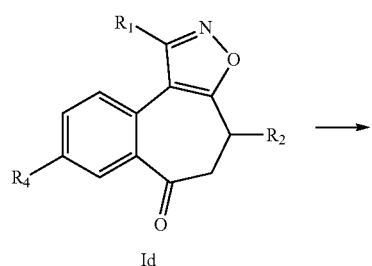
Id
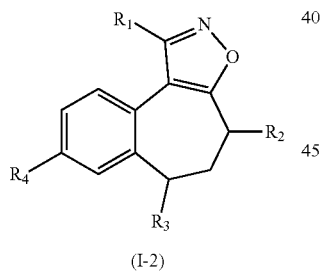
(I-2)
(5) preparing the compound of formula Ie with the compound of formula Ia,
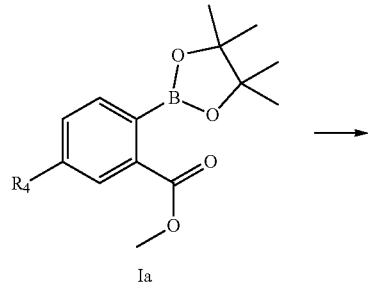
Ia
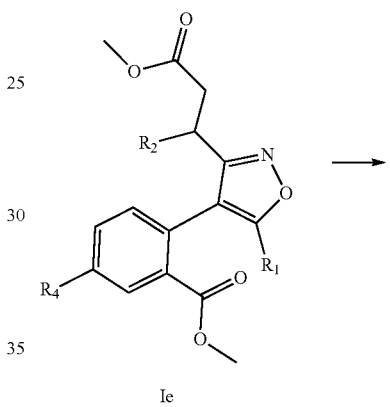
Ie
(6) preparing the compound of formula If with the compound of formula Ie,
Ie
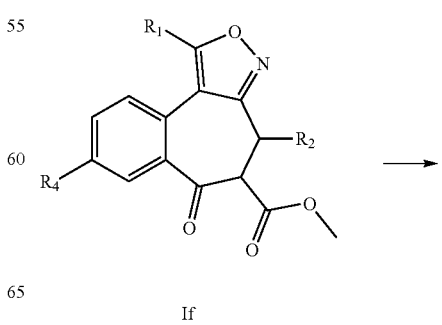
If
(7) preparing the compound of formula Ig with the compound of formula If,
If -continued

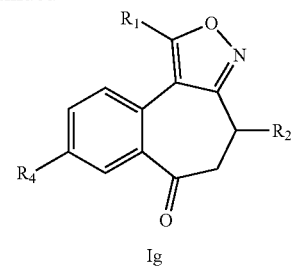
Ig (8) preparing the compound of formula (I-3) with the compound of formula Ig,

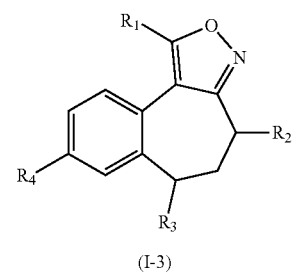
Ig

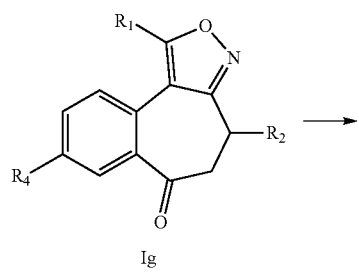
(I-3)

(9) preparing the compound of formula Ii with the compound of formula Ih,

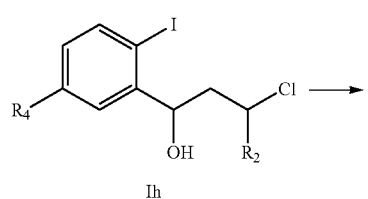
Ih

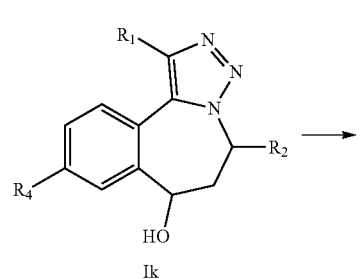
Ii

(10) preparing the compound of formula Ij by reacting the compound of formula Ii with sodium azide,

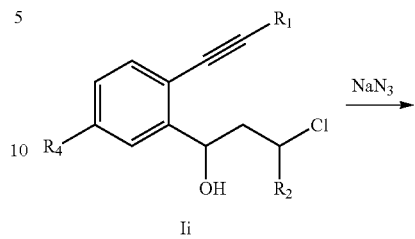

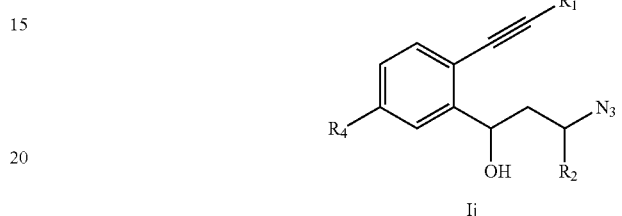
Ij

(11) preparing the compound of formula Ik with the compound of formula Ij,

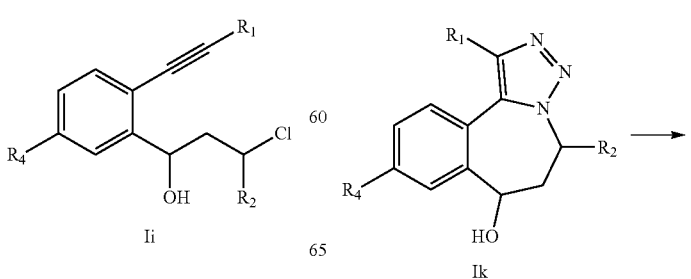

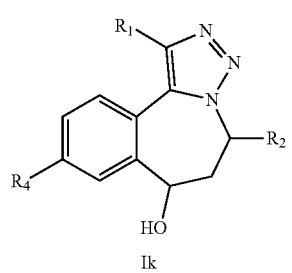
Ik

(12) preparing the compound of formula Il with the compound of formula Ik,

Ik

-continued
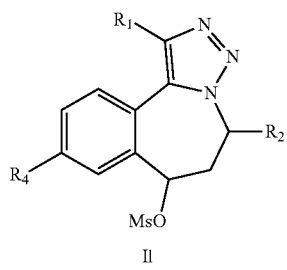
Il
(13) preparing the compound of formula (I-1) with the compound of formula Il,
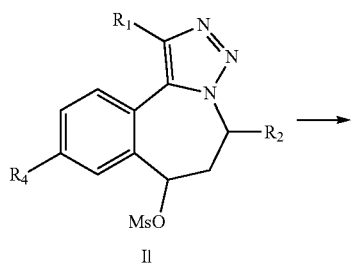
Il
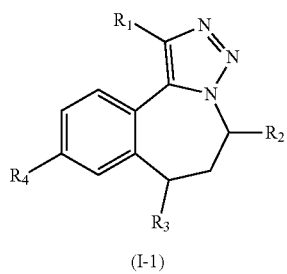
(I-1)
(14) preparing the compound of formula Im with the compound of formula Ik,
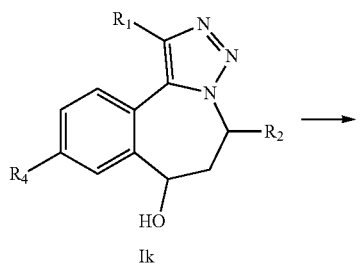
Ik
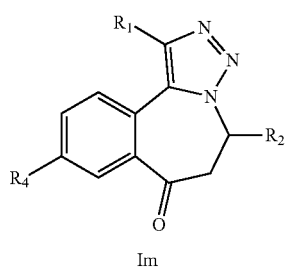
Im
(15) preparing the compound of formula (I-1) with the compound of formula Im,
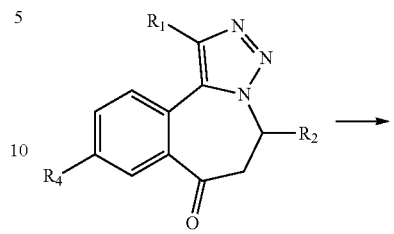
Im
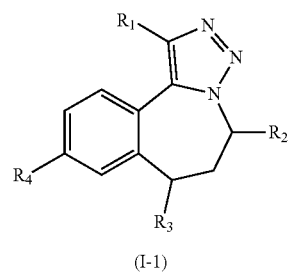
(I-1)
(16) preparing the compound of formula (I-4) and the compound of formula (I-5) by separating and purifying the compound of formula (I-1),
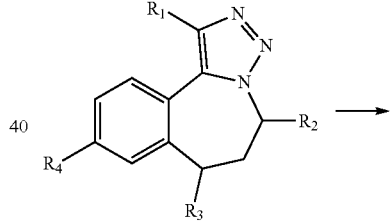
(I-1)
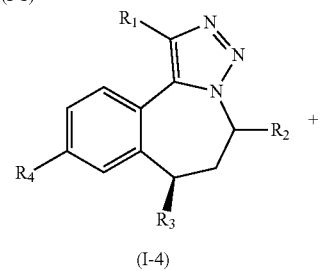
(I-4)
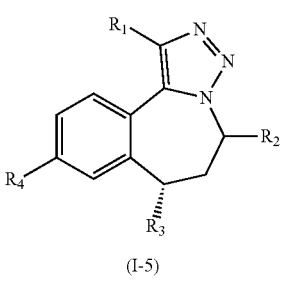
(I-5)

(17) preparing the compound of formula (I-6) and the compound of formula (I-7) by separating and purifying the compound of formula (I-2),
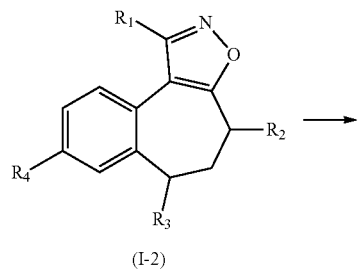
(I-2)
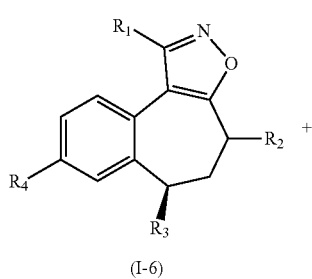
(I-6)
(I-7)
(18) preparing the compound of formula (I-8) and the compound of formula (I-9) by separating and purifying the compound of formula (I-3),
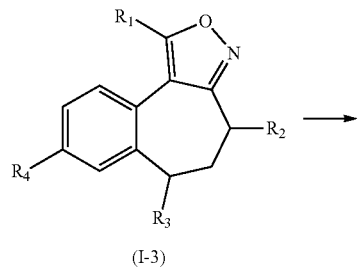
(I-3)
(I-8)
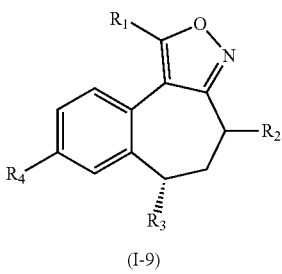
(I-9)
(19) preparing the compound of formula (I-4) by chiral synthesis with the compound of formula Im,
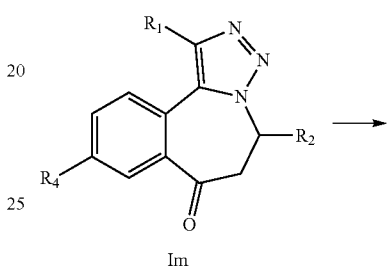
Im
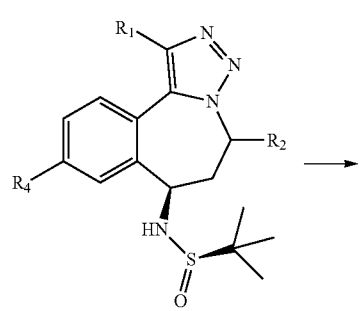
I-10
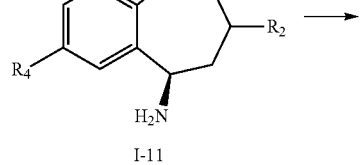
I-11
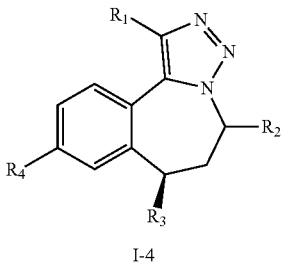
I-4

(20) preparing the compound of formula (I-5) by chiral synthesis with the compound of formula Im,

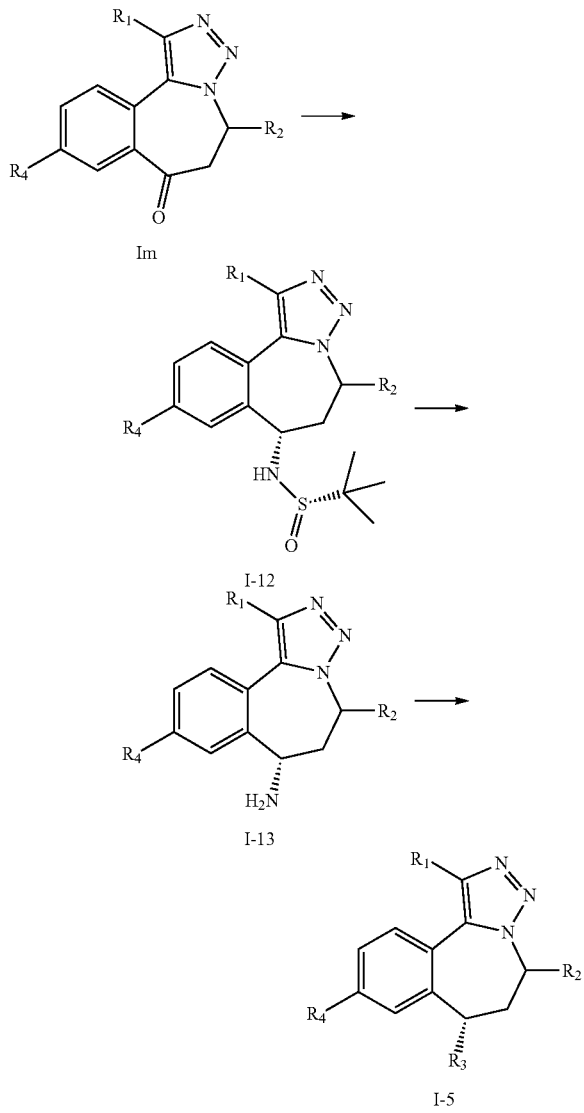

in each of the above schemes, $R_1$, $R_2$, $R_3$, and $R_4$ have the same definitions as those in formula (I).

Further, the present invention provides a pharmaceutical composition comprising one or more selected from the group consisting of the compounds of the present invention, their enantiomers, diastereomers, racemates or mixtures thereof, and chemically acceptable salts, crystalline hydrates, solvent mixtures of the compounds, their enantiomers, diastereomers, racemates and mixtures thereof. In addition, the pharmaceutical composition may optional comprises a pharmaceutically acceptable diluent, carrier, adjuvant, excipient, and the like.

Further, the present invention provides use of the compound or the compound prepared by the preparation method, and its enantiomer, diastereomer, racemate or a mixture thereof, or a chemically acceptable salt, a crystalline hydrate, or a solvent mixture of the compound, its enantiomer, diastereomer, racemate and mixture thereof in preparation of a medicament for treatment of a disease related to the activity or expression of BET Bromodomain BRD4.

Further, the present invention provides a method of treating a disease related to the activity or expression of BET Bromodomain BRD4 comprising administering a subject in need thereof one or more selected from the group consisting of the compounds of claim 1, their enantiomers, diastereomers, racemates or mixtures thereof, and chemically acceptable salts, crystalline hydrates, solvent mixtures of the compounds, their enantiomers, diastereomers, racemates and mixtures thereof.

Further, the disease related to the activity or expression of BET Bromodomain BRD4 includes diabetes, cardiovascular diseases and cancer.

Further, the diabetes include type 1 and type 2 diabetes;
the cardiovascular diseases include heart diseases related to heart failure, arrhythmia and coronary artery lesion;
the cancer includes non-Hodgkin's lymphoma, breast cancer, liver cancer, bowel cancer, esophageal cancer, myelofibrosis, pancreatic cancer, lung cancer, and uterine cancer.

The compounds having a benzo seven-membered ring structure provided by the present invention have a novel structure, and can be prepared by a variety of preparation methods, and the compounds can effectively inhibit the activity of the BRD4 protein, thereby having medical prospects for the treatment of various diseases. Other features and advantages of the present invention will be described in the following description, and become obvious from part of the description, or can be understood by implementing the present invention. The purpose and other advantages of the present invention can be realized and obtained through the structures stated in the description and claims.

MODE OF THE INVENTION

In order to make the objectives, technical solutions, and advantages of the embodiments of the present invention clearer, the technical solutions in the embodiments of the present invention will be illustrated clearly and thoroughly below with reference to the examples of the present invention. Obviously, the examples described are only part but not all of examples of the present invention. Based on the examples of the present invention, all other embodiments obtained by those of ordinary skill in the art without creative work shall fall within the protection scope of the present invention.

Although the existing BET inhibitors have various kinds of structures, no compound having a benzo seven-membered ring structure has ever been reported. Therefore, there are no literature reports on the synthetic method of such compounds, and the binding ability of this class of compounds to BD1/BD2 in BET Bromodomain BRD4 cannot be accurately predicted, neither can the prospects be predicted for using such compounds in treatment of BET Bromodomain-related diseases. The present inventor developed a novel class of compounds having a benzo-seven-membered ring structure and a preparation method thereof, and tested the binding ability of the synthesized compounds to the BD1 domain and BD2 domain of BRD4, and thereby completed the present invention.

The present invention relates to a compound having a benzo seven-membered ring structure represented by formula (I):

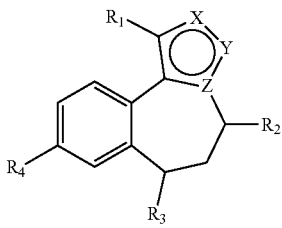

(I)

in formula (I), X, Y, and Z each independently represent CH, N and O, and the formula (I) may be a compound represented by formula (I-1), (I-2) or (I-3), with the proviso that the valence bond rule is satisfied:

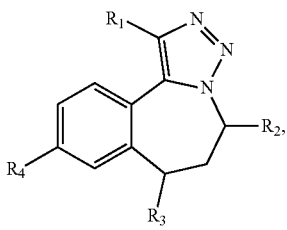

(I-1)

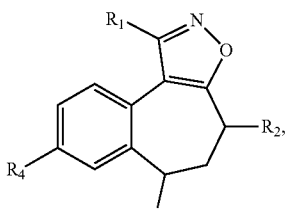

(I-2)

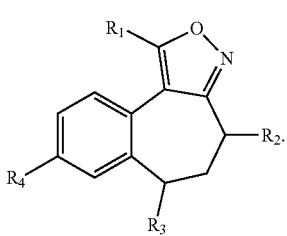

(I-3)

The compounds represented by formulas (I-1), (I-2) and (I-3) contain chiral centers, and thus they have stereoisomers, that is, the compound of formula (I) also includes enantiomers, diastereomers, racemates of the compounds of the formula or mixtures thereof.

The compound represented by formula (I-1) also includes the stereoisomers represented by formulas (I-4) and (I-5):

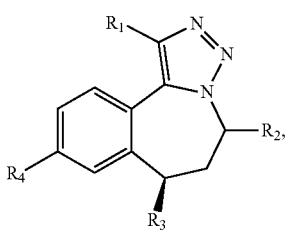

(I-4)

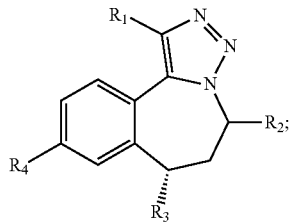

(I-5)

the compound represented by formula (I-2) also includes the stereoisomers represented by formulas (I-6) and (I-7):

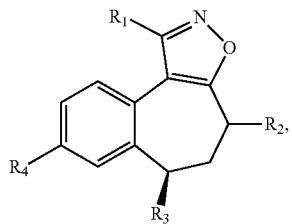

(I-6)

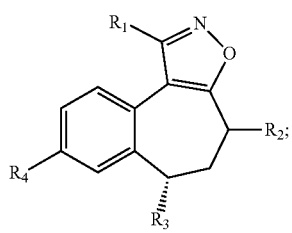

(I-7)

the compound represented by formula (I-3) also includes the stereoisomers represented by formulas (I-8) and (I-9):

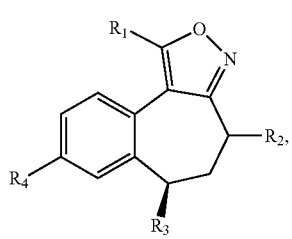

(I-8)

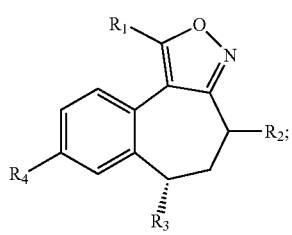

(I-9)

in the above formulas, $R_1$, $R_2$, $R_3$, and $R_4$ have the same definitions as those in the formula (I).

In the definitions of $R_1$, $R_2$, $R_3$, and $R_4$, the terms are defined as below:

In the present invention, unless otherwise specified, the term "substituted" means that one or more atoms or groups on a group are substituted by other substituents, the substituents are selected from the group consisting of, but not limited to, deuterium, halogen, hydroxyl, amino, cyano, an ester group, carboxyl, carbonyl, trifluoromethyl, aminocarbonyl, aminocarbonylamino, aminocarbonylhydroxyl, C1-C6 alkyl, C3-C6 cycloalkyl, C1-C4 alkoxyl, C1-C4 alkylamino, C1-C4 alkylaminocarbonyl, C1-C4 alkylaminocarbonylamino, C1-C4 alkyloxycarbonylamino, C1-C4 alkylcarbamoyloxyl.

The term "heteroaromatic ring" is a heterocyclic structure satisfying Huckel's rule, that is, a heterocyclic structure having aromaticity.

The term "halogen" includes fluorine, chlorine, bromine and iodine.

The term "C3-C6 cycloalkyl" means a cycloalkyl group having 3-6 carbon atoms, such as cyclopropyl, cyclobutyl, cyclopentyl and the like.

The term "C1-C4 alkoxyl" means a straight or branched alkoxyl having 1 to 4 carbon atoms, such as methoxyl, ethoxyl, propoxyl, isopropoxyl, butoxyl, isobutoxyl, sec-butoxyl, tert-butoxyl and the like.

The term "C1-C4 alkylamino" means a C1-C4 alkyl substituted by an amino group, such as groups having structures of "(C1-C4 alkyl)-NH—" or "(C1-C4 alkyl)$_2$-N—", "-(C1-C4 alkylene)-NH$_2$", "(C1-C4 alkyl)-NH—(C1-C4 alkylene)-", or "(C1-C4 alkyl)$_2$-N—(C1-C4 alkylene)-", such as CH$_3$NH—, C$_2$H$_5$NH—, C$_3$H$_7$NH—, (CH$_3$)$_2$N—, —CH$_2$NH$_2$, —C$_2$H$_5$NH$_2$, —C$_3$H$_7$NH$_2$, —C$_2$H$_4$N(CH$_3$)$_2$, and the like. Among others, the C1-C4 alkyl is defined as below.

The term "C1-C4 alkyl" means a straight or branched alkyl having 1 to 4 carbon atoms, such as methyl, ethyl, propyl, isopropyl, butyl, isobutyl, sec-butyl, tert-butyl and the like.

The term "5-12 membered monocyclic or fused heterocyclic ring" means a 5-12 membered saturated or partially unsaturated cyclic group, which comprises 1-4 ring atoms selected from the group consisting of O, S and/or N.

The term "5-12 membered monocyclic or fused heteroaromatic ring" means a 5-12 membered cyclic aromatic group, which comprises 1-4 ring atoms selected from the group consisting of O, S and/or N.

The compound represented by formula (I) can be specifically selected from the group consisting of the compounds listed in the following table:

| No. | Code | Structure | Name |
|---|---|---|---|
| 1 | FA01 | 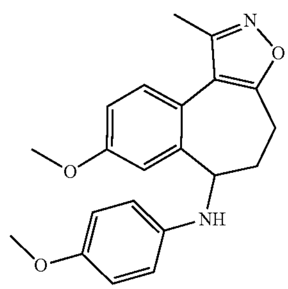 [SMILES: COc1ccc(NC2CCc3onc(C)c3-c3ccc(OC)cc32)cc1] | 8-methoxy-N-(4-methoxyphenyl)-1-methyl-5,6-dihydro-4H-benzo[6,7]cyclohepta[1,2-d]isoxazol-6-amine |
| 2 | FA02 | 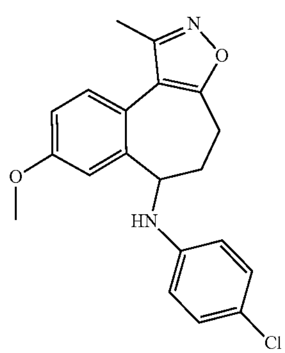 [SMILES: COc1ccc2c(c1)C(Nc1ccc(Cl)cc1)CCc1onc(C)c1-2] | N-(4-chlorophenyl)-8-methoxy-1-methyl-5,6-dihydro-4H-benzo[6,7]cyclohepta[1,2,d]isoxazol-6-amine |
| 3 | FA03 | 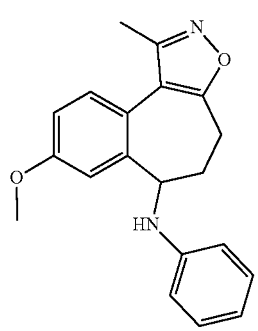 [SMILES: COc1ccc2c(c1)C(Nc1ccccc1)CCc1onc(C)c1-2] | 8-methoxy-1-methyl-N-phenyl-5,6-dihydro-4H-benzo[6,7]cyclohepta[1,2-d]isoxazol-6-amine |

-continued

| No. | Code | Structure | Name |
|---|---|---|---|
| 4 | FA05 | 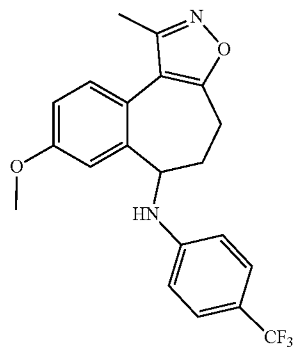 [SMILES: COc1ccc2c(c1)C(Nc1ccc(C(F)(F)F)cc1)CCc1onc(C)c1-2] | 8-methoxy-1-methyl-N-(4-(trifluoromethyl)phenyl)-5,6-dihydro-4H-benzo[6,7]cyclohepta[1,2-d]isoxazol-6-amine |
| 5 | FA06 | 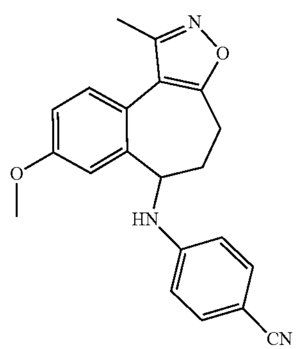 [SMILES: COc1ccc2c(c1)C(Nc1ccc(C#N)cc1)CCc1onc(C)c1-2] | 4-((8-methoxy-1-methyl-5,6-dihydro-4H-benzo[6,7]cyclohepta[1,2-d]isoxazol-6-yl)amino)benzonitrile |
| 6 | BB188 | 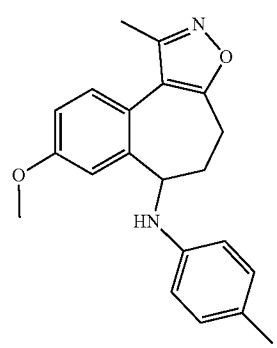 [SMILES: COc1ccc2c(c1)C(Nc1ccc(C)cc1)CCc1onc(C)c1-2] | 8-methoxy-1-methyl-N-(p-tolyl)-5,6-dihydro-4H-benzo[6,7]cyclohepta[1,2-d]isoxazol-6-amine |
| 7 | BB189 | 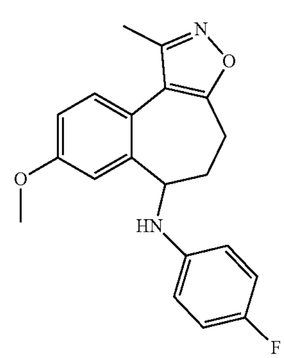 [SMILES: COc1ccc2c(c1)C(Nc1ccc(F)cc1)CCc1onc(C)c1-2] | N-(4-fluorophenyl)-8-methoxy-1-methyl-5,6-dihydro-4H-benzo[6,7]cyclohepta[1,2-d]isoxazol-6-amine |

-continued

| No. | Code | Structure | Name |
|---|---|---|---|
| 8 | BE02 | 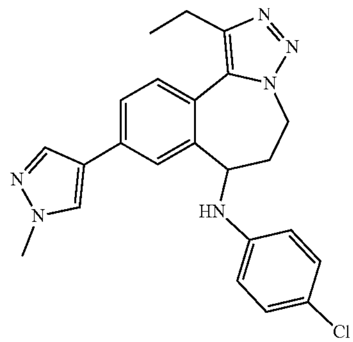 [SMILES: CCc1nnn2c1-c1ccc(-c3cnn(C)c3)cc1C(Nc1ccc(Cl)cc1)CC2] | N-(4-chlorophenyl)-1-ethyl-9-(1-methyl-1H-pyrazol-4-yl)-6,7-dihydro-5H-benzo[c][1,2,3]triazolo[1,5-a]azepin-7-amine |
| 9 | BE25 | 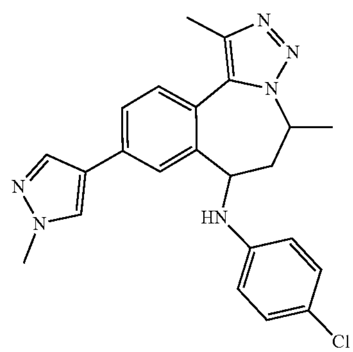 [SMILES: Cc1nnn2c1-c1ccc(-c3cnn(C)c3)cc1C(Nc1ccc(Cl)cc1)CC2C] | N-(4-chlorophenyl)-1,5-dimethyl-9--(1-methyl-1H-pyrazol-4-yl)-6,7-dihydro-5H-benzo[c][1,2,3]triazolo[1,5-a]azepin-7-amine |
| 10 | BE44 | 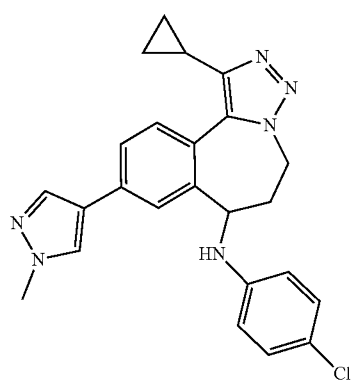 [SMILES: Cn1cc(-c2ccc3c(c2)C(Nc2ccc(Cl)cc2)CCn2nnc(C4CC4)c2-3)cn1] | N-(4-chlorophenyl)-1-cyclopropyl-9-(1-methyl-1H-pyrazol-4-yl)-6,7-dihydro-5H-benzo[c][1,2,3]triazolo[1,5-a]azepin-7-amine |
| 11 | BE95 | 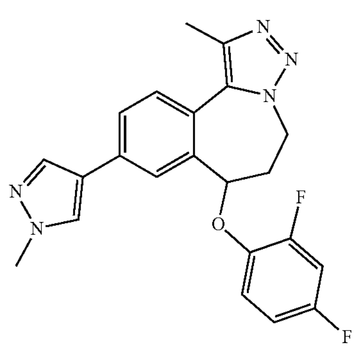 [SMILES: Cc1nnn2c1-c1ccc(-c3cnn(C)c3)cc1C(Oc1ccc(F)cc1F)CC2] | 7-(2,4-difluorophenoxy)-1-methyl-9-(1-methyl-1H-pyrazol-4-yl)-6,7-dihydro-5H-benzo[c][1,2,3]triazolo[1,5-a]azepine |

| No. | Code | Structure | Name |
|---|---|---|---|
| 12 | LA55 | 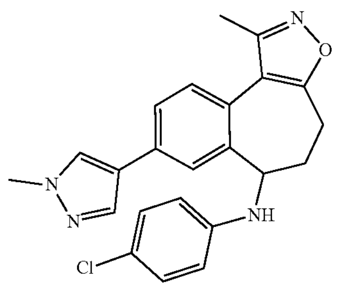 [SMILES: Cc1noc2c1-c1ccc(-c3cnn(C)c3)cc1C(Nc1ccc(Cl)cc1)CC2] | N-(4-chlorophenyl)-1-methyl-8-(1-methyl-1H-pyrazol-4-yl)-5,6-dihydro-4-H-benzo[6,7]cyclohepta[1,2-d]isoxazol-6-amine |
| 13 | LA93 | 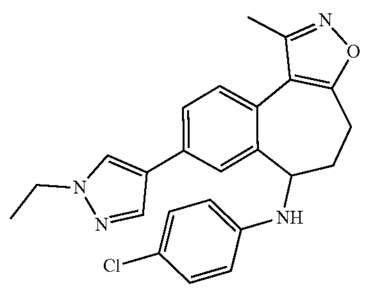 [SMILES: CCn1cc(-c2ccc3c(c2)C(Nc2ccc(Cl)cc2)CCc2onc(C)c2-3)cn1] | N-(4-chlorophenyl)-8-(1-ethyl-1H-pyrazol-4-yl)-1-methyl-5,6-dihydro-4-H-benzo[6,7]cyclohepta[1,2-d]isoxazol-6-amine |
| 14 | LA108 | 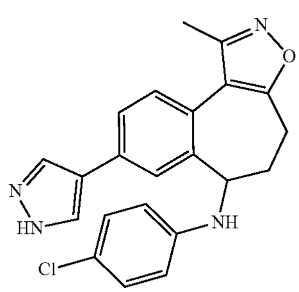 [SMILES: Cc1noc2c1-c1ccc(-c3cn[nH]c3)cc1C(Nc1ccc(Cl)cc1)CC2] | N-(4-chlorophenyl)-1-methyl-8-(1H-pyrazol-4--yl)-5,6-dihydro-4-H-benzo[6,7]cyclohepta[1,2-d]isoxazol-6-amine |
| 15 | LA198 | 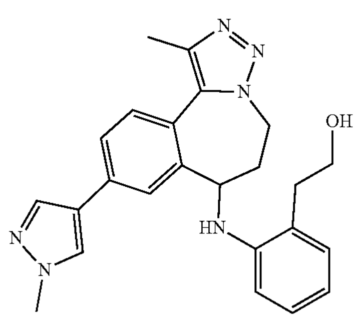 [SMILES: Cc1nnn2c1-c1ccc(-c3cnn(C)c3)cc1C(Nc1ccccc1CCO)CC2] | 2-(2-((1-methyl-9-(1-methyl-1H-pyrazol-4-yl)-6,7-dihydro-5H-benzo[c][1,2,3]triazolo[1,5-a]azepin-7-yl)amino)phenyl)ethan-1-ol |
| 16 | LB01 | 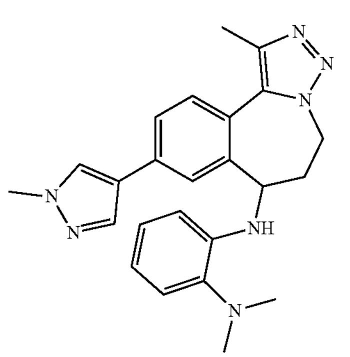 [SMILES: Cc1nnn2c1-c1ccc(-c3cnn(C)c3)cc1C(Nc1ccccc1N(C)C)CC2] | $N^1,N^1$-dimethyl-$N^2$-(1-methyl-9-(1-methyl-1H-pyrazol-4-yl)-6,7-dihydro-5H-benzo[c][1,2,3]triazolo[1,5-a]azepin-7-yl)benzene-1,2-diamine |

-continued

| No. | Code | Structure | Name |
|---|---|---|---|
| 17 | LB17 | 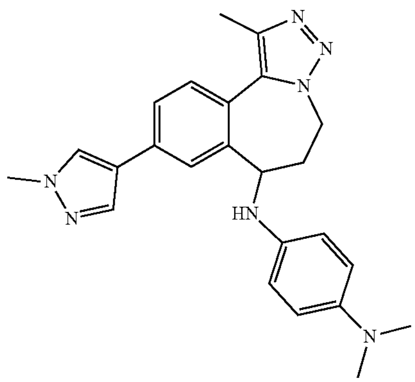 | $N^1,N^1$-dimethyl-$N^4$-(1-methyl-9-(1-methyl-1H-pyrazol-4-yl)-6,7-dihydro-5H-benzo[c][1,2,3]triazolo[1,5-a]azepin-7-yl)benzene-1,4-diamine |
| 18 | LB20 | 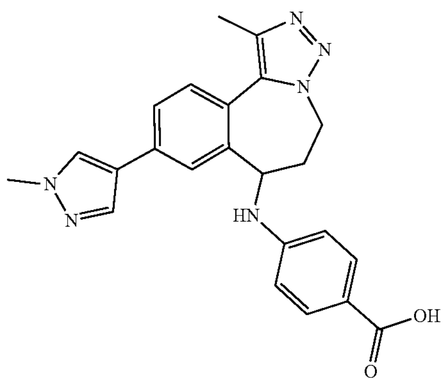 [SMILES: Cc1nnn2c1-c1ccc(-c3cnn(C)c3)cc1C(Nc1ccc(C(=O)O)cc1)CC2] | 4-((1-methyl-9-(1-methyl-1H-pyrazol-4-yl)-6,7-dihydro-5H-benzo[c][1,2,3]triazolo[1,5-a]azepin-7-yl)amino)benzoic acid |
| 19 | LB24 | 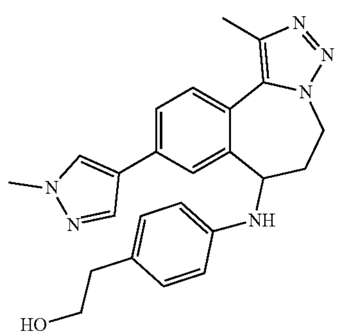 [SMILES: Cc1nnn2c1-c1ccc(-c3cnn(C)c3)cc1C(Nc1ccc(CCO)cc1)CC2] | 2-(4-((1-methyl-9-(1-methyl-1H-pyrazol-4-yl)-6,7-dihydro-5H-benzo[c][1,2,3]triazolo[1,5-a]azepin-7-yl)amino)phenyl)ethan-1-ol |
| 20 | LB32 | 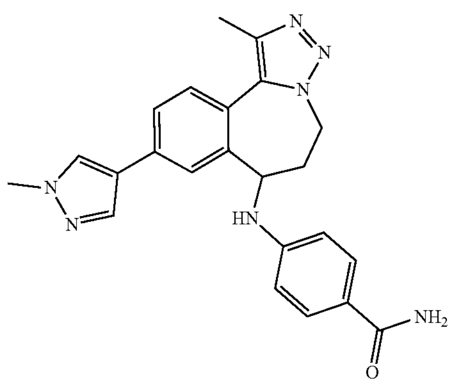 [SMILES: Cc1nnn2c1-c1ccc(-c3cnn(C)c3)cc1C(Nc1ccc(C(N)=O)cc1)CC2] | 4-((1-methyl-9-(1-methyl-1H-pyrazol-4-yl)-6,7-dihydro-5H-benzo[c][1,2,3]triazolo[1,5-a]azepin-7-yl)amino)benzamide |

| No. | Code | Structure | Name |
|---|---|---|---|
| 21 | LB35 | 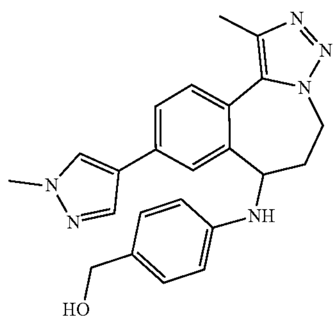 [SMILES: Cc1nnn2c1-c1ccc(-c3cnn(C)c3)cc1C(Nc1ccc(CO)cc1)CC2] | (4-((1-methyl-9-(1-methyl-1H-pyrazol-4-yl)-6,7-dihydro-5H-benzo[c][1,2,3]triazolo[1,5-a]azepin-7-yl)amino)phenyl)methanol |
| 22 | LB36 | 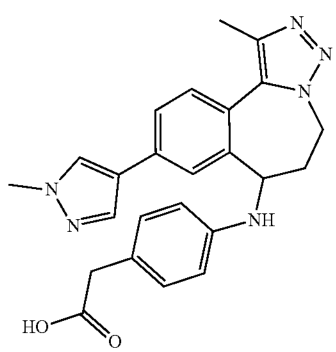 [SMILES: Cc1nnn2c1-c1ccc(-c3cnn(C)c3)cc1C(Nc1ccc(CC(=O)O)cc1)CC2] | 2-(4-((1-methyl-9-(1-methyl-1H-pyrazol-4-yl)-6,7-dihydro-5H-benzo[c][1,2,3]triazolo[1,5-a]azepin-7-yl)amino)phenyl)acetic acid |
| 23 | LB37 | 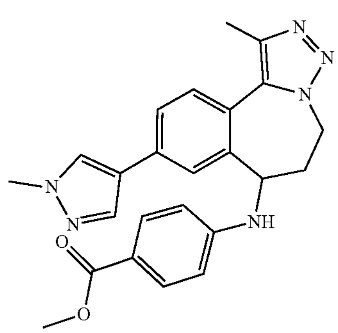 [SMILES: COC(=O)c1ccc(NC2CCn3nnc(C)c3-c3ccc(-c4cnn(C)c4)cc32)cc1] | Methyl-4-((1-methyl-9-(1-methyl-1H-pyrazol-4-yl)-6,7-dihydro-5H-benzo[c][1,2,3]triazolo[15-a]azepin-7-yl)amino)benzoate |
| 24 | LB38 | 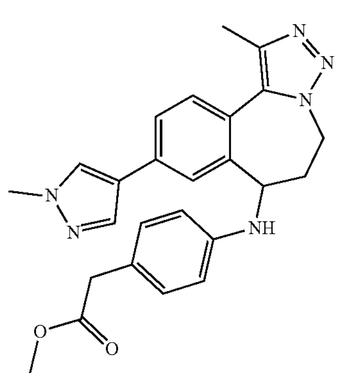 [SMILES: COC(=O)Cc1ccc(NC2CCn3nnc(C)c3-c3ccc(-c4cnn(C)c4)cc32)cc1] | Methyl-2-(4-((1-methyl-9-(1-methyl-1H-pyrazol-4-yl)-6,7-dihydro-5H-benzo[c][1,2,3]triazolo[1,5-a]azepin-7-yl)amino)phenyl)acetate |

| No. | Code | Structure | Name |
|---|---|---|---|
| 25 | RA180 | 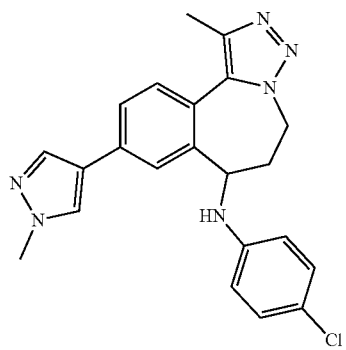 [SMILES: Cc1nnn2c1-c1ccc(-c3cnn(C)c3)cc1C(Nc1ccc(Cl)cc1)CC2] | N-(4-chlorophenyl)-1-methyl-9-(1-methyl-1H-pyrazol-4-yl)-6,7-dihydro-5H-benzo[c][1,2,3]triazolo[1,5-a]azepin-7-amine |
| 26 | RA188 | 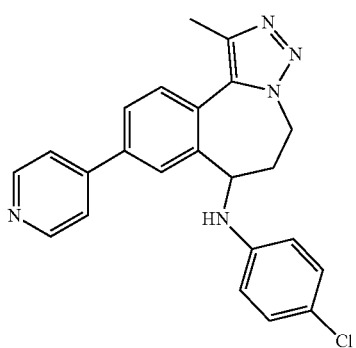 [SMILES: Cc1nnn2c1-c1ccc(-c3ccncc3)cc1C(Nc1ccc(Cl)cc1)CC2] | N-(4-chlorophenyl)-1-methyl-9-(pyridin-4-yl)-6,7-dihydro-5H-benzo[c][1,2,3]triazolo[1,5-a]azepin-7-amine |
| 27 | RA193 | 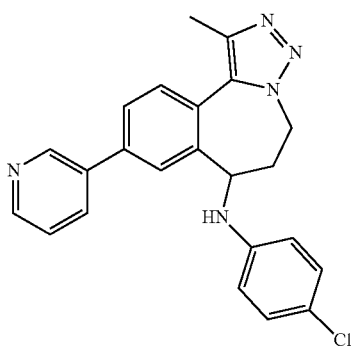 [SMILES: Cc1nnn2c1-c1ccc(-c3cccnc3)cc1C(Nc1ccc(Cl)cc1)CC2] | N-(4-chlorophenyl)-1-methyl-9-(pyridin-3-yl)-6,7-dihydro-5H-benzo[c][1,2,3]triazolo[1,5-a]azepin-7-amine |
| 28 | RA194 | 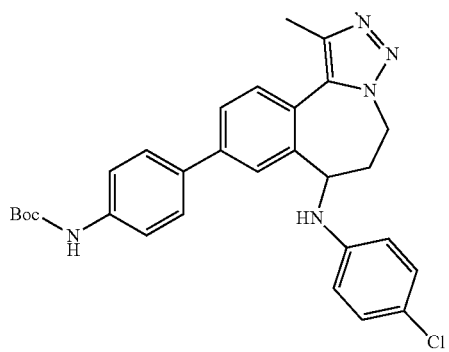 | (4-(7-((4-chlorophenyl)amino)-1-methyl-6,7-dihydro-5H-benzo[c][1,2,3]triazolo[1,5-a]azepin-9-yl)phenyl)carbamate |

| No. | Code | Structure | Name |
|---|---|---|---|
| 29 | RB03 | 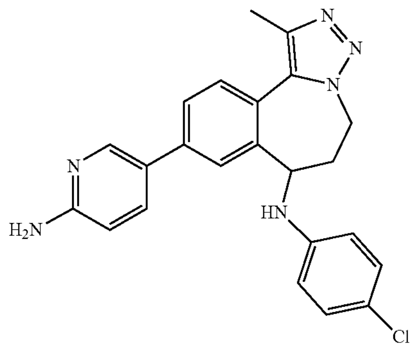 [SMILES: Cc1nnn2c1-c1ccc(-c3ccc(N)nc3)cc1C(Nc1ccc(Cl)cc1)CC2] | 9-(2-aminopyridin-4-yl)-N-(4-chlorophenyl)-1-methyl-6,7-dihydro-5H-benzo[c][1,2,3]triazolo[1,5-a]azepin-7-amine |
| 30 | RB05 | 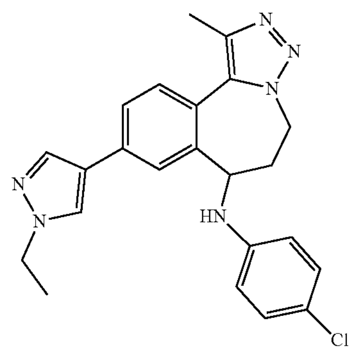 [SMILES: CCn1cc(-c2ccc3c(c2)C(Nc2ccc(Cl)cc2)CCn2nnc(C)c2-3)cn1] | N-(4-chlorophenyl)-9-(1-ethyl-1H-pyrazol-4-yl)-1-methyl-6,7-dihydro-5H-benzo[c][1,2,3]triazolo[1,5-a]azepin-7-amine |
| 31 | RB06 | 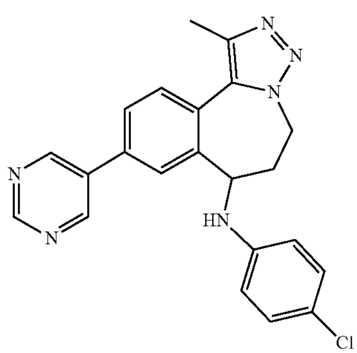 [SMILES: Cc1nnn2c1-c1ccc(-c3cncnc3)cc1C(Nc1ccc(Cl)cc1)CC2] | N-(4-chlorophenyl)-1-methyl-9-(pyrimidin-5-yl)-6,7-dihydro-5H-benzo[c][1,2,3]triazolo[1,5-a]azepin-7-amine |
| 32 | RB07 | 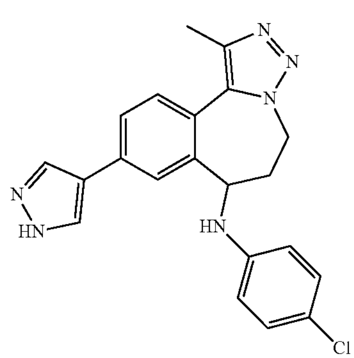 [SMILES: Cc1nnn2c1-c1ccc(-c3cn[nH]c3)cc1C(Nc1ccc(Cl)cc1)CC2] | N-(4-chlorophenyl)-1-methyl-9-(1H-pyrazol-4-yl)-6,7-dihydro-5H-benzo[c][1,2,3]triazolo[1,5-a]azepin-7-amine |

| No. | Code | Structure | Name |
|-----|------|-----------|------|
| 33 | RB11 | 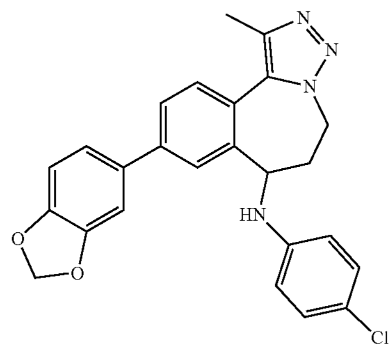 [SMILES: Cc1nnn2c1-c1ccc(-c3ccc4c(c3)OCO4)cc1C(Nc1ccc(Cl)cc1)CC2] | 9-(benzo[d][1,3]dioxol-5-yl)-N-(4-chlorophenyl)-1-methyl-6,7-dihydro-5H-benzo[c][1,2,3]triazolo[1,5-a]azepin-7-amine |
| 34 | RB31 | 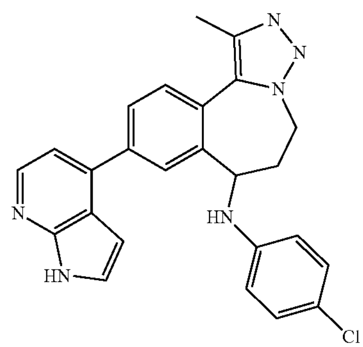 | N-(4-chlorophenyl)-1-methyl-9-(1H-pyrrolo[2,3-b]pyridin-4-yl)-6,7-dihydro-5H-benzo[c][1,2,3]triazolo[1,5-a]azepin-7-amine |
| 35 | RB42 | 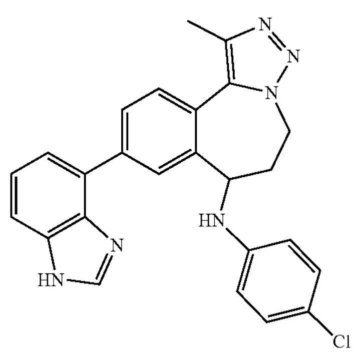 [SMILES: Cc1nnn2c1-c1ccc(-c3cccc4[nH]cnc34)cc1C(Nc1ccc(Cl)cc1)CC2] | 9-(1H-benzo[d]imidazol-4-yl)-N-(4-chlorophenyl)-1-methyl-6,7-dihydro-5H-benzo[c][1,2,3]triazolo[1,5-a]azepin-7-amine |
| 36 | RB43 | 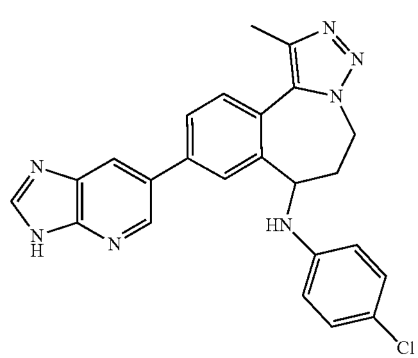 [SMILES: Cc1nnn2c1-c1ccc(-c3cnc4[nH]cnc4c3)cc1C(Nc1ccc(Cl)cc1)CC2] | N-(4-chlorophenyl)-9-(3H-imidazo[4,5-b]pyridin-6-yl)-1-methyl-6,7-dihydro-5H-benzo[c][1,2,3]triazolo[1,5-a]azepin-7-amine |

-continued

| No. | Code | Structure | Name |
|---|---|---|---|
| 37 | RB48 | 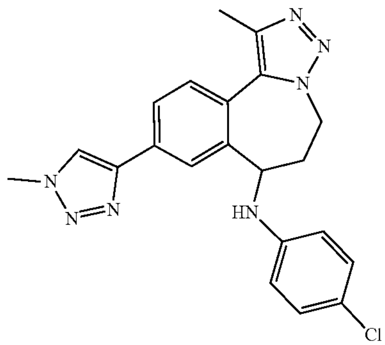 [SMILES: Cc1nnn2c1-c1ccc(-c3cn(C)nn3)cc1C(Nc1ccc(Cl)cc1)CC2] | N-(4-chlorophenyl)-1-methyl-9-(1-methyl-1H-1,2,3-triazol-4-yl)-6,7-dihydro-5H-benzo[c][1,2,3]triazolo[1,5-a]azepin-7-amine |
| 38 | RB66 | 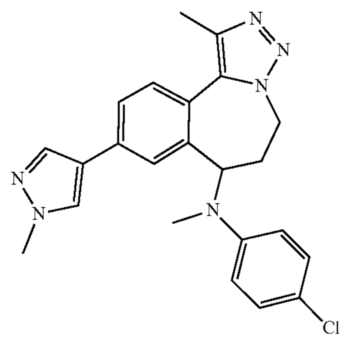 [SMILES: Cc1nnn2c1-c1ccc(-c3cnn(C)c3)cc1C(N(C)c1ccc(Cl)cc1)CC2] | N-(4-chlorophenyl)-N,1-dimethyl-9-(1-methyl-1H-pyrazol-4-yl)-6,7-dihydro-5H-benzo[c][1,2,3]triazolo[1,5-a]azepin-7-amine |
| 39 | BE114 | 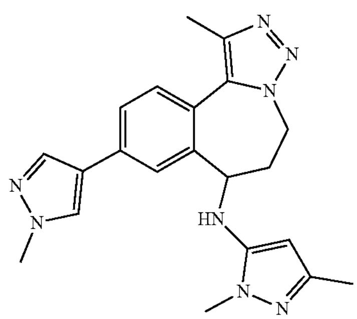 [SMILES: Cc1cc(NC2CCn3nnc(C)c3-c3ccc(-c4cnn(C)c4)cc32)n(C)n1] | N-(1,3-dimethyl-1H-pyrazol-5-yl)-1-methyl-9-(1-methyl-1H-pyrazol-4-yl)-6,7-dihydro-5H-benzo[c][1,2,3]triazolo[1,5-a]azepin-7-amine |
| 40 | BE118 | 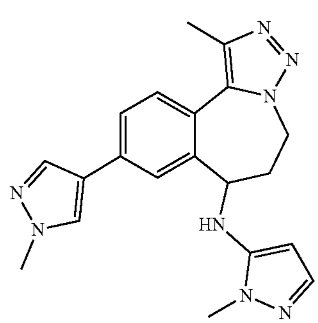 [SMILES: Cc1nnn2c1-c1ccc(-c3cnn(C)c3)cc1C(Nc1ccnn1C)CC2] | 1-methyl-9-(1-methyl-1H-pyrazol-4-yl)-N-(1-methyl-1H-pyrazol-5-yl)-6,7-dihydro-5H-benzo[c][1,2,3]triazolo[1,5-a]azepin-7-amine |

| No. | Code | Structure | Name |
|---|---|---|---|
| 41 | BE128 | 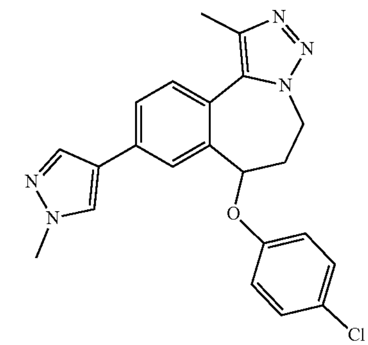 [SMILES: Cc1nnn2c1-c1ccc(-c3cnn(C)c3)cc1C(Oc1ccc(Cl)cc1)CC2] | 7-(4-chlorophenoxy)-1-methyl-9-(1-methyl-1H-pyrazol-4-yl)-6,7-dihydro-5H-benzo[c][1,2,3]triazolo[1,5-a]azepine |
| 42 | BE130 | 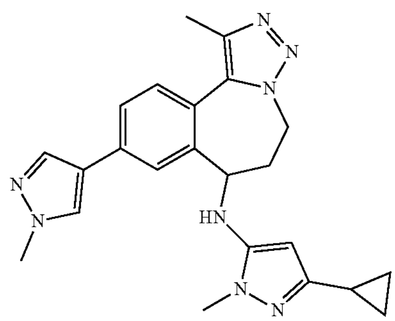 [SMILES: Cc1nnn2c1-c1ccc(-c3cnn(C)c3)cc1C(Nc1cc(C3CC3)nn1C)CC2] | N-(3-cyclopropyl-1-methyl-1H-pyrazol-5-yl)-1-methyl-9-(1-methyl-1H-pyrazol-4-yl)-6,7-dihydro-5H-benzo[c][1,2,3]triazolo[1,5-a]azepin-7-amine |
| 43 | LB42 | 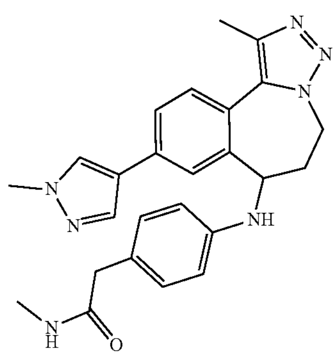 [SMILES: CNC(=O)Cc1ccc(NC2CCn3nnc(C)c3-c3ccc(-c4cnn(C)c4)cc32)cc1] | N-methyl-2-(4-((1-methyl-9-(1-methyl-1H-pyrazol-4-yl)-6,7-dihydro-5H-benzo[c][1,2,3]triazolo[1,5-a]azepin-7-yl)amino)phenyl)acetamide |
| 44 | LB62 | 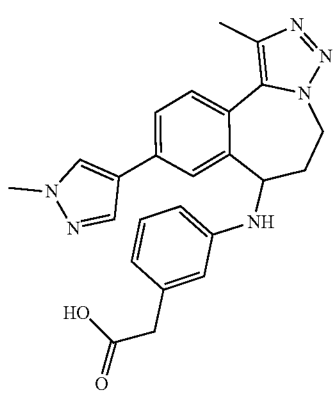 [SMILES: Cc1nnn2c1-c1ccc(-c3cnn(C)c3)cc1C(Nc1cccc(CC(=O)O)c1)CC2] | 2-(3-((1-methyl-9-(1-methyl-1H-pyrazol-4-yl)-6,7-dihydro-5H-benzo[c][1,2,3]triazolo[1,5-a]azepin-7-yl)amino)phenyl)acetic acid |

| No. | Code | Structure | Name |
|---|---|---|---|
| 45 | LB63 | 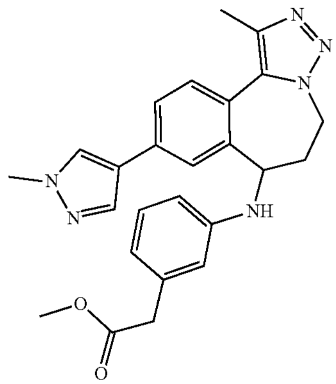 [SMILES: COC(=O)Cc1cccc(NC2CCn3nnc(C)c3-c3ccc(-c4cnn(C)c4)cc32)c1] | methyl 2-(3-((1-methyl-9-(1-methyl-1H-pyrazol-4-yl)-6,7-dihydro-5H-benzo[c][1,2,3]triazolo[1,5-a]azepin-7-yl)amino)phenyl)acetate |
| 46 | LB68 | 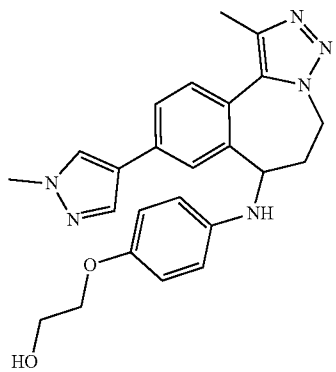 [SMILES: Cc1nnn2c1-c1ccc(-c3cnn(C)c3)cc1C(Nc1ccc(OCCO)cc1)CC2] | 2-(4-((1-methyl-9-(1-methyl-1H-pyrazol-4-yl)-6,7-dihydro-5H-benzo[c][1,2,3]triazolo[1,5-a]azepin-7-yl)amino)phenoxy)ethanol |
| 47 | LB71 | 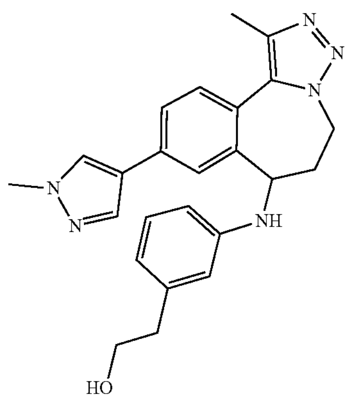 [SMILES: Cc1nnn2c1-c1ccc(-c3cnn(C)c3)cc1C(Nc1cccc(CCO)c1)CC2] | 2-(3-((1-methyl-9-(1-methyl-1H-pyrazol-4-yl)-6,7-dihydro-5H-benzo[c][1,2,3]triazolo[1,5-a]azepin-7-yl)amino)phenyl)ethanol |
| 48 | LB77 | 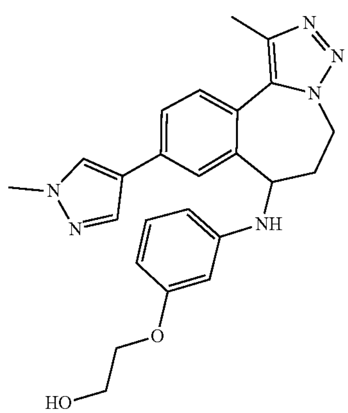 [SMILES: Cc1nnn2c1-c1ccc(-c3cnn(C)c3)cc1C(Nc1cccc(OCCO)c1)CC2] | 2-(3-((1-methyl-9-(1-methyl-1H-pyrazol-4-yl)-6,7-dihydro-5H-benzo[c][1,2,3]triazolo[1,5-a]azepin-7-yl)amino)phenoxy)ethanol |

| No. | Code | Structure | Name |
|---|---|---|---|
| 49 | LB83 | 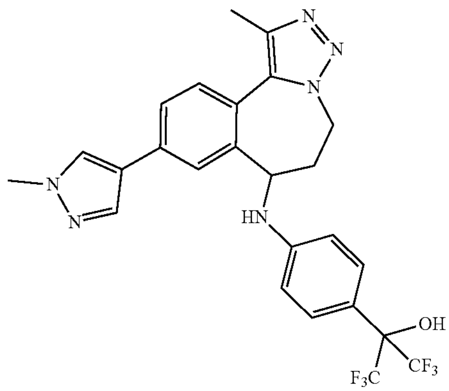 [SMILES: Cc1nnn2c1-c1ccc(-c3cnn(C)c3)cc1C(Nc1ccc(C(O)(C(F)(F)F)C(F)(F)F)cc1)CC2] | 1,1,1,3,3,3-hexafluoro-2-(4-((1-methyl-9-(1-methyl-1H-pyrazol-4-yl)-6,7-dihydro-5H-benzo[c][1,2,3]triazolo[1,5-a]azepin-7-yl)amino)phenyl)propan-2-ol |
| 50 | LB86 | 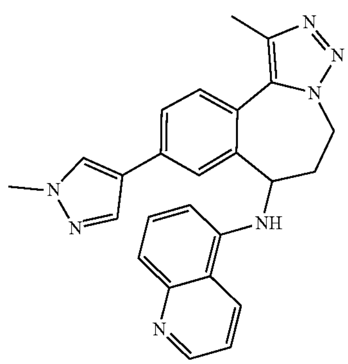 [SMILES: Cc1nnn2c1-c1ccc(-c3cnn(C)c3)cc1C(Nc1cccc3ncccc13)CC2] | 1-methyl-9-(1-methyl-1H-pyrazol-4-yl)-N-(quinolin-5-yl)-6,7-dihydro-5H-benzo[c][1,2,3]triazolo[1,5-a]azepin-7-amine |
| 51 | LB88 | 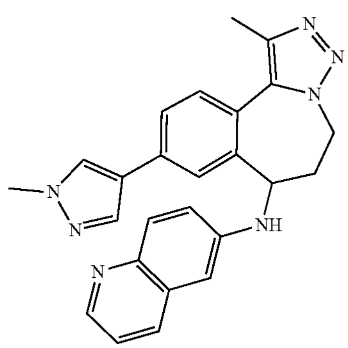 [SMILES: Cc1nnn2c1-c1ccc(-c3cnn(C)c3)cc1C(Nc1ccc3ncccc3c1)CC2] | 1-methyl-9-(1-methyl-1H-pyrazol-4-yl)-N-(quinolin-6-yl)-6,7-dihydro-5H-benzo[c][1,2,3]triazolo[1,5-a]azepin-7-amine |
| 52 | LB89 | 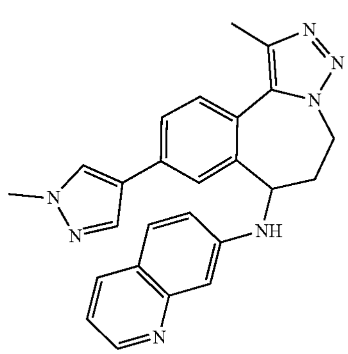 [SMILES: Cc1nnn2c1-c1ccc(-c3cnn(C)c3)cc1C(Nc1ccc3cccnc3c1)CC2] | 1-methyl-9-(1-methyl-1H-pyrazol-4-yl)-N-(quinolin-7-yl)-6,7-dihydro-5H-benzo[c][1,2,3]triazolo[1,5-a]azepin-7-amine |

-continued

| No. | Code | Structure | Name |
|-----|------|-----------|------|
| 53 | LB90 | 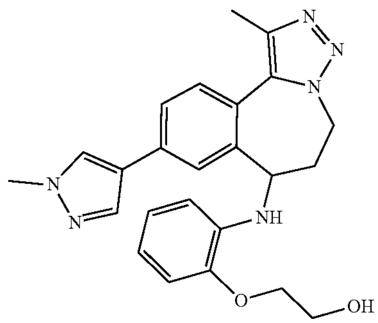 [SMILES: Cc1nnn2c1-c1ccc(-c3cnn(C)c3)cc1C(Nc1ccccc1OCCO)CC2] | 2-(2-((1-methyl-9-(1-methyl-1H-pyrazol-4-yl)-6,7-dihydro-5H-benzo[c][1,2,3]triazolo[1,5-a]azepin-7-yl)amino)phenoxy)ethanol |
| 54 | LB91 | 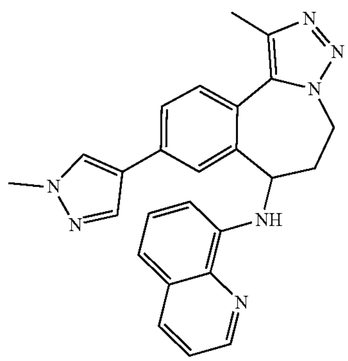 [SMILES: Cc1nnn2c1-c1ccc(-c3cnn(C)c3)cc1C(Nc1cccc3cccnc13)CC2] | 1-methyl-9-(1-methyl-1H-pyrazol-4-yl)-N-(quinolin-8-yl)-6,7-dihydro-5H-benzo[c][1,2,3]triazolo[1,5-a]azepin-7-amine |
| 55 | LB92 | 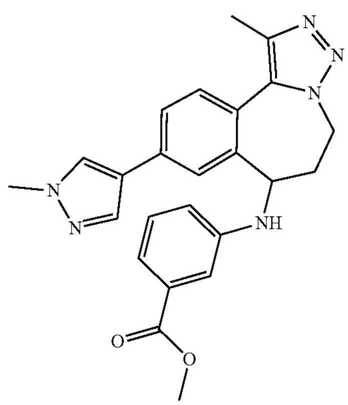 [SMILES: COC(=O)c1cccc(NC2CCn3nnc(C)c3-c3ccc(-c4cnn(C)c4)cc32)c1] | methyl 3-((1-methyl-9-(1-methyl-1H-pyrazol-4-yl)-6,7-dihydro-5H-benzo[c][1,2,3]triazolo[1,5-a]azepin-7-yl)amino)benzoate |
| 56 | LB97 | 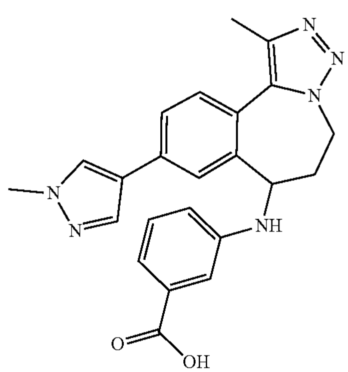 [SMILES: Cc1nnn2c1-c1ccc(-c3cnn(C)c3)cc1C(Nc1cccc(C(=O)O)c1)CC2] | 3-((1-methyl-9-(1-methyl-1H-pyrazol-4-yl)-6,7-dihydro-5H-benzo[c][1,2,3]triazolo[1,5-a]azepin-7-yl)amino)benzoic acid |

| No. | Code | Structure | Name |
|---|---|---|---|
| 57 | LB98 | 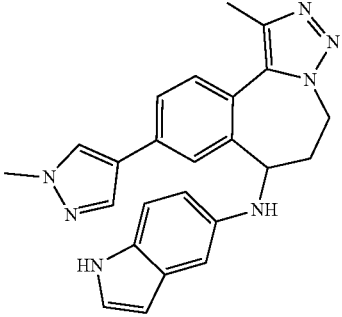 [SMILES: Cc1nnn2c1-c1ccc(-c3cnn(C)c3)cc1C(Nc1ccc3[nH]ccc3c1)CC2] | N-(1H-indol-5-yl)-1-methyl-9-(1-methyl-1H-pyrazol-4-yl)-6,7-dihydro-5H-benzo[c][1,2,3]triazolo[1,5-a]azepin-7-amine |
| 58 | LB103 | 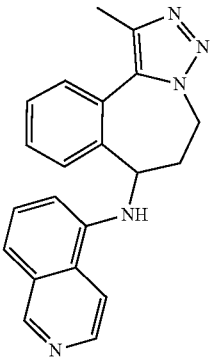 [SMILES: Cc1nnn2c1-c1ccccc1C(Nc1cccc3cnccc13)CC2] | N-(isoquinolin-5-yl)-1-methyl-6,7-dihydro-5H-benzo[c][1,2,3]triazolo[1,5-a]azepin-7-amine |
| 59 | LB113 | 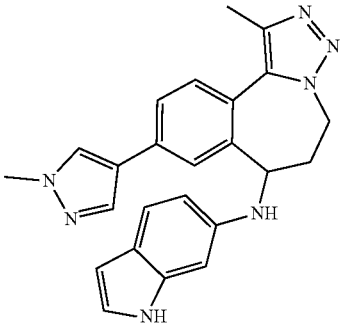 [SMILES: Cc1nnn2c1-c1ccc(-c3cnn(C)c3)cc1C(Nc1ccc3cc[nH]c3c1)CC2] | N-(1H-indol-6-yl)-1-methyl-9-(1-methyl-1H-pyrazol-4-yl)-6,7-dihydro-5H-benzo[c][1,2,3]triazolo[1,5-a]azepin-7-amine |
| 60 | LB114 | 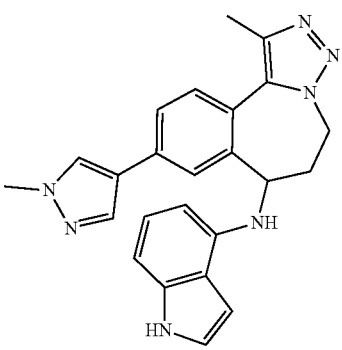 [SMILES: Cc1nnn2c1-c1ccc(-c3cnn(C)c3)cc1C(Nc1cccc3[nH]ccc13)CC2] | N-(1H-indol-4-yl)-1-methyl-9-(1-methyl-1H-pyrazol-4-yl)-6,7-dihydro-5H-benzo[c][1,2,3]triazolo[1,5-a]azepin-7-amine |

| No. | Code | Structure | Name |
|---|---|---|---|
| 61 | LB128 | 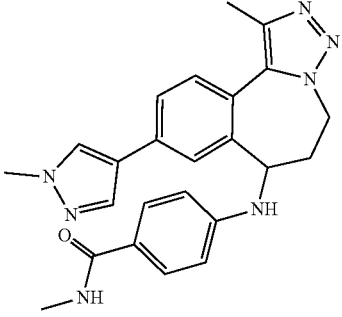 [SMILES: CNC(=O)c1ccc(NC2CCn3nnc(C)c3-c3ccc(-c4cnn(C)c4)cc32)cc1] | N-methyl-4-((1-methyl-9-(1-methyl-1H-pyrazol-4-yl)-6,7-dihydro-5H-benzo[c][1,2,3]triazolo[1,5-a]azepin-7-yl)amino)benzamide |
| 62 | LB138 | 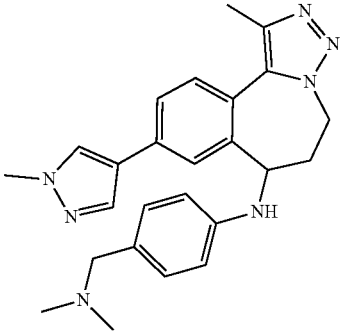 [SMILES: Cc1nnn2c1-c1ccc(-c3cnn(C)c3)cc1C(Nc1ccc(CN(C)C)cc1)CC2] | N-(4-((dimethylamino)methyl)phenyl)-1-methyl-9-(1-methyl-1H-pyrazol-4-yl)-6,7-dihydro-5H-benzo[c][1,2,3]triazolo[1,5-a]azepin-7-amine |
| 63 | LB139 | 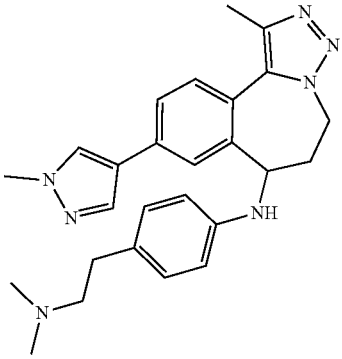 [SMILES: Cc1nnn2c1-c1ccc(-c3cnn(C)c3)cc1C(Nc1ccc(CCN(C)C)cc1)CC2] | N-(4-(2-(dimethylamino)ethyl)phenyl)-1-methyl-9-(1-methyl-1H-pyrazol-[1,2,3]triazolo[1,5-a]azepin-7-amine |
| 64 | LB142 | 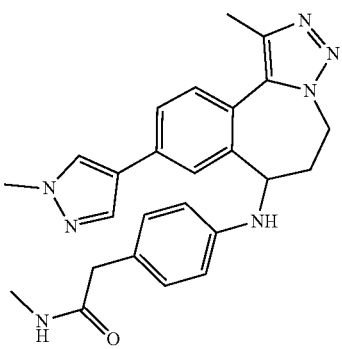 [SMILES: CNC(=O)Cc1ccc(NC2CCn3nnc(C)c3-c3ccc(-c4cnn(C)c4)cc32)cc1] | N-methyl-2-(4-((1-methyl-9-(1-methyl-1H-pyrazol-4-yl)-6,7-dihydro-5H-benzo[c][1,2,3]triazolo[1,5-a]azepin-7-yl)amino)phenyl)acetamide |

| No. | Code | Structure | Name |
|---|---|---|---|
| 65 | LB143 | 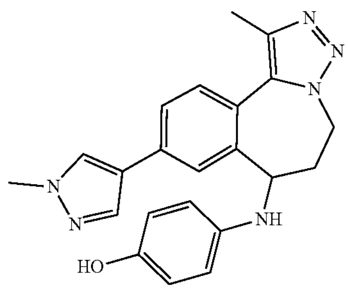 | 4-((1-methyl-9-(1-methyl-1H-pyrazol-4-yl)-6,7-dihydro-5H-benzo[c][1,2,3]triazolo[1,5-a]azepin-7-yl)amino)phenol |
| 66 | RB90 | 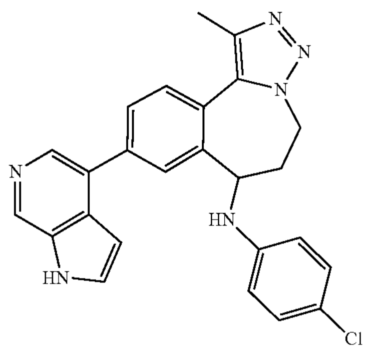 [SMILES: Cc1nnn2c1-c1ccc(-c3cncc4[nH]ccc34)cc1C(Nc1ccc(Cl)cc1)CC2] | N-(4-chlorophenyl)-1-methyl-9-(1H-pyrrolo[2,3-c]pyridin-4-yl)-6,7-dihydro-5H-benzo[c][1,2,3]triazolo[1,5-a]azepin-7-amine |
| 67 | RB99 | 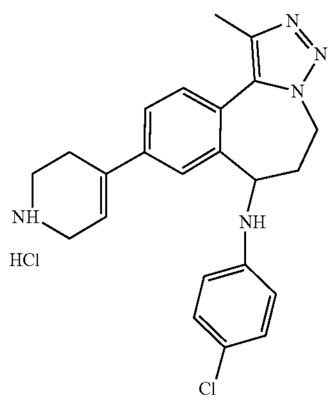 [SMILES: Cl ; Cc1nnn2c1-c1ccc(C3=CCNCC3)cc1C(Nc1ccc(Cl)cc1)CC2] | N-(4-chlorophenyl)-1-methyl-9-(1,2,3,6-tetrahydropyridin-4-yl)-6,7-dihydro-5H-benzo[c][1,2,3]triazolo[1,5-a]azepin-7-amine hydrochloride |
| 68 | LB152 | 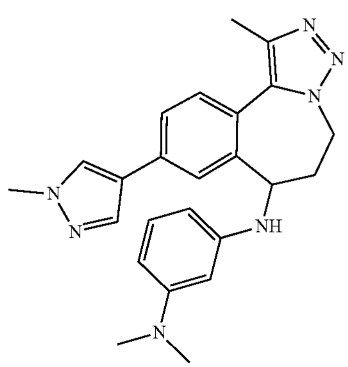 [SMILES: Cc1nnn2c1-c1ccc(-c3cnn(C)c3)cc1C(Nc1cccc(N(C)C)c1)CC2] | $N^1,N^1$-dimethyl-$N^3$-(1-methyl-9-(1-methyl-1H-pyrazol-4-yl)-6,7-dihydro-5H-benzo[c][1,2,3]triazolo[1,5-a]azepin-7-yl)benzene-1,3-diamine |

-continued

| No. | Code | Structure | Name |
|---|---|---|---|
| 69 | LB160 | 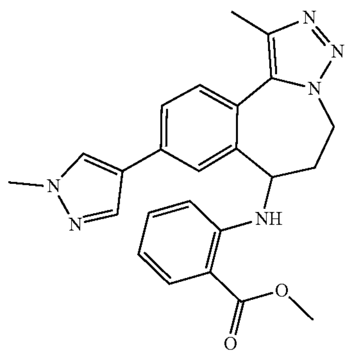 [SMILES: COC(=O)c1ccccc1NC1CCn2nnc(C)c2-c2ccc(-c3cnn(C)c3)cc21] | methyl 2-((1-methyl-9-(1-methyl-1H-pyrazol-4-yl)-6,7-dihydro-5H-benzo[c][1,2,3]triazolo[1,5-a]azepin-7-yl)amino)benzoate |
| 70 | LB164 | 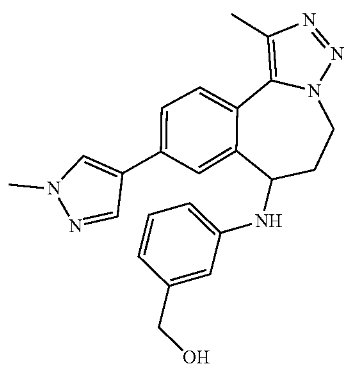 [SMILES: Cc1nnn2c1-c1ccc(-c3cnn(C)c3)cc1C(Nc1cccc(CO)c1)CC2] | (3-((1-methyl-9-(1-methyl-1H-pyrazol-4-yl)-6,7-dihydro-5H-benzo[c][1,2,3]triazolo[1,5-a]azepin-7-yl)amino)phenyl)methanol |
| 71 | LB170 | 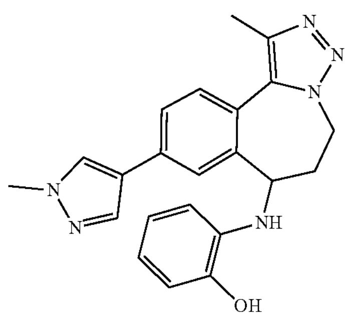 [SMILES: Cc1nnn2c1-c1ccc(-c3cnn(C)c3)cc1C(Nc1ccccc1O)CC2] | 2-((1-methyl-9-(1-methyl-1H-pyrazol-4-yl)-6,7-dihydro-5H-benzo[c][1,2,3]triazolo[1,5-a]azepin-7-yl)amino)phenol |
| 72 | LB171 | 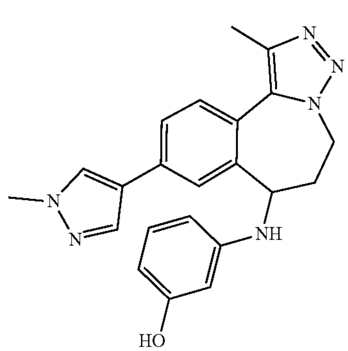 [SMILES: Cc1nnn2c1-c1ccc(-c3cnn(C)c3)cc1C(Nc1cccc(O)c1)CC2] | 3-((1-methyl-9-(1-methyl-1H-pyrazol-4-yl)-6,7-dihydro-5H-benzo[c][1,2,3]triazolo[1,5-a]azepin-7-yl)amino)phenol |

-continued

| No. | Code | Structure | Name |
|---|---|---|---|
| 73 | LB173 | 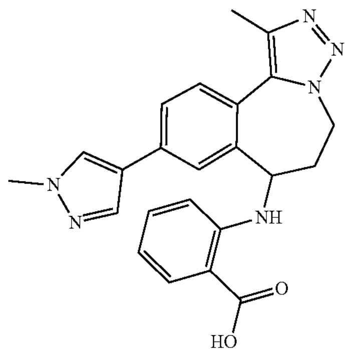 [SMILES: Cc1nnn2c1-c1ccc(-c3cnn(C)c3)cc1C(Nc1ccccc1C(=O)O)CC2] | 2-((1-methyl-9-(1-methyl-1H-pyrazol-4-yl)-6,7-dihydro-5H-benzo[c][1,2,3]triazolo[1,5-a]azepin-7-yl)amino)benzoic acid |
| 74 | LB175 | 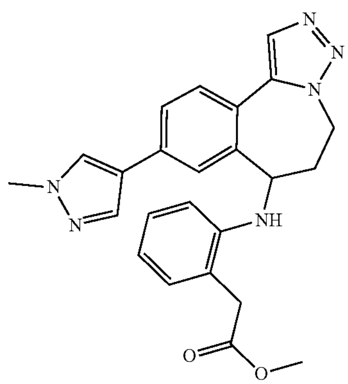 [SMILES: COC(=O)Cc1ccccc1NC1CCn2nncc2-c2ccc(-c3cnn(C)c3)cc21] | methyl 2-(2-((9-(1-methyl-1H-pyrazol-4-yl)-6,7-dihydro-5H-benzo[c][1,2,3]triazolo[1,5-a]azepin-7-yl)amino)phenyl)acetate |
| 75 | LB181 | 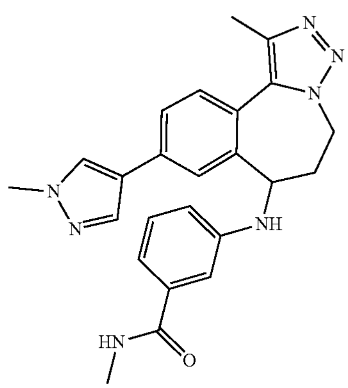 [SMILES: CNC(=O)c1cccc(NC2CCn3nnc(C)c3-c3ccc(-c4cnn(C)c4)cc32)c1] | N-methyl-3-((1-methyl-9-(1-methyl-1H-pyrazol-4-yl)-6,7-dihydro-5H-benzo[c][1,2,3]triazolo[1,5-a]azepin-7-yl)amino)benzamide |
| 76 | LB185 | 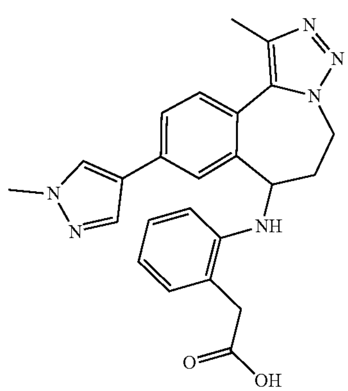 [SMILES: Cc1nnn2c1-c1ccc(-c3cnn(C)c3)cc1C(Nc1ccccc1CC(=O)O)CC2] | 2-(2-((1-methyl-9-(1-methyl-1H-pyrazol-4-yl)-6,7-dihydro-5H-benzo[c][1,2,3]triazolo[1,5-a]azepin-7-yl)amino)phenyl)acetic acid |

-continued

| No. | Code | Structure | Name |
|---|---|---|---|
| 77 | LB186 | 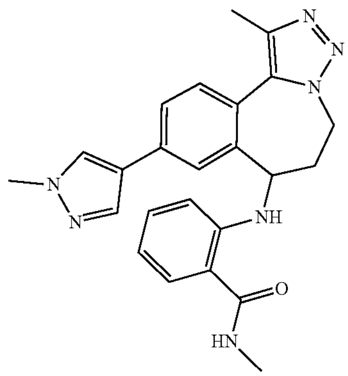 [SMILES: CNC(=O)c1ccccc1NC1CCn2nnc(C)c2-c2ccc(-c3cnn(C)c3)cc21] | N-methyl-2-((1-methyl-9-(1-methyl-1H-pyrazol-4-yl)-6,7-dihydro-5H-benzo[c][1,2,3]triazolo[1,5-a]azepin-7-yl)amino)benzamide |
| 78 | LB192 | 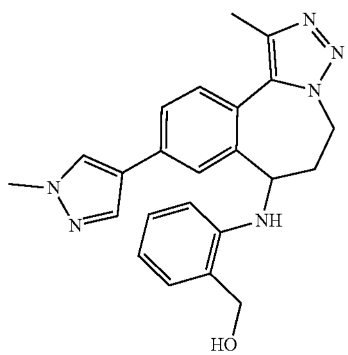 [SMILES: Cc1nnn2c1-c1ccc(-c3cnn(C)c3)cc1C(Nc1ccccc1CO)CC2] | (2-((1-methyl-9-(1-methyl-1H-pyrazol-4-yl)-6,7-dihydro-5H-benzo[c][1,2,3]triazolo[1,5-a]azepin-7-yl)amino)phenyl)methanol |
| 79 | LC01 | 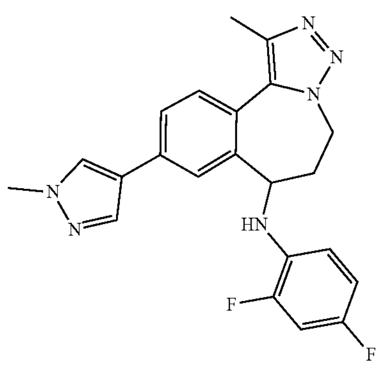 [SMILES: Cc1nnn2c1-c1ccc(-c3cnn(C)c3)cc1C(Nc1ccc(F)cc1F)CC2] | N-(2,4-difluorophenyl)-1-methyl-9-(1-methyl-1H-pyrazol-4-yl)-6,7-dihydro-5H-benzo[c][1,2,3]triazolo[1,5-a]azepin-7-amine |
| 80 | LC03 | 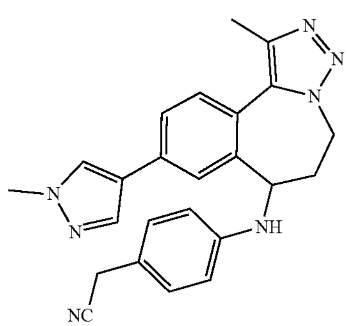 [SMILES: Cc1nnn2c1-c1ccc(-c3cnn(C)c3)cc1C(Nc1ccc(CC#N)cc1)CC2] | 2-(4-((1-methyl-9-(1-methyl-1H-pyrazol-4-yl)-6,7-dihydro-5H-benzo[c][1,2,3]triazolo[1,5-a]azepin-7-yl)amino)phenyl)acetonitrile |

| No. | Code | Structure | Name |
|---|---|---|---|
| 81 | LC07 | 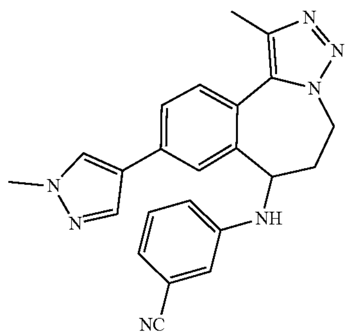 [SMILES: Cc1nnn2c1-c1ccc(-c3cnn(C)c3)cc1C(Nc1cccc(C#N)c1)CC2] | 3-((1-methyl-9-(1-methyl-1H-pyrazol-4-yl)-6,7-dihydro-5H-benzo[c][1,2,3]triazolo[1,5-a]azepin-7-yl)amino)benzonitrile |
| 82 | LC09 | 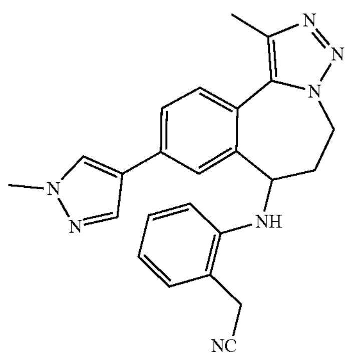 [SMILES: Cc1nnn2c1-c1ccc(-c3cnn(C)c3)cc1C(Nc1ccccc1CC#N)CC2] | 2-(2-((1-methyl-9-(1-methyl-1H-pyrazol-4-yl)-6,7-dihydro-5H-benzo[c][1,2,3]triazolo[1,5-a]azepin-7-yl)amino)phenyl)acetonitrile |
| 83 | LC10 | 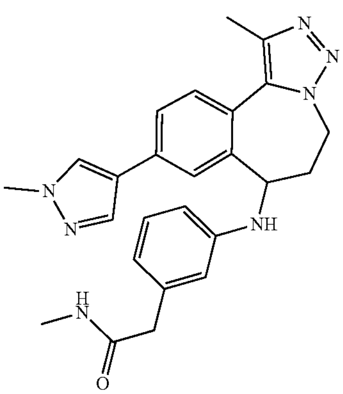 [SMILES: CNC(=O)Cc1cccc(NC2CCn3nnc(C)c3-c3ccc(-c4cnn(C)c4)cc32)c1] | N-methyl-2-(3-((1-methyl-9-(1-methyl-1H-pyrazol-4-yl)-6,7-dihydro-5H-benzo[c][1,2,3]triazolo[1,5-a]azepin-7-yl)amino)phenyl)acetamide |
| 84 | LC11 | 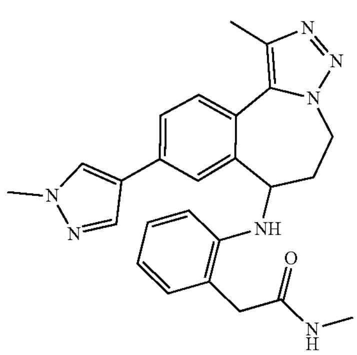 | N-methyl-2-(2-((1-methyl-9-(1-methyl-1H-pyrazol-4-yl)-6,7-dihydro-5H-benzo[c][1,2,3]triazolo[1,5-a]azepin-7-yl)amino)phenyl)acetamide |

| No. | Code | Structure | Name |
|---|---|---|---|
| 85 | LC18 | 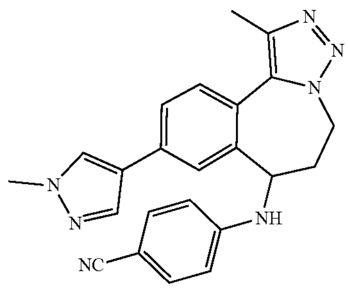 [SMILES: Cc1nnn2c1-c1ccc(-c3cnn(C)c3)cc1C(Nc1ccc(C#N)cc1)CC2] | 4-((1-methyl-9-(1-methyl-1H-pyrazol-4-yl)-6,7-dihydro-5H-benzo[c][1,2,3]triazolo[1,5-a]azepin-7-yl)amino)benzonitrile |
| 86 | LC20 | 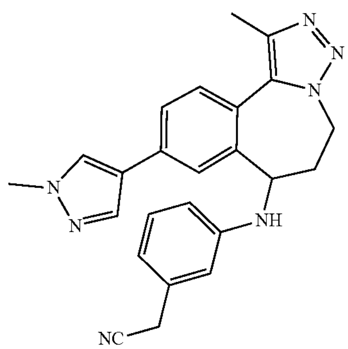 [SMILES: Cc1nnn2c1-c1ccc(-c3cnn(C)c3)cc1C(Nc1cccc(CC#N)c1)CC2] | 2-(3-((1-methyl-9-(1-methyl-1H-pyrazol-4-yl)-6,7-dihydro-5H-benzo[c][1,2,3]triazolo[1,5-a]azepin-7-yl)amino)phenyl)acetonitrile |
| 87 | LC29 | 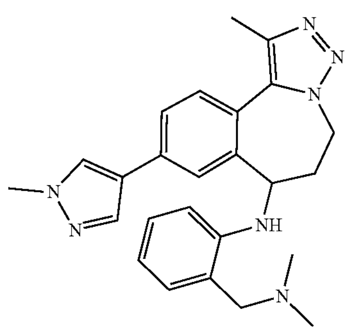 [SMILES: Cc1nnn2c1-c1ccc(-c3cnn(C)c3)cc1C(Nc1ccccc1CN(C)C)CC2] | N-(2-((dimethylamino)methyl)phenyl)-1-methyl-9-(1-methyl-1H-pyrazol-4-yl)-6,7-dihydro-5H-benzo[c][1,2,3]triazolo[1,5-a]azepin-7-amine |
| 88 | LC31 | 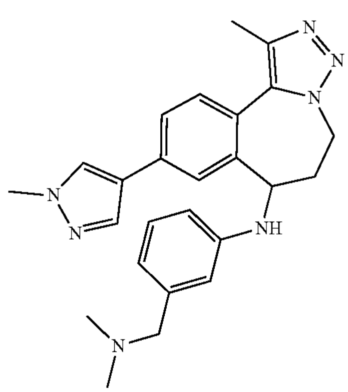 [SMILES: Cc1nnn2c1-c1ccc(-c3cnn(C)c3)cc1C(Nc1cccc(CN(C)C)c1)CC2] | N-(3-((dimethylamino)methyl)phenyl)-1-methyl-9-(1-methyl-1H-pyrazol-4-yl)-6,7-dihydro-5H-benzo[c]triazolo[1,5-a]azepin-7-amine |

| No. | Code | Structure | Name |
|---|---|---|---|
| 89 | LC56 | 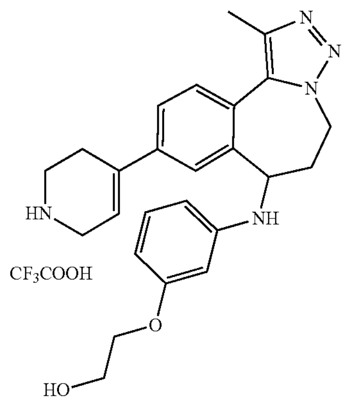 [SMILES: "CF3COOH" ; Cc1nnn2c1-c1ccc(C3=CCNCC3)cc1C(Nc1cccc(OCCO)c1)CC2] | 2-(3-((1-methyl-9-(1,2,3,6-tetrahydropyridin-4-yl)-6,7-dihydro-5H-benzo[c][1,2,3]triazolo[1,5-a]azepin-7-yl)amino)phenoxy)ethan-1-ol 2,2,2-trifluoroacetate |
| 90 | LC75 | 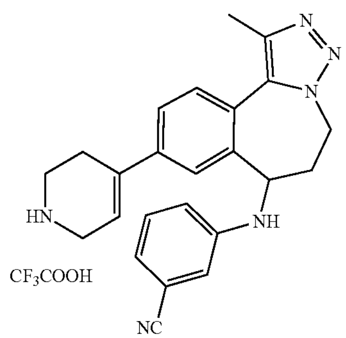 [SMILES: "CF3COOH" ; Cc1nnn2c1-c1ccc(C3=CCNCC3)cc1C(Nc1cccc(C#N)c1)CC2] | 3-((1-methyl-9-(1,2,3,6-tetrahydropyridin-4-yl)-6,7-dihydro-5H-benzo[c][1,2,3]triazolo[1,5-a]azepin-7-yl)amino)benzonitrile 2,2,2-trifluoroacetate |
| 91 | LC79 | 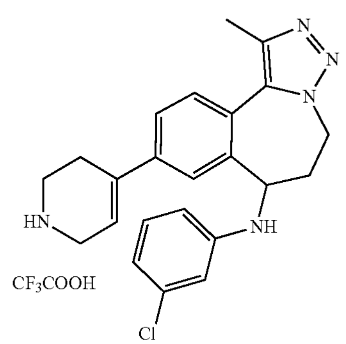 [SMILES: "CF3COOH" ; Cc1nnn2c1-c1ccc(C3=CCNCC3)cc1C(Nc1cccc(Cl)c1)CC2] | N-(3-chlorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate |
| 92 | LC84 | 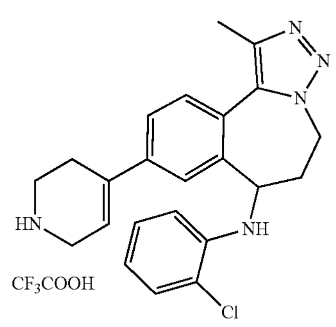 [SMILES: "CF3COOH" ; Cc1nnn2c1-c1ccc(C3=CCNCC3)cc1C(Nc1ccccc1Cl)CC2] | N-(2-chlorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate |

| No. | Code | Structure | Name |
|---|---|---|---|
| 93 | LC87 | 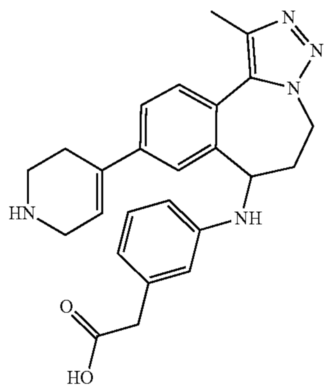 [SMILES: Cc1nnn2c1-c1ccc(C3=CCNCC3)cc1C(Nc1cccc(CC(=O)O)c1)CC2] | 2-(3-((1-methyl-9-(1,2,3,6-tetrahydropyridin-4-yl)-6,7-dihydro-5H-benzo[c][1,2,3]triazolo[1,5-a]azepin-7-yl)amino)phenyl)acetic acid |
| 94 | LC97 | 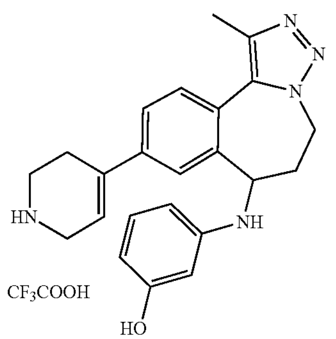 [SMILES: "CF3COOH" ; Cc1nnn2c1-c1ccc(C3=CCNCC3)cc1C(Nc1cccc(O)c1)CC2] | 3-((1-methyl-9-(1,2,3,6-tetrahydropyridin-4-yl)-6,7-dihydro-5H-benzo[c][1,2,3]triazolo[1,5-a]azepin-7-yl)amino)phenol 2,2,2-trifluoroacetate |
| 95 | LC99 | 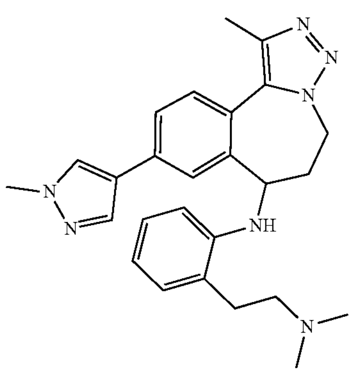 | N-(2-(2-(dimethylamino)ethyl)phenyl)-1-methyl-9-(1-methyl-1H-pyrazol-4-yl)-6,7-dihydro-5H-benzo[c][1,2,3]triazolo[1,5-a]azepin-7-amine |
| 96 | LC101 | 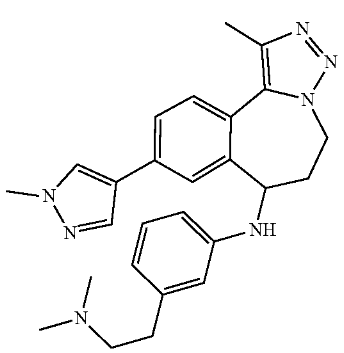 [SMILES: Cc1nnn2c1-c1ccc(-c3cnn(C)c3)cc1C(Nc1cccc(CCN(C)C)c1)CC2] | N-(3-(2-(dimethylamino)ethyl)phenyl)-1-methyl-9-(1-methyl-1H-pyrazol-4-yl)-6,7-dihydro-5H-benzo[c][1,2,3]triazolo[1,5-a]azepin-7-amine |

| No. | Code | Structure | Name |
|---|---|---|---|
| 97 | LC117 | 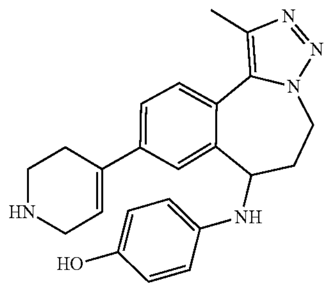 | 4-((1-methyl-9-(1,2,3,6-tetrahydro pyridin-4-yl)-6,7-dihydro-5H-benzo [c][1,2,3]triazolo[1,5-a]azepin-7-yl)amino)phenol 2,2,2-trifluoroacetate |
| 98 | LC127 | 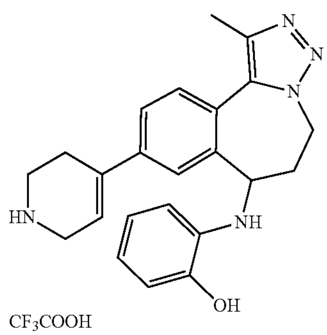 [SMILES: "CF3COOH" ; Cc1nnn2c1-c1ccc(C3=CCNCC3)cc1C(Nc1ccccc1O)CC2] | 2-((1-methyl-9-(1,2,3,6-tetrahydro pyridin-4-yl)-6,7-dihydro-5H-benzo [c][1,2,3]triazolo[1,5-a]azepin-7-yl)amino)phenol 2,2,2-trifluoroacetate |
| 99 | LC128 | 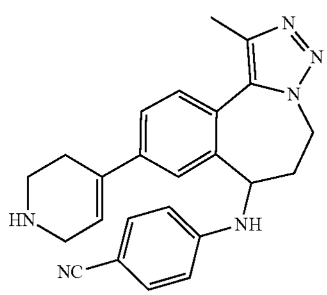 | 4-((1-methyl-9-(1,2,3,6-tetrahydro pyridin-4-yl)-6,7-dihydro-5H-benzo [c][1,2,3]triazolo[1,5-a]azepin-7-yl)amino)benzonitrile 2,2,2-trifluoroacetate |
| 100 | LC131 | 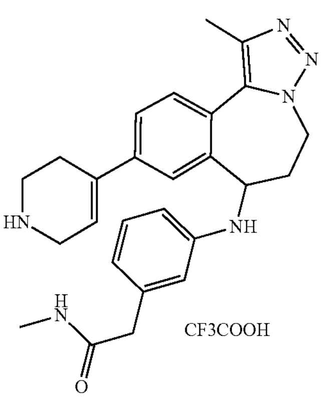 | N-methyl-2-(3-((1-methyl-9-(1,2,3, 6-tetrahydropyridin-4-yl)-6,7-dihydro-5H-benzo[c][1,2,3]triazolo[1,5-a]azepin-7-yl)amino)phenyl)acetamide 2,2,2-trifluoroacetate |

| No. | Code | Structure | Name |
|---|---|---|---|
| 101 | LC132 | 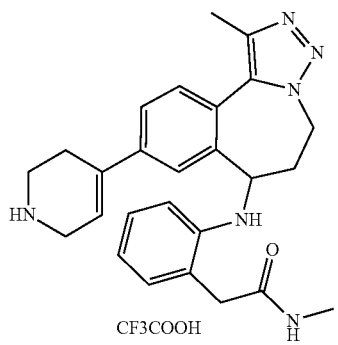 [SMILES: CNC(=O)Cc1ccccc1NC1CCn2nnc(C)c2-c2ccc(C3=CCNCC3)cc21 ; "CF3COOH"] | N-methyl-2-(2-((1-methyl-9-(1,2,3,6-tetrahydropyridin-4-yl)-6,7-dihydro-5H-benzo[c][1,2,3]triazolo[1,5-a]azepin-7-yl)amino)phenyl)acetamide 2,2,2-trifluoroacetate |
| 102 | LC133 | 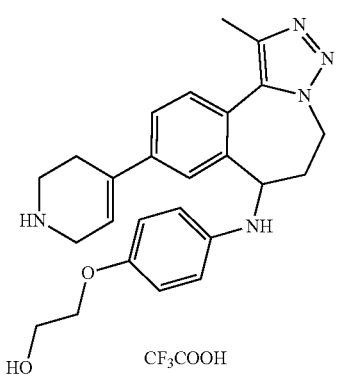 [SMILES: Cc1nnn2c1-c1ccc(C3=CCNCC3)cc1C(Nc1ccc(OCCO)cc1)CC2 ; "CF3COOH"] | 2-(4-((1-methyl-9-(1,2,3,6-tetrahydropyridin-4-yl)-6,7-dihydro-5H-benzo[c][1,2,3]triazolo[1,5-a]azepin-7-yl)amino)phenoxy)ethan-1-ol 2,2,2-trifluoroacetate |
| 103 | LC136 | 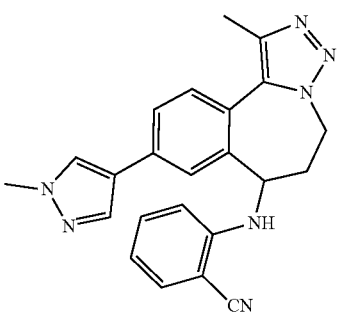 [SMILES: Cc1nnn2c1-c1ccc(-c3cnn(C)c3)cc1C(Nc1ccccc1C#N)CC2] | 2-((1-methyl-9-(1-methyl-1H-pyrazol-4-yl)-6,7-dihydro-5H-benzo[c][1,2,3]triazolo[1,5-a]azepin-7-yl)amino)benzonitrile |
| 104 | LC158 | 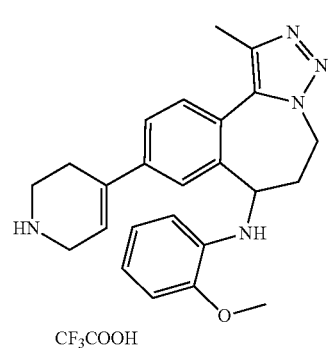 [SMILES: "CF3COOH" ; COc1ccccc1NC1CCn2nnc(C)c2-c2ccc(C3=CCNCC3)cc21] | N-(2-methoxyphenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate |

-continued

| No. | Code | Structure | Name |
|---|---|---|---|
| 105 | LC159 | 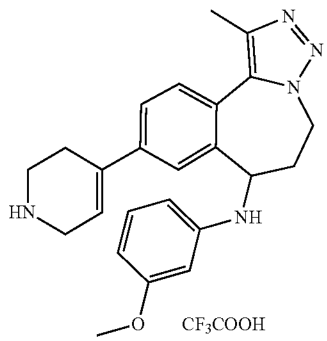 [SMILES: COc1cccc(NC2CCn3nnc(C)c3-c3ccc(C4=CCNCC4)cc32)c1 ; "CF3COOH"] | N-(3-methoxyphenyl)-1-methyl-9-1,2,3,6-tetrahydropyridin-4-yl)-6,7-dihydro-5H-benzo[c][1,2,3]triazolo[1,5-a]azepin-7-amine 2,2,2-trifluoroacetate |
| 106 | LC160 | 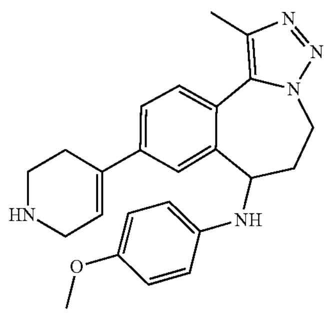 | N-(4-methoxyphenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate |
| 107 | LC174 | 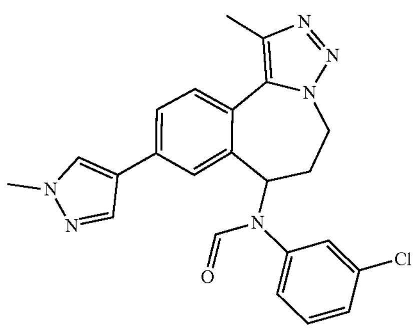 [SMILES: Cc1nnn2c1-c1ccc(-c3cnn(C)c3)cc1C(N(C=O)c1cccc(Cl)c1)CC2] | N-(3-chlorophenyl)-N-(1-methyl-9-(1-methyl-1H-pyrazol-4-yl)-6,7-dihydro-5H-benzo[c][1,2,3]triazolo[1,5-a]azepin-7-yl)formamide |
| 108 | LC185 | 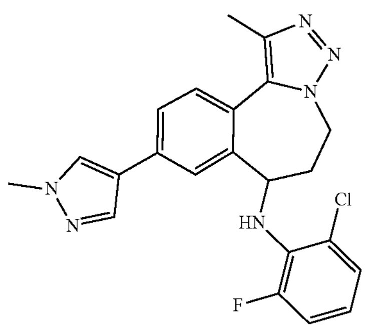 [SMILES: Cc1nnn2c1-c1ccc(-c3cnn(C)c3)cc1C(Nc1c(F)cccc1Cl)CC2] | N-(2-chloro-6-fluorophenyl)-1-methyl-9-(1-methyl-1H-pyrazol-4-yl)-6,7-dihydro-5H-benzo[c][1,2,3]triazolo[1,5-a]azepin-7-amine |

| No. | Code | Structure | Name |
|---|---|---|---|
| 109 | LC186 | 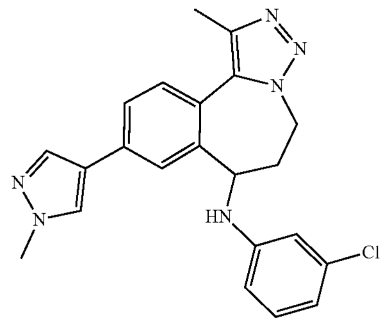 [SMILES: Cc1nnn2c1-c1ccc(-c3cnn(C)c3)cc1C(Nc1cccc(Cl)c1)CC2] | N-(3-chlorophenyl)-1-methyl-9-(1-methyl-1H-pyrazol-4-yl)-6,7-dihydro-5H-benzo[c][1,2,3]triazolo[1,5-a]azepin-7-amine |
| 110 | LC190 | 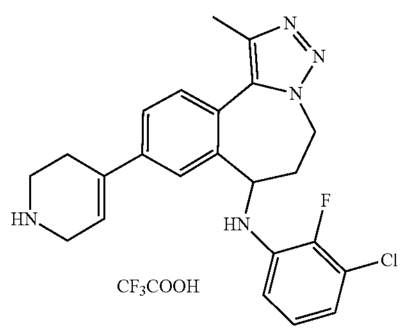 | N-(3-chloro-2-fluorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate |
| 111 | LC191 | 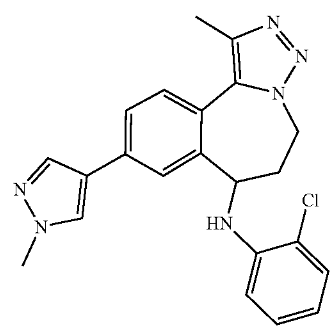 [SMILES: Cc1nnn2c1-c1ccc(-c3cnn(C)c3)cc1C(Nc1ccccc1Cl)CC2] | N-(2-chlorophenyl)-1-methyl-9-(1-methyl-1H-pyrazol-4-yl)-6,7-dihydro-5H-benzo[c][1,2,3]triazolo[1,5-a]azepin-7-amine |
| 112 | LC192 | 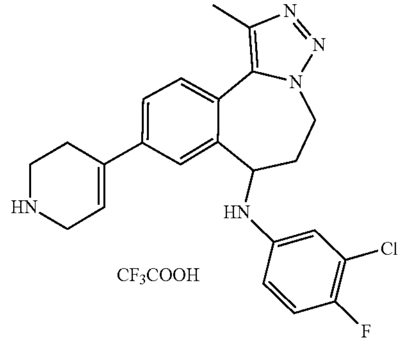 | N-(3-chloro-4-fluorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate |

| No. | Code | Structure | Name |
|---|---|---|---|
| 113 | LC193 | 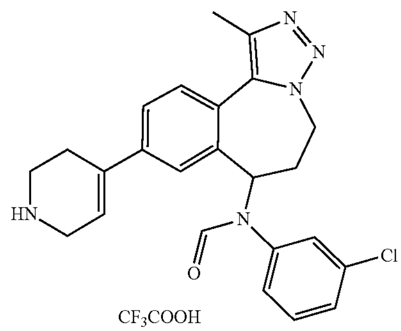 [SMILES: Cc1nnn2c1-c1ccc(C3=CCNCC3)cc1C(N(C=O)c1cccc(Cl)c1)CC2 ; "CF3COOH"] | N-(3-chlorophenyl)-N-(1-methyl-9-(1,2,3,6-tetrahydropyridin-4-yl)-6,7-dihydro-5H-benzo[c][1,2,3]triazolo[1,5-a]azepin-7-yl)formamide 2,2,2-trifluoroacetate |
| 114 | LC198 | 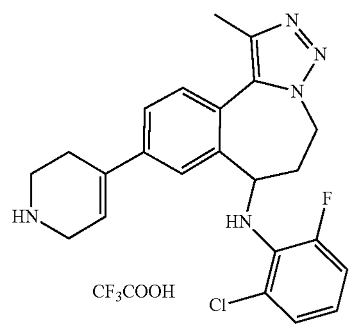 [SMILES: Cc1nnn2c1-c1ccc(C3=CCNCC3)cc1C(Nc1c(F)cccc1Cl)CC2 ; "CF3COOH"] | N-(2-chloro-6-fluorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate |
| 115 | LD07 | 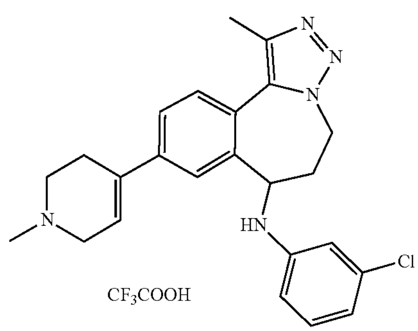 [SMILES: Cc1nnn2c1-c1ccc(C3=CCN(C)CC3)cc1C(Nc1cccc(Cl)c1)CC2 ; "CF3COOH"] | N-(3-chlorophenyl)-1-methyl-9-(1-methyl-1,2,3,6-tetrahydropyridin-4-yl)-6,7-dihydro-5H-benzo[c][1,2,3]triazolo[1,5-a]azepin-7-amine 2,2,2-trifluoroacetate |
| 116 | LD08 | 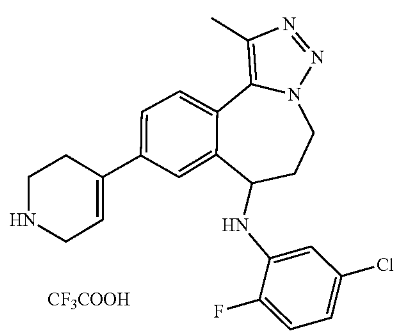 [SMILES: "CF3COOH" ; Cc1nnn2c1-c1ccc(C3=CCNCC3)cc1C(Nc1cc(Cl)ccc1F)CC2] | N-(5-chloro-2-fluorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate |

-continued

| No. | Code | Structure | Name |
|---|---|---|---|
| 117 | LD13 | 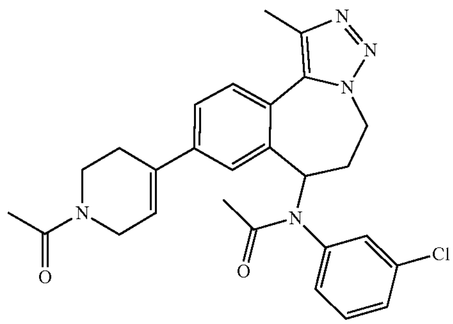 [SMILES: CC(=O)N1CC=C(c2ccc3c(c2)C(N(C(C)=O)c2cccc(Cl)c2)CCn2nnc(C)c2-3)CC1] | N-9-(1,2,3,6-tetrahydropyridin-4-yl)-6,7-dihydro-5H-benzo[c][1,2,3]triazolo[1,5-a]azepin-7-yl)-N-(3-chlorophenyl)acetamide |
| 118 | LD14 | 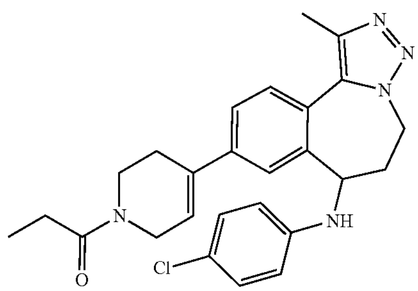 [SMILES: CCC(=O)N1CC=C(c2ccc3c(c2)C(Nc2ccc(Cl)cc2)CCn2nnc(C)c2-3)CC1] | 1-(4-(7-((4-chlorophenyl)amino)-1-methyl-6,7-dihydro-5H-benzo[c][1,2,3]triazolo[1,5-a]azepin-9-yl)-3,6-dihydropyridin-1(2H)-yl)propan-1-one |
| 119 | LD17 | 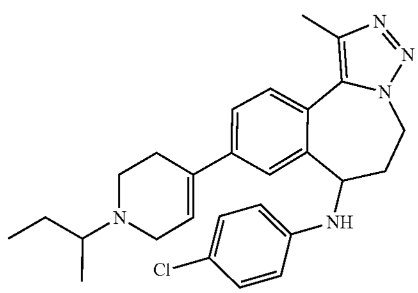 | 9-(1-(sec-butyl)-1,2,3,6-tetrahydropyridin-4-yl)-N-(4-chlorophenyl)-1-methyl-6,7-dihydro-5H-benzo[c][1,2,3]triazolo[1,5-a]azepin-7-amine 2,2,2-trifluoroacetate |
| 120 | LD19 | 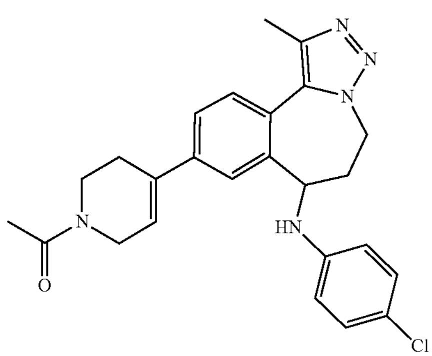 [SMILES: CC(=O)N1CC=C(c2ccc3c(c2)C(Nc2ccc(Cl)cc2)CCn2nnc(C)c2-3)CC1] | 1-(4-(7-((4-chlorophenyl)amino)-1-methyl-6,7-dihydro-5H-benzo[c][1,2,3]triazolo[1,5-a]azepin-9-yl)-3,6-dihydropyridin-1(2H)-yl)ethan-1-one |

| No. | Code | Structure | Name |
|---|---|---|---|
| 121 | LD23 | 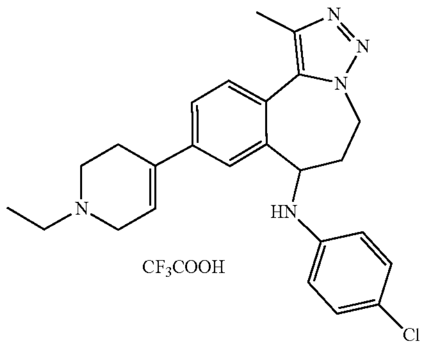 | N-(4-chlorophenyl)-9-(1-ethyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate |
| 122 | LD24 | 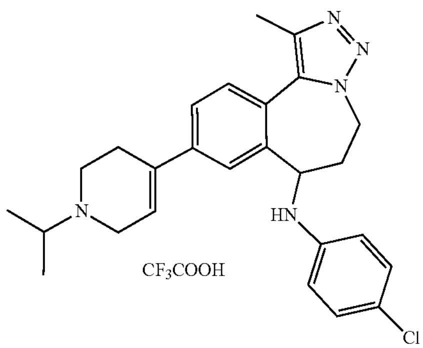 | N-(4-chlorophenyl)-9-(1-isopropyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate |
| 123 | LD31 | 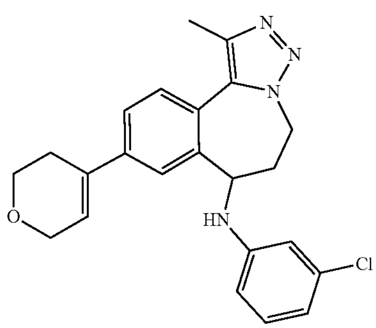 [SMILES: Cc1nnn2c1-c1ccc(C3=CCOCC3)cc1C(Nc1cccc(Cl)c1)CC2] | N-(3-chlorophenyl)-9-(3,6-dihydro-2H-pyran-4-yl)-1-methyl-6,7-dihydro-5H-benzo[c][1,2,3]triazolo[1,5-a]azepin-7-amine |
| 124 | LD76 | 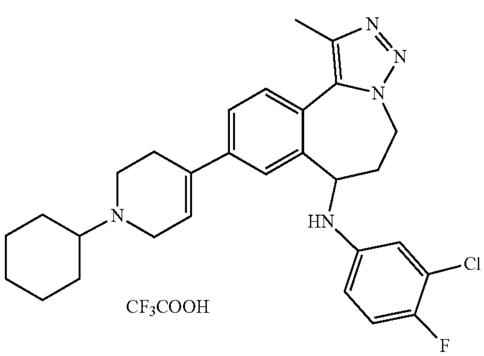 | N-(3-chloro-4-fluorophenyl)-9-(1-cyclohexyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate |

-continued

| No. | Code | Structure | Name |
|---|---|---|---|
| 125 | LD77 | 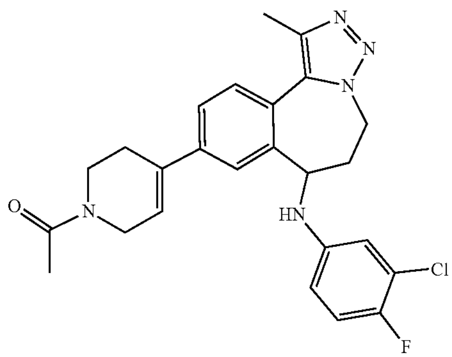 [SMILES: CC(=O)N1CC=C(c2ccc3c(c2)C(Nc2ccc(F)c(Cl)c2)CCn2nnc(C)c2-3)CC1] | 1-(4-(7-((3-chloro-4-fluorophenyl)amino)-1-methyl-6,7-dihydro-5H-benzo[c][1,2,3]triazolo[1,5-a]azepin-9-yl)-3,6-dihydropyridin-1(2H)-yl)ethan-1-one |
| 126 | BF169 | 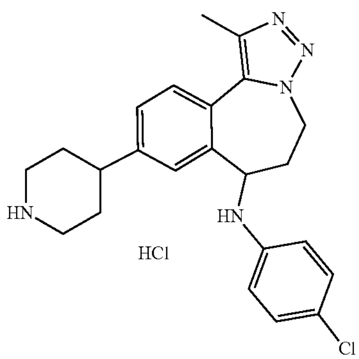 [SMILES: Cc1nnn2c1-c1ccc(C3CCNCC3)cc1C(Nc1ccc(Cl)cc1)CC2 ; Cl] | N-(4-chlorophenyl)-1-methyl-9-(piperidin-4-yl)-6,7-dihydro-5H-benzo[c][1,2,3]triazolo[1,5-a]azepin-7-amine hydrochloride |
| 127 | BF178 | 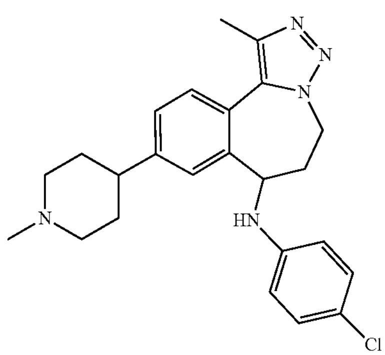 [SMILES: Cc1nnn2c1-c1ccc(C3CCN(C)CC3)cc1C(Nc1ccc(Cl)cc1)CC2] | N-(4-chlorophenyl)-1-methyl-9-(1-methylpiperidin-4-yl)-6,7-dihydro-5H-benzo[c][1,2,3]triazolo[1,5-a]azepin-7-amine |
| 128 | BJ28 | 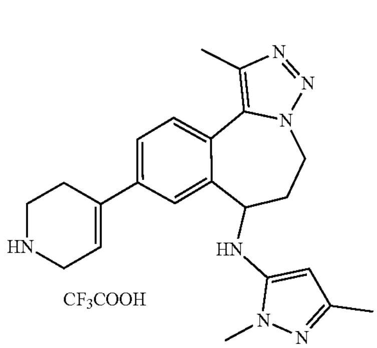 [SMILES: "CF3COOH" ; Cc1cc(NC2CCn3nnc(C)c3-c3ccc(C4=CCNCC4)cc32)n(C)n1] | N-(1,3-dimethyl-1H-pyrazol-5-yl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate |

| No. | Code | Structure | Name |
|---|---|---|---|
| 129 | BJ122 | 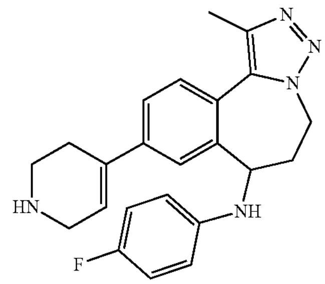 | N-(4-fluorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate |
| 130 | BJ123 | 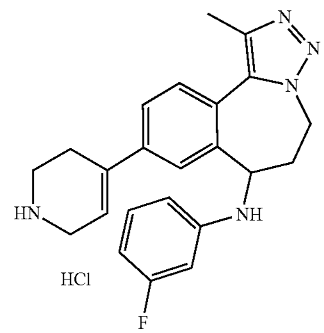 [SMILES: Cc1nnn2c1-c1ccc(C3=CCNCC3)cc1C(Nc1cccc(F)c1)CC2 ; Cl] | N-(3-fluorophenyl)-1-methyl-9-(1,2,3,6-tetrahydropyridin-4-yl)-6,7-dihydro-5H-benzo[c][1,2,3]triazolo[1,5-a]azepin-7-amine hydrochloride |
| 131 | BJ126 | 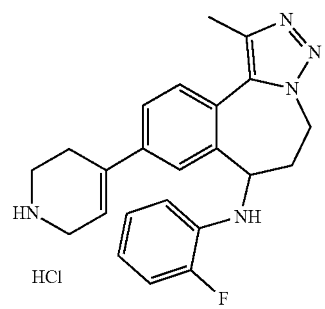 [SMILES: Cc1nnn2c1-c1ccc(C3=CCNCC3)cc1C(Nc1ccccc1F)CC2 ; Cl] | N-(2-fluorophenyl)-1-methyl-9-(1,2,3,6-tetrahydropyridin-4-yl)-6,7-dihydro-5H-benzo[c][1,2,3]triazolo[1,5-a]azepin-7-amine hydrochloride |
| 132 | BJ179 | 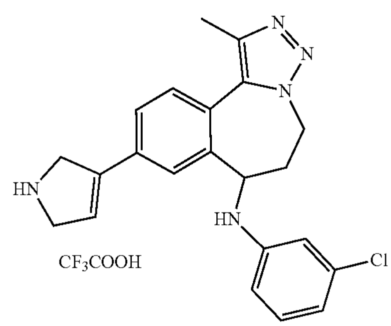 [SMILES: "CF3COOH" ; Cc1nnn2c1-c1ccc(C3=CCNC3)cc1C(Nc1cccc(Cl)c1)CC2] | N-(3-chlorophenyl)-9-(2,5-dihydro-1H-pyrrol-3-yl)-1-methyl-6,7-dihydro-5H-benzo[c][1,2,3]triazolo[1,5-a]azepin-7-amine 2,2,2-trifluoroacetate |
| 133 | BJ183 | 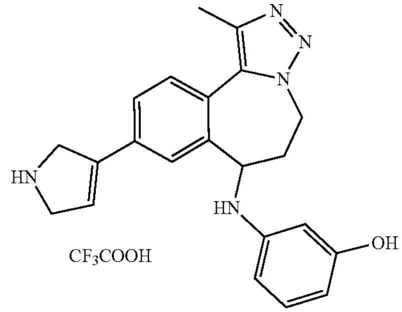 [SMILES: "CF3COOH" ; Cc1nnn2c1-c1ccc(C3=CCNC3)cc1C(Nc1cccc(O)c1)CC2] | 3-((9-(2,5-dihydro-1H-pyrrol-3-yl)-1-methyl-6,7-dihydro-5H-benzo[c][1,2,3]triazolo[1,5-a]azepin-7-yl)amino)phenol 2,2,2-trifluoroacetate |

| No. | Code | Structure | Name |
|---|---|---|---|
| 134 | BJ193 | 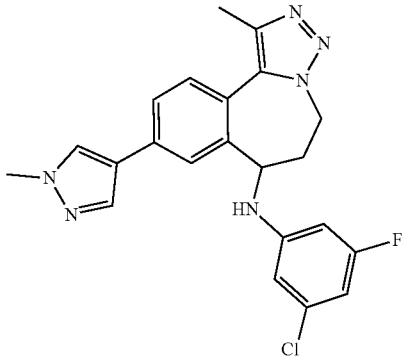 [SMILES: Cc1nnn2c1-c1ccc(-c3cnn(C)c3)cc1C(Nc1cc(F)cc(Cl)c1)CC2] | N-(3-chloro-5-fluorophenyl)-1-methyl-9-(1-methyl-1H-pyrazol-4-yl)-6,7-dihydro-5H-benzo[c][1,2,3]triazolo[1,5-a]azepin-7-amine |
| 135 | BH06 | 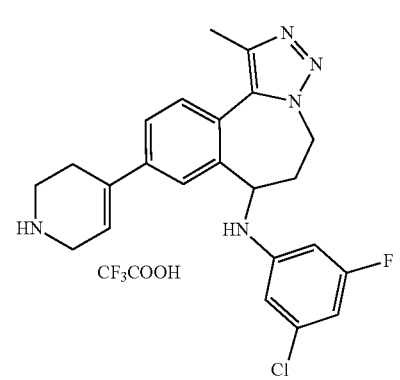 | N-(3-chloro-5-fluorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate |
| 136 | BH23 | 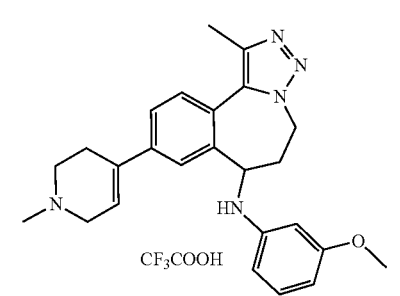 | N-(3-methoxyphenyl)-1-methyl-9-(1-methyl-1,2,3,6-tetrahydropyridin-4-yl)-6,7-dihydro-5H-benzo[c][1,2,3]triazolo[1,5-a]azepin-7-amine 2,2,2-trifluoroacetate |
| 137 | BH27 | 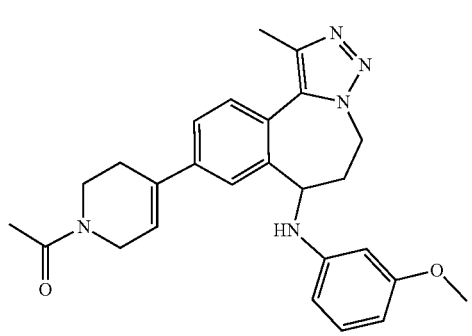 [SMILES: COc1cccc(NC2CCn3nnc(C)c3-c3ccc(C4=CCN(C(C)=O)CC4)cc32)c1] | 1-(4-(7-((3-methoxyphenyl)amino)-1-methyl-6,7-dihydro-5H-benzo[c][1,2,3]triazolo[1,5-a]azepin-9-yl)-3,6-dihydropyridin-1(2H)-yl)ethan-1-one |

-continued

| No. | Code | Structure | Name |
|---|---|---|---|
| 138 | BH29 | 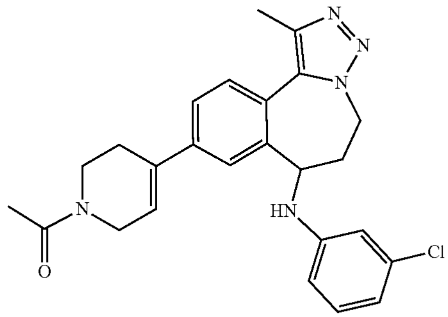 [SMILES: CC(=O)N1CC=C(c2ccc3c(c2)C(Nc2cccc(Cl)c2)CCn2nnc(C)c2-3)CC1] | 1-(4-(7-((3-chlorophenyl)amino)-1-methyl-6,7-dihydro-5H-benzo[c][1,2,3]triazolo[1,5-a]azepin-9-yl)-3,6-dihydropyridin-1(2H)-yl)ethan-1-one |
| 139 | BH32 | 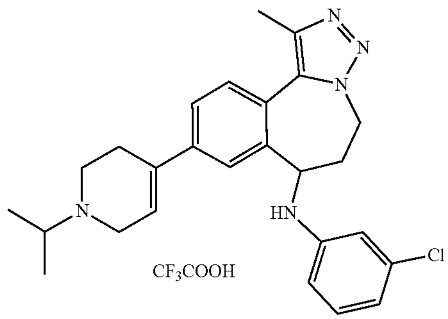 | N-(3-chlorophenyl)-9-(1-isopropyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate |
| 140 | BH33 | 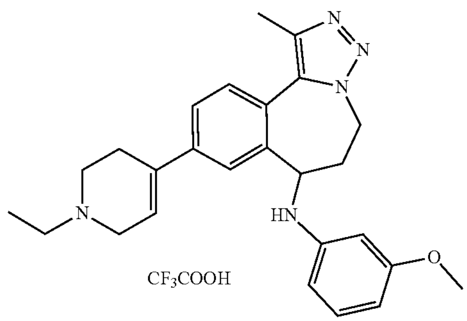 [SMILES: CCN1CC=C(c2ccc3c(c2)C(Nc2cccc(OC)c2)CCn2nnc(C)c2-3)CC1 ; "CF3COOH"] | 9-(1-ethyl-1,2,3,6-tetrahydropyridin-4-yl)-N-(3-methoxyphenyl)-1-methyl-6,7-dihydro-5H-benzo[c][1,2,3]triazolo[1,5-a]azepin-7-amine 2,2,2-trifluoroacetate |
| 141 | BH36 | 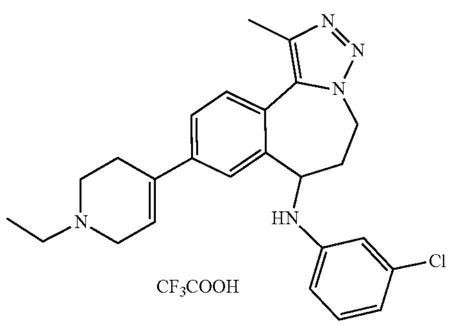 | N-(3-chlorophenyl)-9-(1-ethyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate |
| 142 | BH37 | 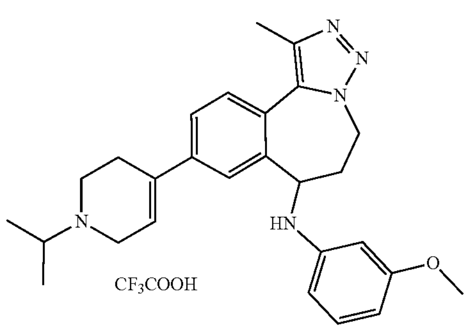 [SMILES: COc1cccc(NC2CCn3nnc(C)c3-c3ccc(C4=CCN(C(C)C)CC4)cc32)c1 ; "CF3COOH"] | 9-(1-isopropyl-1,2,3,6-tetrahydropyridin-4-yl)-N-(3-methoxyphenyl)-1-methyl-6,7-dihydro-5H-benzo[c][1,2,3]triazolo[1,5-a]azepin-7-amine 2,2,2-trifluoroacetate |

| No. | Code | Structure | Name |
|---|---|---|---|
| 143 | BH43 | 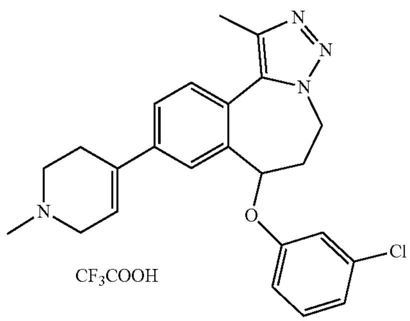 [SMILES: Cc1nnn2c1-c1ccc(C3=CCN(C)CC3)cc1C(Oc1cccc(Cl)c1)CC2 ; "CF3COOH"] | 7-(3-chlorophenoxy)-1-methyl-9-(1-methyl-1,2,3,6-tetrahydropyridin-4-yl)-6,7-dihydro-5H-benzo[c][1,2,3]triazolo[1,5-a]azepine 2,2,2-trifluoroacetate |
| 144 | BH46 | 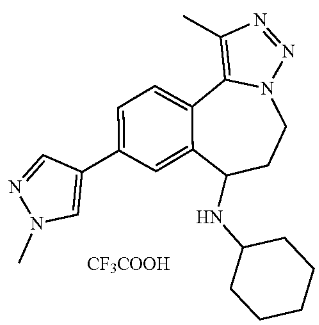 | N-cyclohexyl-1-methyl-9-(1-methyl-1H-pyrazol-4-yl)-6,7-dihydro-5H-benzo[c][1,2,3]triazolo[1,5-a]-azepin-7-amine 2,2,2-trifluoroacetate |
| 145 | BH57 | 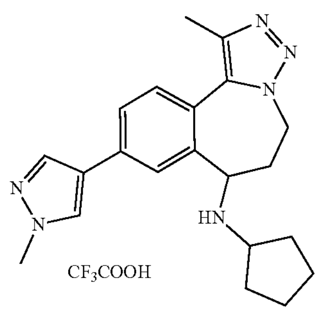 [SMILES: Cc1nnn2c1-c1ccc(-c3cnn(C)c3)cc1C(NC1CCCC1)CC2 ; "CF3COOH"] | N-cyclopentyl-1-methyl-9-(1-methyl-1H-pyrazol-4-yl)-6,7-dihydro-5H-benzo[c][1,2,3]triazolo[1,5-a]azepin-7-amine 2,2,2-trifluoroacetate |
| 146 | BH81 | 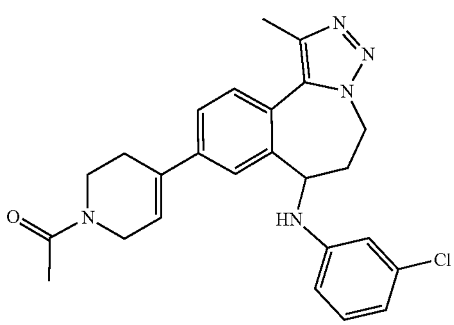 [SMILES: CC(=O)N1CC=C(c2ccc3c(c2)C(Nc2cccc(Cl)c2)CCn2nnc(C)c2-3)CC1] | 1-(4-(7-(3-chlorophenoxy)-1-methyl-6,7-dihydro-5H-benzo[c][1,2,3]triazolo[1,5-a]azepin-9-yl)-3,6-dihydropyridin-1(2H)-yl)ethan-1-one |
| 147 | BH86 | 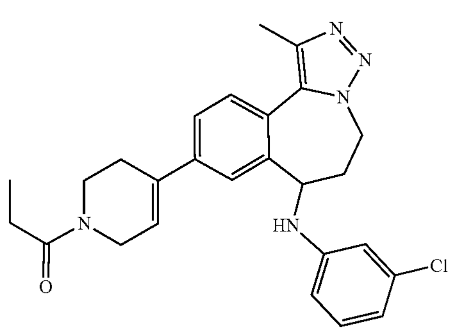 [SMILES: CCC(=O)N1CC=C(c2ccc3c(c2)C(Nc2cccc(Cl)c2)CCn2nnc(C)c2-3)CC1] | 1-(4-(7-((3-chlorophenyl)amino)-1-methyl-6,7-dihydro-5H-benzo[c][1,2,3]triazolo[1,5-a]azepin-9-yl)-3,6-dihydropyridin-1(2H)-yl)propan-1-one |

| No. | Code | Structure | Name |
|---|---|---|---|
| 148 | BH87 | 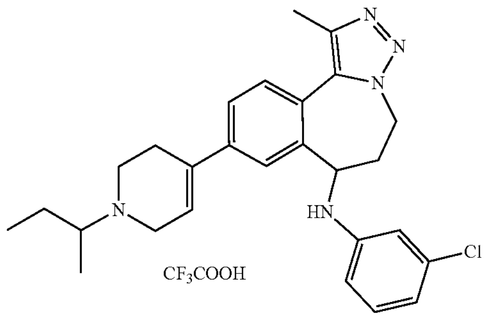 [SMILES: CCC(C)N1CC=C(c2ccc3c(c2)C(Nc2cccc(Cl)c2)CCn2nnc(C)c2-3)CC1 ; "CF3COOH"] | 9-(1-(sec-butyl)-1,2,3,6-tetrahydro pyridin-4-yl)-N-(3-chlorophenyl)-1-methyl-6,7-dihydro-5H-benzo[c][1,2,3]triazolo[1,5-a]azepin-7-amine 2,2,2-trifluoroacetate |
| 149 | BH104 | 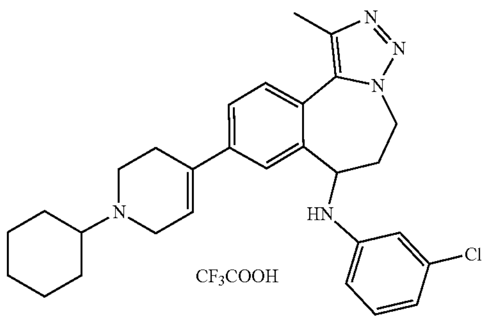 | N-(3-chlorophenyl)-9-(1-cyclohexyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate |
| 150 | BH107 | 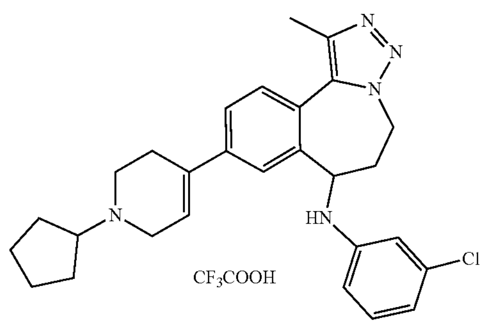 | N-(3-chlorophenyl)-9-(1-cyclopentyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate |
| 151 | BH108 | 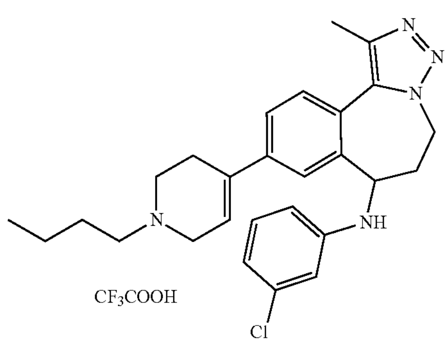 [SMILES: CCCCN1CC=C(c2ccc3c(c2)C(Nc2cccc(Cl)c2)CCn2nnc(C)c2-3)CC1 ; "CF3COOH"] | 9-(1-butyl-1,2,3,6-tetrahydropyridin-4-yl)-N-(3-chlorophenyl)-1-methyl-6,7-dihydro-5H-benzo[c][1,2,3]triazolo[1,5-a]azepin-7-amine 2,2,2-trifluoroacetate |

| No. | Code | Structure | Name |
|---|---|---|---|
| 152 | BH120 | 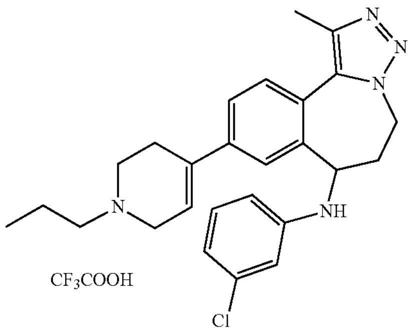 [SMILES: "CF3COOH" ; CCCN1CC=C(c2ccc3c(c2)C(Nc2cccc(Cl)c2)CCn2nnc(C)c2-3)CC1] | N-(3-chlorophenyl)-1-methyl-9-(1-propyl-1,2,3,6-tetrahydropyridin-4-yl)-6,7-dihydro-5H-benzo[c][1,2,3]triazolo[1,5-a]azepin-7-amine 2,2,2-trifluoroacetate |
| 153 | BH123 | 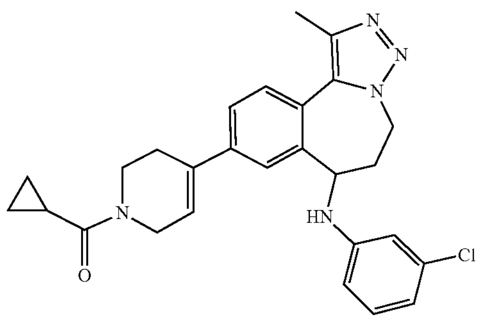 [SMILES: Cc1nnn2c1-c1ccc(C3=CCN(C(=O)C4CC4)CC3)cc1C(Nc1cccc(Cl)c1)CC2] | (4-(7-((3-chlorophenyl)amino)-1-methyl-6,7-dihydro-5H-benzo[c][1,2,3]triazolo[1,5-a]azepin-9-yl)-3,6-dihydropyridin-1(2H)-yl)(cyclopropyl)methanone |
| 154 | BH159 | 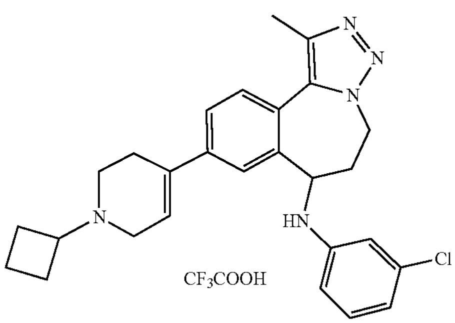 | N-(3-chlorophenyl)-9-(1-cyclobutyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate |
| 155 | BH187 | 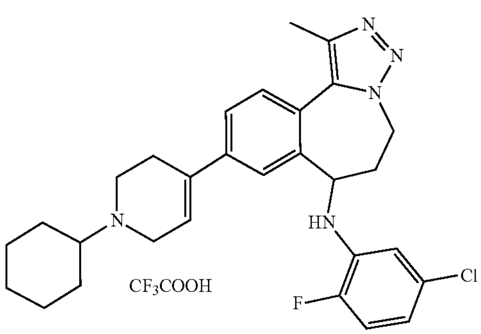 [SMILES: Cc1nnn2c1-c1ccc(C3=CCN(C4CCCCC4)CC3)cc1C(Nc1cc(Cl)ccc1F)CC2 ; "CF3COOH"] | N-(5-chloro-2-fluorophenyl)-9-(1-cyclohexyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate |

| No. | Code | Structure | Name |
|---|---|---|---|
| 156 | BH190 | 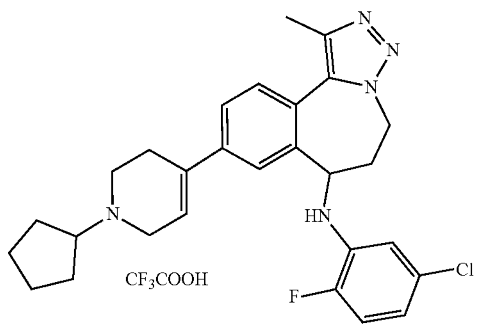 [SMILES: Cc1nnn2c1-c1ccc(C3=CCN(C4CCCC4)CC3)cc1C(Nc1cc(Cl)ccc1F)CC2 ; "CF3COOH"] | N-(5-chloro-2-fluorophenyl)-9-(1-cyclopentyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate |
| 157 | BH192 | 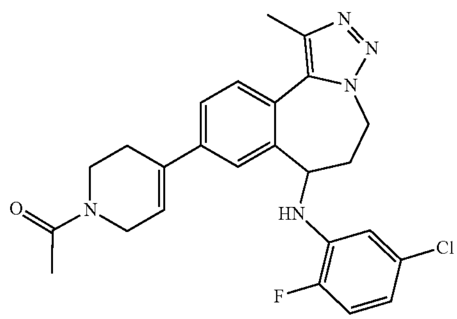 [SMILES: CC(=O)N1CC=C(c2ccc3c(c2)C(Nc2cc(Cl)ccc2F)CCn2nnc(C)c2-3)CC1] | 1-(4-(7-((5-chloro-2-fluorophenyl)amino)-1-methyl-6,7-dihydro-5H-benzo[c][1,2,3]triazolo[1,5-a]azepin-9-yl)-3,6-dihydropyridin-1(2H)-yl)ethan-1-one |
| 158 | BI23 | 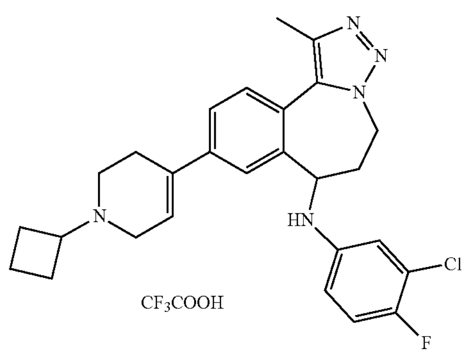 [SMILES: Cc1nnn2c1-c1ccc(C3=CCN(C4CCC4)CC3)cc1C(Nc1ccc(F)c(Cl)c1)CC2 ; "CF3COOH"] | N-(3-chloro-4-fluorophenyl)-9-(1-cyclobutyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate |
| 159 | BI24 | 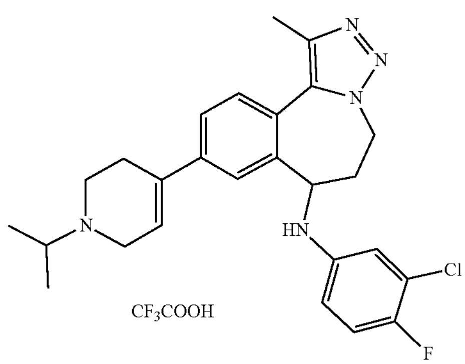 [SMILES: Cc1nnn2c1-c1ccc(C3=CCN(C(C)C)CC3)cc1C(Nc1ccc(F)c(Cl)c1)CC2 ; "CF3COOH"] | N-(3-chloro-4-fluorophenyl)-9-(1-isopropyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate |

-continued

| No. | Code | Structure | Name |
|---|---|---|---|
| 160 | BI26 | 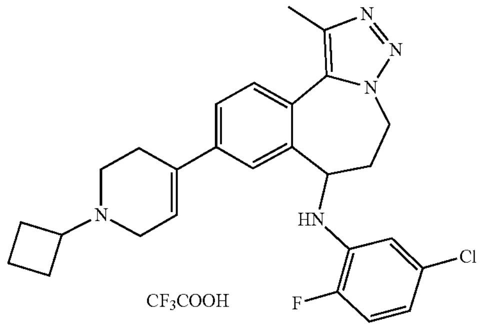 [SMILES: Cc1nnn2c1-c1ccc(C3=CCN(C4CCC4)CC3)cc1C(Nc1cc(Cl)ccc1F)CC2 ; "CF3COOH"] | N-(5-chloro-2-fluorophenyl)-9-(1-cyclobutyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate |
| 161 | BI29 | 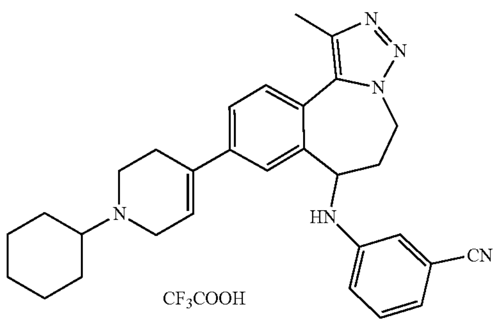 [SMILES: Cc1nnn2c1-c1ccc(C3=CCN(C4CCCCC4)CC3)cc1C(Nc1cccc(C#N)c1)CC2 ; "CF3COOH"] | 3-((9-(1-cyclohexyl-1,2,3,6-tetrahydropyridin-4-yl)-1-methyl-6,7-dihydro-5H-benzo[c][1,2,3]triazolo[1,5-a]azepin-7-yl)amino)benzonitrile 2,2,2-trifluoroacetate |
| 162 | BI31 | 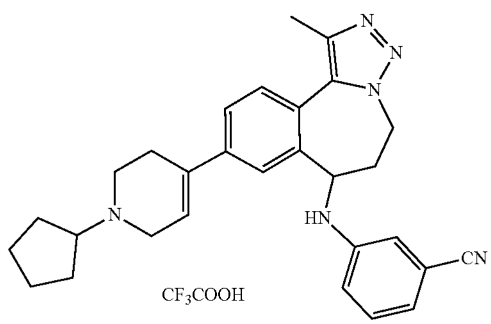 [SMILES: Cc1nnn2c1-c1ccc(C3=CCN(C4CCCC4)CC3)cc1C(Nc1cccc(C#N)c1)CC2 ; "CF3COOH"] | 3-((9-(1-cyclopentyl-1,2,3,6-tetrahydropyridin-4-yl)-1-methyl-6,7-dihydro-5H-benzo[c][1,2,3]triazolo[1,5-a]azepin-7-yl)amino)benzonitrile 2,2,2-trifluoroacetate |
| 163 | BI34 | 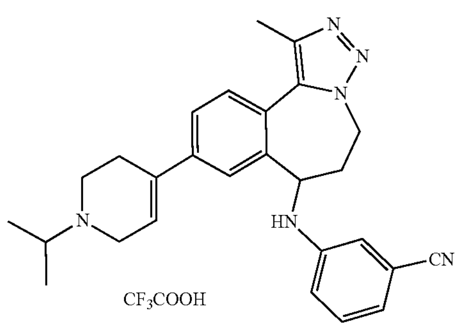 | 3-((9-(1-isopropyl-1,2,3,6-tetrahydropyridin-4-yl)-1-methyl-6,7-dihydro-5H-benzo[c][1,2,3]triazolo[1,5-a]azepin-7-yl)amino)benzonitrile 2,2,2-trifluoroacetate |
| 164 | BI36 | 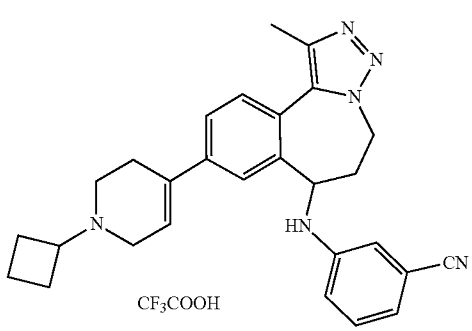 [SMILES: Cc1nnn2c1-c1ccc(C3=CCN(C4CCC4)CC3)cc1C(Nc1cccc(C#N)c1)CC2 ; "CF3COOH"] | 3-((9-(1-cyclobutyl-1,2,3,6-tetrahydropyridin-4-yl)-1-methyl-6,7-dihydro-5H-benzo[c][1,2,3]triazolo[1,5-a]azepin-7-yl)amino)benzonitrile 2,2,2-trifluoroacetate |

| No. | Code | Structure | Name |
|---|---|---|---|
| 165 | BI37 | 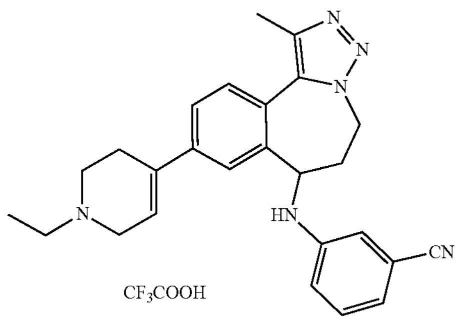 [SMILES: CCN1CC=C(c2ccc3c(c2)C(Nc2cccc(C#N)c2)CCn2nnc(C)c2-3)CC1 ; "CF3COOH"] | 3-((9-(1-ethyl-1,2,3,6-tetrahydropyridin-4-yl)-1-methyl-6,7-dihydro-5H-benzo[c][1,2,3]triazolo[1,5-a]azepin-7-yl)amino)benzonitrile 2,2,2-trifluoroacetate |
| 166 | BI55 | 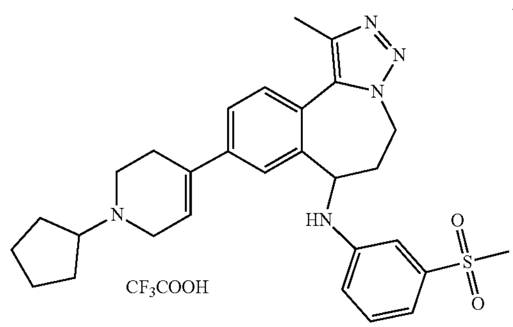 | 9-(1-cyclopentyl-1,2,3,6-tetrahydropyridin-4-yl)-1-methyl-N-(3-(methylsulfonyl)phenyl)-6,7-dihydro-5H-benzo[c][1,2,3]triazolo[1,5-a]azepin-7-amine 2,2,2-trifluoroacetate |
| 167 | BI57 | 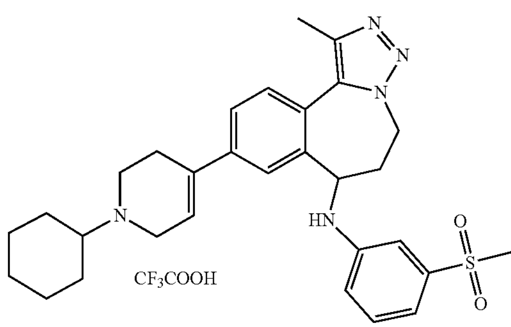 [SMILES: Cc1nnn2c1-c1ccc(C3=CCN(C4CCCCC4)CC3)cc1C(Nc1cccc(S(C)(=O)=O)c1)CC2 ; "CF3COOH"] | 9-(1-cyclohexyl-1,2,3,6-tetrahydropyridin-4-yl)-1-methyl-N-(3-(methylsulfonyl)phenyl)-6,7-dihydro-5H-benzo[c][1,2,3]triazolo[1,5-a]azepin-7-amine 2,2,2-trifluoroacetate |
| 168 | BI60 | 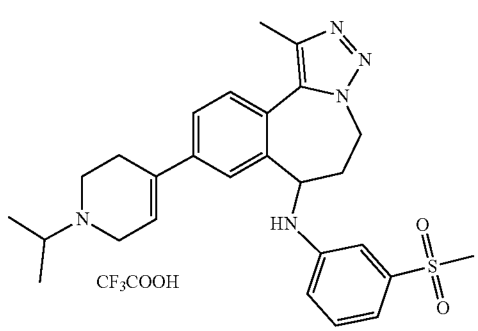 [SMILES: Cc1nnn2c1-c1ccc(C3=CCN(C(C)C)CC3)cc1C(Nc1cccc(S(C)(=O)=O)c1)CC2 ; "CF3COOH"] | 9-(1-isopropyl-1,2,3,6-tetrahydropyridin-4-yl)-1-methyl-N-(3-(methylsulfonyl)phenyl)-6,7-dihydro-5H-benzo[c][1,2,3]triazolo[1,5-a]azepin-7-amine 2,2,2-trifluoroacetate |

| No. | Code | Structure | Name |
|---|---|---|---|
| 169 | BI61 | 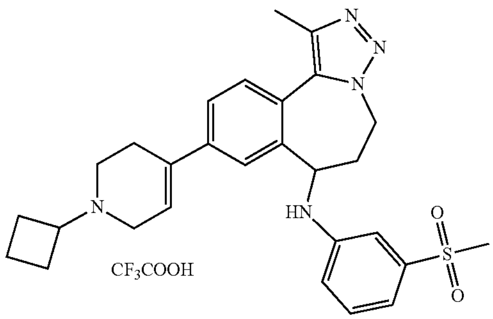 [SMILES: Cc1nnn2c1-c1ccc(C3=CCN(C4CCC4)CC3)cc1C(Nc1cccc(S(C)(=O)=O)c1)CC2 ; "CF3COOH"] | 9-(1-cyclobutyl-1,2,3,6-tetrahydropyridin-4-yl)-1-methyl-N-(3-(methyl sulfonyl)phenyl)-6,7-dihydro-5H-benzo[c][1,2,3]triazolo[1,5-a]azepin-7-amine 2,2,2-trifluoroacetate |
| 170 | BI68 | 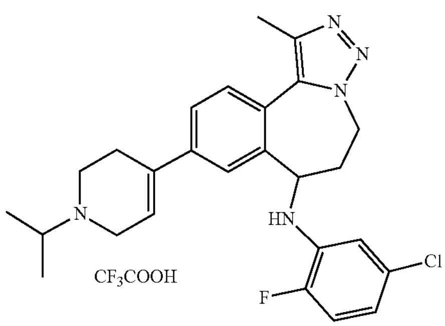 [SMILES: Cc1nnn2c1-c1ccc(C3=CCN(C(C)C)CC3)cc1C(Nc1cc(Cl)ccc1F)CC2 ; "CF3COOH"] | N-(5-chloro-2-fluorophenyl)-9-(1-isopropyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate |
| 171 | WYA10 | 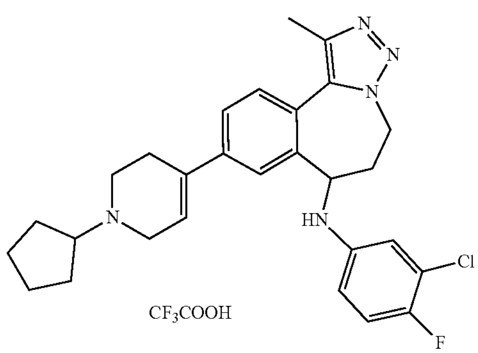 [SMILES: Cc1nnn2c1-c1ccc(C3=CCN(C4CCCC4)CC3)cc1C(Nc1ccc(F)c(Cl)c1)CC2 ; "CF3COOH"] | N-(3-chloro-4-fluorophenyl)-9-(1-cyclopentyl-1,2,3,6-tetrahydropyridin-4-yl)-1-methyl-6,7-dihydro-5H-benzo[c][1,2,3]triazolo[1,5-a]azepin 7-amine 2,2,2-trifluoroacetate |
| 172 | WA78 | 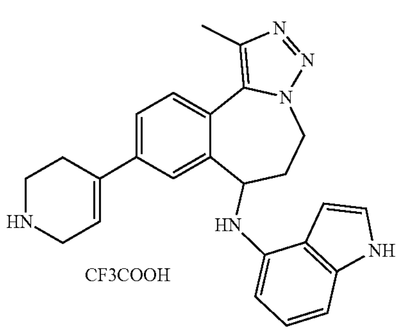 | N-(1H-indol-4-yl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate |

| No. | Code | Structure | Name |
|---|---|---|---|
| 173 | WA82 | 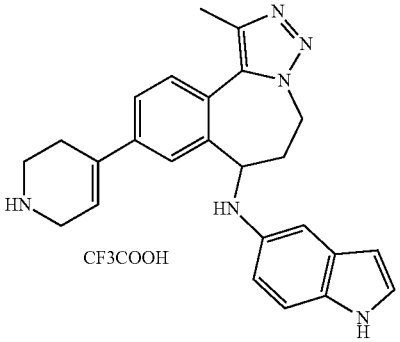 CF3COOH | N-(1H-indol-5-yl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate |
| 174 | WA83 | 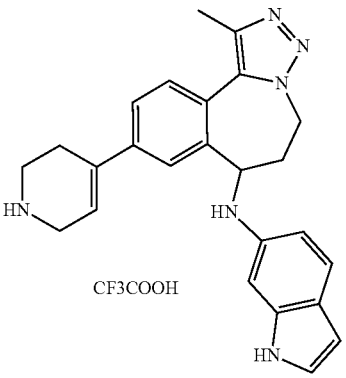 [SMILES: Cc1nnn2c1-c1ccc(C3=CCNCC3)cc1C(Nc1ccc3cc[nH]c3c1)CC2 ; "CF3COOH"] CF3COOH | N-(1H-indol-6-yl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate |
| 175 | RC71 | 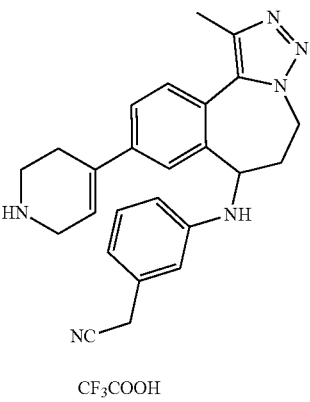 [SMILES: Cc1nnn2c1-c1ccc(C3=CCNCC3)cc1C(Nc1cccc(CC#N)c1)CC2 ; "CF3COOH"] CF$_3$COOH | 2-(3-((1-methyl-9-(1,2,3,6-tetrahydropyridin-4-yl)-6,7-dihydro-5H-benzo[c][1,2,3]triazolo[1,5-a]azepin-7-yl)amino)phenyl)acetonitrile; 2,2,2-trifluoroacetate |
| 176 | RC73 | 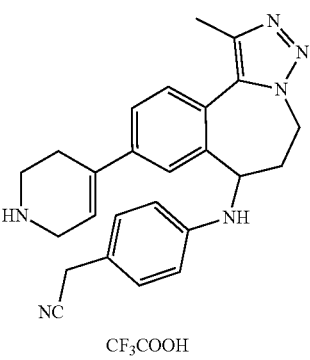 [SMILES: Cc1nnn2c1-c1ccc(C3=CCNCC3)cc1C(Nc1ccc(CC#N)cc1)CC2 ; "CF3COOH"] CF$_3$COOH | 2-(4-((1-methyl-9-(1,2,3,6-tetrahydropyridin-4-yl)-6,7-dihydro-5H-benzo[c][1,2,3]triazolo[1,5-a]azepin-7-yl)amino)phenyl)acetonitrile; 2,2,2-trifluoroacetate |

-continued

| No. | Code | Structure | Name |
|---|---|---|---|
| 177 | RC82 | *CF₃COOH* | 2-(2-((1-methyl-9-(1,2,3,6-tetrahydropyridin-4-yl)-6,7-dihydro-5H-benzo[c][1,2,3]triazolo[1,5-a]azepin-7-yl)amino)phenyl)acetonitrile; 2,2,2-trifluoroacetate |
| 178 | RC116 | *CF₃COOH* | 2-((1-methyl-9-(1,2,3,6-tetrahydropyridin-4-yl)-6,7-dihydro-5H-benzo[c][1,2,3]triazolo[1,5-a]azepin-7-yl)amino)benzonitrile; 2,2,2-trifluoroacetate |
| 179 | RD06 | *CF₃COOH* | N-(2-chlorophenyl)-1-methyl-9-(1-methyl-1,2,3,6-tetrahydropyridin-4-yl)-6,7-dihydro-5H-benzo[c][1,2,3]triazolo[1,5-a]azepin-7-amine; 2,2,2-trifluoroacetate |
| 180 | RD21 | *CF₃COOH* | (3-((1-methyl-9-(1,2,3,6-tetrahydropyridin-4-yl)-6,7-dihydro-5H-benzo[c][1,2,3]triazolo[1,5-a]azepin-7-yl)amino)phenyl)methanol; 2,2,2-trifluoroacetate |

| No. | Code | Structure | Name |
|---|---|---|---|
| 181 | RD41 | 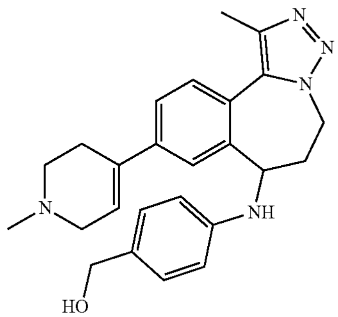 | (4-((1-methyl-9-(1-methyl-1,2,3,6-tetrahydropyridin-4-yl)-6,7-dihydro-5H-benzo[c][1,2,3]triazolo[1,5-a]azepin-7-yl)amino)phenyl)methanol; 2,2,2-trifluoroacetate |
| 182 | RD115 | 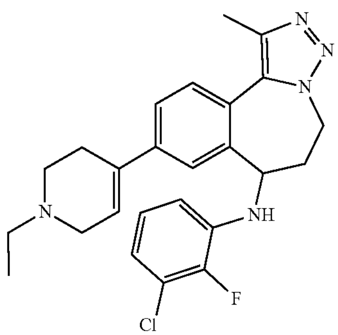 | N-(3-chloro-2-fluorophenyl)-9-(1-ethyl-1,2,3,6-tetrahydropyridin-4-yl) 1-methyl-6,7-dihydro-5H-benzo[c][1,2,3]triazolo[1,5-a]azepin-7-amine; 2,2,2-trifluoroacetate |
| 183 | RD121 | 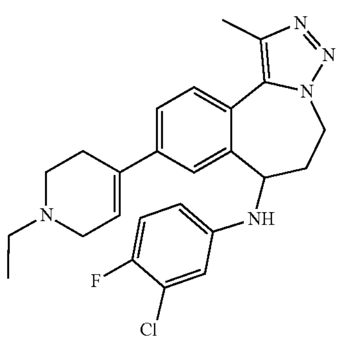 | N-(3-chloro-4-fluorophenyl)-9-(1-ethyl-1,2,3,6-tetrahydropyridin-4-yl) 1-methyl-6,7-dihydro-5H-benzo[c][1,2,3]triazolo[1,5-a]azepin-7-amine; 2,2,2-trifluoroacetate |
| 184 | RD123 | 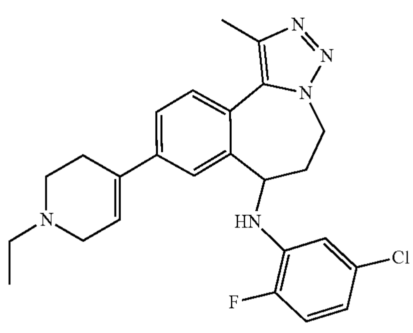 | N-(5-chloro-2-fluorophenyl)-9-(1-ethyl-1,2,3,6-tetrahydropyridin-4-yl)-1-methyl-6,7-dihydro-5H-benzo[c][1,2,3]triazolo[1,5-a]azepin-7-amine; 2,2,2-trifluoroacetate |

| No. | Code | Structure | Name |
|---|---|---|---|
| 185 | RD142 | 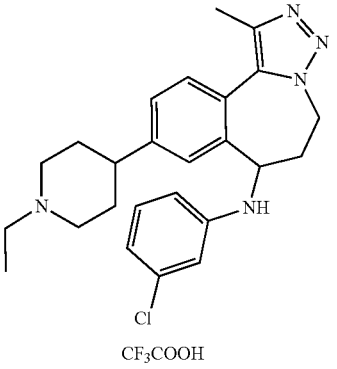 [SMILES: CCN1CCC(c2ccc3c(c2)C(Nc2cccc(Cl)c2)CCn2nnc(C)c2-3)CC1 ; "CF3COOH"] CF₃COOH | N-(3-chlorophenyl)-9-(1-ethylpiperidin-4-yl)-1-methyl-6,7-dihydro-5H-benzo[c][1,2,3]triazolo[1,5-a]azepin-7-amine; 2,2,2-trifluoroacetate |
| 186 | RD178 | 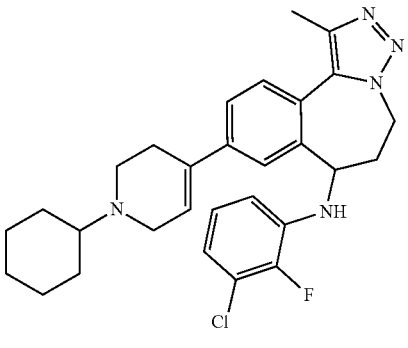 CF₃COOH | N-(3-chloro-2-fluorophenyl)-9-(1-cyclohexyl-1,2,3,6-tetrahydropyridin-4-yl)-1-methyl-6,7-dihydro-5H-benzo[c][1,2,3]triazolo[1,5-a]azepin-7-amine; 2,2,2-trifluoroacetate |
| 187 | RD179 | 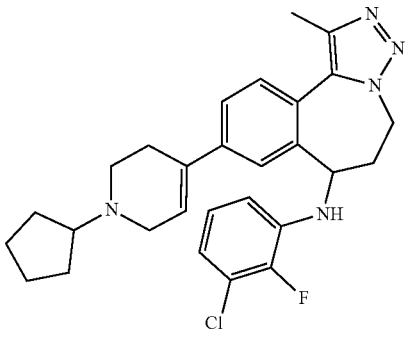 CF₃COOH | N-(3-chloro-2-fluorophenyl)-9-(1-cyclopentyl-1,2,3,6-tetrahydropyridin-4-yl)-1-methyl-6,7-dihydro-5H-benzo[c][1,2,3]triazolo-[1,5-a]azepin-7-amine; 2,2,2-trifluoroacetate |
| 188 | RD180 | 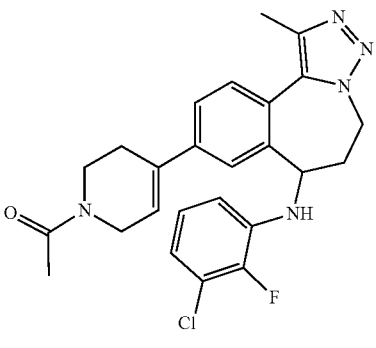 CF₃COOH | N-(3-chloro-2-fluorophenyl)-9-(1-isopropyl-1,2,3,6-tetrahydropyridin-4-yl)-1-methyl-6,7-dihydro-5H-benzo[c][1,2,3]triazolo[1,5-a]azepin-7-amine; 2,2,2-trifluoroacetate |

| No. | Code | Structure | Name |
|-----|------|-----------|------|
| 189 | RE10(S) | 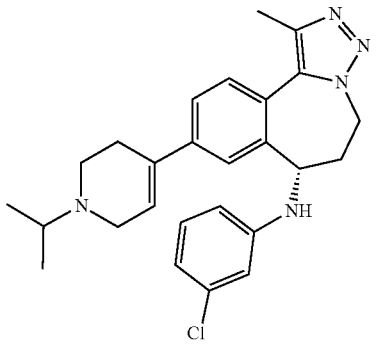<br>CF$_3$COOH | (7 S)-N-(3-chlorophenyl)-9-(1-isopropyl-1,2,3,6-tetrahydropyridin-4-yl)-1-methyl-6,7-dihydro-5H-benzo[c][1,2,3]triazolo[1,5-a]azepin-7-amine; 2,2,2-trifluoroacetate |
| 190 | RE13(R) | 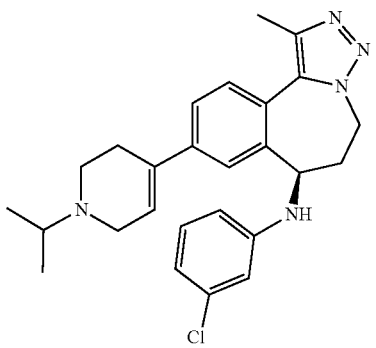<br>CF$_3$COOH | (7R)-N-(3-chlorophenyl)-9-(1-isopropyl-1,2,3,6-tetrahydropyridin-4-yl)-1-methyl-6,7-dihydro-5H-benzo[c][1,2,3]triazolo[1,5-a]azepin-7-amine; 2,2,2-trifluoroacetate |
| 191 | RE29 | 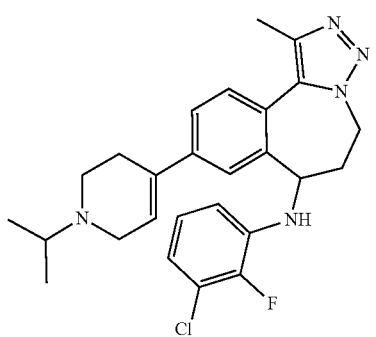<br>CF$_3$COOH | N-(3-chloro-2-fluorophenyl)-9-(1-isopropyl-1,2,3,6-tetrahydropyridin-4-yl)-1-methyl-6,7-dihydro-5H-benzo[c][1,2,3]triazolo[1,5-a]azepin-7-amine; 2,2,2-trifluoroacetate |
| 192 | RE30 | 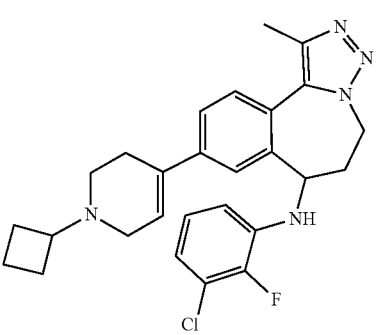<br>CF$_3$COOH | N-(3-chloro-2-fluorophenyl)-9-(1-cyclobutyl-1,2,3,6-tetrahydropyridin-4-yl)-1-methyl-6,7-dihydro-5H-benzo[c][1,2,3]triazolo[1,5-a]azepin-7-amine; 2,2,2-trifluoroacetate |

| No. | Code | Structure | Name |
|---|---|---|---|
| 193 | RE124 | 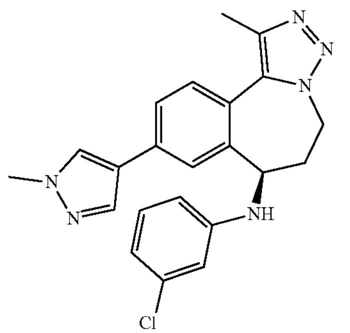 [SMILES: Cc1nnn2c1-c1ccc(-c3cnn(C)c3)cc1[C@H](Nc1cccc(Cl)c1)CC2] | (R)-N-(3-chlorophenyl)-1-methyl-9-(1-methyl-1H-pyrazol-4-yl)-6,7-dihydro-5H-benzo[c][1,2,3]triazolo[1,5-a]azepin-7-amine |
| 194 | RE127 | 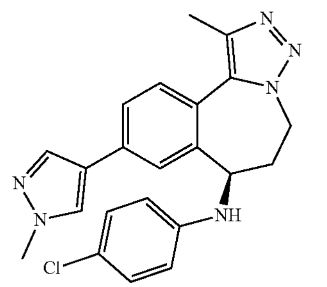 [SMILES: Cc1nnn2c1-c1ccc(-c3cnn(C)c3)cc1[C@H](Nc1ccc(Cl)cc1)CC2] | (R)-N-(4-chlorophenyl)-1-methyl-9-(1-methyl-1H-pyrazol-4-yl)-6,7-dihydro-5H-benzo[c][1,2,3]triazolo[1,5-a]azepin-7-amine |
| 195 | RE136 | 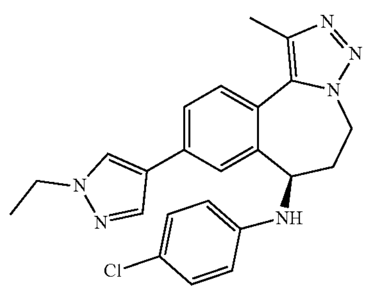 [SMILES: CCn1cc(-c2ccc3c(c2)[C@H](Nc2ccc(Cl)cc2)CCn2nnc(C)c2-3)cn1] | (R)-N-(4-chlorophenyl)-9-(1-ethyl-1H-pyrazol-4-yl)-1-methyl-6,7-dihydro-5H-benzo[c][1,2,3]triazolo[1,5-a]azepin-7-amine |

Specific Preparation Method:

The present invention is illustrated by the preparation processes of the compounds in Table 1, however, they are not intended to limit the present invention adversely. In the following preparation processes, for the test methods in which specific conditions are not indicated the conditions were selected in accordance with conventional methods and conditions, or in accordance with the product specification. The raw materials were obtained from commercial sources, or prepared by methods known in the art or described in the examples of the present invention. The structures of the compounds were identified by nuclear magnetic resonance ($^1$HNMR) or mass spectrometry (MS). The NMR measurement was carried out on a Bruker AV-400 nuclear magnetic resonance instrument in deuterated dimethyl sulfoxide (DMSO-$d_6$), deuterated chloroform (CDCl$_3$) or deuterated methanol (CD$_3$OD) as a solvent using TMS as an internal standard.

The abbreviations used in the description of the specific preparation examples of the present invention have the following meanings: PG means a protecting group, BPin means pinacolborate, brine means saturated brine, DCE means 1,2-dichloroethane, DCM means dichloromethane, DIPEA means diisopropylethylamine, DMAc means N,N-dimethylacetamide, DMF means N,N-dimethylformamide, DMSO means dimethyl sulfoxide, EA means ethyl acetate, THF means tetrahydrofuran, p-TsOH/TsOH means p-toluenesulfonic acid, 1,4-dioxane/dioxane means 1,4-dioxacyclohexane, dppf means 1,1'-bis(diphenylphosphino)ferrocene, Pd(dppf)Cl$_2$ means [1,1,1'-bis(diphenylphosphino)ferrocene]palladium dichloride, S-phos means 2-cyclohexylphosphine-2',6'-dimethoxybiphenyl, TBAF means tetrabutylammonium fluoride, Et$_3$N means triethylamine, toluene means methylbenzene, MsCl means methylsulfonyl chloride, acetone means 2-propanone, TBSC1 means tert-butyldimethylchlorosilane, DMAP means 4-dimethylaminopyridine, ACN means acetonitrile, MTBE means methyl tert-butyl ether, TFA means trifluoroacetic acid, DavePhos means 2-dicyclohexylphosphino-2'-(N,N-dimethylamine)-biphenyl, PLC means thin layer preparative chromatography, TLC means thin layer chromatography, LC-MS/LCMS means liquid chromatography-mass spectrometry combined instrument, ESI-MS means ESI ion source mass spectrometry, and $^1$HNMR means proton nuclear magnetic resonance spectroscopy.

Before Preparing the Final Products, the Following Intermediates Need to be Synthesized:

Intermediate M-1: methyl 5-methoxy-2-(4,4,5,5-tetramethyl-1,3,2-dioxaborolan-2-yl)benzoate (M-1);

Core Intermediate A: 8-Methoxy-1-methyl-4,5-dihydro-6H-benzo[6,7]cyclohepta[1,2-d]isoxazol-6-one;

Core Intermediate B: 8-Chloro-1-methyl-4,5-dihydro-6H-benzo[6,7]cyclohepta[1,2-d] is oxazol-6-one;

Core Intermediate C: 9-Bromo-1-methyl-6,7-dihydro-5H-benzo[C][1,2,3]triazolo[1,5-a]azepin-7-ol;
Core intermediate D: 9-Bromo-1,5-dimethyl-5,6-dihydro-7H-benzo[c][1,2,3]triazolo[1,5-a]azepin-7-one.
(1) Preparation of the Intermediate M-1:

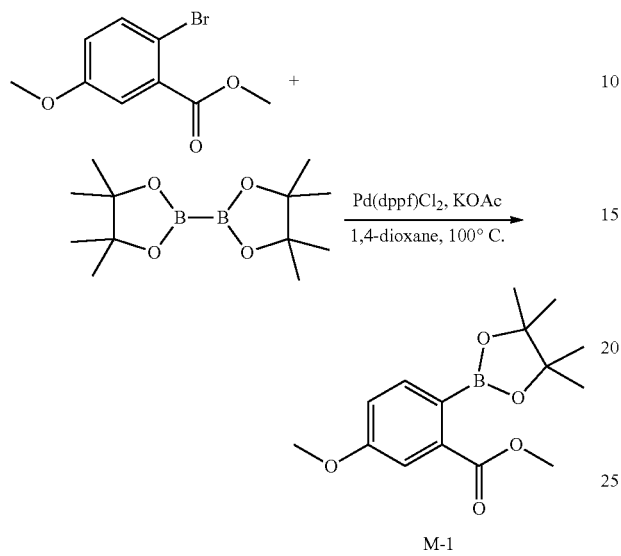

The specific process is as follows. Methyl 2-bromo-5-methoxybenzoate (19.66 g, 80.22 mmol), bis(pinacolato)diboron (23.98 g, 94.43 mmol), potassium acetate (23.61 g, 240.57 mmol) and 1,4-dioxane (350 mL) were added into a 1000 mL glass reaction flask. After deoxygenation, the system was added with [1,1'-bis(diphenylphosphino)ferrocene]dichloropalladium-(2.88 g, 3.94 mmol), and deoxygenated again. The system was stirred overnight at 100° C. under nitrogen protection. After the reaction was complete, the resultant was concentrated under reduced pressure, and the residue was separated by column chromatography to obtain the product M-1 (15.91 g, yield (Y)=67.91%).

The resultant intermediate M-1 was analyzed by proton nuclear magnetic resonance spectroscopy: $^1$HNMR (CDCl$_3$, 400 MHz): 7.40-7.33 (m, 2H), 6.97 (dd, J=8.1, 2.6 Hz, 1H), 3.83 (s, 3H), 3.76 (s, 3H), 1.32 (s, 12H). The analysis result was consistent with the structure of the intermediate M-1, that is, the prepared product is the desired intermediate M-1.
(2) Preparation of the Core Intermediate A:

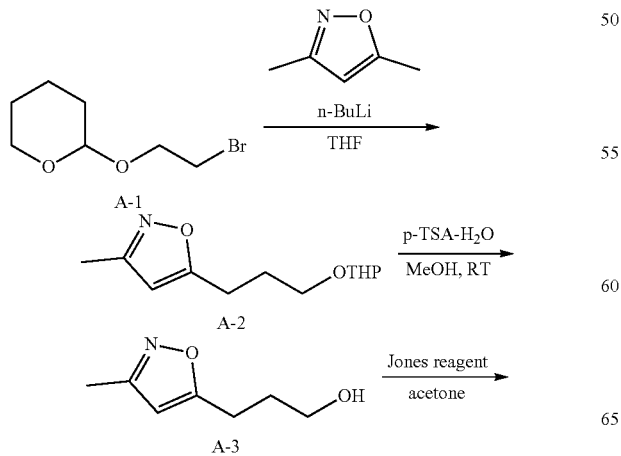

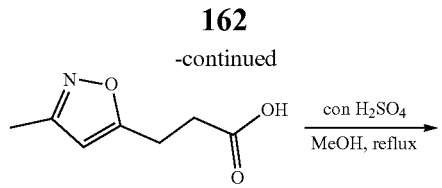

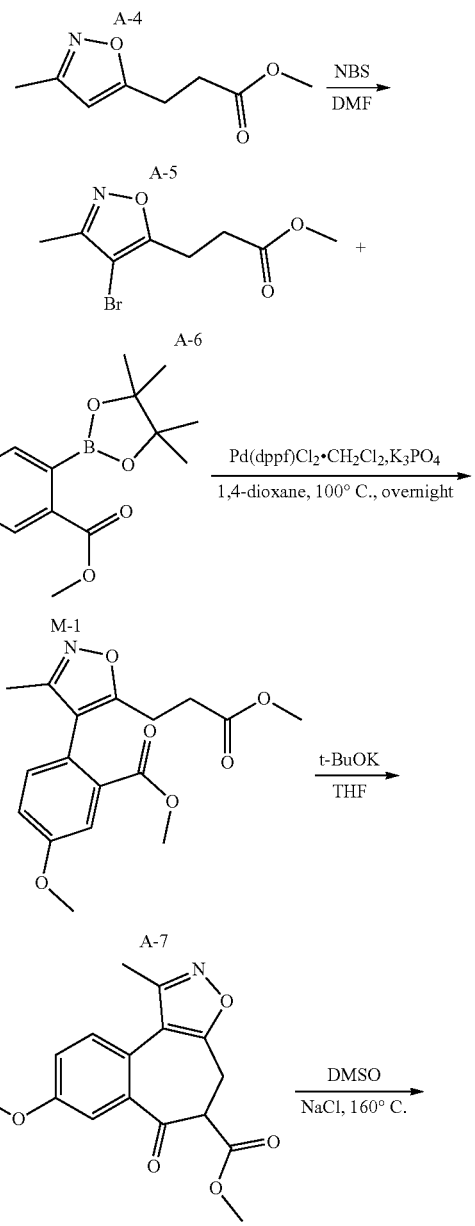

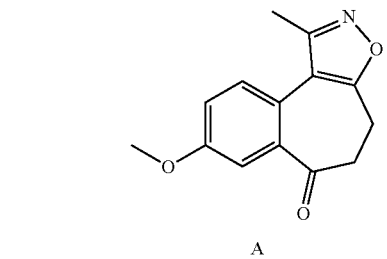

In this process, Step 1: Synthesis of 3-methyl-5-(3-((tetrahydro-2H-pyran-2-yl)oxy)propyl) isoxazol (A-2)

Into a 1 L reaction flask, A-1 (25.02 g, 258.65 mmol) and anhydrous tetrahydrofuran (THF, 280 mL) were added. After the temperature was decreased to −85° C. under nitrogen protection, a solution of n-butyl lithium in n-hexane (162 mL, 1.6M, 259.20 mmol) was added dropwise, while the reaction temperature was controlled at −85~−78° C., and then the system was reacted for 1 hour after the temperature was raised to −65° C. Subsequently, the temperature was decreased to −85° C. again, a solution of 3,5-dimethylisoxazol (51.25 g, 245.12 mmol) in tetrahydrofuran (20 mL) was added dropwise, while the reaction temperature was controlled at −80~−75° C. and then the system was reacted for 2 hours after the temperature was raised to −65° C.~−60° C. Upon the reaction was complete, the system was added with saturated aqueous ammonium chloride solution (300 mL), and extracted with ethyl acetate (300 mL, 100 mL). The combined organic phase was washed with saturated brine (300 mL*2), dried over anhydrous sodium sulfate and filtered with suction, and the filtrate was concentrated under reduced pressure. The residue was separated by column chromatography to obtain the target product A-2 (29.71 g, yield 51.0%).

Analysis results: $^1$HNMR (CDCl$_3$, 400 MHz): 5.84 (s, 1H), 4.59 (dd, J=4.5, 2.7 Hz, 1H), 3.88-3.78 (m, 2H), 3.54-3.41 (m, 2H), 2.85-2.81 (m, 2H), 2.27 (s, 3H), 2.08-1.91 (m, 2H), 1.86-1.68 (m, 2H), 1.63-1.51 (m, 4H).

ESI-MS Calculated for [M+H]$^+$=226.14, Found: 226.00;
The measured results of $^1$HNMR and ESI-MS were consistent with the structure of A-2.

Step 2: Synthesis of 3-(3-methylisoxazol-5-yl)-1-propanol (A-3)

A-2 (2.25 g, 9.98 mmol), methanol (50 mL) and p-toluenesulfonic acid monohydrate (228 mg, 1.20 mmol) were added into a reaction flask and reacted at room temperature for 1 hour. The system was concentrated under reduced pressure, and the residue was separated by column chromatography to obtain the product (0.92 g, yield 65.3%).

$^1$HNMR (CDCl$_3$, 400 MHz): 5.84 (s, 1H), 3.68 (t, J=6.2 Hz, 2H), 2.81 (t, J=7.6 Hz, 2H), 2.25 (br, 1H), 2.246 (s, 3H), 1.96-1.89 (m, 2H).

ESI-MS Calculated for [M+H]$^+$=142.08, Found: 142.00.
The measured results of $^1$HNMR and ESI-MS were consistent with the structure of A-3.

Step 3: Synthesis of 3-(3-methylisoxazol-5-yl)propionic acid (A-4)

A-3 (36.01 g, 255.0 mmol) and 180 mL of acetone were added into a reaction flask and cooled to 0 to 5° C. in an ice-water bath, added dropwise with Jones reagent (124 mL, dropping for 20 minutes), and then reacted at 10 to 20° C. for 30 minutes. After the reaction was complete, the system was quenched by addition of isopropanol (50 mL), added with 200 mL of water, and extracted with ethyl acetate (80 mL, 100*3). The combined organic phase was washed with saturated aqueous sodium thiosulfate solution (200 mL), and then with saturated brine (200 mL), dried over anhydrous sodium sulfate, and filtered. The filtrate was concentrated under reduced pressure to obtain the product (34.10 g), which was directly used in the next reaction. The yield of A-4 in this step was 86.2%.

Step 4: Synthesis of methyl 3-(3-methylisoxazol-5-yl)propionate (A-5)

A-4 (9.14 g, 58.9.0 mmol), methanol (150 mL) and concentrated sulfuric acid (2 mL) were put into a reaction flask, and the system was heated and refluxed for 1 hour. After the reaction was complete, the system was concentrated under reduced pressure, added with ethyl acetate (100 mL), and washed with saturated aqueous sodium bicarbonate solution (20 mL*2), and separated. The ethyl acetate phase was washed with saturated brine (50 mL), dried over anhydrous sodium sulfate, filtered with suction, and concentrated under reduced pressure. The residue was directly used in the next reaction. The product (8.71 g, yield 87.4%) was obtained.

Product identification: $^1$HNMR (CDCl$_3$, 400 MHz): 5.79 (s, 1H), 3.63 (s, 3H), 2.99-2.93 (m, 2H), 2.64 (t, J=7.5 Hz, 2H), 2.18 (s, 3H);

ESI-MS Calculated for [M+1]$^+$=170.07, Found: 170.10;
The test result was consistent with the structure of A-5.

Step 5: Synthesis of methyl 3-(4-bromo-3-methylisoxazol-5-yl)propionate (A-6)

A-5 (3.39 g, 20.0 mmol), N,N-dimethylformamide (40 mL) and N-bromosuccinimide (4.28 g, 24.0 mmol) were put into a reaction flask sequentially, heated to 60° C. and reacted for 2 hours. After the reaction was complete, the system was cooled naturally, added with ethyl acetate (120 mL), and washed with saturated brine (40 mL*3), dried over anhydrous magnesium sulfate, filtered with suction, and concentrated under reduced pressure, and the residue was separated by column chromatography to obtain the product A-6 (3.51 g, yield 70.7%).

Proton spectrum analysis results: $^1$HNMR (CDCl$_3$, 400 MHz): 3.64 (s, 3H), 3.00 (dd, J=8.2, 7.0 Hz, 2H), 2.68 (dd, J=8.1, 7.1 Hz, 2H), 2.19 (s, 3H).

ESI-MS Calculated for [M+1]$^+$=247.98, Found: 247.90.
The result of the product was consistent with the structure of A-6.

Step 6: Synthesis of methyl 5-methoxy-2-(5-(3-methoxy-3-oxopropyl)-3-methylisoxazol-4-yl)benzoate (A-7)

A-6 (18.0 g, 72.6 mmol), M-1 (23.3 g, 79.8 mmol), [1,1'-bis(diphenylphosphino)ferrocene]dichloropalladium-dichloromethane complex (2.30 g, 3.6 mmol), potassium phosphate (30.8 g, 145.1 mmol) and 1,4-dioxane (720 mL) were put into a reaction flask sequentially. After the air in the system was replaced with nitrogen three times, the system was heated to 100° C. and reacted overnight under nitrogen protection. The system was concentrated under reduced pressure, and the residue was separated by column chromatography to obtain the product A-7 (5.51 g, yield 22.8%).

ESI-MS Calculated for [M+1]$^+$=334.12, Found: 334.20.
The experimental result was consistent with the calculated value.

Step 7: Synthesis of methyl 8-methoxy-1-methyl-6-oxo-5,6-dihydro-4H-benzo[6,7] cyclohepta[1,2-d] isoxazol-5-carboxylate (A-8)

A-7 (1.70 g, 5.10 mmol) and anhydrous tetrahydrofuran (35 mL) were added into a reaction flask, and the system was cooled to −5° C. under nitrogen protection, added dropwise with a solution of potassium tert-butoxide (1.43 g, 12.74 mmol) in tetrahydrofuran and then reacted at room temperature for 20 minutes. After the reaction was complete, the system was added with water (15 mL), and adjusted pH to 4 with dilute hydrochloric acid solution (1 mol/L), and then added with ethyl acetate (50 mL) and saturated brine (50 mL), shaken and separated. The aqueous phase was extracted with ethyl ester (50 mL). The combined organic phase was washed with saturated brine (50 mL*2), dried over anhydrous sodium sulfate and filtered with suction, and the filtrate (adding with silica gel pad) was concentrated under reduced pressure. The residue was directly used in the next step. 1.44 g of the product was obtained and the yield of the crude product A-8 was 93.7%.

ESI-MS Calculated for [M+1]$^+$=302.10; Found: 302.20.

Step 8: Synthesis of 8-methoxy-1-methyl-4,5-dihydro-6H-benzo[6,7]cyclohepta[1,2-d]isoxazol-6-one (A)

A-8 (1.44 g, 4.78 mmol), dimethyl sulfoxide (15 mL), sodium chloride (558.7 mg, 9.56 mmol) and water (172.3 mg, 9.56 mmol) were put into a reaction flask, heated to 160° C. and reacted for 2.5 hours at this temperature. After cooled to room temperature, the system was added with water (50 mL), adjusted pH to 3-4 with dilute hydrochloric acid solution (1 mol/L), and extracted with ethyl acetate (30 mL*3). The combined organic phase was washed with saturated brine (50 mL*2), dried over anhydrous sodium sulfate and filtered with suction, and the filtrate was concentrated under reduced pressure. The residue was separated by column chromatography to obtain the product A (501.8 mg, yield 43.2%).

Analysis results of the product A: $^1$HNMR (CDCl$_3$, 400 MHz): 7.47-7.39 (m, 2H), 7.12 (dd, J=8.6, 2.9 Hz, 1H), 3.870 (s, 3H), 3.19-3.10 (m, 2H), 3.10-3.03 (m, 2H), 2.49 (s, 3H);

ESI-MS Calculated for [M+1]$^+$=244.09; Found: 244.10;

From the experimental results, it can be seen that the structure of the core intermediate A was consistent with the test results.

(3) Preparation of Core Intermediate B:

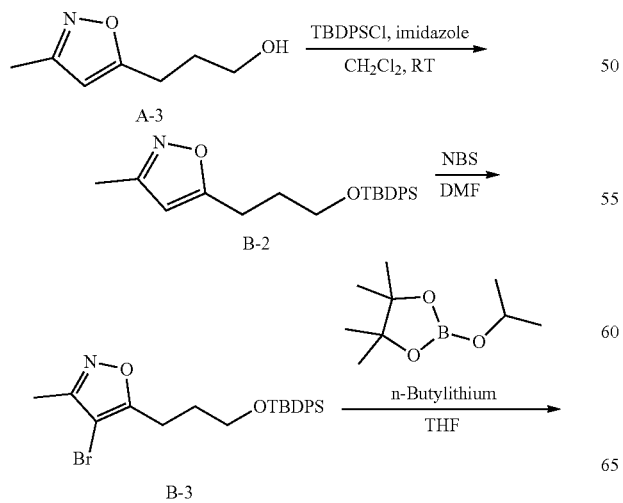

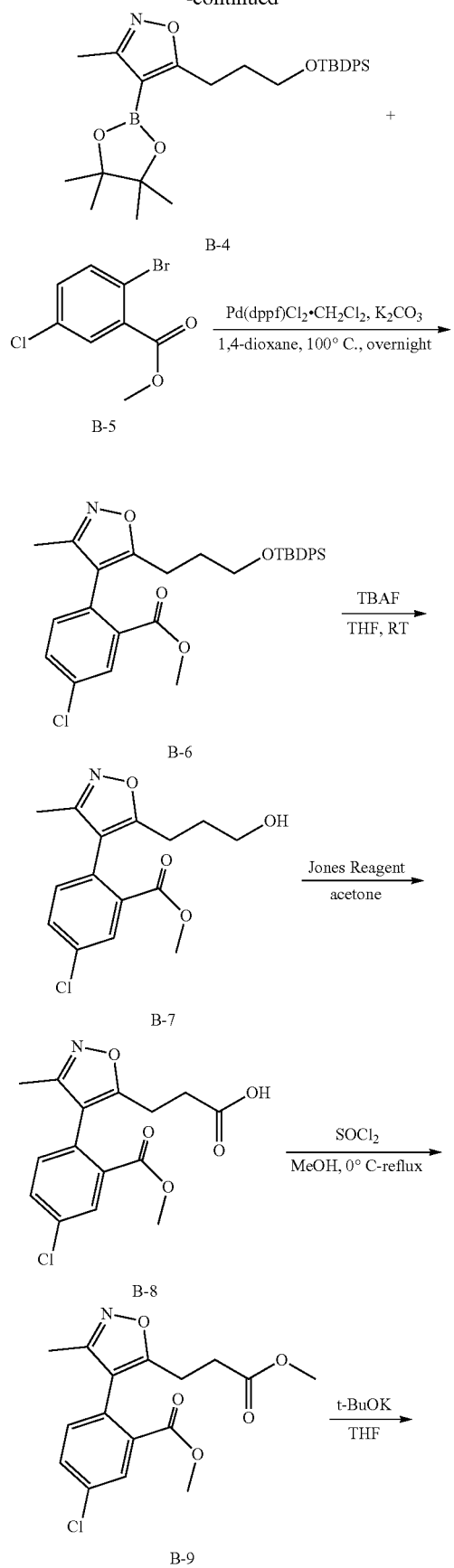

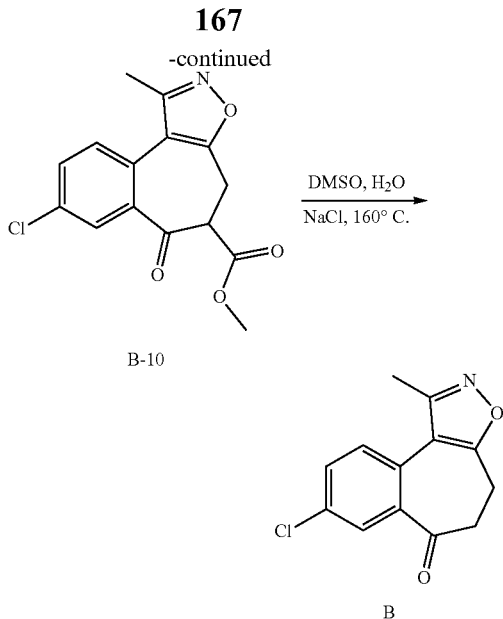

In this process, Step 1: Synthesis of 5-(3-((tert-butyldiphenylsilyl)oxy)propyl)-3-methylisoxazol (B-2)

A-3 (5.12 g, 36.27 mmol), dichloromethane (200 mL), tert-butyldiphenylchlorosilane (12.95 g, 47.11 mmol) and imidazole (3.70 g, 54.35 mmol) were added to a reaction flask sequentially and reacted overnight at room temperature. After the reaction was complete, the solvent was removed by concentration under reduced pressure, and the residue was separated by column chromatography to obtain the product B-2 (11.98 g, yield 87.9%).

ESI-MS Calculated for [M+1]$^+$=380.20, Found: 380.30, which was consistent with the calculated value.

Step 2: Synthesis of 4-bromo-5-(3-((tert-butyldiphenyl)oxy)propyl)-3-methylisoxazol (B-3)

B-2 (5.10 g, 13.50 mmol), N,N-dimethylformamide (100 mL) and N-bromosuccinimide (2.89 g, 16.24 mmol) were added into a reaction flask, and the mixture system was heated to 50° C. and reacted for 4 hours at this temperature. After the reaction was complete, the system was cooled to room temperature naturally, added with water (200 mL), and extracted with ethyl acetate (80 mL*2). The combined organic phase was washed with saturated brine, dried over anhydrous sodium sulfate and filtered with suction, and the filtrate was concentrated under reduced pressure. The residue was separated by column chromatography to obtain the product B-3 (4.59 g, yield 74.2%).

ESI-MS Calculated for [M+1]$^+$=458.11; Found: 458.40, the measured value was consistent with the calculated value.

Step 3: Synthesis of 5-(3-((tert-butyldiphenylsilyl)oxy)propyl)-3-methyl-4-(4,4,5,5-tetramethyl-1,3,2-dioxaborolan-2-yl)isoxazol (B-4)

B-3 (2.31 g, 5.04 mmol), anhydrous tetrahydrofuran (50 mL) and isopropylpinacolylborate (1.14 g, 6.06 mmol) were added into a reaction flask. After the air in the reaction system was replaced with nitrogen three times, the system was cooled to −85° C. under nitrogen protection, and added dropwise with a solution of n-butyllithium in tetrahydrofuran (5 mL), while the reaction temperature was controlled at −85~−78° C. After the addition, the temperature was kept at −60° C. for 0.5 h. After the reaction was complete, the system was quenched by adding saturated ammonium chloride aqueous solution, and extracted with ethyl acetate (50 mL*2), dried over anhydrous sodium sulfate, and filtered, and the filtrate was concentrated under reduced pressure. The residue was separated by column chromatography to obtain the product B-4 (2.05 g, yield 80.5%).

Test results: $^1$HNMR (CDCl$_3$, 400 MHz): 7.71-7.62 (m, 4H), 7.42-7.36 (m, 6H), 3.72 (t, J=6.1 Hz, 2H), 3.08-3.01 (m, 2H), 2.34 (S, 3H), 2.01-1.88 (m, 2H), 1.27 (s, 12H), 1.06 (s, 9H);

ESI-MS Calculated for [M+1]$^+$=506.28, Found: 506.30; The test result was consistent with the theoretical structure.

Step 4: Synthesis of methyl 2-(5-(3(-(tert-butyldiphenylsilyl)oxy)propyl)-3-methylisoxazol-4-yl)-5-chlorobenzoate (B-6)

B-4 (6.25 g, 12.36 mmol), B-5 (3.11 g, 12.47 mmol), Pd(dppf)Cl$_2$-dichloromethane complex (0.53 g, 0.65 mmol), potassium carbonate (5.25 g 24.73 mmol) and 1,4-dioxane (200 mL) were added to a reaction flask sequentially. After the air in the reaction flask was replaced with nitrogen three times, the system was reacted at 100° C. overnight under nitrogen protection. The resultant was concentrated under reduced pressure, and the residue was separated by column chromatography to obtain the product (4.05 g, yield 59.8%).

ESI-MS Calculated for [M+1]$^+$=548.19, Found: 547.80, which was consistent with the calculated value.

Step 5: Synthesis of methyl 5-chloro-2-(5-(3-hydroxypropyl)-3-methylisoxazol-4-yl]benzoate (B-7)

B-6 (4.01 g, 7.32 mmol), tetrahydrofuran (40 mL) and tetrabutylammonium fluoride in tetrahydrofuran (8 mL, 1mol/L, 8 mmol) were added into a reaction flask and reacted at room temperature. After the reaction was complete, the system was concentrated under reduced pressure, and the residue was separated by column chromatography to obtain the product B-7 (1.98 g, yield 87.3%).

Test results: $^1$HNMR (CDCl$_3$, 400 MHz): 7.97 (d, J=2.4 Hz, 1H), 7.54 (dd, J=8.2, 2.4 Hz, 1H), 7.16 (dd, J=8.1, 1.3 Hz, 1H), 3.77 (s, 3H), 3.59-3.57 (t, 2H), 2.71-2.66 (m, 2H), 2.04 (s, 3H), 1.87-1.83 (m, 2H);

The test result was consistent with the structure of B-7.

Step 6: Synthesis of 3-(4-(4-chloro-2-(methoxycarbonyl)phenyl)-3-methylisoxazol-5-yl) propionic acid (B-8)

B-7 (1.96 g, 6.33 mmol) and acetone (50 mL) were added into a reaction flask, and the system was cooled to 10° C. and added dropwise with Jones reagent until the color of system did not fade significantly while the reaction temperature was controlled at 10-15° C. The system was added with 100 mL of water and extracted stepwise with ethyl acetate (50 mL, 30 mL, 15 mL). The combined organic phase was washed with saturated sodium thiosulfate aqueous solution (30 mL) and saturated brine (50 mL*2), dried over anhydrous sodium sulfate, and filtered, and the filtrate was concentrated under reduced pressure to obtain a crude B-8 (1.98 g, yield 96.6%).

Step 7: Synthesis of methyl 5-chloro-2-(5-(3-methoxy-3-oxopropyl)-3-methylisoxazol-4-yl)benzoate (B-9)

B-8 (1.96 g, 6.05 mmol) and methanol (40 mL) were added into a 500 mL three-necked flask, and the system was cooled to 0° C., and added dropwise with dichloromethyl sulfone (1 mL), while the temperature was kept at 0-10° C. After the addition, the system was heated to reflux, and the reaction was monitored by TLC. The system was concentrated under reduced pressure and the residue was added with ethyl acetate (100 mL) and saturated potassium carbonate aqueous solution (30 mL), shaken and separated. The organic phase was washed with saturated brine (50 mL), dried over anhydrous magnesium sulfate, and filtered by suction. After the organic phase was concentrated under reduced pressure, the residue was separated by column chromatography to obtain B-9 (1.18 g, yield 57.7%).

Analysis of the product: $^1$HNMR (CDCl$_3$, 400 MHz): 7.46-7.40 (m, 2H), 7.12 (dd, J=8.6, 2.9 Hz, 1H), 3.87 (s, 3H), 3.17-3.13 (m, 2H), 3.08-3.04 (m, 2H), 2.49 (s, 3H), the test result was consistent with the structure of B-9.

Step 8: Synthesis of methyl 8-chloro-1-methyl-6-oxo-5,6-dihydro-4H-benzo[6,7]cyclohepta[1,2-d]isoxazol-5-carboxylate (B-10)

B-9 (0.98 g, 2.91 mmol) and anhydrous tetrahydrofuran (40 mL) were added into a three-necked flask, and then the system was cooled to −35° C., added with potassium tert-butoxide (0.86 g, 7.66 mmol), and reacted at −20° C., and the reaction was monitored by TLC. After the reaction was complete, the system was added with water (20 mL), adjusted pH to 3~4 with dilute hydrochloric acid aqueous solution (1 mol/L), added with ethyl acetate (30 mL) and water (50 mL), shaken and separated. The aqueous phase was extracted with ethyl acetate (30 mL). The combined organic phase was washed with saturated brine (60 mL), dried over anhydrous sodium sulfate and filtered with suction, and the filtrate was concentrated under reduced pressure. The residue was separated by column chromatography to obtain the product (0.61 g, yield 69.6%).

ESI-MS Calculated for [M+1]$^+$=306.05, Found: 305.80, which was consistent with the calculated value.

Step 9: Synthesis of 8-chloro-1-methyl-4,5-dihydro-6H-benzo[6,7]cyclohepta[1,2-d]isoxazol-6-one (B)

B-10 (14.12 g, 46.19 mmol), dimethyl sulfoxide (140 mL), sodium chloride (5.24 g, 89.24 mmol) and water (1.61 g, 89.61 mmol) were put into a reaction flask, and the system was heated 160° C. and reacted for 1 hour at this temperature. The system was cooled to room temperature, added with water (100 mL), adjusted pH to 3~4 with dilute hydrochloric acid solution (1 mol/L), and extracted with ethyl acetate (100 mL*2). The combined organic phase was washed with saturated brine (50 mL*2), dried over anhydrous sodium sulfate and filtered with suction, and the filtrate was concentrated under reduced pressure. The residue was separated by column chromatography to obtain the product B (6.12 g, yield 53.50%).

Analysis of the product: $^1$HNMR (CDCl$_3$, 400 MHz): 7.92 (d, J=2.4 Hz, 1H), 7.56 (dd, J=8.4, 2.4 Hz, 1H), 7.46 (d, J=8.4 Hz, 1H), 3.24-3.15 (m, 2H), 3.15-3.03 (m, 2H), 2.53 (s, 3H);

ESI-MS Calculated for [M+1]$^+$=248.04, Found: 247.90; The analysis result of the product was consistent with the structure of the core intermediate B.

(4) Preparation of Core Intermediate C:

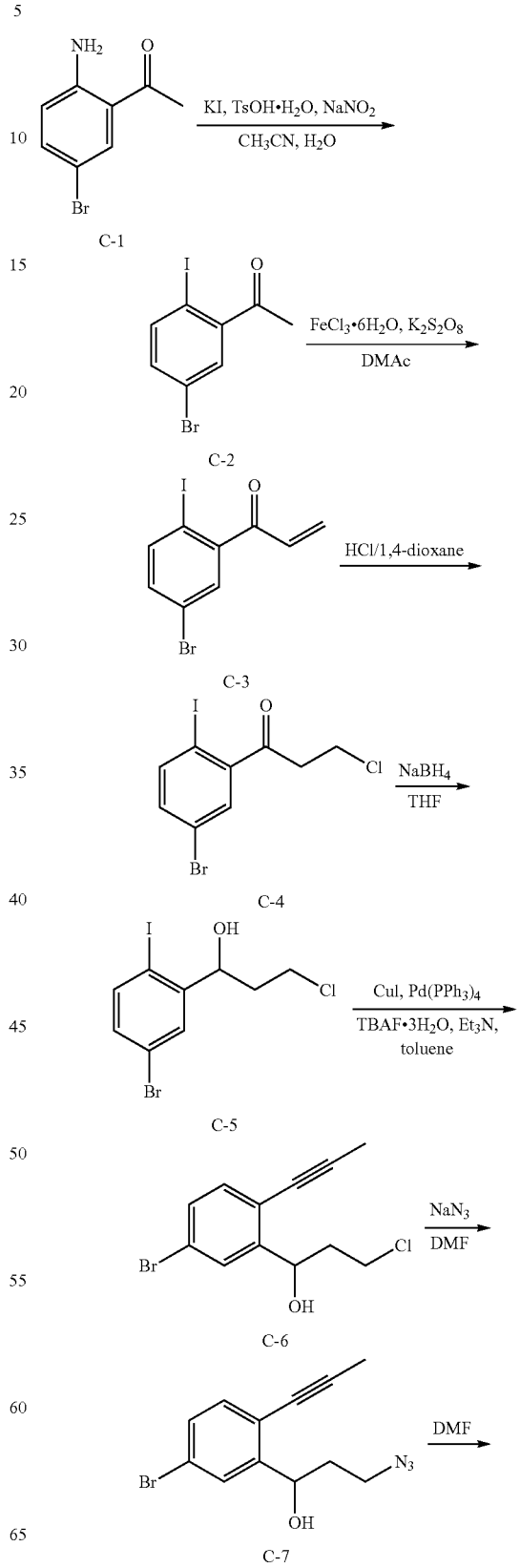

-continued

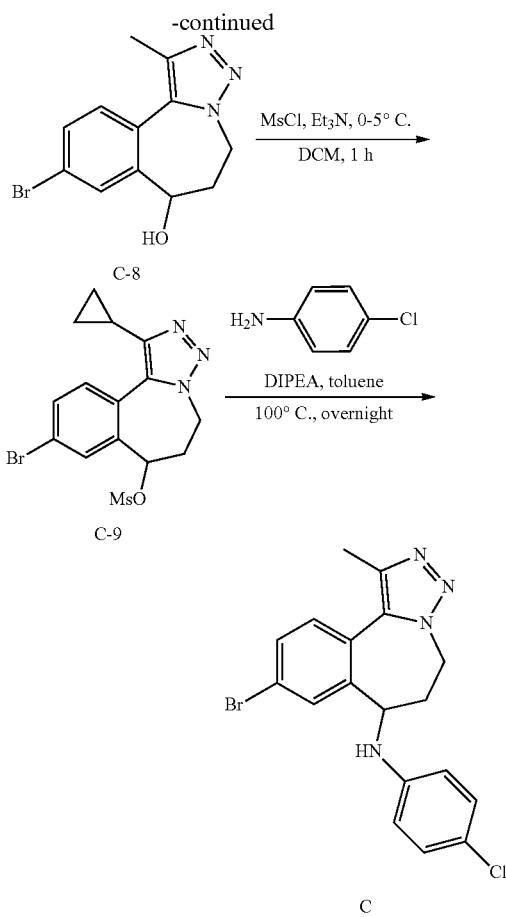

In this process, Step 1: Synthesis of 1-(5-bromo-2-iodophenyl)ethanone (C-2)

C-1 (102.3 g, 0.48 mol) and acetonitrile (1.6 L) were put into a reaction flask, and the system was cooled to 5° C., added with p-toluenesulfonic acid monohydrate (269.7 g, 1.42 mol), and then added dropwise with sodium nitrite (69.15 g, 1.00 mol) in water (150 mL) while the temperature was kept at 0~5° C. After the addition, the system was reacted at 0~5° C. for 1 hour, and added dropwise with potassium iodide (201.1 g, 1.21 mol) in water (150 mL) while the temperature was kept at 0~5° C. After the addition, the system was reacted at 0~5° C. for 0.5 hours. After the reaction was complete, the system was added with water (2 L), saturated sodium bicarbonate (500 mL), and saturated sodium thiosulfate solution (500 mL), and extracted with ethyl acetate (800 mL, 500 mL). The combined organic phase was washed with saturated brine (500 mL*2), dried over anhydrous sodium sulfate, and filtered, and the filtrate was concentrated under reduced pressure. The residue was separated by column chromatography to obtain the product (132.8 g, yield 85.1%).

Product analysis: $^1$HNMR (CDCl$_3$, 400 MHz): 7.77 (d, J=8.4 Hz, 1H), 7.55 (d, J=2.4 Hz, 1H), 7.25 (dd, J=8.3, 2.4 Hz, 1H), 2.60 (s, 3H);

ESI-MS Calculated for [M+1]$^+$=326.86, Found: 326.80;

The analysis result of the product was consistent with the structure of C-2.

Step 2: Synthesis of 1-(5-bromo-2-iodophenyl)prop-2-en-1-one (C-3)

Into a 1 L reaction flask, C-2 (29.98 g, 92.26 mmol), DMAc (360 mL), FeCl$_3$.6H$_2$O (4.22 g, 15.61 mmol) and potassium persulfate (50.45 g, 186.62 mmol) were added, and the system was heated to 110° C. When the temperature reached 110° C., the system exhibited a violent exotherm. After the exotherm was over, the temperature was kept for 10 minutes and then decreased to 80° C. Then, the system was added with an aqueous solution (300 mL), and the aqueous layer was extracted with ethyl acetate (300*2 mL). The combined organic phase was washed with water (300 mL*2), dried over anhydrous sodium sulfate and filtered with suction, and the filtrate was concentrated under reduced pressure to obtain the product (24.34 g, yield 78.30%).

Product analysis: $^1$HNMR (CDCl$_3$, 400 MHz): 7.68 (d, J=8.4 Hz, 1H), 7.35 (d, J=2.4 Hz, 1H), 7.24-7.20 (m, 1H), 6.62 (dd, J=17.5, 10.6 Hz, 1H), 6.12-6.00 (m, 2H);

ESI-MS Calculated for [M+1]+=336.87, Found: 336.60;

The analysis result of the product was consistent with the structure of C-3.

Step 3: Synthesis of 1-(5-bromo-2-iodophenyl)-3-chloroprop-1-one (C-4)

C-3 (24.34 g, 72.24 mmol) and a solution (4 M, 40 mL) of hydrochloric acid in 1,4-dioxane were added to a 250 mL reaction flask and stirred overnight at room temperature. The resultant was rotary evaporated to dryness, extracted with ethyl acetate (200 mL), and washed with water (100 mL*3). The ethyl acetate phase was dried over anhydrous sodium sulfate and filtered with suction, and the filtrate was concentrated under reduced pressure to obtain the product (21.25 g), which was directly used in the next step.

ESI-MS Calculated for [M+1]$^+$=372.85, Found: 372.70, the found value was consistent with the calculated value.

Step 4: Synthesis of 1-(5-bromo-2-iodophenyl)-3-chloroprop-1-ol (C-5)

Into a 500 mL reaction flask, C-4 (19.00 g, 50.88 mmol) and THF (200 mL) were added. The system was controlled to 0-5° C., added with water (1 mL), and added with NaBH$_4$ (1.47 g, 38.73 mmol) in batches. After the reaction is completed in about 30 minutes, aqueous hydrochloric acid solution (1M) was added dropwise until no bubbles emerged. THF was removed by rotary evaporation, and the resultant was extracted with ethyl acetate (200 mL). The ethyl acetate phase was washed with water (100 mL*3), dried over anhydrous sodium sulfate and filtered with suction, and the filtrate was concentrated under reduced pressure. The residue was separated by column chromatography to obtain the product (15.35 g, yield 80.79%).

Product analysis: $^1$HNMR (CDCl$_3$, 400 MHz): 7.68 (d, J=2.5 Hz, 1H), 7.66-7.62 (m, 1H), 7.12 (dd, J=8.4, 2.4 Hz, 1H), 5.05-5.09 (m, 1H), 3.80-3.87 (m, 1H), 3.68-3.74 (m, 1H), 2.14-2.22 (m, 1H), 2.02-1.92 (m, 1H);

ESI-MS Calculated for [M+1]$^+$=374.80, Found: 374.86;

The analysis result of the product was consistent with the structure of C-5.

Step 5: Synthesis of 1-(5-bromo-2-(prop-1-yn-1-yl)phenyl)-3-chloroprop-1-ol (C-6)

C-5 (8.10 g, 21.57 mmol), cuprous iodide (4.35 g, 22.84 mmol), tetrakistriphenylphosphine palladium (1.15 g, 0.99 mmol), tetrabutylammonium fluoride trihydrate (50 mL, 50 mmol), triethylamine (8.74 g, 86.57 mmol) and toluene (100 mL) were added into a reaction flask sequentially, and the air in the flask was replaced with nitrogen three times. Under the protection of nitrogen flow, the system was added with 1-(trimethylsilyl)propyne (4.66 g, 41.51 mmol) and reacted at room temperature for 2 hours under nitrogen protection. After the reaction was complete, the system was added with water (150 mL), and extracted with ethyl acetate (100 mL, 50 mL). The combined organic phase was washed with water (150 mL*2) and saturated brine (100 mL), dried over anhydrous sodium sulfate and filtered with suction, and the filtrate was concentrated under reduced pressure. The residue was separated by column chromatography to obtain the product (4.25 g, yield 68.51%).

Product analysis: $^1$HNMR (CDCl$_3$, 400 MHz): 7.65 (d, J=2.1 Hz, 1H), 7.33 (dd, J=8.2, 2.1 Hz, 1H), 7.22 (d, J=8.2 Hz, 1H), 5.33 (dd, J=9.2, 3.4 Hz, 1H), 3.78-3.86 (m, 1H), 3.65-3.70 (m, 1H), 2.27-2.13 (m, 2H), 2.08 (s, 3H);

ESI-MS Calculated for [M-OH]$^+$=268.98, Found: 269.00;

The analysis result of the product was consistent with the structure of C-6.

Step 6: Synthesis of 3-azido-1-(5-bromo-2-(prop-1-yn-1-yl)phenyl)propan-1-ol (C-7)

C-6 (4.15 g, 14.4 mmol), N,N-dimethylformamide (80 mL) and sodium azide (1.26 g, 1.94 mmol) were added to a reaction flask sequentially, and the system was heated to 80° C. and reacted for 3 hours. After the reaction was complete, the system was cooled to room temperature naturally, added with water (200 mL), and extracted with ethyl acetate (100 mL, 50 mL). The combined organic phase was washed with water (50 mL) and saturated brine (50 mL), dried over anhydrous sodium sulfate, and filtered, and the filtrate was concentrated under reduced pressure. The residue was separated by column chromatography to obtain the product (3.99 g, yield 94.82%).

ESI-MS Calculated for [M-N$_2$—OH]$^+$=248.02, Found: 247.90, the found value was consistent with the calculated value.

Step 7: Synthesis of 9-bromo-1-methyl-6,7-dihydro-5H-benzo[c][1,2,3]triazolo[1,5-a]azepin-7-ol (C-8)

C-7 (3.99 g, 13.65 mmol) and N,N-dimethylformamide (80 mL) were added to a reaction flask, and the system was heated to reflux for 6 hours. After cooled down naturally, the system was added with water (300 mL), and extracted with ethyl acetate (100 mL*4). The combined organic phase was washed with water (400 mL) and saturated brine (100 mL), dried over anhydrous sodium sulfate, and filtered, and the filtrate was concentrated under reduced pressure. The residue was separated by column chromatography to obtain the product (2.67 g, yield 66.91%).

Product analysis: $^1$HNMR (CDCl$_3$, 400 MHz): 7.87 (d, J=2.0 Hz, 1H), 7.51 (dd, J=8.1, 2.1 Hz, 1H), 7.17 (d, J=8.1 Hz, 1H), 4.69-4.58 (m, 2H), 3.85-3.93 (m, 1H), 2.96-2.81 (m, 1H), 2.36 (s, 3H), 2.11-2.18 (m, 1H);

ESI-MS Calculated for [M+1]+=294.02, Found: 294.00;

The analysis result of the product was consistent with the structure of C-8.

Step 8: Synthesis of 9-bromo-1-methyl-6,7-dihydro-5H-benzo[c][1,2,3]triazolo[1,5-a]azepin-7-yl mesylate (C-9)

In a 250 mL glass flask, C-8 (1.54 g, 5.23 mmol), dry DCM (80 mL) and triethylamine (2.82 g, 27.86 mmol) were added, and the system was cooled in an ice bath. After the temperature was controlled at 0-5° C., the system was added dropwise with MsCl (2.60 g, 22.69 mmol) in DCM (10 mL), kept at 0-5° C. and stirred for 1 hour. Thereafter, the system was washed with water (100 mL*2), and the organic layer was dried over anhydrous sodium sulfate, filtered, and rotary evaporated to dryness, and the resultant was put directly into the next step.

ESI-MS Calculated for [M+1]+=372.00, Found: 372.10, the found value was consistent with the calculated value.

Step 9: Synthesis of 9-bromo-N-(4-chlorophenyl)-1-methyl-6,7-dihydro-5H-benzo[c][1,2,3]triazolo[1,5-a]azepin-7-amine (C)

Into a 250 mL glass flask, C-9 (1.95 g, 5.23 mmol), toluene (150 mL), DIPEA (1.47 g, 11.37 mmol) and p-chloroaniline (0.81 g, 6.35 mmol) were added, and the air in the system was replaced with N$_2$ three times. The system was heated to 100° C. and kept for 14 h. After cooled down, the system was washed with water twice, dried over anhydrous sodium sulfate, and filtered, and the filtrate was rotary evaporated to dryness. The residue was purified by column chromatography to obtain the target compound (0.95 g), with a yield of 44.93% in two steps.

Product analysis: $^1$HNMR (CDCl$_3$, 400 MHz): 7.68 (d, J=2.0 Hz, 1H), 7.57 (dd, J=8.1, 2.0 Hz, 1H), 7.29 (d, J=8.0 Hz, 1H), 7.12 6.94 (m, 2H), 6.34 to 6.08 (m, 2H), 4.75 to 4.81 (m, 1H), 4.19 (dd, J=10.6, 6.7 Hz, 1H), 3.94 to 4.02 (m, 1H), 2.93 3.03 (m, 1H), 2.51 (s, 3H), 2.15-2.23 (m, 1H);

ESI-MS Calculated for [M+1]+=403.03, Found: 403.00;

The analysis result of the product was consistent with the structure of C.

(5) Preparation of Core Intermediate D

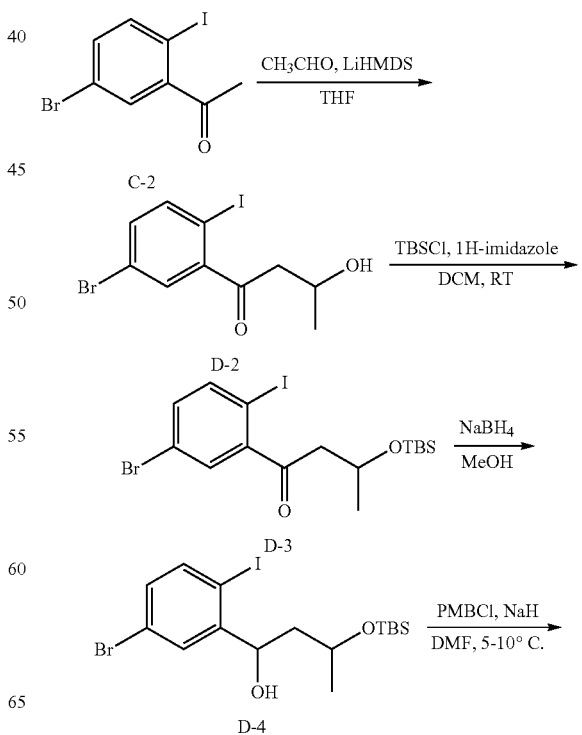

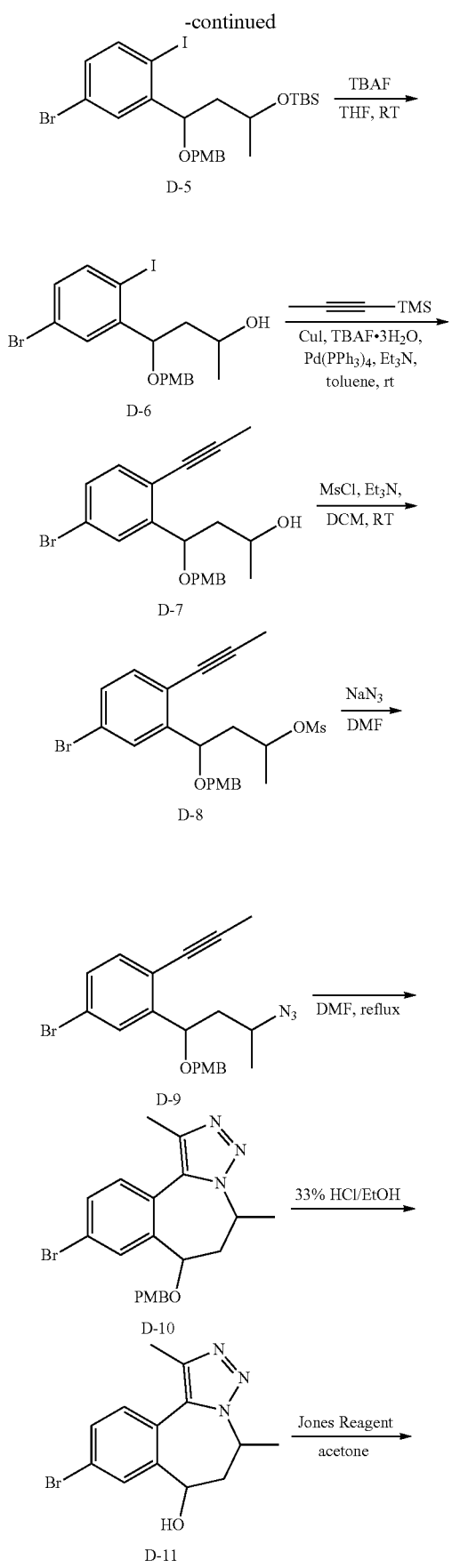

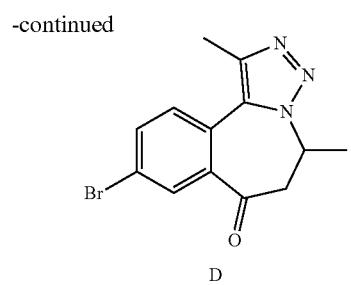

In this process, Step 1: Synthesis of 1-(5-bromo-2-iodophenyl)-3-hydroxybutan-1-one (D-2)

C-2 (9.99 g, 30.74 mmol) and anhydrous tetrahydrofuran (200 mL) were added into a three-necked flask, cooled to −85° C., and added dropwise with a solution of lithium hexamethyldisilaneamide in n-hexane (46 mL, 1.0 mol/L, 46 mmol), while the reaction temperature was kept at −85~−78° C. After the addition, the system was reacted at −60° C. for one hour, cooled to −85° C. again, and added dropwise with a solution of acetaldehyde in tetrahydrofuran (10 mL, 1.0 mol/L, 50 mmol). After the addition, the system was kept at −80~−60° C. to react for 3.5 hours. After the reaction was complete, the system was added with water (500 mL), and extracted with ethyl acetate (150 mL, 50 mL). The combined organic phase was washed with saturated brine (100 mL), dried over anhydrous sodium sulfate and filtered with suction, and the filtrate was concentrated under reduced pressure. The residue was separated by column chromatography to obtain the product D-2 (7.97 g, yield 70.3%).

Product analysis: $^1$HNMR (DMSO-$d_6$, 400 MHz): 7.84 (d, J=8.4 Hz, 1H), 7.74 (d, J=2.4 Hz, 1H), 7.40 (dd, J=8.4, 2.4 Hz, 1H), 4.76 (d, J=5.1 Hz, 1H), 4.11-3.97 (m, 1H), 3.03-2.85 (m, 2H), 1.13 (d, J=6.2 Hz, 3H);

ESI-MS Calculated for $[M+Na]^+$=390.89, Found: 390.80;

The analysis result of the product was consistent with the structure of D-2.

Step 2: Synthesis of 1-(5-bromo-2-iodophenyl)-3-((tert-butyldimethylsilyl)oxy)butan-1-one (D-3)

D-2 (8.67 g, 23.50 mmol), dichloromethane (150 mL), tert-butyldimethylchlorosilane (7.91 g, 52.48 mmol) and imidazole (3.23 g, 47.44 mmol) were added to a reaction flask sequentially and reacted overnight at room temperature. After the reaction was complete, the system was added with 100 mL of water, shaken and separated. The aqueous phase was extracted with dichloromethane (50 mL), and the combined organic phase was washed with saturated brine (50 mL*2) and filtered with suction, and the filtrate was concentrated under reduced pressure. The residue was separated by column chromatography to obtain the product (10.26 g, yield 90.3%).

ESI-MS Calculated for $[M+1]^+$=482.98, Found: 483.00, the found value was consistent with the calculated value.

Step 3: Synthesis of 1-(5-bromo-2-iodophenyl)-3-((tert-butyldimethylsilyl)oxy)butan-1-ol (D-4)

D-3 (1.98 g, 4.10 mmol) and methanol (20 mL) were added to a reaction flask sequentially. After cooled to 5° C., the system was added with sodium borohydride (155.6 mg, 4.10 mmol) and reacted for 0.5 hours while the temperature was kept at 5-10° C. After the reaction was complete, the reaction system was poured into ice water (50 mL), and extracted with ethyl acetate (20 mL*2), and the combined organic phase was washed with saturated brine (35 mL), dried over anhydrous sodium sulfate and filtered with suction, and the filtrate was concentrated under reduced pressure. The residue was separated by column chromatography to obtain the product (1.81 g, yield 91.0%).

Step 4: Synthesis of 44-(5-bromo-2-iodophenyl)-4-((4-methoxybenzyl)oxy)but-2-yl)oxy) (tert-butyl) dimethylsilane (D-5)

D-4 (12.71 g, 26.19 mmol), N,N-dimethylformamide (150 mL) and p-methoxybenzyl chloride (6.69 g, 42.72 mmol) were added to a reaction flask sequentially. After cooled to 5° C., the system was added with sodium hydride (2.06 g, 60% content, 51.50 mmol) in batches, and reacted for 1.5 hours while the temperature was kept at 5-10° C. After the reaction was complete, the reaction system was poured into ice-water (500 mL), and extracted with ethyl acetate (100 mL*2). The combined organic phase was washed with saturated brine (100 mL), dried over anhydrous sodium sulfate and filtered with suction, and the filtrate was concentrated under reduced pressure. The residue was separated by column chromatography to obtain a crude D-5, which was put into the next reaction at a yield of 100%.

Step 5: Synthesis of 4-(5-bromo-2-iodophenyl)-4-((4-methoxybenzyl)oxy)butan-2-ol (D-6)

D-5 (15.86 g, 26.19 mmol) and a solution of tetrabutylammonium fluoride in tetrahydrofuran (30 mL, 1 mol/L, 30 mmol) were added to a reaction flask sequentially, and reacted overnight at room temperature. After the reaction was complete, the system was added with water (200 mL), and extracted with ethyl acetate (100 mL*2). The combined organic phase was washed with saturated brine (100 mL), dried over anhydrous sodium sulfate and filtered with suction, and the filtrate was concentrated under reduced pressure. The residue was separated by column chromatography to obtain the product (10.75 g, 83.6%).

ESI-MS Calculated for [M+Na]$^+$=512.93, Found: 513.00, the found value was consistent with the calculated value.

Step 6: Synthesis of 4-(5-bromo-2-(prop-1-yn-1-yl)phenyl)-4-((4-methoxybenzyl)oxy) butan-2-ol (D-7)

D-6 (9.76 g, 19.87 mmol), cuprous iodide (3.54 g, 36.70 mmol), palladium tetrakistriphenylphosphine (1.09 g, 18.59 mmol), tetrabutylammonium fluoride trihydrate (11.49 g, 36.42 mmol), triethylamine (8.0 mL) and toluene (150 mL) were added to a reaction flask sequentially, and the air in the reaction flask was replaced with nitrogen three times. Under the protection of nitrogen flow, the system was added with 1-(trimethylsilyl)propyne and reacted at room temperature for 1.5 hours under protection of nitrogen. After the reaction was complete, the system was added with water (200 mL), and extracted with ethyl acetate (100 mL, 50 mL). The combined organic phase was washed with saturated brine (100 mL), dried over anhydrous sodium sulfate and filtered with suction, and the filtrate was concentrated under reduced pressure. The residue was separated by column chromatography to obtain the product (7.12 g, yield 88.8%).

Product analysis: $^1$HNMR (CDCl$_3$, 400 MHz): 7.67-7.64 (m, 1H), 7.36-7.33 (m, 1H), 7.26-7.21 (m, 3H), 6.93-6.83 (m, 2H), 5.13-5.00 (m, 1H), 4.42 (t, J=11.1 Hz, 1H), 4.21 (dd, J=11.2, 9.0 Hz, 1H), 3.99-3.94 (m, 1H), 3.80 (d, J=1.0 Hz, 3H), 2.03 (d, J=1.7 Hz, 3H), 1.88-1.65 (m, 3H), 1.14 (d, J=6.3 Hz, 3H);

ESI-MS Calculated for [M+1]$^+$=403.08, Found: 403.00; The test result was consistent with the structure of D-7.

Step 7: Synthesis of Methyl 4-(5-bromo-2-(prop-1-yn-1-yl)phenyl)-4-((4-methoxybenzyl) oxy)but-2-yl mesylate (D-8)

D-7 (4.01 g, 9.94 mmol), dichloromethane (80 mL) and triethylamine (3.09 g, 30.54 mmol) were added into a reaction flask, and the system was cooled to 5° C. in an ice-water bath under nitrogen protection, added with methanesulfonyl chloride (3.52 g, 30.73 mmol) and reacted at room temperature for 2 hours. After the reaction was complete, the system was quenched with 100 mL of water, shaken, and separated. The aqueous phase was extracted with dichloromethane. The combined organic phase was washed with saturated brine, dried over anhydrous sodium sulfate and filtered with suction, and the filtrate was concentrated under reduced pressure. The residue was separated by column chromatography to obtain the product (2.93 g, yield 61.2%).

ESI-MS Calculated for [M+1]$^+$=481.06, Found: 481.00, the experimental result was consistent with the calculated value.

Step 8: Synthesis of 2-(3-azido-1-((4-methoxybenzyl)oxy)butyl)-4-bromo-1-(prop-1-yn-1-yl)benzene (D-9)

D-8 (4.31 g, 10.06 mmol), N,N-dimethylformamide (100 mL) and sodium azide (1.97 g, 30.30 mmol) were added to a reaction flask, heated to 80° C. and reacted for 3 hours. After the reaction was complete, the system was cooled to room temperature naturally, added with 200 mL of water, and extracted with ethyl acetate (100 mL, 50 mL). The combined organic phase was washed with saturated brine (100 mL*2), dried over anhydrous magnesium sulfate and filtered with suction, and the filtrate was concentrated under reduced pressure. The residue was separated by column chromatography to obtain the product (3.34 g, yield 77.5%).

ESI-MS Calculated for [M+1]$^+$=428.09, Found: 428.00, the experimental result was consistent with the calculated value.

Step 9: Synthesis of 9-bromo-7-((4-methoxybenzyl)oxy)-1,5-dimethyl-6,7-dihydro-5H-benzo[c][1,2,3]triazolo[1,5-a]azepine (D-10)

D-9 (5.16 g, 12.0 mmol) and N,N-dimethylformamide (450 mL) were added to a reaction flask, and the system was heated to reflux and reacted for 7 hours. The system was cooled down naturally, added with water (1 L), and extracted with ethyl acetate (200 mL, 150 mL). The combined organic phase was washed with saturated brine (200 mL), dried over anhydrous sodium sulfate, and filtered, and the filtrate was concentrated under reduced pressure. The residue was separated by column chromatography to obtain the product (3.57 g, yield 69.2%).

Product analysis: $^1$HNMR (CDCl$_3$, 400 MHz): 7.67-7.63 (m, 1H), 7.36-7.32 (m, 1H), 7.28-7.20 (m, 3H), 6.92-6.88 (m, 2H), 5.04-4.84 (m, 1H), 4.43-4.37 (m, 1H), 4.26-4.11 (m, 1H), 3.81 (s, 3H), 2.08 (s, 3H), 1.80-1.62 (m, 2H), 1.26 (d, J=6.6 Hz, 3H), 1.18 (dd, J=13.0, 6.5 Hz, 1H);

ESI-MS Calculated for [M+1]+=428.09, Found: 428.10; The test result was consistent with the structure of D-10.

Step 10. Synthesis of 9-bromo-1,5-dimethyl-6,7-dihydro-5H-benzo[c][1,2,3]triazolo[1,5-a]azepin-7-ol (D-11)

D-10 (3.06 g, 7.14 mmol) and hydrogen chloride in ethanol (40 mL, mass fraction 33%) were added to a reaction flask and reacted at room temperature for 4 hours. After the reaction was complete, the system was concentrated under reduced pressure, and the residue was separated by column chromatography to obtain the product (1.72 g, yield 78.2%).

ESI-MS Calculated for [M+1]+=308.03, Found: 308.00, the experimental result was consistent with the calculated value.

Step 11. Synthesis of 9-bromo-1,5-dimethyl-5,6-dihydro-7H-benzo[c][1,2,3]triazolo[1,5-a]azepin-7-one (D)

D-11 (1.72 g, 5.58 mmol), acetone (400 mL) and dichloromethane (150 mL) were added to a reaction flask, cooled to 7° C., and added with Jones reagent (25 mL), while the reaction progress was monitored by TLC. After the reaction was complete, the system was added with water (1 L), and extracted with ethyl acetate (300 mL, 150 mL*2). The combined organic phase was washed with saturated brine (300 mL), saturated sodium thiosulfate aqueous solution (200 mL*2) and saturated brine (250 mL), dried over anhydrous sodium sulfate, and filtered, and the filtrate was concentrated under reduced pressure. The residue was separated by column chromatography to obtain the product (1.23 g, yield 72.0%).

Product analysis: $^1$HNMR (CDCl$_3$, 400 MHz): 8.14 (d, J=2.2 Hz, 1H), 7.80 (dd, J=8.3, 2.2 Hz, 1H), 7.37 (d, J=8.3 Hz, 1H), 5.07-4.94 (m, 1H), 3.21-3.01 (m, 2H), 2.49 (s, 3H), 1.78 (d, J=6.9 Hz, 3H);

ESI-MS Calculated for [M+1]$^+$=306.02, Found: 306.00;

The analysis result of the product was consistent with the structure of D.

The above-mentioned intermediates or the products obtained in the preparation process of the intermediate were used as reactants for synthesis of some compounds in Table 1.

Preparation Example 1, Final Product FA01: 8-methoxy-N-(4-methoxyphenyl)-1-methyl-5,6-dihydro-4H-benzo[6,7]cyclohepta[1,2-d]isoxazol-6-amine

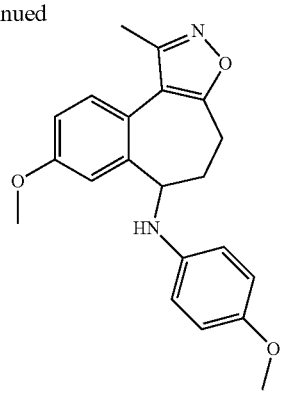

FA01

Synthesis of 8-methoxy-N-(4-methoxyphenyl)-1-methyl-5,6-dihydro-4H-benzo[6,7]cyclohepta[1,2-d]isoxazol-6-amine (FA01)

A (150.0 mg, 0.62 mmol), p-anisidine (152.6 mg, 1.24 mmol), p-toluenesulfonic acid monohydrate (11.8 mg, 0.06 mmol) and toluene (30 mL) were added to a reaction flask in sequence. The system was reacted overnight under reflux for dehydration, and concentrated under reduced pressure. The residue was added with 1,2-dichloroethane (15 mL), acetic acid (0.25 mL) and sodium triacetoxyborohydride (393.9 mg, 1.86 mmol) and reacted at room temperature overnight. After the reaction was complete, the system was added with water (10 mL), shaken and separated. The aqueous phase was extracted with dichloromethane (10 mL*2). The combined organic phase was washed with saturated brine (30 mL), dried over anhydrous sodium sulfate, and filtered. The filtrate was concentrated under reduced pressure, and the residue was separated on a preparative plate to obtain a crude, which was separated by reverse-phase fast medium pressure preparative chromatography to obtain 80.3 mg of the product with a yield of 37.0%.

Product analysis: $^1$HNMR (CDCl$_3$, 400 MHz): 7.38 (d, J=8.5 Hz, 1H), 7.04 (d, J=2.8 Hz, 1H), 6.85 (dd, J=8.5, 2.8 Hz, 1H), 6.76-6.68 (m, 2H), 6.48-6.38 (m, 2H), 4.34 (d, J=8.2 Hz, 1H), 3.77 (s, 1H), 3.75 (s, 3H), 3.71 (s, 3H), 3.24-3.15 (m, 1H), 3.01-2.93 (m, 1H), 2.50 (s, 3H), 2.36-2.25 (m, 2H);

ESI-MS Calculated for [M+1]$^+$=351.16, Found: 351.20;

The product analysis result was consistent with the structure of FA01.

Preparation Example 2, Final Product FA02: N-(4-chlorophenyl)-8-methoxy-1-methyl-5,6-dihydro-4H-benzo[6,7]cyclohepta[1,2-d]isoxazol-6-amine

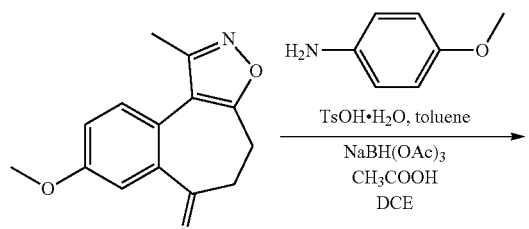

A

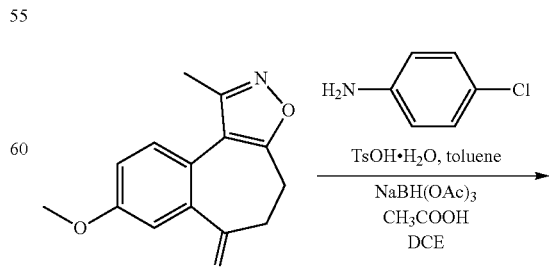

A

-continued

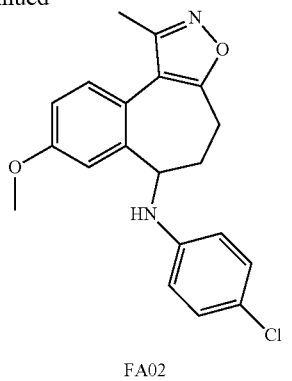

FA02

Synthesis of N-(4-chlorophenyl)-8-methoxy-1-methyl-5,6-dihydro-4H-benzo[6,7]cyclohepta[1,2-d]isoxazol-6-amine (FA02)

A (150.0 mg, 0.62 mmol), p-chloroaniline (158.1 mg, 1.24 mmol), p-toluenesulfonic acid monohydrate (11.8 mg, 0.06 mmol) and toluene (30 mL) were added to a reaction flask in sequence. The system was reacted overnight under reflux and dehydration, and concentrated under reduced pressure. The residue was added with 1,2-dichloroethane (15 mL), acetic acid (0.25 mL) and sodium triacetoxyborohydride (393.9 mg, 1.86 mmol) and reacted at room temperature overnight. After the reaction was complete, the system was added with saturated sodium bicarbonate aqueous solution (10 mL), shaken and separated. The aqueous phase was extracted with dichloromethane (10 mL*2). The combined organic phase was washed with saturated brine (20 mL), dried over anhydrous sodium sulfate and filtered. The filtrate was concentrated under reduced pressure, and the residue was separated on a preparative plate to obtain 76.3 mg of the product with a yield of 34.7%.

Product analysis: $^1$HNMR (CDCl$_3$, 400 MHz): 7.39 (d, J=8.5 Hz, 1H), 7.13-7.01 (m, 2H), 6.97 (d, J=2.8 Hz, 1H), 6.86 (dd, J=8.5, 2.8 Hz, 1H), 6.42-6.33 (m, 2H), 4.36-4.34 (m, 1H), 4.02 (s, 1H), 3.75 (s, 3H), 3.25-3.16 (m, 1H), 3.00-2.92 (m, 1H), 2.50 (s, 3H), 2.41-2.22 (m, 2H);

ESI-MS Calculated for [M+1]$^+$=355.11, Found: 355.20;

The product analysis result was consistent with the structure of FA02.

Preparation Example 3, Final Product FA03: 8-methoxy-1-methyl-N-phenyl-5,6-dihydro-4H-benzo[6,7]cyclohepta[1,2-d]isoxazol-6-amine

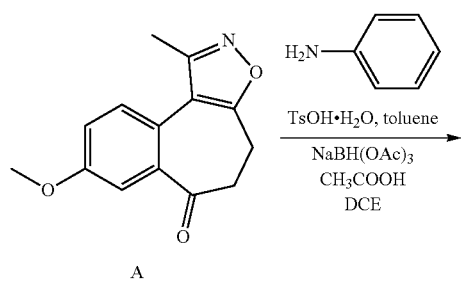

A

-continued

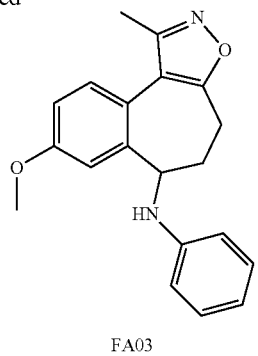

FA03

Synthesis of 8-methoxy-1-methyl-N-phenyl-5,6-dihydro-4H-benzo[6,7]cyclohepta[1,2-d]isoxazol-6-amine (FA03)

A (150.0 mg, 0.62 mmol), aniline (115.4 mg, 1.24 mmol), p-toluenesulfonic acid monohydrate (11.8 mg, 0.06 mmol) and toluene (30 mL) were added to a reaction flask in sequence. The system was reacted overnight under reflux and dehydration, and concentrated under reduced pressure. The residue was added with 1,2-dichloroethane (15 mL), acetic acid (0.25 mL) and sodium triacetoxyborohydride (393.9 mg, 1.86 mmol) and reacted at room temperature overnight. After the reaction was complete, the system was added with saturated sodium bicarbonate aqueous solution (10 mL), shaken and separated. The aqueous phase was extracted with dichloromethane (10 mL*2). The combined organic phase was washed with saturated brine (20 mL), dried over anhydrous sodium sulfate, and filtered. The filtrate was concentrated under reduced pressure, and the residue was separated on a preparative plate to obtain 75 mg product of with a yield of 37.8%.

Product analysis: $^1$HNMR (CDCl$_3$, 400 MHz): 7.39 (d, J=8.5 Hz, 1H), 7.16-7.07 (m, 2H), 7.04 (d, J=2.8 Hz, 1H), 6.86 (dd, J=8.5, 2.8 Hz, 1H), 6.71-6.64 (m, 1H), 6.48-6.45 (m, 2H), 4.41 (d, J=7.4 Hz, 1H), 3.99 (s, 1H), 3.74 (s, 3H), 3.24-3.16 (m, 1H), 3.01-2.94 (m, 1H), 2.50 (s, 3H), 2.39-2.23 (m, 2H);

ESI-MS Calculated for [M+H]$^+$=321.15, Found: 321.20;

The product analysis result was consistent with the structure of FA03.

Preparation Example 4, Final Product FA05: 8-methoxy-1-methyl-N-(4-(trifluoromethyl)phenyl)-5,6-dihydro-4H-benzo[6,7]cyclohepta[1,2-d]isoxazol-6-amine

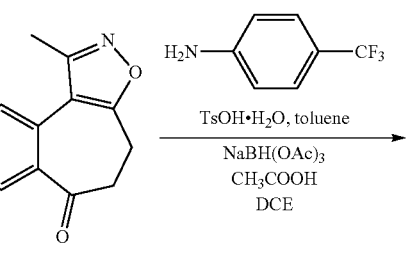

A

-continued

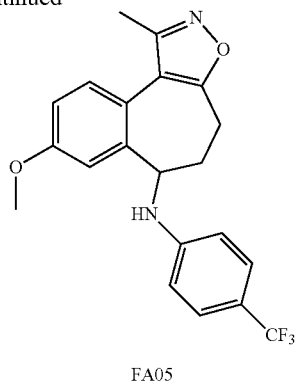

FA05

Synthesis of 8-methoxy-1-methyl-N-(4-(trifluoromethyl)phenyl)-5,6-dihydro-4H-benzo[6,7]cyclohepta[1,2-d]isoxazol-6-amine (FA05)

A (200 mg, 0.83 mmol), 4-trifluoromethylaniline (266.2 mg, 1.65 mmol), p-toluenesulfonic acid monohydrate (15.7 mg, 0.08 mmol) and toluene (30 mL) were added to a reaction flask in sequence. The system was reacted overnight under reflux and dehydration, and concentrated under reduced pressure. The residue was added with 1,2-dichloroethane (15 mL), acetic acid (0.25 mL) and sodium triacetoxyborohydride (525.3 mg, 2.48 mmol) and reacted at room temperature overnight. After the reaction was complete, the system was added with saturated sodium bicarbonate aqueous solution (10 mL), shaken and separated. The aqueous phase was extracted with dichloromethane (10 mL*2). The combined organic phase was washed with saturated brine (20 mL), dried over anhydrous sodium sulfate, and filtered. The filtrate was concentrated under reduced pressure, and the residue was separated on a preparative plate to obtain a crude, which was separated by reverse-phase fast medium pressure preparative chromatography to obtain 39 mg of the product.

Product analysis: $^1$HNMR (CDCl$_3$, 400 MHz): 7.41 (d, J=8.5 Hz, 1H), 7.34 (d, J=8.4 Hz, 2H), 6.95 (d, J=2.7 Hz, 1H), 6.87 (dd, J=8.5, 2.7 Hz, 1H), 6.47 (d, J=8.4 Hz, 2H), 4.26-4.45 (m, 1H), 3.75 (s, 3H), 3.18-3.26 (m, 1H), 2.93-3.01 (m, 1H), 2.51 (s, 3H), 2.32-2.39 (m, 2H);

ESI-MS Calculated for [M+H]$^+$=389.14, Found: 389.20;

The product analysis result was consistent with the structure of FA05.

Preparation Example 5, Final Product FA06: 4-(8-methoxy-1-methyl-5,6-dihydro-4H-benzo[6,7]cyclohepta[1,2-d]isoxazol-6-yl)aminobenzonitrile

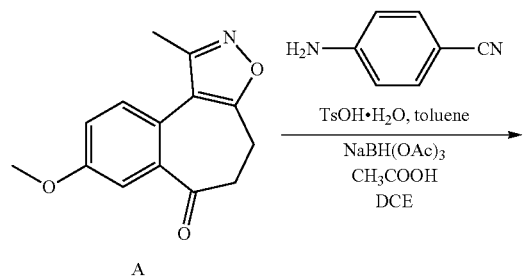

A

-continued

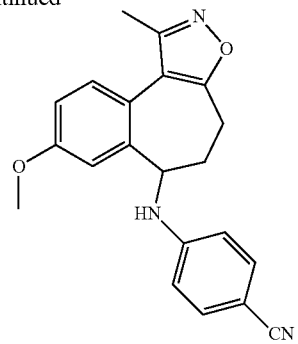

FA06

Synthesis of 4-(8-methoxy-1-methyl-5,6-dihydro-4H-benzo[6,7]cyclohepta[1,2-d]isoxazol-6-yl)aminobenzonitrile (FA06)

A (200 mg, 0.83 mmol), 4-cyanoaniline (195.2 mg, 1.65 mmol), p-toluenesulfonic acid monohydrate (15.7 mg, 0.08 mmol) and toluene (30 mL) were added to a reaction flask in sequence. The system was reacted overnight under reflux and dehydration, and concentrated under reduced pressure. The residue was added with 1,2-dichloroethane (15 mL), acetic acid (0.25 mL) and sodium triacetoxyborohydride (525.3 mg, 2.48 mmol) and reacted at room temperature overnight. After the reaction was complete, the system was added with saturated sodium bicarbonate aqueous solution (10 mL), shaken and separated. The aqueous phase was extracted with dichloromethane (10 mL*2). The combined organic phase was washed with saturated brine (20 mL), dried over anhydrous sodium sulfate, and filtered. The filtrate was concentrated under reduced pressure, and the residue was separated on a preparative plate to obtain a crude, which was separated by reverse-phase fast medium pressure preparative chromatography to obtain 84 mg of the product with a yield of 29.3%.

Product analysis: $^1$HNMR (CDCl$_3$, 400 MHz): 7.39 (dd, J=16.1, 8.6 Hz, 3H), 6.89 (m, 2H), 6.43 (d, J=8.7 Hz, 2H), 4.44 (dd, J=8.6, 2.7 Hz, 1H), 3.75 (s, 3H), 3.27-3.19 (m, 1H), 3.01-2.95 (m, 1H), 2.49 (s, 3H), 2.40-2.30 (m, 2H);

ESI-MS Calculated for [M+H]$^+$=346.15, Found: 346.20;

The product analysis result was consistent with the structure of FA06.

Preparation Example 6, Final Product BB188: 8-methoxy-1-methyl-N-(p-tolyl)-5,6-dihydro-4H-benzo[6,7]cyclohepta[1,2-d]isoxazol-6-amine

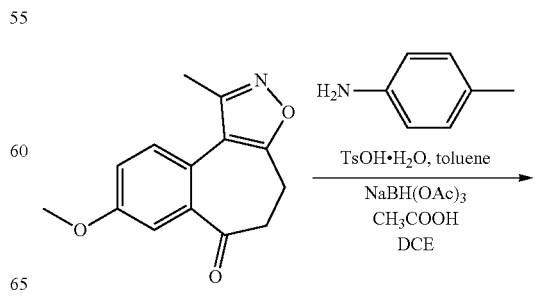

A

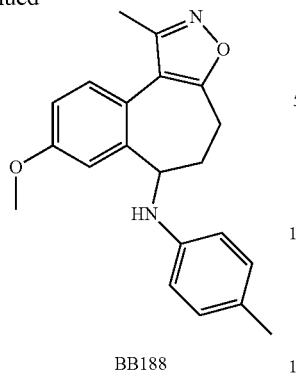

BB188

Synthesis of 8-methoxy-1-methyl-N-(p-tolyl)-5,6-dihydro-4H-benzo[6,7]cyclohepta[1,2-d]isoxazol-6-amine (BB188)

A (100 mg, 0.41 mmol), 4-methylaniline (88.5 mg, 0.83 mmol), p-toluenesulfonic acid monohydrate (7.8 mg, 0.04 mmol) and toluene (15 mL) were added to a reaction flask in sequence. The system was reacted overnight under reflux and dehydration, and concentrated under reduced pressure. The residue was added with 1,2-dichloroethane (15 mL), acetic acid (0.25 mL) and sodium triacetoxyborohydride (262.6 mg, 1.24 mmol) and reacted at room temperature overnight. After the reaction was complete, the system was added with saturated sodium bicarbonate aqueous solution (10 mL), shaken and separated. The aqueous phase was extracted with dichloromethane (10 mL*2). The combined organic phase was washed with saturated brine (20 mL), dried over anhydrous sodium sulfate, and filtered. The filtrate was concentrated under reduced pressure, and the residue was separated on a preparative plate to obtain a crude, which was slurried with dichloromethane and diethylether, respectively and filtered with suction to obtain 28 mg of the product.

Product analysis: $^1$HNMR (CDCl$_3$, 400 MHz): 7.38 (d, J=8.5 Hz, 1H), 7.04 (d, 1H), 6.93 (d, J=8.0 Hz, 2H), 6.85 (dd, J=8.5, 2.8 Hz, 1H), 6.40 (d, J=8.3 Hz, 2H), 4.39-4.37 (m, 1H), 3.87 (s, 1H), 3.75 (s, 3H), 3.28-3.14 (m, 1H), 3.01-2.93 (m, 1H), 2.50 (s, 3H), 2.34-2.27 (m, 2H), 2.21 (s, 3H);

ESI-MS Calculated for [M+1]$^+$=335.17, Found: 335.30;

The product analysis result was consistent with the structure of BB188.

Preparation Example 7, Final Product BB189: N-(4-fluorophenyl)-8-methoxy-1-methyl-5,6-dihydro-4H-benzo[6,7]cyclohepta[1,2-d]isoxazol-6-amine

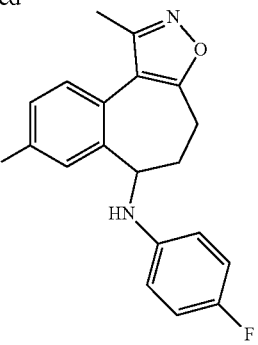

BB189

Synthesis of N-(4-fluorophenyl)-8-methoxy-1-methyl-5,6-dihydro-4H-benzo[6,7]cyclohepta[1,2-d]isoxazol-6-amine (BB189)

A (200 mg, 0.83 mmol), 4-fluoroaniline (183.6 mg, 1.65 mmol), p-toluenesulfonic acid monohydrate (15.7 mg, 0.08 mmol) and toluene (30 mL) were added to a reaction flask in sequence. The system was reacted overnight under reflux and dehydration, and concentrated under reduced pressure. The residue was added with 1,2-dichloroethane (15 mL), acetic acid (0.25 mL) and sodium triacetoxyborohydride (525.3 mg, 2.48 mmol) and reacted at room temperature overnight. After the reaction was complete, the system was added with saturated sodium bicarbonate aqueous solution (10 mL), shaken and separated. The aqueous phase was extracted with dichloromethane (10 mL*2). The combined organic phase was washed with saturated brine (20 mL), dried over anhydrous sodium sulfate, and filtered. The filtrate was concentrated under reduced pressure, and the residue was separated on a preparative plate to obtain a crude, which was slurried with diethylether and filtered with suction to obtain 40 mg of the product.

Product analysis: $^1$HNMR (CDCl$_3$, 400 MHz): 7.39 (d, J=8.4 Hz, 1H), 7.00 (d, J=2.8 Hz, 1H), 6.88-6.80 (m, 3H), 6.40-6.37 (m, 2H), 4.33 (d, J=8.4 Hz, 1H), 3.90 (s, 1H), 3.75 (s, 3H), 3.25-3.17 (m, 1H), 3.01-2.93 (m, 1H), 2.50 (s, 3H), 2.36-2.26 (m, 2H);

ESI-MS Calculated for [M+1]$^+$=339.14, Found: 339.20;

The product analysis result was consistent with the structure of BB189.

Preparation Example 8, Final Product BE02: N-(4-chlorophenyl)-1-ethyl-9-(1-methyl-1H-pyrazol-4-yl)-6,7-dihydro-5H-benzo[c][1,2,3]triazolo[1,5-a]azepin-7-amine

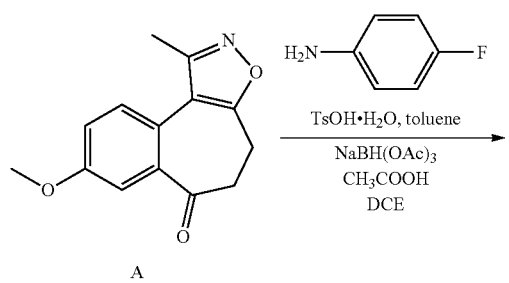

A

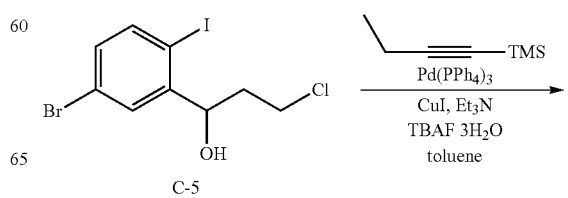

C-5

-continued

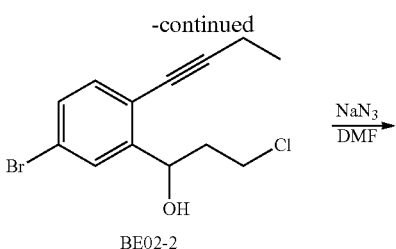
BE02-2

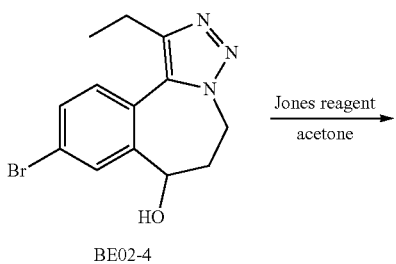
BE02-3

BE02-4

BE02-5

BE02-6

-continued

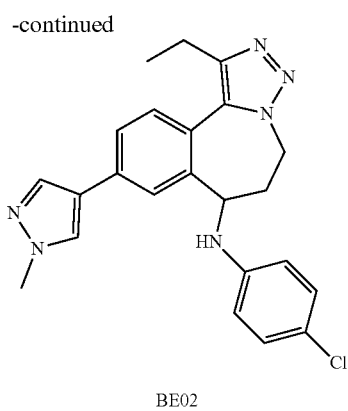
BE02

In the preparation process, Step 1: Synthesis of 1-(5-bromo-2-(but-1-yn-1-yl)phenyl)-3-chloropropan-1-ol (BE02-2)

C-5 (1.48 g, 3.94 mmol), cuprous iodide (0.65 g, 3.41 mmol), tetrakistriphenylphosphine palladium (0.37 g, 0.32 mmol), toluene (25 mL), triethylamine (1.5 mL) and tetrabutylammonium fluoride trihydrate (2.31 g, 7.32 mmol) were added to a reaction flask in sequence, and the air in the reaction flask was replaced with nitrogen three times. Under the protection of nitrogen flow, the system was added with 1-trimethylsilyl-1-butyne (0.76 g, 6.02 mmol) and reacted at room temperature for 45 minutes under nitrogen protection. After the reaction was complete, the system was added with water (50 mL) and extracted with with ethyl acetate (50 mL, 30 mL). The combined organic phase was washed with saturated brine (50 mL), dried over anhydrous magnesium sulfate and filtered with suction. The filtrate was concentrated under reduced pressure. The residue was separated by column chromatography to obtain 915.3 mg of the product BE02-2 with a yield of 77.0%.

ESI-MS Calculated for $[M-OH]^+$=282.99, Found: 283.10. The calculated value was consistent with the found value.

Step 2: Synthesis of 3-azido-1-(5-bromo-2-(but-1-yn-1-yl)phenyl)propan-1-ol (BE02-3)

BE02-2 (1.18 g, 3.91 mmol), N,N-dimethylformamide (20 mL) and sodium azide (0.76 g, 11.70 mmol) were added to a reaction flask in sequence and heated to 80° C. to react for 3 hours. After the reaction was complete, the system was cooled to room temperature naturally, added with water (100 mL) and extracted with ethyl acetate (30 mL*2). The combined organic phase was washed with saturated brine (30 mL), dried over anhydrous sodium sulfate, and filtered. The filtrate was concentrated under reduced pressure. The residue was separated by column chromatography to obtain 0.67 g of the product BE02-3 with a yield of 55.6%.

ESI-MS Calculated for $[M-N_2]^+$=279.03, Found: 279.10. The calculated value was consistent with the found value.

Step 3: Synthesis of 9-bromo-1-ethyl-6,7-dihydro-5H-benzo[c][1,2,3]triazolo[1,5-a]azepin-7-ol (BE02-4)

BE02-3 (0.67 g, 2.17 mmol) and N,N-dimethylformamide (70 mL) were added to a reaction flask and heated to reflux for 4 hours. The system was cooled to room temperature naturally, added with water (200 mL) and extracted with

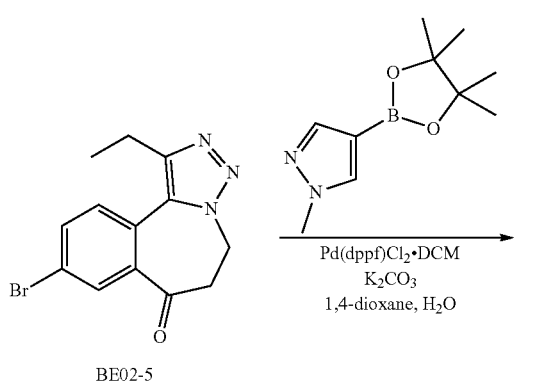

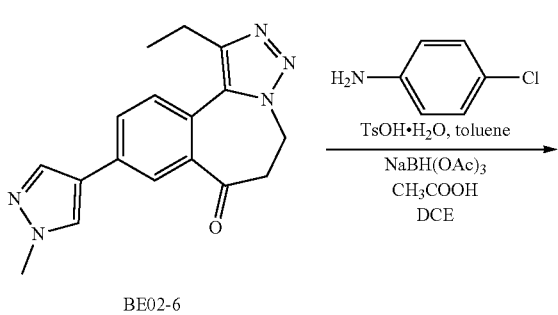

ethyl acetate (50 mL, 20 mL). The combined organic phase was washed with saturated brine (50 mL), dried over anhydrous sodium sulfate, and filtered. The filtrate was concentrated under reduced pressure. The residue was separated by column chromatography to obtain the product BE02-4 (0.44 g, 65.7%).

ESI-MS Calculated for [M+1]$^+$=308.03, Found: 307.90. The calculated value was consistent with the found value.

Step 4: Synthesis of 9-bromo-1-ethyl-5,6-dihydro-7H-benzo[c][1,2,3]triazolo[1,5-a]azepin-7-one (BE02-5)

BE02-4 (0.44 g, 1.43 mmol) and acetone (15 mL) were added to to a reaction flask, cooled to 6° C. and added with Jones reagent (0.5 mL), and the reaction was monitored by TLC (thin layer chromatography). After the reaction was complete, the system was added with water (80 mL) and extracted with ethyl acetate (20 mL*2). The combined organic phase was washed with saturated aqueous sodium thiosulfate solution (20 mL*2) and saturated brine (30 mL), dried over anhydrous sodium sulfate and filtered. The filtrate was concentrated under reduced pressure. The residue was separated by column chromatography to obtain 0.32 g of the product BE02-5 with a yield of 73.1%.

Product analysis: $^1$HNMR (CDCl$_3$, 400 MHz): 8.13 (d, J=2.2 Hz, 1H), 7.83 (dd, J=8.3, 2.2 Hz, 1H), 7.37 (d, J=8.3 Hz, 1H), 4.83-4.75 (m, 2H), 3.24-3.16 (m, 2H), 2.86 (q, J=7.5 Hz, 2H), 1.39 (t, J=7.5 Hz, 3H);

ESI-MS Calculated for [M+1]$^+$=306.02, Found: 306.00;

The product analysis result was consistent with the structure of BE02-5.

Step 5: Synthesis of 1-ethyl-9-(1-methyl-1H-pyrazol-4-yl)-5,6-dihydro-7H-benzo[c][1,2,3]triazolo[1,5-a]azepin-7-one (BE02-6)

BE02-5 (98.3 mg, 0.32 mmol), 1-methyl-4-(4,4,5,5-tetramethyl-1,3,2-dioxaborolan-2-yl)-1H-pyrazole (84.8 mg, 0.41 mmol), potassium carbonate (71.3 mg, 0.52 mmol), [1,1'-bis(diphenylphosphino)ferrocene]dichloropalladium-dichloromethane complex (38.9 mg, 0.047 mmol), 1,4-dioxane (9 mL) and water (0.3 mL) were added to a reaction flask in sequence. The air in the reaction flask was replaced with nitrogen three times. Under nitrogen protection, the system was heated to react under reflux. After the reaction was complete, the resultant was concentrated under reduced pressure. The residue was separated by column chromatography to obtain 82.5 mg of the product BE02-6 with a yield of 83.4%.

ESI-MS Calculated for [M+1]$^+$=308.14, Found: 308.10. The calculated value was consistent with the found value.

Step 6: Synthesis of N-(4-chlorophenyl)-1-ethyl-9-(1-methyl-1H-pyrazol-4-yl)-6,7-dihydro-5H-benzo[c][1,2,3]triazolo[1,5-a]azepin-7-amine (BE02)

BE02-6 (82.5 mg, 0.27 mmol), p-chloroaniline (90.7 mg, 0.71 mmol), p-toluenesulfonic acid monohydrate (49.2 mg, 0.26 mmol) and toluene (30 mL) were added to a reaction flask in sequence. The system was reacted overnight under reflux and dehydration, and concentrated under reduced pressure. The residue was added with 1,2-dichloroethane (30 mL), acetic acid (0.5 mL) and sodium triacetoxyborohydride (200.5 mg, 0.95 mmol) and reacted at room temperature overnight. After the reaction was complete, the system was added with water (10 mL), shaken and separated. The aqueous phase was extracted with dichloromethane (20 mL*2). The combined organic phase was washed with saturated brine (30 mL), dried over anhydrous sodium sulfate and filtered. The filtrate was concentrated under reduced pressure, and the residue was separated on a preparative plate, and further separated by reverse-phase fast medium pressure preparative chromatography to obtain 8.9 mg of the product of with a yield of 7.9%.

Product analysis: $^1$HNMR (CDCl$_3$, 400 MHz): 7.70 (s, 1H), 7.61-7.53 (m, 2H), 7.53-7.34 (m, 2H), 7.08-6.93 (m, 2H), 6.21 (d, J=8.7 Hz, 2H), 4.76 (dd, J=14.5, 7.3 Hz, 1H), 4.22 (s, 1H), 4.08-4.01 (m, 1H), 3.93 (s, 3H), 3.08-2.80 (m, 3H), 1.35 (t, J=7.6 Hz, 2H);

ESI-MS Calculated for [M+1]$^+$=419.17, Found: 419.30;

The product analysis result was consistent with the structure of BE02.

Preparation Example 9, Final Product BE25: N-(4-chlorophenyl)-1,5-dimethyl-9-(1-methyl-1H-pyrazol-4-yl)-6,7-dihydro-5H-benzo[c][1,2,3]triazolo[1,5-a]azepin-7-amine

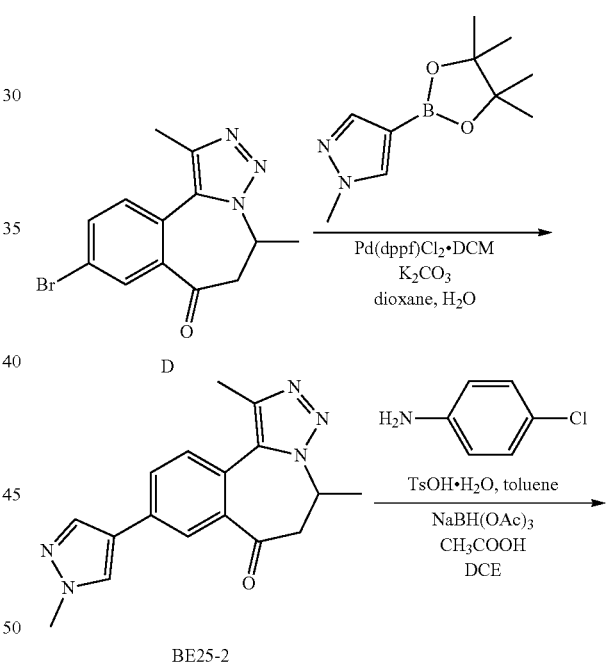

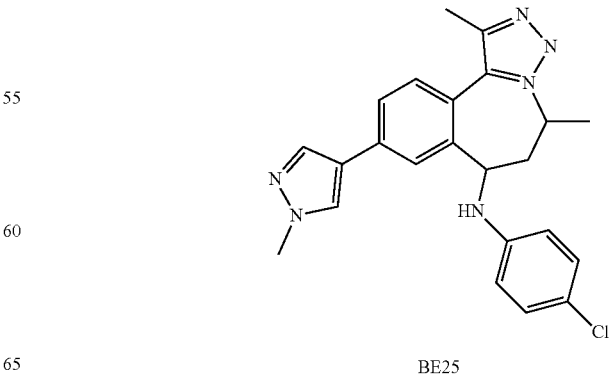

In the preparation process, Step 1: Synthesis of 1,5-dimethyl-9-(1-methyl-1H-pyrazol-4-yl)-5,6-dihydro-7H-benzo[c][1,2,3]triazolo[1,5-a]azepin-7-one (B E25-2)

D (200.4 mg, 0.65 mmol), 1-methyl-4-(4,4,5,5-tetramethyl-1,3,2-dioxaborolan-2-yl)-1H-pyrazole (160.1 mg, 0.77 mmol), potassium carbonate (144.2 mg, 1.04 mmol), [1,1'-bis(diphenylphosphino)ferrocene]dichloropalladium dichloromethane complex (73.9 mg, 0.090 mmol), 1,4-dioxane (13 mL) and water (1 mL) were added added to a reaction flask in sequence. The air in the reaction flask was replaced with nitrogen three times. Under nitrogen protection, the system was heated to react under reflux. After the reaction was complete, the resultant was concentrated under reduced pressure. The residue was separated by column chromatography to obtain 181.3 mg of the product BE25-2 with a yield of 90.7%.

$^1$HNMR (CDCl$_3$, 400 MHz): 8.08 (d, J=2.0 Hz, 1H), 7.85 (s, 1H), 7.80-7.71 (m, 2H), 7.48 (d, J=8.1 Hz, 1H), 5.07-4.96 (m, 1H), 3.98 (s, 3H), 3.17-3.03 (m, 2H), 2.51 (s, 3H), 1.78 (d, J=7.0 Hz, 3H);

ESI-MS Calculated for [M+1]$^+$=308.14, Found: 308.30;
The product analysis result was consistent with the structure of BE25-2.

Step 2: Synthesis of N-(4-chlorophenyl)-1,5-dimethyl-9-(1-methyl-1H-pyrazol-4-yl)-6,7-dihydro-5H-benzo[c][1,2,3]triazolo[1,5-a]azepin-7-amine (BE25)

BE25-2 (177.6 mg, 0.58 mmol), p-chloroaniline (278.1 mg, 2.18 mmol), p-toluenesulfonic acid monohydrate (161.0 mg, 0.85 mmol) and toluene (60 mL) were added to a reaction flask in sequence, reacted overnight under reflux, and concentrated under reduced pressure. The residue was added with 1,2-dichloroethane (15 mL), acetic acid (0.5 mL) and sodium triacetoxyborohydride (502.9 mg, 2.37 mmol) and reacted at room temperature overnight. After the reaction was complete, the system was added with water (50 mL), shaken and separated. The aqueous phase was extracted with dichloromethane (30 mL*2). The combined organic phase was washed with saturated brine (30 mL), dried over anhydrous sodium sulfate and filtered. The filtrate was concentrated under reduced pressure, and the residue was separated on a preparative plate to obtain a crude, which was separated by reverse-phase fast medium pressure preparative chromatography to obtain 25.1 mg of the product with a yield of 10.3%.

ESI-MS Calculated for [M+1]$^+$=419.17, Found: 419.00. The calculated value was consistent with the found value.

Preparation Example 10, Final Product BE44: N-(4-chlorophenyl)-1-cyclopropyl-9-(1-methyl-1H-pyrazol-4-yl)-6,7-dihydro-5H-benzo[c][1,2,3]triazolo[1,5-a]azepin-7-amine

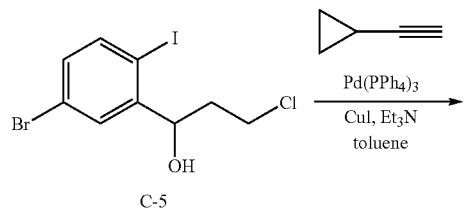

C-5

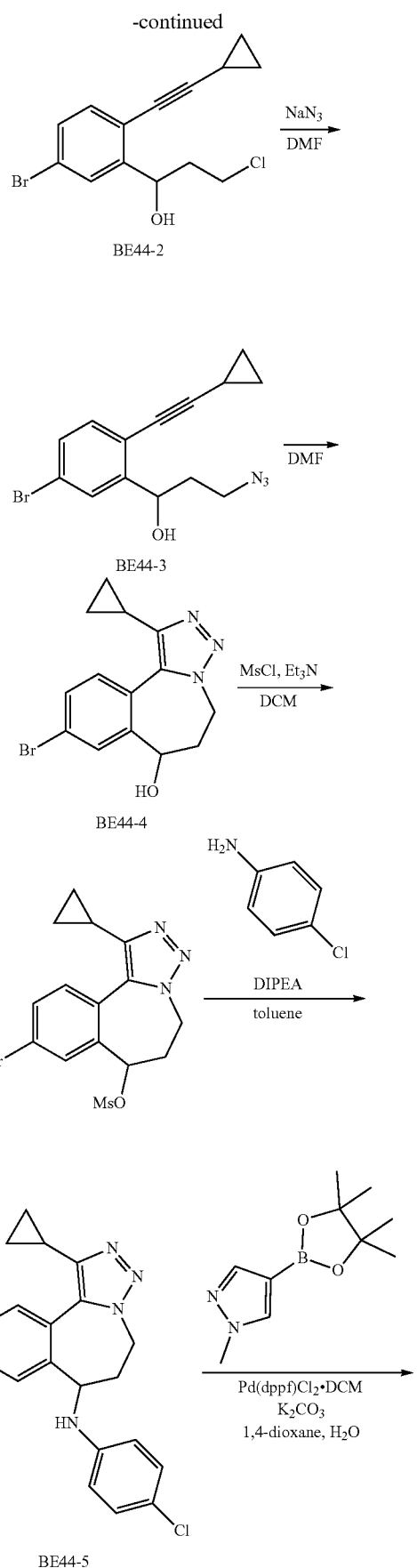

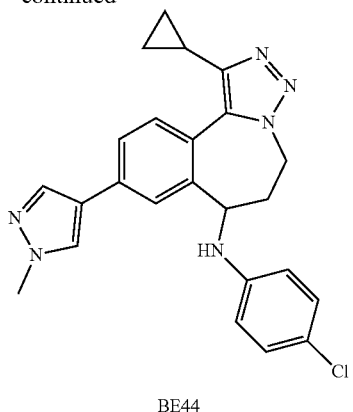

BE44

In the preparation process, Step 1: Synthesis of 1-(5-bromo-2-(cyclopropylethynyl)phenyl)-3-chloropropan-1-ol (B E44-2)

C-5 (1.92 g, 5.11 mmol), cuprous iodide (0.94 g, 4.93 mmol), tetrakistriphenylphosphine palladium (0.26 g, 0.22 mmol), triethylamine (2.0 mL) and toluene (50 mL) were added to a reaction flask in sequence, and the air in the reaction flask was replaced with nitrogen three times. Under the protection of nitrogen flow, the system was added with cyclopropylpropyne (0.63 g, 9.53 mmol) and reacted at room temperature for 1 hour under nitrogen protection. After the reaction was complete, the system was added with water (100 mL) and extracted with ethyl acetate (100 mL, 30 mL). The combined organic phase was washed with saturated brine (80 mL), dried over anhydrous magnesium sulfate and filtered with suction. The filtrate was concentrated under reduced pressure. The residue was separated by column chromatography to obtain 1.21 g of the product BE44-2 with a yield of 75.5%.

Product analysis: $^1$HNMR (CDCl$_3$, 400 MHz): 7.57 (d, J=2.2 Hz, 1H), 7.28-7.10 (m, 2H), 5.22 (dd, J=9.3, 3.3 Hz, 1H), 3.81-3.71 (m, 1H), 3.62-3.58 (m, 1H), 2.16-2.07 (m, 2H), 2.03-1.95 (m, 1H), 1.46-1.32 (m, 1H), 0.88-0.74 (m, 4H);

ESI-MS Calculated for [M-OH]+=294.29, Found: 295.00;

The product analysis result was consistent with the structure of BE44-2.

Step 2: Synthesis of 3-azido-1-(5-bromo-2-(cyclopropylethynyl)phenyl)propan-1-ol (BE44-3)

BE44-2 (1.51 g, 5.25 mmol), N,N-dimethylformamide (60 mL) and sodium azide (0.71 g, 10.92 mmol) were added to a reaction flask in sequence and heated to 75° C. to react for 1.5 hours. After the reaction was complete, the system was cooled to room temperature naturally, added with water (200 mL) and extracted with ethyl acetate (100 mL, 30 mL). The combined organic phase was washed with saturated brine (50 mL*2), dried over anhydrous sodium sulfate and filtered. The filtrate was concentrated under reduced pressure. The residue was separated by column chromatography to obtain 1.49 g of the product BE44-3 with a yield of 88.6%.

$^1$HNMR (CDCl$_3$, 400 MHz): 7.56 (d, J=2.0 Hz, 1H), 7.28-7.10 (m, 2H), 5.13-5.09 (m, 1H), 3.52-3.35 (m, 2H), 2.22 (d, J=3.9 Hz, 1H), 2.01-1.89 (m, 1H), 1.86-1.76 (m, 1H), 1.46-1.34 (m, 1H), 0.89-0.71 (m, 4H);

ESI-MS Calculated for [M-N$_2$—OH]$^+$=274.02, Found: 274.00; The product analysis result was consistent with the structure of BE44-3.

Step 3: Synthesis of 9-bromo-1-cyclopropyl-6,7-dihydro-5H-benzo[c][1,2,3]triazolo[1,5-a]azepin-7-ol (BE44-4)

BE44-3 (1.28 g, 4.00 mmol) and N,N-dimethylformamide (150 mL) were added to a reaction flask and heated to reflux for 3 hours. The system was cooled to room temperature naturally, added with water (500 mL) and extracted with ethyl acetate (100 mL, 50 mL). The combined organic phase was washed with saturated brine (100 mL), dried over anhydrous sodium sulfate, and filtered. The filtrate was concentrated under reduced pressure. The residue was separated by column chromatography to obtain the product BE44-4 (0.94 g, 73.4%).

ESI-MS Calculated for [M+1]$^+$=320.03, Found: 320.10. The calculated value was consistent with the found value.

Step 4: Synthesis of 9-bromo-N-(4-chlorophenyl)-1-cyclopropyl-6,7-dihydro-5H-benzo[c][1,2,3]triazolo [1,5-a]azepin-7-amine (BE44-5)

BE44-4 (197.8 mg, 0.62 mmol), dichloromethane (25 mL) and triethylamine (0.3 g, 2.96 mmol) were added to a reaction flask, cooled to 3° C. in an ice-water bath, added with methanesulfonyl chloride (0.29 g, 2.53 mmol) and kept at 0-10° C. for reaction. After the reaction was complete, the system was added with 50 mL of water, shaken and separated. The aqueous phase was extracted with dichloromethane (20 mL). The combined organic phase was washed with saturated brine (30 mL*2), dried over anhydrous sodium sulfate and filtered. The filtrate was concentrated under reduced pressure. The residue was added with toluene (20 mL), p-chloroaniline (120.8 mg, 0.95 mmol) and diisopropylethylamine (163.6 mg, 1.27 mmol), raised to and kept at 80° C. for 2 hours. The system was concentrated under reduced pressure, and the residue was separated by column chromatography to obtain 110.3 mg of the product BE44-5 with a yield of 41.3%.

$^1$HNMR (CDCl$_3$, 400 MHz): 7.68 (d, J=2.0 Hz, 1H), 7.57 (dd, J=8.1, 2.0 Hz, 1H), 7.46 (d, J=8.1 Hz, 1H), 7.06-6.98 (m, 2H), 6.23-6.16 (m, 2H), 4.79-4.73 (m, 1H), 4.24-4.19 (m, 1H), 4.01-3.89 (m, 2H), 3.03-2.89 (m, 1H), 2.24-2.12 (m, 1H), 1.30-1.16 (m, 4H);

ESI-MS Calculated for [M+H]$^+$=429.04, Found: 429.20; The product analysis result was consistent with the structure of BE44-5.

Step 5: Synthesis of N-(4-chlorophenyl)-1-cyclopropyl-9-(1-methyl-1H-pyrazol-4-yl)-6,7-dihydro-5H-benzo[c][1,2,3]triazolo[1,5-a]azepin-7-amine (BE44)

BE44-5 (102.9 mg, 0.24 mmol), 1-methyl-4-(4,4,5,5-tetramethyl-1,3,2-dioxaborolan-2-yl)-1H-pyrazole (65.2 mg, 0.31 mmol), potassium carbonate (62.4 mg, 0.45 mmol), Pd(dppf)Cl$_2$-dichloromethane complex (48.9 mg, 0.060 mmol), 1,4-dioxane (10 mL) and water (1 mL) were added to a reaction flask in sequence. The air in the reaction flask was replaced with nitrogen three times. Under nitrogen protection, the system was heated to react under reflux. After the reaction was complete, the resultant was concentrated under reduced pressure. The residue was separated by column chromatography to obtain 59.1 mg of a crude, which was separated by reverse-phase fast medium pressure preparative chromatography and lyophilized to obtain 37.3 mg of a pure product with a yield of 36.1%.

Product analysis: $^1$HNMR (CDCl$_3$, 400 MHz): 7.70 (s, 1H), 7.63-7.53 (m, 3H), 7.50 (dd, J=7.9, 1.8 Hz, 1H), 7.03-6.97 (m, 2H), 6.29-6.21 (m, 2H), 4.76-4.71 (m, 1H), 4.32-4.26 (m, 1H), 4.07-3.99 (m, 1H), 3.93 (s, 3H), 3.02-2.92 (m, 1H), 2.22-2.17 (m, 1H), 2.04-1.97 (m, 1H), 1.10-0.89 (m, 4H);

ESI-MS Calculated for [M+1]$^+$=431.17, Found: 431.20;
The product analysis result was consistent with the structure of BE44.

Preparation Example 11, Final Product BE95: 7-(2,4-difluorophenoxy)-1-methyl-9-(1-methyl-1H-pyrazol-4-yl)-6,7-dihydro-5H-benzo[c][1,2,3]triazolo[1,5-a]azepine (BE95)

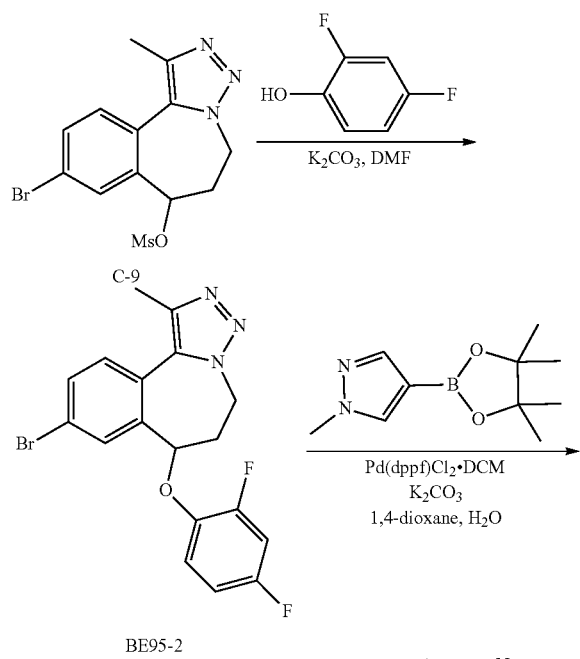

Step 1: Synthesis of 9-bromo-7-(2,4-difluorophenoxy)-1-methyl-6,7-dihydro-5H-benzo[c][1,2,3]triazolo[1,5-a]azepine (BE95-2)

C-9 (100.1 mg, 0.27 mmol), 1,4-difluorophenol (48.5 mg, 0.37 mmol), N,N-dimethylformamide (5 mL) and potassium carbonate (115.3 mg, 0.83 mmol) were added to a reaction flask in sequence and heated to 60° C. to react for 3.5 hours. After the reaction was complete, the system was cooled to room temperature naturally, added with water (50 mL) and extracted with ethyl acetate (20 mL*2). The combined organic phase was washed with saturated brine (30 mL), dried over anhydrous sodium sulfate and filtered. The filtrate was concentrated under reduced pressure. The residue was separated by column chromatography to obtain 107.7 mg of the product BE95-2 with a yield of 98.2%.

Step 2: Synthesis of 7-(2,4-difluorophenoxy)-1-methyl-9-(1-methyl-1H-pyrazol-4-yl)-6,7-dihydro-5H-Benzo[c][1,2,3]triazolo[1,5-a]azepine (BE95)

BE95-2 (105.7 mg, 0.26 mmol), 1-methyl-4-(4,4,5,5-tetramethyl-1,3,2-dioxaborolan-2-yl)-1H-pyrazole (90.5 mg, 0.43 mmol), potassium carbonate (80.2 mg, 0.58 mmol), [1,1'-bis(diphenylphosphino)ferrocene]dichloropalladium-dichloromethane complex (59.2 mg, 0.072 mmol), 1,4-dioxane (15 mL) and water (1 mL) were added to a reaction flask in sequence. The air in the reaction flask was replaced with nitrogen three times, and the system was heated to react under reflux under nitrogen protection. After the reaction was complete, the resultant was concentrated under reduced pressure. The residue was separated by column chromatography to obtain a crude, which was separated by fast medium pressure preparative chromatography to obtain 57.8 mg of the product with a yield of 54.6%.

Product analysis: $^1$HNMR (DMSO-d$_6$, 400 MHz): 8.18 (s, 1H), 7.89 (s, 1H), 7.79 (s, 1H), 7.70-7.41 (m, 2H), 7.18-7.12 (m, 1H), 6.90-6.80 (m, 2H), 5.46 (t, J=5.3 Hz, 1H), 4.53-4.42 (m, 1H), 4.32-4.25 (m, 1H), 3.87 (s, 3H), 2.88-2.78 (m, 1H), 2.73-2.64 (m, 1H), 2.31 (s, 3H);

ESI-MS Calculated for [M+1]$^+$=408.16, Found: 408.00;
The result of the product analysis was consistent with the structure of the compound.

Preparation Example 12, Final Product LA55: N-(4-chlorophenyl)-1-methyl-8-(1-methyl-1H-pyrazol-4-yl)-5,6-dihydro-4H-benzo[6,7]cyclohepta[1,2-d]isoxazol-6-amine

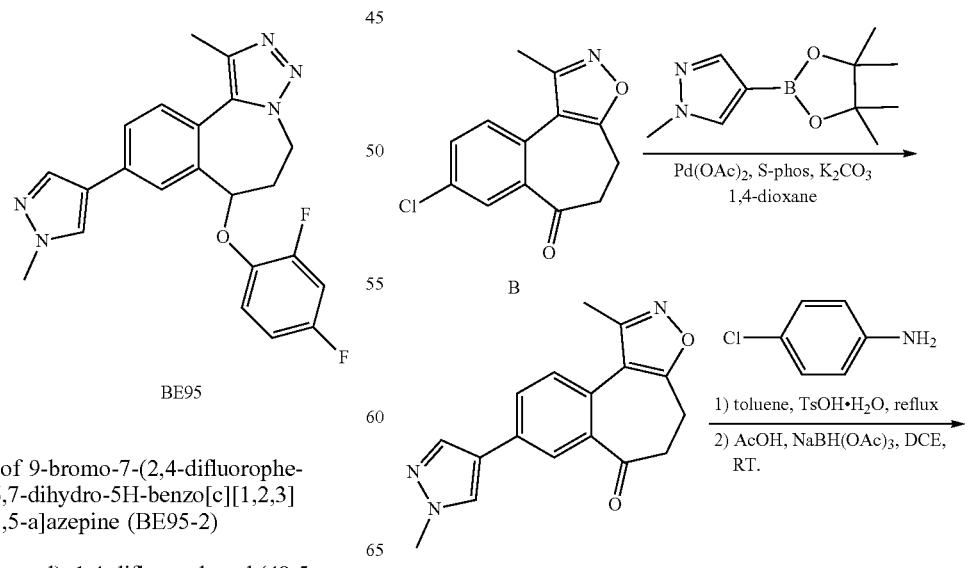

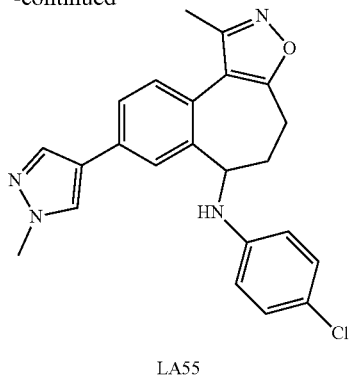

LA55

Step 1: Synthesis of 1-methyl-8-(1-methyl-1H-pyrazol-4-yl)-4,5-dihydro-6H-benzo[6,7]cyclohepta[1,2-d]isoxazol-6-one (LA55-2)

The core intermediate B (500.0 mg, 2.02 mmol), 1-methyl-4-(4,4,5,5-tetramethyl-1,3,2-dioxaborolan-2-yl)-1H-pyrazole (840.0 mg, 4.04 mmol), $K_2CO_3$ (698.0 mg, 5.05 mmol) and 1,4-dioxane (15 mL) were added to a 20 mL microwave tube, purged with $N_2$ for 0.5 h, added with Pd(OAc)$_2$ (25.0 mg, 0.11 mmol) and S-phos (91.0 mg, 0.22 mmol), and purged with nitrogen for 0.5 h. The tube was sealed with a tube sealer to perform microwave reaction (50 W, T=120° C., t=2 h). The system was concentrated under reduced pressure, and the residue was separated by column chromatography to obtain 120.0 mg of a yellow solid with a yield of 20%.

ESI-MS Calculated for [M+H]$^+$=294.12; Found: 294.10. The calculated value was consistent with the found value.

Step 2: Synthesis of N-(4-chlorophenyl)-1-methyl-8-(1-methyl-1H-pyrazol-4-yl)-5,6-dihydro-4H-benzo[6,7]cyclohepta[1,2-d]isoxazol-6-amine (LA55)

LA55-2 (120.0 mg, 0.41 mmol), p-chloroaniline (157.2 mg, 3.00 mmol), p-toluenesulfonic acid monohydrate (39.1 mg, 0.21 mmol) and toluene (40 mL) were added to a 50 mL single necked flask, and the air in the reaction system was replaced with $N_2$ three times. The system was heated to reflux for 16 hours. The reaction was monitored by TLC. The system was concentrated under reduced pressure, added with 1,2-dichloroethane (5 mL), two drops of acetic acid and NaBH(OAc)$_3$ (435.0 mg, 2.05 mmol) and reacted at room temperature for 16 h. The reaction was quenched with water (10 mL) and extracted with DCM (20 mL*2). The combined organic phase was washed with water (20 mL) and saturated brine (20 mL), dried over anhydrous MgSO$_4$ and filtered with suction. The filtrate was concentrated under reduced pressure, and the residue was separated by PLC to obtain 68.0 mg of a crude, which was separated by medium pressure preparative chromatography and lyophilized to obtain 20 mg of an off-white solid with a purity of 98.2%.

$^1$HNMR (DMSO-d$_6$, 400 MHz): 7.98 (s, 1H), 7.68 (s, 1H), 7.54 (d, J=8.5, 1H), 7.51-7.46 (m, 2H), 7.07-7.01 (m, 2H), 6.55-6.47 (m, 2H), 6.42 (d, J=6.7 Hz, 1H), 4.32 (t, J=7.8, 1H), 3.84 (s, 3H), 3.32-3.19 (m, 2H), 2.96-2.80 (m, 1H), 2.46 (s, 3H), 2.39-2.32 (m, 1H), 2.20-2.10 (m, 1H).

ESI-MS Calculated for [M+H]$^+$=405.14; Found: 405.20. The product analysis result was consistent with the structure of LA55.

Preparation Example 13, Final Product LA93: N-(4-chlorophenyl)-1-methyl-8-(1-ethyl-1H-pyrazol-4-yl)-5,6-dihydro-4H-benzo[6,7]cyclohepta[1,2-d]isoxazol-6-amine

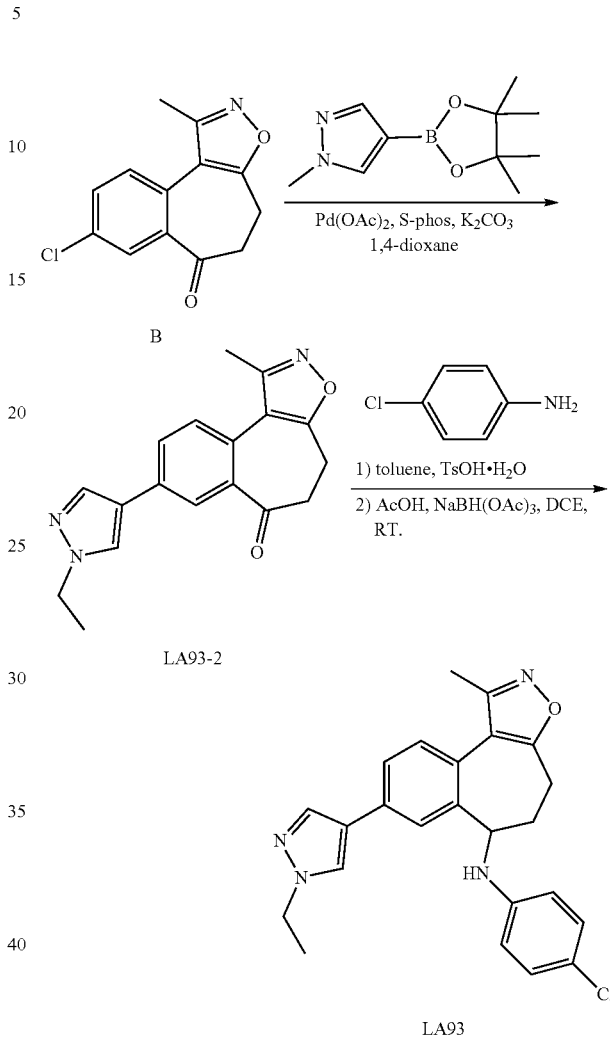

Step 1: Synthesis of 1-methyl-8-(1-ethyl-1H-pyrazol-4-yl)-4,5-dihydro-6H-benzo[6,7]cyclohepta[1,2-d]isoxazol-6-one (LA93-2)

The intermediate B (500.0 mg, 2.02 mmol), (N-ethylpyrazol-4-yl)pinacolborate (900.0 mg, 4.04 mmol), $K_2CO_3$ (700.0 mg, 5.06 mmol) and 1,4-dioxane (15 mL) were added to a 20 mL microwave tube, purged with $N_2$ for 0.5 h, added with Pd(OAc)$_2$ (30.1 mg, 0.12 mmol) and S-phos (100.2 mg, 0.24 mmol) and purged with nitrogen for 0.5 h. The tube was sealed with a tube sealer to perform microwave reaction (50 W, T=110° C., t=1 h). After the reaction was complete, the system was concentrated under reduced pressure, and the residue was separated by column chromatography to obtain 500.0 mg of a yellow solid with a yield of 73%.

ESI-MS Calculated for [M+H]$^+$=308.13; Found: 308.10.

Step 2: Synthesis of N-(4-chlorophenyl)-1-methyl-8-(1-ethyl-1H-pyrazol-4-yl)-5,6-dihydro-4H-benzo[6,7]cyclohepta[1,2-d]isoxazol-6-amine (LA93)

LA93-2 (200.0 mg, 0.65 mmol), p-chloroaniline (415.0 mg, 3.26 mmol), p-toluenesulfonic acid monohydrate (62.0 mg, 0.32 mmol) and toluene (40 mL) were added to a 50 mL single necked flask, and the air in the system was replaced with N$_2$ three times. The system was heated to reflux for 16 hours and concentrated. The residue was added with 1,2-dichloroethane (5 mL), two drops of acetic acid, 1,2-dichloroethane (5 mL) and NaBH(OAc)$_3$ (435.0 mg, 2.05 mmol) and reacted at room temperature for 16 h. The reaction was quenched with water (10 mL) and extracted with DCM (30 mL*2). The combined organic phase was washed with water (20 mL) and saturated brine (20 mL), dried over anhydrous MgSO$_4$ and filtered with suction. The filtrate was concentrated under reduced pressure, and the residue was separated by PLC to obtain 39 mg of a crude, which was separated by medium pressure preparative chromatography and lyophilized to obtain 18.9 mg of an off-white solid with a purity of 98.2%.

$^1$HNMR (DMSO-d$_6$, 400 MHz): 8.05 (s, 1H), 7.67 (s, 1H), 7.53-7.34 (m, 3H), 7.03 (d, J=12.8 Hz, 2H), 6.49 (d, J=8.0 Hz, 2H), 6.39 (d, J=8.8 Hz, 1H), 4.33-4.31 (m, 1H), 4.14-4.11 (m, 2H), 3.33-3.20 (m, 2H), 2.96-2.80 (m, 1H), 2.49 (s,3H), 2.14-2.01 (m, 1H), 1.25 (t, J=3.2 Hz, 3H);

ESI-MS Calculated for [M+H]$^+$=419.16, Found: 419.20;

The product analysis result was consistent with the structure of LA93.

Preparation Example 14, Final Product LA108:
N-(4-chlorophenyl)-1-methyl-8-(1H-pyrazol-4-yl)-5,6-dihydro-4H-benzo[6,7]cyclohepta[1,2-d]isoxazol-6-amine

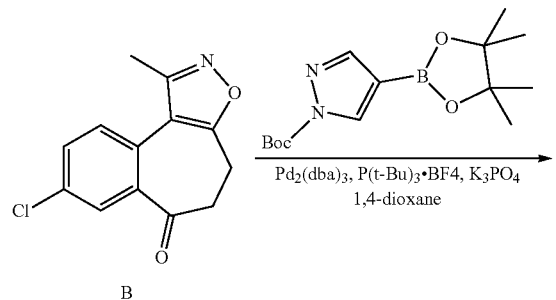

B

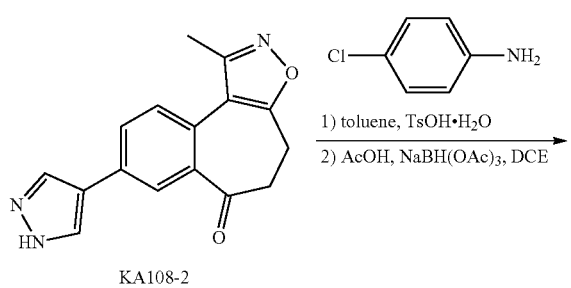

KA108-2

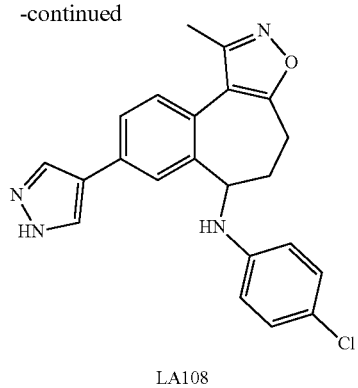

LA108

Step 1: Synthesis of 1-methyl-8-(1H-pyrazole-4-yl)-4,5-dihydro-6H-benzo[6,7]cyclohepta[1,2-d]isoxazol-6-one (LA108-2)

The intermediate B (500.0 mg, 2.02 mmol), (N-tert-butoxycarbonylpyrazole-4-yl) pinacolborate (780.0 mg, 2.63 mmol), K$_3$PO$_4$ (940.1 mg, 4.41 mmol), 1,4-dioxane (20 mL) and H$_2$O (1 mL) were added to a 50 mL two-neck flask, and the air in the system was replaced with N$_2$ three times. The system was added with Pd$_2$(dba)$_3$ (550.0 mg, 0.60 mmol) and P(t-Bu)$_3$·BF$_4$ (360.0 mg, 0.12 mmol) and the air in the system was replaced with N$_2$ three times again. The system was heated to reflux, and the reaction was monitored by LC-MS. The system was cooled to room temperature and filtered (with a diatomite pad). The filtrate was concentrated under reduced pressure, and the residue was separated by column chromatography to obtain 186 mg of LA108-2 with a yield of 73%.

ESI-MS Calculated for [M+H]$^+$=280.10; Found: 280.10.

Step 2: Synthesis of N-(4-chlorophenyl)-1-methyl-8-(1H-pyrazol-4-yl)-5,6-dihydro-4H-benzo[6,7]cyclohepta[1,2-d]isoxazol-6-amine (LA108)

LA108-2 (100 mg, 0.26 mmol), p-chloroaniline (100 mg, 0.78 mmol), p-toluenesulfonic acid monohydrate (25 mg, 0.12 mmol) and toluene (40 mL) were added to a 50 mL single necked flask, and the air in the system was replaced with N$_2$ three times. The system was heated to reflux for 15 h, and the reaction was monitored by TLC. The system was concentrated under reduced pressure, and the residue was added with 1,2-dichloroethane (5 mL), two drops of acetic acid and NaBH(OAc)$_3$ (25 mg, 0.12 mmol) and reacted at room temperature for 16 h. The reaction was monitored by LC-MS. The reaction was quenched with water (10 mL) and extracted with DCM (30 mL*2). The combined organic phase was washed with water (20 mL*2) and saturated brine (25 mL), dried over anhydrous MgSO$_4$ and filtered with suction. The filtrate was concentrated under reduced pressure, and the residue was separated by PLC to obtain 69 mg of a crude, which was separated by medium pressure preparative chromatography and lyophilized to obtain 26.9 mg of an off-white solid with a purity of 97%.

$^1$HNMR (DMSO-d$_6$, 400 MHz): 12.90 (s, 1H), 8.00 (s, 1H), 7.98 (s, 1H), 7.71 (d, J=4.0 Hz, 1H), 7.50 (d, J=8.0 Hz, 2H), 7.01 (d,J=4.4 Hz, 2H), 6.51-6.47 (m, 1H), 6.39 (d, J=8.8 Hz, 1H), 4.34-4.32 (m, 1H), 3.29 (s, 3H), 3.27-3.19 (m, 1H), 2.97-2.89 (m, 1H), 2.64-2.47 (m, 1H), 2.49-2.48 (m, 1H), 2.30-2.14 (m, 1H);

ESI-MS Calculated for [M+H]$^+$=391.12, Found: 391.20;

The product analysis result was consistent with the structure of LA108.

Preparation Example 15, Final Product LA198: 2-(2-((1-methyl-9-(1-methyl-1H-pyrazol-4-yl)-6,7-dihydro-5H-benzo[c][1,2,3]triazolo[1,5-a]azepin-7-yl)amino)phenyl)ethan-1-ol

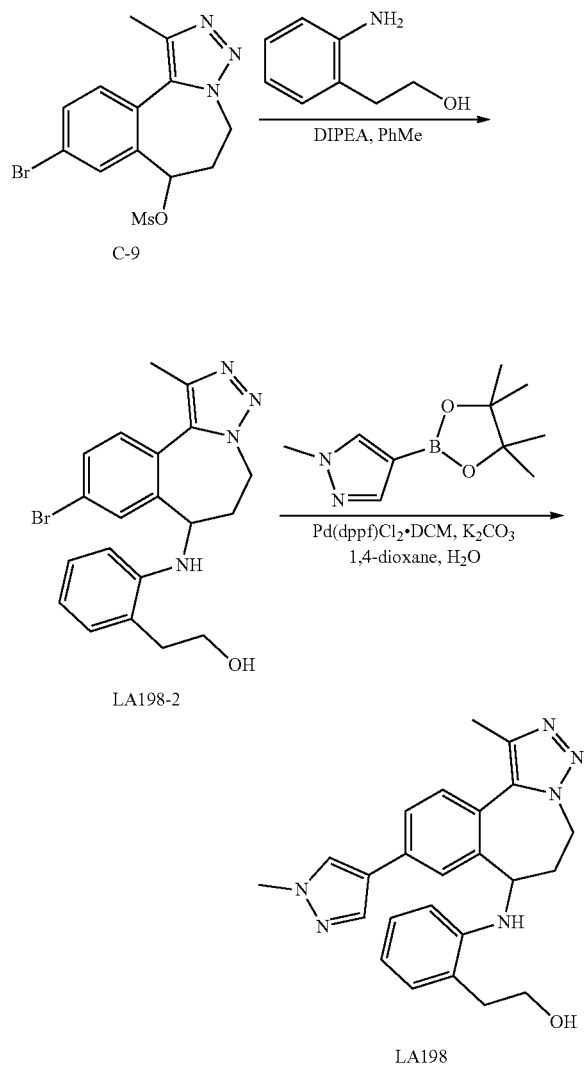

Step 1: Synthesis of 2-(2-((9-bromo-1-methyl-6,7-dihydro-5H-benzo[c][1,2,3]triazolo[1,5-a]azepin-7-yl)amino)phenyl)ethan-1-ol (LA198-2)

C-9 (124.0 mg, 0.33 mmol), 2-(2-aminophenyl)ethan-1-ol (56.8 mg, 0.41 mmol), DIPEA (69.1 mg, 0.54 mmol) and toluene (10 mL) were added to a 100 mL single necked flask and heated to toluene reflux, and the reaction was monitored by LC-MS. The system was added with water (20 mL) and EA (20 mL), shaken and seperated. The aqueous phase was extracted with EA (20 mL*2). The combined organic phase was washed with water (20 mL*2) and saturated brine (20 mL), dried over anhydrous NaSO₄ and filtered with suction. The filtrate was concentrated and the residue separated by PLC to obtain 52.3 mg of the target compound with a yield of 38%.

ESI-MS Calculated for [M+H]⁺=413.09, 415.09; Found: 413.10, 415.00. The calculated value was consistent with the found value.

Step 2: Synthesis of 2-(2-((1-methyl-9-(1-methyl-1H-pyrazol-4-yl)-6,7-dihydro-5H-benzo[c][1,2,3]triazolo[1,5-a]azepin-7-yl)amino)phenyl)ethan-1-ol (LA198)

LA198-2 (52.3 mg, 0.13 mmol), 1-methyl-4-(4,4,5,5-tetramethyl-1,3,2-dioxaborolan-2-yl)-1H-pyrazole (33.8 mg, 0.16 mmol), potassium carbonate (29.1 mg, 0.21 mmol), 1,4-dioxane (5 mL) and water (0.25 mL) were added to a 50 mL single necked flask, and the air in the reaction system was replaced with $N_2$ three times. The system was added with Pd(dppf)Cl₂-dichloromethane complex (5.6 mg, 0.0065 mmol), and the air in the reaction system was replaced with $N_2$ three times again. The system was heated to reflux, and the reaction was monitored by LC-MS. The system was added with water (10 mL) and EA (10 mL), shaken and sepatated. The aqueous phase was extracted with EA (10 mL*2). The combined organic phase was washed with water (10 mL*2) and brine (20 mL), dried over anhydrous NaSO₄ and filtered with suction. The filtrate was concentrated and the residue was separated by PLC to obtain 33.3 mg of a crude mixture, which was separated by fast medium pressure preparative chromatography and lyophilized to obtain 12.1 mg of the target compound LA198.

Product analysis: ¹HNMR (CDCl₃, 400 MHz): 7.70 (s, 1H), 7.57 (s, 1H), 7.51 (s, 1H), 7.49 (d, J=1.6 Hz, 1H), 7.42 (d, J=8.0 Hz, 1H), 7.03 (d, J=8.8 Hz, 1H), 6.95-6.91 (m, 1H), 6.55-6.40 (m, 1H), 6.03-6.01 (m, 1H), 4.75-4.55 (m, 2H), 4.37-4.35 (m, 1H), 4.03-3.94 (m, 1H), 3.93 (s, 3H), 2.90-2.84 (m, 2H), 2.55 (s, 3H), 1.28-1.26 (m, 2H);

ESI-MS Calculated for [M+H]⁺=415.22; found value: 415.20;

The product analysis result was consistent with the structure of LA198.

Preparation Example 16, Final Product LB01: N¹,N¹-dimethyl-N²-(1-methyl-9-(1-methyl-1H-pyrazol-4-yl)-6,7-dihydro-5H-benzo[c][1,2,3]triazolo[1,5-a]azepin-7-yl)benzene-1,2-diamine

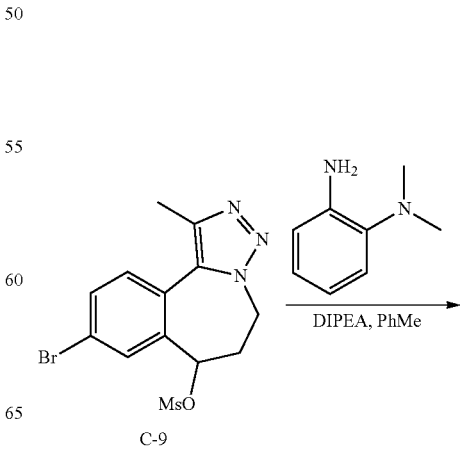

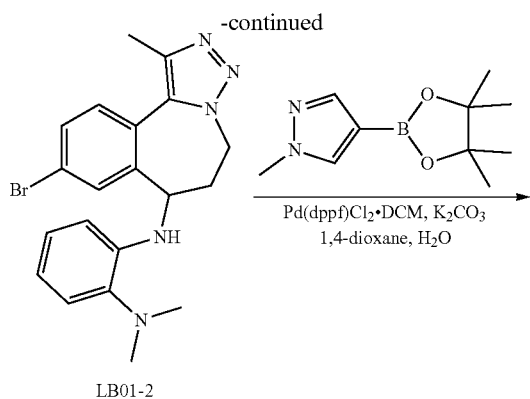

LB01-2

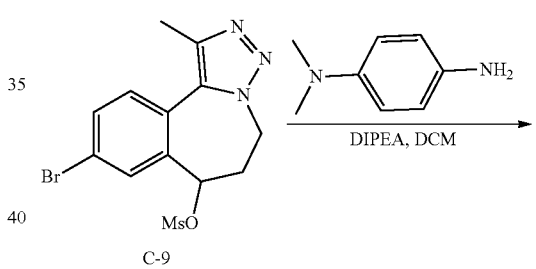

LB01

Step 1: Synthesis of N¹-(9-bromo-1-methyl-6,7-dihydro-5H-benzo[c][1,2,3]triazolo[1,5-a]azepin-7-yl)-N²,N²-dimethylbenzene-1,2-diamine (LB01-2)

C-9 (60.1 mg, 0.16 mmol), N,N-dimethyl-o-phenylenediamine (55.6 mg, 0.41 mmol), DIPEA (34.5 mg, 0.27 mmol) and toluene (10 mL) were added to a 50 mL single necked flask and heated to toluene reflux, and the reaction was monitored by LC-MS. The system was added with water (15 mL) and EA (20 mL), shaken and sepatated. The aqueous phase was extracted with EA (20 mL*2). The combined organic phase was washed with water (20 mL*2) and brine (10 mL), dried over anhydrous NaSO₄ and filtered with suction. The filtrate was concentrated and the residue was separated by PLC to obtain 45.3 mg of the target compound.

ESI-MS Calculated for [M+H]⁺=412.11, Found: 414.10. The calculated value was consistent with the found value.

Step 2: Synthesis of N,N¹-dimethyl-N²-(1-methyl-9-(1-methyl-1H-pyrazol-4-yl)-6,7-dihydro-5H-benzo[c][1,2,3]triazolo[1,5-a]azepin-7-yl)benzene-1,2-diamine (LB01)

LB01-2 (45.3 mg, 0.11 mmol), 1-methyl-4-(4,4,5,5-tetramethyl-1,3,2-dioxaborolan-2-yl)-1H-pyrazole (28.5 mg, 0.14 mmol), potassium carbonate (23.5 mg, 0.17 mmol), 1,4-dioxane (5 mL) and water (0.25 mL) were added to a 50 mL single necked flask, and the air in the reaction system was replaced with N₂ three times. The system was added with Pd(dppf)Cl₂-dichloromethane complex (4.5 mg, 0.0055 mmol), and the air in the reaction system was replaced with N₂ three times again. The system was heated to reflux, and the reaction was monitored by LC-MS. The system was added with water (20 mL) and EA (20 mL), shaken and seperated. The aqueous phase was extracted with EA (20 mL*2). The combined organic phase was washed with water (20 mL*2) and brine (10 mL), dried over anhydrous NaSO₄ and filtered with suction. The filtrate was concentrated and the residue was separated by PLC to obtain 20.3 mg of a crude, which was separated by fast medium pressure preparative chromatography to obtain 8.1 mg of the target compound LB01.

Product analysis: ¹HNMR (CDCl₃, 400 MHz): 7.72 (s, 1H), 7.67 (s, 1H), 7.58 (s, 1H), 7.53 (dd, J=5.7, 3.3 Hz, 1H), 7.41 (s, 1H), 6.97 (d, J=7.4 Hz, 2H), 6.32 (d, J=7.7 Hz, 2H), 4.76 (s, 1H), 4.31 (m, 2H), 4.03 (s, 1H), 3.93 (s, 3H), 3.63 (s, 3H), 3.44 (s, 2H), 2.99 (s, 1H), 2.54 (s, 3H).

ESI-MS Calculated for [M+F1]⁺=414.23; Found: 414.20.

The product analysis result was consistent with the structure of LB01.

Preparation Example 17, Final Product LB17: N¹,N¹-dimethyl-N4-(1-methyl-9-(1-methyl-1H-pyrazol-4-yl)-6,7-dihydro-5H-benzo[c][1,2,3]triazolo[1,5-a]azepin-7-yl)benzene-1,4-diamine

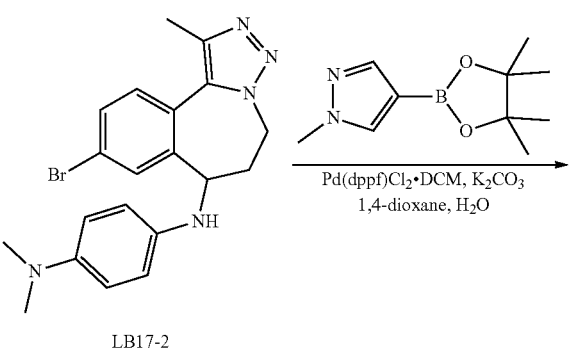

LB17-2

205

-continued

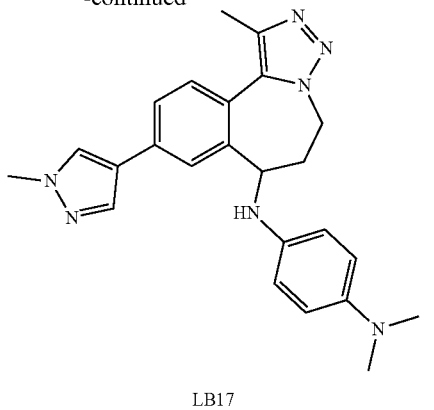

LB17

Step 1: Synthesis of N¹-(9-bromo-1-methyl-6,7-dihydro-5H-benzo[c][1,2,3]triazolo[1,5-a]azepin-7-yl)-N⁴,N⁴-dimethylbenzene-1,4-diamine (LB17-2)

C-9 (103.3 mg, 0.25 mmol), N,N-dimethyl-1,4-phenylenediamine (115.5 mg, 0.85 mmol), DIPEA (183.1 mg, 1.42 mmol) and DCM (10 mL) were added to a 100 mL single necked flask and stirred at room temperature for 16 h, and the reaction was monitored by LC-MS. The system was added with water (20 mL) and DCM (20 mL), shaken and sepatated. The aqueous phase was extracted with DCM (20 mL*2). The combined organic phase was washed with water (20 mL*2) and brine (10 mL), dried over anhydrous $NaSO_4$ and filtered with suction. The filtrate was concentrated and the residue was separated by PLC to obtain 109.1 mg of the target compound.

ESI-MS Calculated for $[M+H]^+$=412.11, 414.11, Found: 412.10, 414.10.

Step 2: Synthesis of N¹,N¹-dimethyl-N⁴-(1-methyl-9-(1-methyl-1H-pyrazol-4-yl)-6,7-dihydro-5H-benzo[c][1,2,3]triazolo[1,5-a]azepin-7-yl)benzene-1,4-diamine (LB17)

LB17-2 (45.3 mg, 0.11 mmol), 1-methyl-4-(4,4,5,5-tetramethyl-1,3,2-dioxaborolan-2-yl)-1H-pyrazole (109.1 mg, 0.26 mmol), potassium carbonate (54.5 mg, 0.41 mmol), 1,4-dioxane (10 mL) and water (0.5 mL) were added to a 50 mL single necked flask, and the air in the reaction system was replaced with $N_2$ three times. The system was added with Pd(dppf)$Cl_2$-dichloromethane complex (10.6 mg, 0.013 mmol), and the air in the reaction system was replaced with $N_2$ three times again. The system was heated to 115° C., and the reaction was monitored by LC-MS. The system was added with water (20 mL) and EA (20 mL), shaken and seperated. The aqueous phase was extracted with EA (20 mL*2). The combined organic phase was washed with water (20 mL*2) and brine (10 mL), dried over anhydrous $NaSO_4$ and filtered with suction. The filtrate was concentrated and the residue was separated by PLC to obtain 18.1 mg of a crude, which was separated by medium pressure preparative chromatography to obtain the target compound LB17, which was lyophilized to obtain 7.8 mg of a white solid.

Product analysis: ¹HNMR (CDCl₃, 400 MHz): 7.71 (s, 1H), 7.65 (s, 1H), 7.58 (s, 1H), 7.50 (d, J=7.7 Hz, 1H), 7.40 (s, 2H), 6.32 (s, 2H), 4.78 (s, 1H), 4.15 (q, J=7.2 Hz, 2H), 3.92 (d, J=7.3 Hz, 3H), 3.00-2.76 (m, 4H), 2.52 (s, 3H), 2.23 (d, J=7.5 Hz, 1H), 2.19 (s, 1H), 1.32-1.21 (m, 3H);

206

ESI-MS Calculated for $[M+H]^+$=414.23, Found: 414.20; The product analysis result was consistent with the structure of LB17.

Preparation Example 18, Final Product LB20: 4-((1-methyl-9-(1-methyl-1H-pyrazol-4-yl)-6,7-dihydro-5H-benzo[c][1,2,3]triazolo[1,5-a]azepin-7-yl)amino)benzoic acid

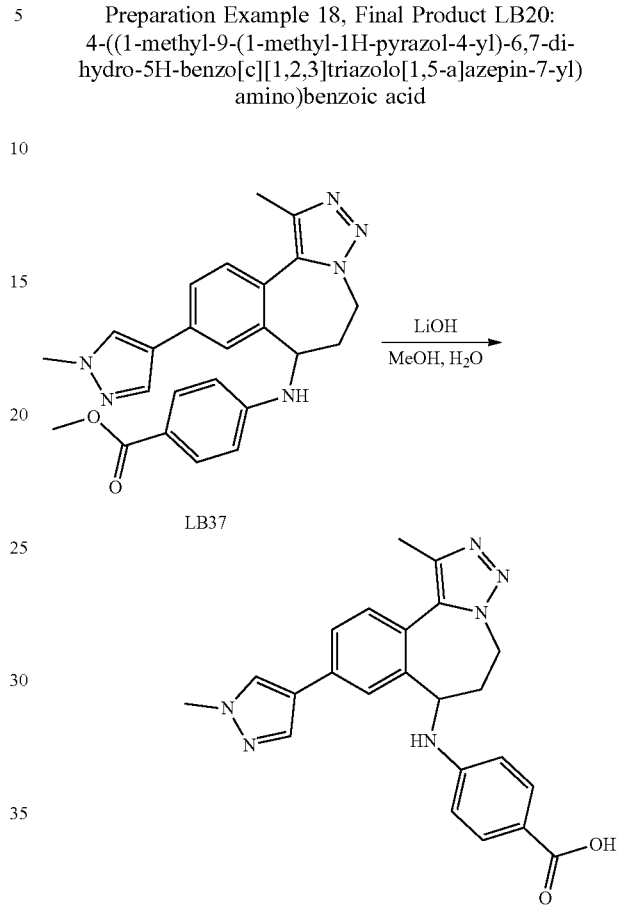

Synthesis of 4-((1-methyl-9-(1-methyl-1H-pyrazol-4-yl)-6,7-dihydro-5H-benzo[c][1,2,3]triazolo[1,5-a]azepin-7-yl)amino)benzoic acid (LB20)

LB37 (14.8 mg, 0.035 mmol), lithium hydroxide (13 mg, 15.08 mmol), methanol (5 mL) and water (5 mL) were added to a 50 mL single necked flask and stirred at room temperature, and the reaction was monitored by LC-MS. The system was distilled under reduced pressure, and the residue was added with water (50 mL) and extracted with EA (20 mL*2). The aqueous phase was adjusted pH to 3 with HCl (1M) and extracted with EA (20 mL*2). The combined organic phase was washed with water (20 mL*2) and brine (20 mL), dried over anhydrous $NaSO_4$ and filtered with suction. The filtrate was concentrated and the residue was separated by fast medium pressure preparative chromatography to obtain 11.7 mg of the target compound LB20.

Product analysis: ¹HNMR (CDCl₃, 400 MHz): 7.79 (d, J=8.5 Hz, 2H), 7.69 (d, J=0.9 Hz, 1H), 7.57-7.47 (m, 3H), 7.42 (d, J=7.8 Hz, 1H), 6.30 (d, J=8.5 Hz, 2H), 4.83-4.72 (m, 1H), 4.41-4.40 (m, 2H), 4.07-3.97 (m, 1H), 3.91 (s, 3H), 3.02-2.97 (m, 1H), 2.53 (s, 3H);

ESI-MS Calculated for $[M+H]^+$=415.18, Found: 415.20; The product analysis result was consistent with the structure of LB20.

Preparation Example 19, Final Product LB24: Synthesis of 2-(4-41-methyl-9-(1-methyl-1H-pyrazol--yl)-6,7-dihydro-5H-benzo[c][1,2,3]triazolo[1,5-a]azepin-7-yl)amino)phenyl)ethan-1-ol

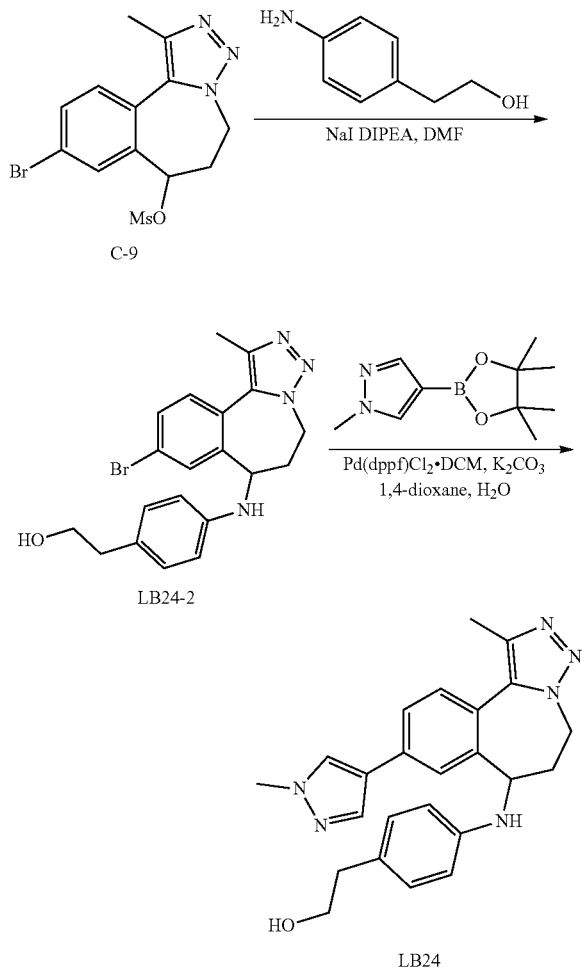

Step 1: Synthesis of 2-(4-((9-bromo-1-methyl-6,7-dihydro-5H-benzo[c][1,2,3]triazolo[1,5-a]azepin-7-yl)amino)phenyl)ethan-1-ol (LB24-2)

C-9 (75.1 mg, 0.20 mmol), 2-(4-aminophenyl)-ethan-1-ol (55.7 mg, 0.41 mmol), DIPEA (95.4 mg, 0.74 mmol), DMF (5 mL) and sodium iodide (3.0 mg, 0.020 mmol) were added to a 100 mL single necked flask and stirred at room temperature, and the reaction was monitored by LC-MS. The system was added with water (80 mL) and EA (20 mL), shaken and sepatated. The aqueous phase was extracted with EA (20 mL*2). The combined organic phase was washed with water (20 mL*3) and brine (10 mL), dried over anhydrous NaSO$_4$ and filtered with suction. The filtrate was concentrated and the residue was separated by PLC to obtain 53.5 mg of the target compound with a yield of 38%.

ESI-MS Calculated for [M+H]$^+$=413.09, 415.09; Found: 413.20, 415.10. The calculated value was consistent with the found value.

Step 2: Synthesis of 2-(4-((1-methyl-9-(1-methyl-1H-pyrazol-4-yl)-6,7-dihydro-5H-benzo[c][1,2,3]triazolo[1,5-a]azepin-7-yl)amino)phenyl)ethan-1-ol (LB24)

LB24-2 (53.5 mg, 0.13 mmol), 1-methyl-4-(4,4,5,5-tetramethyl-1,3,2-dioxaborolan-2-yl)-1H-pyrazole (35.3 mg, 0.17 mmol), potassium carbonate (28.2 mg, 0.21 mmol), 1,4-dioxane (5 mL) and water (0.25 mL) were added to a 50 mL single necked flask, and the air in the reaction system was replaced with N$_2$ three times. The system was added with Pd(dppf)Cl$_2$-dichloromethane complex (5.4 mg, 0.0066 mmol), and the air in the reaction system was replaced with N$_2$ three times again. The system was heated to 115° C., and the reaction was monitored by LC-MS. The system was added with water (20 mL) and EA (20 mL), shaken and seperated. The aqueous phase was extracted with EA (20 mL*2). The combined organic phase was washed with water (20 mL*2) and brine (10 mL), dried over anhydrous NaSO$_4$ and filtered with suction. The filtrate was concentrated and the residue was separated by PLC to obtain 39.9 mg of a crude, which was separated by medium pressure preparative chromatography to obtain the target compound LB24, which was lyophilized to obtain 15.3 mg of a white solid.

Product analysis: $^1$HNMR (CDCl$_3$, 400 MHz): 7.70 (d, J=0.7 Hz, 1H), 7.66 (d, J=1.9 Hz, 1H), 7.57 (s, 1H), 7.49 (dd, J=7.9, 1.7 Hz, 1H), 7.40 (d, J=7.8 Hz, 1H), 6.97-6.87 (m, 2H), 6.33-6.23 (m, 2H), 4.76 (dd, J=14.1, 7.2 Hz, 1H), 4.34-4.21 (m, 1H), 4.09-3.95 (m, 1H), 3.92 (s, 3H), 3.73 (t, J=6.5 Hz, 2H), 2.97-2.89 (m, 1H), 2.68 (m, 2H), 2.53 (s, 3H), 2.26-2.18 (m, 1H);

ESI-MS Calculated for [M+H]$^+$=415.22, Found: 415.40;

The product analysis result was consistent with the structure of LB24.

Preparation Example 20, Final Product LB32: 4-((1-methyl-9-(1-methyl-1H-pyrazol-4-yl)-6,7-dihydro-5H-benzo[c][1,2,3]triazolo[1,5-a]azepin-7-yl)amino)benzamide

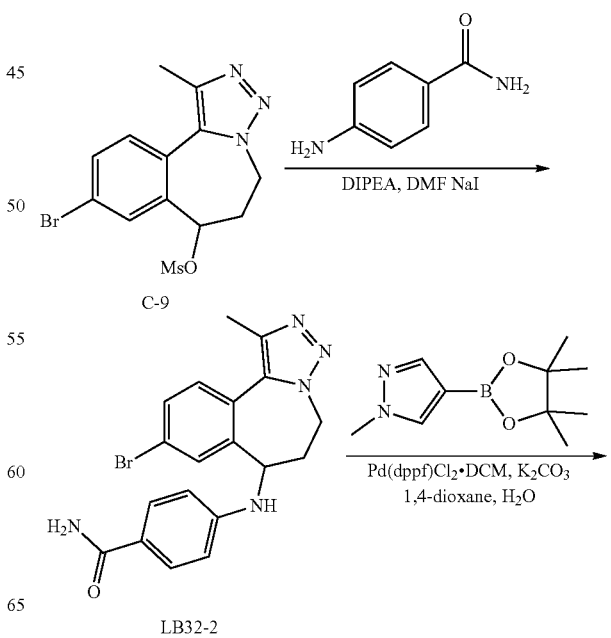

-continued

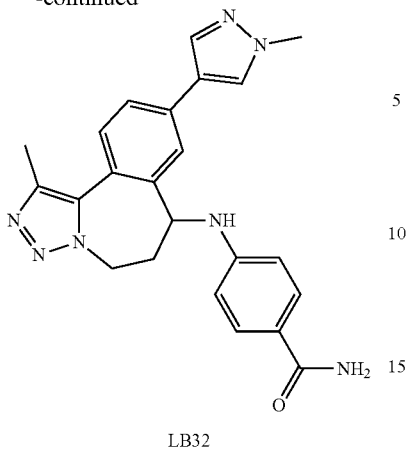

LB32

Step 1: Synthesis of 4-((9-bromo-1-methyl-6,7-dihydro-5H-benzo[c][1,2,3]triazolo[1,5-a]azepin-7-yl)amino)benzamide (LB32-2)

C-9 (88.5 mg, 0.24 mmol), p-aminobenzamide (66.4 mg, 0.49 mmol), DIPEA (158.5 mg, 1.23 mmol), DMF (10 mL) and sodium iodide (7.9 mg, 0.053 mmol) were added to a 50 mL single necked flask and stirred at room temperature, and the reaction was monitored by LC-MS. The system was added with water (40 mL) and EA (20 mL), shaken and sepatated. The aqueous phase was extracted with EA (20 mL*2). The combined organic phase was washed with water (20 mL*3) and brine (10 mL), dried over anhydrous $NaSO_4$ and filtered with suction. The filtrate was concentrated and the residue was separated by PLC to obtain 44.1 mg of the target compound.

ESI-MS Calculated for $[M+H]^+$=412.07, 414.07; Found: 412.00, 414.00. The calculated value was consistent with the found value.

Step 2: Synthesis of 4-((1-methyl-9-(1-methyl-1H-pyrazol-4-yl)-6,7-dihydro-5H-benzo[c][1,2,3]triazolo[1,5-a]azepin-7-yl)amino)benzamide (LB32)

LB32-2 (44.1 mg, 0.11 mmol), 1-methyl-4-(4,4,5,5-tetramethyl-1,3,2-dioxaborolan-2-yl)-1H-pyrazole (29.6 mg, 0.14 mmol), potassium carbonate (23.3 mg, 0.17 mmol), 1,4-dioxane (5 mL) and water (0.25 mL) were added to a 50 mL single necked flask, and the air in the reaction system was replaced with $N_2$ three times. The system was added with Pd(dppf)$Cl_2$-dichloromethane complex (4.5 mg, 0.0055 mmol), and the air in the reaction system was replaced with $N_2$ three times again. The system was heated to reflux, and the reaction was monitored by LCMS. The system was added with water (30 mL) and EA (20 mL), shaken and sepatated. The aqueous phase was extracted with EA (30 mL*2). The combined organic phase was washed with water (20 mL*2) and brine (10 mL), dried over anhydrous $NaSO_4$ and filtered with suction. The filtrate was concentrated and the residue was separated by PLC to obtain 20.6 mg of a crude, which was separated by fast medium pressure preparative chromatography to obtain the target compound LB32, which was lyophilized to obtain 8.1 mg of a white solid.

Product analysis: $^1$HNMR ($CDCl_3$, 400 MHz): 7.69 (s,1H), 7.58-7.48 (m,5H), 7.42 (d,J=7.8 Hz,1H), 6.31 (d,J=8.6 Hz,2H), 4.78 (m,1H), 4.35-4.25 (m,2H), 4.15-4.22 (m,1H), 3.92 (s,3H), 3.11-3.08 (m,1H), 2.53 (s,3H), 2.31-2.18 (m,1H);

ESI-MS Calculated for $[M+H]^+$=414.20, Found: 414.10;

The product analysis result was consistent with the structure of LB32.

Preparation Example 21, Final Product LB35: (4-((1-methyl-9-(1-methyl-1H-pyrazol-4-yl)-6,7-dihydro-5H-benzo[c][1,2,3]triazolo[1,5-a]azepin-7-yl)amino)phenyl)methanol -continued

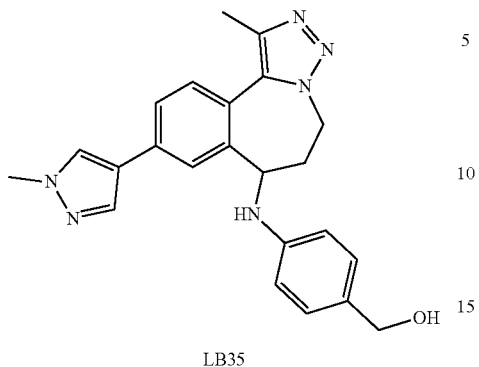

LB35

Step 1: Synthesis of tert-butyldimethyl((4-nitrobenzyl)oxy)silane (LB35-A)

p-Nitrobenzyl alcohol (2.52 g, 16.46 mmol), imidazole (1.41 g, 20.58 mmol) and DMF (15 mL) were added to a 100 mL single necked flask, cooled to 0° C., added dropwise with TBSCl (2.98 g, 19.75 mmol) and warmed to room temperature, and the reaction was monitored by LC-MS. The system was added with water (80 mL) and EA (20 mL), shaken and sepatated. The aqueous phase was extracted with EA (20 mL*2). The combined organic phase was washed with water (20 mL*3) and brine (40 mL), dried over anhydrous $NaSO_4$ and filtered with suction. The filtrate was concentrated to obtain 4.22 g of the target compound, which was not further purified.

Step 2: Synthesis of 4-(((tert-butyldimethylsilyl)oxy)methyl)aniline (LB35-B)

LB35-A (0.50 g, 1.87 mmol), EA (5 mL) and palladium on carbon (52.1 mg, 10%) were added to a 100 mL single necked flask, and the air in the reaction system was replaced with hydrogen three times. The system was stirred at room temperature, and the reaction was monitored by LC-MS. The system was filtration with suction, and the filtrate was concentrated to obtain 416.3 mg of the target compound, which was not further purified.

ESI-MS Calculated for $[M+H]^+=237.15$; Found: 238.10.

Step 3: Synthesis of 9-bromo-N-(4-(((tert-butyldimethylsilyl)oxy)methyl)phenyl)-1-methyl-6,7-dihydro-5H-benzo[c][1,2,3]triazolo[1,5-a]azepin-7-amine (LB35-2)

C-9 (207.5 mg, 0.56 mmol), LB35-B (271.3 mg, 1.14 mmol), DIPEA (369.8 mg, 2.86 mmol), DMF (10 mL) and sodium iodide (10.3 mg, 0.067 mmol) were added to a 100 mL single necked flask and heated to 60° C., and the reaction was monitored by LC-MS. The system was added with water (80 mL) and EA (20 mL), shaken and sepatated. The aqueous phase was extracted with EA (20 mL*2). The combined organic phase was washed with water (40 mL*3) and brine (50 mL), dried over anhydrous $NaSO_4$ and filtered with suction. The filtrate was concentrated and the residue was separated by PLC to obtain 207.1 mg of the target compound.

ESI-MS Calculated for $[M+H]^+=513.16$, 515.16; Found: 513.20, 515.20.

Step 4: Synthesis of N-(4-(((tert-butyldimethylsilyfloxy)methyl)phenyl)-1-methyl-9-(1-methyl-1H-pyrazol-4-yl)-6,7-dihydro-5H-benzo[c][1,2,3]triazolo[1,5-a]azepin-7-amine (LB35-3)

LB35-2 (207.1 mg, 0.40 mmol), 1-methyl-4-(4,4,5,5-tetramethyl-1,3,2-dioxaborolan-2-yl)-1H-pyrazole (109.9 mg, 0.53 mmol), potassium carbonate (84.1 mg, 0.61 mmol), 1,4-dioxane (20 mL) and water (1 mL) were added to a 50 mL single necked flask, and the air in the reaction system was replaced with $N_2$ three times. The system was added with $Pd(dppf)Cl_2$-dichloromethane complex (16.4 mg, 0.0020 mmol), and the air in the reaction system was replaced with $N_2$ three times again. The system was heated to reflux, and the reaction was monitored by LC-MS. The system was added with water (50 mL) and EA (20 mL), shaken and sepatated. The aqueous phase was extracted with EA (50 mL*2). The combined organic phase was washed with water (20 mL*2) and brine (20 mL), dried over anhydrous $NaSO_4$ and filtered with suction. The filtrate was concentrated and the residue was separated by PLC to obtain 132.1 mg of a crude.

ESI-MS Calculated for $[M+H]^+=415.29$; Found: 415.10. The calculated value was consistent with the found value.

Step 5: Synthesis of (4-((1-methyl-9-(1-methyl-1H-pyrazol-4-yl-)-6,7-dihydro-5H-benzo[c][1,2,3]triazolo[1,5-a]azepin-7-yl)amino)phenyl)methanol (LB35)

LB35-3 (132.1 mg, 0.26 mmol), TBAF (1 mL, 1M, 1 mmol) and THF (5 mL) were added to a 50 mL single necked flask and stirred at room temperature, and the reaction was monitored by LC-MS. The system was distilled under reduced pressure, and the residue was dissolved in EA (100 mL), washed with water (20 mL*3) and brine (30 mL), dried over anhydrous $NaSO_4$ and filtered with suction. The filtrate was evaporated to dryness. The residue was separated by medium pressure preparative chromatography to obtain the target compound LB35, which was lyophilized to obtain 16.8 mg of a white solid.

Product analysis: $^1HNMR$ ($CDCl_3$, 400 MHz): 7.70 (d, J=0.8 Hz, 1H), 7.63 (d, J=1.7 Hz, 1H), 7.56 (d, J=0.8 Hz, 1H), 7.50 (dd, J=7.8, 1.8 Hz, 1H), 7.41 (d, J=7.8 Hz, 1H), 7.10-7.02 (m, 2H), 6.35-6.26 (m, 2H), 4.77-4.74 (m, 1H), 4.48 (s, 2H), 4.33-4.28 (m, 1H), 4.03-3.97 (m, 2H), 3.92 (s, 3H), 3.06-2.92 (m, 1H), 2.53 (s, 3H), 2.28-2.15 (m, 1H);

ESI-MS Calculated for $[M+H]^+=401.20$, Found: 401.20;

The product analysis result was consistent with the structure of LB35.

213

Preparation Example 22, Final Product LB36: 2-(4-((1-methyl-9-(1-methyl-1H-pyrazol-4-yl)-6,7-dihydro-5H-benzo[c][1,2,3]triazolo[1,5-a]azepin-7-yl)amino)phenyl)acetic acid

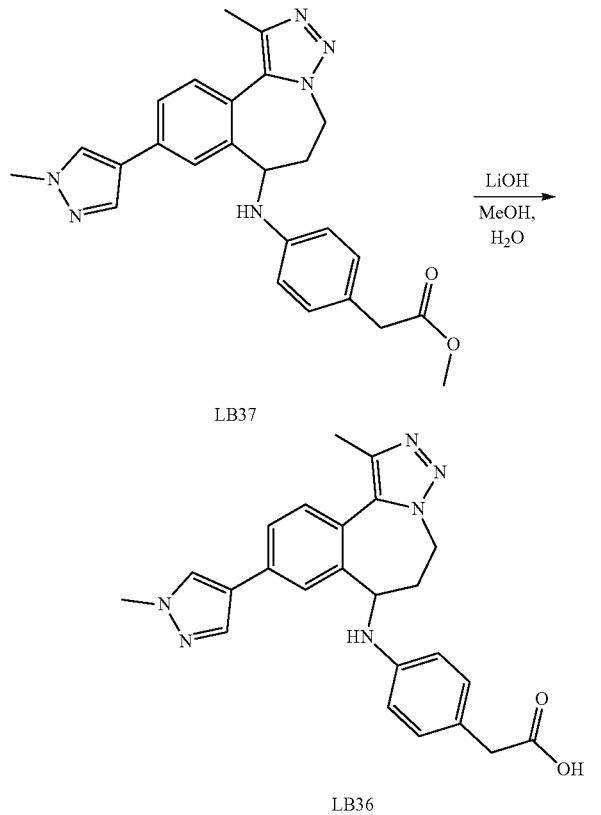

Synthesis of 2-(4-((1-methyl-9-(1-methyl-1H-pyrazol-4-yl)-6,7-dihydro-5H-benzo[c][1,2,3]triazolo[1,5-a]azepin-7-yl)amino)phenyl)acetic acid (LB36)

LB37 (38.8 mg, 0.088 mmol), lithium hydroxide (21.3 mg, 10.07 mmol), methanol (3 mL) and water (3 mL) were added to a 50 mL single necked flask and stirred at room temperature, and the reaction was monitored by LC-MS. The system was distilled under reduced pressure, and the residue was added with water (5 mL) and extracted with EA (20 mL*2). The aqueous phase was adjusted pH to 3 with HCl (1M) and extracted with EA (20 mL*2). The combined organic phase was washed with water (20 mL*2) and brine (10 mL), dried over anhydrous NaSO₄ and filtered with suction. The filtrate was concentrated and the residue was separated by fast medium pressure preparative chromatography to obtain the target compound LB36, which was lyophilized to obtain 18.8 mg of a white solid.

Product analysis: ¹HNMR (CDCl₃, 400 MHz): 7.63 (d, J=0.8 Hz, 1H), 7.62-7.59 (m, 1H), 7.55 (s, 1H), 7.47 (dd, J=7.8, 1.8 Hz, 1H), 7.40 (d, J=7.8 Hz, 1H), 6.98 (d, J=8.4 Hz, 2H), 6.28 (d, J=8.5 Hz, 2H), 4.79-4.72 (m 1H), 4.35-4.22 (m, 2H), 4.01-3.7 (m, 2H), 3.93 (s, 3H), 3.46 (d, J=3.1 Hz, 2H), 2.99-2.87 (m, 1H), 2.53 (s, 3H), 2.19 (s, 1H); ESI-MS Calculated for [M+H]⁺=429.20, Found: 429.00; The product analysis result was consistent with the structure of LB36.

214

Preparation Example 23, Final Product LB37: methyl 4-((1-methyl-9-(1-methyl-1H-pyrazol-4-yl)-6,7-dihydro-5H-benzo[c][1,2,3]triazolol[1,5-a]azepin-7-yl)amino)benzoate

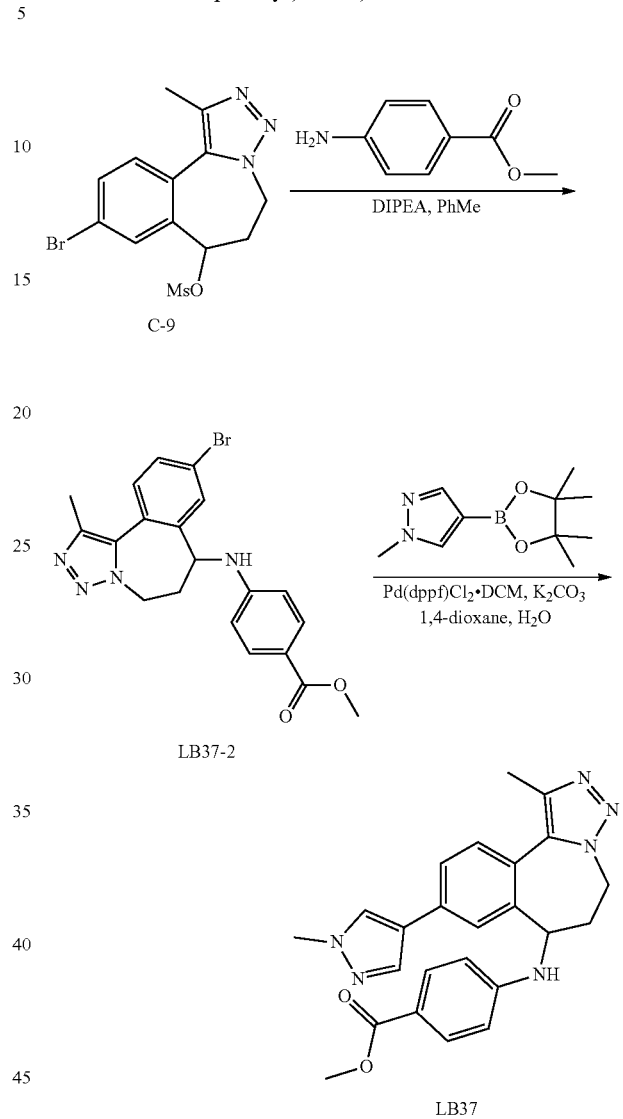

Step 1: Synthesis of methyl 4-((9-bromo-1-methyl-6,7-dihydro-5H-benzo[c][1,2,3]triazolo[1,5-a]azepin-7-yl)amino)benzoate (LB37-2)

C-9 (126.7 mg, 0.34 mmol), methyl 4-aminobenzoate (78.5 mg, 1.53 mmol), DIPEA (148.1 mg, 3.37 mmol) and toluene (10 mL) were added to a 100 mL single necked flask and heated to toluene reflux, and the reaction was monitored by LC-MS. The system was added with water (20 mL) and EA (20 mL), shaken and seperated. The aqueous phase was extracted with EA (20 mL*2). The combined organic phase was washed with water (20 mL*2) and brine (10 mL), dried over anhydrous NaSO₄ and filtered with suction. The filtrate was concentrated and the residue was separated by PLC to obtain 129.9 mg of the target compound.

ESI-MS Calculated for [M+H]⁺=427.08, 429.07; Found: 427.20, 429.20.

Step 2: Synthesis of methyl 4-((1-methyl-9-(1-methyl-1H-pyrazol-4-yl)-6,7-dihydro-5H-benzo[c][1,2,3]triazolo[1,5-a]azepin-7-yl)amino)benzoate (LB37)

LB37-2 (58.9 mg, 0.14 mmol), 1-methyl-4-(4,4,5,5-tetramethyl-1,3,2-dioxaborolan-2-yl)-1H-pyrazole (37.5 mg, 0.18 mmol), potassium carbonate (30.2 mg, 0.22 mmol), 1,4-dioxane (5 mL) and water (0.25 mL) were added to a 50 mL single necked flask, and the air in the reaction system was replaced with $N_2$ three times. The system was added with Pd(dppf)Cl$_2$-dichloromethane complex (5.7 mg, 0.0070 mmol), and the air in the reaction system was replaced with $N_2$ three times again. The system was heated to reflux, and the reaction was monitored by LC-MS. The system was added with water (20 mL) and EA (20 mL), shaken and seperated. The aqueous phase was extracted with EA (20 mL*2). The combined organic phase was washed with water (20 mL*2) and brine (10 mL), dried over anhydrous NaSO$_4$ and filtered with suction. The filtrate was concentrated and the residue was separated by PLC to obtain 57.3 mg of a crude, which was separated by rapid medium pressure preparative chromatography to obtain 58.1 mg of the target compound LB37.

Product analysis: $^1$HNMR (CDCl$_3$, 400 MHz): 7.76 (s, 1H), 7.74 (s, 1H), 7.69 (s, 1H), 7.57-7.48 (m, 3H), 7.42 (d, J=7.8 Hz, 1H), 6.29 (d, J=8.7 Hz, 2H), 4.78 (m, 1H), 4.43-4.29 (m, 2H), 4.08 (s, 1H), 3.92 (s, 3H), 3.80 (s, 3H), 3.02-2.87 (m, 1H), 2.53 (s, 3H), 2.27-2.08 (m, 1H);

ESI-MS Calculated for [M+H]$^+$=429.20, Found: 429.10;

The product analysis result was consistent with the structure of LB37.

Preparation Example 24, Final Product LB38: methyl 2-(4-((1-methyl-9-(1-methyl-1H-pyrazol-4-yl)-6,7-dihydro-5H-benzo[c][1,2,3]triazolo[1,5-a]azepin-7-yl)amino)phenyl)acetate

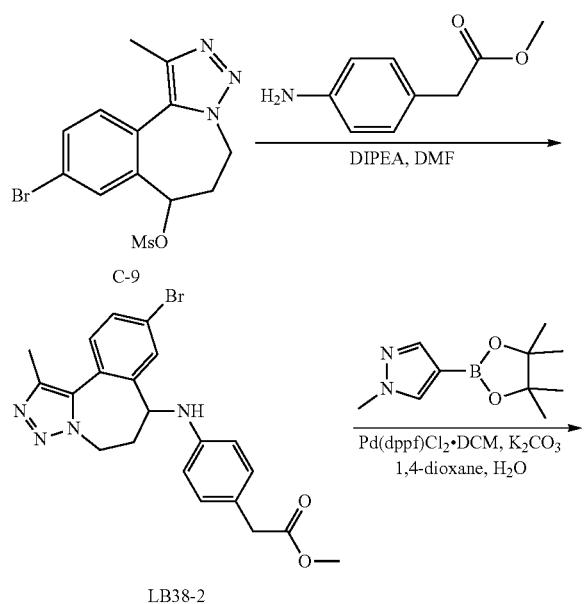

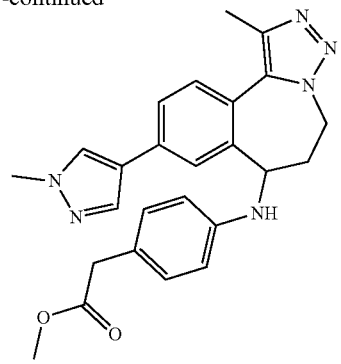

LB38

Step 1: Synthesis of methyl 4-((9-bromo-1-methyl-6,7-dihydro-5H-benzo[c][1,2,3]triazolo[1,5-a]azepin-7-yl)amino)phenyl) acetate (LB38-2)

C-9 (130.4 mg, 0.35 mmol), methyl 4-aminobenzeneacetate (118.5 mg, 2.05 mmol), DIPEA (229.4 mg, 5.07 mmol) and DMF (10 mL) were added to a 100 mL single necked flask and heated to 60° C., and the reaction was monitored by LC-MS. The system was added with water (75 mL) and EA (40 mL), shaken and sepatated. The aqueous phase was extracted with EA (25 mL*2). The combined organic phase was washed with water (30 mL*2) and brine (20 mL), dried over anhydrous NaSO$_4$ and filtered with suction. The filtrate was concentrated and the residue was separated by PLC to obtain 86.3 mg of the target compound.

ESI-MS Calculated for [M+H]$^+$=441.08, 443.08; Found: 440.90, 442.90.

Step 2: Synthesis of methyl 2-(4-((1-methyl-9-(1-methyl-1H-pyrazol-4-yl)-6,7-dihydro-5H-benzo[c][1,2,3]triazolo[1,5-a]azepin-7-yl)amino)phenyl)acetate (LB38)

LB38-2 (86.3 mg, 0.20 mmol), 1-methyl-4-(4,4,5,5-tetramethyl-1,3,2-dioxaborolan-2-yl)-1H-pyrazole (54.9 mg, 0.26 mmol), potassium carbonate (42.6 mg, 0.31 mmol), 1,4-dioxane (10 mL) and water (0.5 mL) were added to a 50 mL single necked flask, and the air in the reaction system was replaced with $N_2$ three times. The system was added with Pd(dppf)Cl$_2$-dichloromethane complex (8.5 mg, 0.011 mmol), and the air in the reaction system was replaced with $N_2$ three times again. The system was heated to reflux, and the reaction was monitored by LC-MS. The system was added with water (50 mL) and EA (20 mL), shaken and sepatated. The aqueous phase was extracted with EA (50 mL*2). The combined organic phase was washed with water (50 mL*2) and brine (20 mL), dried over anhydrous NaSO$_4$ and filtered with suction. The filtrate was concentrated and the residue was separated by PLC to obtain 57.3 mg of a crude, which was separated by rapid medium pressure preparative chromatography to obtain 58.1 mg of the target compound LB38.

Product analysis: $^1$HNMR (CDCl$_3$, 400 MHz): 7.72 (s, 1H), 7.67 (s, 1H), 7.58 (s, 1H), 7.53 (dd, J=5.7, 3.3 Hz, 1H), 7.41 (s, 1H), 6.97 (d, J=7.4 Hz, 2H), 6.32 (d, J=7.7 Hz, 2H), 4.76 (s, 1H), 4.31 (t, J=6.7 Hz, 2H), 4.03 (s, 1H), 3.93 (s, 3H), 3.63 (s, 3H), 3.44 (s, 2H), 2.99 (s, 1H), 2.54 (s, 3H), 2.27 (s, 1H);

ESI-MS Calculated for [M+H]$^+$=429.20, Found: 429.20; The product analysis result was consistent with the structure of LB38.

Preparation Example 25, Final Product RA180: N-(4-chlorophenyl)-1-methyl-9-(1-methyl-1H-pyrazol-4-yl)-6,7-dihydro-5H-benzo[c][1,2,3]triazolo[1,5-a]azepin-7-amine

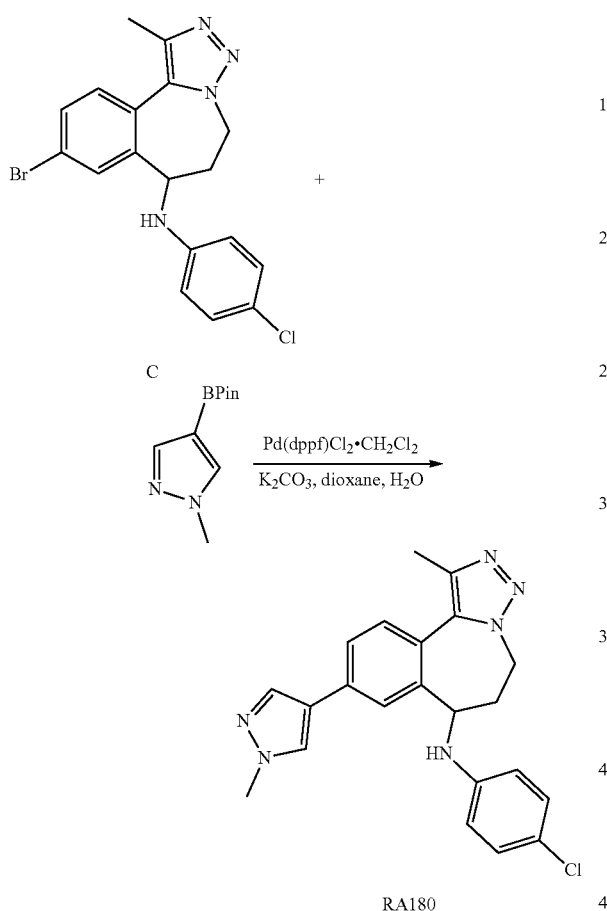

RA180

Synthesis of N-(4-chlorophenyl)-1-methyl-9-(1-methyl-1H-pyrazol-4-yl)-6,7-dihydro-5H-benzo[c][1,2,3]triazolo[1,5-a]azepin-7-amine (RA180)

C (96.6 mg, 0.29 mmol), 1-methylpyrazole-4-pinacolborate (60.6 mg, 0.29 mmol), potassium carbonate (57.0 mg, 0.41 mmol), Pd(dppf)Cl$_2$-dichloromethane complex (47.9 mg, 0.058 mmol), 1,4-dioxane (14 mL) and water (0.5 mL) were added to a reaction flask in sequence. The air in the reaction flask was replaced with nitrogen three times. Under nitrogen protection, the system was heated to react under reflux. After the reaction was complete in 1 hour, the system was concentrated under reduced pressure, and the residue was separated by column chromatography to obtain 25.3 mg of a crude, which was separated by medium pressure preparative chromatography and lyophilized to obtain 12.6 mg of a pure product.

Product analysis: $^1$HNMR (CDCl$_3$, 400 MHz): 7.70 (s, 1H), 7.60-.53 (m, 1H), 7.51-45 (m, 1H), 7.41 (s, 1H), 7.26 (s, 1H), 7.01-6.91 (m, 2H), 6.27-6.16 (m, 2H), 4.73-4.79 (m, 1H), 4.25 (s, 1H), 4.01-4.05 (m, 1H), 3.92 (s, 3H), 2.95-3.03 (m, 1H), 2.62-2.49 (m, 3H), 2.30-2.12 (m, 1H);

ESI-MS Calculated for [M+H]$^+$=405.16, Found: 405.10; The product analysis result was consistent with the structure of RA180.

Preparation Example 26, Final Product RA188: N-(4-chlorophenyl)-1-methyl-9-(pyridin-4-yl)-6,7-dihydro-5H-benzo[c][1,2,3]triazolo[1,5-a]azepin-7-amine

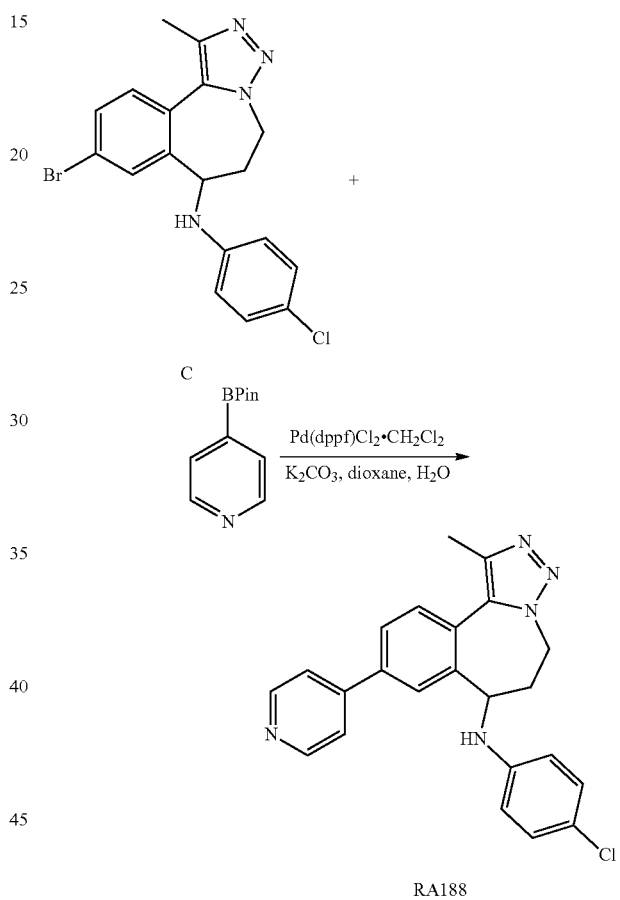

RA188

Synthesis of N-(4-chlorophenyl)-1-methyl-9-(pyridin-4-yl)-6,7-dihydro-5H-benzo[c][1,2,3]triazolo[1,5-a]azepin-7-amine (RA188)

C (115.6 mg, 0.29 mmol), 4-(4,4,5,5-tetramethyl-1,3,2-dioxaborolan-2-yl)pyridine (72.8 mg, 0.36 mmol), potassium carbonate (73.6 mg, 0.53 mmol), Pd(dppf)Cl$_2$-dichloromethane complex (51.2 mg, 0.063 mmol), 1,4-dioxane (10 mL) and water (0.5 mL) were added to a reaction flask in sequence. The air in the reaction flask was replaced with nitrogen three times. Under nitrogen protection, the system was heated to react under reflux. After the reaction was complete, the system was concentrated under reduced pressure, and the residue was separated by column chromatography to obtain 81.1 mg of a crude, which was separated by medium pressure preparative chromatography and lyophilized to obtain 27.4 mg of a pure product.

Product analysis: ¹HNMR (CDCl₃, 400 MHz): 8.80-8.47 (m, 2H), 7.78 (d, J=1.8 Hz, 1H), 7.68 (dd, J=7.9, 1.9 Hz, 1H), 7.55 (d, J=7.9 Hz, 1H), 7.44-7.34 (m, 2H), 7.07-6.90 (m, 2H), 6.27-6.17 (m, 2H), 4.82 (dd, J=14.2, 7.2 Hz, 1H), 4.27-4.33 (m, 1H), 4.10-4.01 (m, 1H), 3.13-2.95 (m, 1H), 2.56 (s, 2H), 2.33-2.17 (m, 1H);

ESI-MS Calculated for [M+1]⁺=402.15, Found: 402.10;

The product analysis result was consistent with the structure of RA188.

Preparation Example 27, Final Product RA193:
N-(4-chlorophenyl)-1-methyl-9-(pyridin-3-yl)-6,7-dihydro-5H-benzo[c][1,2,3]triazolo[1,5-a]azepin-7-amine

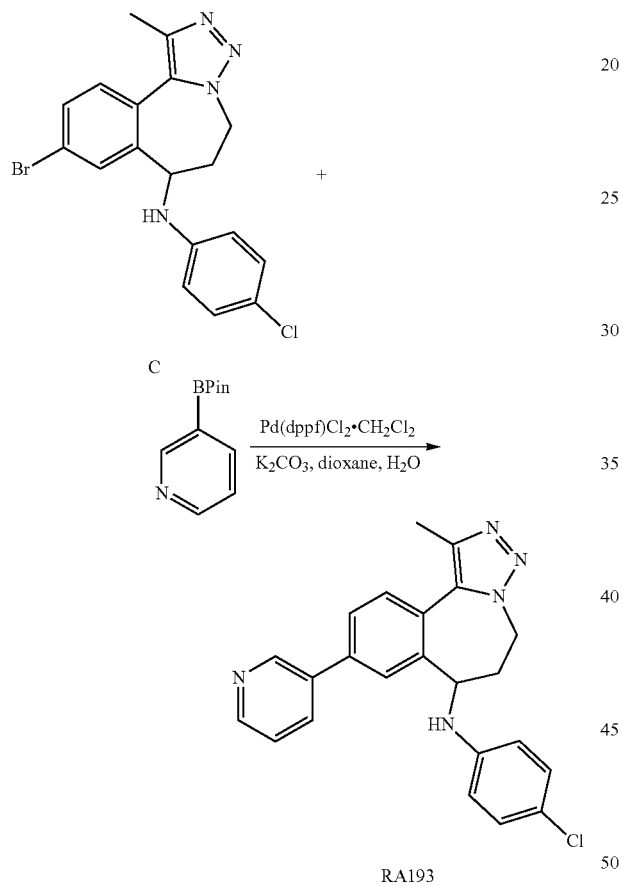

RA193

Synthesis of N-(4-chlorophenyl)-1-methyl-9-(pyridin-3-yl)-6,7-dihydro-5H-benzo[c][1,2,3]triazolo[1,5-a]azepin-7-amine (RA193)

C (101.4 mg, 0.25 mmol), 3-(4,4,5,5-tetramethyl-1,3,2-dioxaborolan-2-yl)pyridine (68.5 mg, 0.33 mmol), Pd(dppf)Cl₂-dichloromethane complex (41.2 mg, 0.050 mmol), potassium carbonate (65.8 mg, 0.48 mmol), 1,4-dioxane (12 mL) and water (0.5 mL) were added to a reaction flask in sequence. The air in the reaction flask was replaced with nitrogen three times. Under nitrogen protection, the system was heated to react under reflux. After the reaction was complete, the system was concentrated under reduced pressure, and the residue was separated by column chromatography to obtain 41.6 mg of a crude, which was separated by medium pressure preparative chromatography and lyophilized to obtain 3.9 mg of a pure product.

ESI-MS Calculated for [M+1]⁺=402.15; Found: 402.10. The found value was consistent with the caculated value.

Preparation Example 28, Final Product RA194:
tert-butyl (4-(7-((4-chlorophenyl)amino)-1-methyl-6,7-dihydro-5H-benzo[c][1,2,3]triazolo[1,5-a]azepin-9-yl)phenyl)carbamate

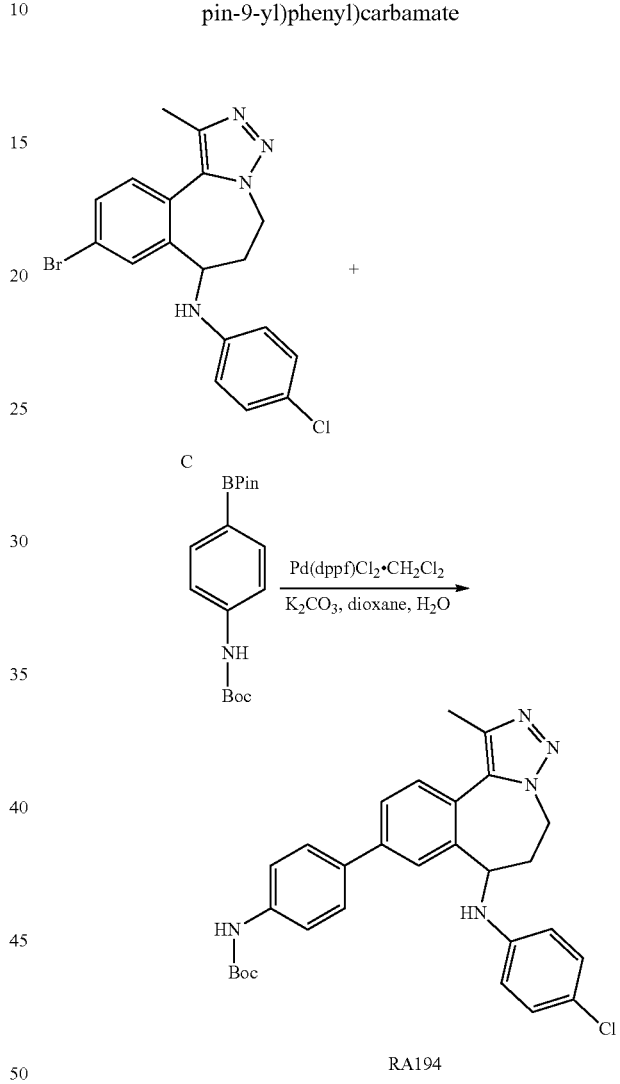

RA194

Synthesis of tert-butyl (4-(7-((4-chlorophenyl)amino)-1-methyl-6,7-dihydro-5H-benzo[c][1,2,3]triazolo[1,5-a]azepin-9-yl)phenyl)carbamate (RA194)

C (117.1 mg, 0.29 mmol), tert-butyl (4-(4,4,5,5-tetramethyl-1,3,2-dioxaborolan-2-yl)phenyl)carbamate (110.0 mg, 0.34 mmol), potassium carbonate (72.5 mg, 0.52 mmol), Pd(dppf)Cl₂-dichloromethane complex (49.5 mg, 0.061 mmol), 1,4-dioxane (12 mL) and water (0.5 mL) were added to a reaction flask in sequence. The air in the reaction flask was replaced with nitrogen three times. Under nitrogen protection, the system was heated to react under reflux. After the reaction was complete, the system was concentrated under reduced pressure, and the residue was separated by column chromatography to obtain 122.5 mg of a crude, which was separated by medium pressure preparative chromatography and lyophilized to obtain 33.5 mg of a pure product.

Product analysis: $^1$HNMR (CDCl$_3$, 400 MHz): 9.47 (s, 1H), 7.65 (s, 2H), 7.61-7.49 (m, 3H), 7.44 (d, J=8.7 Hz, 2H), 7.09-6.92 (m, 2H), 6.58 (d, J=7.5 Hz, 1H), 6.45-6.23 (m, 2H), 4.77 (dd, J=14.4, 7.8 Hz, 1H), 4.12-4.19 (m, 1H), 3.89-3.97 (m, 1H), 2.82-2.88 (m, 1H), 2.45 (s, 3H), 2.24-2.32 (m, 1H), 1.49 (s, 9H);

ESI-MS Calculated for [M+1]$^+$=516.22, Found: 516.30;

The product analysis result was consistent with the structure of RA194.

Preparation Example 29, Final Product RB03: 9-(6-aminopyridin-3-yl)-N-(4-chlorophenyl)-1-methyl-6,7-dihydro-5H-benzo[c][1,2,3]triazolo[1,5-a]azepin-7-amine

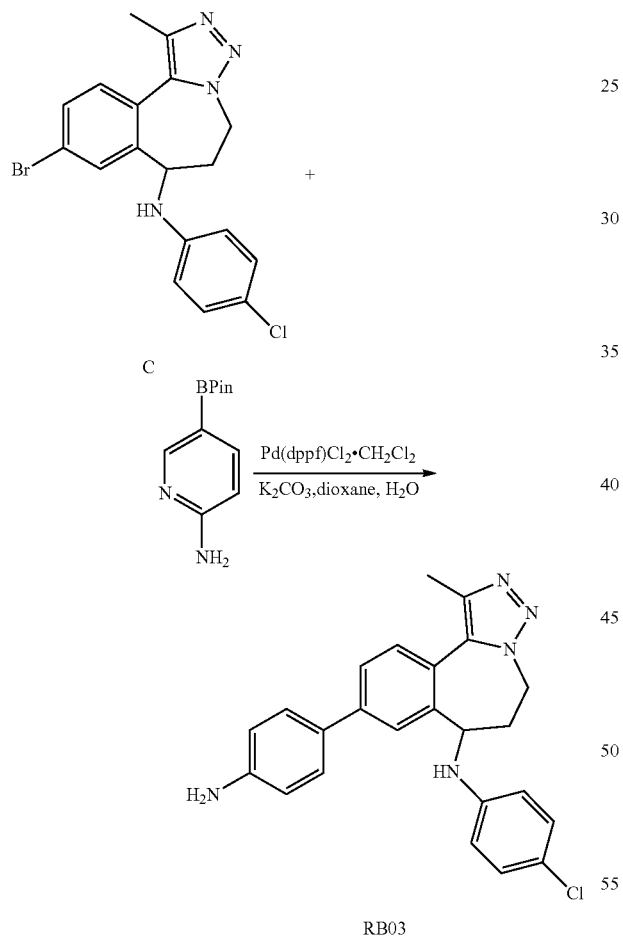

RB03

Synthesis of 9-(6-aminopyridin-3-yl)-N-(4-chlorophenyl)-1-methyl-6,7-dihydro-5H-benzo[c][1,2,3]triazolo[1,5-a]azepin-7-amine (RB03)

C (160.1 mg, 0.40 mmol), 4-(4,4,5,5-tetramethyl-1,3,2-dioxaborolan-2-yl)pyridine-2-amine (107.3 mg, 0.49 mmol), Pd(dppf)Cl$_2$-dichloromethane complex (63.1 mg, 0.077 mmol), potassium carbonate (107.2 mg, 0.76 mmol), 1,4-dioxane (16 mL) and water (0.5 mL) were added to a reaction flask in sequence. The air in the reaction flask was replaced with nitrogen three times. Under nitrogen protection, the system was heated to react under reflux. After the reaction was complete, the system was concentrated under reduced pressure, and the residue was separated by column chromatography to obtain 142.1 mg of a crude, which was separated by medium pressure preparative chromatography and lyophilized to obtain 38.1 mg of a pure product.

Product analysis: $^1$HNMR (CDCl$_3$, 400 MHz): 8.11 (d, J=2.5 Hz, 1H), 7.63-7.51 (m, 4H), 7.07-6.96 (m, 2H), 6.56 (d, J=7.7 Hz, 1H), 6.50 (d, J=8.6 Hz, 1H), 6.40-6.31 (m, 2H), 6.14 (s, 2H), 4.76 (dd, J=14.4, 7.8 Hz, 1H), 4.11-4.18 (m, 1H), 3.88-3.96 (m, 1H), 2.79-2.89 (m, 1H), 2.44 (s, 3H), 2.22-2.30 (m, 1H);

ESI-MS Calculated for [M+1]$^+$=417.16; Found: 417.10;

The product analysis result was consistent with the structure of RB03.

Preparation Example 30, Final Product RB05: N-(4-chlorophenyl)-9-(1-ethyl-1H-pyrazol-4-yl)-1-methyl-6,7-dihydro-5H-benzo[c][1,2,3]triazolo[1,5-a]azepin-7-amine

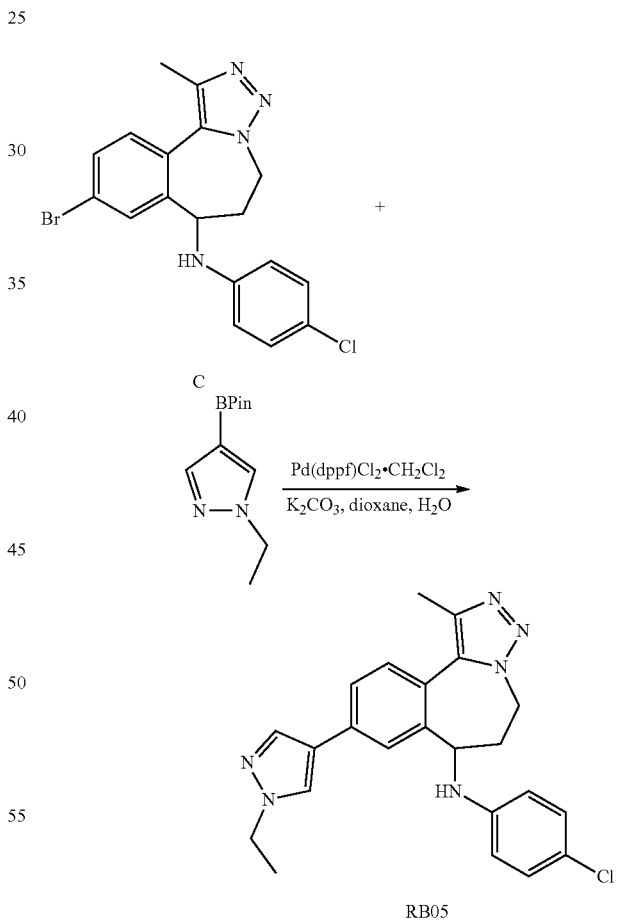

RB05

Synthesis of N-(4-chlorophenyl)-9-(1-ethyl-1H-pyrazol-4-yl)-1-methyl-6,7-dihydro-5H-benzo[c][1,2,3]triazolo[1,5-a]azepin-7-amine (RB05)

C (101.5 mg, 0.25 mmol), 1-ethyl-4-(4,4,5,5-tetramethyl-1,3,2-dioxaborolan-2-yl)-1H-pyrazole (68.7 mg, 0.31 mmol), Pd(dppf)Cl₂-dichloromethane complex (62.5 mg, 0.077 mmol), potassium carbonate (80.3 mg, 0.58 mmol), 1,4-dioxane (12 mL) and water (0.5 mL) were added to a reaction flask in sequence. The air in the reaction flask was replaced with nitrogen three times. Under nitrogen protection, the system was heated to react under reflux. After the reaction was complete, the system was concentrated under reduced pressure, and the residue was separated by column chromatography to obtain 106.1 mg of a crude, which was separated by medium pressure preparative chromatography and lyophilized to obtain 9.8 mg of a pure product.

Product analysis: ¹HNMR (CDCl₃, 400 MHz): 8.16-8.03 (m, 1H), 7.72 (d, J=0.8 Hz, 1H), 7.65-7.56 (m, 2H), 7.49 (d, J=7.8 Hz, 1H), 7.06-6.94 (m, 2H), 6.49 (d, J=7.2 Hz, 1H), 6.38-6.28 (m, 2H), 4.74 (dd, J=14.3, 7.7 Hz, 1H), 4.20-4.04 (m, 3H), 3.99-3.79 (m, 1H), 2.78-2.88 (m, 1H), 2.43 (s, 3H), 2.22-2.29 (m, 1H), 1.38 (t, J=7.3 Hz, 3H);

ESI-MS Calculated for [M+1]⁺=419.18, Found: 419.30;

The product analysis result was consistent with the structure of RB05.

Preparation Example 31, Final Product RB06: N-(4-chlorophenyl)-1-methyl-9-(pyrimidin-5-yl)-6,7-dihydro-5H-benzo[c][1,2,3]triazolo[1,5-a]azepin-7-amine Synthesis of N-(4-chlorophenyl)-1-methyl-9-(pyrimidin-5-yl)-6,7-dihydro-5H-benzo[c][1,2,3]triazolo[1,5-a]azepin-7-amine (RB06)

C (98.2 mg, 0.24 mmol), 5-(4,4,5,5-tetramethyl-1,3,2-dioxaborolan-2-yl)pyrimidine (60.9 mg, 0.29 mmol), Pd(dppf)Cl₂-dichloromethane complex (38.7 mg, 0.047 mmol), potassium carbonate (60.6 mg, 0.44 mmol), 1,4-dioxane (12 mL) and water (0.5 mL) were added to a reaction flask in sequence. The air in the reaction flask was replaced with nitrogen three times. Under nitrogen protection, the system was heated to react under reflux. After the reaction was complete, the system was concentrated under reduced pressure, and the residue was separated by column chromatography to obtain 84.4 mg of a crude, which was separated by medium pressure preparative chromatography and lyophilized to obtain 22.2 mg of a pure product.

Product analysis: ¹HNMR (CDCl₃, 400 MHz): 9.23 (s, 1H), 8.89 (s, 2H), 7.75 (d, J=1.8 Hz, 1H), 7.70-7.57 (m, 2H), 7.12-6.89 (m, 2H), 6.22 (d, J=8.7 Hz, 2H), 4.85 (dd, J=14.2, 7.5 Hz, 1H), 4.31 (dd, J=10.6, 6.7 Hz, 1H), 4.13-3.98 (m, 1H), 3.01-3.11 (m, J=12.9, 7.3 Hz, 1H), 2.57 (s, 3H), 2.41-2.17 (m, 1H);

ESI-MS Calculated for [M+1]⁺=403.14, Found: 403.10;

The product analysis result was consistent with the structure of RB06.

Preparation Example 32, Final Product RB07: N-(4-chlorophenyl)-1-methyl-9-(1H-pyrazol-4-yl)-6,7-dihydro-5H-benzo[c][1,2,3]triazolo[1,5-a]azepin-7-amine

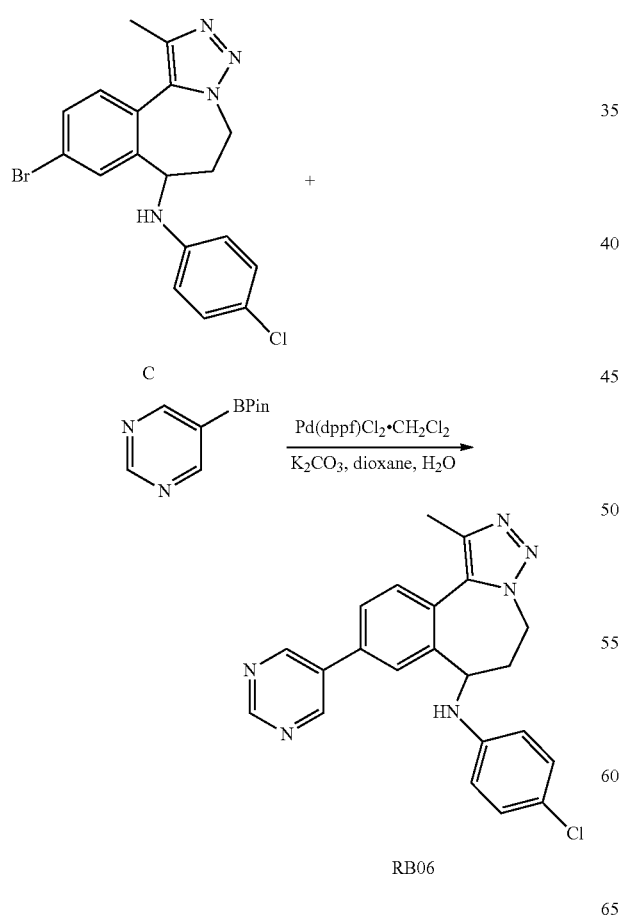

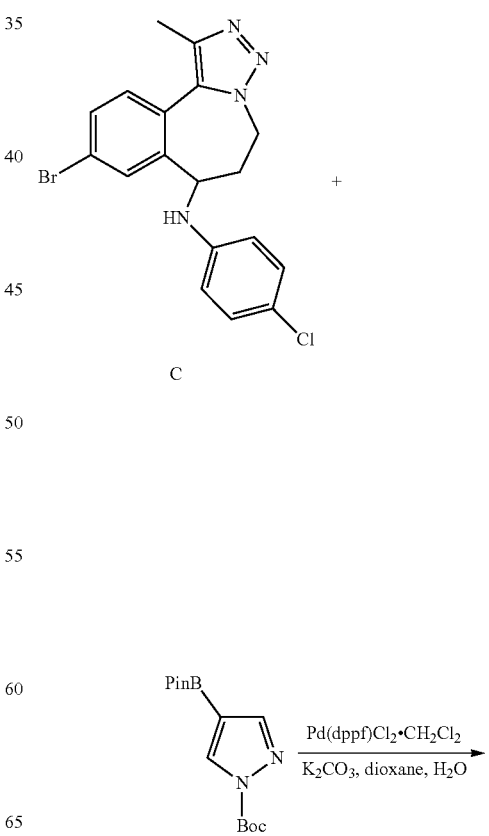

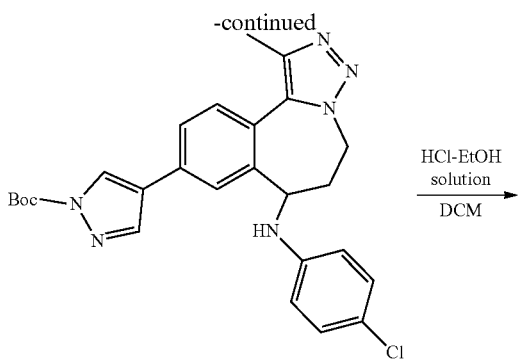

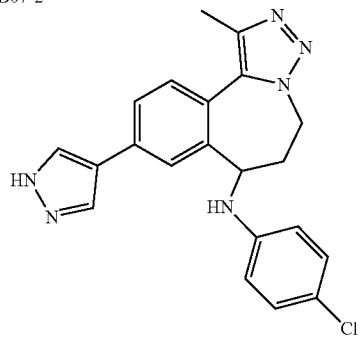

RB07

Synthesis of N-(4-chlorophenyl)-1-methyl-9-(1H-pyrazol-4-yl)-6,7-dihydro-5H-benzo[c][1,2,3]triazolo[1,5-a]azepin-7-amine (RB07)

C (99.5 mg, 0.25 mmol), 4-(4,4,5,5-tetramethyl-1,3,2-dioxaborolan-2-yl)-1H-pyrazole (91.2 mg, 0.31 mmol), Pd(dppf)Cl$_2$-dichloromethane complex (45.2 mg, 0.055 mmol), potassium carbonate (66.9 mg, 0.48 mmol), 1,4-dioxane (16 mL) and water (0.5 mL) were added to a reaction flask in sequence. The air in the reaction flask was replaced with nitrogen three times. Under nitrogen protection, the system was heated to react under reflux. After the reaction was complete, the system was concentrated under reduced pressure, and the residue was separated by column chromatography to obtain 142.1 mg of a crude, which was separated by medium pressure preparative chromatography and lyophilized to obtain 32.9 mg of a pure product RB07-2. To another reaction flask, RB07-2 (32.9 mg, 0.065 mmol), dichloromethane (20 mL) and hydrogen chloride in ethanol (4 M, 10 mL) were added and stirred at room temperature for 3 hours. The system was rotary-evaporated to dryness, extracted with dichloromethane (20 mL) and washed with water (20 mL*2). The organic phase was dried over anhydrous sodium sulfate and filtered with suction, and the filtrate was concentrated under reduced pressure to obtain 20.0 mg of the product, which was lyophilized to obtain 2.8 mg of the product RB07.

Product analysis: $^1$HNMR (CDCl$_3$, 400 MHz): 7.86 (s, 2H), 7.65 (s, 1H), 7.55 (d, J=7.9 Hz, 1H), 7.44 (d, J=7.5 Hz, 1H), 7.00 (d, J=8.0 Hz, 2H), 6.24 (d, J=8.2 Hz, 2H), 4.78 (dd, J=14.1, 7.3 Hz, 1H), 4.28 (t, J=8.2 Hz, 1H), 4.04 (s, 1H), 3.00 (s, 1H), 2.54 (s, 3H), 2.24 (q, J=8.5, 7.4 Hz, 1H);

ESI-MS Calculated for [M+1]$^+$=391.15, Found: 391.10;

The product analysis result was consistent with the structure of RB07.

Preparation Example 33, Final Product RB11: 9-(benzo[d][1,3]dioxol-5-yl)-N-(4-chlorophenyl)-1-methyl-6,7-dihydro-5H-benzo[c][1,2,3]triazolo[1,5-a]azepin-7-amine

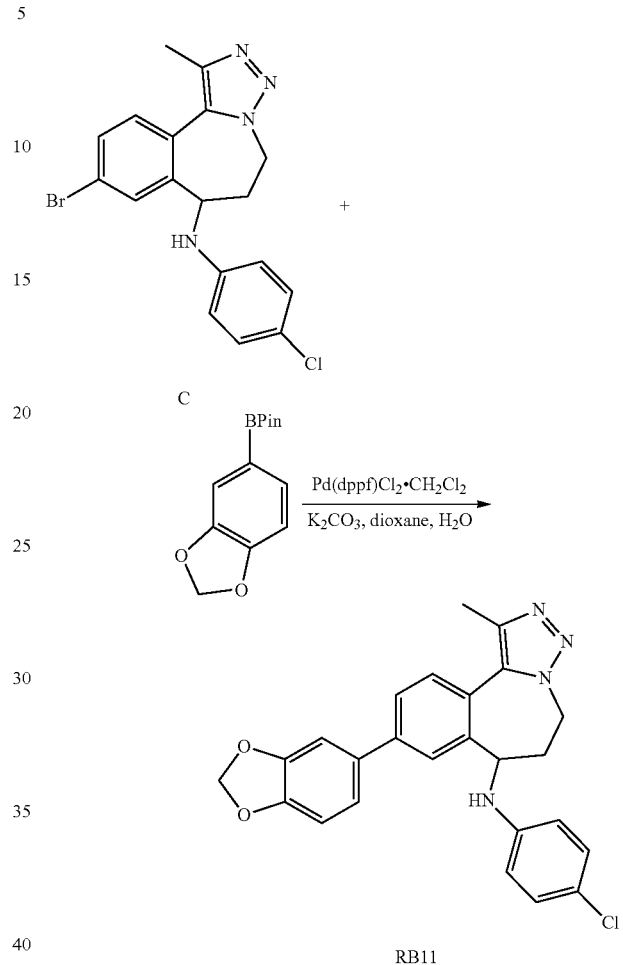

RB11

Synthesis of 9-(benzo[d][1,3]dioxol-5-yl)-N-(4-chlorophenyl)-1-methyl-6,7-dihydro-5H-benzo[c][1,2,3]triazolo[1,5-a]azepin-7-amine (RB11)

C (88.7 mg, 0.22 mmol), 2-(benzo[d][1,3]dioxol-5-yl)-4,4,5,5-tetramethyl-1,3,2-dioxaborolane (65.0 mg, 0.26 mmol), Pd(dppf)Cl$_2$-dichloromethane complex (44.8 mg, 0.055 mmol), potassium carbonate (64.5 mg, 0.47 mmol), 1,4-dioxane (12 mL) and water (0.5 mL) were added to a reaction flask in sequence. The air in the reaction flask was replaced with nitrogen three times. Under nitrogen protection, the system was heated to react under reflux. After the reaction was complete, the system was concentrated under reduced pressure, and the residue was separated by column chromatography to obtain 80.1 mg of a crude, which was separated by medium pressure preparative chromatography and lyophilized to obtain 27.8 mg of a pure product.

Product analysis: $^1$HNMR (CDCl$_3$, 400 MHz): 7.66 (s, 1H), 7.55 (d, J=7.8 Hz, 1H), 7.46 (d, J=7.8 Hz, 1H), 7.05-6.92 (m, 4H), 6.86 (d, J=8.4 Hz, 1H), 6.23 (d, J=8.3 Hz, 2H), 6.00 (s, 2H), 4.77 (s, 1H), 4.29 (s, 1H), 4.01 (d, J=38.7 Hz, 2H), 3.00 (s, 1H), 2.54 (s, 3H), 2.23 (s, 1H);

ESI-MS Calculated for [M+1]$^+$=445.15, Found: 445.20;

The product analysis result was consistent with the structure of RB11.

Preparation Example 34, Final Product RB31: N-(4-chlorophenyl)-1-methyl-9-(1H-pyrrolo[2,3-b]pyridin-4-yl)-6,7-dihydro-5H-benzo[c][1,2,3]triazolo[1,5-a]azepin-7-amine

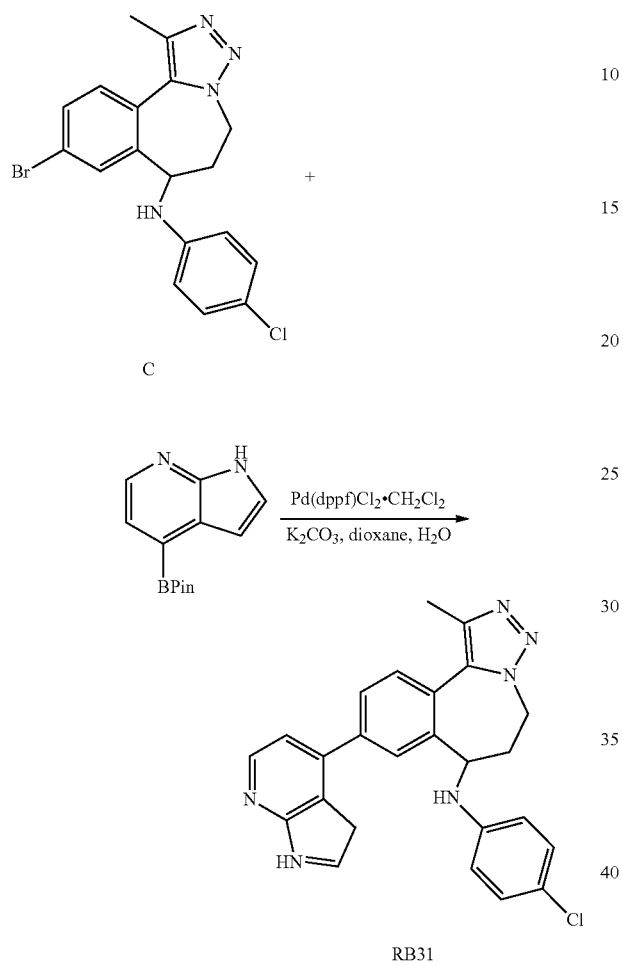

RB31

Synthesis of N-(4-chlorophenyl)-1-methyl-9-(1H-pyrrolo[2,3-b]pyridin-4-yl)-6,7-dihydro-5H-benzo[c][1,2,3]triazolo[1,5-a]azepin-7-amine (RB31)

C (84.9 mg, 0.21 mmol), 4-(4,4,5,5-tetramethyl-1,3,2-dioxaborolan-2-yl)-2,3-dihydro-1H-pyrrolo[2,3-b]pyridine (110.58 mg, 0.45 mmol), Pd(dppf)Cl$_2$-dichloromethane complex (40.5 mg, 0.049 mmol), potassium carbonate (84.8 mg, 0.61 mmol), 1,4-dioxane (10 mL) and water (0.5 mL) were added to a reaction flask in sequence. The air in the reaction flask was replaced with nitrogen three times. Under nitrogen protection, the system was heated to react under reflux. After the reaction was complete, the system was concentrated under reduced pressure, and the residue was separated by column chromatography to obtain 43.4 mg of a crude, which was separated by medium pressure preparative chromatography and lyophilized to obtain 1.9 mg of a pure product.

ESI-MS Calculated for [M+1]$^+$=441.16, Found: 441.10. The calculated value was consistent with the found value.

Preparation Example 35, Final Product RB42: 9-(1H-benzo[d]imidazol-4-yl)-N-(4-chlorophenyl)-1-methyl-6,7-dihydro-5H-benzo[c][1,2,3]triazolo[1,5-a]azepin-7-amine

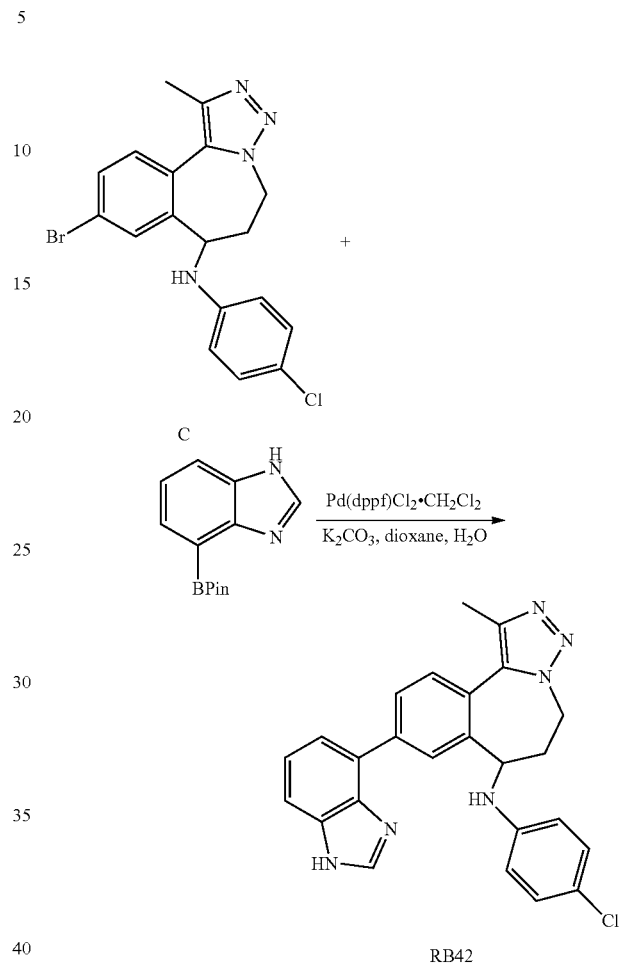

RB42

Synthesis of 9-(1H-benzo[d]imidazol-4-yl)-N-(4-chlorophenyl)-1-methyl-6,7-dihydro-5H-benzo[c][1,2,3]triazolo[1,5-a]azepin-7-amine (RB42)

C (70.4 mg, 0.17 mmol), 4-(4,4,5,5-tetramethyl-1,3,2-dioxaborolan-2-yl)-1H-benzo[d]imidazole (185.51 mg, 0.76 mmol), Pd(dppf)Cl$_2$-dichloromethane complex (36.0 mg, 0.044 mmol), potassium carbonate (78.2 mg, 0.57 mmol), 1,4-dioxane (8 mL) and water (0.5 mL) were added to a reaction flask in sequence. The air in the reaction flask was replaced with nitrogen three times. Under nitrogen protection, the system was heated to react under reflux. After the reaction was complete, the system was concentrated under reduced pressure, and the residue was separated by column chromatography to obtain 122.6 mg of a crude, which was separated by medium pressure preparative chromatography and lyophilized to obtain 23.4 mg of a pure product.

$^1$HNMR (400 MHz, DMSO-d$_6$): 12.61 (s, 1H), 8.38-8.20 (m, 2H), 8.03 (d, J=1.8 Hz, 1H), 7.61 (d, J=8.0 Hz, 1H), 7.52 (dd, J=7.2, 1.7 Hz, 1H), 7.33-7.20 (m, 2H), 7.04-6.88 (m, 2H), 6.60 (d, J=7.0 Hz, 1H), 6.48-6.12 (m, 2H), 4.78 (dd, J=14.2, 7.9 Hz, 1H), 4.12-4.22 (m, 1H), 3.94-4.02 (m, 1H), 2.82-2.89 (m, 1H), 2.48 (s, 3H), 2.39-2.27 (m, 1H);

ESI-MS Calculated for [M+1]$^+$=441.16, Found: 441.00; The product analysis result was consistent with the structure of RB42.

Preparation Example 36, Final Product RB43: N-(4-chlorophenyl)-9-(3H-imidazo[4,5-b]pyridin-6-yl)-1-methyl-6,7-dihydro-5H-benzo[c][1,2,3]triazolo[1,5-a]azepin-7-amine

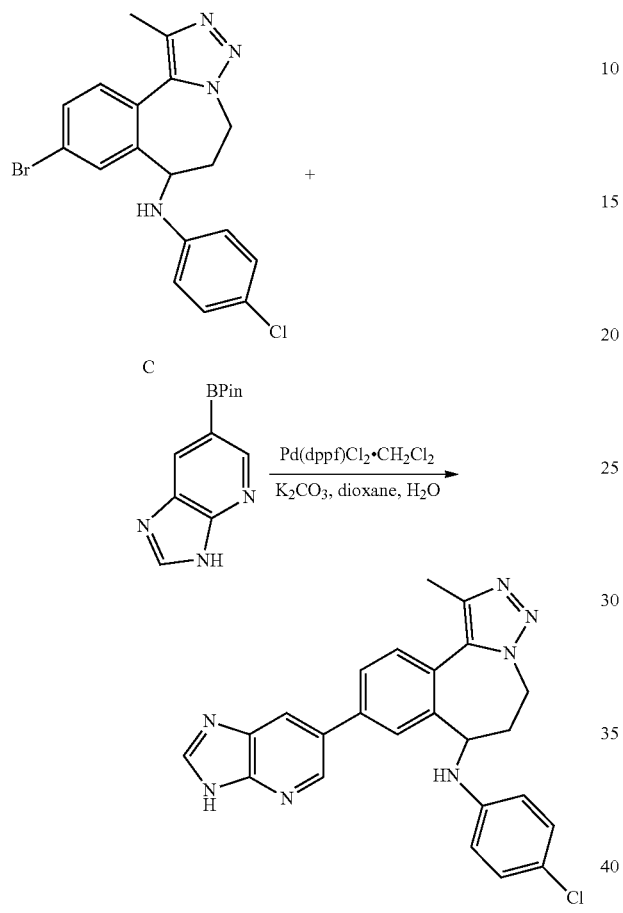

RB43

Synthesis of N-(4-chlorophenyl)-9-(3H-imidazo[4,5-b]pyridin-6-yl)-1-methyl-6,7-dihydro-5H-benzo[c][1,2,3]triazolo[1,5-a]azepin-7-amine (RB43)

C (70.2 mg, 0.17 mmol), 6-(4,4,5,5-tetramethyl-1,3,2-dioxaborolan-2-yl)-3H-imidazo[4,5-b]pyridine (157.19 mg, 0.64 mmol), Pd(dppf)Cl$_2$-dichloromethane complex (44.5 mg, 0.054 mmol), potassium carbonate (78.3 mg, 0.57 mmol), 1,4-dioxane (8 mL) and water (0.5 mL) were added to a reaction flask in sequence. The air in the reaction flask was replaced with nitrogen three times. Under nitrogen protection, the system was heated to react under reflux. After the reaction was complete, the system was concentrated under reduced pressure, and the residue was separated by column chromatography to obtain 134.8 mg of a crude, which was separated by medium pressure preparative chromatography and lyophilized to obtain 16.1 mg of a pure product.

$^1$HNMR (400 MHz, DMSO-d$_6$): 12.88 (s, 1H), 8.50 (d, J=16.4 Hz, 2H), 8.15 (s, 1H), 7.82 (dd, J=7.8, 1.9 Hz, 1H), 7.76 (d, J=1.9 Hz, 1H), 7.63 (d, J=7.9 Hz, 1H), 7.04-6.95 (m, 2H), 6.59 (d, J=7.8 Hz, 1H), 6.41-6.31 (m, 2H), 4.78 (dd, J=14.4, 7.8 Hz, 1H), 4.17-4.23 (m, 1H), 3.92-4.00 (m, 1H), 2.93-2.81 (m, 1H), 2.47 (s, 2H), 2.26-2.34 (m, 1H);

ESI-MS Calculated for [M+1]$^+$=442.15; Found: 442.00; The product analysis result was consistent with the structure of RB43.

Preparation Example 37, Final Product RB48: N-(4-chlorophenyl)-1-methyl-9-(1-methyl-1H-1,2,3-triazol-4-yl)-6,7-dihydro-5H-benzo[c][1,2,3]triazolo[1,5-a]azepin-7-amine

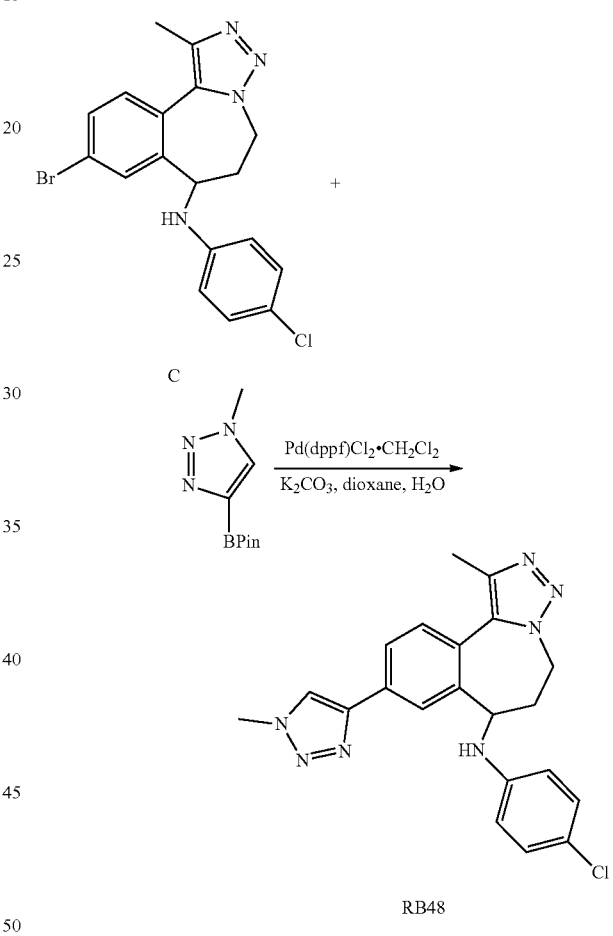

RB48

Synthesis of N-(4-chlorophenyl)-1-methyl-9-(1-methyl-1H-1,2,3-triazol-4-yl)-6,7-dihydro-5H-benzo[c][1,2,3]triazolo[1,5-a]azepin-7-amine (RB48)

C (79.8 mg, 0.2 mmol), 1-methyl-4-(4,4,5,5-tetramethyl-1,3,2-dioxaborolan-2-yl)-1H-1,2,3-triazole (157.19 mg, 0.64 mmol), Pd(dppf)Cl$_2$-dichloromethane complex (27.0 mg, 0.033 mmol), potassium carbonate (68.8 mg, 0.50 mmol), 1,4-dioxane (10 mL) and water (0.5 mL) were added to a reaction flask in sequence. The air in the reaction flask was replaced with nitrogen three times. Under nitrogen protection, the system was heated to react under reflux. After the reaction was complete, the system was concentrated under reduced pressure, and the residue was separated by column chromatography to obtain 176.3 mg of a crude, which was separated by medium pressure preparative chromatography and lyophilized to obtain 1.5 mg of a pure product.

ESI-MS Calculated for [M+1]$^+$=406.15, Found: 406.10. The calculated value was consistent with the found value.

Preparation Example 38, Final Product RB66: N-(4-chlorophenyl)-N,1-dimethyl-9-(1-methyl-1H-pyrazol-4-yl)-6,7-dihydro-5H-benzo[c][1,2,3]triazolo[1,5-a]azepin-7-amine

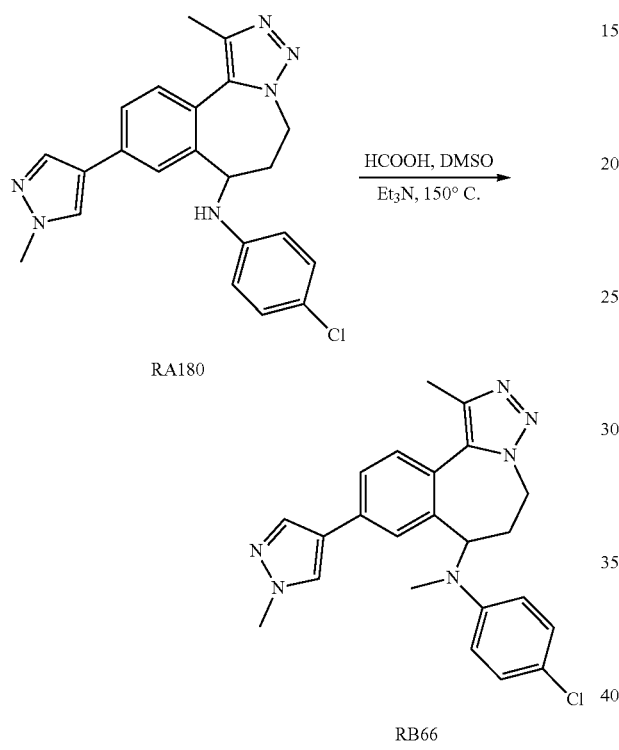

Synthesis of N-(4-chlorophenyl)-N,1-dimethyl-9-(1-methyl-1H-pyrazol-4-yl)-6,7-dihydro-5H-benzo[c][1,2,3]triazolo[1,5-a]azepin-7-amine (RB66)

RA180 (52.1 mg, 0.13 mmol), DMSO (5 mL), formic acid (135.3 mg, 2.94 mmol) and triethylamine (315.7 mg, 3.12 mmol) were added to a reaction flask in sequence. The air in the reaction flask was replaced with nitrogen three times. Under nitrogen protection, the system was heated to 150° C. to react for 24 h. After the reaction was complete, the system was added with a NaOH solution (1M, 4 mL) and dichloromethane (20 mL), shaken and separated. The aqueous layer was extracted with dichloromethane (20 mL). The combined organic phase was washed with water (20 mL*2), dried over anhydrous sodium sulfate and filtered with suction. The filtrate was concentrated under reduced pressure and the residue was separated by PLC to obtain 18.2 mg of a crude, which was separated by medium pressure preparative chromatography and lyophilized to obtain 4.8 mg of a pure product ESI-MS Calculated for [M+1]$^+$=419.18; Found: 419.20. The calculated value was consistent with the found value.

Preparation Example 39, Final Product LB62: 2-(3-((1-methyl-9-(1-methyl-1H-pyrazol-4-yl)-6,7-dihydro-5H-benzo[c][1,2,3]triazolo[1,5-a]azepin-7-yl)amino)phenyl) acetic acid

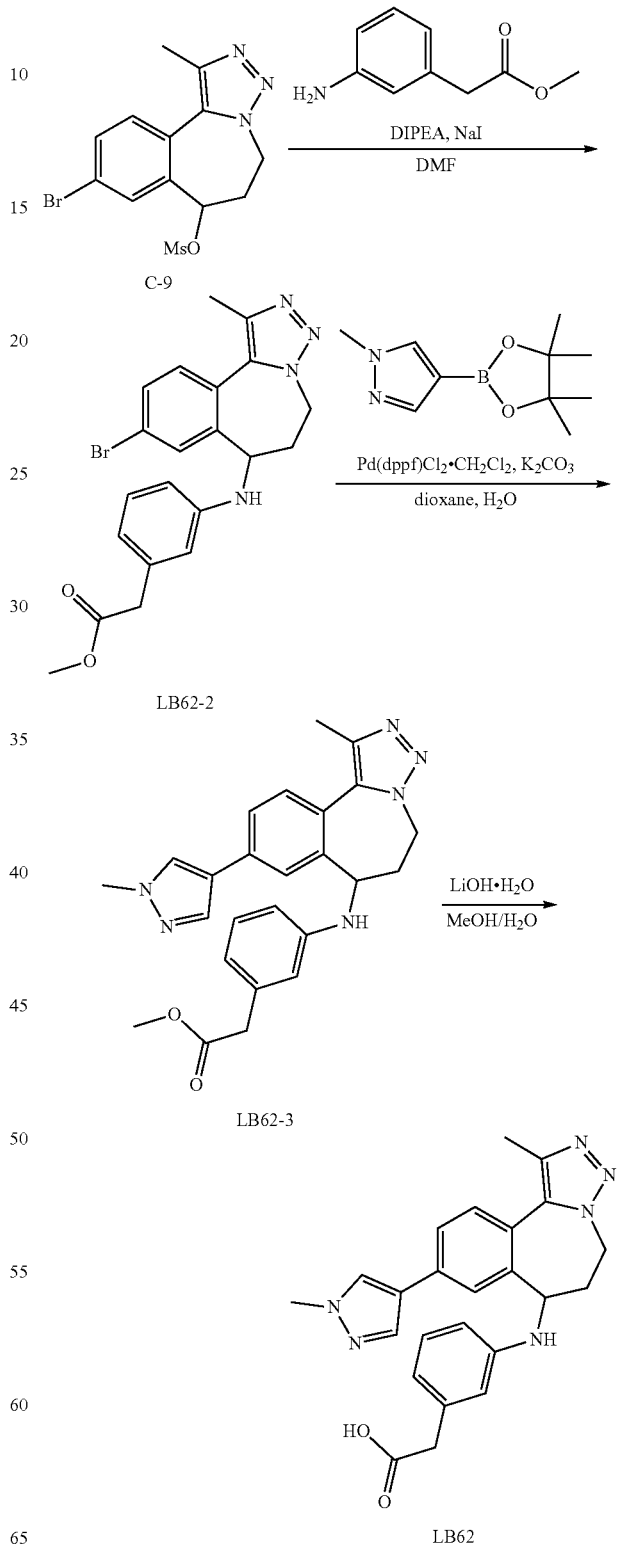

Step 1: Synthesis of methyl 2-(3-((9-bromo-1-methyl-6,7-dihydro-5H-benzo[c][1,2,3]triazolo[1,5-a]azepin-7-yl)amino)phenyl)acetate (LB62-2)

C-9 (234.4 mg, 0.63 mmol), methyl 3-aminophenylacetate (261.1 mg, 1.58 mmol), DMF (20 mL), DIPEA (409.6 mg, 3.17 mmol) and sodium iodide (11.3 mg, 0.076 mmol) were added to a reaction flask and heated to 60° C. After the reaction was complete, the system was cooled down, added with water (100 mL) and EA (20 mL), shaken and separated. The aqueous phase was extracted with EA (20 mL*3). The combined organic phase was washed with water (50 mL*3) and saturated brine (50 mL), dried over anhydrous sodium sulfate and filtered with suction. The filtrate was concentrated under reduced pressure, and the residue was separated by PLC to obtain 180.3 mg of the target compound.

ESI-MS Calculated for [M+H]$^+$=441.00; Found: 441.00. The found value was consistent with the caculated value.

Step 2: Synthesis of methyl 2-(3-((1-methyl-9-(1-methyl-1H-pyrazol-4-yl)-6,7-dihydro-5H-benzo[c][1,2,3]triazolo[1,5-a]azepin-7-yl)amino)phenyl)acetate (LB62-3)

LB62-2 (180.3 mg, 0.41 mmol), 1-methyl-4-(4,4,5,5-tetramethyl-1,3,2-dioxaborolan-2-yl)-1H-pyrazole (111.8 mg, 0.54 mmol), potassium carbonate (92.4 mg, 0.67 mmol), 1,4-dioxane (20 mL) and water (1 mL) were added to a reaction flask. The air in the reaction flask was replaced with nitrogen three times. The system was added with Pd(dppf)Cl$_2$-dichloromethane complex (18.1 mg, 0.023 mmol), and the air in the reaction flask was replaced with nitrogen three times again. The system was heated to reflux for reaction, and the reaction was monitored by LC-MS. After the reaction was complete, the system was cooled down, added with water (40 mL) and EA (20 mL), shaken and separated. The aqueous phase was extracted with EA (20 mL*3). The combined organic phase was washed with water (60 mL) and saturated brine (40 mL), dried over anhydrous sodium sulfate and filtered with suction. The filtrate was concentrated under reduced pressure, and the residue was separated by PLC to obtain 124.6 mg of a crude.

ESI-MS Calculated for [M+H]$^+$=443.21; Found: 443.10. The found value was consistent with the caculated value.

Step 3: Synthesis of 2-(3-((1-methyl-9-(1-methyl-1H-pyrazol-4-yl)-6,7-dihydro-5H-benzo[c][1,2,3]triazolo[1,5-a]azepin-7-yl)amino)phenyl) acetic acid (LB62)

LB62-3 (40.1 mg, 0.091 mmol), methanol (10 mL), water (10 mL) and lithium hydroxide monohydrate (50.1 mg, 1.19 mmol) were added to a reaction flask and stirred at room temperature. After the reaction was complete, the system was concentrated under reduced pressure, and the residue was added with water (50 mL) and washed with EA (20 mL*2), and the organic phase was discarded. The aqueous phase was adjusted pH to 3 with 1 mol/L diluted hydrochloric acid, and extracted with EA (20 mL*2). The combined organic phase was washed with water (20 mL*2) and saturated brine (40 mL), dired with anhydrous sodium sulfate and filtered with suction. The filtrate was concentrated under reduced pressure and the residue was separated by fast medium pressure preparative chromatography to obtain 3.5 mg of the product.

ESI-MS Calculated for [M+H]$^+$=429.20; Found: 429.00. The found value was consistent with the caculated value.

Preparation Example 40, Final Product LB63: methyl 2-(3-((1-methyl-9-(1-methyl-1H-pyrazol-4-yl)-6,7-dihydro-5H-benzo[c][1,2,3]triazolo[1,5-a]azepin-7-yl)amino)phenyl)acetate

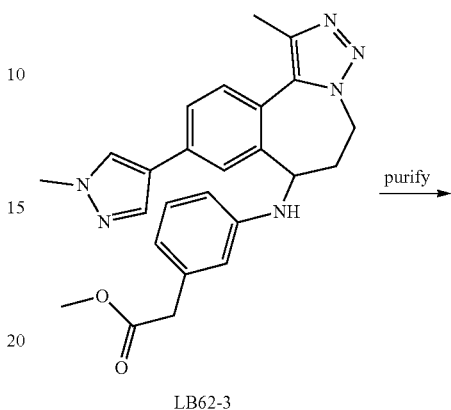

LB62-3 purify →

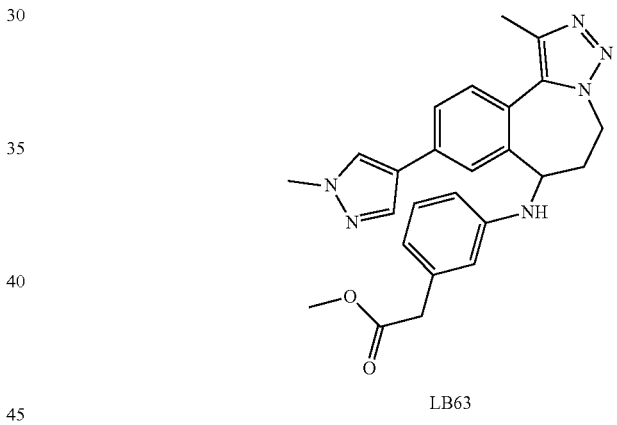

LB63

Synthesis of methyl 2-(3-((1-methyl-9-(1-methyl-1H-pyrazol-4-yl)-6,7-dihydro-5H-benzo[c][1,2,3]triazolo[1,5-a]azepin-7-yl)amino)phenyl)acetate (LB63)

LB62-3 (30.1 mg) was weighed and separated by fast medium pressure preparative chromatography to obtain 15.6 mg of the target compound.

Product analysis: $^1$HNMR (400 MHz, Chloroform-d): δ 7.72 (s, 1H), 7.64 (d, J=1.7 Hz, 1H), 7.60 (s, 1H), 7.49 (dd, J=7.8, 1.8 Hz, 1H), 7.40 (d, J=7.8 Hz, 1H), 6.98 (t, J=7.8 Hz, 1H), 6.56 (d, J=7.6 Hz, 1H), 6.36 (d, J=2.1 Hz, 1H), 6.13 (dd, J=8.0, 2.2 Hz, 1H), 4.76 (dd, J=14.0, 7.5 Hz, 1H), 4.30 (s, 1H), 4.01-1.09 (m, 1H), 3.93 (s, 3H), 3.61 (s, 3H), 3.45 (d, J=2.1 Hz, 2H), 2.95-3.01 (m, 1H), 2.53 (s, 3H), 2.21 (s, 1H).

ESI-MS Calculated for [M+H]$^+$=443.21; Found: 443.10. The found value was consistent with the caculated value.

Preparation Example 41, Final Product LB68: 2-(4-((1-methyl-9-(1-methyl-1H-pyrazol-4-yl)-6,7-di-hydro-5H-benzo[c][1,2,3]triazolo[1,5-a]azepin-7-yl)amino)phenoxy)ethanol

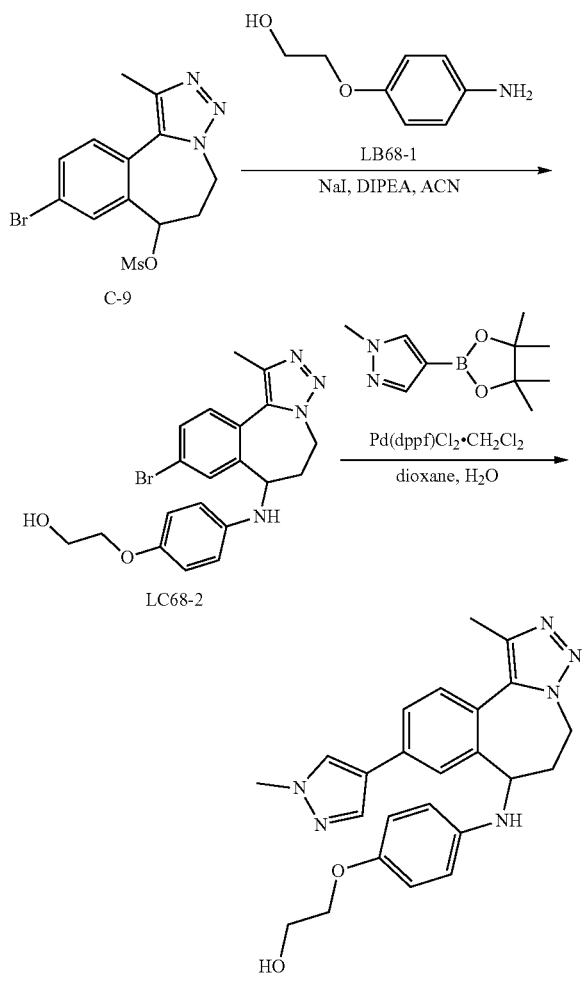

Step 1: Synthesis of 2-(4-((9-bromo-1-methyl-6,7-dihydro-5H-benzo[c][1,2,3]triazolo[1,5-a]azepin-7-yl)amino)phenoxy)ethanol (LB68-2)

C-9 (100.1 mg, 0.27 mmol), LB68-1 (126.6 mg, 0.83 mmol), acetonitrile (10 mL), DIPEA (205.2 mg, 1.59 mmol) and sodium iodide (4.1 mg, 0.027) were added to a reaction flask and heated to 60° C. After the reaction was complete, the system was cooled down, added with water (50 mL) and EA (20 mL), shaken and separated. The aqueous phase was extracted with EA (20 mL*2). The combined organic phase was washed with water (20 mL*2) and saturated brine (40 mL), dried over anhydrous sodium sulfate and filtered with suction. The filtrate was concentrated under reduced pressure, and the residue was separated by PLC to obtain 96.8 mg of the target compound.

ESI-MS Calculated for [M+H]$^+$=429.08; Found: 428.90. The found value was consistent with the caculated value.

Step 2: Synthesis of 2-(4-((1-methyl-9-(1-methyl-1H-pyrazol-4-yl)-6,7-dihydro-5H-benzo[c][1,2,3]triazolo[1,5-a]azepin-7-yl)amino)phenoxy)ethanol (LB68)

LB68-2 (96.8 mg, 0.23 mmol), 1-methyl-4-(4,4,5,5-tetramethyl-1,3,2-dioxaborolan-2-yl)-1H-pyrazole (61.6 mg, 0.30 mmol), potassium carbonate (49.9 mg, 0.36 mmol), 1,4-dioxane (10 mL) and water (0.5 mL) were added to a reaction flask, and the air in the reaction system was replaced with nitrogen three times. The system was added with Pd(dppf)Cl$_2$-dichloromethane complex (9.6 mg, 0.012 mmol), and the air in the reaction flask was replaced with nitrogen three times again. The external temperature of the system was raised to 110° C. After the reaction was complete, the system was cooled down, added with water (30 mL) and EA (20 mL), shaken and separated. The aqueous phase was extracted with EA (20 mL*2). The combined organic phase was washed with water (20 mL*3) and saturated brine (50 mL), dried over anhydrous sodium sulfate and filtered with suction. The filtrate was concentrated under reduced pressure, and the residue was separated by PLC to obtain 16.8 mg of the product.

Product analysis: $^1$HNMR (400 MHz, CDCl$_3$): δ 7.71 (d, J=0.8 Hz, 1H), 7.66 (d, J=1.8 Hz, 1H), 7.57 (d, J=0.8 Hz, 1H), 7.49 (dd, J=7.8, 1.8 Hz, 1H), 7.40 (d, J=7.8 Hz, 1H), 6.70-6.62 (m, 2H), 6.30-6.24 (m, 2H), 4.72-4.78 (m, 1H), 4.23 (dd, J=10.4, 6.8 Hz, 1H), 3.98-4.05 (m, 1H), 3.96-3.90 (m, 5H), 3.87 (d, J=6.0 Hz, 2H), 3.73 (d, J=9.6 Hz, 1H), 2.92-3.02 (m, 1H), 2.52 (s, 3H), 2.16-2.24 (m, 1H).

ESI-MS Calculated for [M+H]$^+$=431.21; Found: 431.00. The found value was consistent with the caculated value.

Preparation Example 42, Final Product LB71: 2-(3-((1-methyl-9-(1-methyl-1H-pyrazol-4-yl)-6,7-di-hydro-5H-benzo[c][1,2,3]triazolo[1,5-a]azepin-7-yl)amino)phenyl)ethanol

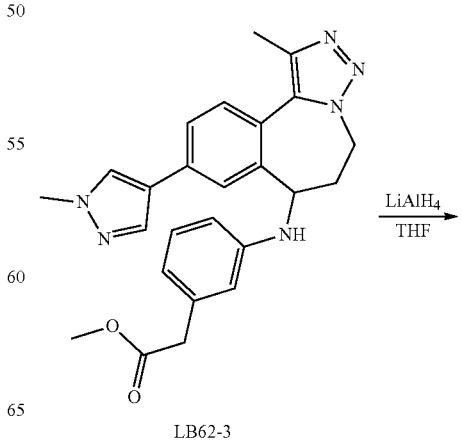

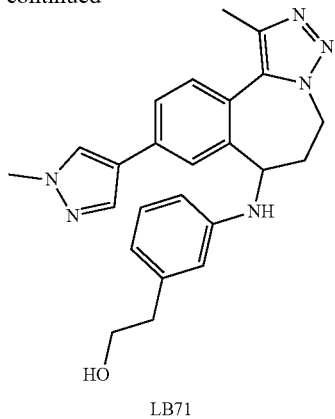

LB71

Synthesis of 2-(3-((1-methyl-9-(1-methyl-1H-pyrazol-4-yl)-6,7-dihydro-5H-benzo[c][1,2,3]triazolo[1,5-a]azepin-7-yl)amino)phenyl)ethanol (LB71)

LB62-3 (47.1 mg, 0.11 mmol) and THF (20 mL) were added to a 50 mL single necked flask, and the air in the reaction system was replaced with nitrogen three times. The system was cooled to 0-10° C. and added with LiAlH$_4$ (42.2 mg, 1.11 mmol) in batches. After completion of addition, the reaction was carried out for 1 h at 0-10° C. The system was quenched by addition of water (20 mL), concentrated under reduced pressure to remove tetrahydrofuran, added with EA (20 mL), shaken and separated. The aqueous phase was extracted with EA (20 mL*2). The combined organic phase was washed with water (20 mL*2) and saturated brine (40 mL), dried over anhydrous sodium sulfate and filtered with suction. The filtrate was concentrated under reduced pressure, and the residue was separated by medium-pressure preparative chromatography and lyophilized to obtain 16.1 mg of the product.

Product analysis: $^1$HNMR (400 MHz, CDC13): δ 7.70 (d, J=0.8 Hz, 1H), 7.65 (d, J=1.8 Hz, 1H), 7.57 (d, J=0.8 Hz, 1H), 7.49 (dd, J=7.8, 1.8 Hz, 1H), 7.40 (d, J=7.9 Hz, 1H), 6.98 (t, J=7.8 Hz, 1H), 6.51-6.54 (m, 1H), 6.27 (t, J=2.0 Hz, 1H), 6.11-6.14 (m, 1H), 4.72-4.78 (m, 1H), 4.28-4.33 (m, 1H), 3.92-4.09 (m, 1H), 3.92 (s, 5H), 3.74 (t, J=6.5 Hz, 2H), 3.05-2.92 (m, 1H), 2.69 (t, J=6.4 Hz, 2H), 2.53 (s, 3H), 2.18-2.26 (m, 1H).

ESI-MS Calculated for [M+H]$^+$=414.22; Found: 414.10. The found value was consistent with the caculated value.

Preparation Example 43, Final Product LB77: 2-(3-((1-methyl-9-(1-methyl-1H-pyrazol-4-yl)-6,7-dihydro-5H-benzo[c][1,2,3]triazolo[1,5-a]azepin-7-yl)amino)phenoxy)ethanol

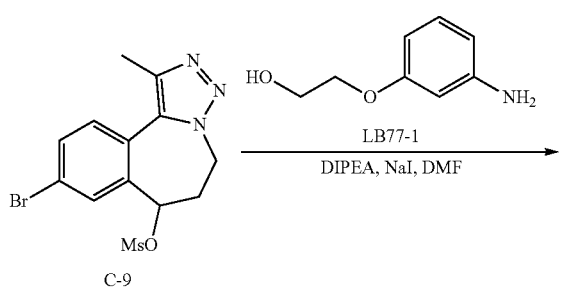

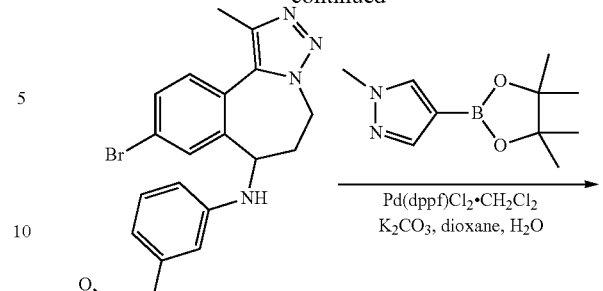

LB77-2

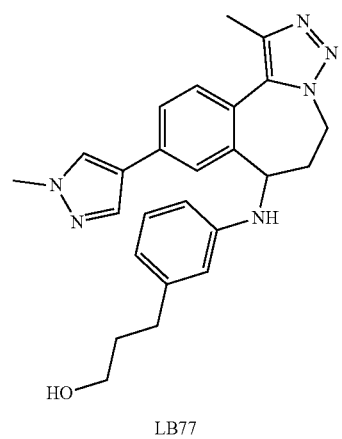

LB77

Step 1: Synthesis of 2-(3-((9-bromo-1-methyl-6,7-dihydro-5H-benzo[c][1,2,3]triazolo[1,5-a]azepin-7-yl)amino)phenoxy)ethanol (LB77-2)

C-9 (100.3 mg, 0.27 mmol), LB77-1 (128.6 mg, 0.84 mmol), DMF (10 mL), DIPEA (205.2 mg, 1.59 mmol) and sodium iodide (4.1 mg, 0.028 mmol) were added to a reaction flask and heated to 60° C. After the reaction was complete, the system was cooled down, added with water (40 mL) and EA (20 mL), shaken and sepatated. The aqueous phase was extracted with EA (20 mL*2). The combined organic phase was washed with water (20 mL*3) and saturated brine (50 mL), dired with anhydrous sodium sulfate and filtered with suction. The filtrate was concentrated under reduced pressure, and the residue was separated by PLC to obtain 77.4 mg of the target compound.

ESI-MS Calculated for [M+H]$^+$=429.08; Found: 429.00. The found value was consistent with the caculated value.

Step 2: Synthesis of 2-(3-((1-methyl-9-(1-methyl-1H-pyrazol-4-yl)-6,7-dihydro-5H-benzo[c][1,2,3]triazolo[1,5-a]azepin-7-yl)amino)phenoxy)ethanol (LB77)

LB77-2 (77.4 mg, 0.18 mmol), 1-methyl-4-(4,4,5,5-tetramethyl-1,3,2-dioxaborolan-2-yl)-1H-pyrazole (49.9 mg, 0.24 mmol), potassium carbonate (39.6 mg, 0.29 mmol), 1,4-dioxane (10 mL) and water (0.5 mL) were added to a reaction flask, and the air in the reaction system was replaced with nitrogen three times. The system was added with Pd(dppf)Cl$_2$-dichloromethane complex (7.8 mg, 0.0096 mmol), and the air in the reaction system was replaced with nitrogen three times again. The system was heated to reflux. After the reaction was complete, the system was cooled down, added with water (40 mL) and EA (20 mL), shaken and sepatated. The aqueous phase was extracted with EA (20 mL*2). The combined organic phase was washed with water (30 mL*2) and saturated brine (50 mL), dried over anhydrous sodium sulfate and filtered with suction. The filtrate was concentrated under reduced pressure, and the residue was separated by medium-pressure preparative chromatography and lyophilized to obtain 24.1 mg of the product.

ESI-MS Calculated for [M+H]$^+$=431.21; Found: 431.20. The found value was consistent with the caculated value.

Preparation Example 44, Final Product LB83: 1,1,1,3,3,3-hexafluoro-2-(4-((1-methyl-9-(1-methyl-1H-pyrazol-4-yl)-6,7-dihydro-5H-Benzo[c][1,2,3]triazolo[1,5-a]azepin-7-yl)amino)phenyl)propan-2-ol

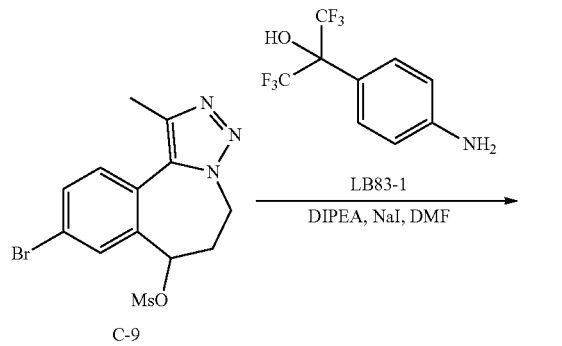

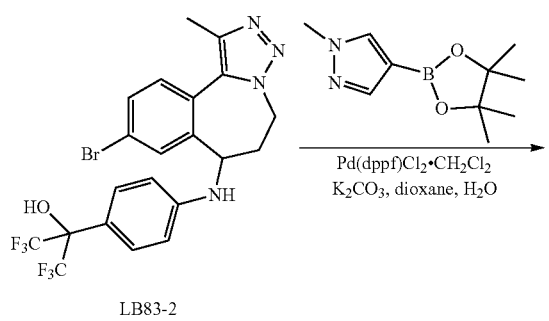

Step 1: Synthesis of 2-(4-((9-bromo-1-methyl-6,7-dihydro-5H-benzo[c][1,2,3]triazolo[1,5-a]azepin-7-yl)amino)phenyl)-1,1,1,3,3,3-hexafluoropropan-2-ol (LB83-2)

C-9 (101.1 mg, 0.27 mmol), LB83-1 (228.8 mg, 0.88 mmol), DMF (10 mL), DIPEA (187.4 mg, 1.45 mmol) and sodium iodide (4.9 mg, 0.032 mmol) were added to a reaction flask and heated to 60° C. for reaction. After the reaction was complete, the system was cooled down, added with water (40 mL) and EA (20 mL), shaken and sepatated. The aqueous phase was extracted with EA (20 mL*2). The combined organic phase was washed with water (20 mL*3) and saturated brine (40 mL), dried over anhydrous sodium sulfate and filtered with suction. The filtrate was concentrated under reduced pressure, and the residue was separated by PLC to obtain 32.3 mg of the target compound.

ESI-MS Calculated for [M+H]$^+$=535.05; Found: 535.00. The found value was consistent with the caculated value.

Step 2: Synthesis of 1,1,1,3,3,3-hexafluoro-2-(4-((1-methyl-9-(1-methyl-1H-pyrazol-4-yl)-6,7-dihydro-5H-Benzo[c][1,2,3]triazolo[1,5-a]azepin-7-yl)amino)phenyl)propan-2-ol (LB83)

LB83-2 (32.3 mg, 0.060 mmol), 1-methyl-4-(4,4,5,5-tetramethyl-1,3,2-dioxaborolan-2-yl)-1H-pyrazole (17.0 mg, 0.082 mmol), potassium carbonate (12.7 mg, 0.092 mmol), 1,4-dioxane (5 mL) and water (0.25 mL) were added to a reaction flask, and the air in the reaction system was replaced with nitrogen three times. The system was added with Pd(dppf)Cl$_2$-dichloromethane complex (2.5 mg, 0.0030 mmol), and the air in the reaction system was replaced with nitrogen three times again. The reaction was carried out in a bath at 110° C. After the reaction was complete, the system was cooled down, added with water (40 mL) and EA (20 mL), shaken and sepatated. The aqueous phase was extracted with EA (20 mL*2). The combined organic phase was washed with water (20 mL*2) and saturated brine (50 mL), dired with anhydrous sodium sulfate and filtered with suction. The filtrate was concentrated under reduced pressure, and the residue was separated by PLC to obtain 15.5 mg of a crude, which was separated by medium pressure preparative chromatography and lyophilized to obtain 12.1 mg of the product.

ESI-MS Calculated for [M+H]$^+$=537.18; Found: 537.00. The found value was consistent with the caculated value.

Preparation Example 45, Final Product LB86: 1-methyl-9-(1-methyl-1H-pyrazol-4-yl)-N-(quinolin-5-yl)-6,7-dihydro-5H-benzo[c][1,2,3]triazolo[1,5-a]azepin-7-amine

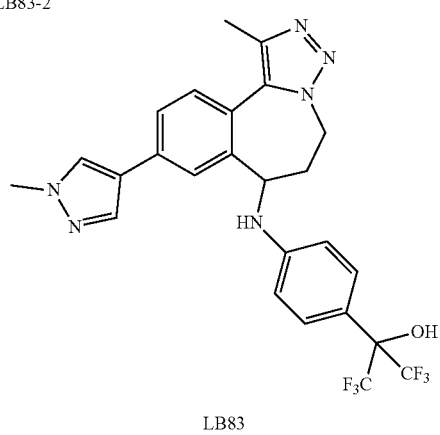

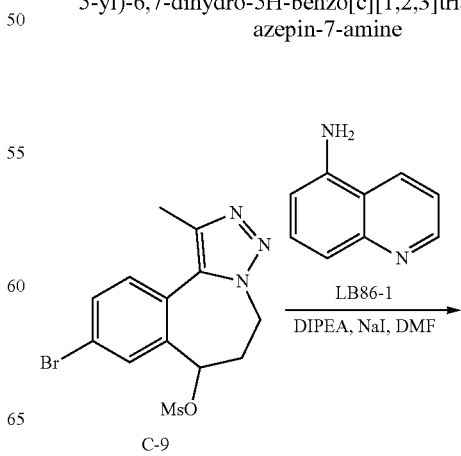

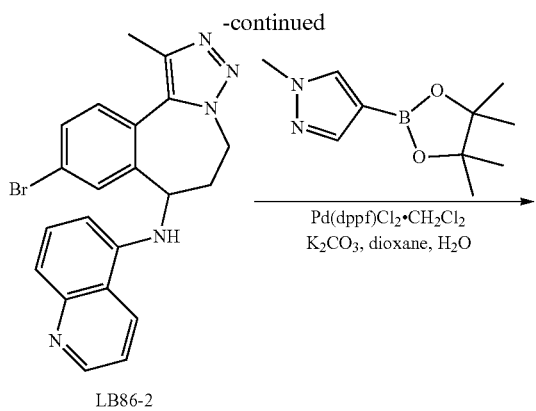

LB86-2

Step 1: Synthesis of 9-bromo-1-methyl-N-(quinolin-5-yl)-6,7-dihydro-5H-benzo[c][1,2,3]triazolo[1,5-a]azepin-7-amine (LB86-2)

C-9 (100.3 mg, 0.27 mmol), LB86-1 (77.9 mg, 0.54 mmol), DMF (10 mL), DIPEA (174.5 mg, 1.35 mmol) and sodium iodide (4.8 mg, 0.032 mmol) were added to a reaction flask and heated to 60° C. for reaction. After the reaction was complete, the system was cooled down, added with water (40 mL) and EA (20 mL), shaken and sepatated. The aqueous phase was extracted with EA (20 mL*2). The combined organic phase was washed with water (20 mL*3) and saturated brine (50 mL), dired with anhydrous sodium sulfate and filtered with suction. The filtrate was concentrated under reduced pressure, and the residue was separated by PLC to obtain 36.1 mg of the target compound.

ESI-MS Calculated for [M+H]$^+$=420.07; Found: 420.10. The found value was consistent with the caculated value.

Step 2: Synthesis of 1-methyl-9-(1-methyl-1H-pyrazol-4-yl)-N-(quinolin-5-yl)-6,7-dihydro-5H-benzo[c][1,2,3]triazolo[1,5-a]azepin-7-amine (LB86)

LB86-2 (36.1 mg, 0.086 mmol), 1-methyl-4-(4,4,5,5-tetramethyl-1,3,2-dioxaborolan-2-yl)-1H-pyrazole (25.1 mg, 0.12 mmol), potassium carbonate (18.9 mg, 0.14 mmol), 1,4-dioxane (5 mL) and water (0.25 mL) were added to a reaction flask, and the air in the reaction system was replaced with nitrogen three times. The system was added with Pd(dppf)Cl$_2$-dichloromethane complex (3.7 mg, 0.0046 mmol), and the air in the reaction system was replaced with nitrogen three times again. The system was heated to 100° C. for reaction. After the reaction was complete, the system was cooled down, added with water (40 mL) and EA (20 mL), shaken and sepatated. The aqueous phase was extracted with EA (20 mL*2). The combined organic phase was washed with water (20 mL*3) and saturated brine (50 mL), dired with anhydrous sodium sulfate and filtered with suction. The filtrate was concentrated under reduced pressure, and the residue was separated by PLC to obtain 27.8 mg of a crude, which was separated by medium pressure preparative chromatography and lyophilized to obtain 11.2 mg of the product.

Product analysis: $^1$HNMR (CDCl$_3$, 400 MHz): δ 7.67-7.63 (m, 1H), 7.60 (d, J=1.8 Hz, 1H), 7.54-7.29 (m, 6H), 4.75 (m, 3.4 Hz, 1H), 4.56 (d, J=7.8 Hz, 2H), 4.22 (m, 1H), 3.87 (s, 3H), 3.16-2.96 (m, 1H), 2.48 (s, 3H).

ESI-MS Calculated for [M+H]$^+$=422.20; Found: 422.10. The found value was consistent with the caculated value.

Preparation Example 46, Final Product LB88: 1-methyl-9-(1-methyl-1H-pyrazol-4-yl)-N-(quinolin-6-yl)-6,7-dihydro-5H-benzo[c][1,2,3]triazolo[1,5-a]azepin-7-amine

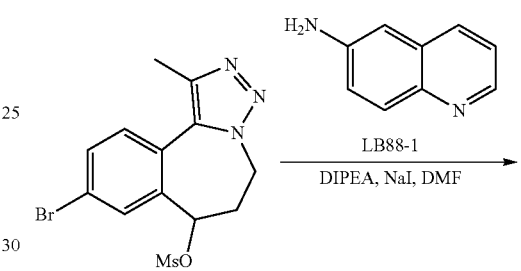

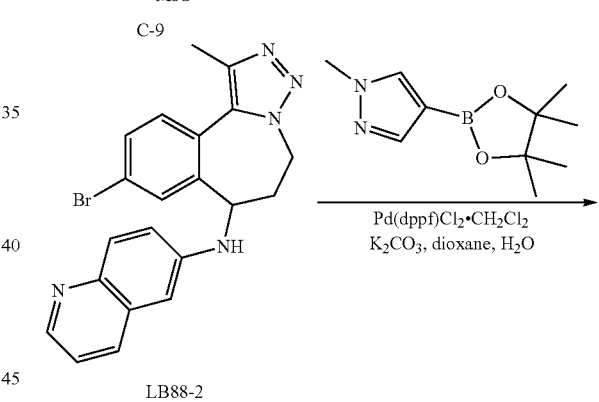

LB88-2

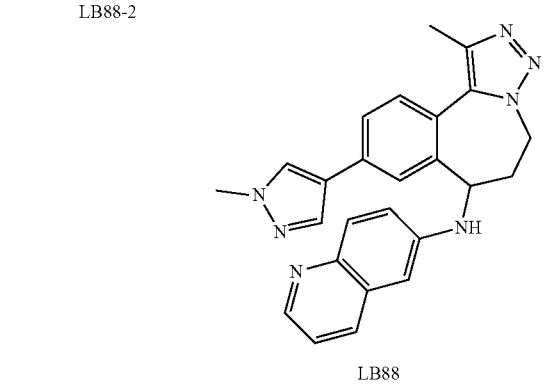

LB88

Step 1: Synthesis of 9-bromo-1-methyl-N-(quinolin-6-yl)-6,7-dihydro-5H-benzo[c][1,2,3]triazolo[1,5-a]azepin-7-amine (LB88-2)

C-9 (99.9 mg, 0.27 mmol), LB88-1 (79.3 mg, 0.55 mmol), DMF (10 mL), DIPEA (175.6 mg, 1.36 mmol) and sodium iodide (5.3 mg, 0.035 mmol) were added to a reaction flask and heated to 60° C. for reaction. After the reaction was complete, the system was cooled down, added with water (40 mL) and EA (20 mL), shaken and sepatated. The aqueous phase was extracted with EA (20 mL*2). The combined organic phase was washed with water (20 mL*2) and saturated brine (50 mL), dired with anhydrous sodium sulfate and filtered with suction. The filtrate was concentrated under reduced pressure, and the residue was separated by PLC to obtain 50.1 mg of the target compound.

ESI-MS Calculated for [M+H]⁺=420.07; Found: 420.10. The found value was consistent with the caculated value.

Step 2: Synthesis of 1-methyl-9-(1-methyl-1H-pyrazol-4-yl)-N-(quinolin-6-yl)-6,7-dihydro-5H-benzo[c][1,2,3]triazolo[1,5-a]azepin-7-amine (LB88)

LB88-2 (50.1 mg, 0.12 mmol), 1-methyl-4-(4,4,5,5-tetramethyl-1,3,2-dioxaborolan-2-yl)-1H-pyrazole (32.5 mg, 0.16 mmol), potassium carbonate (25.6 mg, 0.18 mmol), 1,4-dioxane (5 mL) and water (0.25 mL) were added to a reaction flask, and the air in the reaction system was replaced with nitrogen three times. The system was added with Pd(dppf)Cl₂-dichloromethane complex (5.1 mg, 0.0062 mmol), and the air in the reaction system was replaced with nitrogen three times again. The system was heated to reflux, and the reaction was monitored by LC-MS. The system was added with water (40 mL) and EA (20 mL), shaken and sepatated. The aqueous phase was extracted with EA (20 mL*2). The combined organic phase was washed with water (20 mL*2) and saturated brine (10 mL), dired with anhydrous sodium sulfate and filtered with suction. The filtrate was concentrated under reduced pressure, and the residue was separated by PLC to obtain 30.1 mg of a crude, which was separated by medium pressure preparative chromatography and lyophilized to obtain 12.4 mg of the product.

Product analysis: ¹HNMR (400 MHz, CDCl₃): δ 8.58 (dd, J=4.2, 1.7 Hz, 1H), 7.85 (d, J=9.0 Hz, 1H), 7.74-7.63 (m, 3H), 7.55-7.49 (m, 2H), 7.44 (d, J=7.9 Hz, 1H), 7.18 (dd, J=8.3, 4.2 Hz, 1H), 7.04 (dd, J=9.1, 2.6 Hz, 1H), 6.22 (d, J=2.6 Hz, 1H), 4.77-4.83 (m, 1H), 4.51-4.41 (m, 1H), 4.06-4.14 (m, 1H), 3.88 (s, 3H), 3.13-2.98 (m, 1H), 2.57 (s, 3H), 2.26-2.34 (m, 1H).

ESI-MS Calculated for [M+H]⁺=422.20; Found: 422.10. The found value was consistent with the caculated value.

Preparation Example 47, Final Product LB90: 2-(2-((1-methyl-9-(1-methyl-1H-pyrazol-4-yl)-6,7-dihydro-5H-benzo[c][1,2,3]triazolo[1,5-a]azepin-7-yl)amino)phenoxy)ethanol

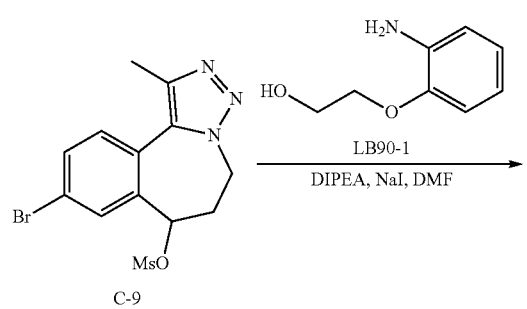

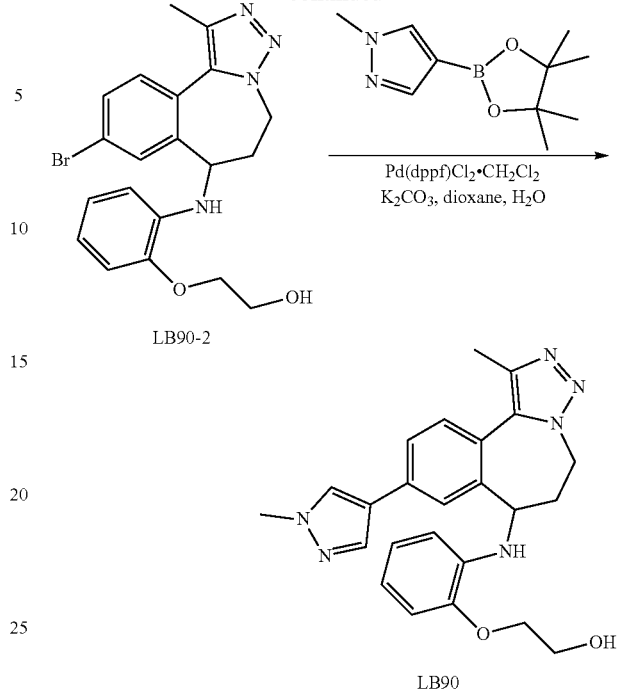

Step 1: Synthesis of 2-(2-((9-bromo-1-methyl-6,7-dihydro-5H-benzo[c][1,2,3]triazolo[1,5-a]azepin-7-yl)amino)phenoxy)ethan-1-ol (LB90-2)

C-9 (100.3 mg, 0.27 mmol), LB90-1 128.6 mg, 0.84 mmol), DMF (10 mL), DIPEA (205.2 mg, 1.59 mmol) and sodium iodide (4.1 mg, 0.028 mmol) were added to a reaction flask and heated to 60° C. for reaction. The system was added with water (50 mL) and EA (20 mL), shaken and sepatated. The aqueous phase was extracted with EA (20 mL*2). The combined organic phase was washed with water (40 mL) and saturated brine (40 mL), dired with anhydrous sodium sulfate and filtered with suction. The filtrate was concentrated under reduced pressure, and the residue was separated by PLC to obtain 86.1 mg of the target compound.

ESI-MS Calculated for [M+H]⁺=429.08; Found: 429.10. The found value was consistent with the caculated value.

Step 2: Synthesis of 2-(2-((1-methyl-9-(1-methyl-1H-pyrazol-4-yl)-6,7-dihydro-5H-benzo[c][1,2,3]triazolo[1,5-a]azepin-7-yl)amino)phenoxy)ethanol (LB90)

LB90-2 (86.1 mg, 0.20 mmol), 1-methyl-4-(4,4,5,5-tetramethyl-1,3,2-dioxaborolan-2-yl)-1H-pyrazole (55.4 mg, 0.27 mmol), potassium carbonate (43.4 mg, 0.32 mmol), 1,4-dioxane (10 mL) and water (0.5 mL) were added to a reaction flask, and the air in the reaction system was replaced with nitrogen three times. The system was added with Pd(dppf)Cl₂-dichloromethane complex (8.6 mg, 0.011 mmol), and the air in the reaction system was replaced with nitrogen three times again. The reaction was carried out in a bath at 110° C. After the reaction was complete, the system was cooled down, added with water (40 mL) and EA (20 mL), shaken and sepatated. The aqueous phase was extracted with EA (20 mL*2). The combined organic phase was washed with water (20 mL*2) and saturated brine (40 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 24.4 mg of the product.

Product analysis: $^1$HNMR (CDCl$_3$, 400 MHz): δ 7.77 (s, 1H), 7.65 (d, J=1.7 Hz, 2H), 7.48 (dd, J=7.8, 1.8 Hz, 1H), 7.36 (d, J=7.9 Hz, 1H), 6.73 (dd, J=7.8, 1.5 Hz, 1H), 6.64 (m, 1H), 6.58 (m, 1H), 6.15 (dd, J=7.8, 1.6 Hz, 1H), 4.52 (m, 2H), 4.33 (m, 1H), 4.20-4.10 (m, 1H), 4.07-3.96 (m, 3H), 3.95 (s, 3H), 2.89 (m, 1H), 2.50 (m, 1H), 2.41 (s, 3H).

ESI-MS Calculated for [M+H]$^+$=431.21; Found: 431.20. The found value was consistent with the caculated value.

Preparation Example 48, Final Product LB91: 1-methyl-9-(1-methyl-1H-pyrazol-4-yl)-N-(quinolin-8-yl)-6,7-dihydro-5H-benzo[c][1,2,3]triazolo[1,5-a]azepin-7-amine

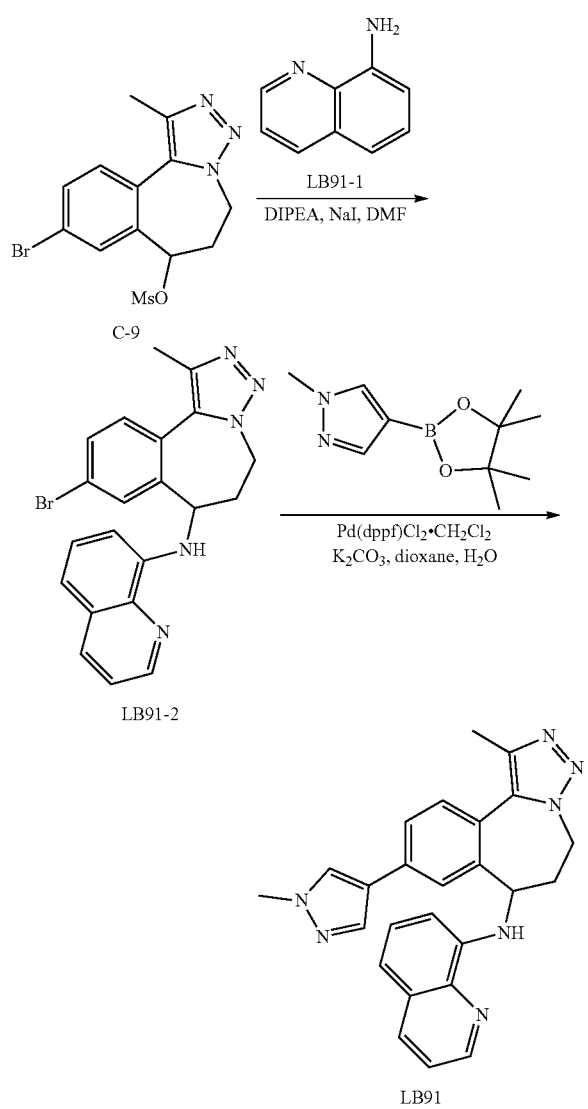

Step 1: Synthesis of 9-bromo-1-methyl-N-(quinolin-8-yl)-6,7-dihydro-5H-benzo[c][1,2,3]triazolo[1,5-a]azepin-7-amine (LB91-2)

C-9 (100.8 mg, 0.27 mmol), LB91-1 (79.8 mg, 0.56 mmol), DMF (10 mL), DIPEA (175.5 mg, 1.36 mmol) and sodium iodide (5.3 mg, 0.035 mmol) were added to a reaction flask and heated to 60° C. for reaction. The system was added with water (50 mL) and EA (20 mL), shaken and sepatated. The aqueous phase was extracted with EA (20 mL*2). The combined organic phase was washed with water (20 mL*3) and saturated brine (50 mL), dired with anhydrous sodium sulfate and filtered with suction. The filtrate was concentrated under reduced pressure, and the residue was separated by PLC to obtain 56.8 mg of the target compound.

ESI-MS Calculated for [M+H]$^+$=420.07; Found: 420.00. The found value was consistent with the caculated value.

Step 2: Synthesis of 1-methyl-9-(1-methyl-1H-pyrazol-4-yl)-N-(quinolin-8-yl)-6,7-dihydro-5H-benzo[c][1,2,3]triazolo[1,5-a]azepin-7-amine LB91-2 (56.8 mg, 0.14 mmol), 1-methyl-4-(4,4,5,5-tetramethyl-1,3,2-dioxaborolan-2-yl)-1H-pyrazole (39.6 mg, 0.19 mmol), potassium carbonate (30.2 mg, 0.22 mmol), 1,4-dioxane (10 mL) and water (0.5 mL) were added to a reaction flask, and the air in the reaction system.was replaced with nitrogen three times. The system was added with Pd(dppf)Cl$_2$-dichloromethane complex (5.9 mg, 0.0073 mmol), and the air in the reaction system was replaced with nitrogen three times again. The system was heated to reflux, and the reaction was monitored by LC-MS. The system was added with water (40 mL) and EA (20 mL), shaken and sepatated. The aqueous phase was extracted with EA (20 mL*2). The combined organic phase was washed with water (40 mL) and saturated brine (50 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 28.8 mg of the product.

Product analysis: $^1$HNMR (CDCl$_3$, 400 MHz): δ 8.81 (dd, J=4.2, 1.7 Hz, 1H), 8.08 (dd, J=8.3, 1.7 Hz, 1H), 7.68 (d, J=1.7 Hz, 1H), 7.58 (d, J=0.8 Hz, 1H), 7.50 (dd, J=7.9, 1.8 Hz, 1H), 7.47-7.39 (m, 3H), 7.15 (t, J=7.9 Hz, 1H), 7.04 (dd, J=8.2, 1.2 Hz, 1H), 6.59 (d, J=6.3 Hz, 1H), 6.07 (dd, J=7.6, 1.2 Hz, 1H), 4.88 (dd, J=14.1, 7.7 Hz, 1H), 4.47 (m, 1H), 4.05 (m, 1H), 3.84 (s, 3H), 3.25-3.03 (m, 1H), 2.56 (s, 3H), 2.46 (m, 1H).

ESI-MS Calculated for [M+H]$^+$=422.20; Found: 422.20. The found value was consistent with the caculated value.

247

Preparation Example 49, Final Product LB92: methyl 3-((1-methyl-9-(1-methyl-1H-pyrazol-4-yl)-6,7-dihydro-5H-benzo[c][1,2,3]triazolo[1,5-a]azepin-7-yl)amino)benzoate

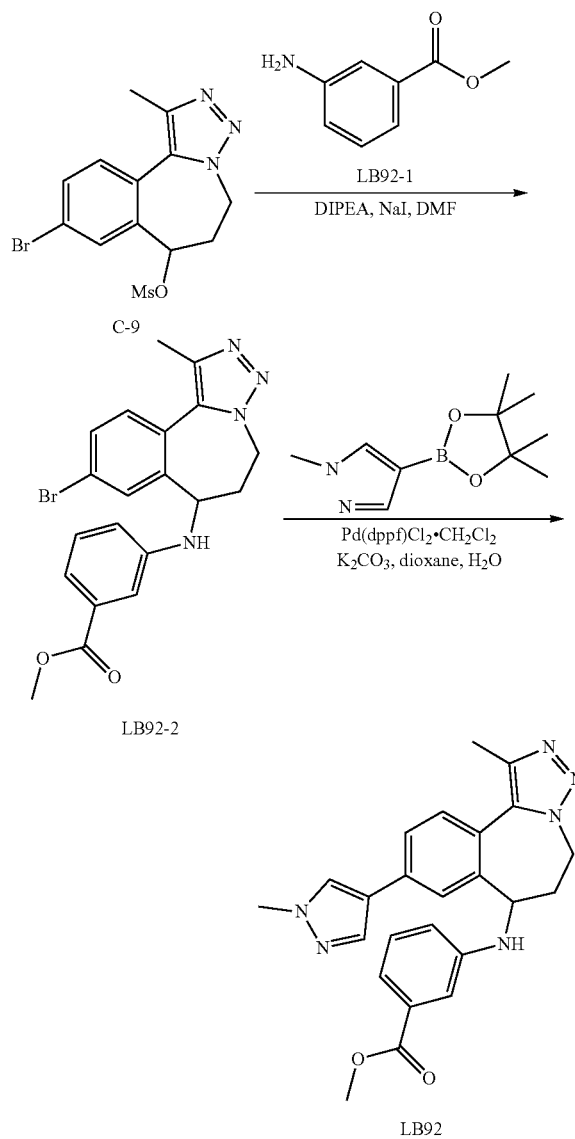

Step 1: Synthesis of methyl 3-((9-bromo-1-methyl-6,7-dihydro-5H-benzo[c][1,2,3]triazolo[1,5-a]azepin-7-yl)amino)benzoate (LB92-2)

C-9 (151.1 mg, 0.41 mmol), LB92-1 (125.4 mg, 0.83 mmol), DMF (15 mL), DIPEA (271.8 mg, 2.11 mmol) and sodium iodide (9.3 mg, 0.062 mmol) were added to a reaction flask and heated to 80° C. for reaction. After the reaction was complete, the system was cooled down, added with water (60 mL) and EA (20 mL), shaken and sepatated. The aqueous phase was extracted with EA (20 mL*3). The combined organic phase was washed with water (60 mL) and saturated brine (50 mL), dired with anhydrous sodium sulfate and filtered with suction. The filtrate was concentrated under reduced pressure, and the residue was separated by PLC to obtain 75.5 mg of the target compound.

248

ESI-MS Calculated for [M+H]$^+$=427.07; Found: 427.10. The found value was consistent with the caculated value.

Step 2: Synthesis of methyl 3-((1-methyl-9-(1-methyl-1H-pyrazol-4-yl)-6,7-dihydro-5H-benzo[c][1,2,3]triazolo[1,5-a]azepin-7-yl)amino)benzoate (LB92)

LB92-2 (75.5 mg, 0.18 mmol), 1-methyl-4-(4,4,5,5-tetramethyl-1,3,2-dioxaborolan-2-yl)-1H-pyrazole (49.9 mg, 0.24 mmol), potassium carbonate (39.3 mg, 0.29 mmol), 1,4-dioxane (10 mL) and water (0.5 mL) were added to a reaction flask, and the air in the reaction system was replaced with nitrogen three times. The system was added with Pd(dppf)Cl$_2$-dichloromethane complex (7.9 mg, 0.0096 mmol), and the air in the reaction system was replaced with nitrogen three times again. The system was heated to reflux. After the reaction was complete, the system was cooled down, added with water (40 mL) and EA (20 mL), shaken and sepatated. The aqueous phase was extracted with EA (20 mL*2). The combined organic phase was washed with water (40 mL) and saturated brine (50 mL), dired with anhydrous sodium sulfate and filtered with suction. The filtrate was concentrated under reduced pressure, and the residue was separated by PLC to obtain 58.3 mg of a crude, which was separated by medium pressure preparative chromatography and lyophilized to obtain 8.1 mg of the product.

Product analysis: $^1$HNMR (CDCl$_3$, 400 MHz): δ 7.70 (d, J=0.8 Hz, 1H), 7.61 (d, J=1.7 Hz, 1H), 7.56 (d, J=0.9 Hz, 1H), 7.50 (dd, J=7.8, 1.8 Hz, 1H), 7.41 (d, J=7.8 Hz, 1H), 7.32 (m, 1H), 7.14-7.04 (m, 2H), 6.38 (m, 1H), 4.75 (m, 1H), 4.36 (m, 1H), 4.16-4.00 (m, 2H), 3.92 (s, 3H), 3.83 (s, 3H), 3.08-2.87 (m, 1H), 2.53 (s, 3H).

ESI-MS Calculated for [M+H]$^+$=429.20; Found: 429.20. The found value was consistent with the caculated value.

Preparation Example 50, Final Product LB97: 3-((1-methyl-9-(1-methyl-1H-pyrazol-4-yl)-6,7-dihydro-5H-benzo[c][1,2,3]triazolo[1,5-a]azepin-7-yl)amino)benzoic acid

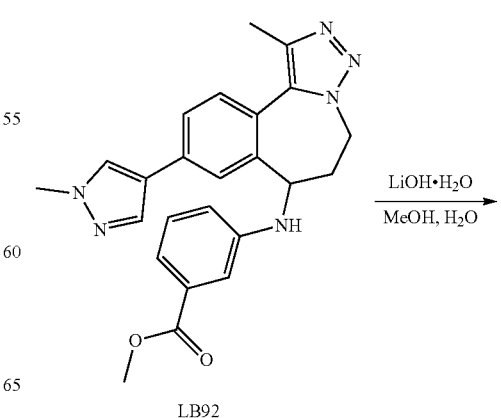

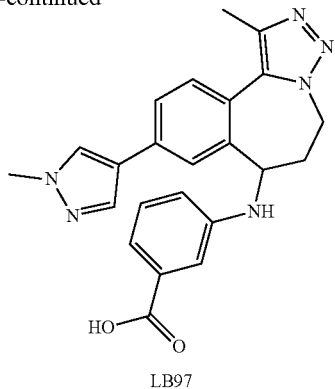

LB97

Synthesis of 3-((1-methyl-9-(1-methyl-1H-pyrazol-4-yl)-6,7-dihydro-5H-benzo[c][1,2,3]triazolo[1,5-a]azepin-7-yl)amino)benzoic acid (LB97)

LB92 (20.0 mg, 0.047 mmol), lithium hydroxide monohydrate (25.70 mg, 1.07 mmol), methanol (10 mL) and water (10 mL) were added to a reaction flask and stirred at room temperature for reaction. After the reaction was complete, the system was concentrated under reduced pressure to remove methanol, added with water (50 mL) and washed with EA (20 mL*2), and the organic phase was discarded. The aqueous phase was adjusted pH to 2-3 with 1 mol/L dilute hydrochloric acid, and extracted with isopropyl acetate (20 mL*2). The combined organic phase was washed with water (20 mL) and saturated brine (40 mL), dired with anhydrous sodium sulfate and filtered with suction. The filtrate was concentrated and the residue was separated by fast medium pressure preparative chromatography to obtain 9.7 mg of the target compound.

ESI-MS Calculated for [M+H]⁺=415.18; Found: 415.10. The found value was consistent with the caculated value.

Preparation Example 51, Final Product LB98: N-(1H-indol-5-yl)-1-methyl-9-(1-methyl-1H-pyrazol-4-yl)-6,7-dihydro-5H-benzo[c][1,2,3]triazolo[1,5-a]azepin-7-amine

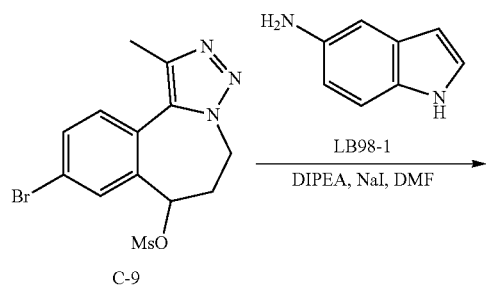

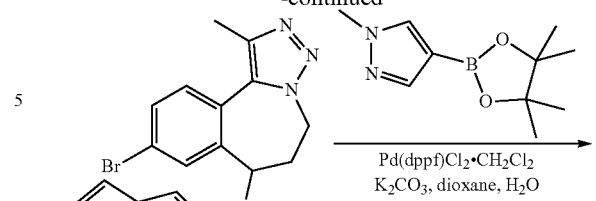

LB98-2

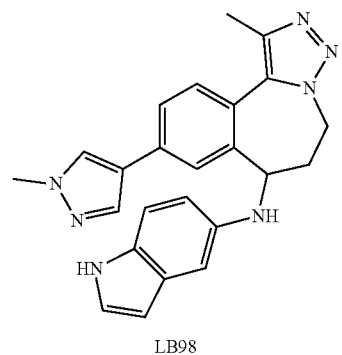

LB98

Step 1: Synthesis of 9-bromo-N-(1H-indol-5-yl)-1-methyl-6,7-dihydro-5H-benzo[c][1,2,3]triazolo[1,5-a]azepin-7-amine (LB98-2)

C-9 (100.8 mg, 0.27 mmol), LB98-1 (72.5 mg, 0.55 mmol), DMF (10 mL), DIPEA (116.6 mg, 1.37 mmol) and sodium iodide (6.2 mg, 0.041 mmol) were added to a reaction flask and heated to 60° C. for reaction. After the reaction was complete, the system was cooled down naturally, added with water (50 mL) and EA (20 mL), shaken and sepatated. The aqueous phase was extracted with EA (20 mL*3). The combined organic phase was washed with water (60 mL) and saturated brine (50 mL), dried over anhydrous sodium sulfate and filtered with suction. The filtrate was concentrated under reduced pressure, and the residue was separated by PLC to obtain 91.5 mg of the target compound.

ESI-MS Calculated for [M+H]⁺=408.07; Found: 408.00. The found value was consistent with the caculated value.

Step 2: Synthesis of N-(1H-indol-5-yl)-1-methyl-9-(1-methyl-1H-pyrazol-4-yl)-6,7-dihydro-5H-benzo[c][1,2,3]triazolo[1,5-a]azepin-7-amine (LB98)

LB98-2 (91.5 mg, 0.23 mmol), 1-methyl-4-(4,4,5,5-tetramethyl-1,3,2-dioxaborolan-2-yl)-1H-pyrazole (63.2 mg, 0.30 mmol), potassium carbonate (49.3 mg, 0.36 mmol), 1,4-dioxane (10 mL) and water (0.5 mL) were added to a reaction flask, and the air in the reaction system was replaced with nitrogen three times. The system was added with Pd(dppf)Cl₂-dichloromethane complex (9.8 mg, 0.012 mmol), and the air in the reaction system was replaced with nitrogen three times again. The system was heated to reflux. After the reaction was complete, the system was cooled down, added with water (50 mL) and EA (20 mL), shaken and sepatated. The aqueous phase was extracted with EA (20 mL*2). The combined organic phase was washed with water (60 mL) and saturated brine (50 mL), dried over anhydrous sodium sulfate and filtered with suction. The filtrate was concentrated under reduced pressure, and the residue was separated by PLC to obtain 68.1 mg of a crude, which was separated by medium pressure preparative chromatography and lyophilized to obtain 28.4 mg of the product.

Product analysis: $^1$HNMR (CDCl$_3$, 400 MHz): δ 7.97 (s, 1H), 7.76 (d, J=1.8 Hz, 1H), 7.70 (d, J=0.8 Hz, 1H), 7.54 (d, J=0.7 Hz, 1H), 7.48 (dd, J=7.9, 1.8 Hz, 1H), 7.40 (d, J=7.8 Hz, 1H), 7.12 (dd, J=9.3, 0.9 Hz, 1H), 7.05 (t, J=2.8 Hz, 1H), 6.47-6.41 (m, 2H), 6.25 (m, 1H), 4.75 (m 1H), 4.33 (dd, J=10.4, 6.7 Hz, 1H), 4.03 (m, 1H), 3.88 (s, 3H), 3.72 (d, J=14.5 Hz, 1H), 3.00 (m, 1H), 2.55 (s, 3H).

ESI-MS Calculated for [M+H]$^+$=410.20; Found: 410.10. The found value was consistent with the caculated value.

Preparation Example 52, Final Product LB113: N-(1H-indol-6-yl)-1-methyl-9-(1-methyl-1H-pyrazol-4-yl)-6,7-dihydro-5H-benzo[c][1,2,3]triazolo[1,5-a]azepin-7-amine

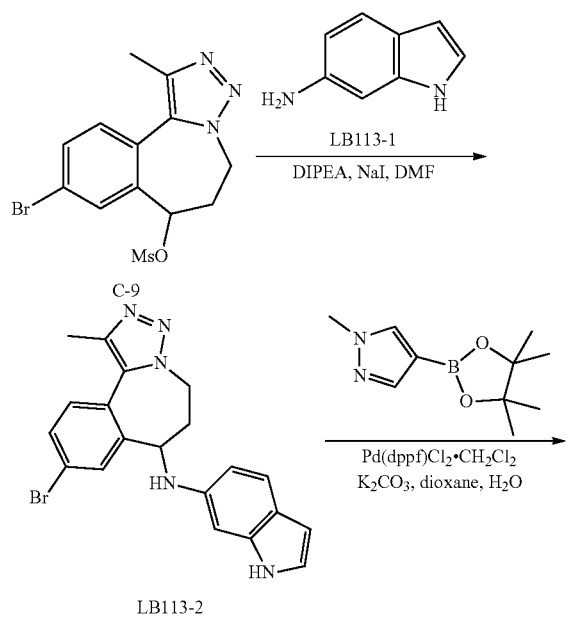

Step 1: Synthesis of 9-bromo-N-(1H-indol-6-yl)-1-methyl-6,7-dihydro-5H-benzo[c][1,2,3]triazolo[1,5-a]azepin-7-amine (LB113-2)

C-9 (110.0 mg, 0.30 mmol), LB113-1 (80.5 mg, 0.61 mmol), DMF (10 mL), DIPEA (195.8 mg, 1.52 mmol) and sodium iodide (6.8 mg, 0.045 mmol) were added to a reaction flask and heated to 60° C., and the reaction was monitored by LC-MS. After the reaction was complete, the system was cooled down, added with water (40 mL) and EA (20 mL), shaken and sepatated. The aqueous phase was extracted with EA (20 mL*2). The combined organic phase was washed with water (20 mL*3) and saturated brine (30 mL), dired with anhydrous sodium sulfate and filtered with suction. The filtrate was concentrated under reduced pressure, and the residue was separated by PLC to obtain 102.1 mg of the target compound.

ESI-MS Calculated for [M+H]$^+$=408.07; Found: 408.00. The found value was consistent with the caculated value.

Step 2: Synthesis of N-(1H-indol-6-yl)-1-methyl-9-(1-methyl-1H-pyrazol-4-yl)-6,7-dihydro-5H-benzo[c][1,2,3]triazolo[1,5-a]azepin-7-amine (LB113)

LB113-2 (102.1 mg, 0.25 mmol), 1-methyl-4-(4,4,5,5-tetramethyl-1,3,2-dioxaborolan-2-yl)-1H-pyrazole (68.2 mg, 0.33 mmol), potassium carbonate (52.6 mg, 0.38 mmol), 1,4-dioxane (10 mL) and water (0.5 mL) were added to a reaction flask, and the air in the reaction system was replaced with nitrogen three times. The system was added with Pd(dppf)Cl$_2$-dichloromethane complex (10.7 mg, 0.013 mmol), and the air in the reaction system was replaced with nitrogen three times again. The system was heated to reflux. After the reaction was complete, the system was cooled down, added with water (40 mL) and EA (20 mL), shaken and sepatated. The aqueous phase was extracted with EA (20 mL*2). The combined organic phase was washed with water (20 mL) and saturated brine (30 mL), dired with anhydrous sodium sulfate and filtered with suction. The filtrate was concentrated under reduced pressure, and the residue was separated by PLC to obtain 68.1 mg of a crude, which was separated by medium pressure preparative chromatography and lyophilized to obtain 32.1 mg of the product.

Product analysis: $^1$HNMR (CDCl$_3$, 400 MHz): δ 7.80 (s, 1H), 7.71 (dd, J=13.3, 1.3 Hz, 2H), 7.56-7.46 (m, 2H), 7.41 (d, J=7.8 Hz, 1H), 7.35 (d, J=8.4 Hz, 1H), 6.91 (dd, J=3.3, 2.3 Hz, 1H), 6.43 (dd, J=8.4, 2.1 Hz, 1H), 6.35 (m, 1H), 6.08 (d, J=2.0 Hz, 1H), 4.78 (m, 1H), 4.32 (dd, J=10.6, 6.7 Hz, 1H), 4.02 (m, 1H), 3.88 (s, 3H), 3.13-2.90 (m, 1H), 2.54 (s, 3H), 2.30-2.13 (m, 1H).

ESI-MS Calculated for [M+H]$^+$=410.20; Found: 410.10. The found value was consistent with the caculated value.

Preparation Example 53, Final Product LB114: N-(1H-indol-4-yl)-1-methyl-9-(1-methyl-1H-pyrazol-4-yl)-6,7-dihydro-5H-benzo[c][1,2,3]triazolo[1,5-a]azepin-7-amine

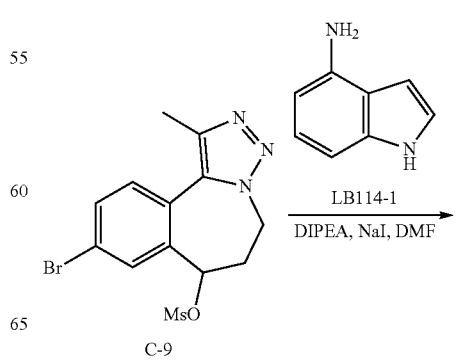

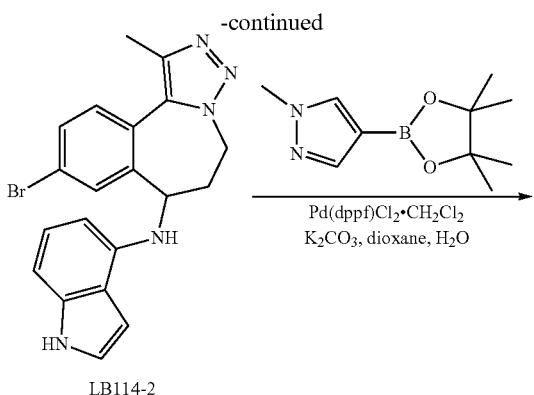

LB114-2

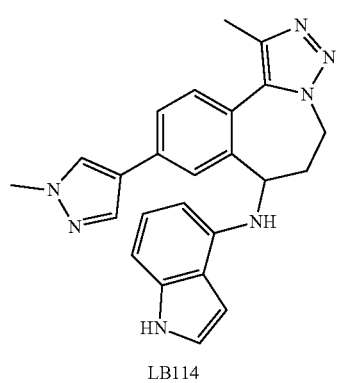

LB114

Step 1: Synthesis of 9-bromo-N-(1H-indol-4-yl)-1-methyl-6,7-dihydro-5H-benzo[c][1,2,3]triazolo[1,5-a]azepin-7-amine (LB114-2)

C-9 (100.0 mg, 0.27 mmol), LB114-1 (71.4 mg, 0.54 mmol), DMF (10 mL), DIPEA (176.6 mg, 1.37 mmol) and sodium iodide (6.5 mg, 0.044 mmol) were added to a reaction flask and heated to 60° C. for reaction. After the reaction was complete, the system was cooled down, added with water (50 mL) and EA (20 mL), shaken and sepatated. The aqueous phase was extracted with EA (20 mL*2). The combined organic phase was washed with water (20 mL*2) and saturated brine (30 mL), dired with anhydrous sodium sulfate and filtered with suction. The filtrate was concentrated under reduced pressure, and the residue was separated by PLC to obtain 83.6 mg of the target compound.

ESI-MS Calculated for [M+H]$^+$=408.07; Found: 408.10. The found value was consistent with the caculated value.

Step 2: Synthesis of N-(1H-indol-4-yl)-1-methyl-9-(1-methyl-1H-pyrazol-4-yl)-6,7-dihydro-5H-benzo[c][1,2,3]triazolo[1,5-a]azepin-7-amine (LB114)

LB114-2 (83.6 mg, 0.21 mmol), 1-methyl-4-(4,4,5,5-tetramethyl-1,3,2-dioxaborolan-2-yl)-1H-pyrazole (58.2 mg, 0.28 mmol), potassium carbonate (43.9 mg, 0.32 mmol), 1,4-dioxane (10 mL) and water (0.5 mL) were added to a reaction flask, and the air in the reaction system was replaced with nitrogen three times. The system was added with Pd(dppf)Cl$_2$-dichloromethane complex (8.6 mg, 0.011 mmol), and the air in the reaction system was replaced with nitrogen twice again. The system was heated to refux. After the reaction was complete, the system was cooled down, added with water (50 mL) and EA (20 mL), shaken and sepatated. The aqueous phase was extracted with EA (20 mL*2). The combined organic phase was washed with water (20 mL*2) and saturated brine (40 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 18.3 mg of the product.

Product analysis: $^1$HNMR (CDCl$_3$, 400 MHz): δ 8.22 (s, 1H), 7.71 (d, J=1.8 Hz, 1H), 7.64 (d, J=0.8 Hz, 1H), 7.52-7.45 (m, 2H), 7.40 (d, J=7.8 Hz, 1H), 7.14 (dd, J=3.3, 2.4 Hz, 1H), 6.88-6.80 (m, 1H), 6.77 (m, 1H), 6.47 (m, 1H), 5.74-5.65 (m, 1H), 4.78 (m, 1H), 4.50 (s, 1H), 4.14-3.92 (m, 1H), 3.87 (s, 3H), 3.05 (m, 1H), 2.53 (s, 3H), 2.43-2.27 (m, 1H).

ESI-MS Calculated for [M+H]$^+$=410.20; Found: 410.10. The found value was consistent with the caculated value.

Preparation Example 54, Final Product LB128: N-methyl-44(1-methyl-9-(1-methyl-1H-pyrazol-4-yl)-6,7-dihydro-5H-benzo[c][1,2,3]triazolo[1,5-a]azepin-7-yl)amino)benzamide

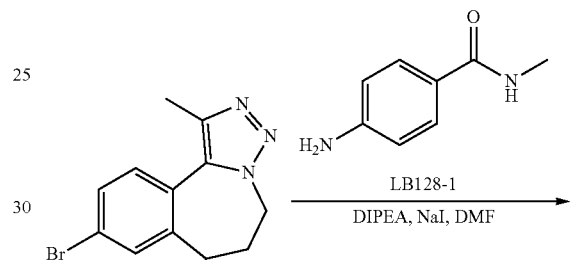

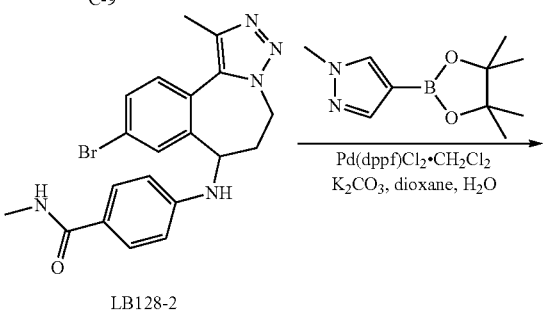

LB128-2

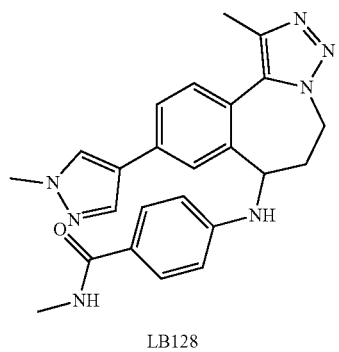

LB128

Step 1: Synthesis of 4-((9-bromo-1-methyl-6,7-dihydro-5H-benzo[c][1,2,3]triazolo[1,5-a]azepin-7-yl)amino)-N-methylbenzamide (LB128-2)

C-9 (200.0 mg, 0.54 mmol), LB128-1 (203.6 mg, 1.36 mmol), DMF (10 mL), DIPEA (374.8 mg, 2.90 mmol) and sodium iodide (12.2 mg, 0.081 mmol) were added to a reaction flask and heated to 60° C. for reaction. After the reaction was complete, the system was cooled down, added with water (50 mL) and EA (20 mL), shaken and sepatated. The aqueous phase was extracted with EA (25 mL*2). The combined organic phase was washed with water (30 mL) and saturated brine (20 mL), dired with anhydrous sodium sulfate and filtered with suction. The filtrate was concentrated under reduced pressure, and the residue was separated by PLC to obtain 89.9 of the target compound mg.

ESI-MS Calculated for [M+H]$^+$=426.09; Found: 426.00. The found value was consistent with the caculated value.

Step 2: Synthesis of N-methyl-4-((1-methyl-9-(1-methyl-1H-pyrazol-4-yl)-6,7-dihydro-5H-benzo[c][1,2,3]triazolo[1,5-a]azepin-7-yl)amino)benzamide (LB128)

LB128-2 (89.9 mg, 0.21 mmol), 1-methyl-4-(4,4,5,5-tetramethyl-1,3,2-dioxaborolan-2-yl)-1H-pyrazole (58.3 mg, 0.28 mmol), potassium carbonate (45.3 mg, 0.33 mmol), 1,4-dioxane (10 mL) and water (0.5 mL) were added to a reaction flask, and the air in the reaction system was replaced with nitrogen three times. The system was added with Pd(dppf)Cl$_2$-dichloromethane complex (8.7 mg, 0.011 mmol), and the air in the reaction system was replaced with nitrogen twice again. The system was heated to reflux. After the reaction was complete, the system was cooled down, added with water (50 mL) and EA (20 mL), shaken and sepatated. The aqueous phase was extracted with EA (30 mL*2). The combined organic phase was washed with water (30 mL) and saturated brine (30 mL), dried over anhydrous sodium sulfate and filtered with suction. The filtrate was concentrated under reduced pressure, and the residue was separated by PLC to obtain a crude, which was separated by medium pressure preparative chromatography and lyophilized to obtain 11.2 mg of the product.

Product analysis: $^1$HNMR (400 MHz, CDCl$_3$): δ 7.68 (d, J=0.8 Hz, 1H), 7.58-7.45 (m, 5H), 7.41 (d, J=7.8 Hz, 1H), 6.34-6.22 (m, 2H), 5.88 (d, J=5.0 Hz, 1H), 4.74-4.80 (m, 1H), 4.32-4.39(m, 1H), 4.02-4.10 (m, 1H), 3.91 (s, 3H), 3.08-2.95 (m, 1H), 2.92 (d, J=4.9 Hz, 3H), 2.52 (s, 3H), 2.20-2.29 (m, 1H). ESI-MS Calculated for [M+H]$^+$=428.21; Found: 428.10. The found value was consistent with the caculated value.

Preparation Example 55, Final Product LB138: N-(4-((dimethylamino)methyl)phenyl)-1-methyl-9-(1-methyl-1H-pyrazol-4-yl)-6,7-dihydro-5H-benzo[c][1,2,3]triazolo[1,5-a]azepin-7-amine

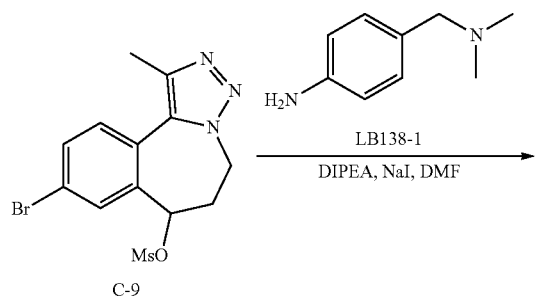

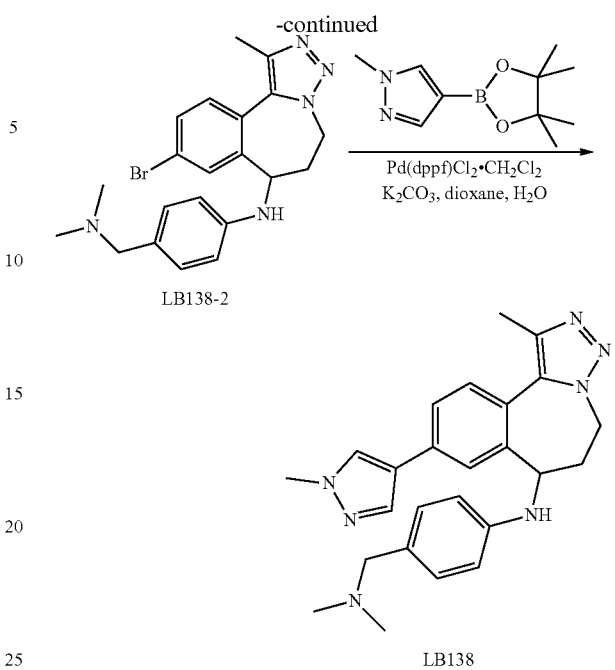

Step 1: Synthesis of 9-bromo-N-(4-((dimethylamino)methyl)phenyl)-1-methyl-6,7-dihydro-5H-benzo[c][1,2,3]triazolo[1,5-a]azepin-7-amine (LB138-2)

C-9 (100.6 mg, 0.27 mmol), LB138-1 (81.7 mg, 0.55 mmol), DMF (10 mL), DIPEA (179.1 mg, 1.39 mmol) and sodium iodide (6.1 mg, 0.041 mmol) were added to a reaction flask and heated to 60° C. for reaction. After the reaction was complete, the system was cooled down, added with water (50 mL) and EA (20 mL), shaken and sepatated. The aqueous phase was extracted with EA (30 mL*3). The combined organic phase was washed with water (35 mL) and saturated brine (35 mL), dried over anhydrous sodium sulfate and filtered with suction. The filtrate was concentrated under reduced pressure, and the residue was separated by PLC to obtain 111.1 mg of the target compound.

ESI-MS Calculated for [M+H]$^+$=426.12; Found: 426.00. The found value was consistent with the caculated value.

Step 2: Synthesis of N-(4-((dimethylamino)methyl) phenyl)-1-methyl-9-(1-methyl-1H-pyrazol-4-yl)-6,7-dihydro-5H-benzo[c][1,2,3]triazolo[1,5-a]azepin-7-amine (LB138)

LB138-2 (111.1 mg, 0.26 mmol), 1-methyl-4-(4,4,5,5-tetramethyl-1,3,2-dioxaborolan-2-yl)-1H-pyrazole (72.0 mg, 0.35 mmol), potassium carbonate (57.2 mg, 0.42 mmol), 1,4-dioxane (10 mL) and water (0.5 mL) were added to a reaction flask, and the air in the reaction system was replaced with nitrogen three times. The system was added with Pd(dppf)Cl$_2$-dichloromethane complex (11.3 mg, 0.014 mmol), and the air in the reaction system was replaced with nitrogen twice again. The system was heated to reflux, and the reaction was monitored by LC-MS. After the reaction was complete, the system was cooled down, added with water (50 mL) and EA (35 mL), shaken and sepatated. The aqueous phase was extracted with EA (35 mL*2). The combined organic phase was washed with water (50 mL*2)

and saturated brine (50 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 10.6 mg of the product.

Product analysis: $^1$HNMR (CDCl$_3$, 400 MHz): δ 7.70 (d, J=0.8 Hz, 1H), 7.64 (d, J=1.8 Hz, 1H), 7.56 (d, J=0.8 Hz, 1H), 7.49 (dd, J=7.9, 1.8 Hz, 1H), 7.40 (d, J=7.8 Hz, 1H), 7.05-6.97 (m, 2H), 6.33-6.22 (m, 2H), 4.77 (m, 1H), 4.30 (d, J=8.9 Hz, 1H), 4.03 (m, 1H), 3.92 (s, 3H), 3.34 (s, 2H), 2.99 (m, 1H), 2.53 (s, 3H), 2.34-2.23 (m, 1H), 2.21 (s, 7H).

ESI-MS Calculated for [M+H]$^+$=428.25; Found: 383.10 (dedimethylamino) The found value was consistent with the caculated value.

Preparation Example 56, Final Product LB139:
N-(4-(2-(dimethylamino)ethyl)phenyl)-1-methyl-9-(1-methyl-1H-pyrazol-4-yl)-6,7-dihydro-5H-benzo[c][1,2,3]triazolo[1,5-a]azepin-7-amine

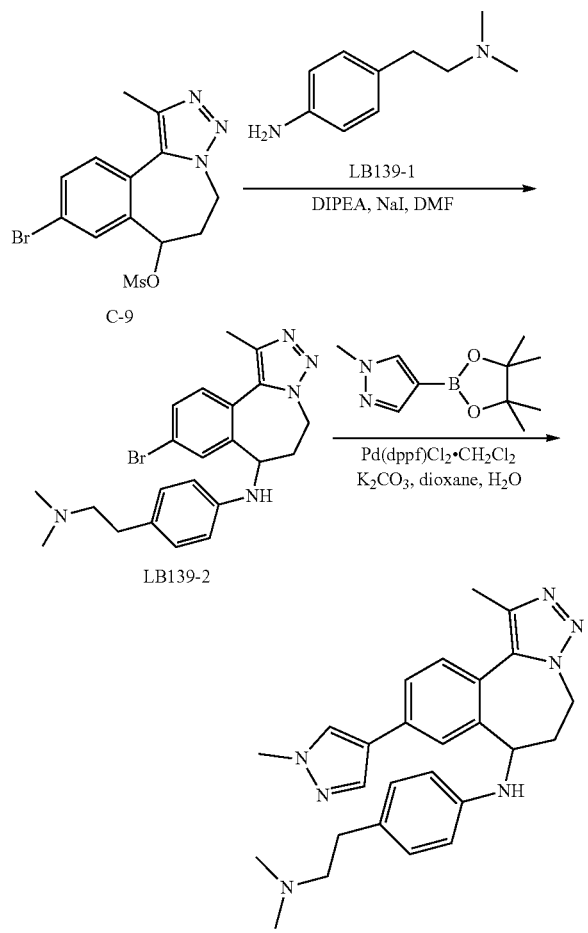

Step 1: Synthesis of 9-bromo-N-(4-(2-(dimethyl-amino)ethyl)phenyl)-1-methyl-6,7-dihydro-5H-benzo[c][1,2,3]triazolo[1,5-a]azepin-7-amine (LB139-2)

C-9 (100.9 mg, 0.27 mmol), LB139-1 (132.6 mg, 0.81 mmol), DMF (10 mL), DIPEA (189.5 mg, 1.47 mmol) and sodium iodide (6.1 mg, 0.041 mmol) were added to a reaction flask and heated to 60° C., and the reaction was monitored by LC-MS. After the reaction was complete, the system was cooled down, added with water (50 mL) and EA (20 mL), shaken and sepatated. The aqueous phase was extracted with EA (30 mL*2). The combined organic phase was washed with water (30 mL*3) and saturated brine (25 mL), dired with anhydrous sodium sulfate and filtered with suction. The filtrate was concentrated under reduced pressure, and the residue was separated by PLC to obtain 88.2 mg of the target compound.

ESI-MS Calculated for [M+H]$^+$=440.14; Found: 440.10. The found value was consistent with the caculated value.

Step 2: Synthesis of N-(4-(2-(dimethyl amino)ethyl)phenyl)-1-methyl-9-(1-methyl-1H-pyrazol-4-yl)-6,7-dihydro-5H-benzo[c][1,2,3]triazolo[1,5-a]azepin-7-amine (LB139)

LB139-2 (88.2 mg, 0.20 mmol), 1-methyl-4-(4,4,5,5-tetramethyl-1,3,2-dioxaborolan-2-yl)-1H-pyrazole (56.2 mg, 0.27 mmol), potassium carbonate (44.5 mg, 0.32 mmol), 1,4-dioxane (10 mL) and water (0.5 mL) were added to a reaction flask, and the air in the reaction system was replaced with nitrogen three times. The system was added with Pd(dppf)Cl$_2$-dichloromethane complex (9.0 mg, 0.011 mmol), and the air in the reaction system was replaced with nitrogen three times again. The system was heated to 100° C. for reaction. After the reaction was complete, the system was cooled down, added with water (50 mL) and EA (30 mL), shaken and sepatated. The aqueous phase was extracted with EA (35 mL*2). The combined organic phase was washed with water (50 mL*2) and saturated brine (50 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 14.3 mg of the product.

Product analysis: $^1$H NMR (CDCl$_3$, 400 MHz): δ 7.71 (d, J=0.8 Hz, 1H), 7.66 (d, J=1.7 Hz, 1H), 7.57 (d, J=0.8 Hz, 1H), 7.49 (dd, J=7.8, 1.8 Hz, 1H), 7.40 (d, J=7.8 Hz, 1H), 6.93-6.85 (m, 2H), 6.26 (d, J=8.5 Hz, 2H), 4.86-4.64 (m, 1H), 4.01 (m, 1H), 3.92 (s, 3H), 3.84 (s, 1H), 2.97 (m, 1H), 2.64 (dd, J=10.1, 6.0 Hz, 2H), 2.53 (s, 3H), 2.51-2.43 (m, 2H), 2.32 (d, J=20.8 Hz, 7H).

ESI-MS Calculated for [M+H]$^+$=442.26; Found: 442.10. The found value was consistent with the caculated value.

Preparation Example 57, Final Product LB142:
N-methyl-2-(4-41-methyl-9-(1-methyl-1H-pyrazol-4-yl)-6,7-dihydro-5H-benzo[c][1,2,3]triazolo[1,5-a]azepin-7-yl)amino)phenyl)acetamide

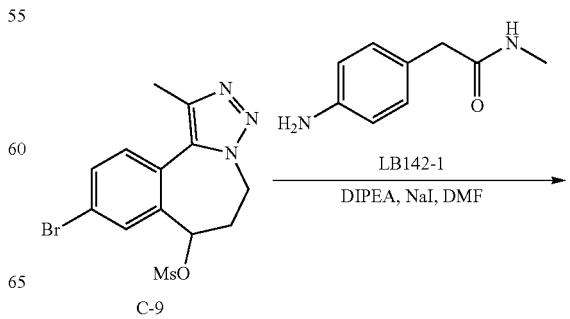

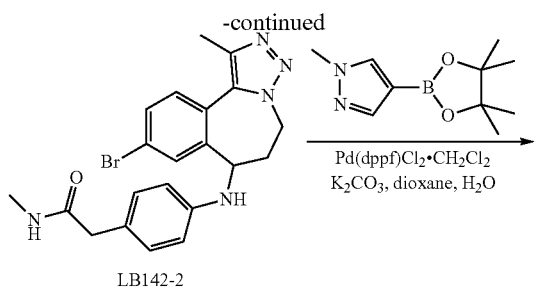

LB142-2

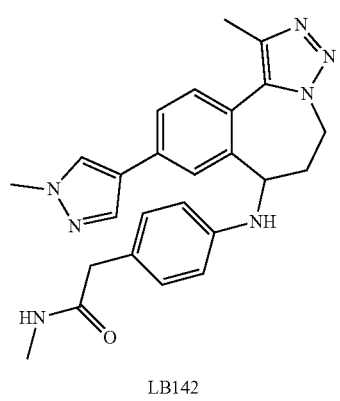

LB142

Step 1: Synthesis of 2-(4-((9-bromo-1-methyl-6,7-dihydro-5H-benzo[c][1,2,3]triazolo[1,5-a]azepin-7-yl)amino)phenyl)-N-methylacetamide (LB142-2)

C-9 (112.1 mg, 0.30 mmol), LB142-1 (99.9 mg, 0.61 mmol), DMF (10 mL), DIPEA (198.9 mg, 1.54 mmol) and sodium iodide (11.3 mg, 0.075 mmol) were added to a reaction flask and heated to 60° C. for reaction. After the reaction was complete, the system was cooled down, added with water (50 mL) and EA (20 mL), shaken and sepatated. The aqueous phase was extracted with EA (30 mL*2). The combined organic phase was washed with water (30 mL*2) and saturated brine (20 mL), dired with anhydrous sodium sulfate and filtered with suction. The filtrate was concentrated under reduced pressure, and the residue was separated by PLC to obtain target compound of 68.2 mg.

ESI-MS Calculated for [M+H]$^+$=440.10; Found: 440.00. The found value was consistent with the caculated value.

Step 2: Synthesis of N-methyl-2-(4-41-methyl-9-(1-methyl-1H-pyrazol-4-yl)-6,7-dihydro-5H-benzo[c][1,2,3]triazolo[1,5-a]azepin-7-yl)amino)phenyl)acet-amide (LB142)

LB142-2 (68.2 mg, 0.16 mmol), 1-methyl-4-(4,4,5,5-tetramethyl-1,3,2-dioxaborolan-2-yl)-1H-pyrazole (45.0 mg, 0.22 mmol), potassium carbonate (34.9 mg, 0.26 mmol), 1,4-dioxane (10 mL) and water (0.5 mL) were added to a reaction flask, and the air in the reaction system was replaced with nitrogen three times. The system was added with Pd(dppf)Cl$_2$-dichloromethane complex (6.9 mg, 0.0085 mmol), and the air in the reaction system was replaced with nitrogen three times again. The reaction was carried out at an extermal temperature of 100° C. After the reaction was complete, the system was cooled down, added with water (50 mL) and EA (30 mL), shaken and sepatated. The aqueous phase was extracted with EA (35 mL*2). The combined organic phase was washed with water (50 mL) and saturated brine (30 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 12.3 mg of the product.

Product analysis: $^1$HNMR (CDCl$_3$, 400 MHz): δ 7.71 (d, J=0.8 Hz, 1H), 7.65 (d, J=1.7 Hz, 1H), 7.59 (d, J=0.8 Hz, 1H), 7.51 (dd, J=7.8, 1.8 Hz, 1H), 7.42 (d, J=7.8 Hz, 1H), 6.95-6.88 (m, 2H), 6.34-6.26 (m, 2H), 5.29 (s, 1H), 4.78 (m, 1H), 4.27 (dt, J=11.3, 6.2 Hz, 1H), 3.98 (d, J=4.9 Hz, 1H), 3.93 (s, 3H), 3.39 (s, 2H), 3.08-2.87 (m, 1H), 2.69 (d, J=4.9 Hz, 3H), 2.53 (s, 3H), 2.29-2.15 (m, 1H).

ESI-MS Calculated for [M+H]$^+$=442.23; Found: 442.20. The found value was consistent with the caculated value.

Preparation Example 58, Final Product LB143: 4-((1-methyl-9-(1-methyl-1H-pyrazol-4-yl)-6,7-dihydro-5H-benzo[c][1,2,3]triazolo[1,5-a]azepin-7-yl)amino)phenol

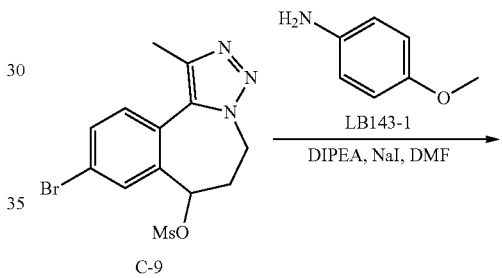

C-9

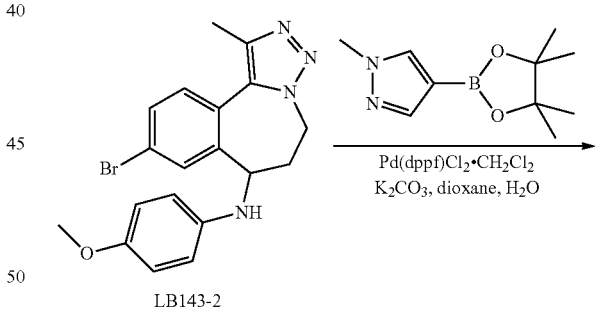

LB143-2

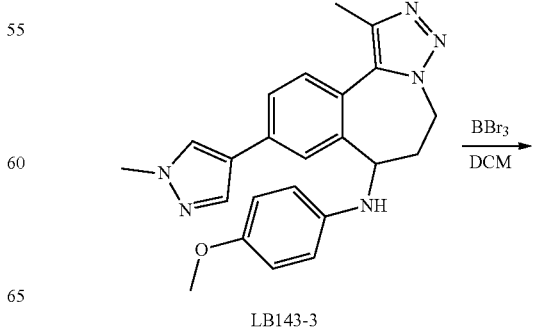

LB143-3

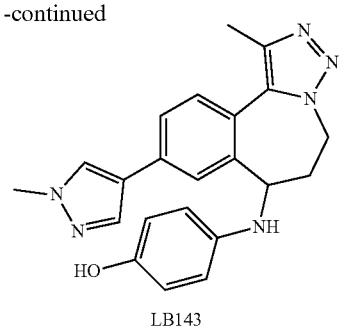

LB143

Step 1: Synthesis of 9-bromo-N-(4-methoxyphenyl)-1-methyl-6,7-dihydro-5H-benzo[c][1,2,3]triazolo[1,5-a]azepin-7-amine (LB143-2)

C-9 (150.4 mg, 0.41 mmol), LB143-1 (100.9 mg, 0.82 mmol), DMF (15 mL), DIPEA (274.1 mg, 2.12 mmol) and sodium iodide (9.3 mg, 0.062 mmol) were added to a reaction flask and heated to 60° C. for reaction. After the reaction was complete, the system was cooled down, added with water (80 mL) and EA (30 mL), shaken and sepatated. The aqueous phase was extracted with EA (30 mL*2). The combined organic phase was washed with water (35 mL*3) and saturated brine (25 mL*3), dried over anhydrous sodium sulfate and filtered with suction. The filtrate was concentrated under reduced pressure, and the residue was separated by PLC to obtain 144.8 mg of the target compound.

ESI-MS Calculated for [M+H]$^+$=399.07; Found: 398.90. The found value was consistent with the caculated value.

Step 2: Synthesis of N-(4-methoxyphenyl)-1-methyl-9-(1-methyl-1H-pyrazol-4-yl)-6,7-dihydro-5H-benzo[c][1,2,3]triazolo[1,5-a]azepin-7-amine (LB143-3)

LB143-2 (144.8 mg, 0.36 mmol), 1-methyl-4-(4,4,5,5-tetramethyl-1,3,2-dioxaborolan-2-yl)-1H-pyrazole (99.6 mg, 0.48 mmol), potassium carbonate (78.8 mg, 0.57 mmol), 1,4-dioxane (15 mL) and water (0.75 mL) were added to a reaction flask, and the air in the reaction system was replaced with nitrogen three times. The system was added with Pd(dppf)Cl$_2$-dichloromethane complex (16.3 mg, 0.020 mmol), and the air in the reaction system was replaced with nitrogen three times again. The system was heated to reflux. After the reaction was complete, the system was cooled down, added with water (50 mL) and EA (20 mL), shaken and sepatated. The aqueous phase was extracted with EA (30 mL*2). The combined organic phase was washed with water (30 mL*2) and saturated brine (25 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 102.1 mg of the product.

ESI-MS Calculated for [M+H]$^+$=401.20; Found: 401.00. The found value was consistent with the caculated value.

Step 3: Synthesis of 4-((1-methyl-9-(1-methyl-1H-pyrazol-4-yl)-6,7-dihydro-5H-benzo[c][1,2,3]triazolo[1,5-a]azepin-7-yl)amino)phenol (LB143)

LB143-3 (55.0 mg, 0.14 mmol) and DCM (5 mL) were added to a reaction flask, added dropwise with BBr$_3$ (0.1 mL) and stirred at room temperature, and the reaction was monitored by LC-MS. After the reaction was complete, 20 mL of an ice-water mixture was added to a 100 mL beaker and the reaction system was carefully dropped into the ice water. After the addition was completed, the system was added with 50 mL of DCM, shaken and sepatated. The aqueous phase was extracted with DCM (50 mL*2). The combined organic phase was washed with water (50 mL*2) and saturated brine (30 mL), dried over anhydrous sodium sulfate and filtered with suction. The filtrate was concentrated under reduced pressure, and the residue was separated by medium-pressure preparative chromatography to obtain 12.4 mg of the product.

Product analysis: $^1$HNMR (CDCl$_3$, 400 MHz): δ 7.71 (d, J=0.8 Hz, 1H), 7.66 (d, J=1.7 Hz, 1H), 7.57 (d, J=0.8 Hz, 1H), 7.48 (dd, J=7.8, 1.8 Hz, 1H), 7.38 (d, J=7.8 Hz, 1H), 6.63-6.56 (m, 2H), 6.25-6.17 (m, 2H), 5.77 (s, 1H), 4.74 (m, 1H), 4.19 (dd, J=10.4, 6.8 Hz, 1H), 4.01 (m, 1H), 3.92 (s, 3H), 3.70 (d, J=31.2 Hz, 1H), 3.05-2.82 (m, 1H), 2.51 (s, 3H).

ESI-MS Calculated for [M+H]$^+$=387.19; Found: 387.00. The found value was consistent with the caculated value.

Preparation Example 59, Final Product RB99: N-(4-chlorophenyl)-1-methyl-9-(1,2,3,6-tetrahydropyridin-4-yl)-6,7-dihydro-5H-benzo[c][1,2,3]triazolo[1,5-a]azepin-7-amine hydrochloride

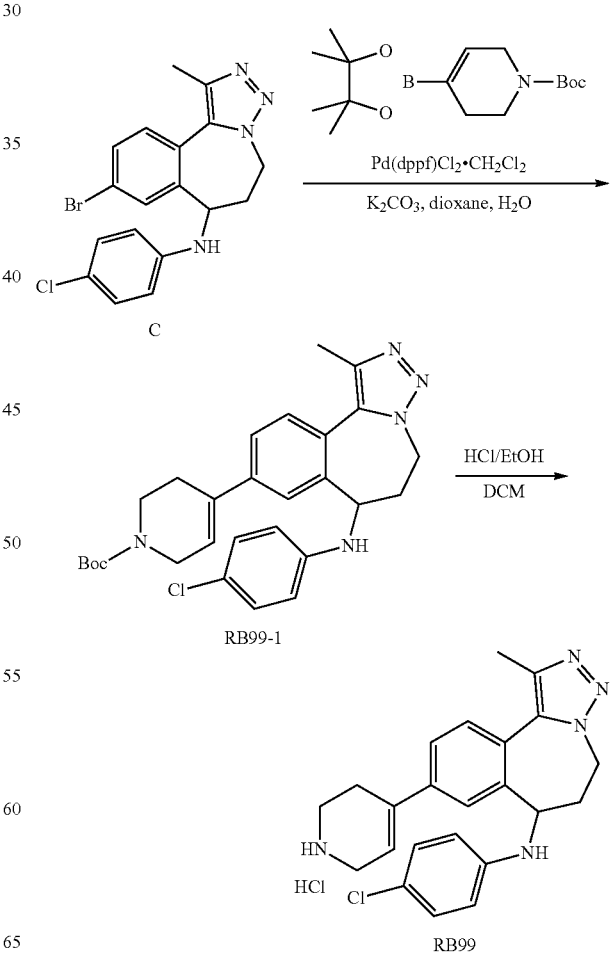

Step 1: Synthesis of tert-butyl 4-(74(4-chlorophenyl)amino)-1-methyl-6,7-dihydro-5H-benzo[c][1,2,3]triazolo[1,5-a]azepin-9-yl)-3,6-dihydropyridine-1(2H)-carboxylate (RB99-1)

C (155.0 mg, 0.38 mmol), N-Boc-1,2,5,6-tetrahydropyridine-4-pinacolborate (132.1 mg, 0.43 mmol), 1,4-dioxane (10 mL), water (0.5 mL) and potassium carbonate (105.7 mg, 0.76 mmol) were added to a reaction flask, and the air in the reaction system was replaced with nitrogen three times. The system was added with Pd(dppf)Cl$_2$-dichloromethane complex (61.5 mg, 0.075 mmol), and the air in the reaction system was replaced with nitrogen three times again. The system was heated to 100° C. for reaction. After the reaction was complete, the system was added with water (100 mL) and EA (50 mL), shaken and sepatated. The aqueous phase was extracted with EA (50 mL*2). The combined organic phase was washed with water (100 mL*2) and saturated brine (50 mL), dired with anhydrous sodium sulfate and filtered with suction. The filtrate was concentrated under reduced pressure, and the residue was separated by column chromatography to obtain 69.0 mg of a crude.

ESI-MS Calculated for [M+H]$^+$=506.22; Found: 506.20. The found value was consistent with the caculated value.

Step 2: Synthesis of N-(4-chlorophenyl)-1-methyl-9-(1,2,3,6-tetrahydropyridin-4-yl)-6,7-dihydro-5H-benzo[c][1,2,3]triazolo[1,5-a]azepin-7-amine hydrochloride (RB99)

RB99-1 (32.9 mg, 0.065 mmol) was added to a reaction flask, added with hydrochloric acid in ethanol/dichloromethane (5/5 mL) and stirred at room temperature for reaction. After the reaction was complete, the system was concentrated under reduced pressure to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 11.5 mg of the product.

ESI-MS Calculated for [M+H]$^+$=406.17; Found: 406.00. The calculated value was consistent with the found value.

Preparation Example 60, Final Product LB152: N$^1$,N$^1$-dimethyl-N$^3$-(1-methyl-9-(1-methyl-1H-pyrazol-4-yl)-6,7-dihydro-5H-benzo[c][1,2,3]triazolo[1,5-a]azepin-7-yl)benzene-1,3-diamine

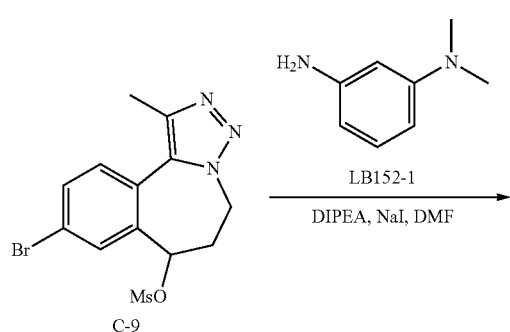

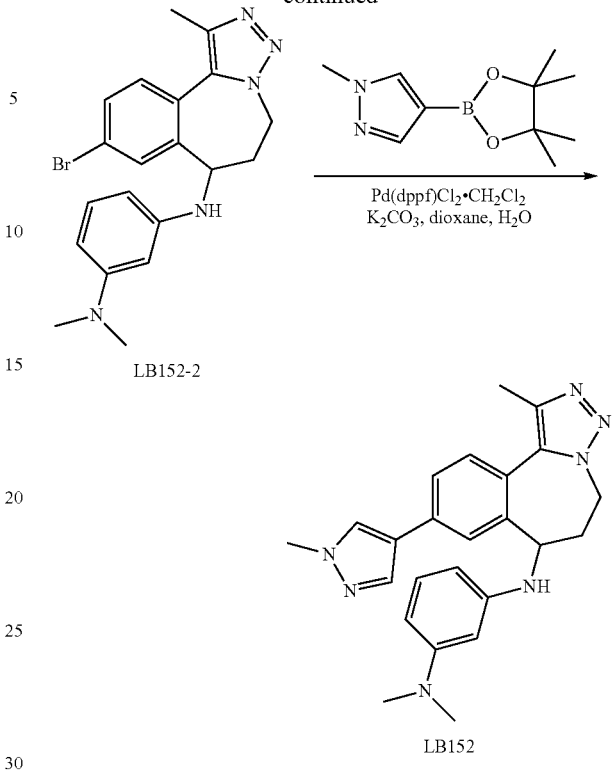

Step 1: Synthesis of N$^1$-(9-bromo-1-methyl-6,7-dihydro-5H-benzo[c][1,2,3]triazolo[1,5-a]azepin-7-yl)-N$^3$,N$^3$-dimethylphenylene-1,3-diamine (LB152-2)

C-9 (152.3 mg, 0.41 mmol), LB152-1 (112.0 mg, 0.82 mmol), DIPEA (266.6 mg, 2.06 mmol), sodium iodide (9.3 mg, 0.062 mmol) and DMF (10 mL) were added to a reaction flask and heated to 60° C., and the reaction was monitored by LC-MS. The system was added with water (50 mL) and EA (25 mL), shaken and sepatated. The aqueous phase was extracted with EA (30 mL*2). The combined organic phase was washed with water (40 mL*2) and saturated brine (20 mL), dired with anhydrous sodium sulfate and filtered with suction. The filtrate was concentrated under reduced pressure, and the residue was separated by PLC to obtain 141.2 mg of the target compound.

ESI-MS Calculated for [M+H]$^+$=412.11; Found: 412.00. The found value was consistent with the caculated value.

Step 2: Synthesis of N$^1$,N$^1$-Dimethyl-N$^3$-(1-methyl-9-(1-methyl-1H-pyrazol-4-yl)-6,7-dihydro-5H-benzo[c][1,2,3]triazolo[1,5-a]azepin-7-yl)benzene-1,3-diamine (LB152)

LB152-2 (141.2 mg, 0.35 mmol), 1-methyl-4-(4,4,5,5-tetramethyl-1,3,2-dioxaborolan-2-yl)-1H-pyrazole (96.1 mg, 0.46 mmol), potassium carbonate (75.9 mg, 0.55 mmol), 1,4-dioxane (15 mL) and water (0.75 mL) were added to a reaction flask, and the air in the reaction system was replaced with nitrogen three times. The system was added with Pd(dppf)Cl$_2$-dichloromethane complex (16.4 mg, 0.020 mmol), and the air in the reaction system was replaced with nitrogen three times again. The system was heated to reflux. After the reaction was complete, the system was cooled down, added with water (50 mL) and EA (30 mL), shaken and sepatated. The aqueous phase was extracted with EA (25 mL*2). The combined organic phase was washed with water (40 mL*2) and saturated brine (25 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 18.9 mg of the product.

Product analysis: $^1$HNMR (CDCl$_3$, 400 MHz): δ 7.76 (d, J=2.9 Hz, 2H), 7.65 (d, J=1.7 Hz, 1H), 7.53 (dd, J=7.9, 1.7 Hz, 1H), 7.42 (d, J=7.9 Hz, 1H), 7.15-7.00 (m, 2H), 6.62 (dd, J=8.1, 1.8 Hz, 1H), 6.07 (d, J=8.5 Hz, 1H), 4.72 (m, 1H), 4.37 (dd, J=9.4, 6.8 Hz, 1H), 4.15(m, 1H), 3.96 (s, 3H), 3.09 (s, 6H), 3.05-2.69 (m, 1H), 2.54 (s, 3H).

ESI-MS Calculated for [M+H]$^+$=414.23; Found: 414.20. The found value was consistent with the caculated value.

Preparation Example 61, Final Product LB160: methyl 2-((1-methyl-9-(1-methyl-1H-pyrazol-4-yl)-6,7-dihydro-5H-benzo[c][1,2,3]triazolo[1,5-a]azepin-7-yl)amino)benzoate

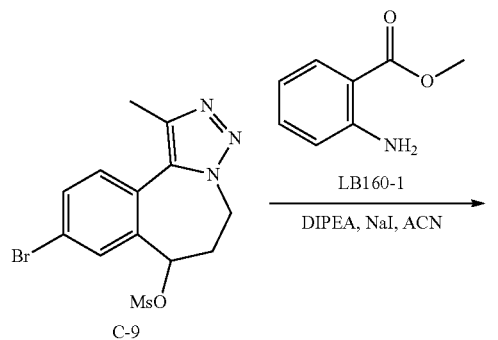

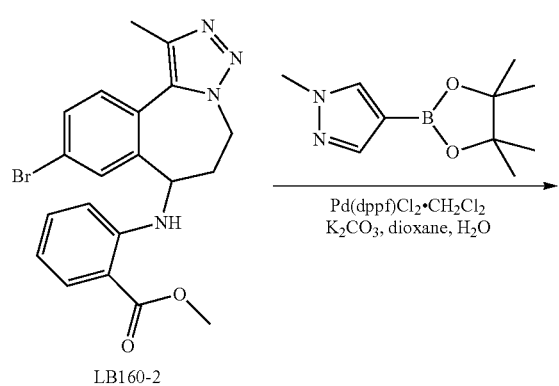

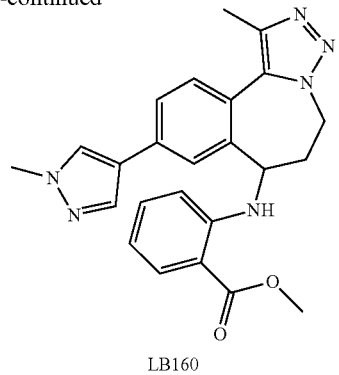

LB160

Step 1: Synthesis of methyl 2-((9-bromo-1-methyl-6,7-dihydro-5H-benzo[c][1,2,3]triazolo[1,5-a]azepin-7-yl)amino)benzoate (LB160-2)

C-9 (200.0 mg, 0.54 mmol), LB160-1 (262.6 mg, 1.68 mmol), acetonitrile (50 mL), DIPEA (311.2 mg, 2.56 mmol) and sodium iodide (12.2 mg, 0.081 mmol) were added to a reaction flask and heated to reflux for reaction. The system was rotary-evaporated to dryness, added with water (100 mL) and EA (80 mL), shaken and sepatated. The aqueous phase was extracted with EA (50 mL*2). The combined organic phase was washed with water (80 mL*3) and saturated brine (50 mL), dired with anhydrous sodium sulfate and filtered with suction. The filtrate was concentrated under reduced pressure, and the residue was separated by PLC to obtain 182.3 mg of the target compound.

ESI-MS Calculated for [M+H]$^+$=427.07; Found: 426.90. The found value was consistent with the caculated value.

Step 2: Synthesis of methyl 2-((1-methyl-9-(1-methyl-1H-pyrazol-4-yl)-6,7-dihydro-5H-benzo[c][1,2,3]triazolo[1,5-a]azepin-7-yl)amino)benzoate (LB160)

LB160-2 (182.3 mg, 0.43 mmol), 1-methyl-4-(4,4,5,5-tetramethyl-1,3,2-dioxaborolan-2-yl)-1H-pyrazole (117.6 mg, 0.57 mmol), potassium carbonate (93.9 mg, 0.68 mmol), 1,4-dioxane (20 mL) and water (1 mL) were added to a reaction flask, and the air in the reaction system was replaced with nitrogen three times. The system was added with Pd(dppf)Cl$_2$-dichloromethane complex (18.9 mg, 0.024 mmol), and the air in the reaction system was replaced with nitrogen three times again. The system was heated to reflux. After the reaction was complete, the system was cooled down, added with water (70 mL) and EA (50 mL), shaken and sepatated. The aqueous phase was extracted with EA (40 mL*2). The combined organic phase was washed with water (50 mL*2) and saturated brine (40 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 40.1 mg of the product.

Product analysis: $^1$HNMR (CDCl$_3$, 400 MHz): δ 8.23 (d, J=6.2 Hz, 1H), 7.92 (dd, J=8.0, 1.7 Hz, 1H), 7.70 (s, 1H), 7.61-7.55 (m, 2H), 7.52 (dd, J=7.9, 1.8 Hz, 1H), 7.43 (d, J=7.9 Hz, 1H), 7.14 (m, 1H), 6.59 (m, 1H), 6.07-5.96 (m, 1H), 4.83 (dd, J=14.1, 7.6 Hz, 1H), 4.39 (m, 1H), 4.14-3.98 (m, 1H), 3.93 (d, J=3.7 Hz, 6H), 3.06 (m, 1H), 2.60 (s, 3H), 2.38 (td, J=11.9, 6.5 Hz, 1H).

ESI-MS Calculated for [M+H]$^+$=429.20; Found: 429.10. The found value was consistent with the caculated value.

Preparation Example 62, Final Product LB164: (3-((1-methyl-9-(1-methyl-1H-pyrazol-4-yl)-6,7-dihydro-5H-benzo[c][1,2,3]triazolo[1,5-a]azepin-7-yl)amino)phenyl)methanol

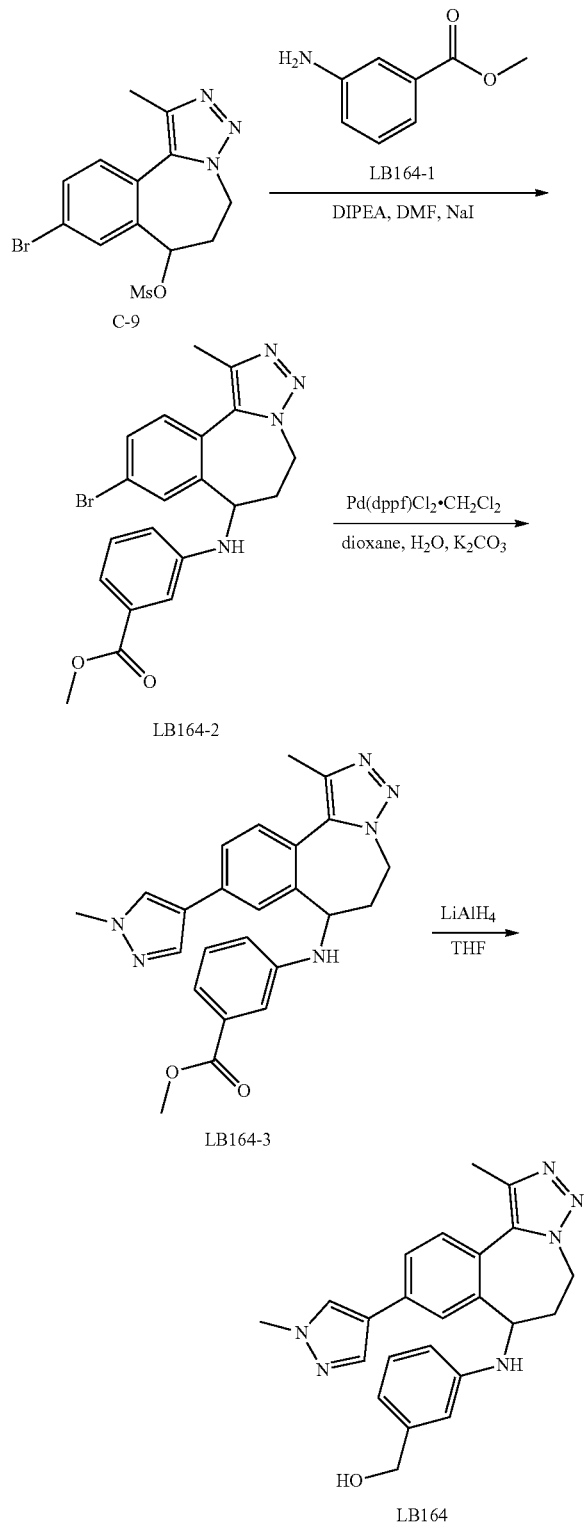

Step 1: Synthesis of methyl 3-((9-bromo-1-methyl-6,7-dihydro-5H-benzo[c][1,2,3]triazolo[1,5-a]azepin-7-yl)amino)benzoate (LB164-2)

C-9 (200.0 mg, 0.54 mmol), LB164-1 (164.9 mg, 1.09 mmol), DMF (15 mL), DIPEA (358.1 mg, 2.77 mmol) and sodium iodide (12.2 mg, 0.081 mmol) were added to a reaction flask and heated to 60° C. for reaction. After the reaction was complete, the system was cooled down, added with water (50 mL) and EA (40 mL), shaken and sepatated. The aqueous phase was extracted with EA (30 mL*2). The combined organic phase was washed with water (40 mL*2) and saturated brine (30 mL), dired with anhydrous sodium sulfate and filtered with suction. The filtrate was concentrated under reduced pressure, and the residue was separated by PLC to obtain 118.2 mg of the target compound.

ESI-MS Calculated for [M+H]⁺=427.07; Found: 426.90. The found value was consistent with the caculated value.

Step 2: Synthesis of methyl 3-((1-methyl-9-(1-methyl-1H-pyrazol-4-yl)-6,7-dihydro-5H-benzo[c][1,2,3]triazolo[1,5-a]azepin-7-yl)amino)benzoate (LB164-3)

LB164-2 (118.2 mg, 0.28 mmol), 1-methyl-4-(4,4,5,5-tetramethyl-1,3,2-dioxaborolan-2-yl)-1H-pyrazole (76.4 mg, 0.37 mmol), potassium carbonate (62.2 mg, 0.45 mmol), 1,4-dioxane (10 mL) and water (0.5 mL) were added to a reaction flask, and the air in the reaction system was replaced with nitrogen three times. The system was added with Pd(dppf)Cl₂-dichloromethane complex (12.4 mg, 0.015 mmol), and the air in the reaction system was replaced with nitrogen three times again. The system was heated to 100° C. for reaction. After the reaction was complete, the system was cooled down, added with water (50 mL) and EA (30 mL), shaken and sepatated. The aqueous phase was extracted with EA (40 mL*2). The combined organic phase was washed with water (40 mL*2) and saturated brine (40 mL), dired with anhydrous sodium sulfate and filtered with suction. The filtrate was concentrated under reduced pressure, and the residue was separated by PLC to obtain a crude, which was separated by medium pressure preparative chromatography to obtain 62.3 mg of the product.

ESI-MS Calculated for [M+H]⁺=429.20; Found: 429.10. The found value was consistent with the caculated value.

Step 2: Synthesis of (3-((1-methyl-9-(1-methyl-1H-pyrazol-4-yl)-6,7-dihydro-5H-benzo[c][1,2,3]triazolo[1,5-a]azepin-7-yl)amino)phenyl)methanol (LB164)

LB164-3 (62.3 mg, 0.15 mmol) and THF (10 mL) were added to a reaction flask, and the air in the reaction system was replaced with nitrogen four times. The system was cooled to 0-10° C., and LiAlH₄ (56.9 mg, 1.50 mmol) was added in batches. After completion of the addition, the system was reacted for 1 h at 0-10° C., quenched by addition of water (10 mL), and concentrated under reduced pressure to remove tetrahydrofuran. The residue was added with EA (20 mL), shaken and sepatated. The aqueous phase was extracted with EA (20 mL*2). The combined organic phase was washed with water (20 mL*2) and saturated brine (30 mL), dried over anhydrous sodium sulfate and filtered with suction. The filtrate was concentrated under reduced pressure to obtain a crude, which was separated by medium pressure preparative chromatography and lyophilized to obtain 1.6 mg of the product.

ESI-MS Calculated for [M+H]$^+$=401.20; Found: 401.10. The found value was consistent with the caculated value.

Preparation Example 63, Final Product LB170: 2-((1-methyl-9-(1-methyl-1H-pyrazol-4-yl)-6,7-dihydro-5H-benzo[c][1,2,3]triazolo[1,5-a]azepin-7-yl)amino)phenol

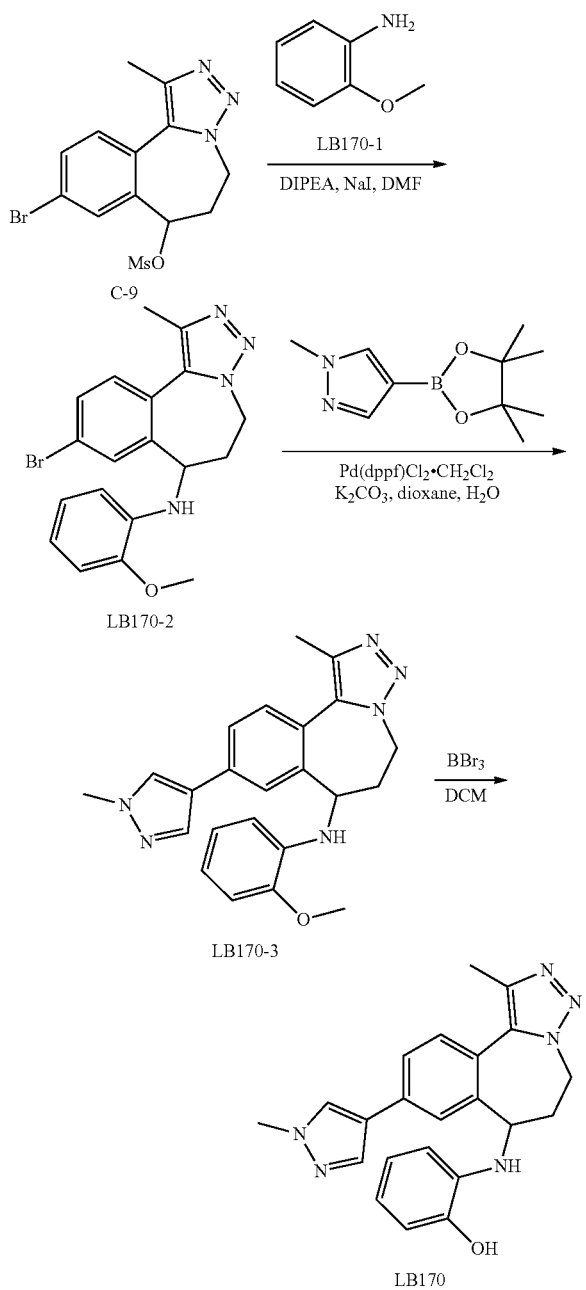

Step 1: Synthesis of 9-bromo-N-(2-methoxyphenyl)-1-methyl-6,7-dihydro-5H-benzo[c][1,2,3]triazolo[1,5-a]azepin-7-amine (LB170-2)

C-9 (100.6 mg, 0.27 mmol), LB170-1 (104.3 mg, 0.85 mmol), DMF (10 mL), DIPEA (174.8 mg, 1.35 mmol) and sodium iodide (6.1 mg, 0.041 mmol) were added to a reaction flask and heated to 60° C. for reaction. After the reaction was complete, the system was cooled down, added with water (50 mL) and EA (40 mL), shaken and sepatated. The aqueous phase was extracted with EA (25 mL*2). The combined organic phase was washed with water (40 mL*2) and saturated brine (30 mL), dired with anhydrous sodium sulfate and filtered with suction. The filtrate was concentrated under reduced pressure, and the residue was separated by PLC to obtain 82.2 mg of the target compound.

ESI-MS Calculated for [M+H]$^+$=399.07; Found: 399.00. The found value was consistent with the caculated value.

Step 2: Synthesis of N-(2-methoxyphenyl)-1-methyl-9-(1-methyl-1H-pyrazol-4-yl)-6,7-dihydro-5H-benzo[c][1,2,3]triazolo[1,5-a]azepin-7-amine (LB170-3)

LB170-2 (82.2 mg, 0.21 mmol), 1-methyl-4-(4,4,5,5-tetramethyl-1,3,2-dioxaborolan-2-yl)-1H-pyrazole (56.2 mg, 0.27 mmol), potassium carbonate (44.7 mg, 0.33 mmol), 1,4-dioxane (10 mL) and water (0.5 mL) were added to a reaction flask, and the air in the reaction system was replaced with nitrogen three times. The system was added with Pd(dppf)Cl$_2$-dichloromethane complex (9.8 mg, 0.012 mmol), and the air in the reaction system was replaced with nitrogen three times again. The reaction was carried out in a bath at 100° C. After the reaction was complete, the reaction system was cooled down, added with water (50 mL) and EA (50 mL), shaken and separated. The aqueous phase was extracted with EA (30 mL*2). The combined organic phase was washed with water (50 mL*2) and saturated brine (40 mL), dired with anhydrous sodium sulfate and filtered with suction. The filtrate was concentrated under reduced pressure, and the residue was separated by PLC to obtain a crude, which was separated by medium pressure preparative chromatography to obtain 44.3 mg of the product.

ESI-MS Calculated for [M+H]$^+$=401.20; Found: 401.10. The found value was consistent with the caculated value.

Step 3: Synthesis of 2-((1-methyl-9-(1-methyl-1H-pyrazol-4-yl)-6,7-dihydro-5H-benzo[c][1,2,3]triazolo[1,5-a]azepin-7-yl)amino)phenol (LB170)

LB170-3 (42.1 mg, 0.053 mmol) and DCM (5 mL) were added into a reaction flask, added dropwise with BBr$_3$ (0.1 mL) and stirred at room temperature, and the reaction was monitored by LC-MS. 50 mL of an ice-water mixture was added into a 100 mL beaker, and the reaction system was carefully added dropwise to the ice water. After completion of the addition, the system was added with 30 mL of DCM, shaken and sepatated. The aqueous phase was extracted with DCM (50 mL*3). The combined organic phase was washed with water (50 mL*3) and saturated brine (50 mL), dried over anhydrous sodium sulfate and filtered with suction. The filtrate was concentrated under reduced pressure, and the residue was separated by medium-pressure preparative chromatography to obtain 0.7 mg of the product.

ESI-MS Calculated for [M+H]$^+$=387.19; Found: 387.10. The found value was consistent with the caculated value.

Preparation Example 64, Final Product LB171: 3-((1-methyl-9-(1-methyl-1H-pyrazol-4-yl)-6,7-dihydro-5H-benzo[c][1,2,3]triazolo[1,5-a]azepin-7-yl)amino)phenol

Step 1: Synthesis of 9-bromo-N-(3-methoxyphenyl)-1-methyl-6,7-dihydro-5H-benzo[c][1,2,3]triazolo[1,5-a]azepin-7-amine (LB171-2)

C-9 (100.3 mg, 0.27 mmol), LB171-1 (104.5 mg, 0.85 mmol), DMF (10 mL), DIPEA (175.5 mg, 1.36 mmol) and sodium iodide (6.1 mg, 0.041 mmol) were added to a reaction flask and heated to 60° C. for reaction. After the reaction was complete, the system was cooled down, added with water (50 mL) and EA (30 mL), shaken and sepatated. The aqueous phase was extracted with EA (30 mL*2). The combined organic phase was washed with water (40 mL*2) and saturated brine (30 mL*2), dired with anhydrous sodium sulfate and filtered with suction. The filtrate was concentrated under reduced pressure, and the residue was separated by PLC to obtain 88.2 mg of the target compound.

ESI-MS Calculated for $[M+H]^+$=399.07; Found: 399.00. The found value was consistent with the caculated value.

Step 2: Synthesis of N-(3-methoxyphenyl)-1-methyl-9-(1-methyl-1H-pyrazol-4-yl)-6,7-dihydro-5H-benzo[c][1,2,3]triazolo[1,5-a]azepin-7-amine (LB171-3)

LB171-2 (88.2 mg, 0.22 mmol), 1-methyl-4-(4,4,5,5-tetramethyl-1,3,2-dioxaborolan-2-yl)-1H-pyrazole (61.2 mg, 0.29 mmol), potassium carbonate (47.6 mg, 0.35 mmol), 1,4-dioxane (10 mL) and water (0.5 mL) were added to a reaction flask, and the air in the reaction system was replaced with nitrogen three times. The system was added with Pd(dppf)Cl$_2$-dichloromethane complex (9.2 mg, 0.011 mmol), and the air in the reaction system was replaced with nitrogen three times again. The reaction was carried out at an external temperature of 100° C. After the reaction was complete, the reaction system was cooled down, added with water (50 mL) and EA (50 mL), shaken and separated. The aqueous phase was extracted with EA (40 mL*2). The combined organic phase was washed with water (50 mL*2) and saturated brine (30 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 74.2 mg of the product.

ESI-MS Calculated for $[M+H]^+$=401.20; Found: 401.10. The found value was consistent with the caculated value.

Step 3: Synthesis of 3-((1-methyl-9-(1-methyl-1H-pyrazol-4-yl)-6,7-dihydro-5H-benzo[c][1,2,3]triazolo[1,5-a]azepin-7-yl)amino)phenol (LB171)

LB171-3 (34.0 mg, 0.085 mmol) and DCM (5 mL) were added into a reaction flask, added dropwise with BBr$_3$ (0.1 mL) and stirred at room temperature, and the reaction was monitored by LC-MS. 40 mL of an ice-water mixture was added to a 100 mL beaker, and the reaction system was carefully added dropwise to the ice water. After completion of the dropwise addition, the system was added with 30 mL of DCM, shaken and sepatated. The aqueous phase was extracted with DCM (50 mL*3). The combined organic phase was washed with water (50 mL*3) and saturated brine (50 mL), dried over anhydrous sodium sulfate and filtered with suction. The filtrate was concentrated under reduced pressure, and the residue was separated by medium-pressure preparative chromatography to obtain 12.1 mg of the product.

ESI-MS Calculated for $[M+H]^+$=387.19; Found: 387.10. The found value was consistent with the caculated value.

Preparation Example 65, Final Product LB173: 2-((1-methyl-9-(1-methyl-1H-pyrazol-4-yl)-6,7-dihydro-5H-benzo[c][1,2,3]triazolo[1,5-a]azepin-7-yl)amino)benzoic acid

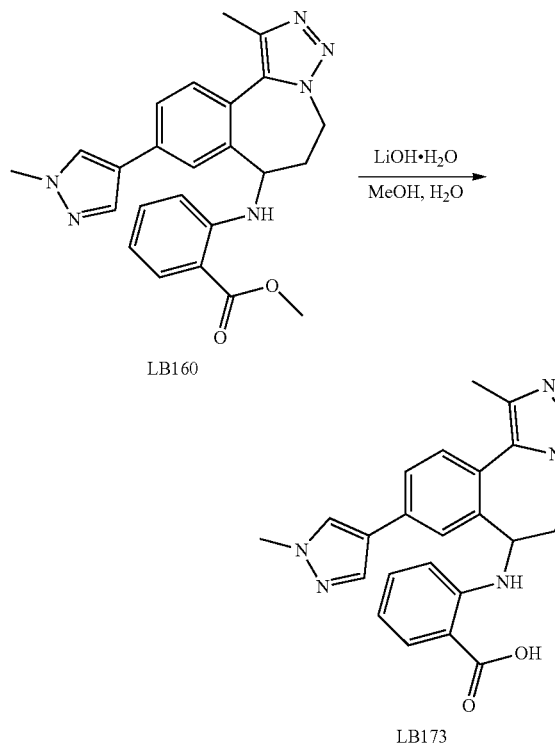

Synthesis of 2-((1-methyl-9-(1-methyl-1H-pyrazol-4-yl)-6,7-dihydro-5H-benzo[c][1,2,3]triazolo[1,5-a]azepin-7-yl)amino)benzoic acid (LB173)

LB160 (12.1 mg, 0.028 mmol), lithium hydroxide monohydrate (12.6 mg, 0.53 mmol), methanol (2.5 mL) and water (2.5 mL) were added to a 25 mL single necked flask and stirred at room temperature. After the reaction was complete, the system was concentrated under reduced pressure, and the residue was added with water (50 mL) and methyl tert-butyl ether (MTBE, 50 mL) and seperated. The aqueous phase was extracted with MTBE (50 mL*2), and the organic phase was discarded. The aqueous phase was adjusted pH to 2-3 with 1 mol/L dilute hydrochloric acid and extracted with MTBE (30 mL*2). The combined organic phase was washed with water (30 mL*3) and saturated brine (30 mL), dired with anhydrous sodium sulfate and filtered with suction. The filtrate was concentrated and the residue was separated by fast medium pressure preparative chromatography to obtain 8.1 mg of the target compound.

Product analysis: $^1$HNMR (CDCl$_3$, 400 MHz): δ 7.95 (d, J=7.9 Hz, 1H), 7.84 (s, 1H), 7.65 (s, 1H), 7.53 (s, 1H), 7.41 (s, 1H), 7.17 (t, J=7.6 Hz, 1H), 6.61 (t, J=7.5 Hz, 1H), 6.13 (d, J=8.3 Hz, 1H), 4.72 (s, 1H), 4.56 (s, 1H), 4.26 (s, 1H), 3.98 (s, 3H), 3.04 (s, 1H), 2.54 (s, 4H).

ESI-MS Calculated for [M+H]$^+$=415.18; Found: 415.20. The found value was consistent with the caculated value.

Preparation Example 66, Final Product LB175: methyl 2-(2-((9-(1-methyl-1H-pyrazol-4-yl)-6,7-dihydro-5H-benzo[c][1,2,3]triazolo[1,5-a]azepin-7-yl)amino)phenyl)acetate

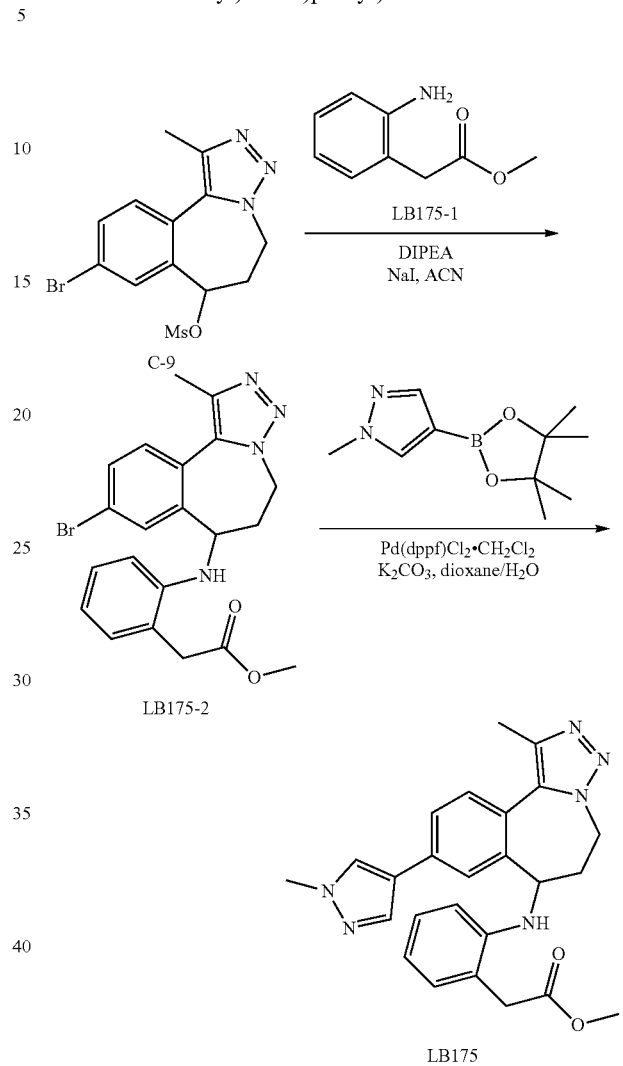

Step 1: Synthesis of methyl 2-(2-((9-bromo-1-methyl-6,7-dihydro-5H-benzo[c][1,2,3]triazolo[1,5-a]azepin-7-yl)amino)phenyl)acetate (LB175-2)

C-9 (300.5 mg, 0.81 mmol), LB175-1: methyl 2-aminophenylacetate (404.1 mg, 2.45 mmol), acetonitrile (40 mL), DIPEA (527.6 mg, 4.09 mmol) and sodium iodide (18.0 mg, 0.12 mmol) were added to a reaction flask and heated to react under reflux. After the reaction was complete, the system was concentrated under reduced pressure, and the residue was added with water (100 mL) and EA (80 mL), shaken and sepatated. The aqueous phase was extracted with EA (50 mL*2). The combined organic phase was washed with water (80 mL*2) and saturated brine (50 mL), dired with anhydrous sodium sulfate and filtered with suction. The filtrate was concentrated under reduced pressure, and the residue was separated by PLC to obtain 266.1 mg of the target compound.

ESI-MS Calculated for [M+H]$^+$=441.08; Found: 441.10. The found value was consistent with the caculated value.

Step 2: Synthesis of methyl 2-(2-((9-(1-methyl-1H-pyrazol-4-yl)-6,7-dihydro-5H-benzo[c][1,2,3]triazolo[1,5-a]azepin-7-yl)amino)phenyl)acetate (LB175)

LB175-2 (266.1 mg, 0.60 mmol), 1-methyl-4-(4,4,5,5-tetramethyl-1,3,2-dioxaborolan-2-yl)-1H-pyrazole (164.4 mg, 0.79 mmol), potassium carbonate (130.2 mg, 0.95 mmol), 1,4-dioxane (20 mL) and water (1 mL) were added to a reaction flask, and the air in the reaction system was replaced with nitrogen three times. The system was added with Pd(dppf)Cl$_2$-dichloromethane complex (26.6 mg, 0.033 mmol), and the air in the reaction system was replaced with nitrogen three times again. The reaction was carried out at an external temperature of 100° C. After the reaction was complete, the system was cooled down, added with water (80 mL) and EA (50 mL), shaken and sepatated. The aqueous phase was extracted with EA (50 mL*2). The combined organic phase was washed with water (50 mL*3) and saturated brine (50 mL), dired with anhydrous sodium sulfate and filtered with suction. The filtrate was concentrated under reduced pressure, and the residue was separated by PLC to obtain 184.0 mg of the product.

Product analysis: $^1$HNMR (CDCl$_3$, 400 MHz): δ 7.85 (s, 1H), 7.75 (d, J=1.6 Hz, 1H), 7.68 (s, 1H), 7.53 (d, J=6.6 Hz, 1H), 7.44 (d, J=7.7 Hz, 1H), 7.09 (dd, J=7.4, 1.6 Hz, 1H), 6.94 (m,1H), 6.66 (td, J=7.4, 1.0 Hz, 1H), 5.98 (d, J=8.0 Hz, 1H), 4.83 (dd, J=14.0, 7.5 Hz, 1H), 4.38 (dd, J=10.7, 6.5 Hz, 1H), 4.09 (m, 1H), 3.97 (s, 3H), 3.75 (s, 3H), 3.66 (d, J=6.7 Hz, 2H), 3.05 (m, 1H), 2.63 (s, 3H), 2.41-2.27 (m, 1H).

ESI-MS Calculated for [M+H]$^+$=443.50; Found: 443.10; the found value was consistent with the caculated value.

Preparation Example 67, Final Product LB181: N-methyl-34(1-methyl-9-(1-methyl-1H-pyrazol-4-yl)-6,7-dihydro-5H-benzo[c][1,2,3]triazolo[1,5-a]azepin-7-yl)amino)benzamide

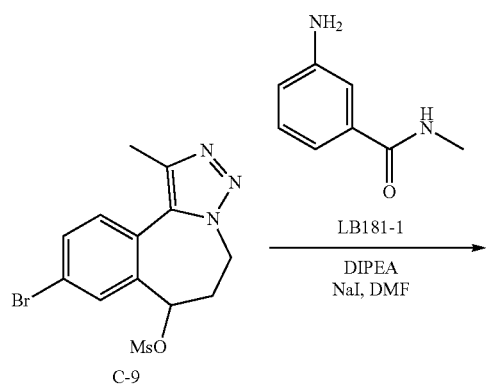

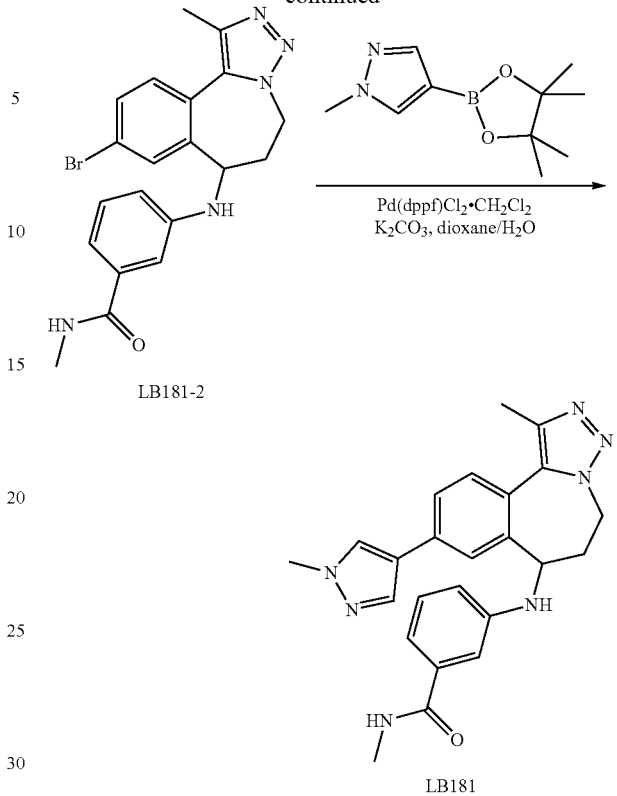

Step 1: Synthesis of 3-((9-bromo-1-methyl-6,7-dihydro-5H-benzo[c][1,2,3]triazolo[1,5-a]azepin-7-yl)amino)-N-methylbenzamide (LB181-2)

C-9 (120.6 mg, 0.33 mmol), LB181-1 (147.2 mg, 0.98 mmol), DMF (10 mL), DIPEA (214.6 mg, 1.66 mmol) and sodium iodide (7.5 mg, 0.050 mmol) were added to a reaction flask and heated to 60° C. for reaction. After the reaction was complete, the system was cooled down, added with water (50 mL) and EA (30 mL), shaken and sepatated. The aqueous phase was extracted with EA (30 mL*2). The combined organic phase was washed with water (40 mL*2) and saturated brine (30 mL), dired with anhydrous sodium sulfate and filtered with suction. The filtrate was concentrated under reduced pressure, and the residue was separated by PLC to obtain 66.6 mg of the target compound.

ESI-MS Calculated for [M+H]$^+$=426.09; Found: 426.00. The found value was consistent with the caculated value.

Step 2: Synthesis of N-methyl-3-((1-methyl-9-(1-methyl-1H-pyrazol-4-yl)-6,7-dihydro-5H-benzo[c][1,2,3]triazolo[1,5-a]azepin-7-yl)amino)benzamide (LB181)

LB181-2 (66.6 mg, 0.16 mmol), 1-methyl-4-(4,4,5,5-tetramethyl-1,3,2-dioxaborolan-2-yl)-1H-pyrazole (45.8 mg, 0.22 mmol), potassium carbonate (34.8 mg, 0.25 mmol), 1,4-dioxane (10 mL) and water (0.5 mL) were added to a reaction flask, and the air in the reaction system was replaced with nitrogen three times. The system was added with Pd(dppf)Cl$_2$-dichloromethane complex (7.2 mg, 0.0088 mmol), and the air in the reaction system was replaced with nitrogen three times again. The system was heated to 100° C. for reaction. The system was cooled down, added with water (50 mL) and EA (40 mL), shaken and sepatated. The aqueous phase was extracted with EA (40 mL*2). The combined organic phase was washed with water (50 mL*2) and saturated brine (40 mL), dired with anhydrous sodium sulfate and filtered with suction. The filtrate was concentrated under reduced pressure, and the residue was separated by PLC to obtain a crude, which was separated by medium pressure preparative chromatography to obtain 21.1 mg of the product.

Product analysis: ¹HNMR (CDCl₃, 400 MHz): δ 7.75 (d, J=0.8 Hz, 1H), 7.66-7.59 (m, 2H), 7.52 (dd, J=7.9, 1.8 Hz, 1H), 7.42 (d, J=7.8 Hz, 1H), 7.06 (t, J=7.9 Hz, 1H), 7.00 (t, J=2.0 Hz, 1H), 6.93-6.88 (m, 1H), 6.29-6.24 (m, 1H), 6.19 (d, J=5.4 Hz, 1H), 4.85-4.68 (m, 1H), 4.37 (dd, J=10.0, 6.7 Hz, 1H), 4.11 (m, 1H), 3.94 (s, 3H), 2.96 (d, J=4.8 Hz, 4H), 2.55 (s, 3H), 2.46-2.07 (m, 1H).

ESI-MS Calculated for [M+H]⁺=428.21; Found: 428.30. The found value was consistent with the caculated value.

Preparation Example 68, Final Product LB185:
2-(2-((1-methyl-9-(1-methyl-1H-pyrazol-4-yl)-6,7-dihydro-5H-benzo[c][1,2,3]triazolo[1,5-a]azepin-7-yl)amino)phenyl)acetic acid

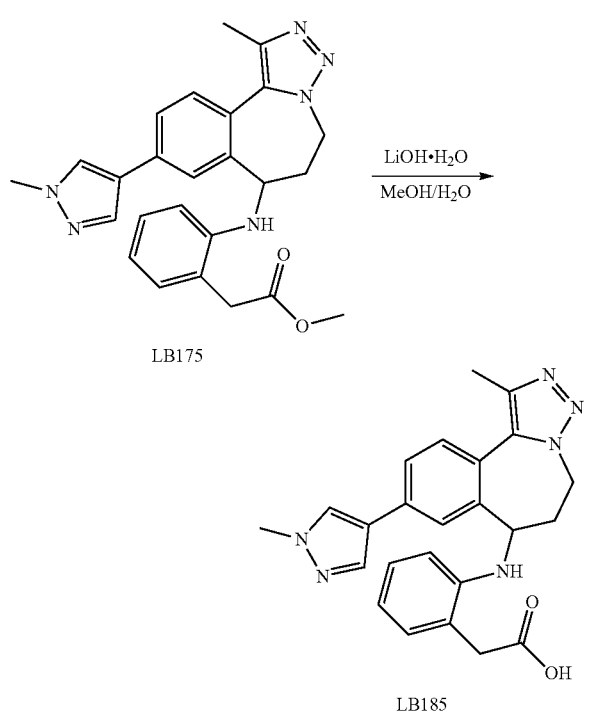

Synthesis of 2-(2-((1-methyl-9-(1-methyl-1H-pyrazol-4-yl)-6,7-dihydro-5H-benzo[c][1,2,3]triazolo[1,5-a]azepin-7-yl)amino)phenyl)acetic acid (LB185)

LB175 (144.3 mg, 0.10 mmol), methanol (5 mL), water (5 mL) and lithium hydroxide monohydrate (24.3 mg, 1.01 mmol) were added to a 25 mL single necked flask and stirred at room temperature, and the reaction was monitored by LC-MS. After the reaction was complete, the system was concentrated under reduced pressure, and the residue was added with water (50 mL) and washed with MTBE (50 mL*2). The organic phase was discarded, and the aqueous phase was adjusted pH to 1-3 with 1 mol/L dilute hydrochloric acid and extracted with MTBE (30 mL*2). The combined organic phase was washed with water (40 mL*3) and saturated brine (30 mL), dired with anhydrous sodium sulfate and filtered with suction. The filtrate was concentrated and the residue was separated by fast medium pressure preparative chromatography to obtain 48.1 mg of the target compound.

ESI-MS Calculated for [M+H]⁺=429.20; Found: 429.10. The found value was consistent with the caculated value.

Preparation Example 69, Final Product LB186:
N-methyl-24(1-methyl-9-(1-methyl-1H-pyrazol-4-yl)-6,7-dihydro-5H-benzo[c][1,2,3]triazolo[1,5-a]azepin-7-yl)amino)benzamide

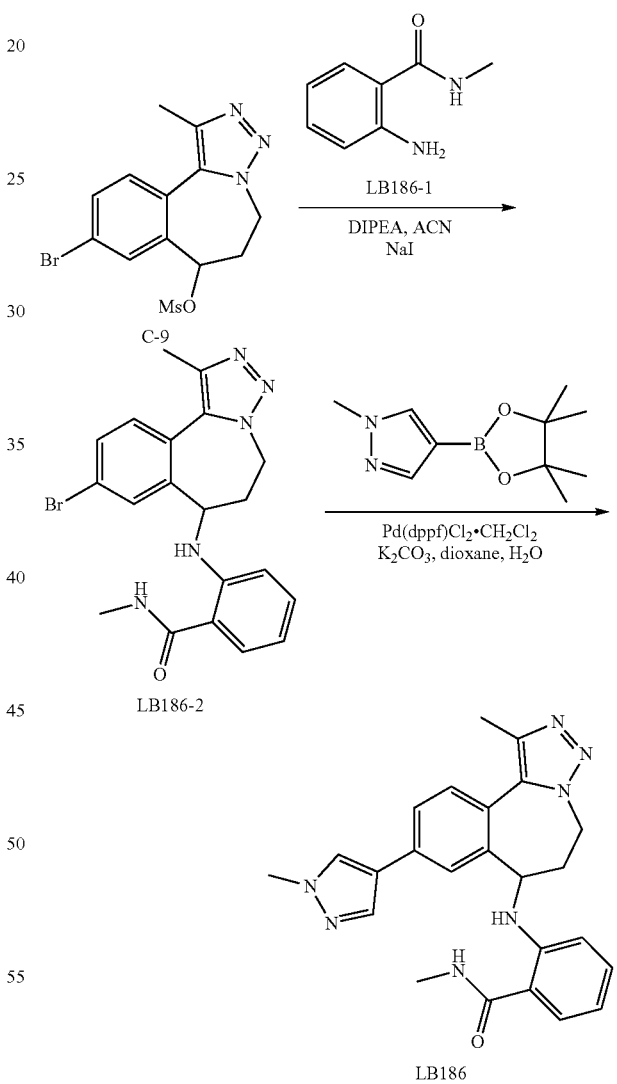

Step 1: Synthesis of 2-((9-bromo-1-methyl-6,7-dihydro-5H-benzo[c][1,2,3]triazolo[1,5-a]azepin-7-yl)amino)-N-methylbenzamide (LB186-2)

C-9 (200.1 mg, 0.53 mmol), LB186-1 (243.3 mg, 1.62 mmol), DIPEA (347.7 mg, 2.68 mmol), sodium iodide (12.0 mg, 0.080 mmol) and acetonitrile (30 mL) were added to a reaction flask and heated to reflux, and the reaction was monitored by LC-MS. The system was added with water (50 mL) and EA (100 mL), shaken and sepatated. The aqueous phase was extracted with EA (40 mL*2). The combined organic phase was washed with water (50 mL*2) and saturated brine (50 mL), dired with anhydrous sodium sulfate and filtered with suction. The filtrate was concentrated under reduced pressure, and the residue was separated by PLC to obtain 186.3 mg of the target compound.

ESI-MS Calculated for [M+H]$^+$=426.09; Found: 426.00. The found value was consistent with the caculated value.

Step 2: Synthesis of N-methyl-2-((1-methyl-9-(1-methyl-1H-pyrazol-4-yl)-6,7-dihydro-5H-benzo[c][1,2,3]triazolo[1,5-a]azepin-7-yl)amino)benzamide (LB186)

LB186-2 (186.3 mg, 0.44 mmol), 1-methyl-4-(4,4,5,5-tetramethyl-1,3,2-dioxaborolan-2-yl)-1H-pyrazole (121.9 mg, 0.59 mmol), potassium carbonate (94.9 mg, 0.69 mmol), 1,4-dioxane (20 mL) and water (1 mL) were added to a reaction flask, and the air in the reaction system was replaced with nitrogen three times. The system was added with Pd(dppf)Cl$_2$-dichloromethane complex (19.1 mg, 0.024 mmol), and the air in the reaction system was replaced with nitrogen three times again. The system was heated to reflux, and the reaction was monitored by LC-MS. The system was added with water (80 mL) and EA (50 mL), shaken and sepatated. The aqueous phase was extracted with EA (50 mL*2). The combined organic phase was washed with water (80 mL*2) and saturated brine (50 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 70.8 mg of the product.

Product analysis: $^1$HNMR (CDCl$_3$, 400 MHz): δ 7.82 (d, J=0.8 Hz, 1H), 7.74-7.65 (m, 2H), 7.54 (dd, J=7.9, 1.8 Hz, 1H), 7.45 (d, J=7.8 Hz, 1H), 7.36 (dd, J=7.9, 1.5 Hz, 1H), 7.09 (m, 1H), 6.68-6.55 (m, 1H), 6.43 (s, 1H), 6.04 (d, J=8.3 Hz, 1H), 4.83 (dd, J=14.1, 7.4 Hz, 1H), 4.38 (dd, J=10.7, 6.7 Hz, 1H), 4.12 (m, 1H), 3.99 (s, 3H), 3.13-2.96 (m, 4H), 2.64 (s, 3H), 2.51-2.32 (m, 1H).

ESI-MS Calculated for [M+H]$^+$=428.21; Found: 428.10. The found value was consistent with the caculated value.

Preparation Example 70, Final Product LB192: (2-((1-methyl-9-(1-methyl-1H-pyrazol-4-yl)-6,7-dihydro-5H-benzo[c][1,2,3]triazolo[1,5-a]azepin-7-yl)amino)phenyl)methanol

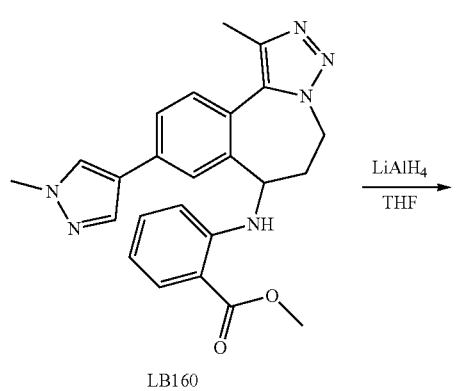

LB160

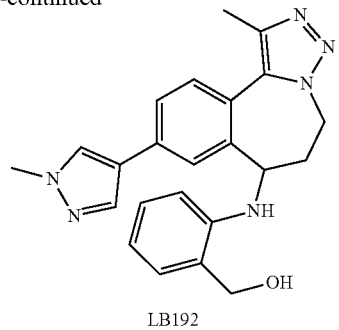

LB192

Synthesis of 2-((1-methyl-9-(1-methyl-1H-pyrazol-4-yl)-6,7-dihydro-5H-benzo[c][1,2,3]triazolo[1,5-a]azepin-7-yl)amino)phenyl)methanol (LB192)

LB160 (15.3 mg, 0.036 mmol) and THF (5 mL) were added to a reaction flask, and the air in the reaction system was replaced with nitrogen three times. The system was cooled to 0-10° C., and LiAlH$_4$ (13.6 mg, 0.36 mmol) was added in batches. After completion of the addition, the reaction was carried out for 1 h at 0-10° C. After the reaction was complete, the system was quenched by addition of water (20 mL). The organic phase was concentrated under reduced pressure. The residue was added with EA (20 mL), shaken and sepatated. The aqueous phase was extracted with EA (20 mL*2). The combined organic phase was washed with water (20 mL*2) and saturated brine (40 mL), dried over anhydrous sodium sulfate and filtered with suction. The filtrate was concentrated under reduced pressure to obtain a crude, which was separated by medium pressure preparative chromatography and lyophilized to obtain 7.1 mg of the product.

Product analysis: $^1$HNMR (CDCl$_3$, 400 MHz): δ 7.75 (d, J=0.7 Hz, 1H), 7.68 (d, J=1.7 Hz, 1H), 7.59 (s, 1H), 7.51 (dd, J=7.8, 1.7 Hz, 1H), 7.42 (d, J=7.9 Hz, 1H), 7.06-6.93 (m, 2H), 6.61 (m, 1H), 6.08 (d, J=8.1 Hz, 1H), 4.72 (s, 3H), 4.50-4.37 (m, 1H), 4.16 (m, 1H), 3.94 (s, 3H), 2.99 (m, 1H), 2.56 (s, 4H).

ESI-MS Calculated for [M+H]$^+$=401.20; Found: 401.10. The found value was consistent with the caculated value.

Preparation Example 71, Final Product LCO1: N-(2,4-difluorophenyl)-1-methyl-9-(1-methyl-1H-pyrazol-4-yl)-6,7-dihydro-5H-benzo[c][1,2,3]triazolo[1,5-a]azepin-7-amine

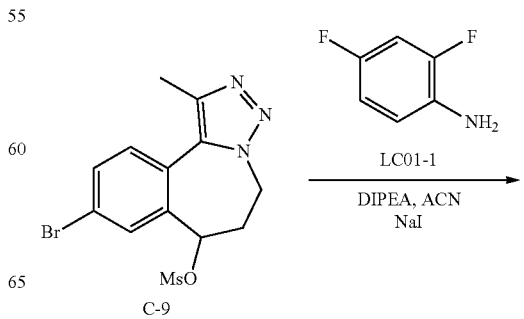

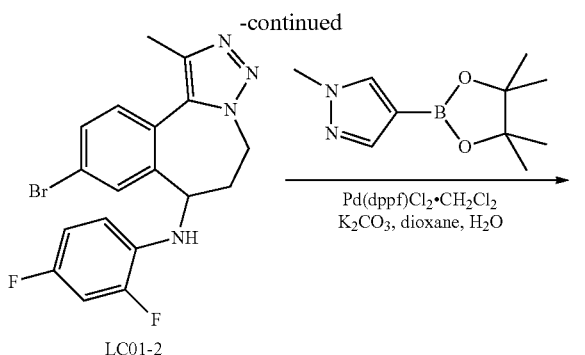

Step 1: Synthesis of 9-bromo-N-(2,4-difluorophenyl)-1-methyl-6,7-dihydro-5H-benzo[c][1,2,3]triazolo[1,5-a]azepin-7-amine (LC01-2)

C-9 (150.3 mg, 0.40 mmol), LC01-1 (104.8 mg, 0.81 mmol), acetonitrile (15 mL), DIPEA (260.1 mg, 2.01 mmol) and sodium iodide (9.1 mg, 0.060 mmol) were added to a reaction flask and heated to react under reflux. After the reaction was complete, the system was added with water (50 mL) and EA (100 mL), shaken and sepatated. The aqueous phase was extracted with EA (40 mL*2). The combined organic phase was washed with water (50 mL*2) and saturated brine (30 mL), dired with anhydrous sodium sulfate and filtered with suction. The filtrate was concentrated under reduced pressure, and the residue was separated by PLC to obtain 93.1 mg of the target compound.

ESI-MS Calculated for [M+H]$^+$=407.04; Found: 407.00. The found value was consistent with the caculated value.

Step 2: Synthesis of N-(2,4-difluorophenyl)-1-methyl-9-(1-methyl-1H-pyrazol-4-yl)-6,7-dihydro-5H-benzo[c][1,2,3]triazolo[1,5-a]azepin-7-amine (LC01)

LC01-2 (93.1 mg, 0.23 mmol), 1-methyl-4-(4,4,5,5-tetramethyl-1,3,2-dioxaborolan-2-yl)-1H-pyrazole (64.4 mg, 0.31 mmol), 1,4-dioxane (10 mL), water (0.5 mL) and potassium carbonate (50.0 mg, 0.36 mmol) were added to a reaction flask, and the air in the reaction system was replaced with nitrogen three times. The system was added with Pd(dppf)Cl$_2$-dichloromethane complex (10.0 mg, 0.012 mmol), and the air in the reaction system was replaced with nitrogen three times again. The reaction was carried out in a bath at 100° C. After the reaction was complete, the system was cooled down, added with water (30 mL) and EA (50 mL), shaken and sepatated. The aqueous phase was extracted with EA (40 mL*2). The combined organic phase was washed with water (50 mL*2) and saturated brine (40 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 16.8 mg of the product.

Product analysis: $^1$HNMR (CDCl$_3$, 400 MHz): δ 7.73 (d, J=0.7 Hz, 1H), 7.66-7.56 (m, 2H), 7.52 (dd, J=7.8, 1.8 Hz, 1H), 7.42 (d, J=7.8 Hz, 1H), 6.79 (m, 1H), 6.52 (m, 1H), 5.97 (m, 1H), 4.92-4.73 (m, 1H), 4.25 (dd, J=10.7, 6.8 Hz, 1H), 4.05 (m, 1H), 3.94 (s, 3H), 3.03 (m, 1H), 2.57 (s, 3H), 2.28 (m, 1H).

ESI-MS Calculated for [M+H]$^+$=407.17; Found: 407.00. The found value was consistent with the caculated value.

Preparation Example 72, Final Product LC03: 2-(4-((1-methyl-9-(1-methyl-1H-pyrazol-4-yl)-6,7-dihydro-5H-benzo[c][1,2,3]triazolo[1,5-a]azepin-7-yl) amino)phenyl)acetonitrile

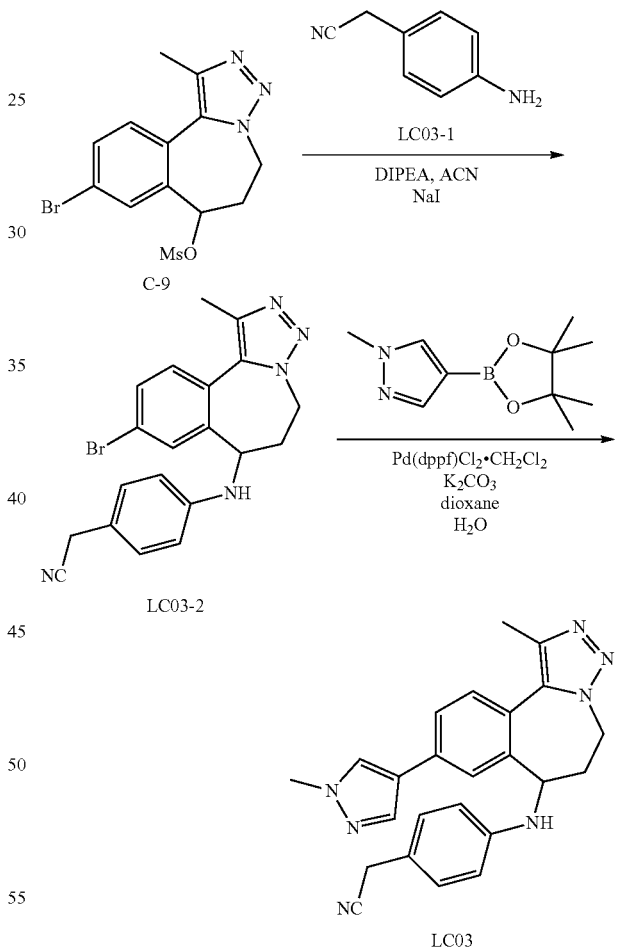

Step 1: Synthesis of 2-(4-((9-bromo-1-methyl-6,7-dihydro-5H-benzo[c][1,2,3]triazolo[1,5-a]azepin-7-yl)amino)phenyl)acetonitrile (LC03-2)

C-9 (150.8 mg, 0.41 mmol), LC03-1 (107.7 mg, 0.82 mmol), acetonitrile (25 mL), DIPEA (267.6 mg, 2.07 mmol) and sodium iodide (11.1 mg, 0.074 mmol) were added to a reaction flask and heated to react under reflux. After the reaction was complete, the system was cooled down, added with water (80 mL) and EA (100 mL), shaken and sepatated. The aqueous phase was extracted with EA (50 mL*2). The combined organic phase was washed with water (100 mL*2) and saturated brine (50 mL), dired with anhydrous sodium sulfate and filtered with suction. The filtrate was concentrated under reduced pressure, and the residue was separated by PLC to obtain 120.9 mg of the target compound.

ESI-MS Calculated for [M+H]$^+$=410.07; Found: 409.90. The found value was consistent with the caculated value.

Step 2: Synthesis of 2-(4-((1-methyl-9-(1-methyl-1H-pyrazol-4-yl)-6,7-dihydro-5H-benzo[c][1,2,3]triazolo[1,5-a]azepin-7-yl)amino)phenyl)acetonitrile (LC03)

LC03-2 (120.9 mg, 0.30 mmol), 1-methyl-4-(4,4,5,5-tetramethyl-1,3,2-dioxaborolan-2-yl)-1H-pyrazole (81.9 mg, 0.40 mmol), 1,4-dioxane (15 mL) and water (0.75 mL), potassium carbonate (65.1 mg, 0.47 mmol) were added to a reaction flask, and the air in the reaction system was replaced with nitrogen three times. The system was added with Pd(dppf)Cl$_2$-dichloromethane complex (13.5 mg, 0.017 mmol), and the air in the reaction system was replaced with nitrogen three times again. The system was heated to reflux. After the reaction was complete, the system was cooled down, added with water (50 mL) and EA (40 mL), shaken and sepatated. The aqueous phase was extracted with EA (40 mL*2). The combined organic phase was washed with water (50 mL*3) and saturated brine (40 mL), dired with anhydrous sodium sulfate and filtered with suction. The filtrate was concentrated under reduced pressure, and the residue was separated by PLC to obtain a crude, which was separated by medium pressure preparative chromatography to obtain 46.8 mg of the product.

Product analysis: $^1$HNMR (CDCl$_3$, 400 MHz): δ 7.72 (s, 1H), 7.63 (d, J=1.7 Hz, 1H), 7.58 (s, 1H), 7.51 (dd, J=7.8, 1.8 Hz, 1H), 7.41 (d, J=7.9 Hz, 1H), 7.02-6.96 (m, 2H), 6.36-6.28 (m, 2H), 4.77 (m, 1H), 4.30 (dd, J=10.3, 6.7 Hz, 1H), 4.07 (m, 1H), 3.93 (s, 3H), 3.55 (s, 2H), 3.01 (m, 1H), 2.55 (s, 3H).

ESI-MS Calculated for [M+H]$^+$=410.20; Found: 410.00. The found value was consistent with the caculated value.

Preparation Example 73, Final Product LC07: 3-((1-methyl-9-(1-methyl-1H-pyrazol-4-yl)-6,7-dihydro-5H-benzo[c][1,2,3]triazolo[1,5-a]azepin-7-yl)amino)benzonitrile

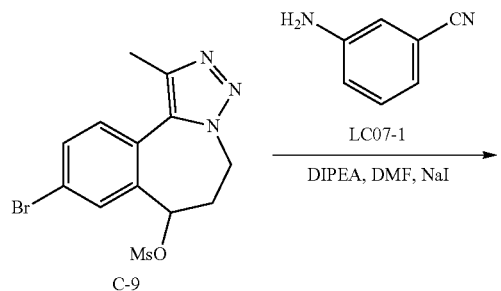

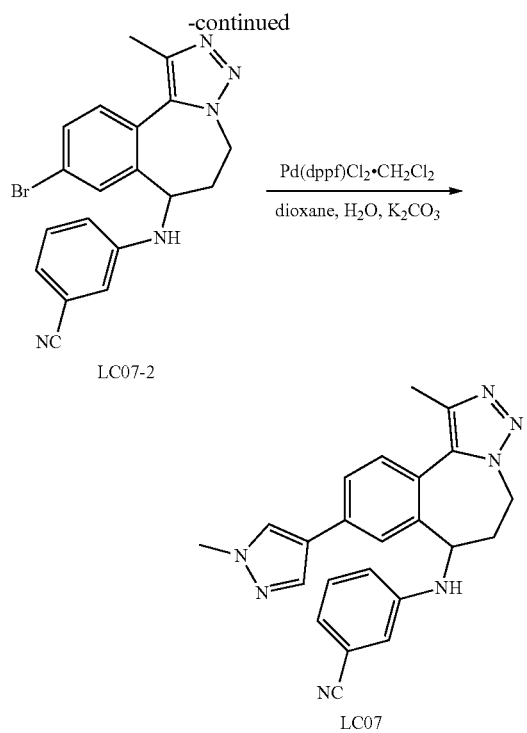

Step 1: Synthesis of 3-((9-bromo-1-methyl-6,7-dihydro-5H-benzo[c][1,2,3]triazolo[1,5-a]azepin-7-yl)amino)benzonitrile (LC07-2)

C-9 (150.9 mg, 0.41 mmol), LC07-1 (98.4 mg, 0.83 mmol), acetonitrile (30 mL), DIPEA (270.3 mg, 2.09 mmol) and sodium iodide (9.9 mg, 0.066 mmol) were added to a reaction flask, and heated to react under reflux. After the reaction was complete, the reaction system was added with water (50 mL) and EA (50 mL), shaken and separated. The aqueous phase was extracted with EA (30 mL*2). The combined organic phase was washed with water (50 mL*2) and saturated brine (20 mL), dired with anhydrous sodium sulfate and filtered with suction. The filtrate was concentrated under reduced pressure, and the residue was separated by PLC to obtain 72.1 mg of the target compound.

ESI-MS Calculated for [M+H]$^+$=394.06; Found: 393.90. The found value was consistent with the caculated value.

Step 2: Synthesis of 3-((1-methyl-9-(1-methyl-1H-pyrazol-4-yl)-6,7-dihydro-5H-benzo[c][1,2,3]triazolo[1,5-a]azepin-7-yl)amino)benzonitrile (LC07)

LC07-2 (72.1 mg, 0.18 mmol), 1-methyl-4-(4,4,5,5-tetramethyl-1,3,2-dioxaborolan-2-yl)-1H-pyrazole (50.7 mg, 0.25 mmol), 1,4-dioxane (10 mL), water (0.5 mL) and potassium carbonate (38.6 mg, 0.28 mmol) were added to a reaction flask, and the air in the reaction system was replaced with nitrogen three times. The system was added with Pd(dppf)Cl$_2$-dichloromethane complex (9.0 mg, 0.011 mmol), and the air in the reaction system was replaced with nitrogen three times again. The system was heated to 100° C. for reaction. After the reaction was complete, the reaction system was added with water (50 mL) and EA (50 mL), shaken and separated. The aqueous phase was extracted with EA (50 mL*2). The combined organic phase was washed with water (50 mL*2) and saturated brine (40 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 14.8 mg of the product.

Product analysis: $^1$HNMR (CDCl$_3$, 400 MHz): δ 7.70 (s, 1H), 7.62-7.48 (m, 3H), 7.44 (d, J=7.8 Hz, 1H), 7.18-7.06 (m, 1H), 6.93 (dt, J=7.6, 1.2 Hz, 1H), 6.51 (dd, J=8.1, 1.3 Hz, 2H), 4.78 (dd, J=14.5, 7.4 Hz, 1H), 4.30 (s, 1H), 4.17-4.00 (m, 2H), 3.93 (s, 3H), 3.01 (m, 1H), 2.54 (s, 3H), 2.25 (m, 1H), 2.10 (s, 1H), 1.81-1.40 (m, OH), 1.26 (s, OH), 0.86 (d, J=15.2 Hz, 1H).

ESI-MS Calculated for [M+H]$^+$=396.19; Found: 396.00. The found value was consistent with the caculated value.

Preparation Example 74, Final Product LC09: 2-(2-((1-methyl-9-(1-methyl-1H-pyrazol-4-yl)-6,7-dihydro-5H-benzo[c][1,2,3]triazolo[1,5-a]azepin-7-yl)amino)phenyl)acetonitrile

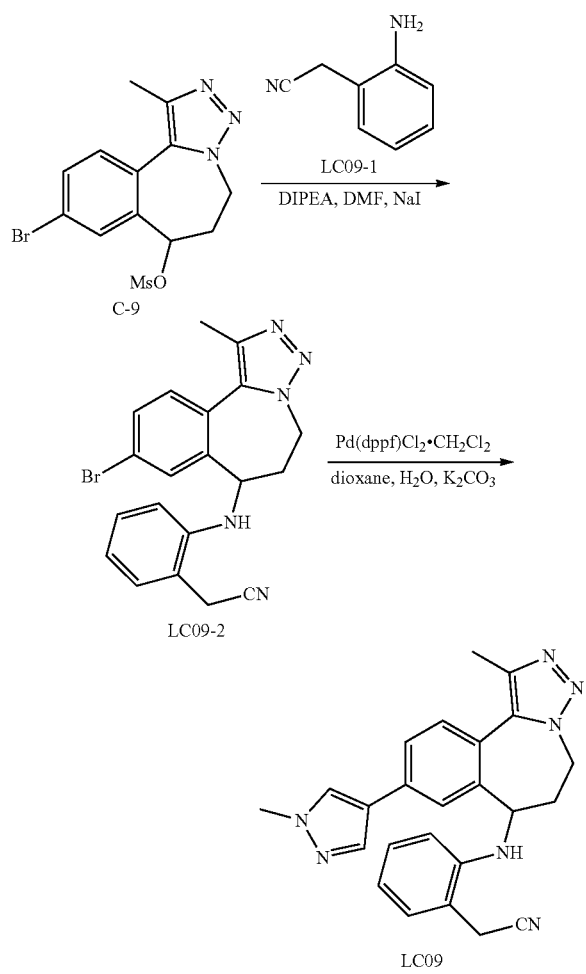

Step 1: Synthesis of 2-(2-((9-bromo-1-methyl-6,7-dihydro-5H-benzo[c][1,2,3]triazolo[1,5-a]azepin-7-yl)amino)phenyl)acetonitrile (LC09-2)

C-9 (150.1 mg, 0.40 mmol), LC09-1 (107.3 mg, 0.81 mmol), acetonitrile (30 mL), DIPEA (264.5 mg, 2.04 mmol) and sodium iodide (9.1 mg, 0.060 mmol) were added to a reaction flask, and heated to react under reflux. After the reaction was complete, the system was added with water (50 mL) and EA (100 mL), shaken and sepatated. The aqueous phase was extracted with EA (50 mL*2). The combined organic phase was washed with water (100 mL*3) and saturated brine (50 mL), dired with anhydrous sodium sulfate and filtered with suction. The filtrate was concentrated under reduced pressure, and the residue was separated by PLC to obtain 26.7 mg of the target compound.

ESI-MS Calculated for [M+H]$^+$=408.07; Found: 407.90. The found value was consistent with the caculated value.

Step 2: Synthesis of 2-(2-((1-methyl-9-(1-methyl-1H-pyrazol-4-yl)-6,7-dihydro-5H-benzo[c][1,2,3]triazolo[1,5-a]azepin-7-yl)amino)phenyl)acetonitrile (LC09)

LC09-2 (26.7 mg, 0.066 mmol), 1-methyl-4-(4,4,5,5-tetramethyl-1,3,2-dioxaborolan-2-yl)-1H-pyrazole (18.4 mg, 0.088 mmol), 1,4-dioxane (10 mL), water (0.5 mL) and potassium carbonate (14.5 mg, 0.11 mmol) were added to a reaction flask, and the air in the reaction system was replaced with nitrogen three times. The system was added with Pd(dppf)Cl$_2$-dichloromethane complex (3.1 mg, 0.0037 mmol), and the air in the reaction system was replaced with nitrogen three times again. The system was heated to reflux. After the reaction was complete, the system was added with water (50 mL) and EA (50 mL), shaken and sepatated. The aqueous phase was extracted with EA (30 mL*2). The combined organic phase was washed with water (50 mL*3) and saturated brine (40 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 4.8 mg of the product.

Product analysis: $^1$HNMR (CDCl$_3$, 400 MHz): δ 7.74 (s, 1H), 7.67-7.60 (m, 2H), 7.53 (dd, J=7.8, 1.8 Hz, 1H), 7.42 (d, J=7.9 Hz, 1H), 7.13 (dd, J=7.5, 1.5 Hz, 1H), 7.07-6.93 (m, 1H), 6.70 (m, 1H), 6.08 (d, J=8.2 Hz, 1H), 4.86-4.70 (m, 1H), 4.45 (m, 1H), 4.07 (m, 1H), 3.90 (s, 3H), 3.81 (d, J=6.3 Hz, 1H), 3.62 (s, 2H), 3.10-2.91 (m, 1H), 2.55 (s, 3H), 2.33 (dd, J=17.7, 10.7 Hz, OH).

ESI-MS Calculated for [M+H]$^+$=410.20; Found: 410.00. The found value was consistent with the caculated value.

Preparation Example 75, Final Product LC10: N-methyl-2-(3-((1-methyl-9-(1-methyl-1H-pyrazol-4-yl)-6,7-dihydro-5H-benzo[c][1,2,3]triazolo[1,5-a]azepin-7-yl)amino)phenyl)acetamide

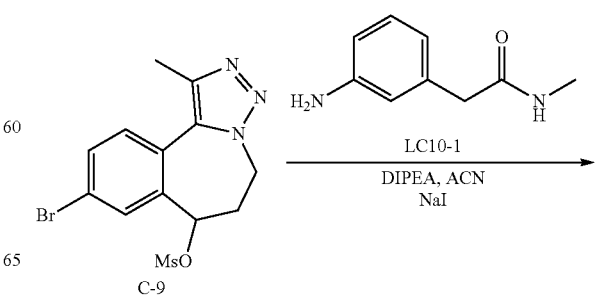

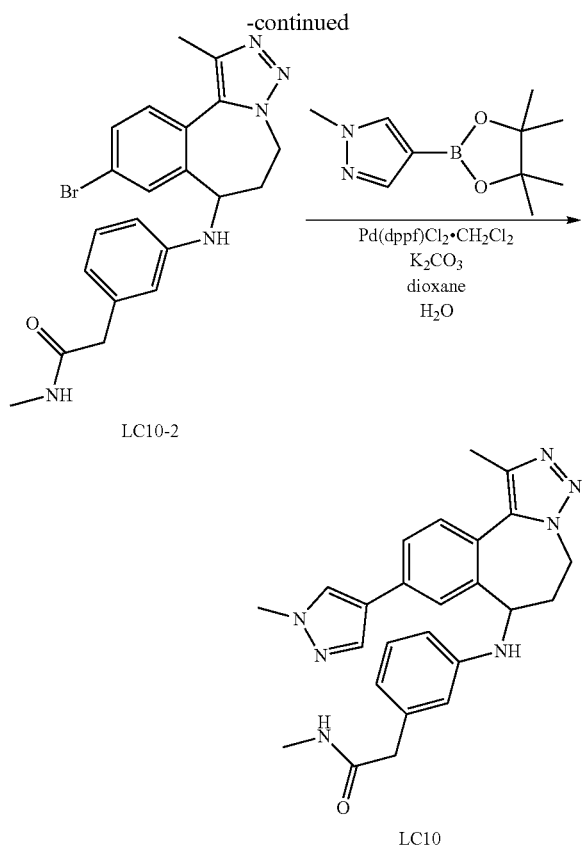

LC10-2

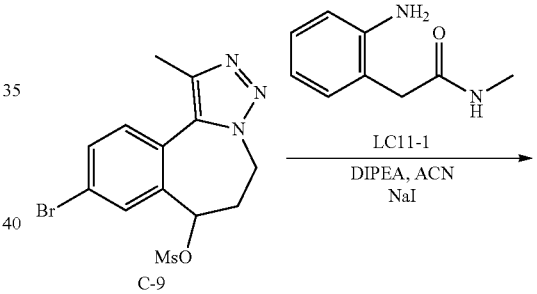

LC10

Step 1: Synthesis of 2-(3-((9-bromo-1-methyl-6,7-dihydro-5H-benzo[c][1,2,3]triazolo[1,5-a]azepin-7-yl)amino)phenyl)-N-methylacetamide (LC10-2)

C-9 (156.5 mg, 0.42 mmol), LC10-1 (144.3 mg, 0.88 mmol), acetonitrile (30 mL), DIPEA (275.3 mg, 2.13 mmol) and sodium iodide (11.4 mg, 0.076 mmol) were added to a reaction flask and heated to react under reflux. After the reaction was complete, the system was concentrated under reduced pressure, and the residue was added with water (50 mL) and EA (50 mL), shaken and sepatated. The aqueous phase was extracted with EA (30 mL*2). The combined organic phase was washed with water (50 mL*2) and saturated brine (30 mL), dired with anhydrous sodium sulfate and filtered with suction. The filtrate was concentrated under reduced pressure, and the residue was separated by PLC to obtain 88.6 mg of the target compound.

ESI-MS Calculated for [M+H]$^+$=440.10; Found: 439.90. The found value was consistent with the caculated value. The found value was consistent with the caculated value.

Step 2: Synthesis of N-methyl-2-(3-41-methyl-9-(1-methyl-1H-pyrazol-4-yl)-6,7-dihydro-5H-benzo[c][1,2,3]triazolo[1,5-a]azepin-7-yl)amino)phenyl)acetamide (LC10)

LC10-2 (88.6 mg, 0.20 mmol), 1-methyl-4-(4,4,5,5-tetramethyl-1,3,2-dioxaborolan-2-yl)-1H-pyrazole (56.2 mg, 0.27 mmol), 1,4-dioxane (10 mL) and water (0.5 mL) and potassium carbonate (44.0 mg, 0.32 mmol) were added to a reaction flask, and the air in the reaction system was replaced with nitrogen three times. The system was added with Pd(dppf)Cl$_2$-dichloromethane complex (9.4 mg, 0.012 mmol), and the air in the reaction system was replaced with nitrogen three times again. The system was heated to 100° C. for reaction. After the reaction was complete, the reaction system was added with water (50 mL) and EA (50 mL), shaken and separated. The aqueous phase was extracted with EA (40 mL*2). The combined organic phase was washed with water (50 mL*2) and saturated brine (50 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 10.4 mg of the product.

Product analysis: $^1$HNMR (CDCl$_3$, 400 MHz): δ 7.69 (d, J=0.9 Hz, 1H), 7.65-7.56 (m, 2H), 7.50 (dd, J=7.9, 1.8 Hz, 1H), 7.41 (d, J=7.8 Hz, 1H), 7.02 (t, J=7.8 Hz, 1H), 6.51 (dd, J=7.4, 1.5 Hz, 1H), 6.24 (t, J=1.9 Hz, 1H), 6.22-6.17 (m, 1H), 5.25 (s, 1H), 4.82-4.70 (m, 1H), 4.31 (dd, J=10.2, 6.8 Hz, 1H), 4.05 (m, 1H), 3.93 (s, 3H), 3.38 (s, 2H), 2.99 (m, 1H), 2.64 (d, J=4.8 Hz, 3H), 2.53 (s, 3H), 2.31-2.17 (m, 1H).

ESI-MS Calculated for [M+H]$^+$=442.23; Found: 442.00. The found value was consistent with the caculated value.

Preparation Example 76, Final Product LC11: N-methyl-2-(2-((1-methyl-9-(1-methyl-1H-pyrazol-4-yl)-6,7-dihydro-5H-benzo[c][1,2,3]triazolo[1,5-a]azepin-7-yl)amino)phenyl)acetamide

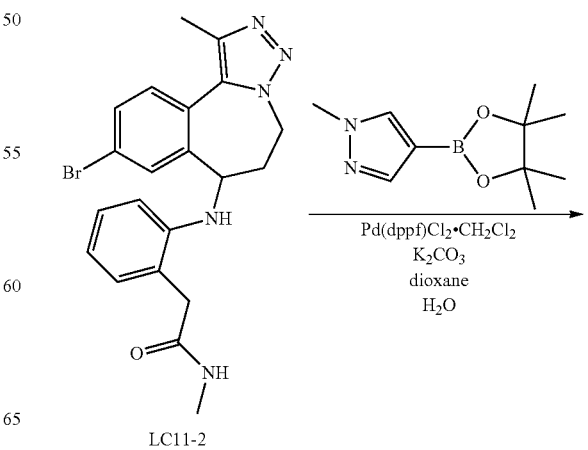

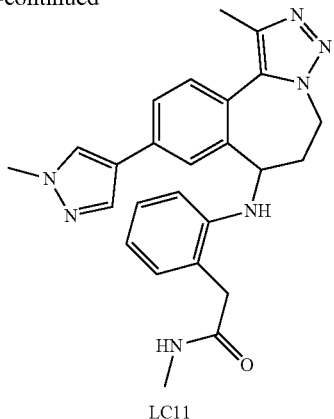

LC11

Step 1: Synthesis of 2-(2-((9-bromo-1-methyl-6,7-dihydro-5H-benzo[c][1,2,3]triazolo[1,5-a]azepin-7-yl)amino)phenyl)-N-methylacetamide (LC11-2)

C-9 (100.3 mg, 0.27 mmol), LC11-1 (89.9 mg, 0.55 mmol), acetonitrile (20 mL), DIPEA (178.3 mg, 1.38 mmol) and sodium iodide (6.9 mg, 0.046 mmol) were added to a reaction flask and heated to react under reflux. After the reaction was complete, the system was concentrated under reduced pressure, and the residue was added with water (50 mL) and EA (50 mL), shaken and sepatated. The aqueous phase was extracted with EA (40 mL*2). The combined organic phase was washed with water (50 mL*2) and saturated brine (50 mL), dried with anhydrous sodium sulfate and filtered with suction. The filtrate was concentrated under reduced pressure, and the residue was separated by PLC to obtain 105.1 mg of the target compound.

ESI-MS Calculated for [M+H]$^+$=440.10; Found: 440.00. The found value was consistent with the caculated value.

Step 2: Synthesis of N-methyl-2-(2-41-methyl-9-(1-methyl-1H-pyrazol-4-yl)-6,7-dihydro-5H-benzo[c][1,2,3]triazolo[1,5-a]azepin-7-yl)amino)phenyl)acetamide (LC11)

LC11-2 (105.1 mg, 0.24 mmol), 1-methyl-4-(4,4,5,5-tetramethyl-1,3,2-dioxaborolan-2-yl)-1H-pyrazole (66.6 mg, 0.32 mmol), 1,4-dioxane (10 mL), water (0.5 mL) and potassium carbonate (52.1 mg, 0.38 mmol) were added to a reaction flask, and the air in the reaction system was replaced with nitrogen three times. The system was added with Pd(dppf)Cl$_2$-dichloromethane complex (10.8 mg, 0.014 mmol), and the air in the reaction system was replaced with nitrogen three times again. The system was heated to reflux. After the reaction was complete, the reaction system was cooled down, added with water (50 mL) and EA (50 mL), shaken and separated. The aqueous phase was extracted with EA (40 mL*2). The combined organic phase was washed with water (50 mL*2) and saturated brine (50 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 33.3 mg of the product.

Product analysis: $^1$HNMR (CDCl$_3$, 400 MHz): δ 7.72 (d, J=2.0 Hz, 2H), 7.66 (s, 1H), 7.48 (dd, J=7.8, 1.7 Hz, 1H), 7.40 (d, J=7.8 Hz, 1H), 7.00 (m, 1H), 6.92 (m, 1H), 6.61 (m, 1H), 5.99 (d, J=8.1 Hz, 1H), 5.77 (s, 1H), 4.81 (dd, J=14.3, 7.7 Hz, 1H), 4.33 (dd, J=11.0, 6.5 Hz, 1H), 4.00 (s, 1H), 3.91 (s, 3H), 3.61 (d, J=14.2 Hz, 1H), 3.57-3.45 (m, 1H), 3.01 (m, 1H), 2.84 (d, J=4.7 Hz, 3H), 2.54 (d, J=10.5 Hz, 3H), 2.38-2.28 (m, 1H).

ESI-MS Calculated for [M+H]$^+$=442.23; Found: 442.00. The found value was consistent with the caculated value.

Preparation Example 77, Final Product LC18: 4-((1-methyl-9-(1-methyl-1H-pyrazol-4-yl)-6,7-dihydro-5H-benzo[c][1,2,3]triazolo[1,5-a]azepin-7-yl)amino)benzonitrile

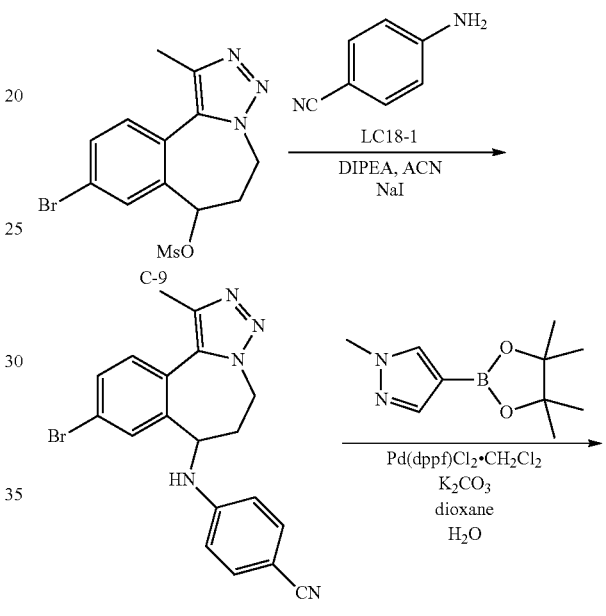

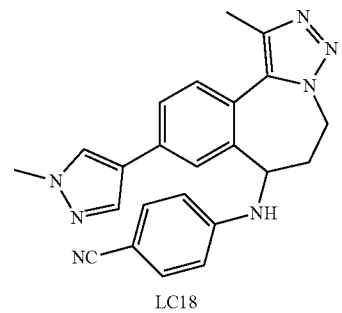

LC18

Step 1: Synthesis of 4-((9-bromo-1-methyl-6,7-dihydro-5H-benzo[c][1,2,3]triazolo[1,5-a]azepin-7-yl)amino)benzonitrile (LC18-2)

C-9 (151.1 mg, 0.41 mmol), LC18-1 (239.8 mg, 2.03 mmol), acetonitrile (20 mL), DIPEA (293.1 mg, 2.27 mmol) and sodium iodide (620.6 mg, 4.14 mmol) were added to a reaction flask and heated to react under reflux. After the reaction was complete, the reaction system was added with water (50 mL) and EA (50 mL), shaken and separated. The aqueous phase was extracted with EA (30 mL*2). The combined organic phase was washed with water (50 mL*2) and saturated brine (30 mL), dired with anhydrous sodium sulfate and filtered with suction. The filtrate was concentrated under reduced pressure, and the residue was separated by PLC to obtain 42.1 mg of the target compound.

ESI-MS Calculated for [M+H]$^+$=394.06; Found: 393.70. The found value was consistent with the caculated value.

Step 2: Synthesis of 4-((I-methyl-941-methyl-1H-pyrazol-4-yl)-6,7-dihydro-5H-benzo[c][1,2,3]triazolo[1,5-a]azepin-7-yl)amino)benzonitrile (LC18)

LC18-2 (42.1 mg, 0.11 mmol), 1-methyl-4-(4,4,5,5-tetramethyl-1,3,2-dioxaborolan-2-yl)-1H-pyrazole (30.3 mg, 0.15 mmol), 1,4-dioxane (5 mL), water (0.25 mL) and potassium carbonate (23.9 mg, 0.17 mmol) were added to a reaction flask, and the air in the reaction system was replaced with nitrogen three times. The system was added with Pd(dppf)Cl$_2$-dichloromethane complex (5.0 mg, 0.0061 mmol), and the air in the reaction system was replaced with nitrogen three times again. The system was heated to 100° C. for reaction. After the reaction was complete, the system was added with water (50 mL) and EA (20 mL), shaken and sepatated. The aqueous phase was extracted with EA (40 mL*2). The combined organic phase was washed with water (50 mL*2) and saturated brine (40 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 12.8 mg of the product.

Product analysis: $^1$HNMR (CDCl$_3$, 400 MHz): δ 7.69 (d, J=0.9 Hz, 1H), 7.58-7.47 (m, 3H), 7.47-7.39 (m, 1H), 7.32 (d, J=8.7 Hz, 2H), 6.44-6.21 (m, 2H), 4.84-4.68 (m, 1H), 4.44-4.31 (m, 2H), 4.07 (m, 1H), 3.93 (s, 3H), 3.09-2.93 (m, 1H), 2.52 (s, 3H).

ESI-MS Calculated for [M+H]$^+$=396.19; Found: 395.80. The found value was consistent with the caculated value.

Preparation Example 78, Final Product LC20: 2-(3-((1-methyl-9-(1-methyl-1H-pyrazol-4-yl)-6,7-dihydro-5H-benzo[c][1,2,3]triazolo[1,5-a]azepin-7-yl)amino)phenyl)acetonitrile

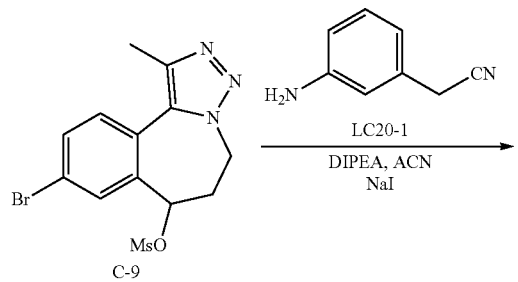

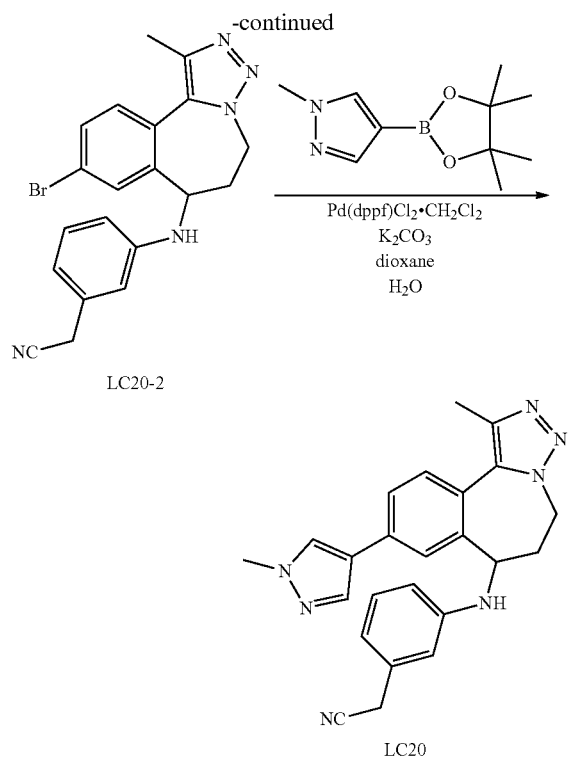

Step 1: Synthesis of 2-(3-((9-bromo-1-methyl-6,7-dihydro-5H-benzo[c][1,2,3]triazolo[1,5-a]azepin-7-yl)amino)phenyl)acetonitrile (LC20-2)

C-9 (120.3 mg, 0.33 mmol), LC20-1 (86.6 mg, 0.66 mmol), acetonitrile (30 mL), DIPEA (215.8 mg, 1.67 mmol) and sodium iodide (8.9 mg, 0.060 mmol) were added to a reaction flask and heated to react under reflux. After the reaction was complete, the system was concentrated under reduced pressure, and the residue was added with water (100 mL) and EA (100 mL), shaken and sepatated. The aqueous phase was extracted with EA (40 mL*2). The combined organic phase was washed with water (50 mL*3) and saturated brine (50 mL), dired with anhydrous sodium sulfate and filtered with suction. The filtrate was concentrated under reduced pressure, and the residue was separated by PLC to obtain 110.1 mg of the target compound.

ESI-MS Calculated for [M+H]$^+$=408.07; Found: 407.70. The found value was consistent with the caculated value.

Step 2: Synthesis of 2-(3-((1-methyl-9-(1-methyl-1H-pyrazol-4-yl)-6,7-dihydro-5H-benzo[c][1,2,3]triazolo[1,5-a]azepin-7-yl)amino)phenyl)acetonitrile (LC20)

LC20-2 (110.1 mg, 0.27 mmol), 1-methyl-4-(4,4,5,5-tetramethyl-1,3,2-dioxaborolan-2-yl)-1H-pyrazole (77.0 mg, 0.37 mmol), 1,4-dioxane (15 mL), water (0.75 mL) and potassium carbonate (59.0 mg, 0.43 mmol) were added to a reaction flask, and the air in the reaction system was replaced with nitrogen three times. The system was added with Pd(dppf)Cl$_2$-dichloromethane complex (12.2 mg, 0.015 mmol), and the air in the reaction system was replaced with nitrogen three times again. The system was heated to reflux fro reaction. After the reaction was complete, the reaction system was added with water (50 mL) and EA (50 mL), shaken and separated. The aqueous phase was extracted with EA (40 mL*2). The combined organic phase was washed with water (50 mL*2) and saturated brine (50 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 24.6 mg of the product.

Product analysis: $^1$HNMR (CDCl$_3$, 400 MHz): δ 7.71 (d, J=0.8 Hz, 1H), 7.64-7.57 (m, 2H), 7.51 (dd, J=7.8, 1.8 Hz, 1H), 7.41 (d, J=7.8 Hz, 1H), 7.01 (m, 1H), 6.56 (d, J=7.6 Hz, 1H), 6.38 (s, 1H), 6.22-6.11 (m, 1H), 4.82-4.68 (m, 1H), 4.31 (m, 1H), 4.13-3.96 (m, 2H), 3.92 (s, 3H), 3.57 (s, 2H), 2.98 (m, 1H), 2.53 (s, 3H).

ESI-MS Calculated for [M+H]$^+$=410.20; Found: 410.90. The found value was consistent with the caculated value.

Preparation Example 79, Final Product LC29:
N-(2-((dimethylamino)methyl)phenyl)-1-methyl-9-(1-methyl-1H-pyrazol-4-yl)-6,7-dihydro-5H-benzo[c][1,2,3]triazolo[1,5-a]azepin-7-amine

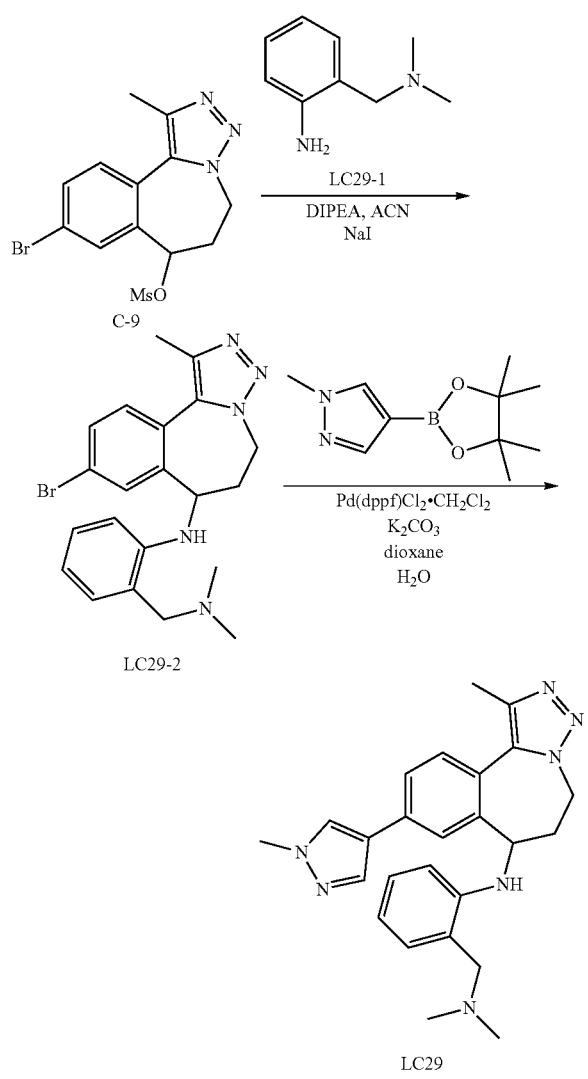

Step 1: Synthesis of 9-bromo-N-(2-((dimethylamino)methyl)phenyl)-1-methyl-6,7-dihydro-5H-benzo[c][1,2,3]triazolo[1,5-a]azepin-7-amine (LC29-2)

C-9 (151.1 mg, 0.41 mmol), LC29-1 (125.1 mg, 0.83 mmol), acetonitrile (30 mL), DIPEA (268.7 mg, 2.08 mmol) and sodium iodide (17.9 mg, 0.21 mmol) were added to a reaction flask, and heated to react under reflux. After the reaction was complete, the system was concentrated under reduced pressure, and the residue was added with water (50 mL) and EA (30 mL), shaken and sepatated. The aqueous phase was extracted with EA (30 mL*2). The combined organic phase was washed with water (40 mL*2) and saturated brine (50 mL), dried over anhydrous magnesium sulfate and filtered with suction. The filtrate was concentrated under reduced pressure, and the residue was separated by PLC to obtain 96.1 mg of the target compound.

ESI-MS Calculated for [M+H]$^+$=426.12; Found: 426.10.

Step 2: Synthesis of N-(2-((dimethylamino)methyl)phenyl)-1-methyl-9-(1-methyl-1H-pyrazol-4-yl)-6,7-dihydro-5H-benzo[c][1,2,3]triazolo[1,5-a]azepin-7-amine (LC29)

LC29-2 (96.1 mg, 0.23 mmol), 1-methyl-4-(4,4,5,5-tetramethyl-1,3,2-dioxaborolan-2-yl)-1H-pyrazole (64.3 mg, 0.31 mmol), potassium carbonate (49.8 mg, 0.36 mmol), 1,4-dioxane (15 mL) and water (0.75 mL) were added to a reaction flask, and the air in the reaction system was replaced with nitrogen three times. The system was added with Pd(dppf)Cl$_2$-dichloromethane complex (10.7 mg, 0.013 mmol), and the air in the reaction system was replaced with nitrogen three times again. The system was heated to 100° C. for reaction. After the reaction was complete, the reaction system was added with water (50 mL) and EA (50 mL), shaken and separated. The aqueous phase was extracted with EA (30 mL*3). The combined organic phase was washed with water (50 mL*2) and saturated brine (40 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 24.4 mg of the product.

Product analysis: $^1$HNMR (CDCl$_3$, 400 MHz): δ 7.66 (d, J=0.8 Hz, 1H), 7.58 (d, J=1.7 Hz, 1H), 7.53 (s, 1H), 7.47 (dd, J=7.8, 1.8 Hz, 1H), 7.40 (d, J=7.8 Hz, 1H), 6.95 (dd, J=7.2, 1.6 Hz, 1H), 6.90 (dd, J=7.7, 1.7 Hz, 1H), 6.54 (m, 1H), 5.90 (d, J=8.0 Hz, 1H), 4.83-4.72 (m, 1H), 4.29 (m, 1H), 4.01 (m, 1H), 3.90 (s, 3H), 3.48 (s, 2H), 2.97 (m, 1H), 2.54 (s, 3H), 2.26 (s, 6H).

ESI-MS Calculated for [M+H]$^+$=428.25; Found: 428.10. The found value was consistent with the caculated value.

Preparation Example 80, Final Product LC31:
N-(3-((dimethylamino)methyl)phenyl)-1-methyl-9-(1-methyl-1H-pyrazol-4-yl)-6,7-dihydro-5H-benzo[c][1,2,3]triazolo[1,5-a]azepin-7-amine

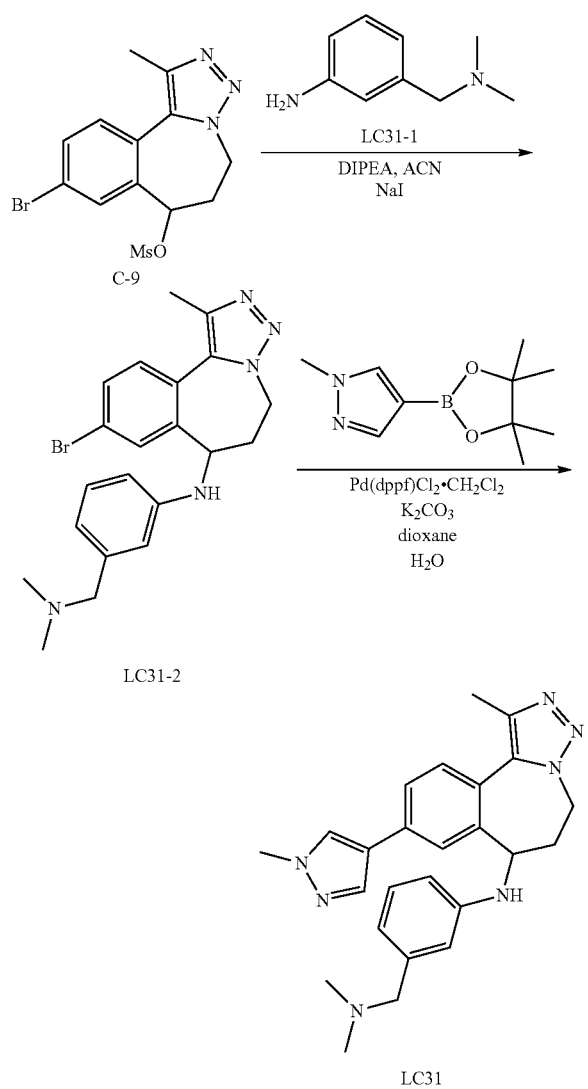

Step 1: Synthesis of 9-bromo-N-(3-((dimethylamino)methyl)phenyl)-1-methyl-6,7-dihydro-5H-benzo[c][1,2,3]triazolo[1,5-a]azepin-7-amine (LC31-2)

C-9 (154.1 mg, 0.41 mmol), LC31-1 (127.7 mg, 0.85 mmol), acetonitrile (30 mL), DIPEA (269.8 mg, 2.09 mmol) and sodium iodide (17.9 mg, 0.21 mmol) were added to a reaction flask, and heated to react under reflux. After the reaction was complete, the system was concentrated under reduced pressure, and the residue was added with water (50 mL) and EA (50 mL), shaken and sepatated. The aqueous phase was extracted with EA (50 mL*2). The combined organic phase was washed with water (50 mL*2) and saturated brine (50 mL), dried over anhydrous magnesium sulfate and filtered with suction. The filtrate was concentrated under reduced pressure, and the residue was separated by PLC to obtain 83.1 mg of the target compound.

ESI-MS Calculated for [M+H]$^+$=426.12; Found: 426.40. The found value was consistent with the caculated value.

Step 2: Synthesis of N-(3-((dimethylamino)methyl)phenyl)-1-methyl-9-(1-methyl-1H-pyrazol-4-yl)-6,7-dihydro-5H-benzo[c][1,2,3]triazolo[1,5-a]azepin-7-amine (LC31)

LC31-2 (83.1 mg, 0.20 mmol), 1-methyl-4-(4,4,5,5-tetramethyl-1,3,2-dioxaborolan-2-yl)-1H-pyrazole (57.5 mg, 0.28 mmol), 1,4-dioxane (15 mL), water (0.75 mL) and potassium carbonate (43.7 mg, 0.32 mmol) were added to a reaction flask, and the air in the reaction system was replaced with nitrogen three times. The system was added with Pd(dppf)Cl$_2$-dichloromethane complex (9.4 mg, 0.012 mmol), and the air in the reaction system was replaced with nitrogen three times again. The system was heated to reflux for reaction. After the reaction was complete, the system was added with water (50 mL) and EA (30 mL), shaken and sepatated. The aqueous phase was extracted with EA (30 mL*3). The combined organic phase was washed with water (40 mL*3) and saturated brine (40 mL), dried with anhydrous sodium sulfate and filtered with suction. The filtrate was concentrated under reduced pressure, and the residue was separated by PLC to obtain a crude, which was separated by medium pressure preparative chromatography and lyophilized to obtain 14.8 mg of the product.

Product analysis: $^1$HNMR (CDCl$_3$, 400 MHz): δ 7.69 (d, J=0.8 Hz, 1H), 7.64 (d, J=1.7 Hz, 1H), 7.55 (s, 1H), 7.48 (dd, J=7.8, 1.8 Hz, 1H), 7.39 (d, J=7.8 Hz, 1H), 6.97 (t, J=7.7 Hz, 1H), 6.57 (d, J=7.5 Hz, 1H), 6.42 (s, 1H), 6.17-6.06 (m, 1H), 4.75 (dd, J=14.2, 7.5 Hz, 1H), 4.32 (m, 1H), 4.04 (m, 1H), 3.91 (s, 3H), 3.64 (s, 1H), 3.24 (d, J=4.8 Hz, 2H), 3.05-2.89 (m, 1H), 2.52 (s, 3H), 2.14 (s, 6H).

ESI-MS Calculated for [M+H]$^+$=428.25; Found: 428.20. The found value was consistent with the caculated value.

Preparation Example 81, Final Product LC56: 2-(3-((1-methyl-9-(1,2,3,6-tetrahydropyridin-4-yl)-6,7-dihydro-5H-benzo[c][1,2,3]triazolo[1,5-a]azepin-7-yl)amino)pheno xy)ethan-1-ol 2,2,2-trifluoroacetate

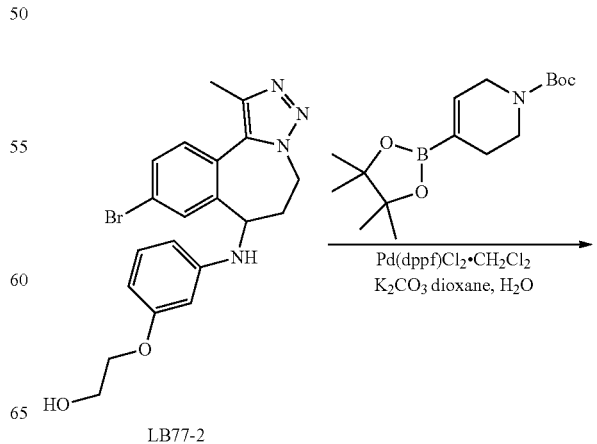

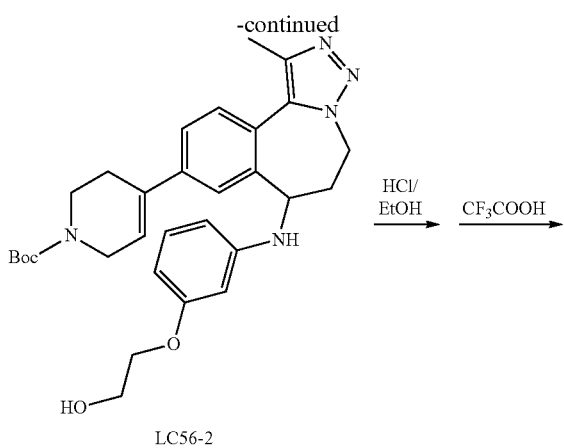

LC56-2

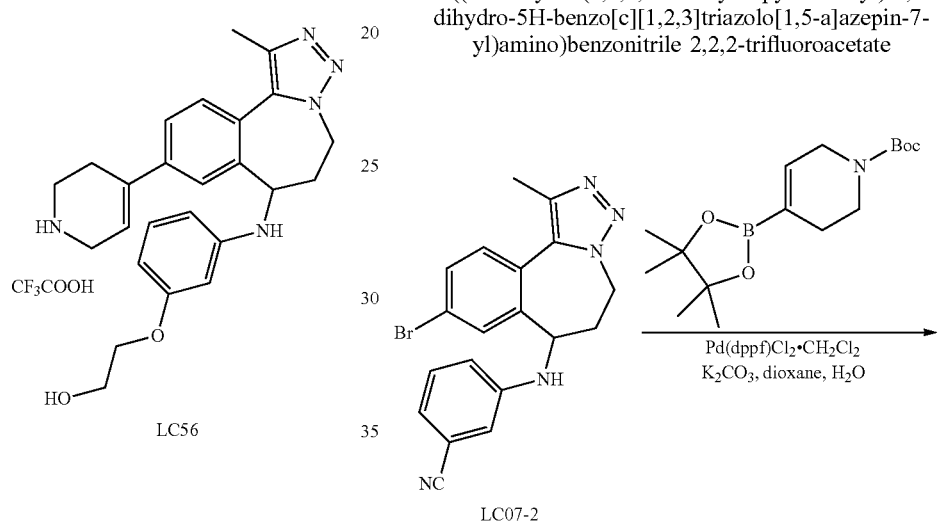

LC56

Step 1: Synthesis of tert-butyl 4-(7-((3-(2-hydroxy-ethoxy)phenyl)amino)-1-methyl-6,7-dihydro-5H-benzo[c][1,2,3]triazolo[1,5-a]azepin-9-yl)-3,6-dihydropyridine-1 (2H)-carboxylate (LC56-2)

LB77-2 (149.3 mg, 0.35 mmol), tert-butyl 4-(4,4,5,5-tetramethyl-1,3,2-dioxaboran-2-yl)-3,6-dihydropyridine-1 (2H)-carboxylate (140.9 mg, 0.46 mmol), 1,4-dioxane (15 mL), water (0.75 mL) and potassium carbonate (75.5 mg, 0.55 mmol) were added to a reaction flask, and the air in the reaction system was replaced with nitrogen three times. The system was added with Pd(dppf)Cl$_2$-dichloromethane complex (14.9 mg, 0.018 mmol), and the air in the reaction system was replaced with nitrogen three times again. The system was heated to 100° C. for reaction. After the reaction was complete, the reaction system was added with water (50 mL) and EA (50 mL), shaken and separated. The aqueous phase was extracted with EA (30 mL*2). The combined organic phase was washed with water (50 mL) and saturated brine (50 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 125.5 mg of the product.

ESI-MS Calculated for [M+H]$^+$=532.28; Found: 532.40. The found value was consistent with the caculated value.

Step 2: Synthesis of 2-(3-((1-methyl-9-(1,2,3,6-tetrahydropyridin-4-yl)-6,7-dihydro-5H-benzo[c][1,2,3]triazolo[1,5-a]azepin-7-yl)amino)phenoxy)ethan-1-ol 2,2,2-trifluoro acetate (LC56)

LC56-2 (90.3 mg, 0.17 mmol) was added Mo a reaction flask, added with hydrochloric acid in ethanol (5 mL, 33% content) and stirred at room temperature for reaction. After the reaction was complete, the system was concentrated under reduced pressure, and the residue was separted by medium-pressure preparative chromatography (mobile phase: A: purified water with 0.05% trifluoroacetic acid, B: acetonitrile with 0.05% trifluoroacetic acid) and lyophilized to obtain 14.1 mg of the product.

ESI-MS Calculated for [M+H]$^+$=432.23; Found: 432.10. The found value was consistent with the caculated value.

Preparation Example 82, Final Product LC75: 3-((1-methyl-9-(1,2,3,6-tetrahydropyridin-4-yl)-6,7-dihydro-5H-benzo[c][1,2,3]triazolo[1,5-a]azepin-7-yl)amino)benzonitrile 2,2,2-trifluoroacetate

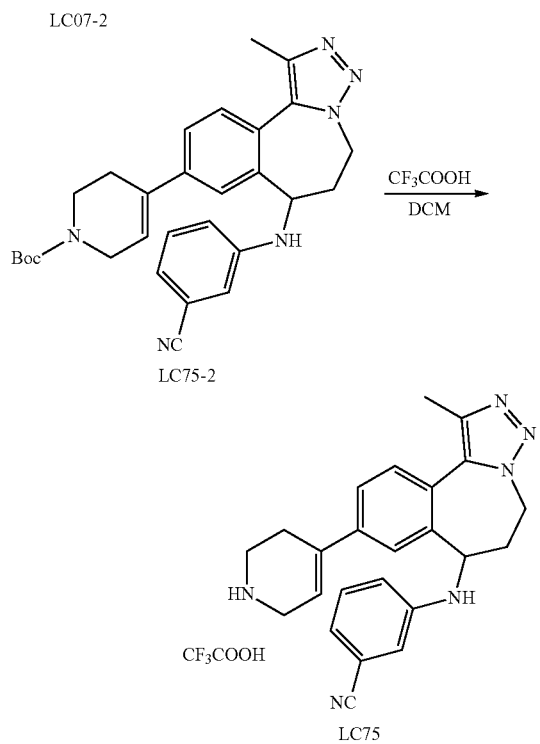

Step 1: Synthesis of tert-butyl 4-(7-((3-cyanophenyl)amino)-1-methyl-6,7-dihydro-5H-benzo[c][1,2,3]triazolo[1,5-a]azepin-9-yl)-3,6-dihydropyridine-1(2H)-carboxylate (LC75-2)

LC07-2 (142.3 mg, 0.36 mmol), tert-butyl 4-(4,4,5,5-tetramethyl-1,3,2-dioxaboran-2-yl)-3,6-dihydropyridine-1(2H)-carboxylate (150.7 mg, 0.49 mmol), 1,4-dioxane (15 mL), water (0.75 mL) and potassium carbonate (78.7 mg, 0.57 mmol) were added to a reaction flask, and the air in the reaction system was replaced with nitrogen three times. The system was added with Pd(dppf)Cl$_2$-dichloromethane complex (16.2 mg, 0.020 mmol), and the air in the reaction system was replaced with nitrogen three times again. The system was heated to reflux for reaction. After the reaction was complete, the reaction system was cooled down, added with water (50 mL) and EA (50 mL), shaken and separated. The aqueous phase was extracted with EA (50 mL*2). The combined organic phase was washed with water (50 mL*3) and saturated brine (50 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 45.3 mg of the product.

ESI-MS Calculated for [M+H]$^+$=497.26; Found: 497.20. The found value was consistent with the caculated value.

Step 2: Synthesis of 3-((1-methyl-9-(1,2,3,6-tetrahydropyridin-4-yl)-6,7-dihydro-5H-benzo[c][1,2,3]triazolo[1,5-a]azepin-7-yl)amino)benzonitrile 2,2,2-trifluoroacetate (LC75)

LC75-2 (34.5 mg, 0.069 mmol) was added into a reaction flask, added with dichloromethane (10 mL) and trifluoroacetic acid (1 mL), and stirred at room temperature for reaction. After the reaction was complete, the system was concentrated under reduced pressure, and the residue was separated by medium-pressure preparative chromatography (mobile phase: A: purified water with 0.05% trifluoroacetic acid, B: acetonitrile with 0.05% trifluoroacetic acid) and lyophilized to obtain 14.2 mg of the product.

ESI-MS Calculated for [M+H]$^+$=397.21; Found: 397.20. The found value was consistent with the caculated value.

Preparation Example 83, Final Product LC79: N-(3-chlorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate

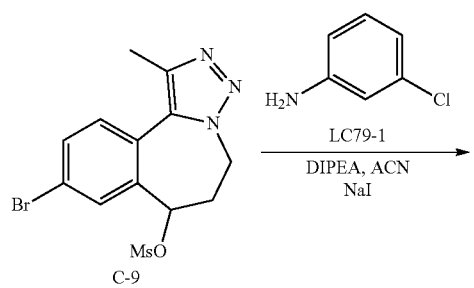

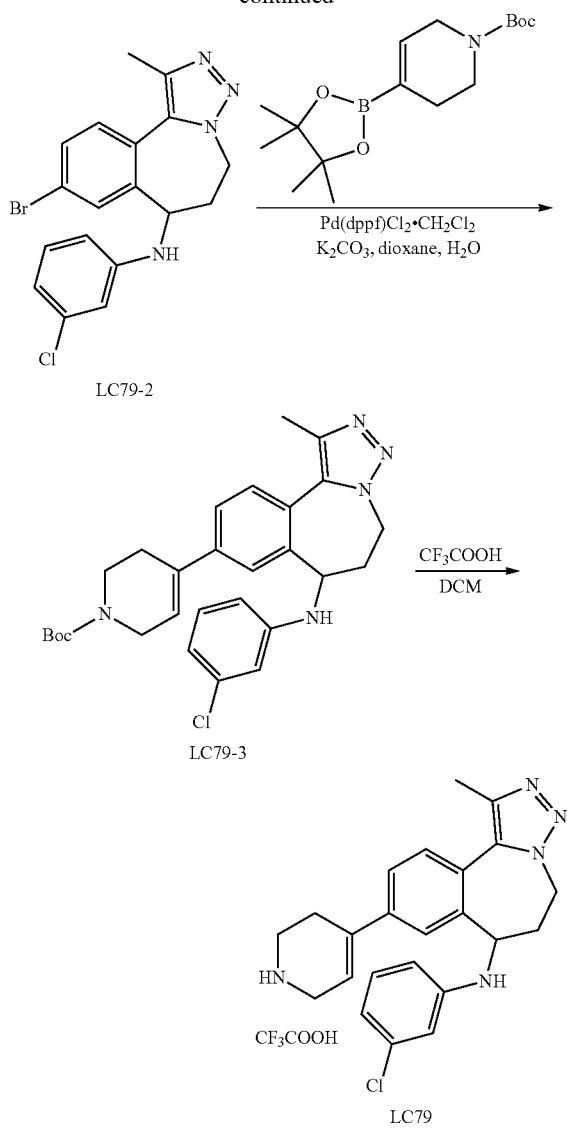

Step 1: Synthesis of 9-bromo-N-(3-chlorophenyl)-1-methyl-6,7-dihydro-5H-benzo[c][1,2,3]triazolo[1,5-a]azepin-7-amine (LC79-2)

C-9 (250.3 mg, 0.67 mmol), LC79-1 (257.3 mg, 2.02 mmol), acetonitrile (40 mL), DIPEA (439.1 mg, 3.40 mmol) and sodium iodide (32.2 mg, 0.22 mmol) were added to a reaction flask and heated to react under reflux. After the reaction was complete, the system was concentrated under reduced pressure, and the residue was added with water (50 mL) and EA (50 mL), shaken and sepatated. The aqueous phase was extracted with EA (30 mL*2). The combined organic phase was washed with water (50 mL*2) and saturated brine (50 mL), dried over anhydrous magnesium sulfate and filtered with suction. The filtrate was concentrated under reduced pressure, and the residue was separated by PLC to obtain 186.1 mg of the target compound.

ESI-MS Calculated for [M+H]$^+$=403.02; Found: 403.00. The found value was consistent with the caculated value.

Step 2: Synthesis of tert-butyl 4-(7-((3-chlorophenyl)amino)-1-methyl-6,7-dihydro-5H-benzo[c][1,2,3]triazolo[1,5-a]azepin-9-yl)-3,6-dihydropyridine-1(2H)-carboxylate (LC79-3)

LC79-2 (186.1 mg, 0.46 mmol), tert-butyl 4-(4,4,5,5-tetramethyl-1,3,2-dioxaboran-2-yl)-3,6-dihydropyridine-1(2H)-carboxylate (192.4 mg, 0.62 mmol), 1,4-dioxane (20 mL), water (1 mL) and potassium carbonate (99.8 mg, 0.72 mmol) were added to a reaction flask, and the air in the reaction system was replaced with nitrogen three times. The system was added with Pd(dppf)Cl₂-dichloromethane complex (20.7 mg, 0.025 mmol), and the air in the reaction system was replaced with nitrogen three times again. The system was heated to 100° C. for reaction. After the reaction was complete, the reaction system was cooled down, added with water (50 mL) and EA (50 mL), shaken and separated. The aqueous phase was extracted with EA (50 mL*2). The combined organic phase was washed with water (50 mL) and saturated brine (50 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 87.8 mg of the product.

ESI-MS Calculated for $[M+H]^+$=506.22; Found: 506.20. The found value was consistent with the caculated value.

Step 3: Synthesis of N-(3-chlorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate (LC79)

LC79-3 (38.8 mg, 0.076 mmol) was added into a reaction flask, added with dichloromethane (10 mL) and trifluoroacetic acid (1 mL) and stirred at room temperature for reaction. After the reaction was complete, the system was concentrated under reduced pressure, and the residue was separated by medium-pressure preparative chromatography (mobile phase: A: purified water with 0.05% trifluoroacetic acid, B: acetonitrile with 0.05% trifluoroacetic acid) and lyophilized to obtain 28.8 mg of the product.

Product analysis: ¹HNMR (CDCl₃, 400 MHz): δ 7.47 (d, J=1.3 Hz, 1H), 7.40-7.31 (m, 2H), 6.89 (m, 1H), 6.57 (d, J=8.0 Hz, 1H), 6.25 (m, 1H), 6.07-5.99 (m, 1H), 5.91 (s, 1H), 4.72 (dd, J=14.2, 7.5 Hz, 1H), 4.20 (dd, J=10.6, 6.7 Hz, 1H), 4.06-3.88 (m, 1H), 3.77 (s, 2H), 3.35 (s, 2H), 3.20-2.91 (m, 3H), 2.48 (s, 3H), 2.22-2.04 (m, 1H).

ESI-MS Calculated for $[M+H]^+$=406.17; Found: 406.10. The found value was consistent with the caculated value.

Preparation Example 84, Final Product LC84: N-(2-chlorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate

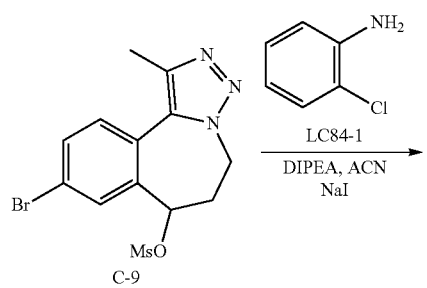

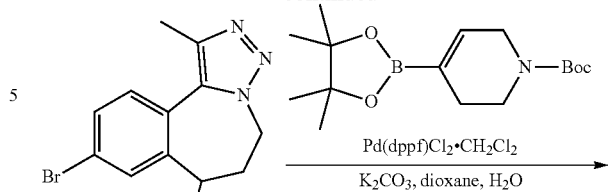

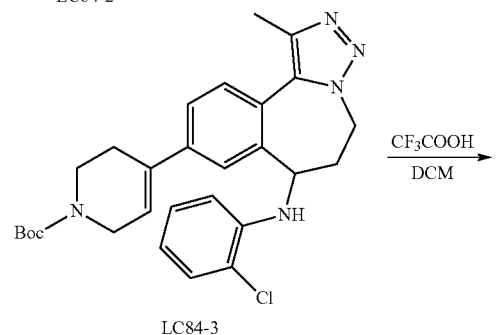

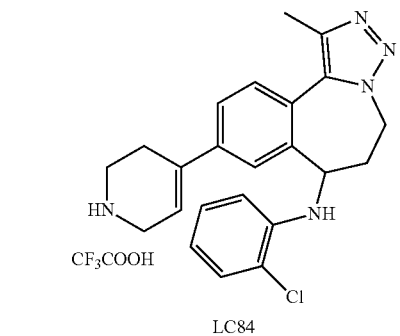

Step 1: Synthesis of 9-bromo-N-(2-chlorophenyl)-1-methyl-6,7-dihydro-5H-benzo[c][1,2,3]triazolo[1,5-a]azepin-7-amine (LC84-2)

C-9 (300.4 mg, 0.81 mmol), LC84-1 (311.6 mg, 2.44 mmol), acetonitrile (40 mL), DIPEA (530.6 mg, 4.11 mmol) and sodium iodide (38.9 mg, 0.26 mmol) were added to a reaction flask and heated to react under reflux. After the reaction was complete, the system was concentrated under reduced pressure, and the residue was added with water (50 mL) and EA (50 mL), shaken and separated. The aqueous phase was extracted with EA (50 mL*2). The combined organic phase was washed with water (50 mL*2) and saturated brine (40 mL), dried over anhydrous magnesium sulfate and filtered with suction. The filtrate was concentrated under reduced pressure, and the residue was separated by PLC to obtain 100.7 mg of the target compound.

ESI-MS Calculated for $[M+H]^+$=405.02; Found: 405.10. The found value was consistent with the caculated value.

Step 2: Synthesis of tert-butyl 4-(74(2-chlorophenyl)amino)-1-methyl-6,7-dihydro-5H-benzo[c][1,2,3]triazolo[1,5-a]azepin-9-yl)-3,6-dihydropyridine-1(2H)-carboxylate (LC84-3)

LC84-2 (100.7 mg, 0.25 mmol), tert-butyl 4-(4,4,5,5-tetramethyl-1,3,2-dioxaborolan-2-yl)-3,6-dihydropyridine-1

(2H)-carboxylate (102.9 mg, 0.33 mmol), 1,4-dioxane (10 mL), water (0.5 mL) and potassium carbonate (53.3 mg, 0.39 mmol) were added to a reaction flask, and the air in the reaction system was replaced with nitrogen three times. The system was added with Pd(dppf)Cl$_2$-dichloromethane complex (11.2 mg, 0.014 mmol), and the air in the reaction system was replaced with nitrogen three times again. The system was heated to reflux for reaction. After the reaction was complete, the reaction system was added with water (50 mL) and EA (50 mL), shaken and separated. The aqueous phase was extracted with EA (30 mL*2). The combined organic phase was washed with water (50 mL*2) and saturated brine (40 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 67.1 mg of the product.

ESI-MS Calculated for [M+H]$^+$=506.22; Found: 506.10. The found value was consistent with the caculated value.

Step 3: Synthesis of N-(2-chlorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate (LC84)

LC84-3 (38.8 mg, 0.076 mmol) was added into a reaction flask, added with dichloromethane (3 mL) and trifluoroacetic acid (1 mL) and stirred at room temperature for reaction. After the reaction was complete, the system was concentrated under reduced pressure, and the residue was separated by medium-pressure preparative chromatography (mobile phase: A: purified water with 0.05% trifluoroacetic acid, B: acetonitrile with 0.05% trifluoroacetic acid) and lyophilized to obtain 24.6 mg of the product.

Product analysis: $^1$HNMR (CDCl$_3$, 400 MHz): δ 7.49 (s, 1H), 7.47-7.39 (m, 2H), 7.27 (d, J=3.1 Hz, 1H), 6.91 (m, 1H), 6.62 (m, 1H), 5.96 (d, J=8.1 Hz, 2H), 4.83 (dd, J=14.2, 7.5 Hz, 1H), 4.39-4.28 (m, 1H), 4.10-3.96 (m, 1H), 3.83 (s, 2H), 3.41 (s, 2H), 3.19-2.97 (m, 4H), 2.55 (s, 3H).

ESI-MS Calculated for [M+H]$^+$=406.17; Found: 406.00. The found value was consistent with the caculated value.

Preparation Example 85, Final Product LC87: 2-(3-((1-methyl-9-(1,2,3,6-tetrahydropyridin-4-yl)-6,7-dihydro-5H-benzo[c][1,2,3]triazolo[1,5-a]azepin-7-yl)amino)pheny1)acetic acid

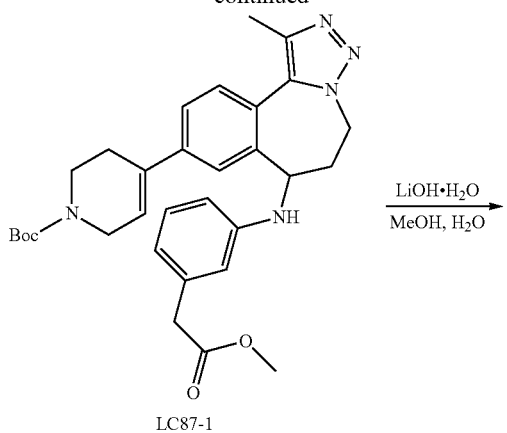

LC87-1

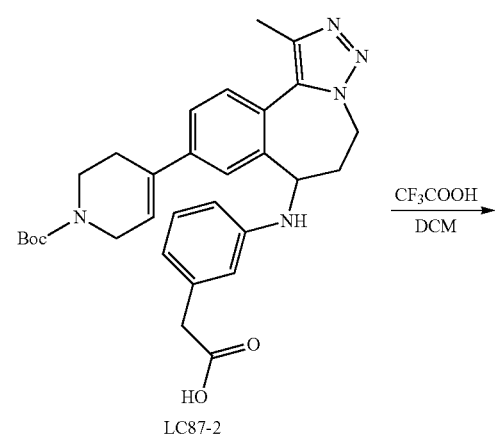

LC87-2

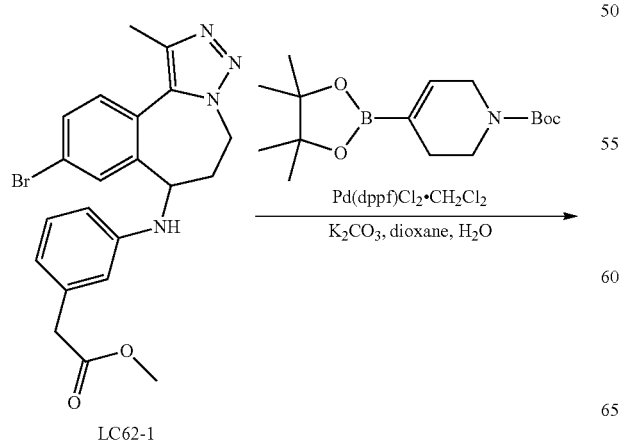

LC87

Step 1: Synthesis of tert-butyl 4-(7-((3-(2-methoxy-2-oxoethyl)phenyl)amino)-1-methyl-6,7-dihydro-5H-benzo[c][1,2,3]triazolo[1,5-a]azepin-9-yl)-3,6-dihydropyridine-1(2H)-carboxylate (LC87-1)

LB62-1 (238.3 mg, 0.54 mmol), tert-butyl 4-(4,4,5,5-tetramethyl-1,3,2-dioxaboran-2-yl)-3,6-dihydropyridine-1(2H)-carboxylate (218.7 mg, 0.71 mmol), 1,4-dioxane (20 mL), water (1 mL) and potassium carbonate (117.2 mg, 0.85 mmol) were added to a reaction flask, and the air in the reaction system was replaced with nitrogen three times. The system was added with Pd(dppf)Cl$_2$-dichloromethane complex (24.2 mg, 0.030 mmol), and the air in the reaction system was replaced with nitrogen three times again. The system was heated to 100° C. for reaction. After the reaction was complete, the reaction system was added with water (50 mL) and EA (50 mL), shaken and separated. The aqueous phase was extracted with EA (50 mL*2). The combined organic phase was washed with water (50 mL*2) and saturated brine (50 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 110.1 mg of the product.

ESI-MS Calculated for [M+H]$^+$=544.28; Found: 544.30. The found value was consistent with the caculated value.

Step 2: Synthesis of 2-(3-((9-(1-(tert-butoxycarbonyl)-1,2,3,6-tetrahydropyridin-4-yl)-1-methyl-6,7-dihydro-5H-benzo[c][1,2,3]triazolo[1,5-a]azepin-7-yl)amino)phenyl)acetic acid (LC87-2)

LC87-1 (70 mg, 0.13 mmol), lithium hydroxide monohydrate (31.3 mg, 1.30 mmol), methanol (3 mL) and water (3 mL) were added to a 25 mL single necked flask and stirred at room temperature for reaction. After the reaction was complete, the system was concentrated under reduced pressure, and the residue was added with water (20 mL) and washed with MTBE (50 mL*2). The organic phase was discarded, and the aqueous phase was adjusted pH to 3-5 with 1 mol/L dilute hydrochloric acid and extracted with EA (30 mL*2). The combined organic phase was washed with water (30 mL*3) and saturated brine (40 mL), dired with anhydrous sodium sulfate and filtered with suction. The filtrate was concentrated under reduced pressure, and the residue was separated by medium-pressure preparative chromatography to obtain 56.6 mg of the target compound.

ESI-MS Calculated for [M+H]$^+$=530.27; Found: 530.00. The found value was consistent with the caculated value.

Step 3: Synthesis of 2-(3-((1-methyl-9-(1,2,3,6-tetrahydropyridin-4-yl)-6,7-dihydro-5H-benzo[c][1,2,3]triazolo[1,5-a]azepin-7-yl)amino)phenyl) acetic acid (LC87)

LC87-2 (56.6 mg, 0.11 mmol) was added into a reaction flask, added with trifluoroacetic acid/dichloromethane (1:10, 5 mL) and stirred at room temperature for reaction. After the reaction was complete, the system was concentrated under reduced pressure, and the residue was separated by medium-pressure preparative chromatography and lyophilized to obtain 24.9 mg of the product.

ESI-MS Calculated for [M+H]$^+$=430.22; Found: 430.10. The found value was consistent with the caculated value.

Preparation Example 86, Final Product LC97: 3-((1-methyl-9-(1,2,3,6-tetrahydropyridin-4-yl)-6,7-dihydro-5H-benzo[c][1,2,3]triazolo[1,5-a]azepin-7-yl)amino)phenol 2,2,2-trifluoroacetate

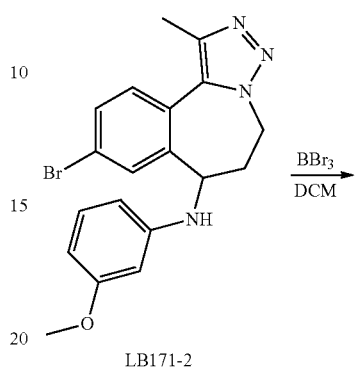

LB171-2

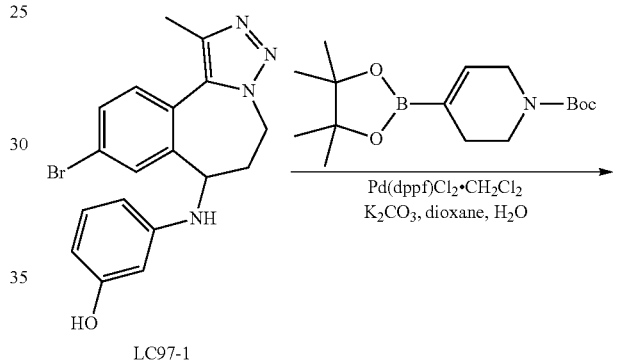

LC97-1

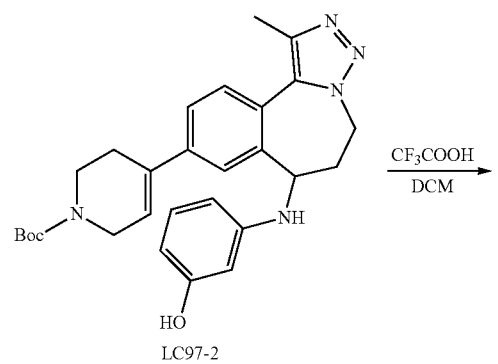

LC97-2

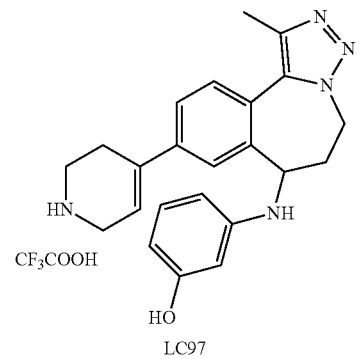

LC97

Step 1: Synthesis of 3-((9-bromo-1-methyl-6,7-dihydro-5H-benzo[c][1,2,3]triazolo[1,5-a]azepin-7-yl)amino)phenol (LC97-1)

LB171-2 (100.5 mg, 0.25 mmol) and DCM (10 mL) were added into a reaction flask and added dropwise with BBr$_3$ (2.5 mL) in an ice bath. After completion of the addition, the system was warmed to room temperature for reaction. After the reaction was complete, 100 mL of an ice-water mixture was added to a 100 mL beaker, and the reaction system was carefully added dropwise to the ice water. After completion of the dropwise addition, the system was extracted with DCM (30 mL). The aqueous phase was extracted with DCM (30 mL) again. The combined organic phase was washed with water (20 mL*2) and saturated brine (50 mL), dried over anhydrous sodium sulfate and filtered with suction. The filtrate was concentrated under reduced pressure, and the residue was separated by medium-pressure preparative chromatography and lyophilized to obtain 88.2 mg of the product.

ESI-MS Calculated for [M+H]$^+$=385.06; Found: 384.90. The found value was consistent with the caculated value.

Step 2: Synthesis of tert-butyl 4-(7-((3-hydroxyphenyl)amino)-1-methyl-6,7-dihydro-5H-benzo[c][1,2,3]triazolo[1,5-a]azepin-9-yl)-3,6-dihydropyridine-1(2H)-carboxylate (LC97-2)

LC97-1 (88.2 mg, 0.23 mmol), tert-butyl 4-(4,4,5,5-tetramethyl-1,3,2-dioxaboran-2-yl)-3,6-dihydropyridine-1(2H)-carboxylate (94.2 mg, 0.30 mmol), 1,4-dioxane (10 mL), water (0.5 mL) and potassium carbonate (49.9 mg, 0.36 mmol) were added to a reaction flask, and the air in the reaction system was replaced with nitrogen three times. The system was added with Pd(dppf)Cl$_2$-dichloromethane complex (10.6 mg, 0.013 mmol), and the air in the reaction system was replaced with nitrogen three times again. The system was heated to reflux for reaction. After the reaction was complete, the reaction system was added with water (50 mL) and EA (50 mL), shaken and separated. The aqueous phase was extracted with EA (30 mL*2). The combined organic phase was washed with water (50 mL*2) and saturated brine (30 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 36.6 mg of the product.

ESI-MS Calculated for [M+H]$^+$=488.26; Found: 487.80. The found value was consistent with the caculated value.

Step 3: Synthesis of 3-((1-methyl-9-(1,2,3,6-tetrahydropyridin-4-yl)-6,7-dihydro-5H-benzo[c][1,2,3]triazolo[1,5-a]azepin-7-yl)amino)phenol 2,2,2-trifluoroacetate (LC97)

LC97-2 (18.2 mg, 0.038 mmol) was added into a reaction flask, added with trifluoroacetic acid/dichloromethane (1:10, 5 mL) and stirred at room temperature for reaction. After the reaction was complete, the system was concentrated under reduced pressure, and the residue was separated by medium-pressure preparative chromatography (mobile phase: A: purified water with 0.05% trifluoroacetic acid, B: acetonitrile with 0.05% trifluoroacetic acid) and lyophilized to obtain 12.1 mg of the product.

ESI-MS Calculated for [M+H]$^+$=388.21; Found: 388.10. The found value was consistent with the caculated value.

Preparation Example 87, Final Product LC99: N-(2-(2-(dimethylamino)ethyl)phenyl)-1-methyl-9-(1-methyl-1H-pyrazol-4-yl)-6,7-dihydro-5H-benzo[c][1,2,3]triazolo azepin-7-amine

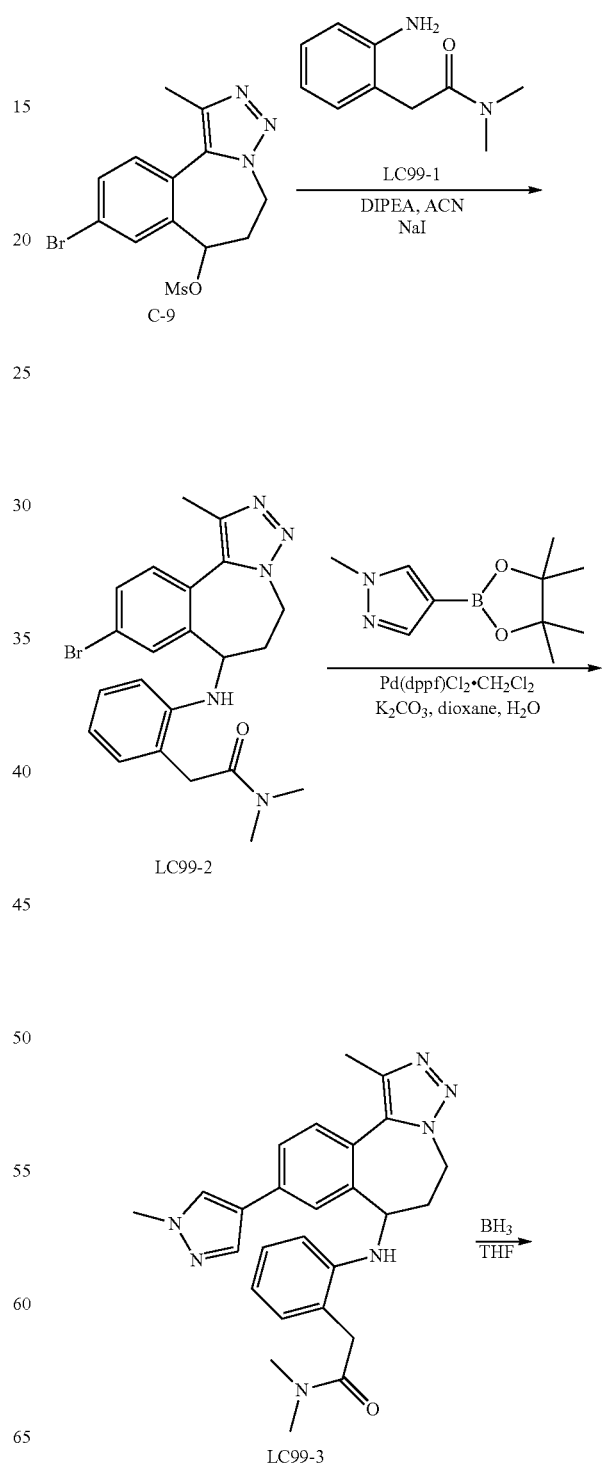

-continued

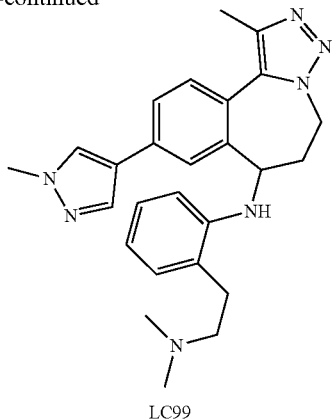

LC99

Step 1: Synthesis of 2-(2-((9-bromo-1-methyl-6,7-dihydro-5H-benzo[c][1,2,3]triazolo[1,5-a]azepin-7-yl)amino)phenyl)-N,N-dimethylacetamide (LC99-2)

C-9 (300.0 mg, 0.80 mmol), LC99-1 (175.5 mg, 0.97 mmol), acetonitrile (40 mL), DIPEA (516.9 mg, 4.01 mmol) and sodium iodide (38.4 mg, 0.26 mmol) were added to a reaction flask and heated to react under reflux. After the reaction was complete, the system was concentrated under reduced pressure, and the residue was added with water (50 mL) and EA (30 mL), shaken and sepatated. The aqueous phase was extracted with EA (30 mL*2). The combined organic phase was washed with water (80 mL*2) and saturated brine (30 mL), dired with anhydrous sodium sulfate and filtered with suction. The filtrate was concentrated under reduced pressure, and the residue was separated by PLC to obtain 105.5 mg of the target compound.

ESI-MS Calculated for [M+H]$^+$=456.12; Found: 456.00. The found value was consistent with the caculated value.

Step 2: Synthesis of N,N-dimethyl-2-(2-((1-methyl-9-(1-methyl-1H-pyrazol-4-yl)-6,7-dihydro-5H-benzo[c][1,2,3]triazolo[1,5-a]azepin-7-yl)amino)phenyl)acetamide (LC99-3)

LC99-2 (105.5 mg, 0.23 mmol), 1-methyl-4-(4,4,5,5-tetramethyl-1,3,2-dioxaborolan-2-yl)-1H-pyrazole (64.3 mg, 0.31 mmol), 1,4-dioxane (10 mL), water (0.50 mL) and potassium carbonate (50.0 mg, 0.36 mmol) were added to a reaction flask, and the air in the reaction system was replaced with nitrogen three times. The system was added with Pd(dppf)Cl$_2$-dichloromethane complex (10.6 mg, 0.013 mmol), and the air in the reaction system was replaced with nitrogen three times again. The system was heated to 100° C. for reaction. After the reaction was complete, the reaction system was added with water (50 mL) and EA (50 mL), shaken and separated. The aqueous phase was extracted with EA (50 mL*2). The combined organic phase was washed with water (100 mL*2) and saturated brine (50 mL), dired with anhydrous sodium sulfate and filtered with suction. The filtrate was concentrated under reduced pressure, and the residue was separated by PLC and lyophilized to obtain 68.9 mg of the product.

ESI-MS Calculated for [M+H]$^+$=456.24; Found: 456.00.

Step 3: Synthesis of N-(2-(2-(dimethylamino)ethyl)phenyl)-1-methyl-9-(1-methyl-1H-pyrazol-4-yl)-6,7-dihydro-5H-benzo[c][1,2,3]triazolo[1,5-a]azepin-7-amine (LC99)

LC99-2 (68.9 mg, 0.15 mmol), tetrahydrofuran (5 mL) and boron tribromide in tetrahydrofuran (2 mL) were added to a reaction flask and heated to react under reflux. After the reaction was complete, the system was concentrated under reduced pressure, and the residue was separated by medium-pressure preparative chromatography and lyophilized to obtain 10.8 mg of the product.

Product analysis: $^1$HNMR (CDCl$_3$, 400 MHz): δ 7.65 (s, 1H), 7.58 (s, 1H), 7.55 (d, J=1.7 Hz, 1H), 7.50-7.44 (m, 1H), 7.40 (d, J=7.8 Hz, 1H), 6.97-6.93 (m, 1H), 6.92-6.86 (m, 1H), 6.56 (m, 1H), 5.92 (d, J=8.3 Hz, 1H), 4.79 (dd, J=14.1, 7.4 Hz, 1H), 4.31 (dd, J=11.0, 6.7 Hz, 1H), 4.05-3.93 (m, 1H), 3.92 (s, 3H), 3.35-3.01 (m, 3H), 2.92 (dd, J=13.5, 3.5 Hz, 7H), 2.82-2.69 (m, 1H), 2.55 (s, 3H), 2.53-2.44 (m, 1H).

ESI-MS Calculated for [M+H]$^+$=442.26; Found: 442.00. The found value was consistent with the caculated value.

Preparation Example 88, Final Product LC101: N-(3-(2-(dimethylamino)ethyl)phenyl)-1-methyl-9-(1-methyl-1H-pyrazol-4-yl)-6,7-dihydro-5H-benzo[c][1,2,3]triazolo[1,5-a]azepin-7-amine

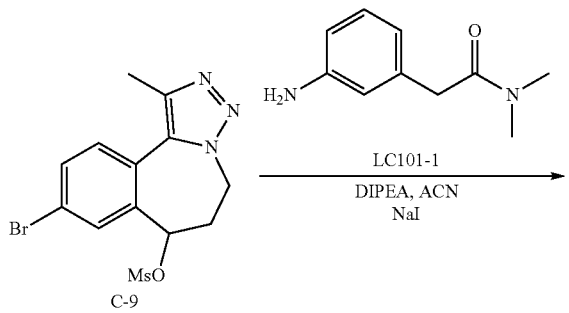

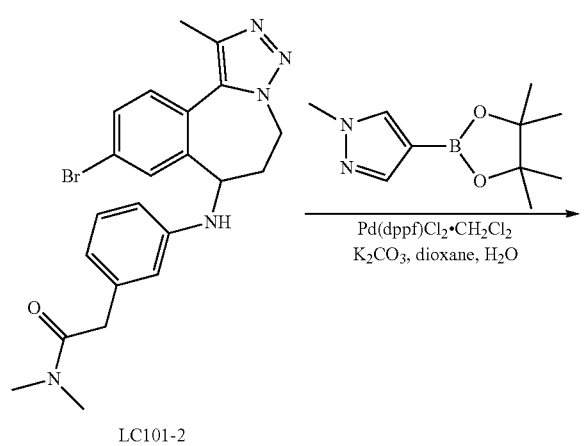

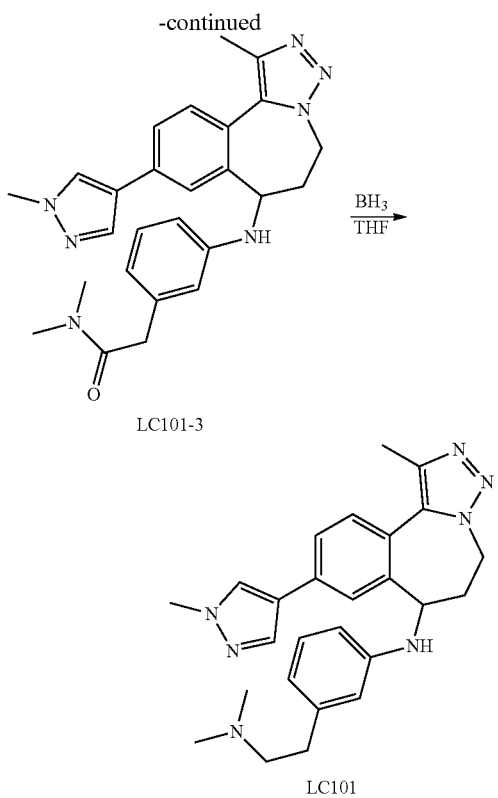

LC101-3

LC101

Step 1: Synthesis of 2-(3-((9-bromo-1-methyl-6,7-dihydro-5H-benzo[c][1,2,3]triazolo[1,5-a]azepin-7-yl)amino)phenyl)-N,N-dimethylacetamide (LC101-2)

C-9 (500.1 mg, 1.34 mmol), LC101-1 (486.1 mg, 2.73 mmol), acetonitrile (50 mL), DIPEA (876.3 mg, 6.78 mmol) and sodium iodide (64.3 mg, 0.43 mmol) were added to a reaction flask and heated to react under reflux. After the reaction was complete, the system was concentrated under reduced pressure, and the residue was added with water (50 mL) and EA (30 mL), shaken and sepatated. The aqueous phase was extracted with EA (30 mL*2). The combined organic phase was washed with water (80 mL*2) and saturated brine (30 mL), dired with anhydrous sodium sulfate and filtered with suction. The filtrate was concentrated under reduced pressure, and the residue was separated by PLC to obtain 313.3 mg of the target compound.

ESI-MS Calculated for [M+H]$^+$=454.12; Found: 454.00. The found value was consistent with the caculated value.

Step 2: Synthesis of N,N-dimethyl-2-(3-((1-methyl-9-(1-methyl-1H-pyrazol-4-yl)-6,7-dihydro-5H-benzo[c][1,2,3]triazolo[1,5-a]azepin-7-yl)amino)phenyl)acetamide (LC101-3)

LC101-2 (313.3 mg, 0.69 mmol), 1-methyl-4-(4,4,5,5-tetramethyl-1,3,2-dioxaborolan-2-yl)-1H-pyrazole (188.0 mg, 0.90 mmol), potassium carbonate (149.8 mg, 1.09 mmol), 1,4-dioxane (30 mL) and water (1.5 mL) were added to a reaction flask, and the air in the reaction system was replaced with nitrogen three times. The system was added with Pd(dppf)Cl$_2$-dichloromethane complex (31.0 mg, 0.038 mmol), and the air in the reaction system was replaced with nitrogen twice again. The reaction was carried out at an external temperature of 100° C. After the reaction was complete, the reaction system was cooled down, added with water (50 mL) and EA (50 mL), shaken and separated. The aqueous phase was extracted with EA (50 mL*2). The combined organic phase was washed with water (50 mL*2) and saturated brine (50 mL), dired with anhydrous sodium sulfate and filtered with suction. The filtrate was concentrated under reduced pressure, and the residue was separated by PLC and lyophilized to obtain 132.9 mg of the product.

ESI-MS Calculated for [M+H]$^+$=456.24; Found: 456.10. The found value was consistent with the caculated value.

Step 3: Synthesis of N-(3-(2-(dimethyl amino)ethyl)phenyl)-1-methyl-9-(1-methyl-1H-pyrazol-4-yl)-6,7-dihydro-5H-benzo[c][1,2,3]triazolo[1,5-a]azepin-7-amine (LC101)

LC101-2 (52.4 mg, 0.12 mmol), tetrahydrofuran (8 mL) and borane in tetrahydrofuran (2 mL) were added to a reaction flask and heated to react under reflux. After the reaction was complete, the system was concentrated under reduced pressure, and the residue was separated by medium-pressure preparative chromatography and lyophilized to obtain 12.4 mg of the product.

ESI-MS Calculated for [M+H]$^+$=442.26; Found: 442.00. The found value was consistent with the caculated value.

Preparation Example 89, Final Product LC117: 4-((1-methyl-9-(1,2,3,6-tetrahydropyridin-4-yl)-6,7-dihydro-5H-benzo[c][1,2,3]triazolo[1,5-a]azepin-7-yl)amino)phenol 2,2,2-trifluoroacetate

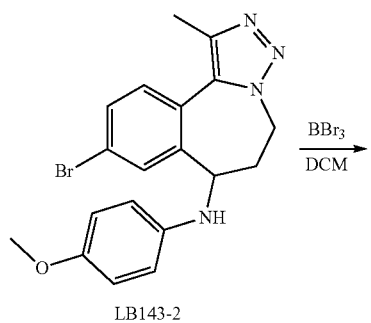

LB143-2

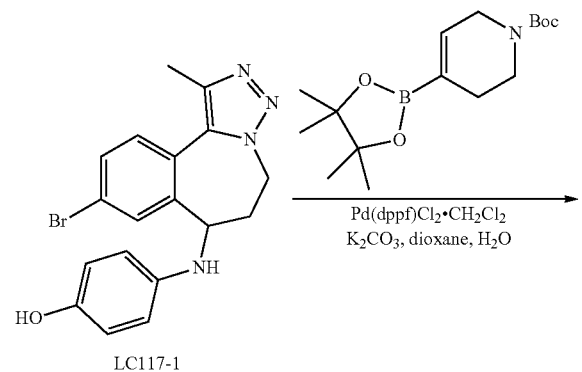

LC117-1

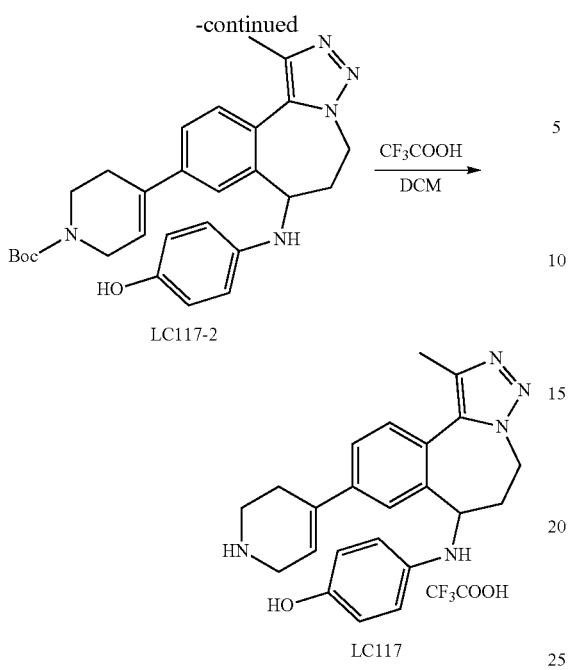

LC117-2

LC117

Step 1: Synthesis of 4-((9-bromo-1-methyl-6,7-dihydro-5H-benzo[c][1,2,3]triazolo[1,5-a]azepin-7-yl)amino)phenol (LC117-1)

LB143-2 (178.4 mg, 0.45 mmol) and DCM (10 mL) were added into a reaction flask and added dropwise with BBr$_3$ (4.5 mL) in an ice bath. After completion of the dropwise addition, the system was warmed to room temperature naturally. After the reaction was complete, an ice-water mixture (50 mL) was added to a 100 mL beaker, and the reaction system was carefully added dropwise to the ice water. After completion of the dropwise addition, the system was added with DCM (30 mL), shaken and sepatated. The aqueous phase was extracted with DCM (50 mL*2). The combined organic phase was washed with water (50 mL*3) and saturated brine (30 mL), dried over anhydrous sodium sulfate and filtered with suction. The filtrate was concentrated under reduced pressure, and the residue was separated by medium-pressure preparative chromatography and lyophilized to obtain 104.3 mg of the product.

ESI-MS Calculated for [M+H]$^+$=387.06; Found: 387.00. The found value was consistent with the caculated value.

Step 2: Synthesis of tert-butyl 4-(7-((4-hydroxyphenyl)amino)-1-methyl-6,7-dihydro-5H-benzo[c][1,2,3]triazolo[1,5-a]azepin-9-yl)-3,6-dihydropyridine-1(2H)-carboxylate (LC117-2)

LC117-1 (104.3 mg, 0.27 mmol), tert-butyl 4-(4,4,5,5-tetramethyl-1,3,2-dioxaboran-2-yl)-3,6-dihydropyridine-1(2H)-carboxylate (111.1 mg, 0.36 mmol), 1,4-dioxane (10 mL), water (0.5 mL) and potassium carbonate (58.6 mg, 0.43 mmol) were added to a reaction flask, and the air in the reaction system was replaced with nitrogen three times. The system was added with Pd(dppf)Cl$_2$-dichloromethane complex (12.4 mg, 0.015 mmol), and the air in the reaction system was replaced with nitrogen three times again. The system was heated to 100° C. for reaction. After the reaction was complete, the reaction system was cooled down, added with water (50 mL) and EA (50 mL), shaken and separated. The aqueous phase was extracted with EA (50 mL*2). The combined organic phase was washed with water (50 mL*2) and saturated brine (50 mL), dired with anhydrous sodium sulfate and filtered with suction. The filtrate was concentrated under reduced pressure, and the residue was separated by PLC to obtain a crude, which was separated by medium pressure preparative chromatography (mobile phase: A: purified water with 0.05% trifluoroacetic acid, B: acetonitrile with 0.05% trifluoroacetic acid) and lyophilized to obtain 28.8 mg of the product.

ESI-MS Calculated for [M+H]$^+$=488.26; Found: 488.10. The found value was consistent with the caculated value.

Step 3: Synthesis of 4-((1-methyl-9-(1,2,3,6-tetrahydropyridin-4-yl)-6,7-dihydro-5H-benzo[c][1,2,3]triazolo[1,5-a]azepin-7-yl)amino)phenol 2,2,2-trifluoro acetate (LC117)

LC117-2 (18.8 mg, 0.039 mmol) was added into a reaction flask, added with trifluoroacetic acid/dichloromethane (1:5, 5 mL) and stirred at room temperature for reaction. After the reaction was complete, the system was concentrated under reduced pressure, and the residue was separated by medium-pressure preparative chromatography and lyophilized to obtain 10.2 mg of the product.

ESI-MS Calculated for [M+H]$^+$=388.21; Found: 388.00. The found value was consistent with the caculated value.

Preparation Example 90, Final Product LC127: 2-((1-methyl-9-(1,2,3,6-tetrahydropyridin-4-yl)-6,7-dihydro-5H-benzo[c][1,2,3]triazolo[1,5-a]azepin-7-yl)amino)phenol 2,2,2-trifluoroacetate

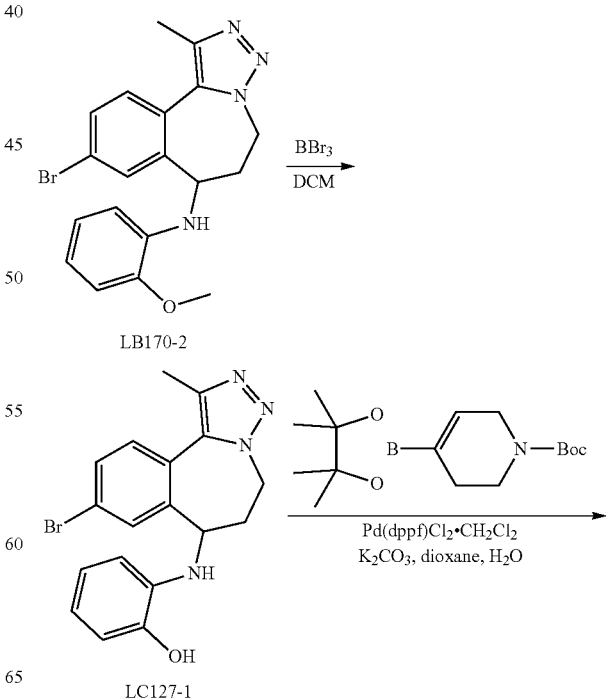

LB170-2

LC127-1

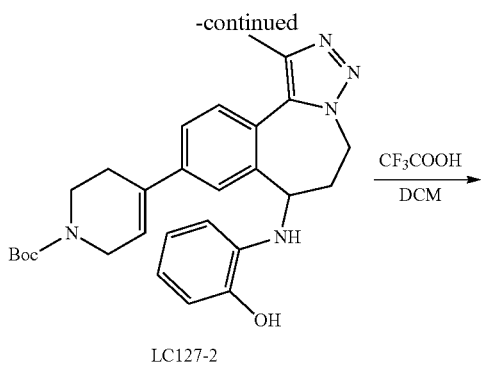

LC127-2

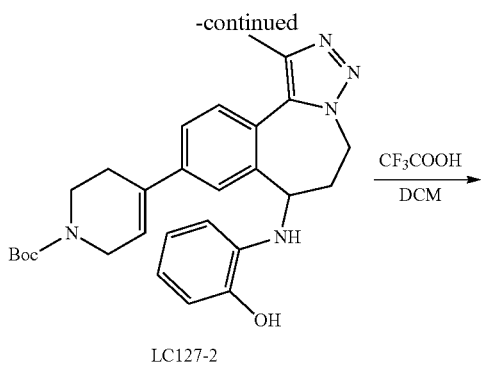

LC127

Step 1: Synthesis of 2-((9-bromo-1-methyl-6,7-dihydro-5H-benzo[c][1,2,3]triazolo[1,5-a]azepin-7-yl)amino)phenol (LC127-1)

LB170-2 (172.4 mg, 0.43 mmol) and DCM (10 mL) were added into a reaction flask and added dropwise with BBr$_3$ (4.5 mL) in an ice bath. After completion of the dropwise addition, the system was warmed to room temperature for reaction. After the reaction was complete, 50 mL of an ice-water mixture was added to a 100 mL beaker, and the reaction system was slowly added dropwise to the ice water. After completion of the dropwise addition, the system was extracted with DCM (30 mL). The aqueous phase was extracted with DCM (50 mL*2). The combined organic phase was washed with water (50 mL) and saturated brine (30 mL), dried over anhydrous sodium sulfate and filtered with suction. The filtrate was concentrated under reduced pressure, and the residue was separated by medium-pressure preparative chromatography and lyophilized to obtain 88.3 mg of the product.

ESI-MS Calculated for [M+H]$^+$=387.06; Found: 386.90. The found value was consistent with the caculated value.

Step 2: Synthesis of tert-butyl 4-(7-((2-hydroxyphenyl)amino)-1-methyl-6,7-dihydro-5H-benzo[c][1,2,3]triazolo[1,5-a]azepin-9-yl)-3,6-dihydropyridine-1(2H)-carboxylate (LC127-2)

LC127-1 (88.3 mg, 0.35 mmol), tert-butyl 4-(4,4,5,5-tetramethyl-1,3,2-dioxaboran-2-yl)-3,6-dihydropyridine-1(2H)-carboxylate (144.1 mg, 0.47 mmol), 1,4-dioxane (10 mL), water (0.5 mL) and potassium carbonate (76.0 mg, 0.55 mmol) were added to a reaction flask, and the air in the reaction system was replaced with nitrogen three times. The system was added with Pd(dppf)Cl$_2$-dichloromethane complex (16.1 mg, 0.020 mmol), and the air in the reaction system was replaced with nitrogen three times again. The system was heated to 105° C. for reaction. After the reaction was complete, the reaction system was cooled down, added with water (50 mL) and EA (50 mL), shaken and separated. The aqueous phase was extracted with EA (50 mL*2). The combined organic phase was washed with water (50 mL*2) and saturated brine (50 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 48.8 mg of the product.

ESI-MS Calculated for [M+H]$^+$=488.26; Found: 488.10.

Step 3: Synthesis of 2-((1-methyl-9-(1,2,3,6-tetrahydropyridin-4-yl)-6,7-dihydro-5H-benzo[c][1,2,3]triazolo[1,5-a]azepin-7-yl)amino)phenol 2,2,2-trifluoroacetate (LC127)

LC127-2 (25 mg, 0.051 mmol) was added into a reaction flask, added with trifluoroacetic acid/dichloromethane (1:5, 5 mL) and stirred at room temperature for reaction. After the reaction was complete, the system was concentrated under reduced pressure, and the residue was separated by medium-pressure preparative chromatography (mobile phase: A: purified water with 0.05% trifluoroacetic acid, B: acetonitrile with 0.05% trifluoroacetic acid) and lyophilized to obtain 12.7 mg of the product.

ESI-MS Calculated for [M+H]$^+$=388.21; Found: 388.10. The found value was consistent with the caculated value.

Preparation Example 91, Final Product LC128: 4-((1-methyl-9-(1,2,3,6-tetrahydropyridin-4-yl)-6,7-dihydro-5H-benzo[c][1,2,3]triazolo[1,5-a]azepin-7-yl)amino)benzonitrile 2,2,2-trifluoroacetate

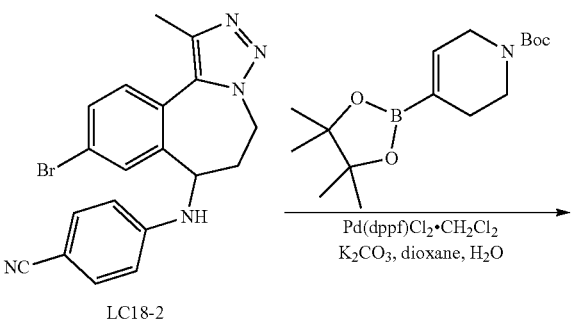

LC18-2

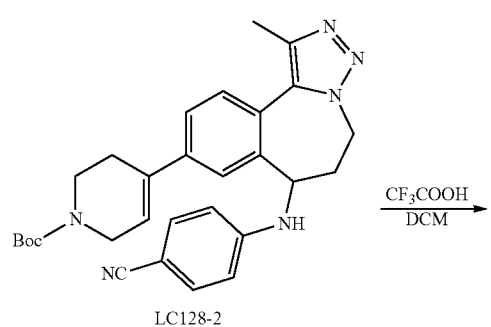

LC128-2

Step 1: Synthesis of tert-butyl 4-(7-((4-cyanophenyl)amino)-1-methyl-6,7-dihydro-5H-benzo[c][1,2,3]triazolo[1,5-a]azepin-9-yl)-3,6-dihydropyridine-1(2H)-carboxylate (LC128-2)

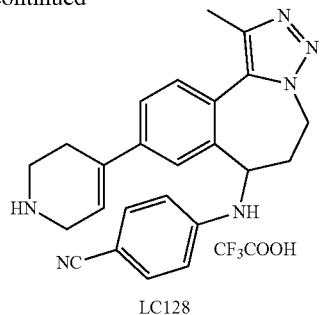

LC18-2 (117.1 mg, 0.30 mmol), tert-butyl 4-(4,4,5,5-tetramethyl-1,3,2-dioxaboran-2-yl)-3,6-dihydropyridine-1(2H)-carboxylate (122.2 mg, 0.40 mmol), 1,4-dioxane (10 mL), water (0.5 mL) and potassium carbonate (65.1 mg, 0.47 mmol) were added to a reaction flask, and the air in the reaction system was replaced with nitrogen three times. The system was added with Pd(dppf)Cl$_2$-dichloromethane complex (13.8 mg, 0.017 mmol), and the air in the reaction system was replaced with nitrogen three times again. The system was heated to 100° C. for reaction. After the reaction was complete, the reaction system was added with water (50 mL) and EA (50 mL), shaken and separated. The aqueous phase was extracted with EA (50 mL*2). The combined organic phase was washed with water (50 mL*3) and saturated brine (50 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 101.1 mg of the product.

ESI-MS Calculated for [M+H]$^+$=497.26; Found: 497.00. The found value was consistent with the caculated value.

Step 2: Synthesis of 4-((1-methyl-9-(1,2,3,6-tetrahydropyridin-4-yl)-6,7-dihydro-5H-benzo[c][1,2,3]triazolo[1,5-a]azepin-7-yl)amino)benzonitrile 2,2,2-trifluoroacetate (LC128)

LC128-2 (20.0 mg, 0.040 mmol) was added into a reaction flask, added with trifluoroacetic acid/dichloromethane (1:10, 5 mL) and stirred at room temperature for reaction. After the reaction was complete, the system was concentrated under reduced pressure, and the residue was separated by medium-pressure preparative chromatography (mobile phase: A: purified water with 0.05% trifluoroacetic acid, B: acetonitrile with 0.05% trifluoroacetic acid) and lyophilized to obtain 12.6 mg of the product.

Product analysis: $^1$HNMR (CDCl$_3$, 400 MHz): δ 7.38 (d, J=6.7 Hz, 3H), 7.26 (d, J=8.5 Hz, 2H), 6.21 (d, J=8.5 Hz, 2H), 5.87 (s, 1H), 3.76 (s, 2H), 3.34 (s, 2H), 2.48 (s, 3H), 1.83 (m, 7H).

ESI-MS Calculated for [M+H]$^+$=397.21; Found: 397.10. The found value was consistent with the caculated value.

Preparation Example 92, Final Product LC131: N-methyl-2-(34(1-methyl-9-(1,2,3,6-tetrahydropyridin-4-yl)-6,7-dihydro-5H-benzo[c][1,2,3]triazolo[1,5-a]azepin-7-yl)amino)pheny 1)acetamide 2,2,2-trifluoroacetate

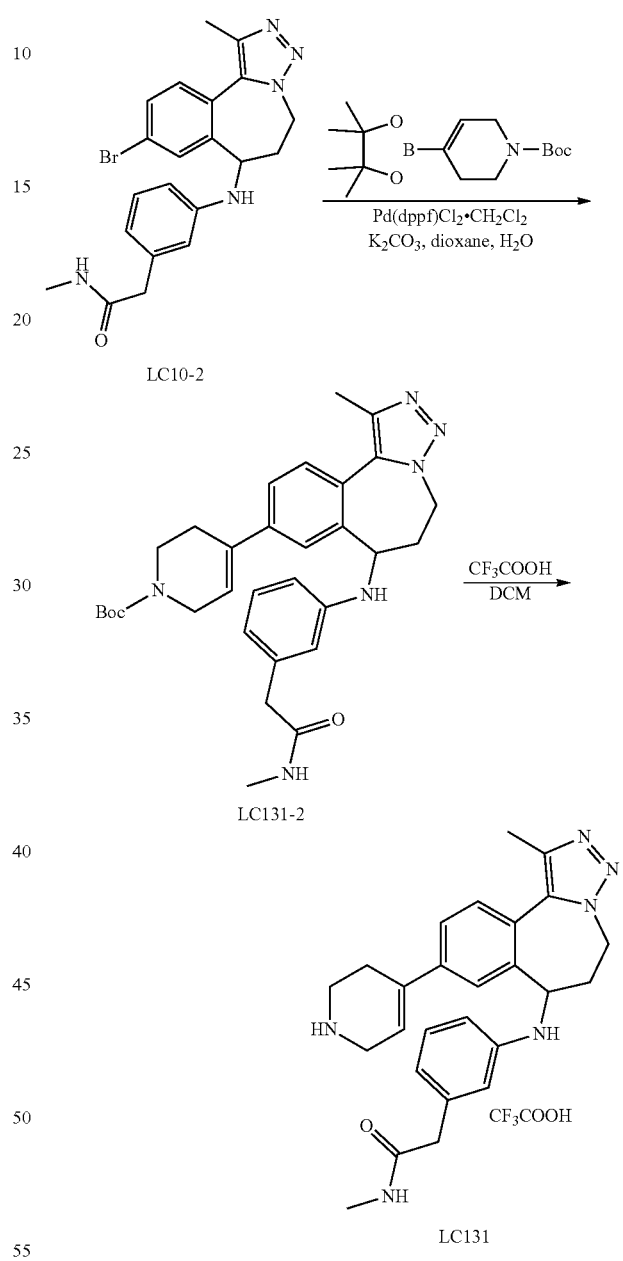

Step 1: Synthesis of tert-butyl 4-(1-methyl-7-((3-(2-(methylamino)-2-oxoethyl)phenyl)amino)-6,7-dihydro-5H-benzo[c][1,2,3]triazolo[1,5-a]azepin-9-yl)-3,6-dihydropyridine-1(2H)-carboxylate (LC131-2)

LC10-2 (86.1 mg, 0.20 mmol), tert-butyl 4-(4,4,5,5-tetramethyl-1,3,2-dioxaboran-2-yl)-3,6-dihydropyridine-1(2H)-carboxylate (82.3 mg, 0.27 mmol), 1,4-dioxane (10 mL), water (0.5 mL) and potassium carbonate (44.3 mg, 0.32 mmol) were added to a reaction flask, and the air in the reaction system was replaced with nitrogen three times. The system was added with Pd(dppf)Cl$_2$-dichloromethane complex (9.2 mg, 0.011 mmol), and the air in the reaction system was replaced with nitrogen three times again. The system was heated to 100° C. for reaction. After the reaction was complete, the reaction system was added with water (50 mL) and EA (50 mL), shaken and separated. The aqueous phase was extracted with EA (50 mL*2). The combined organic phase was washed with water (100 mL*2) and saturated brine (50 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 80.1 mg of the product.

ESI-MS Calculated for [M+H]$^+$=543.30; Found: 543.10. The found value was consistent with the caculated value.

Step 2: Synthesis of N-methyl-2-(34(1-methyl-9-(1,2,3,6-tetrahydropyridin-4-yl)-6,7-dihydro-5H-benzo[c][1,2,3]triazolo[1,5-a]azepin-7-yl)amino)phenyl)acetamide 2,2,2-trifluoroacetate (LC131)

LC131-2 (40.1 mg, 0.074 mmol) was added into a reaction flask, added with trifluoroacetic acid/dichloromethane (1:10, 5 mL) and stirred at room temperature for reaction. After the reaction was complete, the system was concentrated under reduced pressure, the residue was separated by medium-pressure preparative chromatograph (mobile phase: A: purified water with 0.05% trifluoroacetic acid, B: acetonitrile with 0.05% trifluoroacetic acid) and lyophilized to obtain 12.30 mg of the product.

ESI-MS Calculated for [M+H]$^+$=443.25; Found: 443.10. The found value was consistent with the caculated value.

Preparation Example 93, Final Product LC132: N-methyl-2-(2-4(1-methyl-9-(1,2,3,6-tetrahydropyridin-4-yl))-6,7-dihydro-5H-benzo[c][1,2,3]triazolo[1,5-a]azepin-7-yl)amino)phen yl)acetamide 2,2,2-trifluoroacetate

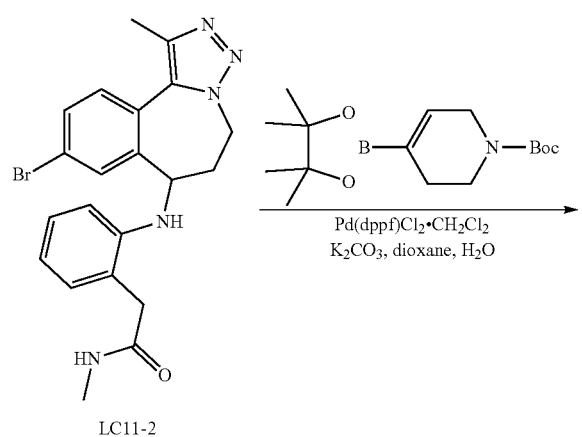

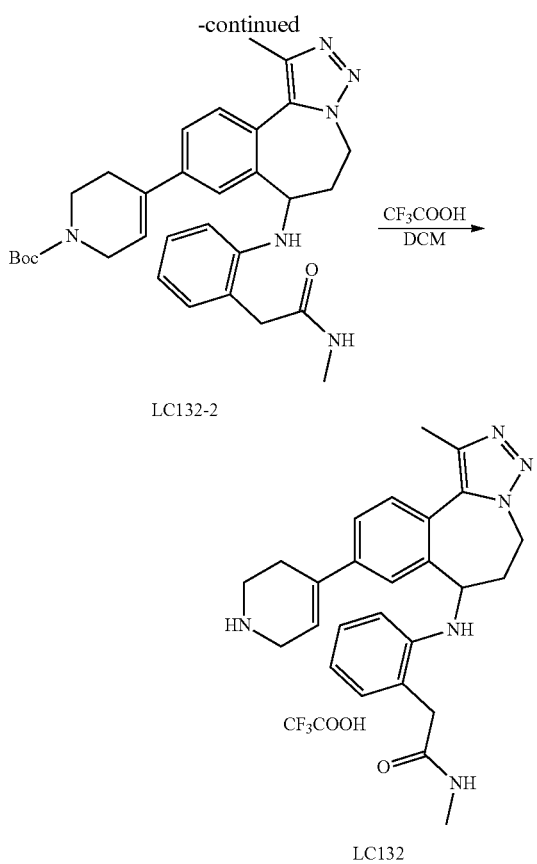

Step 1: Synthesis of tert-butyl 4-(1-methyl-7-((2-(2-(methylamino)-2-oxoethyl)phenyl)amino)-6,7-dihydro-5H-benzo[c][1,2,3]triazolo[1,5-a]azepin-9-yl)-3,6-dihydropyridine-1 (2H)-carboxylate (LC132-2)

LC11-2 (230.5 mg, 0.53 mmol), tert-butyl 4-(4,4,5,5-tetramethyl-1,3,2-dioxaboran-2-yl)-3,6-dihydropyridine-1 (2H)-carboxylate (215.3 mg, 0.70 mmol), 1,4-dioxane (20 mL), water (1 mL) and potassium carbonate (115.1 mg, 0.83 mmol) were added to a reaction flask, and the air in the reaction system was replaced with nitrogen three times. The system was added with Pd(dppf)Cl$_2$-dichloromethane complex (24.4 mg, 0.030 mmol), and the air in the reaction system was replaced with nitrogen three times again. The system was heated to 100° C. for reaction. After the reaction was complete, the reaction system was added with water (50 mL) and EA (50 mL), shaken and separated. The aqueous phase was extracted with EA (50 mL*2). The combined organic phase was washed with water (100 mL*2) and saturated brine (50 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 203.7 mg of the product.

ESI-MS Calculated for [M+H]$^+$=543.30; Found: 543.10 the found value was consistent with the caculated value.

Step 2: Synthesis of N-methyl-2-(2-(41-methyl-9-(1,2,3,6-tetrahydropyridin-4-yl))-6,7-dihydro-5H-benzo[c][1,2,3]triazolo[1,5-a]azepin-7-yl)amino)phenyl)acetamide 2,2,2-trifluoroacetate (LC132)

LC132-2 (50.0 mg, 0.081 mmol) was added into a reaction flask, added with trifluoroacetic acid/dichloromethane (1:10, 5 mL) and stirred at room temperature for reaction. After the reaction was complete, the system was concentrated under reduced pressure, the residue was separated by medium-pressure preparative chromatography (mobile phase: A: purified water with 0.05% trifluoroacetic acid, B: acetonitrile with 0.05% trifluoroacetic acid) and lyophilized to obtain 28.8 mg of the product.

ESI-MS Calculated for [M+H]$^+$=443.25; Found: 443.10. The found value was consistent with the caculated value.

Preparation Example 94, Final Product LC133: 2-(4-((1-methyl-9-(1,2,3,6-tetrahydropyridin-4-yl)-6,7-dihydro-5H-benzo[c][1,2,3]triazolo[1,5-a]azepin-7-yl)amino)pheno xy)ethan-1-ol 2,2,2-trifluoroacetate

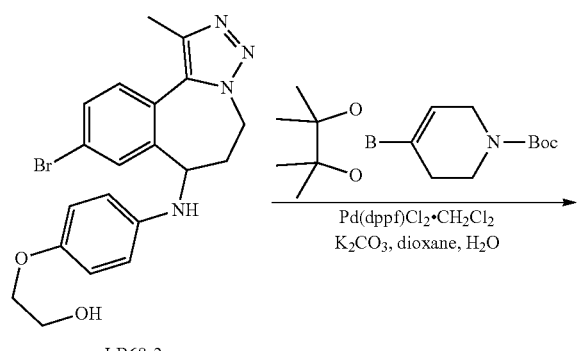

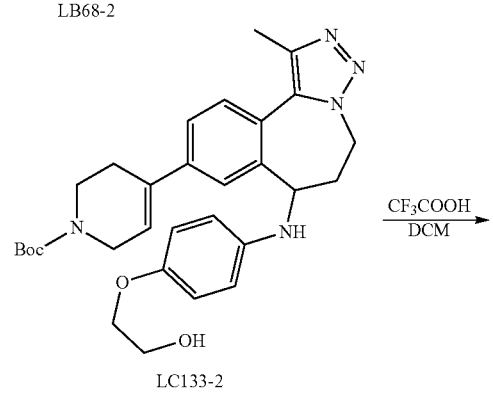

Step 1: Synthesis of tert-butyl 4-(7-((4-(2-hydroxyethoxy)phenyl)amino)-1-methyl-6,7-dihydro-5H-benzo[c][1,2,3]triazolo[1,5-a]azepin-9-yl)-3,6-dihydropyridine-1 (2H)-carboxylate (LC133-2)

LB68-2 (190.5 mg, 0.45 mmol), tert-butyl 4-(4,4,5,5-tetramethyl-1,3,2-dioxaboran-2-yl)-3,6-dihydropyridine-1 (2H)-carboxylate (182.6 mg, 0.59 mmol), 1,4-dioxane (20 mL), water (1 mL) and potassium carbonate (97.7 mg, 0.71 mmol) were added to a reaction flask, and the air in the reaction system was replaced with nitrogen three times. The system was added with Pd(dppf)Cl$_2$-dichloromethane complex (21.8 mg, 0.025 mmol), and the air in the reaction system was replaced with nitrogen three times again. The system was heated to 100° C. for reaction. After the reaction was complete, the reaction system was added with water (50 mL) and EA (50 mL), shaken and separated. The aqueous phase was extracted with EA (30 mL*2). The combined organic phase was washed with water (50 mL*3) and saturated brine (50 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 58.8 mg of the product.

ESI-MS Calculated for [M+H]$^+$=532.28; Found: 532.00. The found value was consistent with the caculated value.

Step 2: Synthesis of 2-(4-((1-methyl-9-(1,2,3,6-tetrahydropyridin-4-yl)-6,7-dihydro-5H-benzo[c][1,2,3]triazolo[1,5-a]azepin-7-yl)amino)phenoxy)ethan-1-ol 2,2,2-trifluoroacetate (LC133)

LC133-2 (38.1 mg, 0.072 mmol) was added into a reaction flask, added with trifluoroacetic acid/dichloromethane (1:10, 5 mL) and stirred at room temperature for reaction. After the reaction was complete, the system was concentrated under reduced pressure, and the residue was separated by medium-pressure preparative chromatography (mobile phase: A: purified water with 0.05% trifluoroacetic acid, B: acetonitrile with 0.05% trifluoroacetic acid) and lyophilized to obtain 12.7 mg of the product.

ESI-MS Calculated for [M+H]$^+$=432.23; Found: 432.10. The found value was consistent with the caculated value.

Preparation Example 95, Final Product LC136: 2-((1-methyl-9-(1-methyl-1H-pyrazol-4-yl)-6,7-dihydro-5H-benzo[c][1,2,3]triazolo[1,5-a]azepin-7-yl)amino)benzonitrile

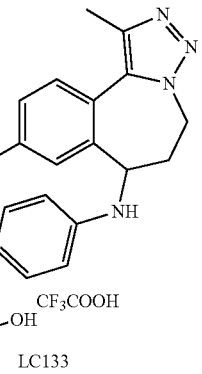

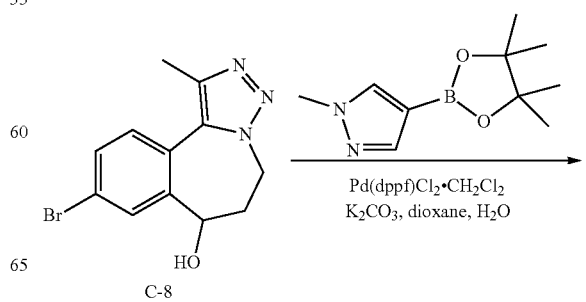

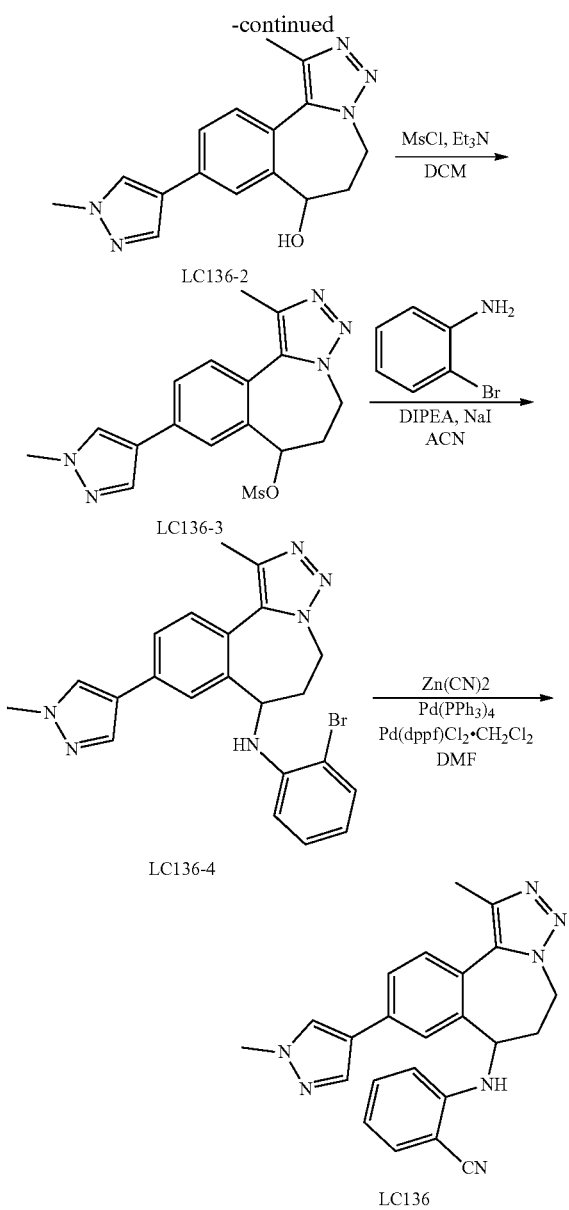

Step 1: Synthesis of 1-methyl-9-(1-methyl-1H-pyrazol-4-yl)-6,7-dihydro-5H-benzo[c][1,2,3]triazolo[1,5-a]azepin-7-ol (LC136-2)

C-8 (501.1 mg, 1.71 mmol), 1-methyl-4-(4,4,5,5-tetramethyl-1,3,2-dioxaborolan-2-yl)-1H-pyrazole (480.4 mg, 2.31 mmol), 1,4-dioxane (50 mL), water (2.5 mL) and potassium carbonate (373.2 mg, 2.70 mmol) were added to a reaction flask, and the air in the reaction system was replaced with nitrogen three times. The system was added with Pd(dppf)Cl$_2$-dichloromethane complex (80.1 mg, 0.098 mmol), and the air in the reaction system was replaced with nitrogen three times again. The system was heated to reflux for reaction. After the reaction was complete, the reaction system was added with water (50 mL) and EA (50 mL), shaken and separated. The aqueous phase was extracted with EA (50 mL*3). The combined organic phase was washed with water (50 mL*2) and saturated brine (50 mL), dired with anhydrous sodium sulfate and filtered with suction. The filtrate was concentrated under reduced pressure, and the residue was separated by column chromatography to obtain 320.1 mg of the target compound.

ESI-MS Calculated for [M+H]$^+$=296.14; Found: 296.00. The found value was consistent with the caculated value.

Step 2: Synthesis of 1-methyl-9-(1-methyl-1H-pyrazol-4-yl)-6,7-dihydro-5H-benzo[c][1,2,3]triazolo[1,5-a]azepin-7-yl methanesulfonate (LC136-3)

LC136-2 (480.0 mg, 1.63 mmol), triethylamine (498.9 mg, 4.94 mmol) and dichloromethane (50 ml) were added to a 250 mL single necked flask. The system was cooled to 2° C., added dropwise with methanesulfonyl chloride (297.8 mg) and kept at 0-10° C. After completion of the dropwise addition, the system was stirred at room temperature for reaction. The system was added with water (100 mL), shaken and sepatated. The aqueous phase was extracted with dichloromethane (50 mL*3). The combined organic phase was washed with water (100 mL*2) and saturated brine (50 mL), dired with anhydrous sodium sulfate and filtered with suction. The filtrate was concentrated under reduced pressure, and the residue was added with ethyl acetate/petroleum ether (1:10, 30 mL), slurried and filtered with suction to obtain 402.1 mg of the target compound.

Step 3: Synthesis of N-(2-bromophenyl)-1-methyl-9-(1-methyl-1H-pyrazol-4-yl)-6,7-dihydro-5H-benzo[c][1,2,3]triazolo[1,5-a]azepin-7-amine (LC136-4)

LC136-3 (170.8 mg, 0.46 mmol), o-bromoaniline (236.1 mg, 1.73 mmol), acetonitrile (50 mL), DIPEA (301.0 mg, 2.33 mmol) and sodium iodide (22.1 mg, 0.15 mmol) were added to a reaction flask and heated to reflux. After the reaction was complete, the system was cooled down and concentrated under reduced pressure, and the residue was added with water (100 mL) and EA (100 mL), shaken and sepatated. The aqueous phase was extracted with EA (50 mL*3). The combined organic phase was washed with water (100 mL*2) and saturated brine (80 mL), dired with anhydrous sodium sulfate and filtered with suction. The filtrate was concentrated under reduced pressure, and the residue was separated by PLC to obtain 180.3 mg of the target compound.

ESI-MS Calculated for [M+H]$^+$=451.10; Found: 451.00. The found value was consistent with the caculated value.

Step 4: Synthesis of 2-((1-methyl-9-(1-methyl-1H-pyrazol-4-yl)-6,7-dihydro-5H-benzo[c][1,2,3]triazolo[1,5-a]azepin-7-yl)amino)benzonitrile (LC136)

LC136-4 (80.4 mg, 0.18 mmol), DMF (5 mL), zinc cyanide (21.4 mg, 0.18 mmol), tetratriphenylphosphine palladium (124.8 mg,0.11) and Pd(dppf)Cl$_2$-dichloromethane complex (23.6 mg, 0.029 mmol) were added to a 20 mL microwave tube. The tube was purged with nitrogen for 10 minutes and sealed. The reaction was carried out at T=120° C. for 0.5 h. After the reaction was complete, the reaction system was added with water (50 mL) and EA (50 mL), shaken and separated. The aqueous phase was extracted with EA (20 mL*2). The combined organic phase was washed with water (100 mL*2) and saturated brine (50 mL), dired with anhydrous sodium sulfate and filtered with suction. The filtrate was concentrated under reduced pressure, and the residue was separated by column chromatography to obtain 42.2 mg of the target compound.

Product analysis: ¹HNMR (CDCl₃, 400 MHz): δ 7.71 (d, J=0.8 Hz, 1H), 7.59 (d, J=0.8 Hz, 1H), 7.56-7.50 (m, 2H), 7.43 (m, 2H), 7.18 (m, 1H), 6.68 (m, 1H), 6.02 (d, J=8.6 Hz, 1H), 4.95-4.76 (m, 2H), 4.37 (m, 1H), 4.00 (m, 1H), 3.93 (s, 3H), 3.07 (m, 1H), 2.55 (s, 3H), 2.29 (m, 1H).

ESI-MS Calculated for [M+H]⁺=396.19; Found: 395.90. The found value was consistent with the caculated value.

Preparation Example 96, Final Product LC158: N-(2-methoxyphenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate

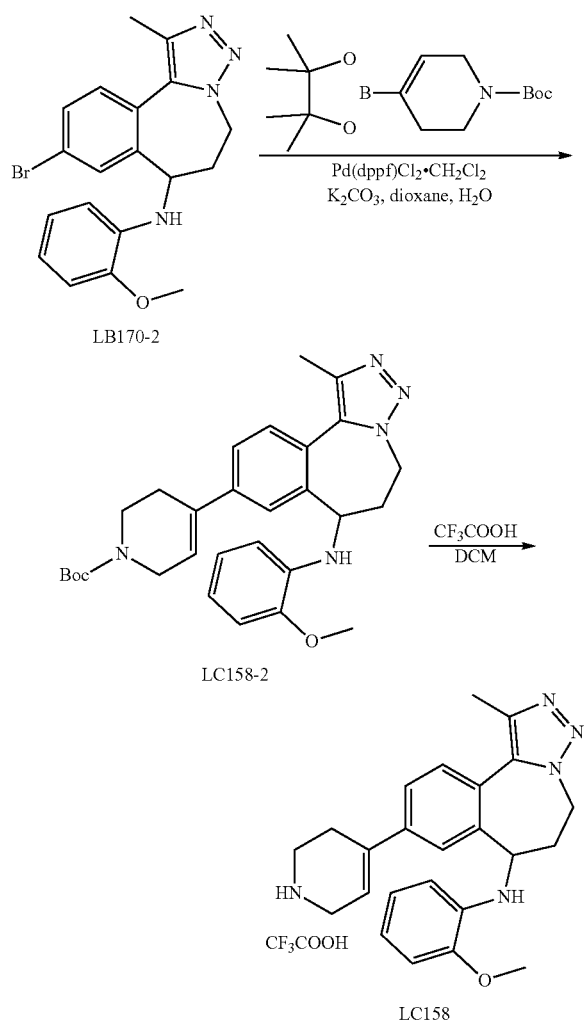

Step 1: Synthesis of tert-butyl 4-(7-((2-methoxyphenyl)amino)-1-methyl-6,7-dihydro-5H-benzo[c][1,2,3]triazolo[1,5-a]azepin-9-yl)-3,6-dihydropyridine-1(2H)-carboxylate (LC158-2)

LB170-2 (161.2 mg, 0.41 mmol), tert-butyl 4-(4,4,5,5-tetramethyl-1,3,2-dioxaboran-2-yl)-3,6-dihydropyridine-1(2H)-carboxylate (166.1 mg, 0.54 mmol), 1,4-dioxane (15 mL), water (0.75 mL) and potassium carbonate (90.0 mg, 0.65 mmol) were added to a reaction flask, and the air in the reaction system was replaced with nitrogen three times. The system was added with Pd(dppf)Cl₂-dichloromethane complex (18.8 mg, 0.023 mmol), and the air in the reaction system was replaced with nitrogen three times again. The system was heated to 100° C. for reaction. After the reaction was complete, the system was added with water (50 mL), extracted with EA (40 mL) and separated. The aqueous phase was extracted with EA (40 mL*2). The combined organic phase was washed with water (100 mL*2) and saturated brine (30 mL), dired with anhydrous sodium sulfate and filtered with suction. The filtrate was concentrated under reduced pressure, and the residue was separated by PLC (mobile phase: A: purified water with 0.05% trifluoroacetic acid, B: acetonitrile with 0.05% trifluoroacetic acid) to obtain a crude, which was separated by medium pressure preparative chromatography and lyophilized to obtain 101.1 mg of the product.

ESI-MS Calculated for [M+H]⁺=502.27; Found: 502.00. The found value was consistent with the caculated value.

Step 2: Synthesis of N-(2-methoxyphenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate (LC158)

LC158-2 (101.1 mg, 0.20 mmol) was added into a reaction flask, added with trifluoroacetic acid/dichloromethane (1:10, 5 mL) and stirred at room temperature for reaction. After the reaction was complete, the system was concentrated under reduced pressure, and the residue was separated by medium-pressure preparative chromatography (mobile phase: A: purified water with 0.05% trifluoroacetic acid, B: acetonitrile with 0.05% trifluoroacetic acid) and lyophilized to obtain 42.1 mg of the product.

Product analysis: ¹HNMR (400 MHz, Methanol-d₄): δ 7.64 (s, 1H), 7.56 (d, J=2.8 Hz, 2H), 6.82 (dd, J=7.2, 2.0 Hz, 1H), 6.63-6.48 (m, 2H), 6.15 (s, 1H), 5.91 (dd, J=7.2, 2.1 Hz, 1H), 4.83-4.72 (m, 1H), 4.31 (dd, J=10.3, 6.8 Hz, 1H), 4.09 (m, 1H), 3.90 (s, 3H), 3.84 (s, 2H), 3.45 (t, J=6.1 Hz, 2H), 3.08-2.86 (m, 2H), 2.74 (s, 2H), 2.51 (d, J=2.6 Hz, 3H).

ESI-MS Calculated for [M+H]⁺=402.22; Found: 402.00. The found value was consistent with the caculated value.

Preparation Example 97, Final Product LC159: N-(3-methoxyphenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate

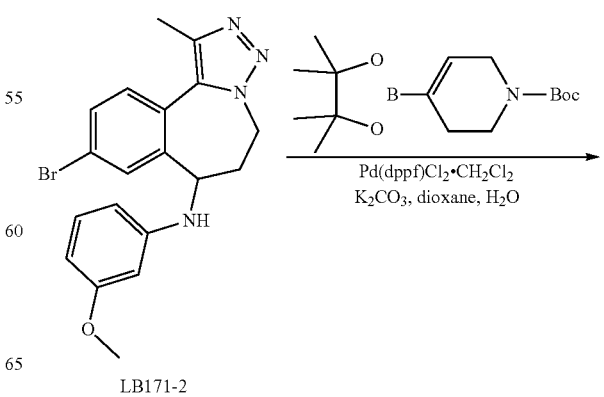

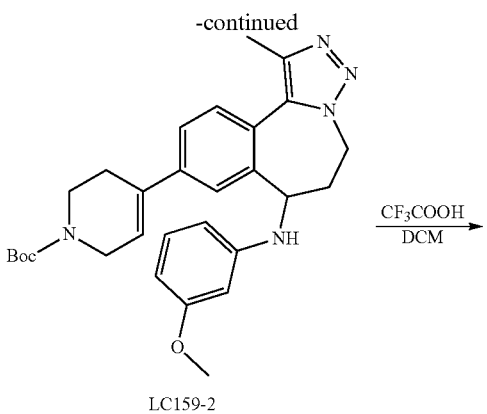

LC159-2

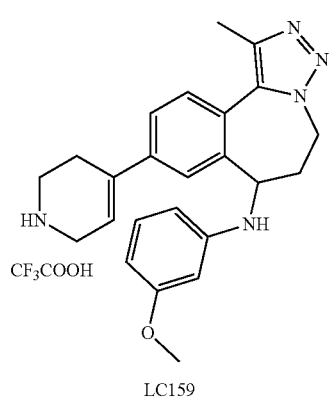

LC159

Step 1: Synthesis of tert-butyl 4-(7-((3-methoxyphenyl)amino)-1-methyl-6,7-dihydro-5H-benzo[c][1,2,3]triazolo[5-a]azepin-9-yl)-3,6-dihydropyridine-1(2H)-carboxylate (LC159-2)

LB171-2 (127.5 mg, 0.32 mmol), tert-butyl 4-(4,4,5,5-tetramethyl-1,3,2-dioxaboran-2-yl)-3,6-dihydropyridine-1(2H)-carboxylate (131.4 mg, 0.43 mmol), 1,4-dioxane (15 mL), water (0.75 mL) and potassium carbonate (69.5 mg, 0.51 mmol) were added to a reaction flask, and the air in the reaction system was replaced with nitrogen three times. The system was added with Pd(dppf)Cl₂-dichloromethane complex (14.7 mg, 0.018 mmol), and the air in the reaction system was replaced with nitrogen three times again. The system was heated to 100° C. for reaction. After the reaction was complete, the reaction system was added with water (50 mL) and EA (50 mL), shaken and separated. The aqueous phase was extracted with EA (50 mL*2). The combined organic phase was washed with water (100 mL*2) and saturated brine (50 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 80.3 mg of the product.

ESI-MS Calculated for [M+H]⁺=502.27; Found: 502.00. The found value was consistent with the caculated value.

Step 2: Synthesis of N-(3-methoxyphenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate (LC159)

LC159-2 (80.3 mg, 0.16 mmol) was added into a reaction flask, added with trifluoroacetic acid/dichloromethane (1:10, 5 mL) and stirred at room temperature for reaction. After the reaction was complete, the system was concentrated under reduced pressure, and the residue was separated by medium-pressure preparative chromatography (mobile phase: A: purified water with 0.05% trifluoroacetic acid, B: acetonitrile with 0.05% trifluoroacetic acid) and lyophilized to obtain 26.5 mg of the product.

Product analysis: ¹HNMR (400 MHz, Methanol-d₄): δ 7.69 (d, J=1.7 Hz, 1H), 7.63-7.52(m, 2H), 6.88 (t, J=8.1 Hz, 1H), 6.21-6.10 (m, 2H), 5.98-5.87 (m, 1H), 5.84 (t, J=2.3 Hz, 1H), 4.82 (t, J=7.5 Hz, 1H), 4.18 (dd, J=11.3, 6.8 Hz, 1H), 4.00 (m, 1H), 3.84 (m, 2H), 3.62(s, 3H), 3.45 (t, J=6.1 Hz, 2H), 3.34 (s, 2H), 2.96 (m, 1H), 2.52 (s, 3H), 2.31 (m, 1H).

ESI-MS Calculated for [M+H]⁺=402.22; Found: 402.00. The found value was consistent with the caculated value.

Preparation Example 98, Final Product LC160: N-(4-methoxyphenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate

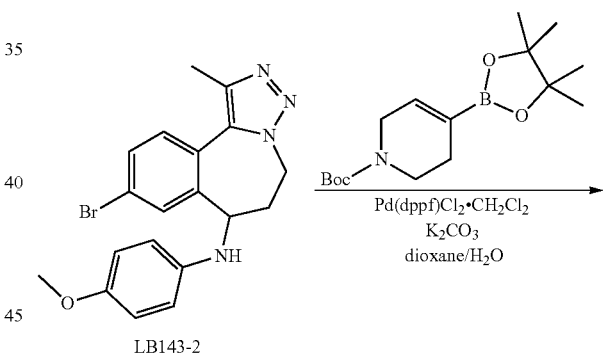

LB143-2

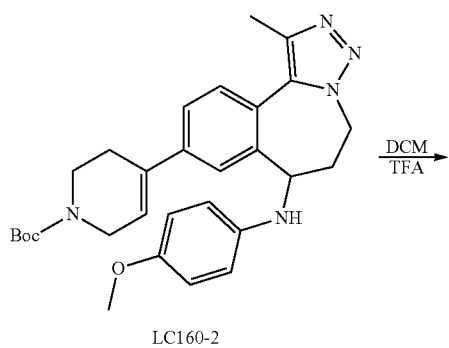

LC160-2

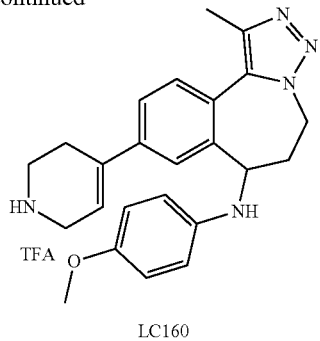

LC160

Step 1: Synthesis of tert-butyl 4-(7-((4-methoxyphenyl)amino)-1-methyl-6,7-dihydro-5H-benzo[c][1,2,3]triazolo[1,5-a]azepin-9-yl)-3,6-dihydropyridine-1(2H)-carboxylate (LC160-2)

LB143-2 (170.1 mg, 0.43 mmol), tert-butyl 4-(4,4,5,5-tetramethyl-1,3,2-dioxaboran-2-yl)-3,6-dihydropyridine-1(2H)-carboxylate (176.6 mg, 0.57 mmol), 1,4-dioxane (17 mL), water (0.85 mL) and potassium carbonate (93.9 mg, 0.68 mmol) were added to a reaction flask, and the air in the reaction system was replaced with nitrogen three times. The system was added with Pd(dppf)Cl$_2$-dichloromethane complex (19.7 mg, 0.024 mmol), and the air in the reaction system was replaced with nitrogen three times again. The system was heated to 100° C. for reaction. After the reaction was complete, the system was added with water (50 mL) and EA (50 mL), shaken and separated. The aqueous phase was extracted with EA (50 mL*2). The combined organic phase was washed with water (100 mL*2) and saturated brine (50 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 101.1 mg of the product.

ESI-MS Calculated for [M+H]$^+$=502.27; Found: 502.00. The found value was consistent with the caculated value.

Step 2: Synthesis of N-(4-methoxyphenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate (LC160)

LC160-2 (101.1 mg, 0.20 mmol) was added into a reaction flask, added with trifluoroacetic acid/dichloromethane (1:10, 5 mL) and stirred at room temperature for reaction. After the reaction was complete, the system was concentrated under reduced pressure, and the residue was separated by medium-pressure preparative chromatography and lyophilized to obtain 62.6 mg of the product.

Product analysis: $^1$HNMR (400 MHz, Methanol-d$_4$): δ 7.70 (s, 1H), 7.63-7.50 (m, 2H), 6.69-6.59 (m, 2H), 6.38-6.31 (m, 2H), 6.16 (d, J=4.0 Hz, 1H), 4.81 (dt, J=15.1, 6.7 Hz, 1H), 4.22 (dd, J=10.9, 6.9 Hz, 1H), 4.03 (m, 1H), 3.85 (d, J=3.7 Hz, 2H), 3.66 (s, 3H), 3.46 (m, 2H), 2.95 (m, 1H), 2.81-2.69 (m, 2H), 2.52 (s, 3H), 2.32 (m, 1H).

ESI-MS Calculated for [M+H]$^+$=402.22; Found: 402.00. The found value was consistent with the caculated value.

Preparation Example 99, Final Product LC174: N-(3-chlorophenyl)-N-(1-methyl-9-(1-methyl-1H-pyrazol-4-yl)-6,7-dihydro-5H-benzo[c][1,2,3]triazolo[1,5-a]azepin-7-yl)formamide

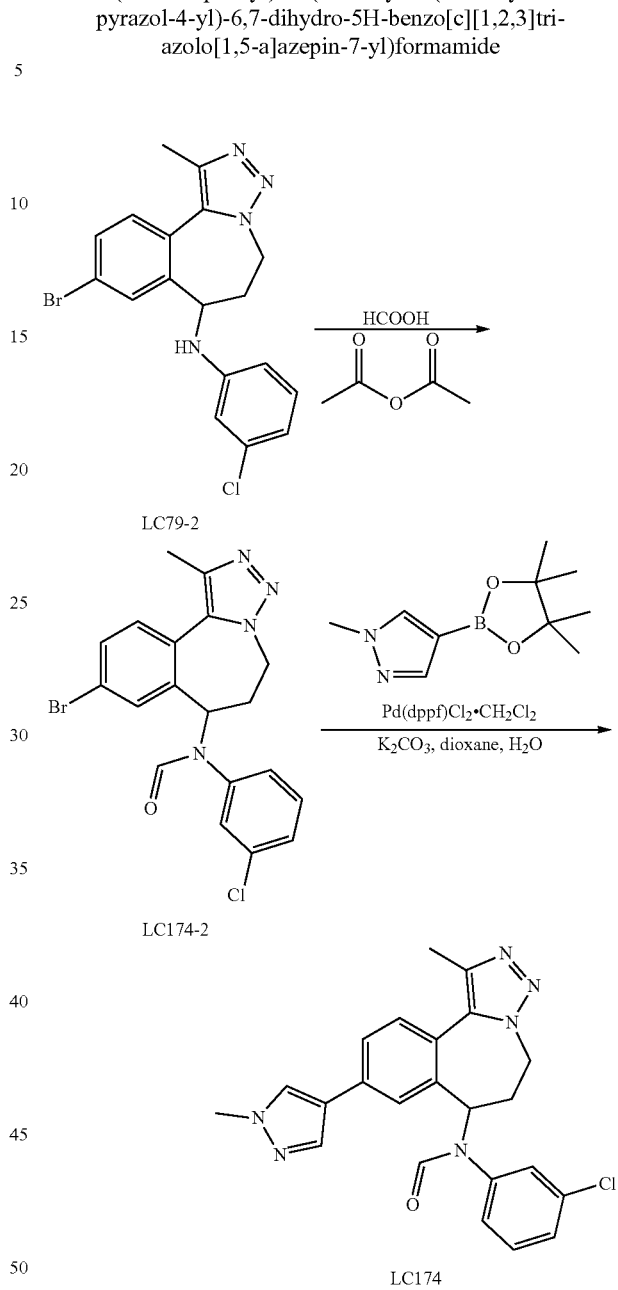

Step 1: Synthesis of N-(9-bromo-1-methyl-6,7-dihydro-5H-benzo[c][1,2,3]triazolo[1,5-a]azepin-7-yl)-N-(3-chlorophenyl)formamide (LC174-2)

LC79-2 (150.0 mg, 0.37 mmol) and formic acid (15 mL) were added to a reaction flask. Under nitrogen protection, the system was cooled to 0° C., added dropwise with acetic anhydride (4.5 mL) and kept at 0-10° C. After completion of the dropwise addition, the system was warmed to room temperature for reaction. After the reaction was complete, the system was added with water (50 mL), extracted with EA (50 mL) and seperated. The aqueous phase was extracted with EA (40 mL*3). The combined organic phase was washed with saturated sodium bicarbonate solution (50 mL*3), water (50 mL*2) and saturated brine (50 mL), dired over anhydrous sodium sulfate and filtered with suction. The filtrate was concentrated under reduced pressure, and the residue was separated by column chromatography to obtain 203.3 mg of the product.

Step 2: Synthesis of N-(3-chlorophenyl)-N-(1-methyl-9-(1-methyl-1H-pyrazol-4-yl)-6,7-dihydro-5H-benzo[c][1,2,3]triazolo[1,5-a]azepin-7-yl)formamide (LC174)

LC174-2 (80.0 mg, 0.19 mmol), 1-methyl-4-(4,4,5,5-tetramethyl-1,3,2-dioxaborolan-2-yl)-1H-pyrazole (53.4 mg, 0.26 mmol), 1,4-dioxane (10 mL), water (0.5 mL) and potassium carbonate (41.5 mg, 0.30 mmol) were added to a reaction flask, and the air in the reaction system was replaced with nitrogen three times. The system was added with Pd(dppf)Cl$_2$-dichloromethane complex (8.6 mg, 0.011 mmol), and the air in the reaction system was replaced with nitrogen three times again. The system was heated to reflux for reaction. After the reaction was complete, the reaction system was added with water (50 mL) and EA (50 mL), shaken and separated. The aqueous phase was extracted with EA (50 mL*3). The combined organic phase was washed with water (100 mL*2) and saturated brine (50 mL), dired with anhydrous sodium sulfate and filtered with suction. The filtrate was concentrated under reduced pressure, and the residue was separated by column chromatography to obtain 25.5 mg of the target compound.

Product analysis: $^1$HNMR (400 MHz, Methanol-d$_4$): δ 8.39 (s, 1H), 8.10 (s, 1H), 7.93 (s, 1H), 7.80 (s, 1H), 7.72 (d, J=7.9 Hz, 1H), 7.47 (d, J=8.1 Hz, 1H), 7.35 (d, J=2.8 Hz, 1H), 7.09-6.98 (m, 2H), 5.72 (m, 1H), 4.62-4.49 (m, 1H), 4.41 (m, 1H), 3.97 (s, 3H), 2.96-2.62 (m, 1H), 2.34 (s, 3H).

ESI-MS Calculated for [M+H]$^+$=433.15; Found: 432.90. The found value was consistent with the caculated value.

Preparation Example 100, Final Product LC185: N-(2-chloro-6-fluorophenyl)-1-methyl-9-(1-methyl-1H-pyrazol-4-yl)-6,7-dihydro-5H-benzo[c][1,2,3]triazolo[1,5-a]azepin-7-amine

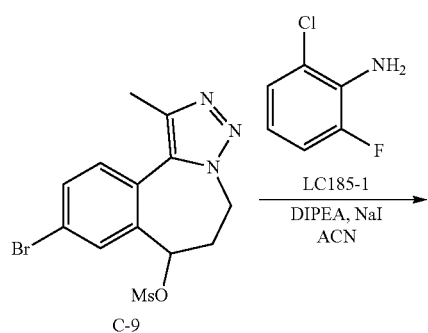

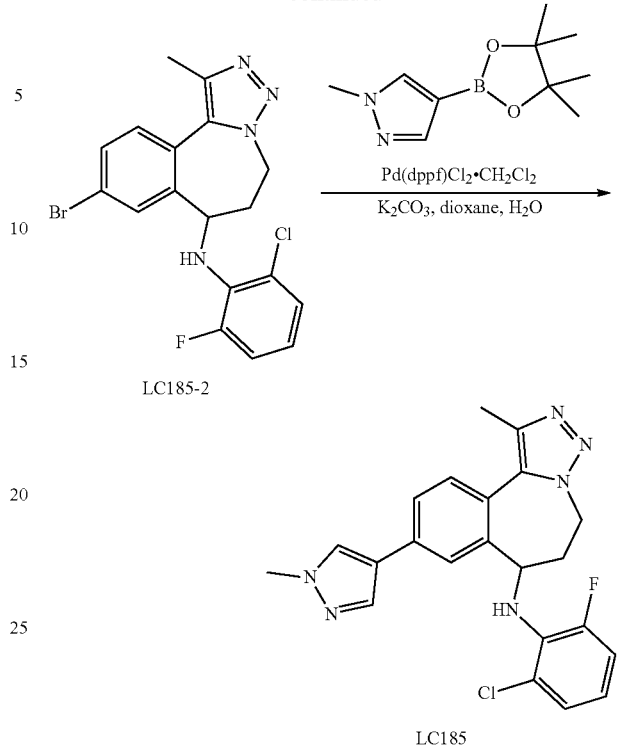

Step 1: Synthesis of 9-bromo-N-(2-chloro-6-fluorophenyl)-1-methyl-6,7-dihydro-5H-benzo[c][1,2,3]triazolo[1,5-a]azepin-7-amine (LC185-2)

C-9 (200.0 mg, 0.54 mmol), LC185-1 (236.6 mg, 1.63 mmol), acetonitrile (40 mL), DIPEA (348.9 mg, 2.70 mmol) and sodium iodide (52.5 mg, 0.19 mmol) were added to a reaction flask, and heated to react under reflux. After the reaction was complete, the reaction system was added with water (50 mL) and EA (50 mL), shaken and separated. The aqueous phase was extracted with EA (50 mL*2). The combined organic phase was washed with water (100 mL*2) and saturated brine (50 mL), dried over anhydrous magnesium sulfate and filtered with suction. The filtrate was concentrated under reduced pressure, and the residue was separated by PLC to obtain 52.1 mg of the target compound.

ESI-MS Calculated for [M+H]$^+$=423.02; Found: 423.00. The found value was consistent with the caculated value.

Step 2: Synthesis of N-(2-chloro-6-fluorophenyl)-1-methyl-9-(1-methyl-1H-pyrazol-4-yl)-6,7-dihydro-5H-benzo[c][1,2,3]triazolo[1,5-a]azepin-7-amine (LC185)

LC185-2 (52.1 mg, 0.12 mmol), 1-methyl-4-(4,4,5,5-tetramethyl-1,3,2-dioxaborolan-2-yl)-1H-pyrazole (33.2 mg, 0.16 mmol), potassium carbonate (26.2 mg, 0.19 mmol), 1,4-dioxane (5 mL) and water (0.25 mL) were added to a reaction flask, and the air in the reaction system was replaced with nitrogen three times. The system was added with Pd(dppf)Cl$_2$-dichloromethane complex (5.4 mg, 0.0066 mmol), and the air in the reaction system was replaced with nitrogen three times again. The system was heated to 100° C. for reaction. After the reaction was complete, the reaction system was added with water (50 mL)

and EA (50 mL), shaken and separated. The aqueous phase was extracted with EA (30 mL*3). The combined organic phase was washed with water (50 mL*3) and saturated brine (40 mL), dired with anhydrous sodium sulfate and filtered with suction. The filtrate was concentrated under reduced pressure, and the residue was separated by PLC to obtain a crude, which was separated by medium pressure preparative chromatography and lyophilized to obtain 12.2 mg of the product.

Product analysis: $^1$HNMR (400 MHz, Methanol-$d_4$): δ 7.96 (s, 1H), 7.80 (s, 1H), 7.72 (d, J=1.6 Hz, 1H), 7.62 (dd, J=7.9, 1.8 Hz, 1H), 7.46 (d, J=7.9 Hz, 1H), 7.12 (d, J=8.1 Hz, 1H), 6.84 (dd, J=12.9, 8.3 Hz, 1H), 6.69 (m, 1H), 4.82-4.86 (m,1H),4.66 (m, 1H), 4.18 (m, 1H), 3.95 (s, 3H), 2.98 (m, 1H), 2.48-2.56 (m,1H),2.46 (s, 3H).

ESI-MS Calculated for $[M+H]^+$=423.14; Found: 422.90. The found value was consistent with the caculated value.

Preparation Example 101, Final Product LC186:
N-(3-chlorophenyl)-1-methyl-9-(1-methyl-1H-pyrazol-4-yl)-6,7-dihydro-5H-benzo[c][1,2,3]triazolo[1,5-a]azepin-7-amine

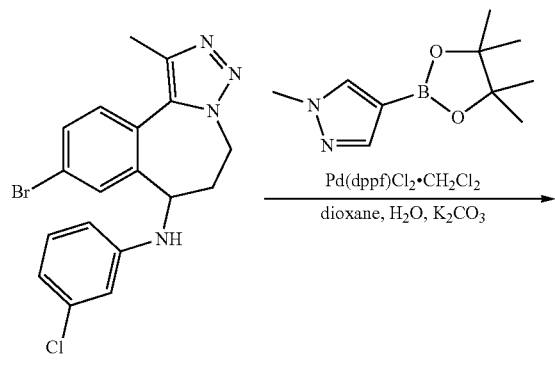

Synthesis of N-(3-chlorophenyl)-1-methyl-9-(1-methyl-1H-pyrazol-4-yl)-6,7-dihydro-5H-benzo[c][1,2,3]triazolo[1,5-a]azepin-7-amine (LC186)

LC79-2 (72.6 mg, 0.18 mmol), 1-methyl-4-(4,4,5,5-tetramethyl-1,3,2-dioxaborolan-2-yl)-1H-pyrazole (49.8 mg, 0.24 mmol), 1,4-dioxane (8 mL), water (0.4 mL) and potassium carbonate (39.4 mg, 0.28 mmol) were added into a reaction flask. The air in the reaction system was replaced with nitrogen three times, and Pd(dppf)Cl$_2$-dichloromethane complex (8.1 mg, 0.0099 mmol) was added. The air in the reaction system was replaced with nitrogen again three times, and the system was heated to react under reflux. After the reaction was complete, the system was added with water (50 mL) and EA (50 mL), shaken and separated. The aqueous phase was extracted with EA (50 mL*3). The combined organic phase was washed with water (100 mL*2) and saturated brine (50 mL), dried over anhydrous sodium sulfate and filtered under suction. The filtrate was concentrated under reduced pressure, and the residue was separated by rapid medium-pressure preparative chromatography to obtain 5.3 mg of the product.

Product analysis: $^1$HNMR (400 MHz, Methanol-$d_4$): δ 7.86 (s, 1H), 7.81 (s, 1H), 7.73 (s, 1H), 7.69 (d, J=1.7 Hz, 1H), 7.64-7.59 (m, 1H), 7.49 (d, J=7.8 Hz, 1H), 6.94 (m, 1H), 6.52 (d, J=7.9 Hz, 1H), 6.38 (s, 1H), 6.20-6.15 (m, 1H), 4.78 (d, J=10.2 Hz, 1H), 4.21 (dd, J=11.1, 6.8 Hz, 1H), 4.03 (m, 1H), 3.92 (s, 3H), 2.97 (m, 1H), 2.52 (s, 3H), 2.39-2.25 (m, 1H).

ESI-MS Calculated for $[M+H]^+$=405.15; Found: 405.00. The calculated value was consistent with the found value.

Preparation Example 102, Final Product LC190:
N-(3-chloro-2-fluorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate

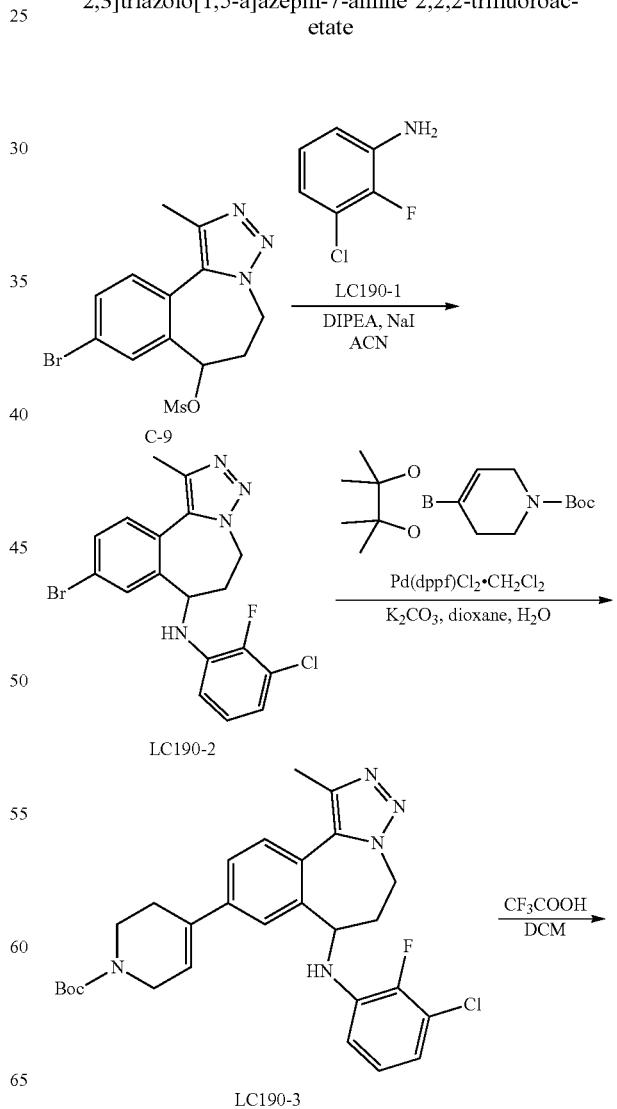

-continued

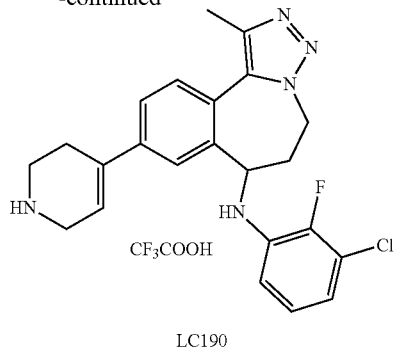

LC190

Step 1: Synthesis of 9-bromo-N-(3-chloro-2-fluorophenyl)-1-methyl-6,7-dihydro-5H-benzo[c][1,2,3]triazolo[1,5-a]azepin-7-amine (LC190-2)

C-9 (200.0 mg, 0.54 mmol), LC190-1 (158.9 mg, 1.09 mmol), acetonitrile (40 mL), DIPEA (353.9 mg, 2.74 mmol) and sodium iodide (25.9 mg, 0.17 mmol) were added into a reaction flask, and heated to react under reflux. After the reaction was complete, the system was concentrated under reduced pressure, and the residue was added with water (50 mL) and EA (50 mL), shaken and separated. The aqueous phase was extracted with EA (50 mL*2). The combined organic phase was washed with water (50 mL*2) and saturated brine (50 mL), dried over anhydrous magnesium sulfate and filtered under suction. The filtrate was concentrated under reduced pressure, and the residue was separated by PLC to obtain 143.1 mg of the target compound.

ESI-MS Calculated for [M+H]$^+$=423.02; Found: 422.80. The calculated value was consistent with the found value.

Step 2: Synthesis of tert-butyl 4-(7-((3-chloro-2-fluorophenyl)amino)-1-methyl-6,7-dihydro-5H-benzo[c][1,2,3]triazolo[1,5-a]azepin-9-yl)-3,6-dihydropyridine-1 (2H)-carboxylate (LC190-3)

LC190-2 (143.1 mg, 0.34 mmol), tert-butyl 4-(4,4,5,5-tetramethyl-1,3,2-dioxaborolan-2-yl)-3,6-dihydropyridine-1 (2H)-carboxylate (139.6 mg, 0.45 mmol), 1,4-dioxane (15 mL), water (0.75 mL) and potassium carbonate (74.7 mg, 0.54 mmol) were added into a reaction flask, and the air in the reaction system was replaced with nitrogen three times. The system was added with Pd(dppf)Cl$_2$-dichloromethane complex (15.6 mg, 0.019 mmol), and the air in the reaction system was replaced with nitrogen again three times. The system was heated to 100° C. for reaction. After the reaction was complete, the reaction system was added with water (50 mL) and EA (50 mL), shaken and separated. The aqueous phase was extracted with EA (30 mL*2). The combined organic phase was washed with water (50 mL*3) and saturated brine (50 mL), dried over anhydrous sodium sulfate and filtered under suction. The filtrate was concentrated under reduced pressure, and the residue was separated by PLC to obtain a crude, which was separated by medium-pressure preparative chromatography and lyophilized to obtain 48.8 mg of the product.

ESI-MS Calculated for [M+H]$^+$=524.22; Found: 524.00. The calculated value was consistent with the found value.

Step 3: Synthesis of N-(3-chloro-2-fluorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate (LC190)

LC190-3 (48.8 mg, 0.093 mmol) was added into a reaction flask, added with trifluoroacetic acid/dichloromethane (1:10, 5 mL) and stirred at room temperature for reaction. After the reaction was complete, the system was concentrated under reduced pressure, and the residue was separated by medium-pressure preparative chromatography (mobile phase: A: purified water with 0.05% trifluoroacetic acid; B: acetonitrile with 0.05% trifluoroacetic acid) and lyophilized to obtain 28.1 mg of the product.

Product analysis: $^1$HNMR (400 MHz, Methanol-d$_4$): δ 7.67-7.53 (m, 3H), 6.70 (m, 1H), 6.61 (m, 1H), 6.16 (s, 1H), 5.92 (m, 1H), 4.82 (d, J=7.6 Hz, 1H), 4.33 (dd, J=10.8, 6.7 Hz, 1H), 4.03 (m, 1H), 3.85 (d, J=3.0 Hz, 2H), 3.46 (m, 2H), 3.10-2.89 (m, 1H), 2.75 (s, 2H), 2.52 (s, 3H), 2.50-2.42 (m, 1H).

ESI-MS Calculated for [M+H]$^+$=424.16; Found: 424.10. The calculated value was consistent with the found value.

Preparation Example 103, Final Product LC191: N-(2-chlorophenyl)-1-methyl-9-(1-methyl-1H-pyrazol-4-yl)-6,7-dihydro-5H-benzo[c][1,2,3]triazolo[1,5-a]azepin-7-amine

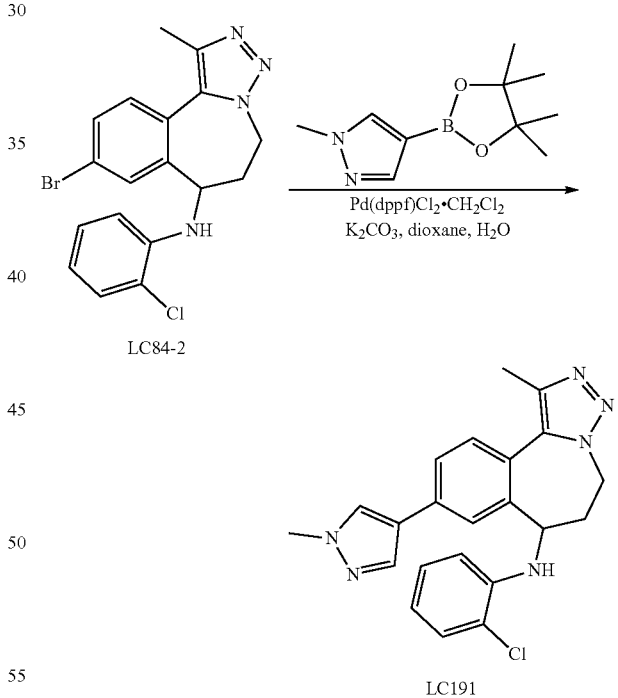

Synthesis of N-(2-chlorophenyl)-1-methyl-9-(1-methyl-1H-pyrazol-4-yl)-6,7-dihydro-5H-benzo[c][1,2,3]triazolo[1,5-a]azepin-7-amine (LC191)

LC84-2 (45.1 mg, 0.11 mmol), 1-methyl-4-(4,4,5,5-tetramethyl-1,3,2-dioxaborolan-2-yl)-1H-pyrazole (30.9 mg, 0.15 mmol), potassium carbonate (24.1 mg, 0.18 mmol), 1,4-dioxane (5 mL) and water (0.25 mL) were added into a reaction flask, and the air in the reaction system was replaced with nitrogen three times. The system was added with Pd(dppf)Cl$_2$-dichloromethane complex (5.0 mg, 0.0061 mmol), and the air in the reaction system was replaced with nitrogen again three times. The system was heated to react under reflux. After the reaction was complete, the system was added with water (50 mL) and EA (50 mL), shaken and separated. The aqueous phase was extracted with EA (50 mL*3). The combined organic phase was washed with water (50 mL*2) and saturated brine (50 mL), dried over anhydrous sodium sulfate and filtered under suction. The filtrate was concentrated under reduced pressure, and the residue was separated by medium-pressure preparative chromatography to obtain 15.5 mg of the target compound.

Product analysis: $^1$HNMR (400 MHz, Methanol-d$_4$): δ 7.93 (s, 1H), 7.76 (s, 1H), 7.65 (d, J=12.0 Hz, 2H), 7.52 (d, J=7.8 Hz, 1H), 7.24 (d, J=7.9 Hz, 1H), 6.91 (t, J=7.8 Hz, 1H), 6.57 (m, 1H), 6.16 (d, J=8.2 Hz, 1H), 4.73 (dd, J=15.6, 7.5 Hz, 1H), 4.47 (d, J=8.5 Hz, 1H), 4.24-4.09 (m, 1H), 3.92 (s, 3H), 3.00 (m, 1H), 2.50-2.67(m,1H), 2.50 (s, 3H).

ESI-MS Calculated for [M+H]$^+$=405.15; Found: 404.90. The calculated value was consistent with the found value.

Preparation Example 104, Final Product LC192: N-(3-chloro-4-fluorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate

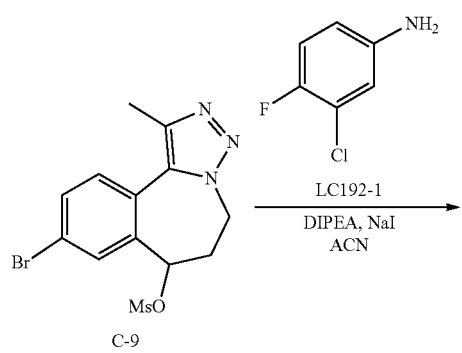

Step 1: Synthesis of 9-bromo-N-(3-chloro-4-fluorophenyl)-1-methyl-6,7-dihydro-5H-benzo[c][1,2,3]triazolo[1,5-a]azepin-7-amine (LC192-2)

C-9 (200.1 mg, 0.54 mmol), LC192-1 (158.9 mg, 1.09 mmol), acetonitrile (40 mL), DIPEA (353.9 mg, 2.74 mmol) and sodium iodide (25.9 mg, 0.17 mmol) were added into a reaction flask, and heated to react under reflux. After the reaction was complete, the system was concentrated under reduced pressure, added with water (50 mL) and EA (50 mL), shaken and separated. The aqueous phase was extracted with EA (50 mL*2). The combined organic phase was washed with water (50 mL*2) and saturated brine (50 mL), dried over anhydrous magnesium sulfate and filtered under suction. The filtrate was concentrated under reduced pressure, and the residue was separated by PLC to obtain 157.1 mg of the target compound.

ESI-MS Calculated for [M+H]$^+$=423.02; Found: 422.80. The calculated value was consistent with the found value.

Step 2: Synthesis of tert-butyl 4-(74(3-chloro-4-fluorophenyl)amino)-1-methyl-6,7-dihydro-5H-benzo[c][1,2,3]triazolo[1,5-a]azepin-9-yl)-3,6-dihydropyridine-1 (2H)-carboxylate (LC192-3)

LC192-2 (157.1 mg, 0.37 mmol), tert-butyl 4-(4,4,5,5-tetramethyl-1,3,2-dioxaborolan-2-yl)-3,6-dihydropyridine-1 (2H)-carboxylate (153.2 mg, 0.50 mmol), 1,4-dioxane (15 mL), water (0.75 mL) and potassium carbonate (80.3 mg, 0.58 mmol) were added into a reaction flask, and the air in the reaction system was replaced with nitrogen three times. The system was added with Pd(dppf)Cl$_2$-dichloromethane complex (16.7 mg, 0.020 mmol), and the air in the reaction system was replaced with nitrogen again three times. The system was heated to 100° C. for reaction. After the reaction was complete, the reaction system was added with water (50 mL) and EA (50 mL), shaken and separated. The aqueous phase was extracted with EA (30 mL*2). The combined organic phase was washed with water (100 mL*2) and saturated brine (50 mL), dried over anhydrous sodium sulfate and filtered under suction. The filtrate was concentrated under reduced pressure, and the residue was separated by PLC to obtain 124.1 mg of a crude.

ESI-MS Calculated for [M+H]$^+$=524.22; Found: 524.00. The calculated value was consistent with the found value.

Step 3: Synthesis of N-(3-chloro-4-fluorophenyl)-1-methyl-9-(1,2,3,6-tetrahydropyridin-4-yl)-6,7-dihydro-5H-benzo[c][1,2,3]triazolo[1,5-a]azepin-7-amine (LC192)

LC190-3 (56.6 mg, 0.11 mmol) was added into a reaction flask, added with trifluoroacetic acid/dichloromethane (1:10, 5 mL) and stirred at room temperature for reaction. After the reaction was complete, the system was concentrated under reduced pressure, and the residue was separated by medium-pressure preparative chromatography (mobile phase: A: purified water with 0.05% trifluoroacetic acid, B: acetonitrile with 0.05% trifluoroacetic acid) and lyophilized to obtain 48.8 mg of the product.

Product analysis: $^1$HNMR (400 MHz, Methanol-d$_4$): δ 7.74-7.50 (m, 3H), 6.85 (m, 1H), 6.37 (dd, J=6.2, 2.9 Hz, 1H), 6.21-6.09 (m, 2H), 4.83-4.72 (m, 1H), 4.17 (dd, J=11.1, 6.8 Hz, 1H), 4.09-3.90 (m, 1H), 3.85 (m, 2H), 3.46 (m, 2H), 3.09-2.84 (m, 1H), 2.84-2.69 (m, 2H), 2.52 (s, 3H), 2.31 (m, 1H).

ESI-MS Calculated for [M+H]$^+$=424.16; Found: 424.00. The calculated value was consistent with the found value.

Preparation Example 105, Final Product LC193: N-(3-chlorophenyl)-N-(1-methyl-9-(1,2,3,6-tetrahydropyridin-4-yl)-6,7-dihydro-5H-benzo[c][1,2,3]triazolo[1,5-a]azepin-7-yl)form amide 2,2,2-trifluoroacetate

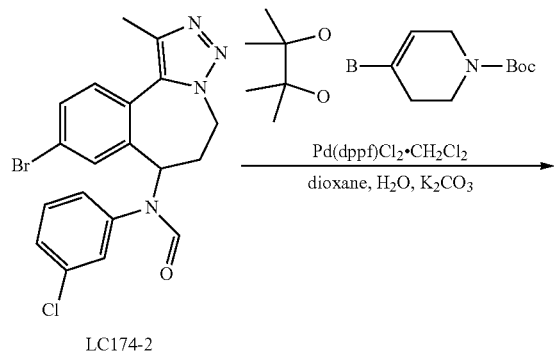

LC174-2

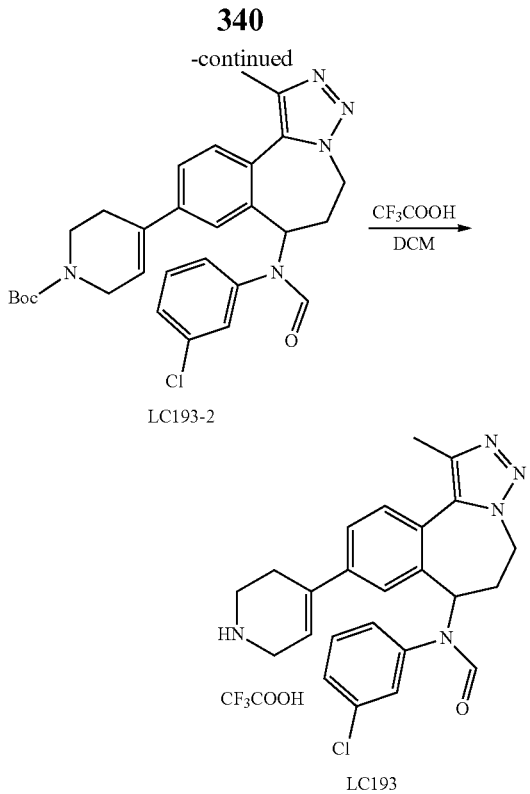

Step 1: Synthesis of tert-butyl 4-(7-(N-(3-chlorophenyl)formamido)-1-methyl-6,7-dihydro-5H-benzo[c][1,2,3]triazolo[1,5-a]azepin-9-yl)-3,6-dihydropyridine-1(2H)-carboxylate (LC193-2)

LC174-2 (100.0 mg, 0.23 mmol), tert-butyl 4-(4,4,5,5-tetramethyl-1,3,2-dioxaborolan-2-yl)-3,6-dihydropyridine-1(2H)-carboxylate (94.6 mg, 0.31 mmol), 1,4-dioxane (10 mL), water (0.5 mL) and potassium carbonate (49.9 mg, 0.36 mmol) were added into a reaction flask, and the air in the reaction system was replaced with nitrogen for three times. The system was added with Pd(dppf)Cl$_2$-dichloromethane complex (10.4 mg, 0.013 mmol), and the air in the reaction system was replaced with nitrogen again three times. The system was heated to 100° C. for reaction. After the reaction was complete, the reaction system was added with water (50 mL) and EA (50 mL), shaken and separated. The aqueous phase was extracted with EA (30 mL*2). The combined organic phase was washed with water (100 mL*2) and saturated brine (50 mL), dried over anhydrous sodium sulfate and filtered under suction. The filtrate was concentrated under reduced pressure, and the residue was separated by PLC to obtain 64.4 mg of a crude.

ESI-MS Calculated for [M+H]$^+$=534.22; Found: 534.00. The calculated value was consistent with the found value.

Step 2: N-(3-chlorophenyl)-N-(1-methyl-9-(1,2,3,6-tetrahydropyridin-4-yl)-6,7-dihydro-5H-benzo[c][1,2,3]triazolo[1,5-a]azepin-7-yl)formamide 2,2,2-trifluoroacetate (LC193)

LC193-2 (64.4 mg, 0.12 mmol) was added into a reaction flask, added with trifluoroacetic acid/dichloromethane (1:10, 5 mL) and stirred at room temperature. After the reaction was complete, the system was concentrated under reduced pressure, and the residue was separated by medium-pressure preparative chromatography (mobile phase: A: purified water with 0.05% trifluoroacetic acid, B: acetonitrile with 0.05% trifluoroacetic acid) and lyophilized to obtain 31.6 mg of the product.

Product analysis: ¹HNMR (400 MHz, Methanol-$d_4$): δ 8.40 (s, 1H), 7.72 (s, 1H), 7.70-7.62 (m, 1H), 7.53 (d, J=8.0 Hz, 1H), 7.41-7.32 (m, 2H), 7.10-6.97 (m, 2H), 6.32 (s, 1H), 5.67 (m, 1H), 4.65-4.51 (m, 1H), 4.38 (m, 1H), 3.92 (d, J=3.3 Hz, 2H), 3.53 (m 2H), 2.98-2.70 (m, 5H), 2.35 (s, 3H).

ESI-MS Calculated for [M+H]⁺=434.17; Found: 434.00. The calculated value was consistent with the found value.

Preparation Example 106, Final Product LC198: N-(2-chloro-6-fluorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate

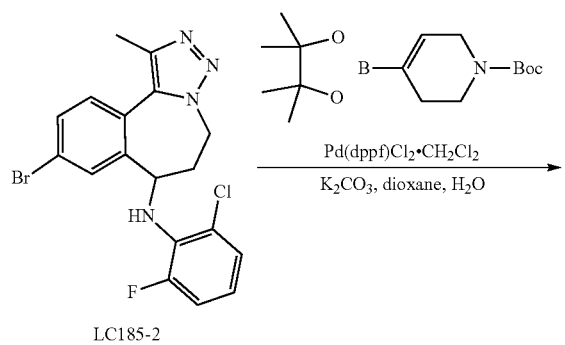

LC185-2

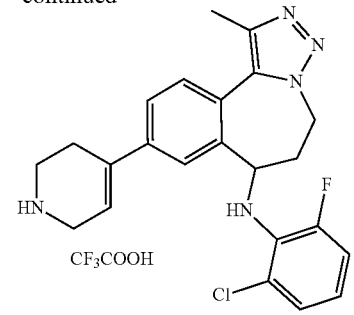

LC198

Step 1: Synthesis of tert-butyl 4-(7-((2-chloro-6-fluorophenyl)amino)-1-methyl-6,7-dihydro-5H-benzo[c][1,2,3]triazolo[1,5-a]azepin-9-yl)-3,6-dihydropyridine-1(2H)-carboxylate (LC198-3)

LC185-2 (34.7 mg, 0.083 mmol), tert-butyl 4-(4,4,5,5-tetramethyl-1,3,2-dioxaborolan-2-yl)-3,6-dihydropyridine-1(2H)-carboxylate (34.2 mg, 0.11 mmol), 1,4-dioxane (5 mL), water (0.25 mL) and potassium carbonate (18.1 mg, 0.13 mmol) were added into a reaction flask, and the air in the reaction system was replaced with nitrogen three times. The system was added with Pd(dppf)Cl₂-dichloromethane complex (3.8 mg, 0.0046 mmol), and the air in the reaction system was replaced with nitrogen again three times. The system was heated to 100° C. for reaction. After the reaction was complete, the system was added with water (30 mL) and EA (30 mL), and shaken and separated. The aqueous phase was extracted with EA (30 mL*2). The combined organic phase was washed with water (30 mL*2) and saturated brine (50 mL), dried over anhydrous sodium sulfate and filtered under suction. The filtrate was concentrated under reduced pressure, and the residue was separated by PLC to obtain 20.0 mg of the crude product.

ESI-MS Calculated for [M+H]⁺=524.22; Found: 523.90. The calculated value was consistent with the found value.

Step 2: Synthesis of N-(2-chloro-6-fluorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate (LC198)

LC198-3 (20.0 mg, 0.039 mmol) was added into a reaction flask, added with trifluoroacetic acid/dichloromethane (1:10, 5 mL) and stirred at room temperature for reaction. After the reaction was complete, the system was concentrated under reduced pressure, and the residue was sepeated under medium-pressure chromatography (mobile phase: A: purified water with 0.05% trifluoroacetic acid, B: acetonitrile with 0.05% trifluoroacetic acid) and lyophilized to obtain 10.8 mg of the product.

Product analysis: ¹HNMR (400 MHz, DMSO-$d_6$): δ 6.74 (d, J=1.8 Hz, 1H), 6.65 (dd, J=8.0, 1.9 Hz, 1H), 6.59 (d, J=8.0 Hz, 1H), 6.18 (m, 1H), 5.90 (m, 1H), 5.76 (m, 1H), 5.33-5.25 (m, 1H), 3.90 (s, 1H), 3.75 (m, 1H), 3.23 (m, 1H), 2.96 (d, J=3.2 Hz, 2H), 2.57 (m, 2H), 2.17-1.73 (m, 2H), 151-1.54(m, 1H),1.53 (s, 3H).

ESI-MS Calculated for [M+H]⁺=434.17; Found: 434.00. The calculated value was consistent with the found value.

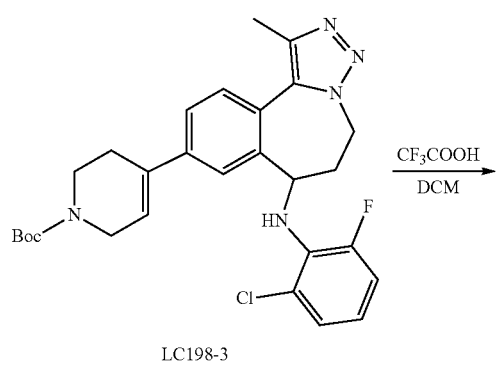

LC198-3

Preparation Example 107, Final Product LD07: N-(3-chlorophenyl)-1-methyl-9-(1-methyl-1,2,3,6-tetrahydropyridin-4-yl)-6,7-dihydro-5H-benzo[c][1,2,3]triazolo[1,5-a]azepin-7-amine 2,2,2-trifluoroacetate

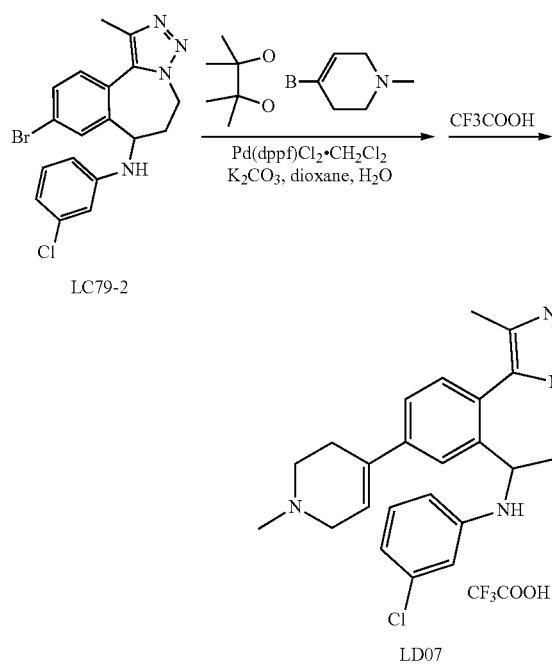

Synthesis of N-(3-chlorophenyl)-1-methyl-9-(1-methyl-1,2,3,6-tetrahydropyridin-4-yl)-6,7-dihydro-5H-benzo[c][1,2,3]triazolo[1,5-a]azepin-7-amine 2,2,2-trifluoroacetate (LD07)

LC79-2 (100.0 mg, 0.25 mmol), 1-methyl-4-(4,4,5,5-tetramethyl-1,3,2-dioxaborolan-2-yl)-1,2,3,6-tetrahydropyridine (74.2 mg, 0.33 mmol), 1,4-dioxane (10 mL), water (0.5 mL) and potassium carbonate (54.6 mg, 0.40 mmol) were added into a reaction flask, and the air in the reaction system was replaced with nitrogen three times. The system was added with Pd(dppf)Cl$_2$-dichloromethane complex (11.3 mg, 0.0014 mmol), and the air in the reaction system was replaced with nitrogen again three times. The system was heated to 100° C. for reaction. The system was added with water (50 mL) and EA (50 mL), and shaken and separated. The aqueous phase was extracted with EA (50 mL*2). The combined organic phase was washed with water (50 mL*2) and saturated brine (50 mL), dried over anhydrous sodium sulfate and filtered under suction. The filtrate was concentrated under reduced pressure, and the residue was separated by medium-pressure preparative chromatography (mobile phase: A: purified water with 0.05% trifluoroacetic acid, B: acetonitrile with 0.05% trifluoroacetic acid) and lyophilized to obtain 26.1 mg of the product.

Product analysis: $^1$HNMR (400 MHz, Methanol-d$_4$): δ 7.68-7.57 (m, 3H), 6.93 (m,1H), 6.52 (dd, J=8.0, 1.9 Hz, 1H), 6.32 (m, 1H), 6.15 (dd, J=8.2, 2.4 Hz, 2H), 4.84-4.77 (m, 1H), 4.20 (dd, J=11.2, 6.8 Hz, 1H), 4.01 (m, 2H), 3.88-3.63 (m, 2H), 2.99 (s, 4H), 2.83 (s, 2H), 2.52 (s, 4H), 2.32 (m, 1H).

ESI-MS Calculated for [M+H]$^+$=420.19; Found: 419.80. The calculated value was consistent with the found value.

Preparation Example 108, Final Product LD08: N-(5-chloro-2-fluorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate

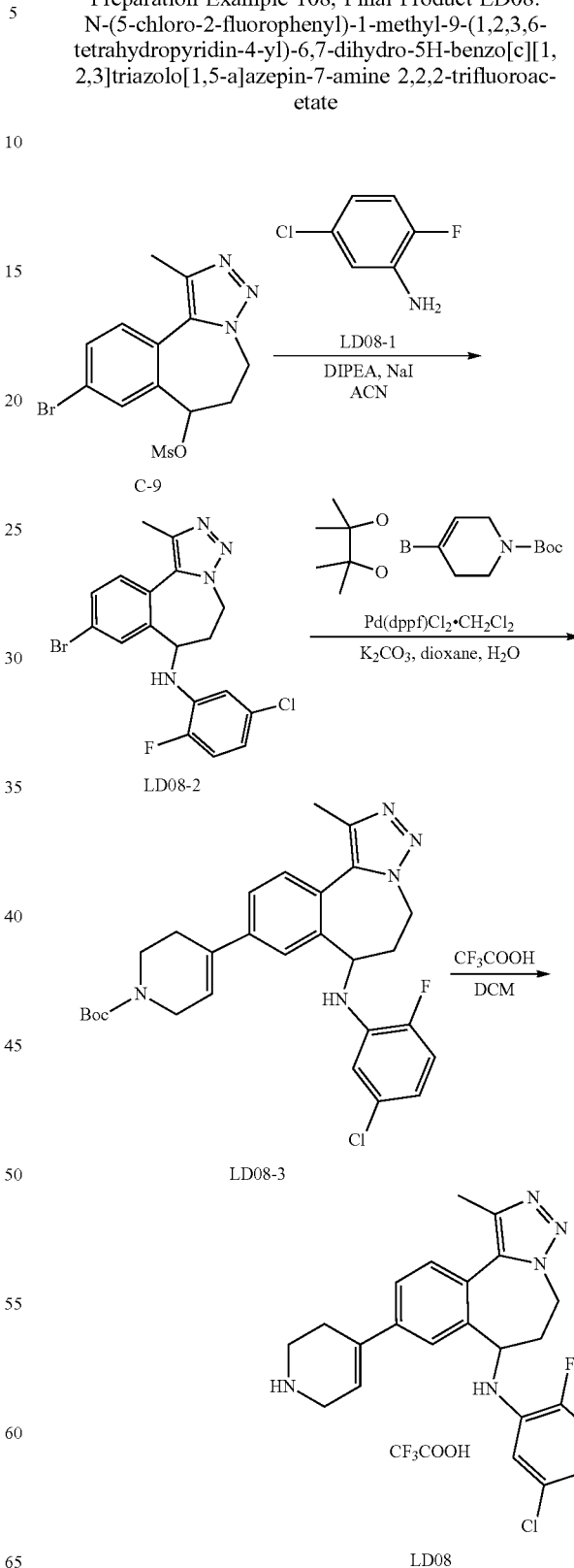

Step 1: Synthesis of 9-bromo-N-(5-chloro-2-fluorophenyl)-1-methyl-6,7-dihydro-5H-benzo[c][1,2,3]triazolo[1,5-a]azepin-7-amine (LD08-2)

C-9 (300.0 mg, 0.81 mmol), LD08-1 (351.9 mg, 2.42 mmol), acetonitrile (40 mL), DIPEA (523.5 mg, 4.05 mmol) and sodium iodide (46.1 mg, 0.29 mmol) were added into a reaction flask, and reacted in a bath at 90° C. After the reaction was complete, the system was concentrated under reduced pressure, added with water (50 mL) and EA (50 mL), shaken and separated. The aqueous phase was extracted with EA (50 mL*2). The combined organic phase was washed with water (100 mL*2) and saturated brine (50 mL), dried over anhydrous magnesium sulfate and filtered under suction. The filtrate was concentrated under reduced pressure, and the residue was separated by column chromatography to obtain 170.5 mg of the target compound.

ESI-MS Calculated for [M+H]$^+$=421.02; Found: 420.80. The calculated value was consistent with the found value.

Step 2: Synthesis of tert-butyl 4-(7-((5-chloro-2-fluorophenyl)amino)-1-methyl-6,7-dihydro-5H-benzo[c][1,2,3]triazolo[1,5-a]azepin-9-yl)-3,6-dihydropyridine-1 (2H)-carboxylate (LD08-3)

LD08-2 (100.4 mg, 0.24 mmol), tert-butyl 4-(4,4,5,5-tetramethyl-1,3,2-dioxaborolan-2-yl)-3,6-dihydropyridine-1 (2H)-carboxylate (99.0 mg, 0.32 mmol), 1,4-dioxane (10 mL), water (0.5 mL) and potassium carbonate (52.1 mg, 0.38 mmol) were added into a reaction flask, and the air in the reaction system was replaced with nitrogen three times. The system was added with Pd(dppf)Cl$_2$-dichloromethane complex (10.8 mg, 0.014 mmol), and the air in the reaction system was replaced with nitrogen again three times. The system was heated to 100° C. for reaction. After the reaction was complete, the reaction system was added with water (50 mL) and EA (50 mL), shaken and separated. The aqueous phase was extracted with EA (30 mL*2). The combined organic phase was washed with water (100 mL*2) and saturated brine (50 mL), dried over anhydrous sodium sulfate and filtered under suction. The filtrate was concentrated under reduced pressure, and the residue was separated by PLC to obtain 20.3 mg of the crude product.

ESI-MS Calculated for [M+H]$^+$=524.22; Found: 524.00. The calculated value was consistent with the found value.

Step 3: Synthesis of N-(5-chloro-2-fluorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate (LD08)

LD08-3 (20.0 mg, 0.038 mmol) was added into a reaction flask, added with trifluoroacetic acid/dichloromethane (1:10, 5 mL) and stirred at room temperature for reaction. After the reaction was complete, the system was concentrated under reduced pressure, and the residue was separated by medium-pressure preparative chromatography (mobile phase: A: purified water with 0.05% trifluoroacetic acid, B: acetonitrile with 0.05% trifluoroacetic acid) and lyophilized to obtain 10.1 mg of the product.

Product analysis: $^1$HNMR(CDCl$_3$, 400 MHz): $^1$H NMR (400 MHz, Methanol-d$_4$) δ 7.64-7.40 (m, 3H), 6.82 (dd, J=11.5, 8.5 Hz, 1H), 6.39 (m, 1H), 6.08 (s, 1H), 5.82 (dd, J=7.6, 2.5 Hz, 1H), 4.74-4.59 (m, 1H), 4.18 (dd, J=10.7, 6.8 Hz, 1H), 3.93 (m, 1H), 3.74 (d, J=3.5 Hz, 2H), 3.35 (m, 2H), 2.85 (m, 1H), 2.66 (s, 2H), 2.40 (s, 3H), 2.38-2.40 (m, 1H).

ESI-MS Calculated for [M+H]$^+$=424.16; Found: 424.00. The calculated value was consistent with the found value.

Preparation Example 109, Final Product LD13: N-(9-(1-acetyl-1,2,3,6-tetrahydropyridin-4-yl)-1-methyl-6,7-dihydro-5H-benzo[c][1,2,3]triazolo azepin-7-yl)-N-(4-chlorophenyl) acetamide

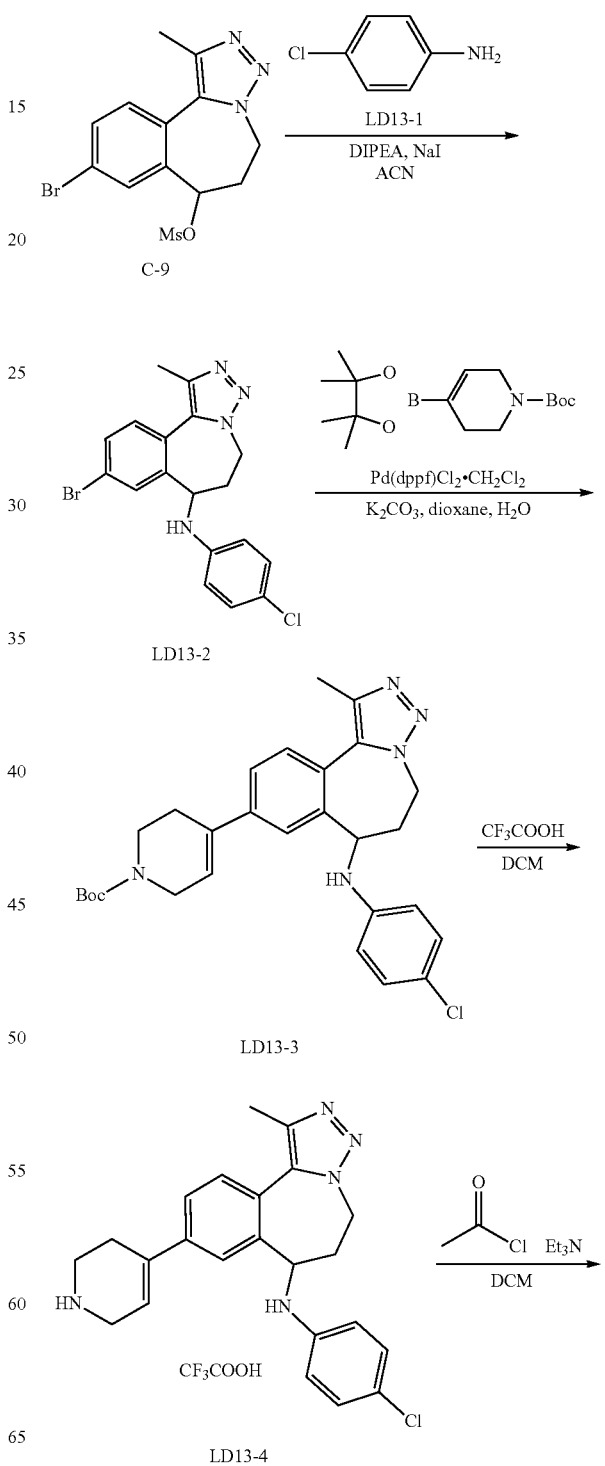

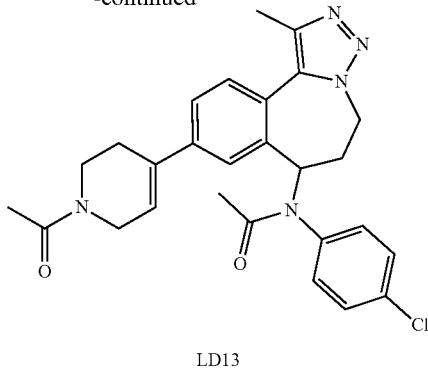

LD13

Step 1: Synthesis of 9-bromo-N-(4-chlorophenyl)-1-methyl-6,7-dihydro-5H-benzo[c][1,2,3]triazolo[1,5-a]azepin-7-amine (LD13-2)

C-9 (1.00 g, 2.69 mmol), LD13-1 (1.03 g, 8.07 mmol), acetonitrile (100 mL), DIPEA (1.74 g, 13.45 mmol) and sodium iodide (121.1 mg, 0.81 mmol) were added into a reaction flask, and heated to 90° C. for reaction. The system was concentrated under reduced pressure, added with water (100 mL) and EA (50 mL), shaken and separated. The aqueous phase was extracted with EA (50 mL*2). The combined organic phase was washed with water (100 mL*2) and saturated brine (50 mL), dried over anhydrous magnesium sulfate and filtered under suction. The filtrate was concentrated under reduced pressure, and the residue was separated by PLC to obtain 678.3 mg of the target compound.

ESI-MS Calculated for [M+H]$^+$=403.02; Found: 403.00. The calculated value was consistent with the found value.

Step 2: Synthesis of tert-butyl 4-(74(4-chlorophenyflamino)-1-methyl-6,7-dihydro-5H-benzo[c][1,2,3]triazolo[1,5-a]azepin-9-yl)-3,6-dihydropyridine-1(2H)-carboxylate (LD13-3)

LD13-2 (1.11 g, 2.73 mmol), tert-butyl 4-(4,4,5,5-tetramethyl-1,3,2-dioxaborolan-2-yl)-3,6-dihydropyridine-1(2H)-carboxylate (1.13 g, 3.63 mmol), 1,4-dioxane (100 mL), water (5 mL) and potassium carbonate (596.2 mg, 4.31 mmol) were added into a reaction flask, and the air in the reaction system was replaced with nitrogen three times. The system was added with Pd(dppf)Cl$_2$-dichloromethane complex (122.7 mg, 0.15 mmol), and the air in the reaction system was replaced with nitrogen again three times. The system was was heated to 100° C. for reaction. After the reaction was complete, the system was added with water (100 mL) and EA (50 mL), shaken and separated. The aqueous phase was extracted with EA (50 mL*2). The combined organic phase was washed with water (100 mL*2) and saturated brine (50 mL), dried over anhydrous sodium sulfate and filtered under suction. The filtrate was concentrated under reduced pressure, and the residue was separated by column chromatography to obtain 786.6 mg of a crude.

ESI-MS Calculated for [M+H]$^+$=506.22; Found: 506.00. The calculated value was consistent with the found value.

Step 3: Synthesis of N-(4-chlorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate (LD13-4)

LD13-3 (250.1 mg, 0.50 mmol) was added into a reaction flask, added with trifluoroacetic acid/dichloromethane (1:10, 27.5 mL) and stirred at room temperature for reaction. After the reaction was complete, the system was concentrated under reduced pressure to obtain 200.0 mg of a crude.

ESI-MS Calculated for [M+H]$^+$=424.16; Found: 424.00. The calculated value was consistent with the found value.

Step 4: Synthesis of N-(9-(1-acetyl-1,2,3,6-tetrahydropyridin-4-yl)-1-methyl-6,7-dihydro-5H-benzo[c][1,2,3]triazolo[1,5-a]azepin-7-yl)-N-(4-chlorophenyl) acetamide (LD13)

LD13-4 (50.0 mg, 0.12 mmol), triethylamine (36.4 mg, 0.36 mmol), DCM (5 mL) were added into a reaction flask, added dropwise and slowly with acetyl chloride (0.24 mL) and stirred at room temperature for reaction. After the reaction was complete, the system was added with water (100 ml) and DCM (50 mL), and shaken and separated. The aqueous phase was extracted with DCM (50 mL*2). The combined organic phase was washed with water (50 mL*2) and saturated brine (50 mL), dried over anhydrous sodium sulfate and filtered under suction. The filtrate was concentrated under reduced pressure, and the residue was separated by medium-pressure preparative chromatography and lyophilized to obtain 12.4 mg of the product.

ESI-MS Calculated for [M+H]$^+$=490.19; Found: 490.20. The calculated value was consistent with the found value.

Preparation Example 110, Final Product LD14: 1-(4-(7-((4-chlorophenyl)amino)-1-methyl-6,7-dihydro-5H-benzo[c][1,2,3]triazolo[1,5-a]azepin-9-yl)-3,6-dihydropyridin-1(2H)-yl)propan-1-one

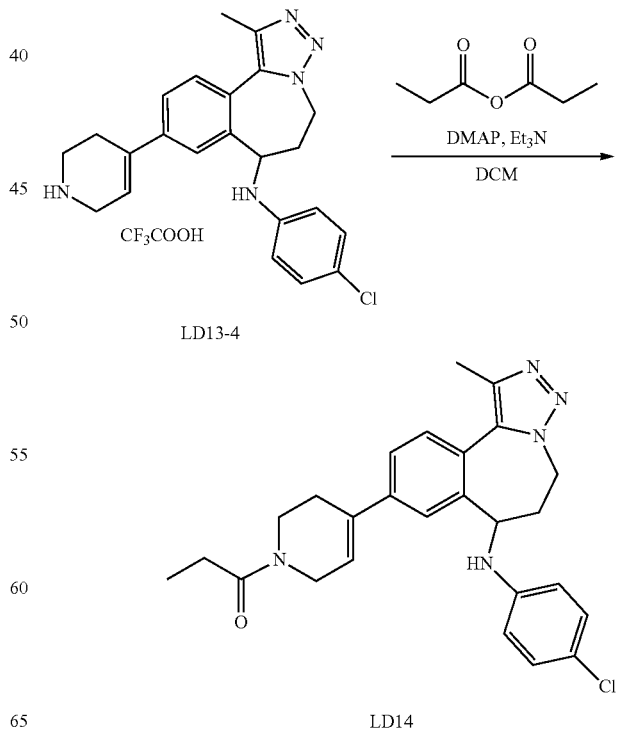

LD13-4

LD14

Synthesis of 1-(4-(7-((4-chlorophenyl)amino)-1-methyl-6,7-dihydro-5H-benzo[c][1,2,3]triazolo[1,5-a]azepin-9-yl)-3,6-dihydropyridin-1(2H)-yl)propan-1-one (LD14)

LD13-4 (50.0 mg, 0.12 mmol), triethylamine (1 mL), DCM (10 mL), DMAP (1.5 mg, 0.012 mmol) and propionic anhydride (32.3 mg, 0.24 mmol) were added into a reaction flask and stirred at room temperature for reaction. After the reaction was complete, the system was added with water (50 mL) and DCM (50 mL), shaken and separated. The aqueous phase was extracted with DCM (50 mL*2). The combined organic phase was washed with water (50 mL*2) and saturated brine (50 mL), dried over anhydrous sodium sulfate and filtered under suction. The filtrate was concentrated under reduced pressure, and the residue was separated by medium-pressure preparative chromatography and lyophilized to obtain 16.8 mg of the product.

Product analysis: $^1$HNMR (400 MHz, Methanol-$d_4$): δ 7.61 (s, 1H), 7.56-7.46 (m, 2H), 6.97 (d, J=8.7 Hz, 2H), 6.28 (d, J=8.7 Hz, 2H), 6.11 (d, J=8.8 Hz, 1H), 4.80 (dd, J=14.3, 7.6 Hz, 1H), 4.21 (d, J=11.9 Hz, 3H), 4.01 (m, 1H), 3.81-3.66 (m, 2H), 2.96 (m, 1H), 2.64-2.36 (m, 5H), 2.31 (m, 1H), 1.15 (m, 3H).

ESI-MS Calculated for [M+H]$^+$=462.20; Found: 462.20. The calculated value was consistent with the found value.

Preparation Example 111, Final Product LD17: 9-(1-(sec-butyl)-1,2,3,6-tetrahydropyridin-4-yl)-N-(4-chlorophenyl)-1-methyl-6,7-dihydro-5H-benzo[c][1,2,3]triazolo[1,5-a]azepin-7-amine 2,2,2-trifluoroacetate Synthesis of 9-(1-(s ec-butyl)-1,2,3,6-tetrahydropyridin-4-yl)-N-(4-chlorophenyl)-1-methyl-6,7-dihydro-5H-benzo[c][1,2,3]triazolo[1,5-a]azepin-7-amine 2,2,2-trifluoroacetate (LD17)

LD13-4 (50.0 mg, 0.12 mmol), methanol (10 mL), 2-butanone (0.2 mL) and sodium cyanoborohydride (0.21 g) were added into a reaction flask and stirred at room temperature for reaction. After the reaction was complete, the system was added with water (50 ml) and DCM (50 mL), shaken and separated. The aqueous phase was extracted with DCM (50 mL*2). The combined organic phase was washed with water (50 mL*2) and saturated brine (50 mL), dried over anhydrous sodium sulfate and filtered under suction. The filtrate was concentrated under reduced pressure, and the residue was separated by medium-pressure preparative chromatography (mobile phase: A: purified water with 0.05% trifluoroacetic acid, B: acetonitrile with 0.05% trifluoroacetic acid) and lyophilized to obtain 11.4 mg of the product.

Product analysis: $^1$HNMR (400 MHz, Methanol-$d_4$): δ 7.61 (d, J=24.1 Hz, 3H), 6.95 (d, J=8.7 Hz, 2H), 6.25 (d, J=8.6 Hz, 2H), 6.16 (d, J=14.0 Hz, 1H), 4.82 (d, J=7.2 Hz, 1H), 4.31 (m, 1H), 4.19 (dd, J=11.3, 6.8 Hz, 1H), 4.06-3.84 (m, 1H), 3.68 (d, J=11.8 Hz, 1H), 3.27-3.16 (m, 1H), 2.97 (m, 1H), 2.84 (s, 2H), 2.52 (d, J=4.9 Hz, 4H), 2.32 (m, 1H), 1.91 (s, 2H), 1.80-1.58 (m, 1H), 1.42 (dd, J=23.9, 6.6 Hz, 3H), 1.16-0.86 (m, 3H).

ESI-MS Calculated for [M+H]$^+$=462.20; Found: 462.30. The calculated value was consistent with the found value.

Preparation Example 112, Final Product LD19: 1-(4-(7-((4-chlorophenyl)amino)-1-methyl-6,7-dihydro-5H-benzo[c][1,2,3]triazolo[1,5-a]azepin-9-yl)-3,6-dihydropyridin-1(2H)-yl)ethan-1-one

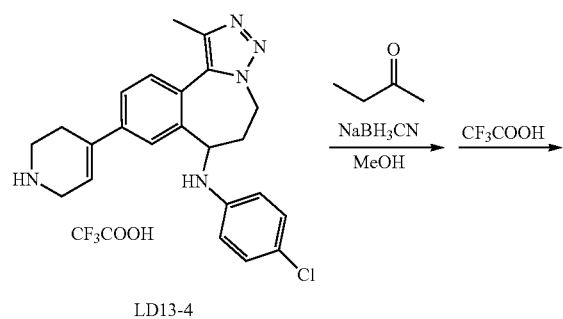

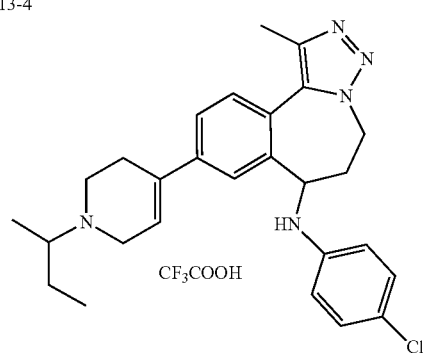

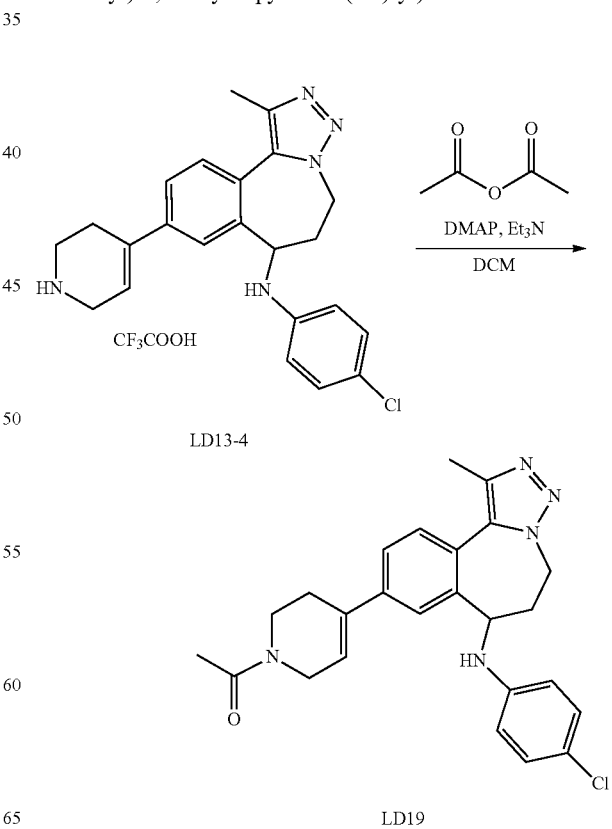

Synthesis of 1-(4-(7-((4-chlorophenyl)amino)-1-methyl-6,7-dihydro-5H-benzo[c][1,2,3]triazolo[1,5-a]azepin-9-yl)-3,6-dihydropyridin-1(2H)-yl)ethan-1-one (LD19)

LD13-4 (50.0 mg, 0.12 mmol), DCM (10 mL), triethylamine (1 mL), DMAP (1.5 mg, 0.012 mmol) and acetic anhydride (0.1 mL) were added into a reaction flask and stirred at room temperature for reaction. After the reaction was complete, the system was added with water (50 mL) and DCM (50 mL), shaken and separated. The aqueous phase was extracted with DCM (50 mL*2). The combined organic phase was washed with water (50 mL*2) and saturated brine (50 mL), dried over anhydrous sodium sulfate and filtered under suction. The filtrate was concentrated under reduced pressure, and the residue was separated by medium-pressure preparative chromatography and lyophilized to obtain 18.8 mg of the product.

Product analysis: $^1$HNMR (400 MHz, Methanol-$d_4$): δ 7.61 (s, 1H), 7.53 (d, J=3.0 Hz, 2H), 6.97 (d, J=8.7 Hz, 2H), 6.28 (d, J=8.7 Hz, 2H), 6.11 (s, 1H), 4.81 (dd, J=14.2, 7.7 Hz, 2H), 4.20 (dd, J=10.8, 6.8 Hz, 3H), 4.08-3.94 (m, 1H), 3.83-3.67 (m, 2H), 2.96 (m, 1H), 2.52 (m, 4H), 2.32 (m, 1H), 2.17 (s, 2H), 2.13 (s, 1H).

ESI-MS Calculated for [M+H]$^+$=448.18; Found: 448.30. The calculated value was consistent with the found value.

Preparation Example 113, Final Product LD23: N-(4-chlorophenyl)-9-(1-ethyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate Synthesis of N-(4-chlorophenyl)-9-(1-ethyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate (LD23)

LD13-4 (50.0 mg, 0.12 mmol), methanol (10 mL), an aqueous acetaldehyde solution (0.2 mL, 40% content) and sodium cyanoborohydride (0.20 g) were added into a reaction flask and reacted at room temperature. After the reaction was complete, the system was added with water (50 mL), extracted with DCM (50 mL) and separated. The aqueous phase was extracted with DCM (30 mL). The combined organic phase was washed with water (50 mL*2) and saturated brine (50 mL), dried over anhydrous sodium sulfate and filtered under suction. The filtrate was concentrated under reduced pressure, and the residue was separated by medium-pressure preparative chromatography (mobile phase: A: purified water with 0.05% trifluoroacetic acid, B: acetonitrile with 0.05% trifluoroacetic acid) and lyophilized to obtain 13.1 mg of the product.

Product analysis: $^1$HNMR (400 MHz, Methanol-$d_4$): δ 7.61 (d, J=25.4 Hz, 3H), 7.03-6.86 (m, 3H), 6.26 (d, J=8.7 Hz, 3H), 6.15 (s, 1H), 4.82 (d, J=7.6 Hz, 1H), 4.19 (dd, J=11.2, 6.8 Hz, 1H), 4.06-3.95 (m, 2H), 3.78 (d, J=17.1 Hz, 3H), 2.98 (m, 1H), 2.83 (s, 2H), 2.52 (s, 4H), 2.32 (m, 1H), 1.40 (m, 4H).

ESI-MS Calculated for [M+H]$^+$=434.20; Found: 434.10. The calculated value was consistent with the found value.

Preparation Example 114, Final Product LD24: N-(4-chlorophenyl)-9-(1-isopropyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate

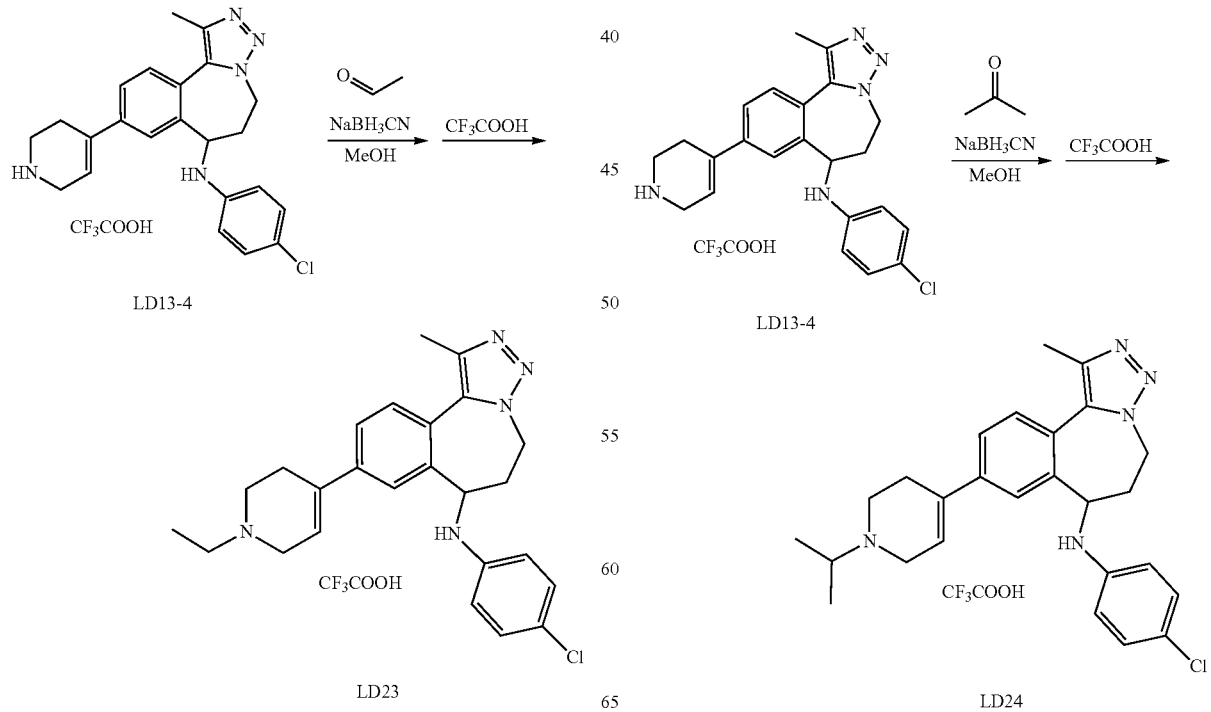

Synthesis of N-(4-chlorophenyl)-9-(1-isopropyl-1,2,
3,6-tetrahydropyridin-4-yl)-1-methyl-6,7-dihydro-
5H-benzo[c][1,2,3]triazolo[1,5-a]azepin-7-amine
2,2,2-trifluoroacetate (LD24)

LD13-4 (50.0 mg, 0.12 mmol), methanol (10 mL), acetone (0.2 mL) and sodium cyanoborohydride (0.20 g) were added into a reaction flask and reacted at room temperature. After the reaction was complete, the system was added with water (50 mL), extracted with DCM (50 mL) and separated. The aqueous phase was extracted with DCM (25 mL). The combined organic phase was washed with water (50 mL*2) and saturated brine (50 mL), dried over anhydrous sodium sulfate and filtered under suction. The filtrate was concentrated under reduced pressure, and the residue was separated by medium-pressure preparative chromatography (mobile phase: A: purified water with 0.05% trifluoroacetic acid, B: acetonitrile with 0.05% trifluoroacetic acid) and lyophilized to obtain 21.1 mg of the product.

Product analysis: $^1$HNMR (400 MHz, Methanol-$d_4$): δ 7.64 (s, 1H), 7.59 (d, J=6.9 Hz, 2H), 7.00-6.90 (m, 2H), 6.25 (d, J=8.7 Hz, 2H), 6.17 (d, J=13.9 Hz, 1H), 4.82 (d, J=7.8 Hz, 1H), 4.19 (dd, J=11.3, 6.8 Hz, 1H), 4.00 (m, 1H), 3.92 (d, J=3.2 Hz, 2H), 3.71 (d, J=11.6 Hz, 1H), 3.63 (m, 1H), 2.98 (m, 1H), 2.84 (s, 2H), 2.52 (s, 3H), 2.32 (m, 1H), 1.41 (d, J=6.7 Hz, 7H).

ESI-MS Calculated for [M+H]$^+$=448.18; Found: 448.20. The calculated value was consistent with the found value.

Preparation Example 115, Final Product LD31:
N-(4-chlorophenyl)-9-(3,6-dihydro-2H-pyran-4-yl)-
1-methyl-6,7-dihydro-5H-benzo[c][1,2,3]triazolo[1,
5-a]azepin-7-amine Synthesis of N-(4-chlorophenyl)-9-(3,6-dihydro-2H-
pyran-4-yl)-1-methyl-6,7-dihydro-5H-benzo[c][1,2,
3]triazolo[1,5-a]azepin-7-amine (LD31)

LD13-2 (100.1 mg, 0.25 mmol), 2-(3,6-dihydro-2H-pyran-4-yl)-4,4,5,5'-tetramethyl-1,3,2-dioxaborolane (69.9 mg, 0.33 mmol), potassium carbonate (54.6 mg, 0.40 mmol), 1,4-dioxane (10 mL) and water (0.5 mL) were added into a reaction flask, and the air in the reaction system was replaced with nitrogen three times. The system was added with Pd(dppf)Cl$_2$-dichloromethane complex (11.3 mg, 0.014 mmol), and the air in the reaction system was replaced with nitrogen again three times. The system was heated to react under reflux. After the reaction was complete, the system was cooled down, added with water (100 mL) and EA (50 mL), shaken and separated. The aqueous phase was extracted with EA (50 mL*2). The combined organic phase was washed with water (50 mL*2) and saturated brine (50 mL*2), dried over anhydrous sodium sulfate and filtered under suction. The filtrate was concentrated under reduced pressure, and the residue was separated by PLC to obtain 44.4 mg of a crude.

Product analysis: $^1$HNMR (400 MHz, Methanol-$d_4$): δ 7.61 (s, 1H), 7.58-7.48 (m, 2H), 7.03-6.93 (m, 2H), 6.32-6.25 (m, 2H), 6.17 (s, 1H), 4.81 (dd, J=14.0, 7.6 Hz, 2H), 4.28 (m, 2H), 4.21 (dd, J=11.1, 6.7 Hz, 1H), 4.08-3.94 (m, 1H), 3.89 (m, 2H), 2.96 (m, 1H), 2.51 (d, J=5.1 Hz, 3H), 2.43-2.25 (m, 2H).

ESI-MS Calculated for [M+H]$^+$=407.16; Found: 407.00. The calculated value was consistent with the found value.

Preparation Example 116, Final Product LD76:
N-(3-chloro-4-fluorophenyl)-9-(1-cyclohexyl-1,2,3,
6-tetrahydropyridin-4-yl)-1-methyl-6,7-dihydro-5H-
benzo[c][1,2,3]triazolo[1,5-a]azepin-7-amine 2,2,2-
trifluoroacetate

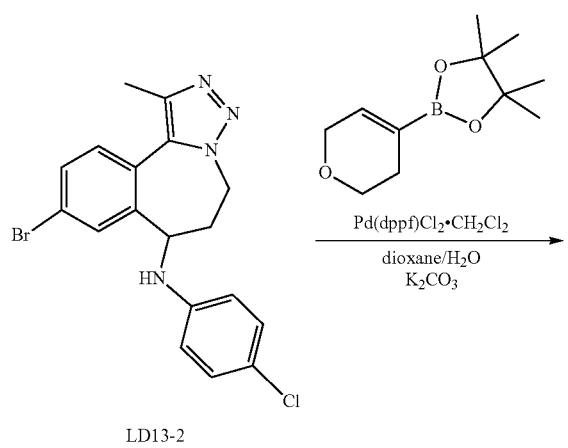

LD13-2

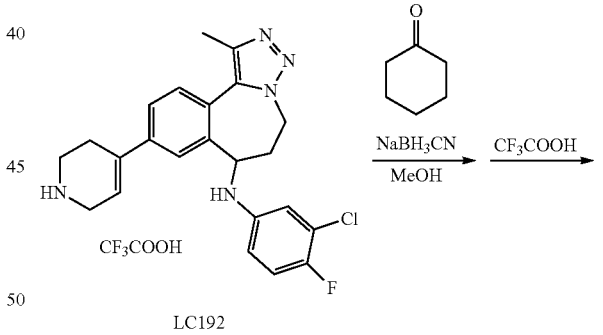

LC192

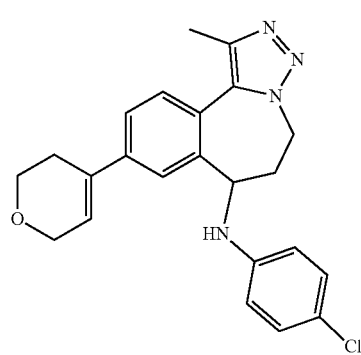

LD31

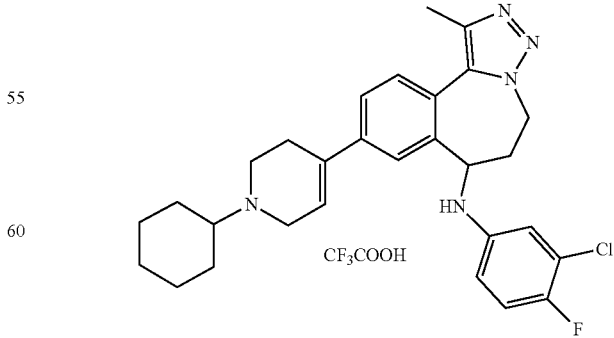

LD76

Synthesis of N-(3-chloro-4-fluorophenyl)-9-(1-cyclohexyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate (LD76)

LC192 (40.5 mg, 0.096 mmol), methanol (5 mL), cyclohexanone (1 mL) and sodium cyanoborohydride (0.25 g, 3.98 mmol) were added into a reaction flask and reacted at room temperature. After the reaction was complete, the system was added with water (100 mL) and extracted with DCM (30 mL*2). The combined DCM phase was washed with saturated brine (100 mL), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 10.1 mg of the product.

ESI-MS Calculated for $[M+H]^+=506.24$; Found: 506.10. The calculated value was consistent with the found value.

Preparation Example 117, Final Product LD77: 1-(4-(7-((3-chloro-4-fluorophenyl)amino)-1-methyl-6,7-dihydro-5H-benzo[c][1,2,3]triazolo[1,5-a]azepin-9-yl)-3,6-dihydropyridin-1(2H)-yl)ethan-1-one LC192 (40.5 mg, 0.096 mmol), DCM (10 mL), acetic anhydride (0.1 mL), triethylamine (1 mL) and DMAP (1.5 mg, 0.0096 mmol) were added into a reaction flask and reacted at room temperature under nitrogen protection. After the reaction was complete, the system was added with DCM (20 mL), washed with water (50 mL) and saturated brine (50 mL), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 8.4 mg of the product.

ESI-MS Calculated for $[M+H]^+=466.17$; Found: 466.20. The calculated value was consistent with the found value.

Preparation Example 118, Final Product BF169: N-(4-chlorophenyl)-1-methyl-9-(piperidin-4-yl)-6,7-dihydro-5H-benzo[c][1,2,3]triazolo[1,5-a]azepin-7-amine hydrochloride

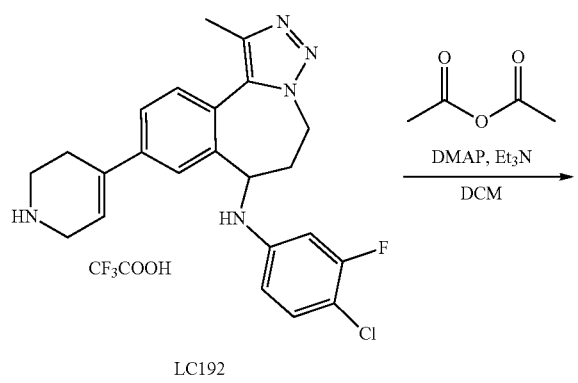

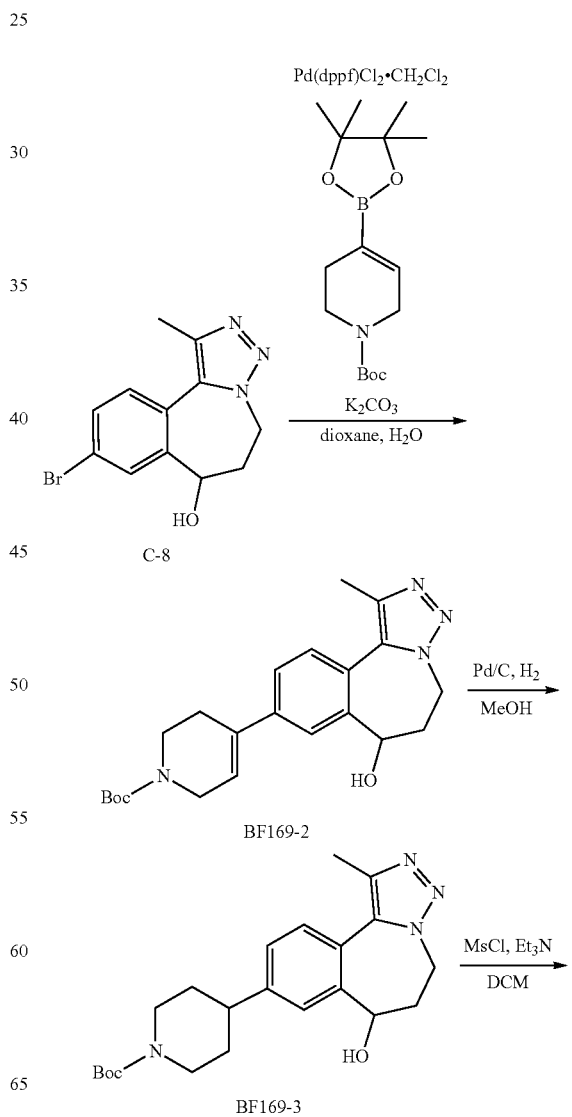

-continued

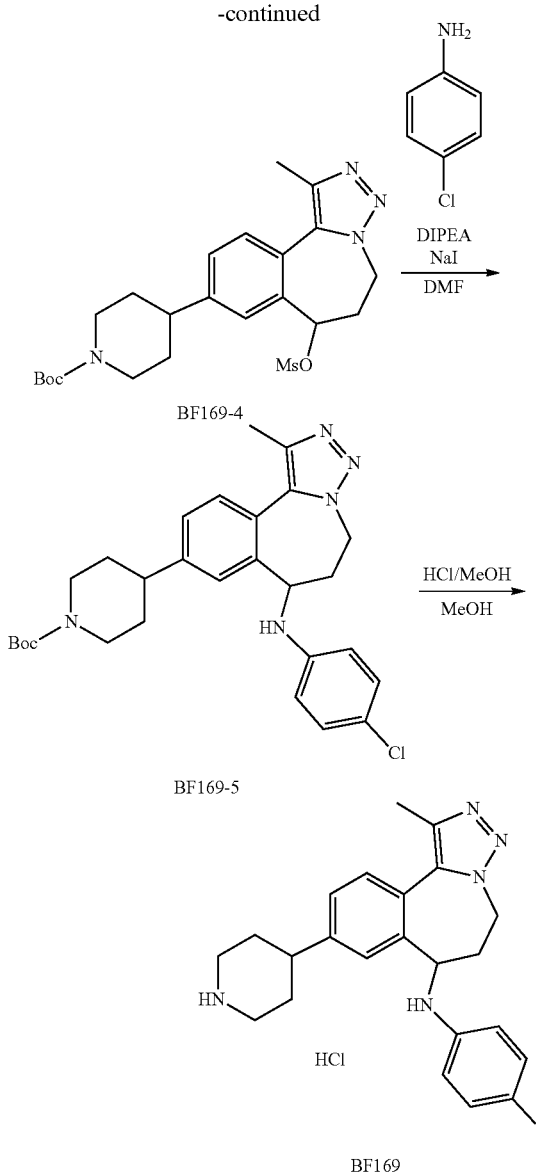

BF169-4

BF169-5

BF169

Step 1: Synthesis of tert-butyl 4-(7-hydroxyl-1-methyl-6,7-dihydro-5H-benzo[c][1,2,3]triazolo[1,5-a]azepin-9-yl)-3,6-dihydropyridine-1 (2H)-carboxylate (BF169-2)

C-8 (1.00 g, 3.40 mmol), tert-butyl 4-(4,4,5,5-tetramethyl-1,3,2-dioxaborolan-2-yl)-3,6-dihydropyridine-1(2H)-carboxylate (1.35 g, 4.36 mmol), potassium carbonate (0.95 g, 6.87 mmol), [1,1'-bis(diphenylphosphino)ferrocene]dichloropalladium-dichloromethane complex (249.7 mg, 0.31 mmol), 1,4-dioxane (30 mL) and water (3 mL) were added into a reaction flask in sequence. The air in the reaction flask was replaced with nitrogen three times, and the system was heated to react under reflux under nitrogen protection. After the reaction was complete, the system was concentrated under reduced pressure, and the residue was separated by column chromatography to obtain 1.16 g of the product with a yield of 86.1%.

Product analysis: $^1$HNMR (CDCl$_3$, 400 MHz): δ 7.79 (d, J=1.9 Hz, 1H), 7.41 (dd, J=8.0, 1.9 Hz, 1H), 7.33 (d, J=8.0 Hz, 1H), 6.17 (s, 1H), 4.79-4.59 (m, 2H), 4.12-4.08(m, 2H), 4.00-3.95(m, 1H), 3.64 (t, J=5.7 Hz, 2H), 2.97-2.87 (m, 2H), 2.56 (d, J=5.6 Hz, 2H), 2.41 (s, 3H), 2.26-2.19 (m, 1H), 1.48 (s, 9H).

Step 2: Synthesis of tert-butyl 4-(7-hydroxyl-1-methyl-6,7-dihydro-5H-benzo[c][1,2,3]triazolo[1,5-a]azepin-9-yl)-3,6-dihydropyridine-1 (2H)-carboxylate (B F169-3)

BF169-2 (1.01 g, 2.53 mmol), 30 mL of methanol, 0.51 g of palladium on carbon (palladium content 10%, water content 52%) were added into a 100 mL single necked flask. The air in a reaction flask was replaced with hydrogen three times, and the system was reacted at room temperature under hydrogen balloon pressure. After the reaction was complete, the system was filtered under suction, and the filter cake was rinsed with methanol (10 mL). The filtrate was concentrated under reduced pressure, and the residue was used directly in the next reaction. The yield was calculated as 100%.

ESI-MS Calculated for [M+H]$^+$=399.23; Found: 399.20. The calculated value was consistent with the found value.

Step 3: Synthesis of tert-butyl 4-(1-methyl-7-((methylsulfonyl)oxy)-6,7-dihydro-5H-benzo[c][1,2,3]triazolo[1,5-a]azepin-9-yl)piperidine-1-carboxylate (BF169-4)

BF169-3 (302.3 mg, 0.76 mmol), dichloromethane (30 mL) and triethylamine (236.4 mg, 2.34 mmol) were added into a reaction flask, cooled to 6° C. in an ice-water bath under nitrogen protection, added with methanesulfonyl chloride (167.2 mg, 1.28 mmol) and kept at 0-10° C. for reaction. After the reaction was complete, the system was added with 50 mL of water, shaken and separated. The aqueous phase was extracted with dichloromethane (20 mL). The combined organic phase was washed with saturated brine (30 mL), dried over anhydrous magnesium sulfate and filtered. The filtrate was concentrated under reduced pressure, and the residue was directly used in the next reaction. The yield was calculated as 100%.

Step 4: Synthesis of tert-butyl 4-(7-((4-chlorophenyl)amino)-1-methyl-6,7-dihydro-5H-benzo[c][1,2,3]triazolo[1,5-a]azepin-9-yl)piperidine-1-carboxylate (BF169-5)

BF169-4 (obtained in the previous step), p-chloroaniline (250.9 mg, 1.97 mmol), DMF (25 mL), DIPEA (416.7 mg, 3.22 mmol) and NaI (809.7 mg, 5.40 mmol) were added to a 100 mL single necked bottle and heated to 70° C., and the reaction was monitored by LC-MS. After the reaction was complete, the system was added with ice water (50 mL) and extected with EA (20 mL). The aqueous phase was extracted with EA (20 mL*2). The combined organic phase was washed with water (30 mL) and saturated brine (30 mL), dried over anhydrous magnesium sulfate and filtered under suction. The filtrate was concentrated under reduced pressure, and the residue was separated by medium-pressure preparative column chromatography (mobile phase: A: purified water, B: acetonitrile) and lyophilized to obtain 82.7 mg of the product.

ESI-MS Calculated for [M+H]$^+$=508.24; Found: 508.20. The calculated value was consistent with the found value.

Step 5: Synthesis of N-(4-chlorophenyl)-1-methyl-9-(piperidin-4-yl)-6,7-dihydro-5H-benzo[c][1,2,3]triazolo[1,5-a]azepin-7-amine hydrochloride (BF169)

BF169-5 (82.7 mg, 0.16 mmol), methanol (5 mL) and hydrogen chloride in methanol (0.5 mL, 5 mol/L) were added into a reaction flask. After the reaction was complete, the system was concentrated under reduced pressure and lyophilized to obtain 32.8 mg of the product.

ESI-MS Calculated for [M+H]$^+$=408.19; Found: 408.20. The calculated value was consistent with the found value.

Preparation Example 119, Final Product BF178: N-(4-chlorophenyl)-1-methyl-9-(1-methylpiperidin-4-yl)-6,7-dihydro-5H-benzo[c][1,2,3]triazolo[1,5-a]azepin-7-amine

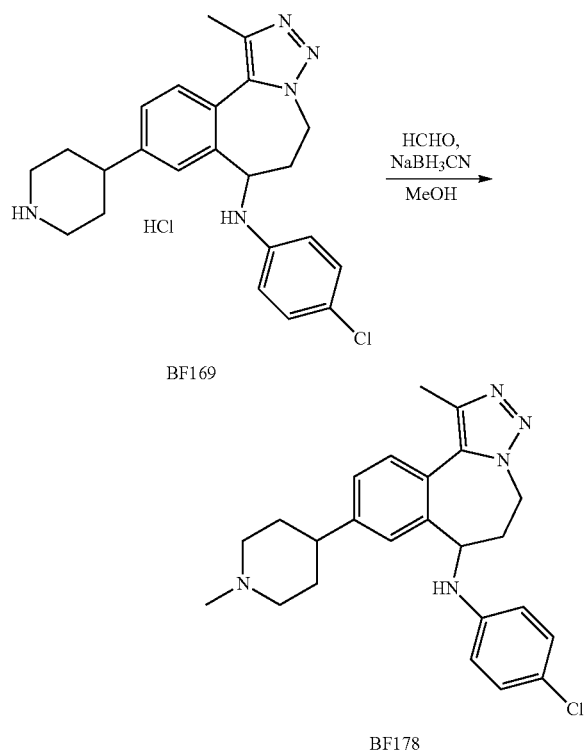

Synthesis of N-(4-chlorophenyl)-1-methyl-9-(1-methylpiperidin-4-yl)-6,7-dihydro-5H-benzo[c][1,2,3]triazolo[1,5-a]azepin-7-amine (BF178)

BF169 (10.6 mg, 0.024 mmol), methanol (5 mL), aqueous formaldehyde solution (3 drops, 40% content) and sodium cyanoborohydride (80.3 mg) were added into a reaction flask and reacted at room temperature. After the reaction was complete, the system was concentrated under reduced pressure. The residue was separated by PLC to obtain 6.1 mg of the product BF178.

ESI-MS Calculated for [M+H]$^+$=422.20; Found: 422.00. The calculated value was consistent with the found value.

Preparation Example 120, Final Product BJ28: N-(1,3-dimethyl-1H-pyrazol-5-yl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate

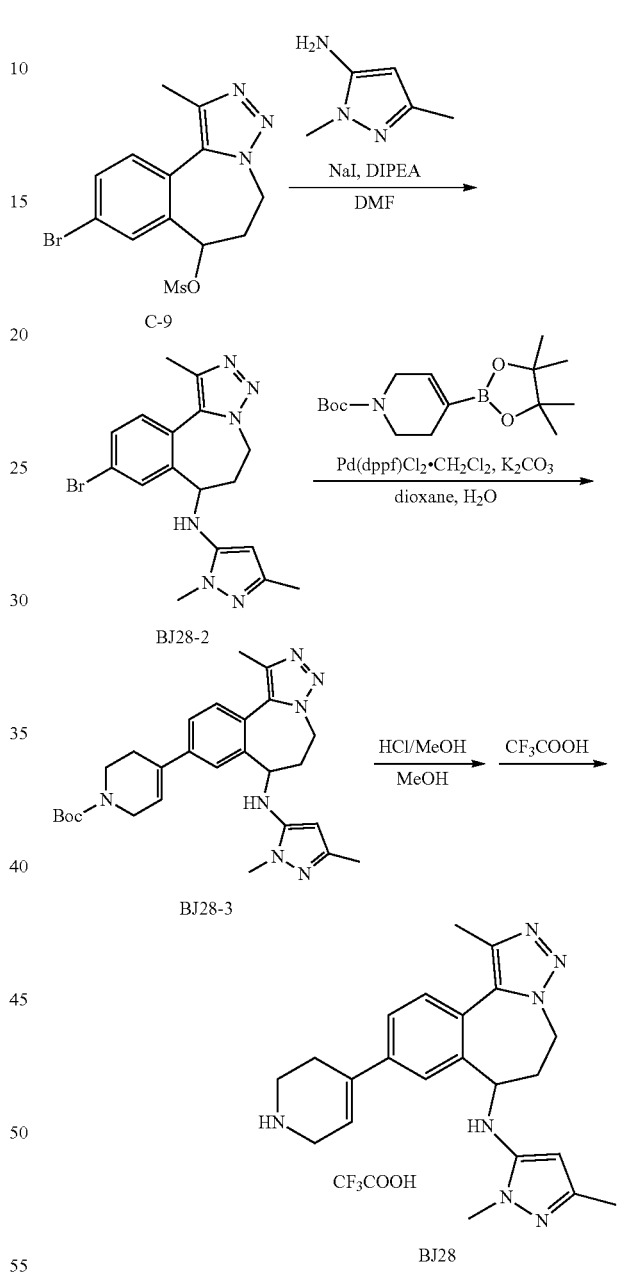

Step 1: Synthesis of 9-bromo-N-(1,3-dimethyl-1H-pyrazol-5-yl)-1-methyl-6,7-dihydro-5H-benzo[c][1,2,3]triazolo[1,5-a]azepin-7-amine (BJ28-2)

C-9 (198.6 mg, 0.53 mmol), 1,3-dimethyl-1H-pyrazol-5-amine (123.9 mg, 2.15 mmol), DMF (15 mL), DIPEA (280.7 mg, 4.09 mmol) and NaI (510.3 mg, 6.41 mmol) were added into a reaction flask and heated to 70° C., and the reaction was monitored by TLC. After the reaction was complete, the system was cooled down, added with water (50 mL) and extracted with EA (30 mL, 15 mL). The combined EA phase was washed with saturated brine (50 mL), dried over anhydrous magnesium sulfate and filtered under suction. The filtrate was concentrated under reduced pressure, and the residue was separated by column chromatography to obtain 75.4 mg of the product with a yield of 35.8%.

ESI-MS Calculated for [M+H]⁺=387.09; Found: 387.00. The calculated value was consistent with the found value.

Step 2: Synthesis of tert-butyl 4-(7-((1,3-dimethyl-1H-pyrazol-5-yl)amino)-1-methyl-6,7-dihydro-5H-benzo[c][1,2,3]triazolo[1,5-a]azepin-9-yl)-3,6-dihydropyridine-1 (2H)-carboxylate (BJ28-3)

BJ28-2 (75.4 mg, 0.19 mmol), tert-butyl 4-(4,4,5,5-tetramethyl-1,3,2-dioxaborolan-2-yl)-3,6-dihydropyridine-1 (2H)-carboxylate (71.4 mg, 0.23 mmol), potassium carbonate (87.3 mg, 0.63 mmol), [1,1'-bis(diphenylphosphino) ferrocene]dichloropalladium-dichloromethane complex (25.0 mg, 0.031 mmol), 1,4-dioxane (10 mL) and water (1 mL) were added into a reaction flask in sequence. The air in the reaction flask was replaced with nitrogen three times, and the system was heated to react under reflux under nitrogen protection. After the reaction was complete, the system was cooled down, added with water (50 mL) and extracted with EA (20 mL*2). The combined EA phase was washed with saturated brine (50 mL), dried over anhydrous magnesium sulfate and filtered under suction. The filtrate was concentrated under reduced pressure, and the residue was separated by PLC to obtain 53.6 mg of the product.

ESI-MS Calculated for [M+H]⁺=490.29; Found: 490.10. The calculated value was consistent with the found value.

Step 3: Synthesis of N-(1,3-dimethyl-1H-pyrazol-5-yl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate (BJ28)

BJ28-3 (53.6 mg), methanol (5 mL) and hydrogen chloride in methanol (1 mL, 5 mol/L) were added into a reaction flask and reacted at room temperature. After the reaction was complete, the system was concentrated under reduced pressure, and the residue was separated by thin layer preparative chromatography to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 3.9 mg of the product.

ESI-MS Calculated for [M+H]⁺=390.23; Found: 390.10. The calculated value was consistent with the found value.

Preparation Example 121, Final Product BJ122: N-(4-fluorophenyl)-1-methyl-9-(1,2,3,6-tetrahydropyridin-4-yl)-6,7-dihydro-5H-benzo[c][1,2,3]triazolo [1,5-a]azepin-7-amine 2,2,2-trifluoroacetate

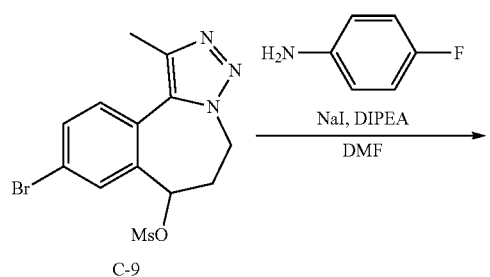

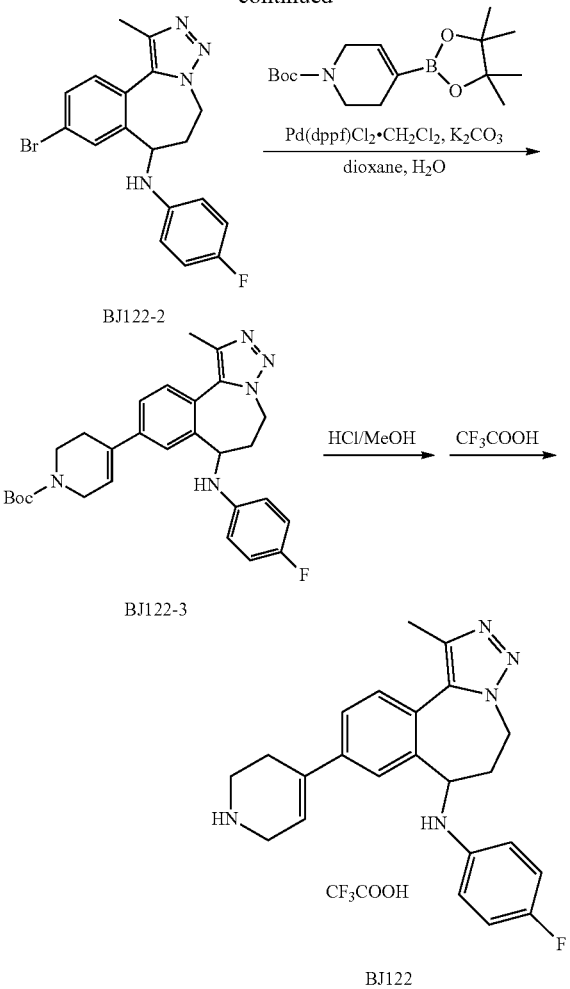

Step 1: Synthesis of 9-bromo-N-(4-fluorophenyl)-1-methyl-6,7-dihydro-5H-benzo[c][1,2,3]triazolo[1,5-a]azepin-7-amine (BJ122-2)

C-9 (198.6 mg, 0.53 mmol), p-fluoroaniline (150.6 mg, 1.14 mmol), DMF (25 mL), DIPEA (309.3 mg, 2.39 mmol) and NaI (0.47 g, 3.14 mmol) were added into a reaction flask and heated to 55° C., and the reaction was monitored by TLC. After the reaction was complete, the system was cooled down, added with water (100 mL) and extracted with EA (20 mL, 15 mL). The combined EA phase was washed with saturated brine (30 mL), dried over anhydrous magnesium sulfate and filtered under suction. The filtrate was concentrated under reduced pressure, and the residue was separated by column chromatography to obtain 100 mg of the product with a yield of 48.7%.

ESI-MS Calculated for [M+H]⁺=387.05; Found: 386.80. The calculated value was consistent with the found value.

Step 2: Synthesis of tert-butyl 4-(7-((4-fluorophenyl)amino)-1-methyl-6,7-dihydro-5H-benzo[c][1,2,3]triazolo[1,5-a]azepin-9-yl)-5,6-dihydropyridine-1 (2H)-carboxylate (BJ122-3)

BJ122-2 (100 mg, 0.26 mmol), tert-butyl 4-(4,4,5,5-tetramethyl-1,3,2-dioxaborolan-2-yl)-3,6-dihydropyridine-1

(2H)-carboxylate (103.9 mg, 0.34 mmol), potassium carbonate (90.1 mg, 0.65 mmol), [1,1'-bis(diphenylphosphino)ferrocene]dichloropalladium-dichloromethane complex (17.3 mg, 0.021 mmol), 1,4-dioxane (10 mL) and water (1 mL) were added into a reaction flask in sequence. The air in the reaction flask was replaced with nitrogen three times, and the system was heated to react under reflux under nitrogen protection. After the reaction was complete, the system was cooled down, added with water (50 mL) and extracted with (25 mL, 20 mL). The combined EA phase was washed with saturated brine (30 mL), dried over anhydrous magnesium sulfate and filtered under suction. The filtrate was concentrated under reduced pressure, and the residue was separated by PLC to obtain 91.3 mg of the product with a yield of 71.8%.

ESI-MS Calculated for [M+H]$^+$=490.25; Found: 490.10. The calculated value was consistent with the found value.

Step 3: Synthesis of N-(4-fluorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate (BJ122)

BJ122-3 (91.3 mg), methanol (10 mL) and hydrogen chloride in methanol (2 mL, 5 mol/L) were added into a reaction flask and reacted at room temperature. After the reaction was complete, the system was concentrated under reduced pressure. The residue was separated by medium-pressure preparative column chromatography (mobile phase: A: purified water with 0.05% trifluoroacetic acid, B: acetonitrile with 0.05% trifluoroacetic acid) and lyophilized to obtain 40.7 mg of the product.

Product analysis: $^1$HNMR (CD$_3$OD, 400 MHz): δ 7.67 (s, 1H), 7.57 (d, J=2.7 Hz, 2H), 6.73 (t, J=8.8 Hz, 2H), 6.27 (dd, J=9.0, 4.3 Hz, 2H), 6.15 (s, 1H), 4.81 (d, J=7.8 Hz, 1H), 4.17 (dd, J=11.2, 6.8 Hz, 1H), 4.07-3.91 (m, 1H), 3.84 (d, J=3.0 Hz, 2H), 3.45 (t, J=6.1 Hz, 2H), 2.90-3.02 (m, 1H), 2.78-2.69 (m, 2H), 2.52 (s, 3H), 2.27-2.36 (m, 1H).

ESI-MS Calculated for [M+H]$^+$=390.20; Found: 390.00. The calculated value was consistent with the found value.

Preparation Example 122, Final Product BJ123: N-(3-fluorophenyl)-1-methyl-9-(1,2,3,6-tetrahydropyridin-4-yl)-6,7-dihydro-5H-benzo[c][1,2,3]triazolo[1,5-a]azepin-7-amine hydrochloride

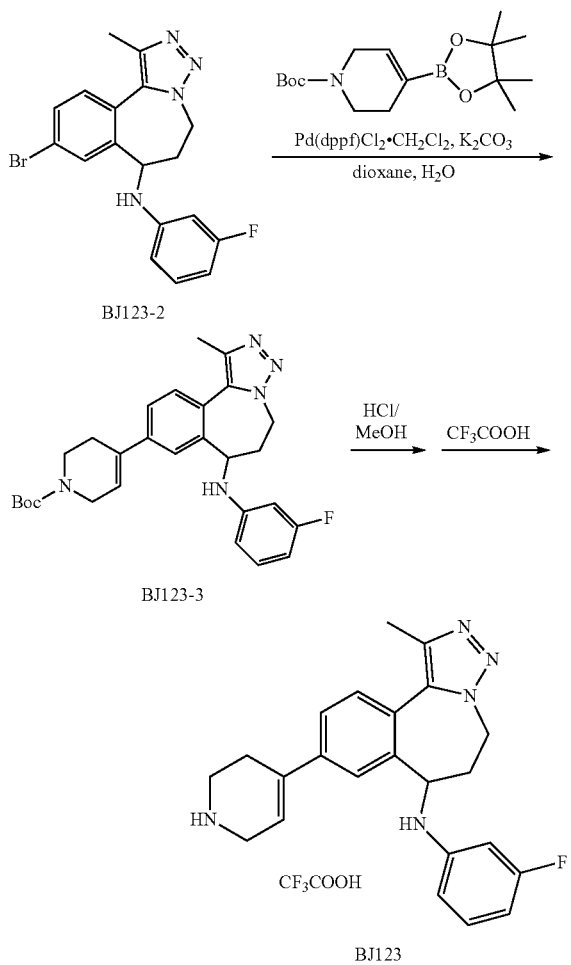

The final product BJ123A was prepared ccording to the method of Preparation Example 121, except that the used reactant p-fluoroaniline was replaced with m-fluoroaniline.

ESI-MS Calculated for [M+H]$^+$=390.20; Found: 389.90. The calculated value was consistent with the found value.

Preparation Example 123, Final Product BJ126: N-(2-fluorophenyl)-1-methyl-9-(1,2,3,6-tetrahydropyridin-4-yl)-6,7-dihydro-5H-benzo[c][1,2,3]triazolo[1,5-a]azepin-7-amine hydrochloride

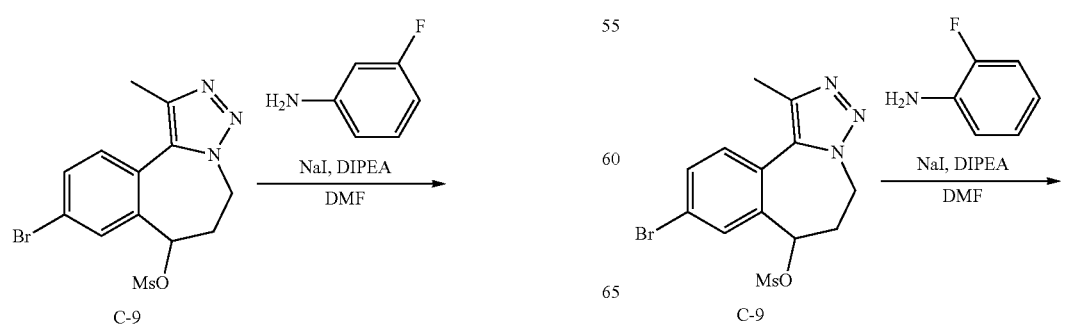

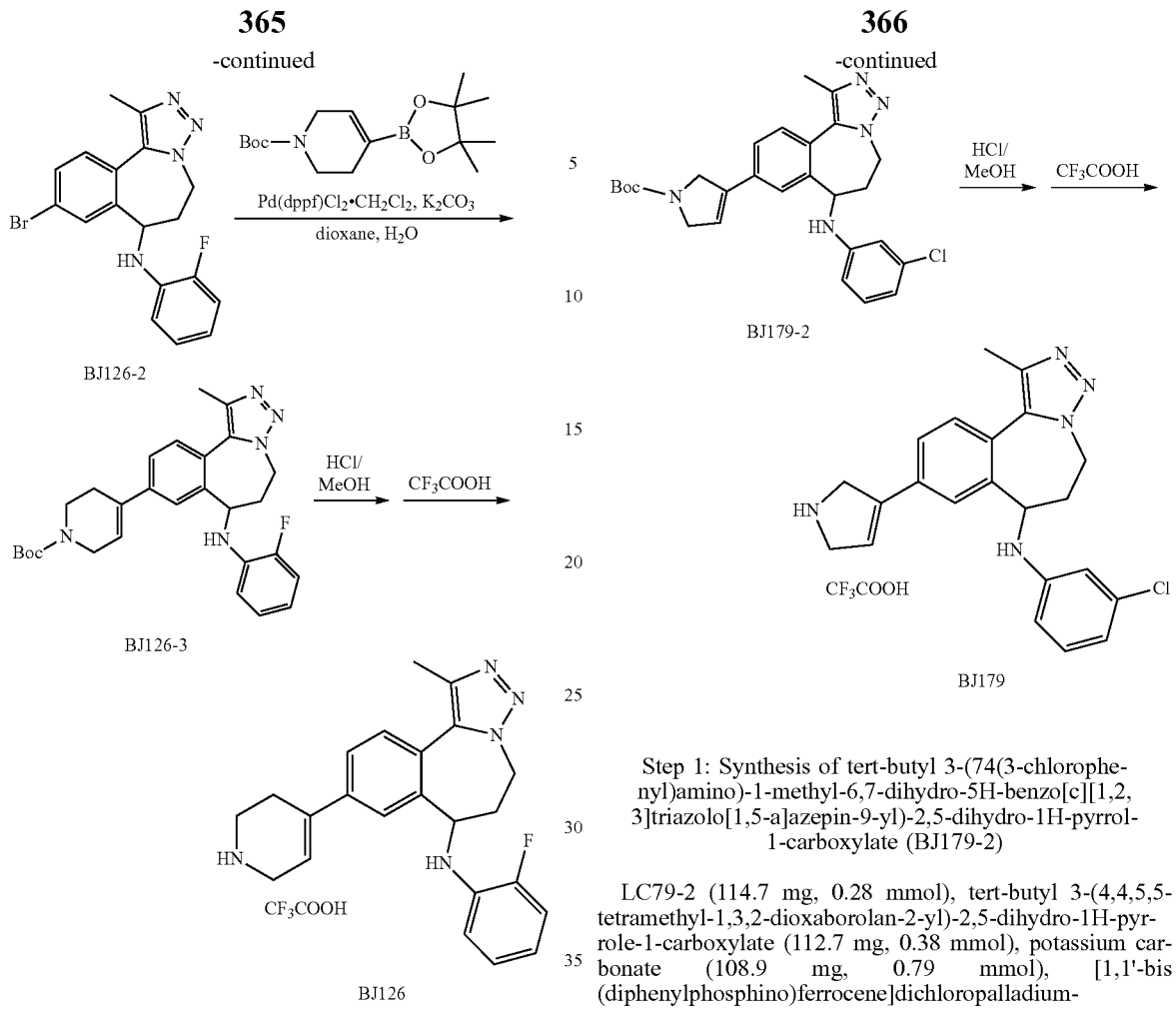

The final product BJ126 was prepared according to the method of Preparation Example 121, except that the used reactant p-fluoroaniline was replaced with o-fluoroanilin.

ESI-MS Calculated for [M+H]$^+$=390.20; Found: 390.00. The calculated value was consistent with the found value.

Preparation Example 124, Final Product BJ179: N-(3-chlorophenyl)-9-(2,5-dihydro-1H-pyrrol-3-yl)-1-methyl-6,7-dihydro-5H-benzo[c][1,2,3]triazolo[1,5-a]azepin-7-amine 2,2,2-trifluoroacetate

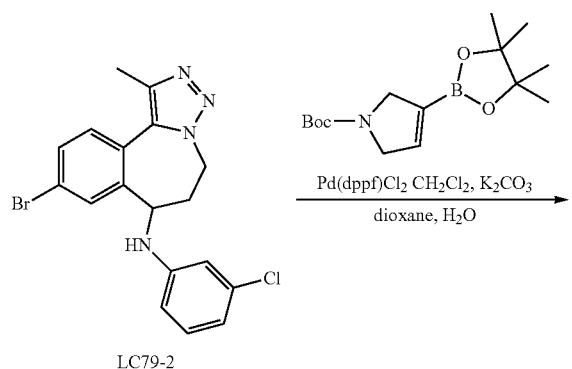

Step 1: Synthesis of tert-butyl 3-(74(3-chlorophenyl)amino)-1-methyl-6,7-dihydro-5H-benzo[c][1,2,3]triazolo[1,5-a]azepin-9-yl)-2,5-dihydro-1H-pyrrol-1-carboxylate (BJ179-2)

LC79-2 (114.7 mg, 0.28 mmol), tert-butyl 3-(4,4,5,5-tetramethyl-1,3,2-dioxaborolan-2-yl)-2,5-dihydro-1H-pyrrole-1-carboxylate (112.7 mg, 0.38 mmol), potassium carbonate (108.9 mg, 0.79 mmol), [1,1'-bis(diphenylphosphino)ferrocene]dichloropalladium-dichloromethane complex (37.2 mg, 0.046 mmol), 1,4-dioxane (15 mL) and water (1 mL) were added into a reaction flask in sequence. The air in the reaction flask was replaced with nitrogen three times, and the system was heated to react under reflux under nitrogen protection. After the reaction was complete, the system was added with water (50 mL) and extracted with EA (25 mL*2). The combined EA phase was washed with saturated brine (50 mL), dried over anhydrous magnesium sulfate and filtered under suction. The filtrate was concentrated under reduced pressure, and the residue was separated by PLC to obtain 110.0 mg of the product with a yield of 80.0%.

ESI-MS Calculated for [M+H]$^+$=492.21; Found: 492.00. The calculated value was consistent with the found value.

Step 2: Synthesis of N-(3-chlorophenyl)-9-(2,5-dihydro-1H-pyrrol-3-yl)-1-methyl-6,7-dihydro-5H-benzo[c][1,2,3]triazolo[1,5-a]azepin-7-amine 2,2,2-trifluoroacetate (BJ179)

BJ179-2 (110.0 mg), methanol (20 mL) and hydrogen chloride in methanol (3 mL, 5 mol/L) were added into a reaction flask and reacted at room temperature. After the reaction was complete, the system was concentrated under reduced pressure. The residue was separated by medium-pressure preparative column chromatography (mobile phase: A: purified water with 0.05% trifluoroacetic acid, B: acetonitrile with 0.05% trifluoroacetic acid) and lyophilized to obtain 39.9 mg of the product.

ESI-MS Calculated for [M+H]$^+$=392.16; Found: 391.90. The calculated value was consistent with the found value.

Preparation Example 125, Final Product BJ183: 3-((9-(2,5-dihydro-1H-pyrrol-3-yl)-1-methyl-6,7-dihydro-5H-benzo[d][1,2,3]triazolo[1,5-a]azepin-7-yl)amino)phenol 2,2,2-trifluoroacetate

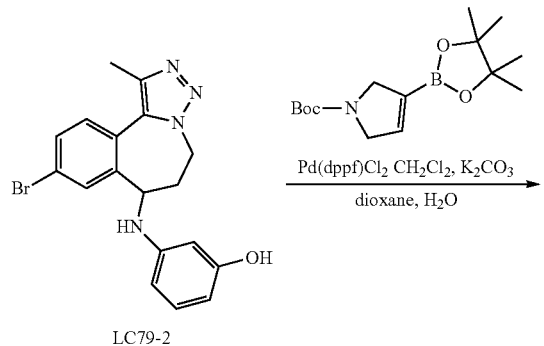

The final product BJ183 was prepared by using LC97-2 as a raw material according to the method and reactants of Preparation Example 124.

ESI-MS Calculated for [M+H]$^+$=374.19; Found: 374.10. The calculated value was consistent with the found value.

Preparation Example 126, Final Product BJ193: N-(3-chloro-5-fluorophenyl)-1-methyl-9-(1-methyl-1H-pyrazol-4-yl)-6,7-dihydro-5H-benzo[c][1,2,3]triazolo[1,5-a]azepin-7-amine

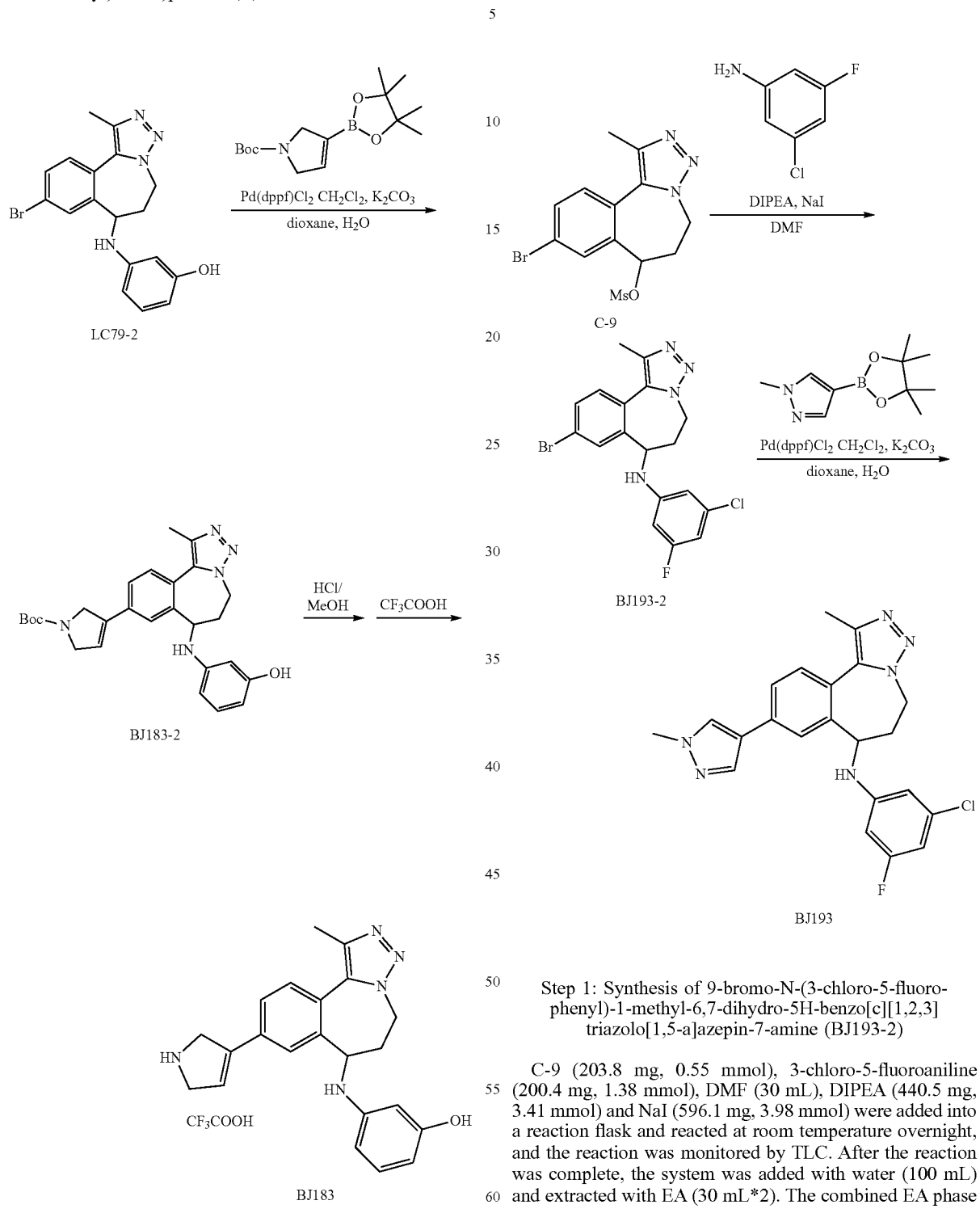

Step 1: Synthesis of 9-bromo-N-(3-chloro-5-fluorophenyl)-1-methyl-6,7-dihydro-5H-benzo[c][1,2,3]triazolo[1,5-a]azepin-7-amine (BJ193-2)

C-9 (203.8 mg, 0.55 mmol), 3-chloro-5-fluoroaniline (200.4 mg, 1.38 mmol), DMF (30 mL), DIPEA (440.5 mg, 3.41 mmol) and NaI (596.1 mg, 3.98 mmol) were added into a reaction flask and reacted at room temperature overnight, and the reaction was monitored by TLC. After the reaction was complete, the system was added with water (100 mL) and extracted with EA (30 mL*2). The combined EA phase was washed with saturated brine (50 mL), dried over anhydrous magnesium sulfate and filtered under suction. The filtrate was concentrated under reduced pressure, and the residue was separated by column chromatography to obtain 71.3 mg of the product with a yield of 24.7%.

ESI-MS Calculated for [M+H]$^+$=422.70; Found: 423.00. The calculated value was consistent with the found value.

Step 2: Synthesis of N-(3-chloro-5-fluorophenyl)-1-methyl-9-(1-methyl-1H-pyrazol-4-yl)-6,7-dihydro-5H-benzo[c][1,2,3]triazolo[1,5-a]azepin-7-amine (BJ193)

BJ193-2 (49.3 mg, 0.12 mmol), 1-methyl-4-(4,4,5,5-tetramethyl-1,3,2-dioxaborolan-2-yl)-1H-pyrazole (37.9 mg, 0.18 mmol), potassium carbonate (54.8 mg, 0.40 mmol), [1,1'-bis(diphenylphosphino)ferrocene]dichloropalladium-dichloromethane complex (15.0 mg, 0.018 mmol), 1,4-dioxane (20 mL) and water (1 mL) were added into a reaction flask. The air in the reaction flask was replaced with nitrogen three times, and the system was heated to react under reflux under nitrogen protection. After the reaction was complete, the system was cooled down, added with water (60 mL) and extracted with EA (25 mL*2). The combined EA phase was washed with saturated brine (50 mL), dried over anhydrous magnesium sulfate and filtered under suction. The filtrate was concentrated under reduced pressure, and the residue was separated by medium-pressure preparative column chromatography and lyophilized to obtain 4.1 mg of the product.

ESI-MS Calculated for [M+H]$^+$=423.14; Found: 422.80. The calculated value was consistent with the found value.

Preparation Example 127, Final Product BH06: N-(3-chloro-5-fluorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate

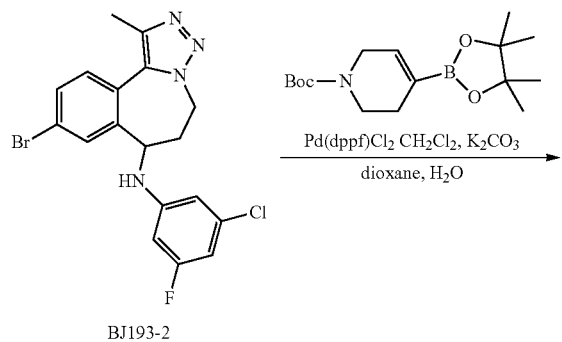

BJ193-2

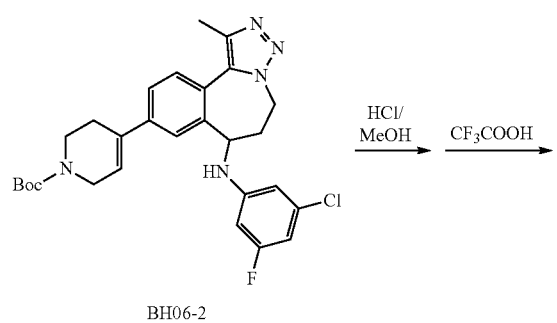

BH06-2

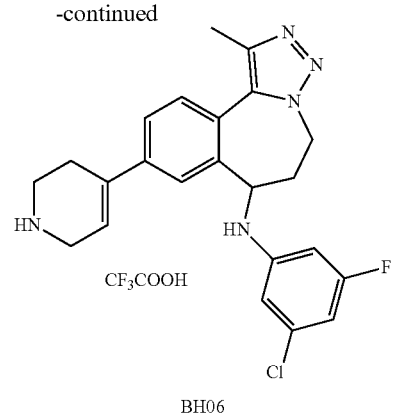

BH06

Step 1: Synthesis of tert-butyl 4-(7-((3-chloro-5-fluorophenyl)amino)-1-methyl-6,7-dihydro-5H-benzo[c][1,2,3]triazolo[1,5-a]azepin-9-yl)-3,6-dihydropyridine-1 (2H)-carboxylate (BH06-2)

BJ193-2 (100 mg, 0.14 mmol), tert-butyl 4-(4,4,5,5-tetramethyl-1,3,2-dioxaborolan-2-yl)-3,6-dihydropyridine-1 (2H)-carboxylate (75.7 mg, 0.24 mmol), potassium carbonate (62.0 mg, 0.45 mmol), [1,1'-bis(diphenylphosphino)ferrocene]dichloropalladium-dichloromethane complex (20.3 mg, 0.025 mmol), 1,4-dioxane (20 mL) and water (1 mL) were added into a reaction flask in sequence. The air in the reaction flask was replaced with nitrogen three times, and the system was heated to react under reflux under nitrogen protection. After the reaction was complete, the system was cooled down, added with water (80 mL) and extracted with EA (25 mL). The combined EA phase was washed with saturated brine (50 mL), dried over anhydrous magnesium sulfate and filtered under suction. The filtrate was concentrated under reduced pressure, and the residue was separated by PLC to obtain 37.0 mg of the product.

Step 2: N-(3-chloro-5-fluorophenyl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate (BH06)

BH06-2 (37.0 mg), methanol (5 mL) and hydrogen chloride in methanol (1.5 mL, 5 mol/L) were added into a reaction flask and reacted at room temperature. After the reaction was complete, the system was concentrated under reduced pressure, the residue was added with methanol (15 mL), and continually concentrated under reduced pressure. The residue was separated by medium-pressure preparative column chromatography (mobile phase: A: purified water with 0.05% trifluoroacetic acid; B: acetonitrile with 0.05% trifluoroacetic acid) and lyophilized to obtain 13.6 mg of the product.

Product analysis: $^1$HNMR(CD$_3$OD, 400 MHz): δ 7.65-7.55 (m, 3H), 6.28-6.32 (m, 1H), 6.18 (d, J=9.8 Hz, 2H), 5.86 (d, J=11.5 Hz, 1H), 4.84-4.78 (m, 1H), 4.20 (dd, J=11.0, 6.7 Hz, 1H), 4.07-3.95 (m, 1H), 3.85 (d, J=3.1 Hz, 2H), 3.47 (t, J=6.2 Hz, 2H), 2.92-3.02 (m, 1H), 2.77 (s, 2H), 2.52 (s, 3H), 2.28-2.36 (m, 1H).

ESI-MS Calculated for [M+H]$^+$=424.16; Found: 424.10. The calculated value was consistent with the found value.

Preparation Example 128, Final Product BH23:
N-(3-methoxyphenyl)-1-methyl-9-(1-methyl-1,2,3,6-tetrahydropyridin-4-yl)-6,7-dihydro-5H-benzo[c][1,2,3]triazolo[1,5-a]azepin-7-amine 2,2,2-trifluoroacetate

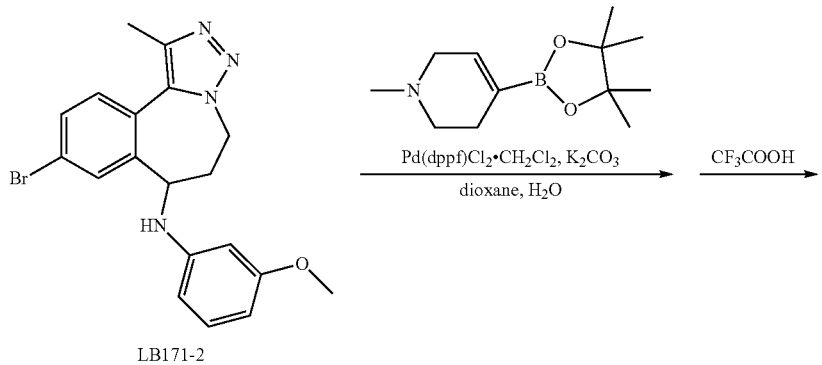

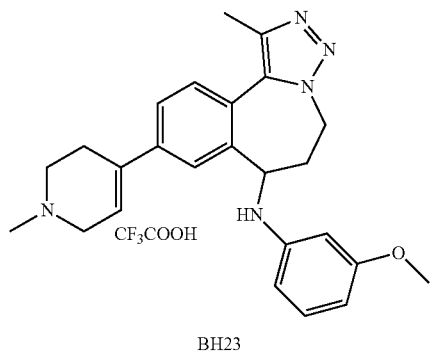

BH23

Synthesis of N-(3-methoxyphenyl)-1-methyl-9-(1-methyl-1,2,3,6-tetrahydropyridin-4-yl)-6,7-dihydro-5H-benzo[c][1,2,3]triazolo[1,5-a]azepin-7-amine 2,2,2-trifluoroacetate (BH23)

LB171-2 (63.5 mg, 0.16 mmol), 1-methyl-4-(4,4,5,5-tetramethyl-1,3,2-dioxaborolan-2-yl)-1,2,3,6-tetrahydropyridine (54.4 mg, 0.24 mmol), potassium carbonate (63.8 mg, 0.46 mmol), 1,1'-bis(diphenylphosphino)ferroceneldichloropalladium-dichloromethane complex (26.9 mg, 0.033 mmol), 1,4-dioxane (20 mL) and water (1 mL) were added into a reaction flask in sequence. The air in the reaction flask was replaced with nitrogen three times, and the system was heated to react under reflux under nitrogen protection. After the reaction was complete, the system was added with water (80 mL) and extracted with DCM (30 mL*2). The combined DCM phase was washed with saturated brine (50 mL), dried over anhydrous magnesium sulfate and filtered under suction. The filtrate was concentrated under reduced pressure and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 30.6 mg of the product.

ESI-MS Calculated for [M+H]$^+$=415.24; Found: 416.00. The calculated value was consistent with the found value.

Preparation Example 129, Final Product BH27:
1-(4-(7-((3-methoxyphenyl)amino)-1-methyl-6,7-dihydro-5H-benzo[c][1,2,3]triazolo[1,5-a]azepin-9-yl)-3,6-dihydropyridin-1(2H)-yl) ethan-1-one

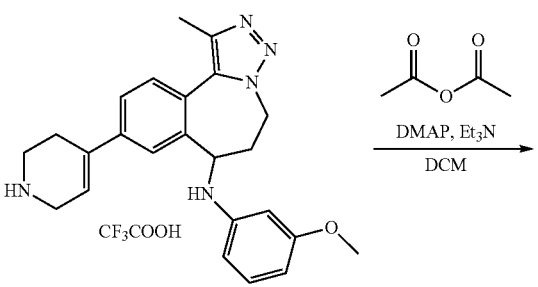

LC159

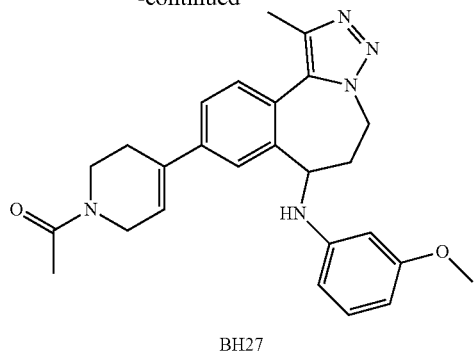

BH27

Synthesis of 1-(4-(7-((3-methoxyphenyl)amino)-1-methyl-6,7-dihydro-5H-benzo[c][1,2,3]triazolo[1,5-a]azepin-9-yl)-3,6-dihydropyridin-1(2H)-yl)ethan-1-one (BH27)

LC159 (56.7 mg, 0.11 mmol), DCM (10 mL), acetic anhydride (53.9 mg, 0.53 mmol), triethylamine (103.6 mg, 1.02 mmol) and DMAP (7.3 mg, 0.06 mmol) were added into a reaction flask and stirred under nitrogen protection at room temperature. The system was concentrated under reduced pressure, and the residue was separated by medium-pressure preparation column chromatography (mobile phase: A: purified water with 0.05% trifluoroacetic acid, B: acetonitrile with 0.05% trifluoroacetic acid) and lyophilized to obtain 12.6 mg of the product.

ESI-MS Calculated for $[M+H]^+$=444.23; Found: 444.00. The calculated value was consistent with the found value.

Preparation Example 130, Final Product BH29: 1-(4-(7-((3-chlorophenyl)amino)-1-methyl-6,7-dihydro-5H-benzo[c][1,2,3]triazolo[1,5-a]azepin-9-yl)-3,6-dihydropyridin-1 (2H)-yl)ethan-1-one

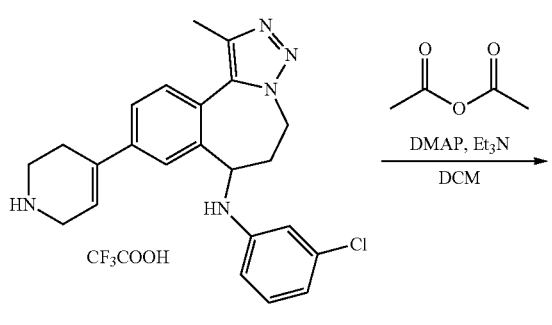

LC79

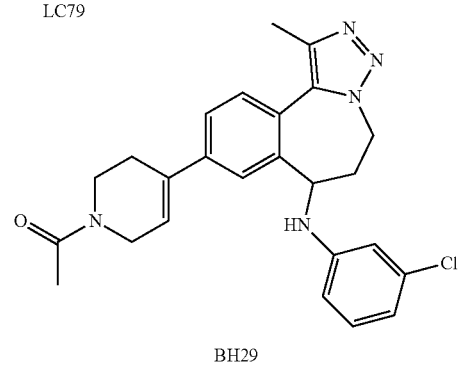

BH29

Synthesis of 1-(4-(7-((3-chlorophenyl)amino)-1-methyl-6,7-dihydro-5H-benzo[c][1,2,3]triazolo[1,5-a]azepin-9-yl)-3,6-dihydropyridin-1(2H)-yl)ethan-1-one (BH29)

LC79 (48.2 mg, 0.093 mmol), DCM (10 mL), acetic anhydride (70.9 mg, 0.69 mmol), triethylamine (105.8 mg, 1.04 mmol) and DMAP (10.3 mg, 0.084 mmol) were added into a reaction flask and reacted under nitrogen protection at room temperature. The system was concentrated under reduced pressure, and the residue was separated by medium-pressure preparation column chromatography (mobile phase: A: purified water with 0.05% trifluoroacetic acid, B: acetonitrile with 0.05% trifluoroacetic acid) and lyophilized to obtain 7.6 mg of the product.

ESI-MS Calculated for $[M+H]^+$=448.18; Found: 447.90. The calculated value was consistent with the found value.

Preparation Example 131, Final Product BH32: N-(3-chlorophenyl)-9-(1-isopropyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate

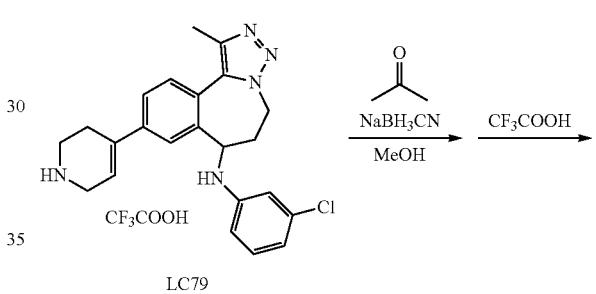

LC79

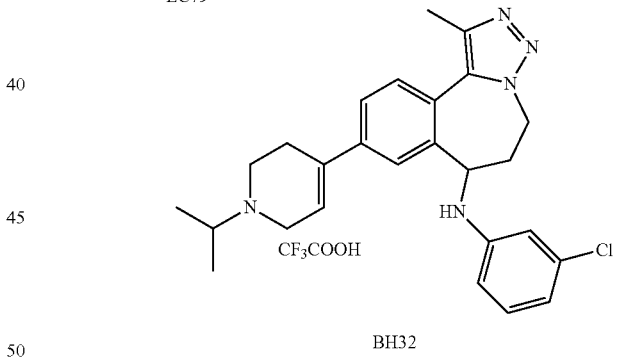

BH32

N-(3-chlorophenyl)-9-(1-isopropyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate (BH32)

LC79 (50.6 mg, 0.095 mmol), methanol (10 mL), acetone (2 mL) and sodium cyanoborohydride (362.6 mg, 5.77 mmol) were added into a reaction flask and reacted at room temperature. After the reaction was complete, the system was added with water (80 mL) and extracted with DCM (30 mL*2). The combined DCM phase was washed with saturated brine (50 mL), dried over anhydrous magnesium sulfate and filtered under suction. The filtrate was concentrated under reduced pressure, and the residue was separated by medium-pressure preparative column chromatography (mobile phase: A: purified water with 0.05% trifluoroacetic acid, B: acetonitrile with 0.05% trifluoroacetic acid) and lyophilized to obtain 8.4 mg of the product.

Product analysis: $^1$HNMR (CD$_3$OD, 400 MHz): δ 7.72-7.54 (m, 3H), 6.92 (t, J=8.1 Hz, 1H), 6.57-6.47 (m, 1H), 6.31 (t, J=2.1 Hz, 1H), 6.17 (t, J=11.8 Hz, 2H), 4.85-4.78 (m, 1H), 4.20 (dd, J=11.3, 6.8 Hz, 1H), 3.97-4.05 (m, 1H), 3.92 (s, 2H), 3.72 (d, J=12.3 Hz, 1H), 3.68-3.58 (m, 1H), 2.93-3.03 (m, 1H), 2.86 (s, 2H), 2.53 (s, 3H), 2.29-2.36 (m, 1H), 1.41 (d, J=6.8 Hz, 5H).

ESI-MS Calculated for [M+H]$^+$=448.22; Found: 447.90. The calculated value was consistent with the found value.

Preparation Example 132, Final Product BH33:
9-(1-ethyl-1,2,3,6-tetrahydropyridin-4-yl)-N-(3-methoxyphenyl)-1-methyl-6,7-dihydro-5H-benzo[c][1,2,3]triazolo[1,5-a]azepin-7-amine 2,2,2-trifluoroacetate

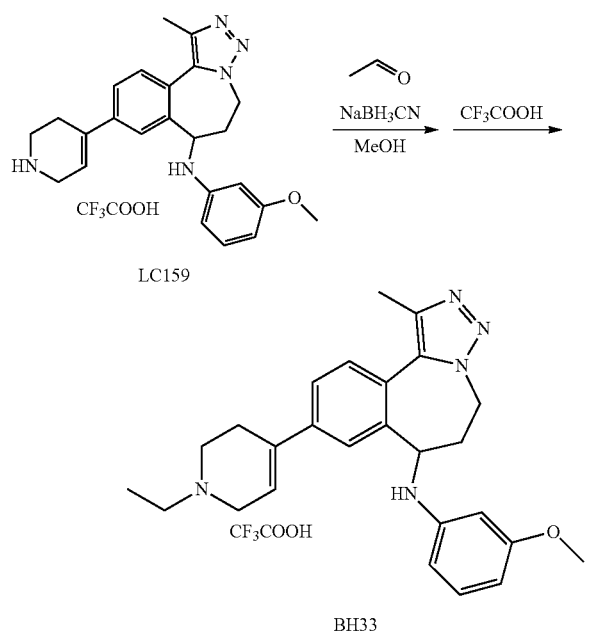

BH33

Synthesis of 9-(1-ethyl-1,2,3,6-tetrahydropyridin-4-yl)-N-(3-methoxyphenyl)-1-methyl-6,7-dihydro-5H-benzo[c][1,2,3]triazolo[1,5-a]azepin-7-amine 2,2,2-trifluoroacetate (BH33)

LC159 (57.2 mg, 0.11 mmol), methanol (10 mL), 40% acetaldehyde aqueous solution (0.5 mL) and sodium cyanoborohydride (128.8 mg, 2.05 mmol) were added into a reaction flask and reacted at room temperature. After the reaction was complete, the system was added with water (50 mL) and extracted with DCM (30 mL*2). The combined DCM phase was washed with saturated brine (50 mL), dried over anhydrous magnesium sulfate and filtered under suction. The filtrate was concentrated under reduced pressure, and the residue was separated by medium-pressure preparative column chromatography (mobile phase: A: purified water with 0.05% trifluoroacetic acid, B: acetonitrile with 0.05% trifluoroacetic acid) and lyophilized to obtain 6.9 mg of the product.

ESI-MS Calculated for [M+H]$^+$=430.25; Found: 430.00. The calculated value was consistent with the found value.

Preparation Example 133, Final Product BH36:
N-(3-chlorophenyl)-9-(1-ethyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate

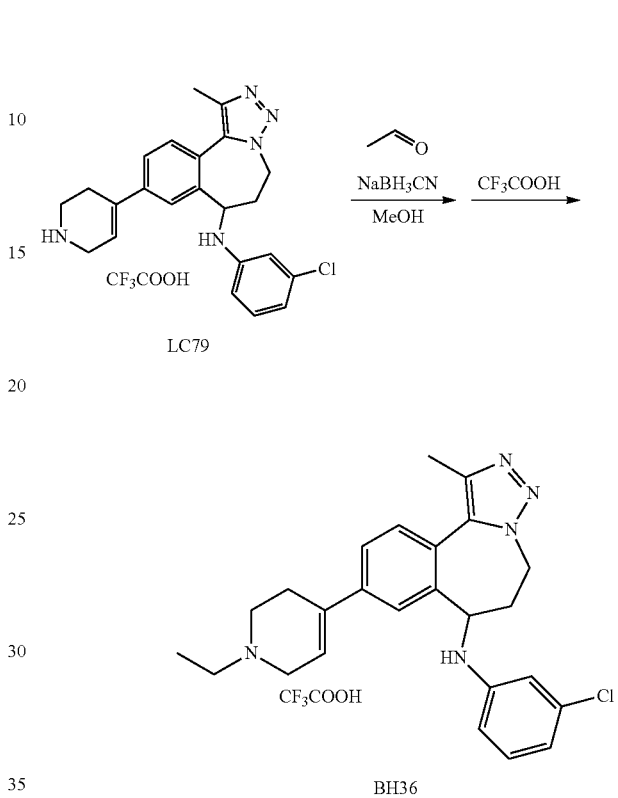

BH36

Synthesis of N-(3-chlorophenyl)-9-(1-ethyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate (BH36)

LC79 (57.2 mg, 0.11 mmol), methanol (10 mL), 40% acetaldehyde aqueous solution (0.5 mL) and sodium cyanoborohydride (128.8 mg, 2.05 mmol) were added into a reaction flask and reacted at room temperature. After the reaction was complete, the system was added with water (50 mL) and extracted with DCM (30 mL*2). The combined DCM phase was washed with saturated brine (50 mL), dried over anhydrous magnesium sulfate and filtered under suction. The filtrate was concentrated under reduced pressure, and the residue was separated by medium-pressure preparative column chromatography (mobile phase: A: purified water with 0.05% trifluoroacetic acid, B: acetonitrile with 0.05% trifluoroacetic acid) and lyophilized to obtain 6.9 mg of the product.

Product analysis: $^1$HNMR (CD$_3$OD, 400 MHz): δ 7.69-7.55 (m, 3H), 6.93 (t, J=8.1 Hz, 1H), 6.52 (dd, J=7.9, 1.9 Hz, 1H), 6.32 (t, J=2.1 Hz, 1H), 6.15 (dd, J=8.1, 2.3 Hz, 2H), 4.20 (dd, J=11.2, 6.8 Hz, 1H), 4.13-3.90 (m, 2H), 3.78 (d, J=17.5 Hz, 2H), 3.32-3.25 (m, 3H), 2.93-3.02 (m, 1H), 2.84 (s, 2H), 2.52 (s, 3H), 2.29-2.36 (m, 1H), 1.40 (t, J=7.4 Hz, 3H).

ESI-MS Calculated for [M+H]$^+$=434.20; Found: 434.00. The calculated value was consistent with the found value.

Preparation Example 134, Final Product BH37: 9-(1-isopropyl-1,2,3,6-tetrahydropyridin-4-yl)-N-(3-methoxyphenyl)-1-methyl-6,7-dihydro-5H-benzo[c][1,2,3]triazolo[1,5-a]azepin-7-amine 2,2,2-trifluoroacetate

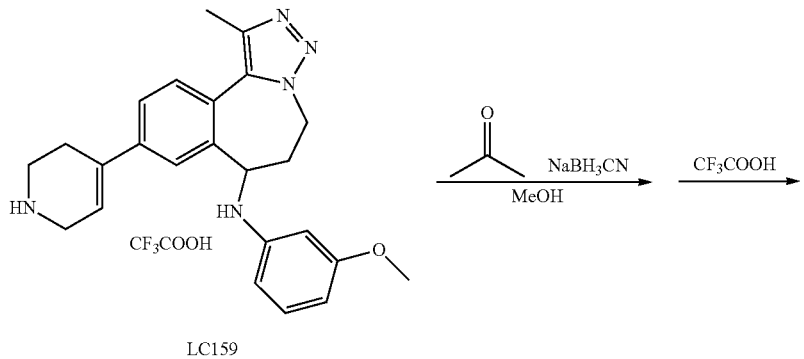

LC159

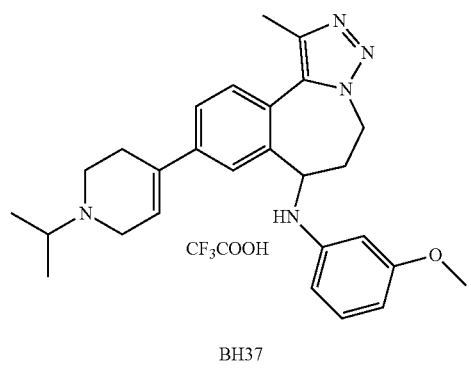

BH37

Synthesis of 9-(1-isopropyl-1,2,3,6-tetrahydropyridin-4-yl)-N-(methoxyphenyl)-1-methyl-6,7-dihydro-5H-benzo[c][1,2,3]triazolo[1,5-a]azepin-7-amine 2,2,2-trifluoroacetate (BH37)

LC159 (56.3 mg, 0.11 mmol), methanol (10 mL), acetone (1 mL) and sodium cyanoborohydride (290.3 mg, 4.62 mmol) were added into a reaction flask and reacted at room temperature overnight. After the reaction was complete, the system was added with water (100 mL) and extracted with DCM (30 mL*2). The combined DCM phase was washed with saturated brine (50 mL*2), dried over anhydrous magnesium sulfate and filtered under suction. The filtrate was concentrated under reduced pressure, and the residue was separated by medium-pressure preparative column chromatography (mobile phase: A: purified water with 0.05% trifluoroacetic acid, B: acetonitrile with 0.05% trifluoroacetic acid) and lyophilized to obtain 9.1 mg of the product.

ESI-MS Calculated for [M+H]$^+$=444.27; Found: 444.10. The calculated value was consistent with the found value.

Preparation Example 135, Final Product BH43: 7-(3-chlorophenoxy)-1-methyl-9-(1-methyl-1,2,3,6-tetrahydropyridin-4-yl)-6,7-dihydro-5H-benzo[c][1,2,3]triazolo[1,5-a]azepine 2,2,2-trifluoroacetate

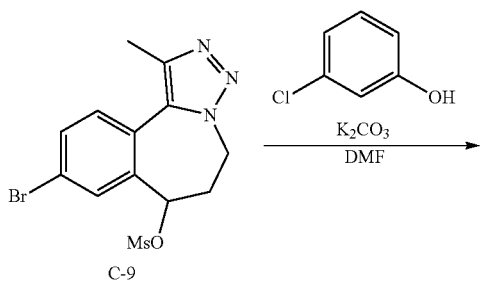

C-9

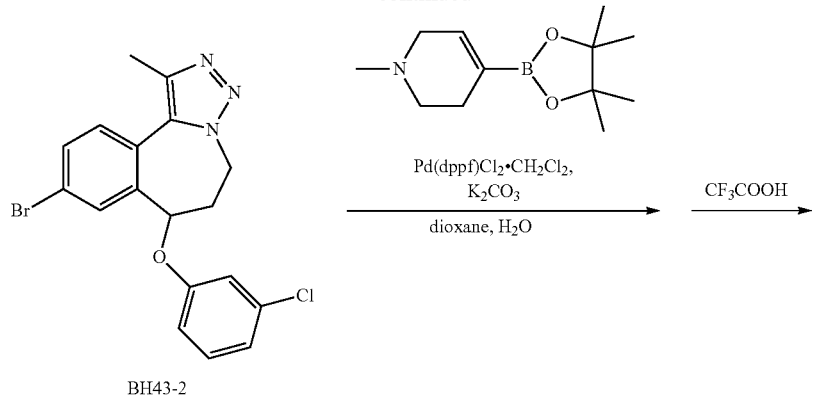

BH43-2

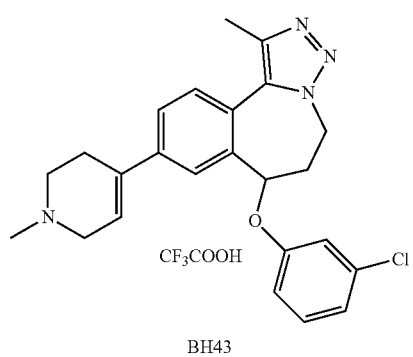

BH43

Step 1: Synthesis of 9-bromo-7-(3-chlorophenoxy)-1-methyl-6,7-dihydro-5H-benzo[c][1,2,3]triazolo[1,5-a]azepine (BH$_{43}$-2)

C-9 (196.8 mg, 0.53 mmol), 3-chlorophenol (145.6 mg, 1.13 mmol), DMF (15 mL), and anhydrous potassium carbonate (337.0 mg, 2.44 mmol) were added into a reaction flask and reacted at room temperature overnight. After the reaction was complete, the system was added with water (80 mL) and extracted with EA (20 mL, 15 mL). The combined EA phase was washed with saturated brine (50 mL), dried over anhydrous magnesium sulfate and filtered under suction. The filtrate was concentrated under reduced pressure, and the residue was separated by PLC to obtain 165.6 mg of the product with a yield of 77.2%.

ESI-MS Calculated for [M+H]$^+$=404.01; Found: 404.00. The calculated value was consistent with the found value.

Step 2: Synthesis of 7-(3-chlorophenoxy)-1-methyl-9-(1-methyl-1,2,3,6-tetrahydropyridin-4-yl)-6,7-dihydro-5H-benzo[c][1,2,3]triazolo[1,5-a]azepine2,2,2-trifluoroacetate (BH$_{43}$)

BH$_{43}$-2 (165.6 mg, 0.41 mmol), 1-methyl-4-(4,4,5,5-tetramethyl-1,3,2-dioxaborolan-2-yl)-1,2,3,6-tetrahydropyridine (130.4 mg, 0.58 mmol), potassium carbonate (160.2 mg, 1.16 mmol), [1,1'-bis(diphenylphosphino)ferrocene]dichloropalladium-dichloromethane complex (36.1 mg, 0.044 mmol), 1,4-dioxane (20 mL) and water (1 mL) were added into a reaction flask. The air in the reaction flask was replaced with nitrogen five times, and the system was heated to react under reflux under nitrogen protection. After the reaction was complete, the system was cooled to room temperature, added with water (60 mL) and extracted with DCM (30 mL*2). The combined DCM phase was washed with saturated brine (50 mL*2), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 36.8 mg of the product.

ESI-MS Calculated for [M+H]$^+$=421.17; Found: 421.00. The calculated value was consistent with the found value.

Preparation Example 136, Final Product BH46: N-cyclohexyl-1-methyl-9-(1-methyl-1H-pyrazol-4-yl)-6,7-dihydro-5H-benzo[c][1,2,3]triazolo[1,5-a]azepin-7-amine 2,2,2-trifluoroacetate

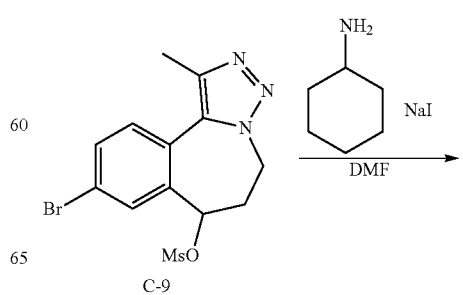

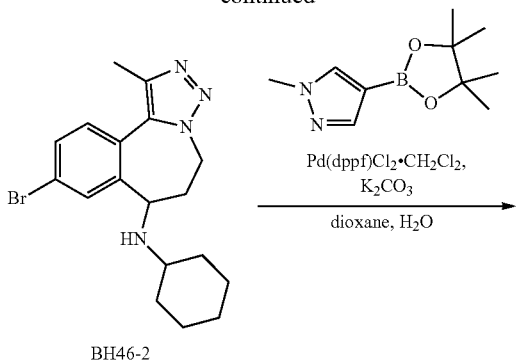

system was cooled to room temperature, added with water (50 mL) and extracted with EA (15 mL*2). The combined organic phase was washed with saturated brine (50 mL), dried over anhydrous magnesium sulfate and filtered under suction. The filtrate was concentrated under reduced pressure, and the residue was separated by PLC to obtain a crude, which was separated by medium-pressure preparative chromatography (mobile phase: A: purified water with 0.05% trifluoroacetic acid, B: acetonitrile with 0.05% trifluoroacetic acid) and lyophilized to obtain 2.6 mg of the product.

ESI-MS Calculated for [M+H]$^+$=377.26; Found: 376.90. The calculated value was consistent with the found value.

Preparation Example 137, Final Product BH57: N-cyclopentyl-1-methyl-9-(1-methyl-1H-pyrazol-4-yl)-6,7-dihydro-5H-benzo[c][1,2,3]triazolo[1,5-a]azepin-7-amine 2,2,2-trifluoroacetate Step 1: Synthesis of 9-bromo-N-cyclohexyl-1-methyl-6,7-dihydro-5H-benzo[c][1,2,3]triazolo[1,5-a]azepin-7-amine (BH$_{46}$-2)

C-9 (67.1 mg, 0.18 mmol), cyclohexylamine (180.3 mg, 1.82 mmol), DMF (5 mL) and sodium iodide (100.6 mg, 0.67 mmol) were added into a reaction flask and reacted at room temperature overnight under nitrogen protection. After the reaction was complete, the system was added with water (50 mL) and extracted with EA (15 mL*2). The combined EA phase was washed with saturated brine (30 mL), dried over anhydrous magnesium sulfate and filtered under suction. The filtrate was concentrated under reduced pressure, and the residue was separated by PLC to obtain 40.5 mg of the product with a yield of 60.0%.

ESI-MS Calculated for [M+H]$^+$=375.11; Found: 374.90. The calculated value was consistent with the found value.

Step 2: Synthesis of N-cyclohexyl-1-methyl-9-(1-methyl-1H-pyrazol-4-yl)-6,7-dihydro-5H-benzo[c][1,2,3]triazolo[1,5-a]azepin-7-amine 2,2,2-trifluoroacetate (BH$_{46}$)

BH$_{46}$-2 (40.5 mg, 0.11 mmol), 1-methyl-4-(4,4,5,5-tetramethyl-1,3,2-dioxaborolan-2-yl)-1H-pyrazole(44.3 mg, 0.21 mmol), potassium carbonate (46.2 mg, 0.33 mmol), 1,4-dioxane (15 mL) and water (0.6 mL) were added into a reaction flask, and the air in the flask was replaced with nitrogen three times. The system was added with Pd(dppf)Cl$_2$-dichloromethane complex (12.0 mg, 0.015 mmol), and the air in the flask was replaced with nitrogen again three times. The system was heated to reflux, and the reaction was monitored by LC-MS. After the reaction was complete, the The final product BH57 was prepared according to the preparation method of Preparation Example 136 except that the reactant cyclohexylamine in Preparation Example 136 was replaced with cyclopentylamine.

ESI-MS Calculated for [M+H]$^+$=363.22; Found: 363.00. The calculated value was consistent with the found value.

Preparation Example 138, Final Product BH81: 1-(4-(7-(3-chlorophenoxy)-1-methyl-6,7-dihydro-5H-benzo[c][1,2,3]triazolo[1,5-a]azepin-9-yl)-3,6-dihydropyridin-1(2H)-yl)ethan-1-one

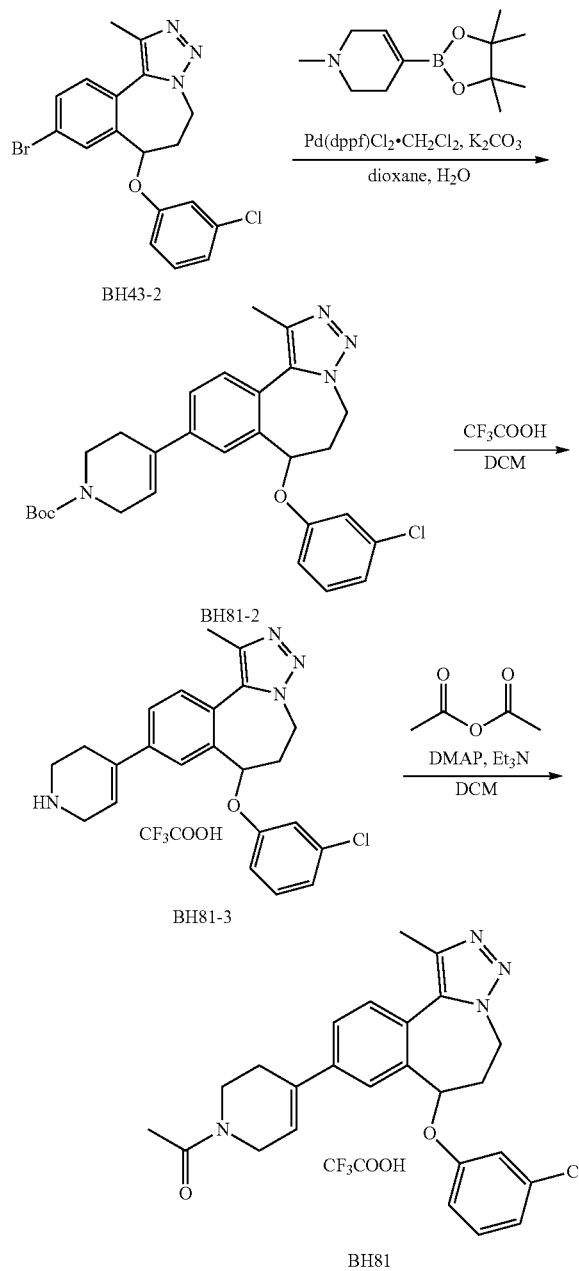

Step 1: Synthesis of tert-butyl 4-(7-(3-chlorophenoxy)-1-methyl-6,7-dihydro-5H-benzo[c][1,2,3]triazolo[1,5-a]azepin-9-yl)-3,6-dihydropyridine-1(2H)-carboxylate (BH81-2)

$BH_{43}$-2 (1.11 g, 2.74 mmol), tert-butyl 4-(4,4,5,5-tetramethyl-1,3,2-dioxaborolan-2-yl)-3,6-dihydropyridine-1(2H)-carboxylate (1.45 g, 4.69 mmol), potassium carbonate (1.16 g, 8.39 mmol), [1,1'-bis(diphenylphosphino)ferrocene]dichloropalladium-dichloromethane complex (0.31 g, 0.38 mmol), 1,4-dioxane (50 mL) and water (2 mL) were added into a reaction flask in sequence. The air in the reaction flask was replaced with nitrogen three times, and the system was heated to react under reflux under nitrogen protection. After the reaction was complete, the system was cooled down, added with water (100 mL) and extracted with EA (40 mL*2). The combined EA phase was washed with saturated brine (100 mL), dried over anhydrous magnesium sulfate and filtered under suction. The filtrate was concentrated under reduced pressure, and the residue was separated by column chromatography to obtain 863.4 mg of the product with a yield of 62.0%.

Step 2: Synthesis of 7-(3-chlorophenoxy)-1-methyl-9-(1,2,3,6-tetrahydropyridin-4-yl)-6,7-dihydro-5H-benzo[c][1,2,3]triazolo[1,5-a]azepine (BH81-3)

BH81-2 (86.7 mg, 0.21 mmol), DCM (10 mL), and trifluoroacetic acid (1 mL) were added into a reaction flask and reacted at room temperature. After the reaction was complete, the system was concentrated under reduced pressure. The residue was added with DCM (20 mL), and continually concentrated to dryness under reduced pressure, and the residue was directly used in the next reaction. The reaction yield of this step was calculated as 100%.
ESI-MS Calculated for $[M+H]^+$=407.16; Found: 407.10. The calculated value was consistent with the found value.

Step 3: Synthesis of 1-(4-(7-(3-chlorophenoxy)-1-methyl-6,7-dihydro-5H-benzo[c][1,2,3]triazolo[1,5-a]azepin-9-yl)-3,6-dihydropyridin-1(2H)-yl)ethan-1-one (BH81)

BH81-3 (obtained in the previous step, 0.21 mmol), DCM (20 mL), acetic anhydride (142.1 mg, 1.39 mmol), triethylamine (145.9 mg, 1.44 mmol) and DMAP (10.1 mg, 0.08 mmol) were added into a reaction flask and reacted at room temperature under nitrogen protection. After the reaction was complete, the system was added with 20 mL of DCM, washed with water (30 mL) and saturated brine (30 mL). The DCM phase was dried over anhydrous magnesium sulfate and filtered under suction. The filtrate was concentrated under reduced pressure, and the residue was separated by medium-pressure preparative column chromatography (mobile phase: A: purified water with 0.05% trifluoroacetic acid, B: acetonitrile with 0.05% trifluoroacetic acid) and lyophilized to obtain 14.1 mg of the product.
ESI-MS Calculated for $[M+H]^+$=449.17; Found: 449.10. The calculated value was consistent with the found value.

Preparation Example 139, Final Product BH86: 1-(4-(7-((3-chlorophenyl)amino)-1-methyl-6,7-dihydro-5H-benzo[c][1,2,3]triazolo[1,5-a]azepin-9-yl)-3,6-dihydropyridin-1 (2H)-yl)propan-1-one

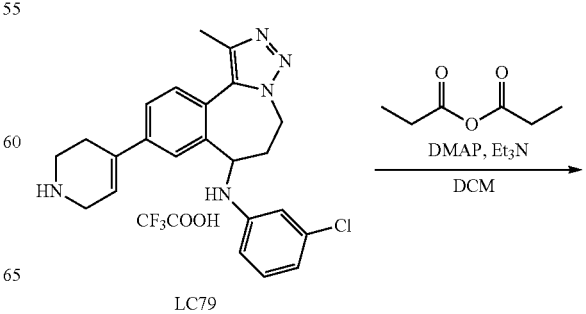

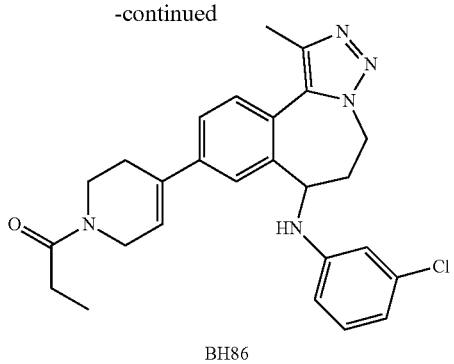

BH86

Synthesis of 1-(4-(7-((3-chlorophenyl)amino)-1-methyl-6,7-dihydro-5H-benzo[c][1,2,3]triazolo[1,5-a]azepin-9-yl)-3,6-dihydropyridin-1(2H)-yl)propan-1-one (BH86)

LC79 (52.0 mg, 0.10 mmol), DCM (20 mL), propionic anhydride (103.2 mg, 0.79 mmol), triethylamine (200.9 mg, 1.99 mmol) and DMAP (11.6 mg, 0.095 mmol) were added into a reaction flask and reacted at room temperature under nitrogen protection. After the reaction was complete, the system was concentrated under reduced pressure, and the residue was separated by medium-pressure preparative column chromatography (mobile phase: A: purified water with 0.05% trifluoroacetic acid, B: acetonitrile with 0.05% trifluoroacetic acid) and lyophilized to obtain 8.7 mg of the product.

Product analysis: $^1$HNMR (CDCl$_3$, 400 MHz): δ 7.55 (d, J=5.0 Hz, 1H), 7.48-7.40 (m, 2H), 6.98 (t, J=8.0 Hz, 1H), 6.69-6.63 (m, 1H), 6.35 (q, J=2.2 Hz, 1H), 6.19-6.07 (m, 2H), 4.78 (dd, J=14.2, 7.2 Hz, 1H), 4.39-4.22 (m, 2H), 4.13 (d, J=3.2 Hz, 1H), 4.00-4.08 (m, 2H), 3.77-3.89 (m, 1H), 3.67 (t, J=5.7 Hz, 1H), 2.96-3.05 (m, 1H), 2.54 (s, 3H), 2.36-2.47 (m, 3H), 2.18-2.26 (m, 1H), 1.20 (q, J=7.1 Hz, 3H).

ESI-MS Calculated for [M+H]$^+$=462.20; Found: 462.20. The calculated value was consistent with the found value.

Preparation Example 140, Final Product BH87: 9-(1-(sec-butyl)-1,2,3,6-tetrahydropyridin-4-yl)-N-(3-chlorophenyl)-1-methyl-6,7-dihydro-5H-benzo[c][1,2,3]triazolo[1,5-a]azepin-7-amine 2,2,2-trifluoroacetate

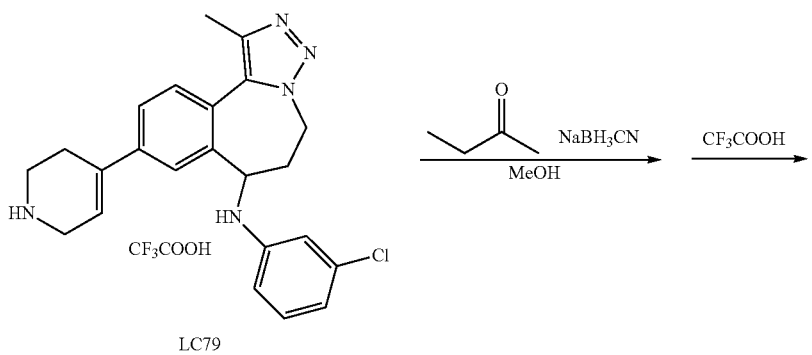

LC79

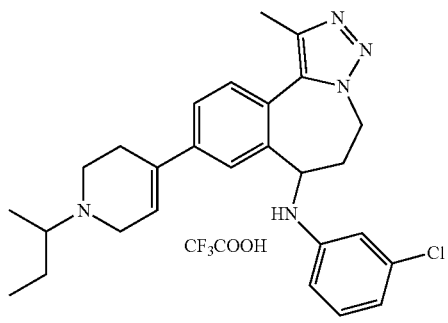

BH87

Synthesis of 9-(1-(s ec-butyl)-1,2,3,6-tetrahydro-pyridin-4-yl)-N-(3-chlorophenyl)-1-methyl-6,7-dihydro-5H-benzo[c][1,2,3]triazolo[1,5-a]azepin-7-amine 2,2,2-trifluoroacetate (BH87)

LC79 (100.3 mg, 0.19 mmol), methanol (15 mL), 2-butanone (0.49 g, 6.80 mmol) and sodium cyanoborohydride (0.39 g, 6.21 mmol) were added into a reaction flask and reacted at room temperature overnight. After the reaction was complete, the system was added with water (100 mL) and extracted with DCM (30 mL*2). The combined DCM phase was washed with saturated brine (80 mL), dried over anhydrous magnesium sulfate and filtered under suction. The filtrate was concentrated under reduced pressure, and the residue was separated by medium-pressure preparative column chromatography (mobile phase: A: purified water with 0.05% trifluoroacetic acid, B: acetonitrile with 0.05% trifluoroacetic acid) and lyophilized to obtain 30.9 mg of the product.

ESI-MS Calculated for [M+H]$^+$=462.23; Found: 462.20. The calculated value was consistent with the found value.

Preparation Example 141, Final Product BH104: N-(3-chlorophenyl)-9-(1-cyclohexyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate

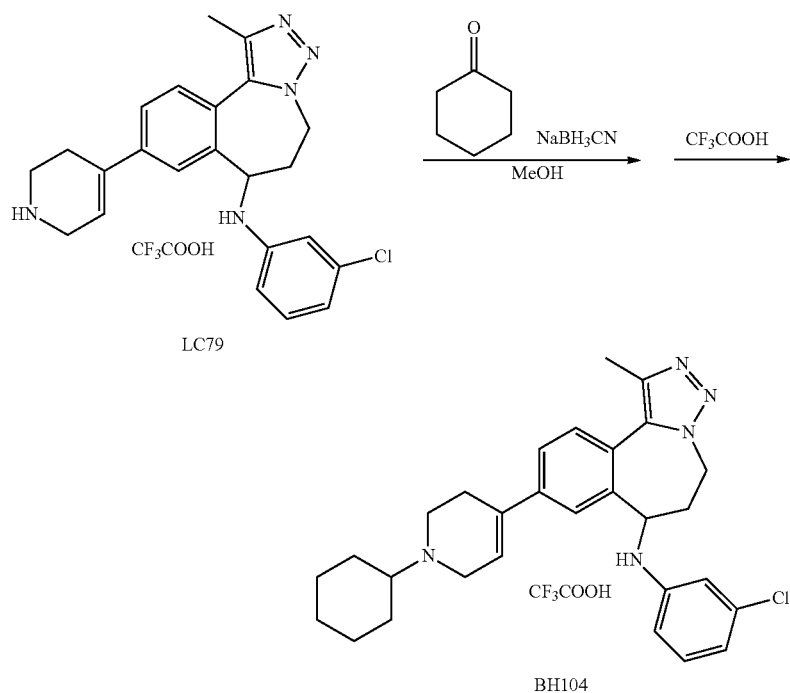

Synthesis of N-(3-chlorophenyl)-9-(1-cyclohexyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate (BH104)

LC79 (54.9 mg, 0.11 mmol), methanol (15 mL), cyclohexanone (0.62 g, 6.32 mmol) and sodium cyanoborohydride (0.36 g, 5.73 mmol) were added into a reaction flask and reacted at room temperature. After the reaction was complete, the system was added with water (80 mL) and extracted with DCM (30 mL*2). The combined DCM phase was washed with saturated brine (60 mL), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 18.8 mg of the product.

ESI-MS Calculated for [M+H]$^+$=488.25; Found: 488.30. The calculated value was consistent with the found value.

Preparation Example 142, Final Product BH107:
N-(3-chlorophenyl)-9-(1-cyclopentyl-1,2,3,6-tetra-hydropyridin-4-yl)-1-methyl-6,7-dihydro-5H-benzo[c][1,2,3]triazolo[1,5-a]azepin-7-amine 2,2,2-trifluoroacetate

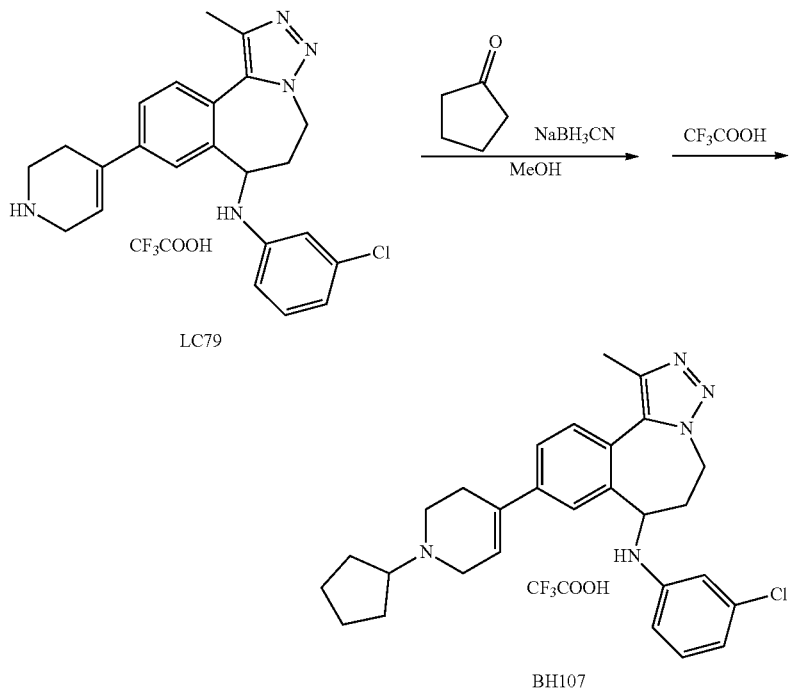

Synthesis of N-(3-chlorophenyl)-9-(1-cyclopentyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate (BH107)

LC79 (54.3 mg, 0.10 mmol), methanol (25 mL), cyclopentanone (0.26 g, 3.09 mmol) and sodium cyanoborohydride (0.37 g, 5.89 mmol) were added into a reaction flask and reacted at room temperature. After the reaction was complete, the system was added with water (100 mL) and extracted with DCM (30 mL*2). The combined DCM phase was washed with saturated brine (100 mL), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 7.4 mg of the product.

ESI-MS Calculated for $[M+H]^+$=474.23; Found: 474.20. The calculated value was consistent with the found value.

Preparation Example 143, Final Product BH108:
9-(1-butyl-1,2,3,6-tetrahydropyridin-4-yl)-N-(3-chlorophenyl)-1-methyl-6,7-dihydro-5H-benzo[c][1,2,3]triazolo[1,5-a]azepin-7-amine 2,2,2-trifluoroacetate

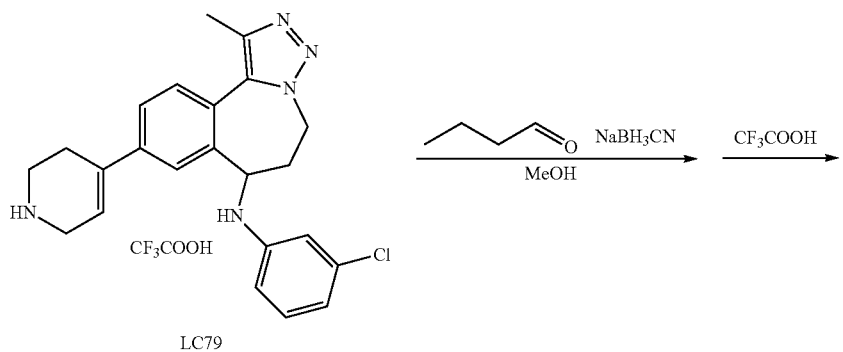

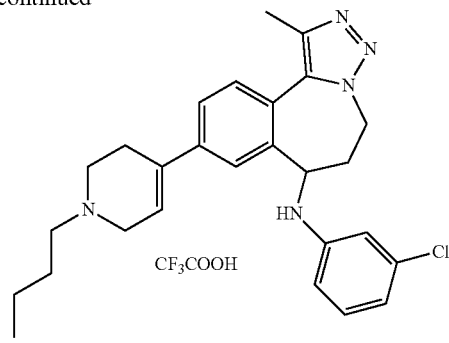

BH108

Synthesis of 9-(1-butyl-1,2,3,6-tetrahydropyridin-4-yl)-N-(3-chlorophenyl)-1-methyl-6,7-dihydro-5H-benzo[c][1,2,3]triazolo[1,5-a]azepin-7-amine 2,2,2-trifluoroacetate (BH108)

LC79 (57.8 mg, 0.11 mmol), methanol (15 mL), n-butyraldehyde (0.16 g, 2.22 mmol) and sodium cyanoborohydride (0.21 g, 3.34 mmol) were added into a reaction flask and reacted at room temperature. After the reaction was complete, the system was added with water (100 mL) and extracted with DCM (35 mL*2). The combined DCM phase was washed with saturated brine (100 mL), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 10.2 mg of the product.

ESI-MS Calculated for [M+H]$^+$=463.23; Found: 463.20. The calculated value was consistent with the found value.

Preparation Example 144, Final Product BH120: N-(3-chlorophenyl)-1-methyl-9-(1-propyl-1,2,3,6-tetrahydropyridin-4-yl)-6,7-dihydro-5H-benzo[c][1,2,3]triazolo[1,5-a]azepin-7-amine 2,2,2-trifluoroacetate

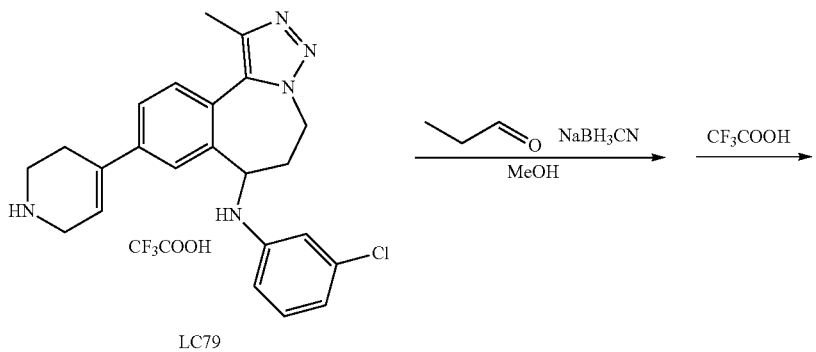

LC79

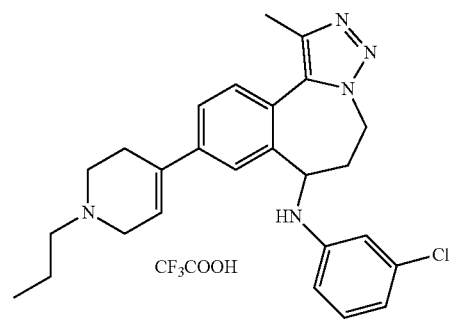

BH120

Synthesis of N-(3-chlorophenyl)-1-methyl-9-(1-propyl-1,2,3,6-tetrahydropyridin-4-yl)-6,7-dihydro-5H-benzo[c][1,2,3]triazolo[1,5-a]azepin-7-amine 2,2,2-trifluoroacetate (BH120)

LC79 (57.2 mg, 0.11 mmol), methanol (15 mL), n-propionaldehyde (63.3 mg, 1.10 mmol) and sodium cyanoborohydride (0.13 g, 2.07 mmol) were added into a reaction flask and reacted at room temperature. After the reaction was complete, the system was added with water (100 mL) and extracted with DCM (25 mL*3). The combined DCM phase was washed with saturated brine (50 mL*2), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 9.7 mg of the product.

ESI-MS Calculated for $[M+H]^+$=448.22; Found: 448.10. The calculated value was consistent with the found value.

Preparation Example 145, Final Product BH123: (4-(7-((3-chlorophenyl)amino)-1-methyl-6,7-dihydro-5H-benzo[c][1,2,3]triazolo[1,5-a]azepin-9-yl)-3,6-dihydropyridin-1 (2H)-yl) (cyclopropyl) methanone

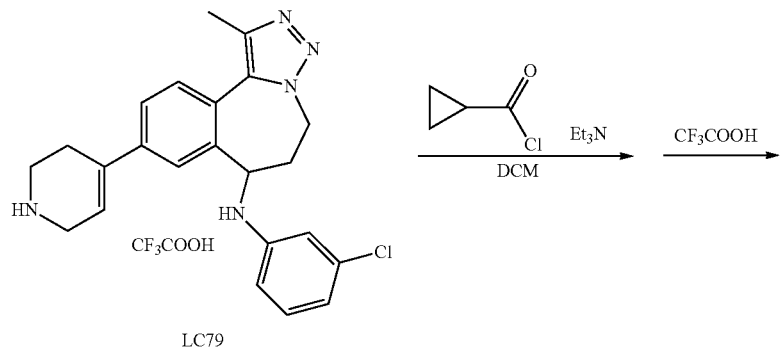

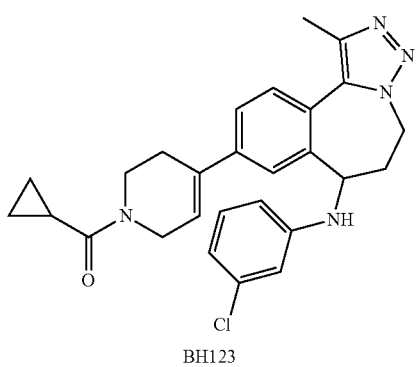

Synthesis of 4-(7-((3-chlorophenyl)amino)-1-methyl-6,7-dihydro-5H-benzo[c][1,2,3]triazolo[1,5-a]azepin-9-yl)-3,6-dihydropyridin-1(2H)-yl) (cyclopropyl)methanone (BH123)

LC79 (57.2 mg, 0.11 mmol), DCM (20 mL), cyclopropanecarbonyl chloride (36.2 mg, 0.35 mmol) and triethylamine (103.6 mg, 1.02 mmol) were added into a reaction flask and reacted at room temperature under nitrogen protection. After the reaction was complete, the residue was concentrated under reduced pressure, and the residue was separated by medium-pressure preparative column chromatography (mobile phase: A: purified water with 0.05% trifluoroacetic acid, B: acetonitrile with 0.05% trifluoroacetic acid) and lyophilized to obtain 6.7 mg of the product.

ESI-MS Calculated for $[M+H]^+$=474.20; Found: 474.20. The calculated value was consistent with the found value.

Preparation Example 146, Final Product BH159: N-(3-chlorophenyl)-9-(1-cyclobutyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate

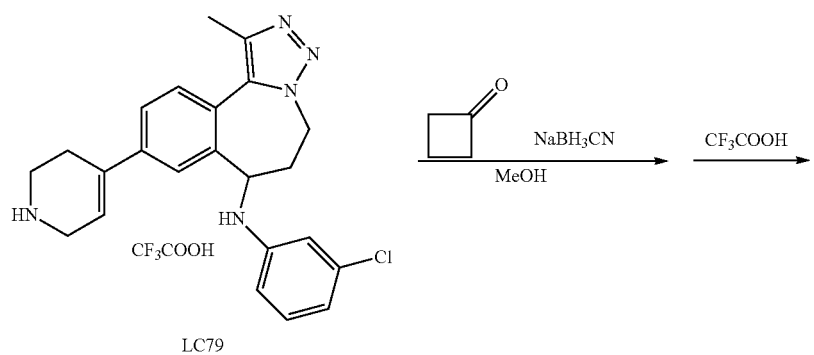

LC79

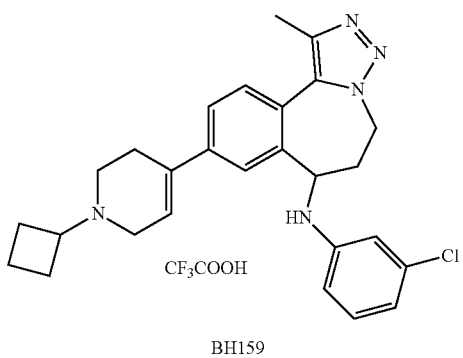

BH159

Synthesis of N-(3-chlorophenyl)-9-(1-cyclobutyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate (BH159)

LC79 (52.0 mg, 0.10 mmol), methanol (15 mL), cyclobutanone (60.2 mg, 0.86 mmol) and sodium cyanoborohydride (0.12 g, 1.91 mmol) were added into a reaction flask and reacted at room temperature. After the reaction was complete, the system was added with water (50 mL) and extracted with DCM (30 mL*2). The combined DCM phase was washed with saturated brine (50 mL*2), dried over anhydrous magnesium sulfate and filtered under suction. The filtrate was concentrated under reduced pressure, and the residue was separated by medium-pressure preparative column chromatography (mobile phase: A: purified water with 0.05% trifluoroacetic acid, B: acetonitrile with 0.05% trifluoroacetic acid) and lyophilized to obtain 25.6 mg of the product.

ESI-MS Calculated for [M+H]$^+$=460.22; Found: 460.20.
The calculated value was consistent with the found value.

Preparation Example 147, Final Product BH187:
N-(5-chloro-2-fluorophenyl)-9-(1-cyclohexyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate

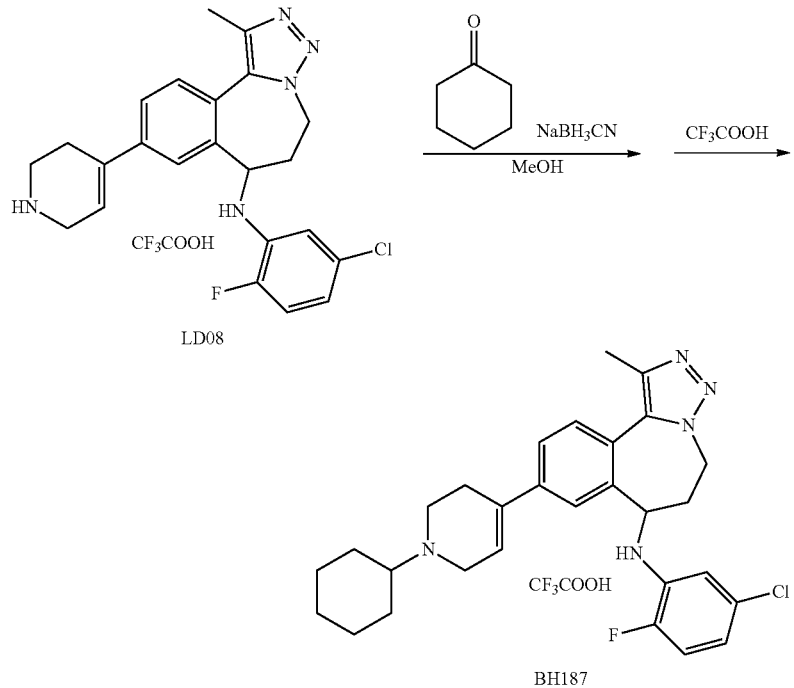

Synthesis of N-(5-chloro-2-fluorophenyl)-9-(1-cyclohexyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate (BH187)

LD08 (46.7 mg, 0.087 mmol), methanol (15 mL), cyclohexanone (0.5 mL) and sodium cyanoborohydride (0.19 g, 3.02 mmol) were added into a reaction flask and reacted at room temperature. After the reaction was complete, the system was added with water (80 mL) and extracted with DCM (35 mL*2). The combined DCM phase was washed with saturated brine (100 mL), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 13.0 mg of the product.

ESI-MS Calculated for [M+H]$^+$=506.24; Found: 506.40.
The calculated value was consistent with the found value.

Preparation Example 148, Final Product BH190:
N-(5-chloro-2-fluorophenyl)-9-(1-cyclopentyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate

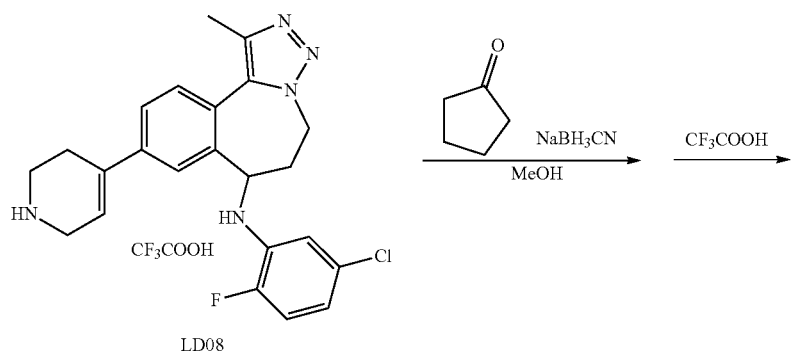

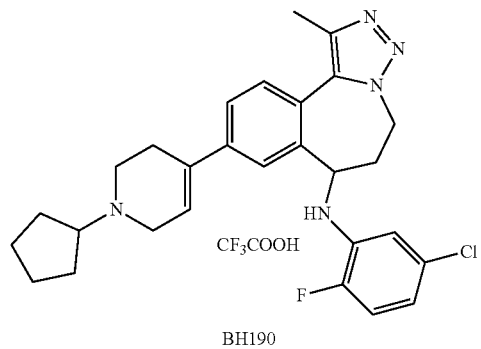

BH190

Synthesis of N-(5-chloro-2-fluorophenyl)-9-(1-cyclopentyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate (BH190)

LD08 (47.9 mg, 0.089 mmol), methanol (15 mL), cyclopentanone (0.5 mL) and sodium cyanoborohydride (0.16 g, 2.55 mmol) were added into a reaction flask and reacted at room temperature. After the reaction was complete, the system was added with water (80 mL) and extracted with DCM (30 mL*2). The combined DCM phase was washed with saturated brine (100 mL), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 17.6 mg of the product.

ESI-MS Calculated for $[M+H]^+$=492.23; Found: 492.00. The calculated value was consistent with the found value.

Preparation Example 149, Final Product BH192: 1-(4-(7-((5-chloro-2-fluorophenyl)amino)-1-methyl-6,7-dihydro-5H-benzo[c][1,2,3]triazolo[1,5-a]azepin-9-yl)-3,6-dihydropyridin-1 (2H)-yl)ethan-1-one

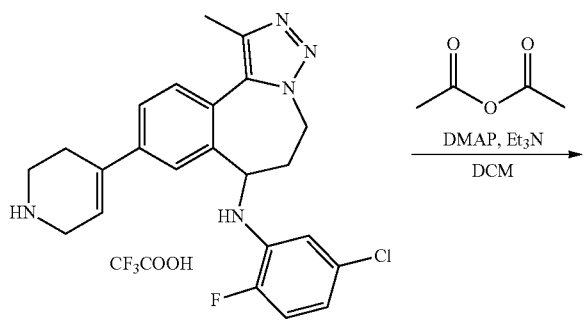

LD08

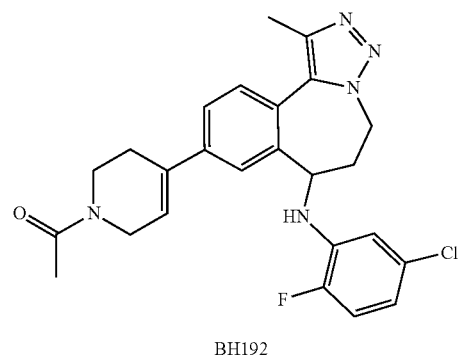

BH192

Synthesis of 1-(4-(7-((5-chloro-2-fluorophenyl) amino)-1-methyl-6,7-dihydro-5H-benzo[c][1,2,3] triazolo[1,5-a]azepin-9-yl)-3,6-dihydropyridin-1 (2H)-yl)ethan-1-one (BH192)

LD08 (66.4 mg, 0.12 mmol), DCM (20 mL), acetic anhydride (118.0 mg, 1.16 mmol), triethylamine (126.8 mg, 1.25 mmol) and DMAP (10.9 mg, 0.089 mmol) were added into a reaction flask, and under nitrogen protection, the reaction was carried out at room temperature. After the reaction was complete, the system was added with DCM (20 mL), washed with water (50 mL) and saturated brine (50 mL), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 10.6 mg of the product.

ESI-MS Calculated for $[M+H]^+$=466.17; Found: 466.20. The calculated value was consistent with the found value.

Preparation Example 150, Final Product BI23:
N-(3-chloro-4-fluorophenyl)-9-(1-cyclobutyl-1,2,3,6-tetrahydropyridin-4-yl)-1-methyl-6,7-dihydro-5H-benzo[c][1,2,3]triazolo[1,5-a]azeuin-7-amine 2,2,2-trifluoroacetate

Preparation Example 151, Final Product BI24:
N-(3-chloro-4-fluorophenyl)-9-(1-isopropyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate

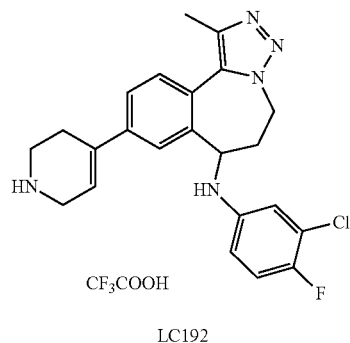

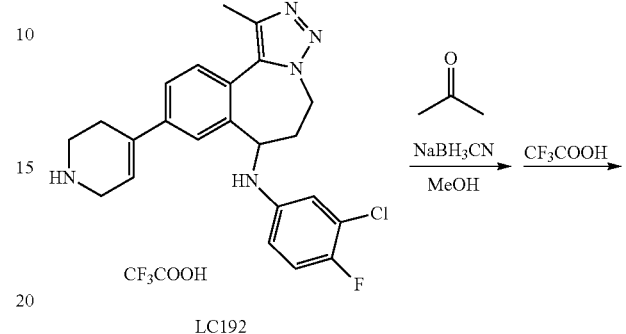

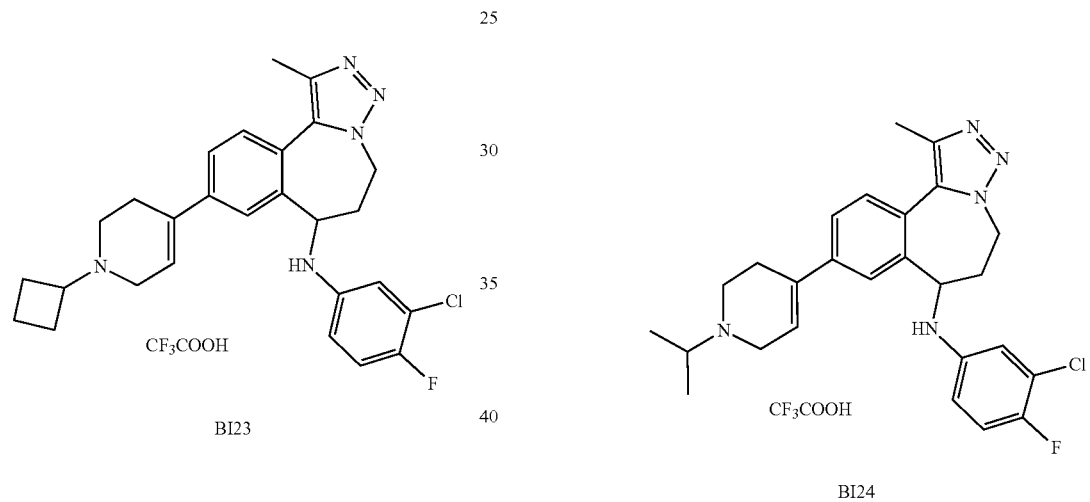

Synthesis of N-(3-chloro-4-fluorophenyl)-9-(1-cyclobutyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate (BI23)

LC192 (51.1 mg, 0.095 mmol), methanol (15 mL), cyclobutanone (0.51 g, 7.27 mmol) and sodium cyanoborohydride (0.25 g, 3.98 mmol) were added into a reaction flask and reacted at room temperature. After the reaction was complete, the system was added with water (100 mL) and extracted with DCM (30 mL*2). The combined DCM phase was washed with saturated brine (100 mL), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 3.8 mg of the product.

ESI-MS Calculated for NA-W=478.21; Found: 478.50. The calculated value was consistent with the found value.

Synthesis of N-(3-chloro-4-fluorophenyl)-9-(1-isopropyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate (BI24)

LC192 (51.7 mg, 0.97 mmol), methanol (20 mL), acetone (0.7 mL) and sodium cyanoborohydride (0.32 g, 5.09 mmol) were added into a reaction flask and reacted at room temperature. After the reaction was complete, the system was added with water (100 mL) and extracted with DCM (30 mL*2). The combined DCM phase was washed with saturated brine (100 mL), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 9.0 mg of the product.

ESI-MS Calculated for [M+H]$^+$=466.21; Found: 466.40. The calculated value was consistent with the found value.

403

Preparation Example 152, Final Product BI26:
N-(5-chloro-2-fluorophenyl)-9-(1-cyclobutyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate

404

Preparation Example 153, Final Product BI29:
3-((9-(1-cyclohexyl-1,2,3,6-tetrahydropyridin-4-yl)-1-methyl-6,7-dihydro-5H-benzo[c][1,2,3]triazolo[1,5-a]azepin-7-yl)amino)benzonitrile 2,2,2-trifluoroacetate

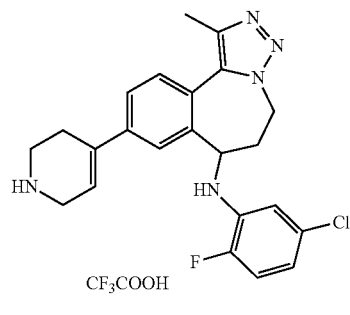

LD08

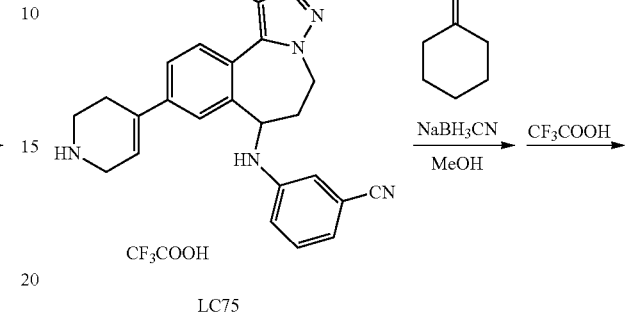

LC75

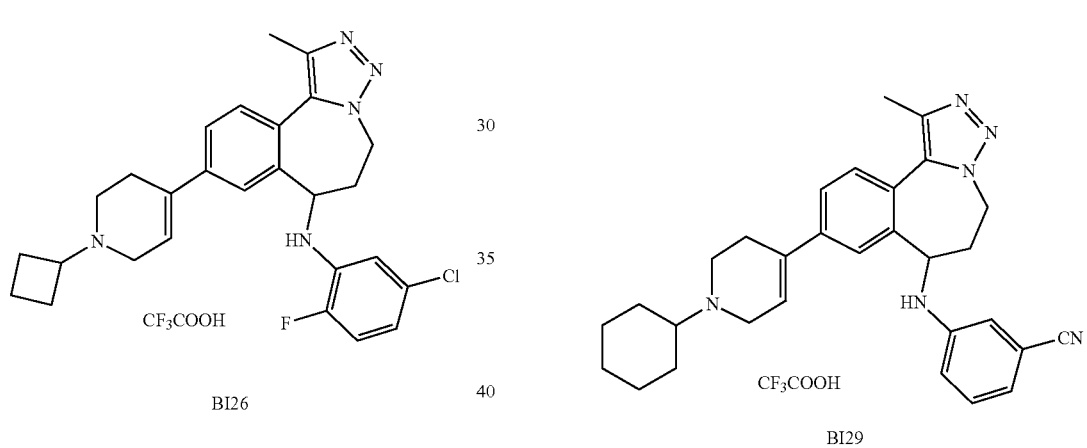

BI26

BI29

Synthesis of N-(5-chloro-2-fluorophenyl)-9-(1-cyclobutyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate (BI26)

LD08 (75.3 mg, 0.14 mmol), methanol (15 mL), cyclobutanone (0.26 g, 3.71 mmol) and sodium cyanoborohydride (0.26 g, 4.14 mmol) were added into a reaction flask and reacted at room temperature. After the reaction was complete, the system was added with water (100 mL) and extracted with DCM (50 mL, 25 mL). The combined DCM phase was washed with saturated brine (50 mL*2), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 30.5 mg of the product.

ESI-MS Calculated for NA-W=478.21; Found: 478.80. The calculated value was consistent with the found value.

Synthesis of 3-((9-(1-cyclohexyl-1,2,3,6-tetrahydropyridin-4-yl)-1-methyl-6,7-dihydro-5H-benzo[c][1,2,3]triazolo[1,5-a]azepin-7-yl)amino)benzonitrile 2,2,2-trifluoroacetate (BI29)

LC75 (49.0 mg, 0.096 mmol), methanol (15 mL), cyclohexanone (0.8 mL) and sodium cyanoborohydride (0.26 g, 4.14 mmol) were added into a reaction flask and reacted at room temperature. After the reaction was complete, the system was added with water (100 mL) and extracted with DCM (30 mL*2). The combined DCM phase was washed with saturated brine (50 mL*2), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 7.6 mg of the product.

ESI-MS Calculated for [M+H]$^+$=479.28; Found: 479.40. The calculated value was consistent with the found value.

Preparation Example 154, Final Product BI31:
3-((9-(1-cyclopentyl-1,2,3,6-tetrahydropyridin-4-yl)-1-methyl-6,7-dihydro-5H-benzo[c][1,2,3]triazolo[1,5-a]azepin-7-yl)amino)benzonitrile 2,2,2-trifluoroacetate

Preparation Example 155, Final Product BI34:
3-((9-(1-isopropyl-1,2,3,6-tetrahydropyridin-4-yl)-1-methyl-6,7-dihydro-5H-benzo[c][1,2,3]triazolo[1,5-a]azepine7-yl)amino)benzonitrile 2,2,2-trifluoroacetate

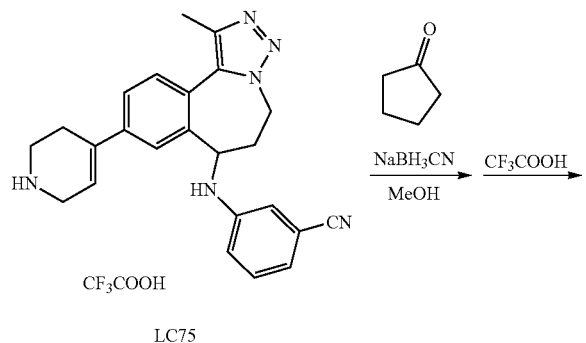

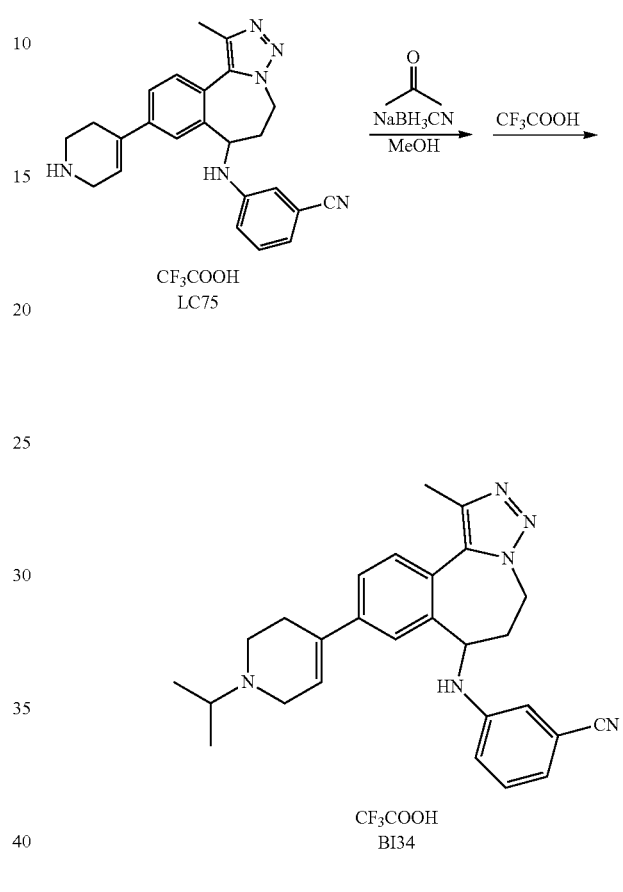

Synthesis of 3-((9-(1-cyclopentyl-1,2,3,6-tetrahydropyridin-4-yl)-1-methyl-6,7-dihydro-5H-benzo[c][1,2,3]triazolo[1,5-a]azepin-7-yl)amino)benzonitrile 2,2,2-trifluoro acetate (BI31)

LC75 (44.9 mg, 0.088 mmol), methanol (15 mL), cyclopentanone (0.5 mL) and sodium cyanoborohydride (0.23 g, 3.66 mmol) were added into a reaction flask and reacted at room temperature. After the reaction was complete, the system was added with water (100 mL) and extracted with DCM (40 mL*2). The combined DCM phase was washed with saturated brine (50 mL*2), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 5.0 mg of the product.

ESI-MS Calculated for [M+H]$^+$=465.27; Found: 465.40. The calculated value was consistent with the found value.

Synthesis of 3-((9-(1-isopropyl-1,2,3,6-tetrahydropyridin-4-yl)-1-methyl-6,7-dihydro-5H-benzo[c][1,2,3]triazolo[1,5-a]azepine7-yl)amino)benzonitrile 2,2,2-trifluoroacetate (BI34)

LC75 (47.5 mg, 0.093 mmol), methanol (15 mL), acetone (1 mL) and sodium cyanoborohydride (0.26 g, 4.14 mmol) were added into a reaction flask and reacted at room temperature. After the reaction was complete, the system was added with water (100 mL) and extracted with DCM (50 mL, 25 mL). The combined DCM phase was washed with saturated brine (100 mL), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 4.4 mg of the product.

ESI-MS Calculated for [M+H]$^+$=439.25; Found: 439.40. The calculated value was consistent with the found value.

407

Preparation Example 156, Final Product BI36:
3-(((9-(1-cyclobutyl-1,2,3,6-tetrahydropyridin-4-yl))-1-methyl-6,7-dihydro-5H-benzo[c][1,2,3]triazolo[1,5-a]azepin-7-yl)amino)benzonitrile 2,2,2-trifluoroacetate

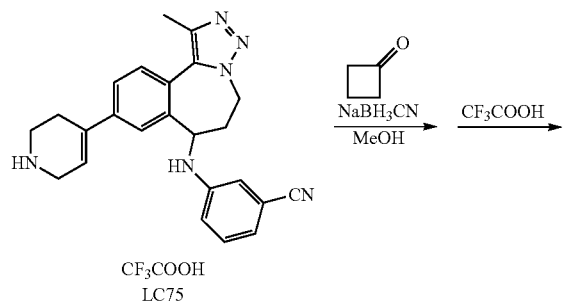

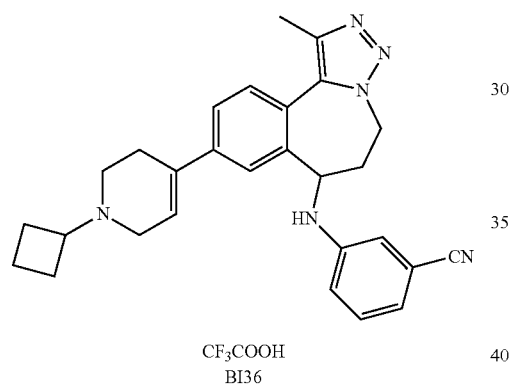

Synthesis of 3-(((9-(1-cyclobutyl-1,2,3,6-tetrahydropyridin-4-yl))-1-methyl-6,7-dihydro-5H-benzo[c][1,2,3]triazolo[1,5-a]azepin-7-yl)amino)benzonitrile 2,2,2-trifluoroacetate (BI36)

LC75 (46.5 mg, 0.091 mmol), methanol (15 mL), cyclobutanone (0.18 g, 2.56 mmol) and sodium cyanoborohydride (0.21 g, 3.34 mmol) were added into a reaction flask and reacted at room temperature. After the reaction was complete, the system was added with water (50 mL) and extracted with DCM (25 mL*2). The combined DCM phase was washed with saturated brine (50 mL*2), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 9.1 mg of the product.

ESI-MS Calculated for [M+H]$^+$=451.25; Found: 451.40. The calculated value was consistent with the found value.

408

Preparation Example 157, Final Product BI37:
3-((9-(1-ethyl-1,2,3,6-tetrahydropyridin-4-yl)-1-methyl-6,7-dihydro-5H-benzo[c][1,2,3]triazolo[1,5-a]azepin-7-yl)amino)benzonitrile 2,2,2-trifluoroacetate

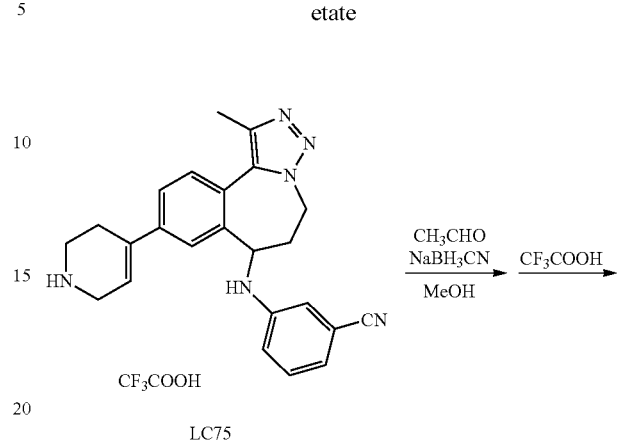

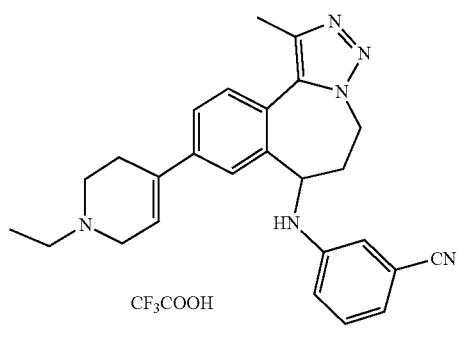

Synthesis of 3-((9-(1-ethyl-1,2,3,6-tetrahydropyridin-4-yl)-1-methyl-6,7-dihydro-5H-benzo[c][1,2,3]triazolo[1,5-a]azepin-7-yl)amino)benzonitrile 2,2,2-trifluoroacetate (BI37)

LC75 (51.4 mg, 0.10 mmol), methanol (15 mL), acetaldehyde aqueous solution (1 mL, content 40%) and sodium cyanoborohydride (0.36 g, 5.73 mmol) were added into a reaction flask and reacted at room temperature. After the reaction was complete, the system was added with water (100 mL) and extracted with DCM (50 mL*2). The combined DCM phase was washed with saturated brine (50 mL*2), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 14.6 mg of the product.

ESI-MS Calculated for [M+H]$^+$=425.24; Found: 425.50. The calculated value was consistent with the found value.

Preparation Example 158, Final Product BI55: 9-(1-cyclopentyl-1,2,3,6-tetrahydropyridin-4-yl)-1-methyl-N-(3-(methylsulfonyl)phenyl)-6,7-dihydro-5H-benzo[c][1,2,3]triazolo[1,5-a]azepin-7-amine 2,2,2-trifluoroacetate

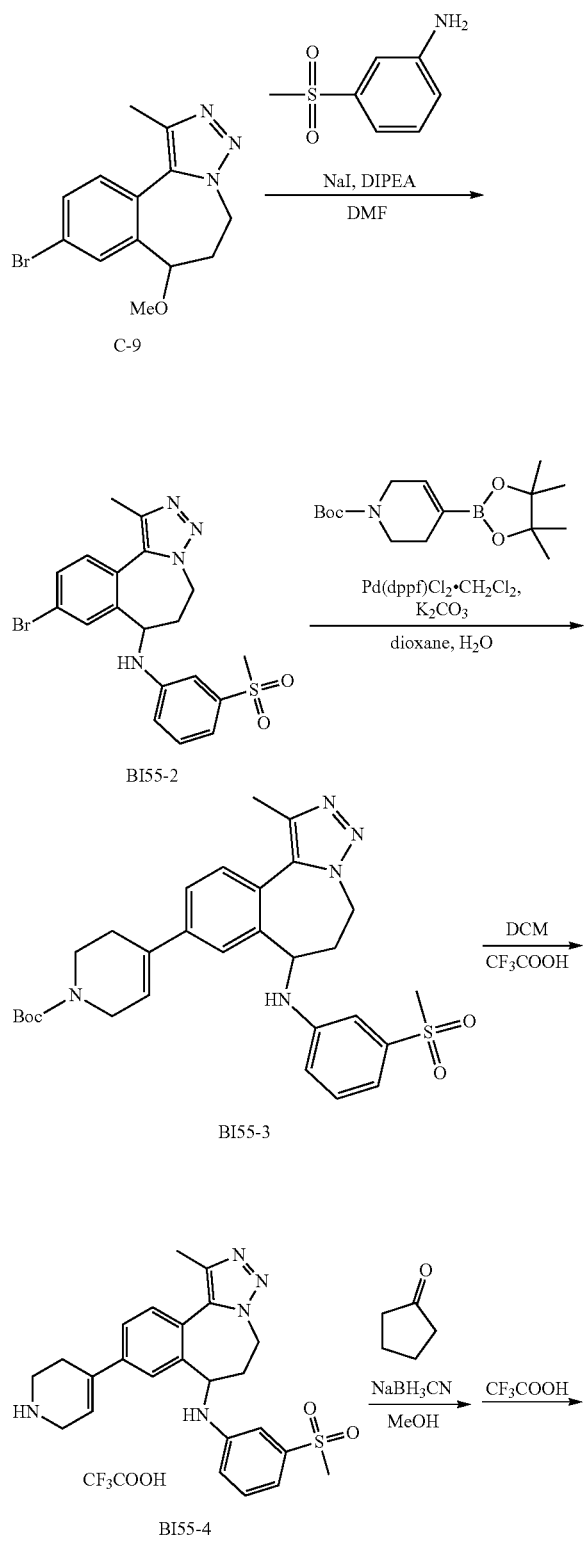

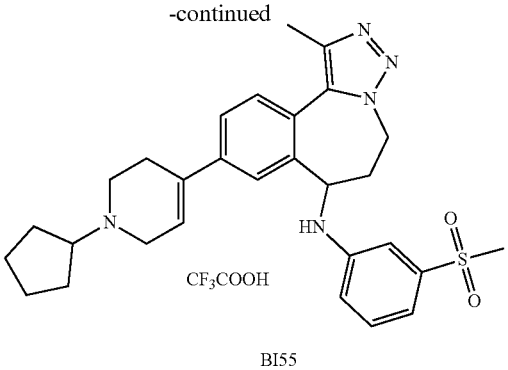

Step 1: Synthesis of 9-bromo-1-methyl-N-(3-(methylsulfonyl)phenyl)-6,7-dihydro-5H-benzo[c][1,2,3]triazolo[1,5-a]azepin-7-amine (BI55-2)

C-9 (801.3 mg, 2.15 mmol), 3-methylsulfonylaniline (751.9 mg, 4.39 mmol), DMF (100 mL), DIPEA (2 mL) and NaI (1.20 g, 8.00 mmol) were added into a reaction flask and heated to 35° C., and the reaction was monitored by TLC. After the reaction was complete, the system was cooled down, added with water (100 mL) and extracted with EA (30 mL, 15 mL*2). The combined EA phase was washed with saturated brine (60 mL), dried over anhydrous magnesium sulfate and filtered under suction. The filtrate was concentrated under reduced pressure, and the residue was separated by column chromatography to obtain 201.5 mg of the product.

ESI-MS Calculated for $[M+H]^+$=447.04; Found: 447.30. The calculated value was consistent with the found value.

Step 2: Synthesis of tert-butyl 4-(1-methyl-7-4(3-methylsulfonyl)phenyl)amino)-6,7-dihydro-5H-benzo[c][1,2,3]triazolo[1,5-a]azepin-9-yl)-3,6-dihydropyridine-1 (2H)-carboxylate (BI55-3)

BI55-2 (201.5 mg, 0.45 mmol), tert-butyl 4-(4,4,5,5-tetramethyl-1,3,2-dioxaborolan-2-yl)-3,6-dihydropyridine-1 (2H)-carboxylate (283.9 mg, 0.92 mmol), potassium carbonate (191.7 mg, 1.39 mmol), 11,1'-bis (diphenylphosphino)ferroceneldichloropalladium-dichloromethane complex (73.9 mg, 0.090 mmol), 1,4-dioxane (25 mL) and water (1.5 mL) were added into a reaction flask in sequence. The air in the reaction flask was replaced with nitrogen three times, and the system was heated to react under reflux under nitrogen protection. After the reaction was complete, the system was cooled down, added with water (100 mL) and extracted with EA (40 mL, 30 mL). The combined EA phase was washed with saturated brine (50 mL), dried over anhydrous magnesium sulfate and filtered under suction. The filtrate was concentrated under reduced pressure, and the residue was separated by column chromatography to obtain 202.8 mg of the product.

ESI-MS Calculated for $[M+H]^+$=550.24; Found: 550.40. The calculated value was consistent with the found value.

Step 3: Synthesis of 1-methyl-N-(3-(methylsulfonyl)phenyl)-9-(1,2,3,6-tetrahydropyridin-4-yl)-6,7-dihydro-5H-benzo[c][1,2,3]triazolo[1,5-a]azepin-7-amine (BI55-4)

BI55-3 (38.0 mg), DCM (10 mL), and trifluoroacetic acid (1 mL) were added into a reaction flask and reacted at room temperature. After the reaction was complete, the system was concentrated under reduced pressure, and the residue was directly used in the next reaction. The yield was calculated as 100%.

ESI-MS Calculated for [M+H]$^+$=450.19; Found: 450.30. The calculated value was consistent with the found value.

Step 4: Synthesis of 9-(1-cyclopentyl-1,2,3,6-tetrahydropyridin-4-yl)-1-methyl-N-(3-(methylsulfonyl)phenyl)-6,7-dihydro-5H-benzo[c][1,2,3]triazolo[1,5-a]azepin-7-amine 2,2,2-trifluoroacetate (BI55)

BI55-4 (used directly from the previous step), methanol (15 mL), cyclopentanone (0.5 mL) and sodium cyanoborohydride (0.26 g) were added into a reaction flask and reacted at room temperature. After the reaction was complete, the system was added with water (50 mL) and extracted with DCM (30 mL*2). The combined DCM phase was washed with saturated brine (50 mL*2), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 6.2 mg of the product.

ESI-MS Calculated for NA-W=518.25; Found: 518.40. The calculated value was consistent with the found value.

Preparation Example 159, Final Product BI57:
9-(1-cyclohexyl-1,2,3,6-tetrahydropyridin-4-yl)-1-methyl-N-(3-(methylsulfonyl)phenyl)-6,7-dihydro-5H-benzo[c][1,2,3]triazolo[1,5-a]azepin-7-amine 2,2,2-trifluoroacetate Synthesis of 9-(1-cyclohexyl-1,2,3,6-tetrahydropyridin-4-yl)-1-methyl-N-(3-(methylsulfonyl)phenyl)-6,7-dihydro-5H-benzo[c][1,2,3]triazolo[1,5-a]azepin-7-amine 2,2,2-trifluoroacetate (BH57)

BI55-4 (38.9 mg, 0.069 mmol), methanol (10 mL), cyclohexanone (0.5 mL) and sodium cyanoborohydride (0.19 g, 3.02 mmol) were added into a reaction flask and reacted at room temperature. After the reaction was complete, the system was added with water (50 mL) and extracted with DCM (25 mL*2). The combined DCM phase was washed with saturated brine (50 mL*2), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 2.1 mg of the product.

ESI-MS Calculated for NA-W=532.27; Found: 532.50. The calculated value was consistent with the found value.

Preparation Example 160, Final Product BI60:
9-(1-isopropyl-1,2,3,6-tetrahydropyridin-4-yl)-1-methyl-N-(3-(methylsulfonyl)phenyl)-6,7-dihydro-5H-benzo[c][1,2,3]triazolo[1,5-a]azepin-7-amine 2,2,2-trifluoroacetate

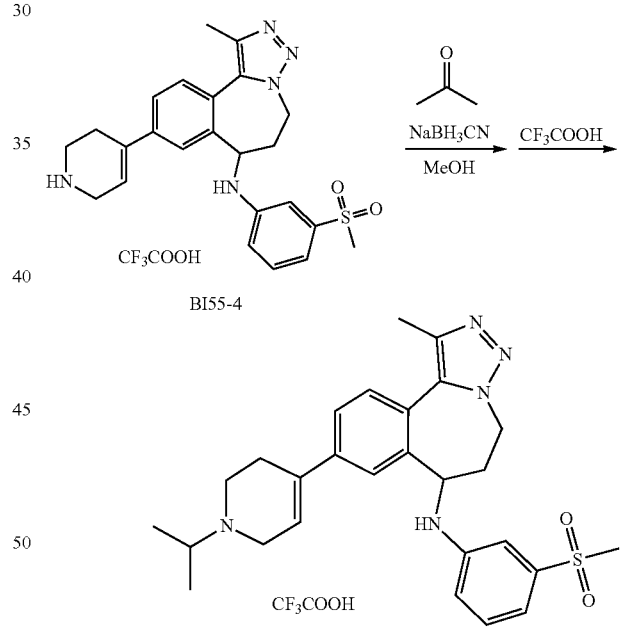

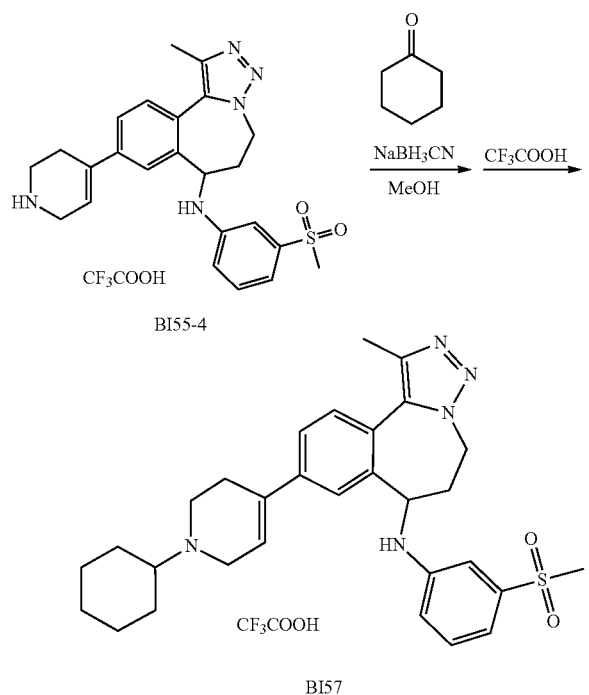

Synthesis of 9-(1-isopropyl-1,2,3,6-tetrahydropyridin-4-yl)-1-methyl-N-(3-(methylsulfonyl)phenyl)-6,7-dihydro-5H-benzo[c][1,2,3]triazolo[1,5-a]azepin-7-amine 2,2,2-trifluoroacetate (BH60)

BI55-4 (47.3 mg, 0.084 mmol), methanol (15 mL), acetone (1 mL) and sodium cyanoborohydride (0.22 g, 3.50 mmol) were added into a reaction flask and reacted at room temperature. After the reaction was complete, the system was added with water (50 mL) and extracted with DCM (30 mL*2). The combined DCM phase was washed with saturated brine (50 mL*2), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 3.1 mg of the product.

ESI-MS Calculated for [M+H]⁺=492.24; Found: 492.40. The calculated value was consistent with the found value.

Preparation Example 161, Final Product BI61:
9-(1-cyclobutyl-1,2,3,6-tetrahydropyridin-4-yl)-1-methyl-N-(3-(methylsulfonyl)phenyl)-6,7-dihydro-5H-benzo[c][1,2,3]triazolo[1,5-a]azepin-7-amine 2,2,2-trifluoroacetate

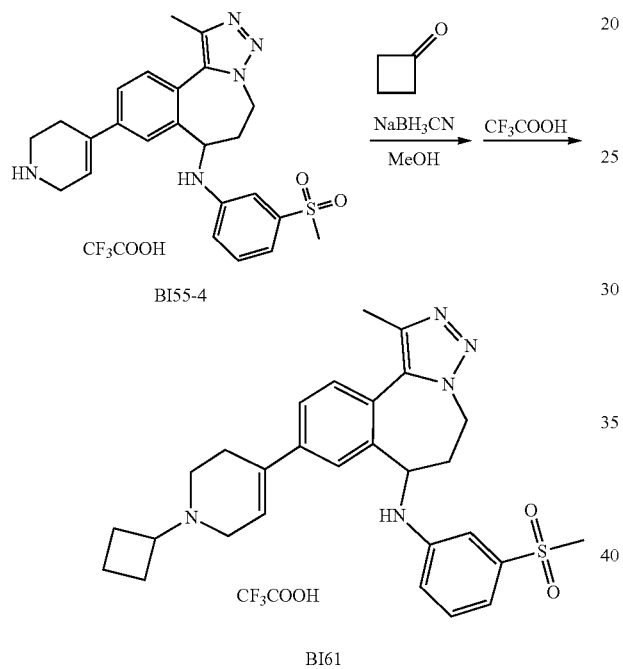

Synthesis of 9-(1-cyclobutyl-1,2,3,6-tetrahydropyridin-4-yl)-1-methyl-N-(3-(methylsulfonyl)phenyl)-6,7-dihydro-5H-benzo[c][1,2,3]triazolo[1,5-a]azepin-7-amine 2,2,2-trifluoroacetate (BH61)

BI55-4 (42.3 mg, 0.075 mmol), methanol (10 mL), cyclobutanone (0.21 g) and sodium cyanoborohydride (0.23 g, 3.66 mmol) were added into a reaction flask and reacted at room temperature. After the reaction was complete, the system was added with water (50 mL) and extracted with DCM (30 mL*2). The combined DCM phase was washed with saturated brine (50 mL*2), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 7.3 mg of the product.

ESI-MS Calculated for [M+H]⁺=504.24; Found: 504.50. The calculated value was consistent with the found value.

Preparation Example 162, Final Product BI68:
N-(5-chloro-2-fluorophenyl)-9-(1-isopropyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate

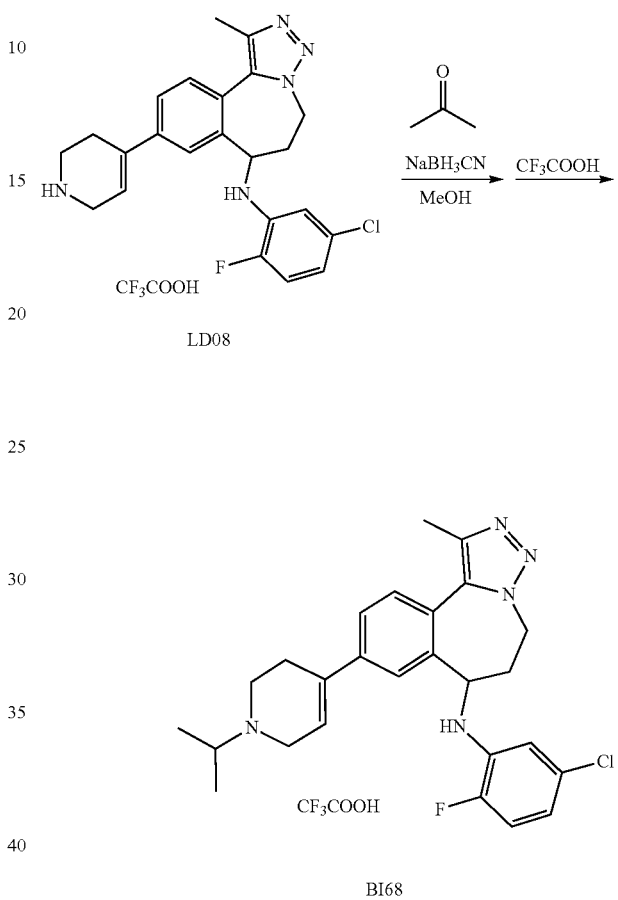

Synthesis of N-(5-chloro-2-fluorophenyl)-9-(1-isopropyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate (BI68)

LD08 (31.8 mg, 0.059 mmol), methanol (10 mL), acetone (1 mL) and sodium cyanoborohydride (0.21 g, 3.34 mmol) were added into a reaction flask and reacted at room temperature. After the reaction was complete, the system was added with water (50 mL) and extracted with DCM (20 mL*2). The combined DCM phase was washed with saturated brine (50 mL*2), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 18.6 mg of the product.

ESI-MS Calculated for [M+H]⁺=466.21; Found: 466.20. The calculated value was consistent with the found value.

Preparation Example 163, Final Product WYA10:
N-(3-chloro-4-fluorophenyl)-9-(1-cyclopentyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate

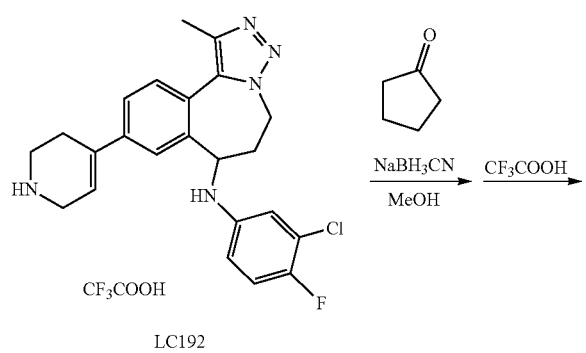

Synthesis of N-(3-chloro-4-fluorophenyl)-9-(1-cyclopentyl-1,2,3,6-tetrahydropyridin-4-yl)-1-methyl-6,7-dihydro-5H-benzo[c][1,2,3]triazolo[1,5-a]azepin-7-amine 2,2,2-trifluoro acetate (WYA10)

LC192 (51.1 mg, 0.095 mmol), methanol (10 mL), cyclopentanone (1 mL) and sodium cyanoborohydride (0.18 g, 2.86 mmol) were added into a reaction flask and reacted at room temperature. After the reaction was complete, the system was added with water (100 mL) and extracted with DCM (25 mL*2). The combined DCM phase was washed with saturated brine (50 mL*2), dried over anhydrous magnesium sulfate and filtered under suction. The filtrate was concentrated under reduced pressure, and the residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 8.5 mg of the product.

ESI-MS Calculated for [M+H]$^+$=492.23; Found: 492.40. The calculated value was consistent with the found value.

Preparation Example 164, Final Product WA78:
N-(1H-indol-5-yl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate

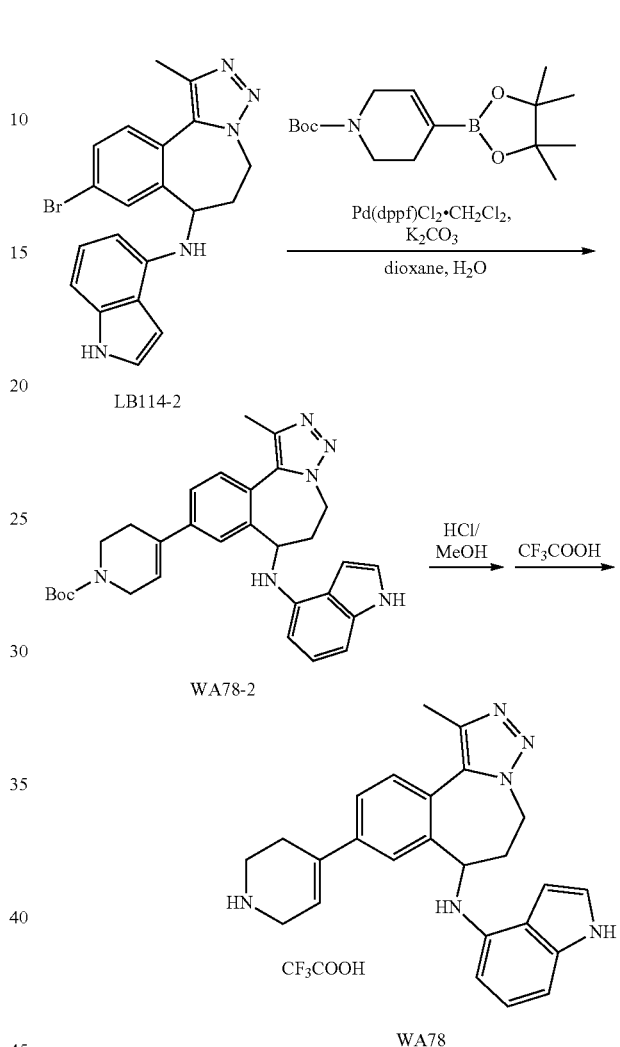

Step 1: Synthesis of tert-butyl 4-(7-((1H-indol-4-yl)amino)-1-methyl-6,7-dihydro-5H-benzo[c][1,2,3]triazolo[1,5-a]azepin-9-yl)-3,6-dihydropyridine-1(2H)-carboxylate (WA78-2)

LB114-2 (151.5 mg, 0.37 mmol), tert-butyl 4-(4,4,5,5-tetramethyl-1,3,2-dioxaborolan-2-yl)-3,6-dihydropyridine-1(2H)-carboxylate (165.7 mg, 0.54 mmol), potassium carbonate (127.2 mg, 0.92 mmol), [1,1'-bis(diphenylphosphino)ferrocene]dichloropalladium-dichloromethane complex (24.8 mg, 0.030 mmol), 1,4-dioxane (20 mL) and water (2 mL) were added into a reaction flask in sequence. The air in the reaction flask was replaced with nitrogen three times, and the system was heated to react under reflux under nitrogen protection. After the reaction was complete, the system was cooled down, added with water (50 mL) and extracted with EA (25 mL, 20 mL). The combined EA phase was washed with saturated brine (35 mL), dried over anhydrous magnesium sulfate and filtered under suction. The filtrate was concentrated under reduced pressure, and the residue was separated by PLC to obtain 113.9 mg of the product.

ESI-MS Calculated for [M+H]$^+$=511.27; Found: 511.10. The calculated value was consistent with the found value.

Step 2: Synthesis of N-(1H-indol-5-yl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate (WA78)

WA78-2 (105.0 mg), methanol (10 mL) and hydrogen chloride in methanol (2 mL, 5 mol/L) were added into a reaction flask and reacted at room temperature. After the reaction was complete, the system was concentrated under reduced pressure, the residuce was added with methanol (10 mL), and continually concentrated under reduced pressure. The residue was separated by medium-pressure preparative column chromatography (mobile phase: A: purified water with 0.05% trifluoroacetic acid; B: acetonitrile with 0.05% trifluoroacetic acid) and lyophilized to obtain 30.6 mg of the product.

ESI-MS Calculated for [M+H]$^+$=411.22; Found: 411.00. The calculated value was consistent with the found value.

Preparation Example 165, Final Product WA82: N-(1H-indol-5-yl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate

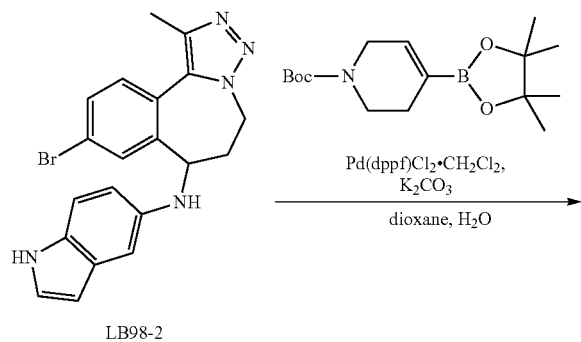

LB98-2

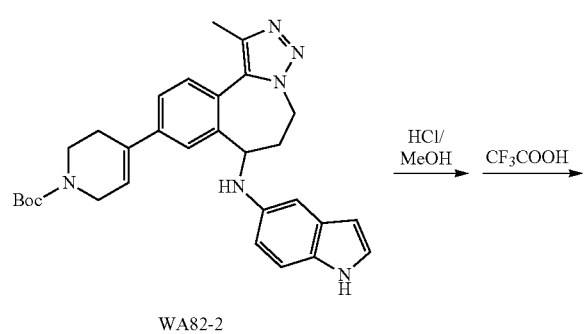

WA82-2

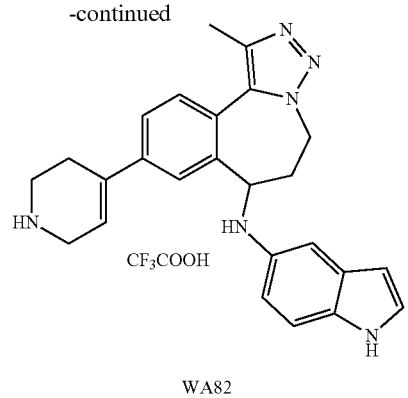

WA82

Step 1: Synthesis of tert-butyl 4-(7-((1H-indol-5-yl)amino)-1-methyl-6,7-dihydro-5H-benzo[c][1,2,3]triazolo[1,5-a]azepin-9-yl)-3,6-dihydropyridine-1(2H)-carboxylate (WA82-2)

LB98-2 (186.9 mg, 0.46 mmol), tert-butyl 4-(4,4,5,5-tetramethyl-1,3,2-dioxaborolan-2-yl)-3,6-dihydropyridine-1(2H)-carboxylate (182.6 mg, 0.59 mmol), potassium carbonate (136.8 mg, 0.99 mmol), [1,1'-bis(diphenylphosphino)ferrocene]dichloropalladium-dichloromethane complex (22.3 mg, 0.027 mmol), 1,4-dioxane (20 mL) and water (2 mL) were added into a reaction flask in sequence. The air in the reaction flask was replaced with nitrogen three times, and the system was heated to react under reflux under nitrogen protection. After the reaction was complete, the system was cooled down, added with water (50 mL) and extracted with EA (25 mL*2). The combined EA phase was washed with saturated brine (50 mL), dried over anhydrous magnesium sulfate and filtered under suction. The filtrate was concentrated under reduced pressure, and the residue was separated by column chromatography to obtain 175.3 mg of the product.

ESI-MS Calculated for [M+H]$^+$=511.27; Found: 511.10. The calculated value was consistent with the found value.

Step 2: Synthesis of N-(1H-indol-5-yl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate (WA82)

WA82-2 (175.3 mg), methanol (20 mL) and hydrogen chloride in methanol (2 mL, 5 mol/L) were added into a reaction flask and reacted at room temperature. After the reaction was complete, the system was concentrated under reduced pressure, and the residue was added with methanol (20 mL) and continually concentrated under reduced pressure. The residue was separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 27.8 mg of the product.

ESI-MS Calculated for [M+H]$^+$=411.22; Found: 411.00. The calculated value was consistent with the found value.

Preparation Example 166, Final Product WA83: N-(1H-indol-6-yl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate

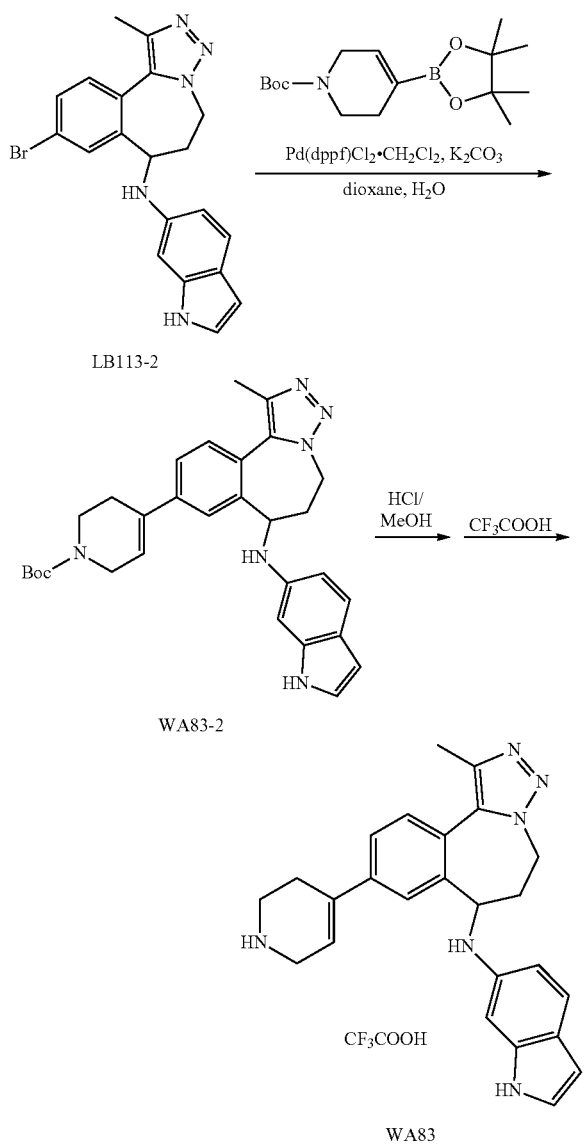

Step 1: Synthesis of tert-butyl 4-(7-((1H-indol-6-yl)amino)-1-methyl-6,7-dihydro-5H-benzo[c][1,2,3]triazolo[1,5-a]azepin-9-yl)-3,6-dihydropyridine-1(2H)-carboxylate (WA83-2)

LB113-2 (225.7 mg, 0.55 mmol), tert-butyl 4-(4,4,5,5-tetramethyl-1,3,2-dioxaborolan-2-yl)-3,6-dihydropyridine-1(2H)-carboxylate (216.9 mg, 0.70 mmol), potassium carbonate (176.3 mg, 1.28 mmol), [1,1'-bis(diphenylphosphino)ferrocene]dichloropalladium-dichloromethane complex (32.1 mg, 0.039 mmol), 1,4-dioxane (20 mL) and water (2 mL) were added into a reaction flask in sequence. The air in the reaction flask was replaced with nitrogen three times, and the system was heated to react under reflux under nitrogen protection. After the reaction was complete, the system was cooled down, added with water (50 mL) and extracted with EA (25 mL*2). The combined EA phase was washed with saturated brine (50 mL), dried over anhydrous magnesium sulfate and filtered under suction. The filtrate was concentrated under reduced pressure, and the residue was separated by column chromatography to obtain 192.8 mg of the product.

ESI-MS Calculated for [M+H]$^+$=511.27; Found: 511.10. The calculated value was consistent with the found value.

Step 2: Synthesis of N-(1H-indol-6-yl)-1-methyl-9-(1,2,3,6-tetrahydropyridin-4-yl)-6,7-dihydro-5H-benzo[c][1,2,3]triazolo[1,5-a]azepin-7-amine 2,2,2-trifluoroacetate (WA83)

WA83-2 (192.8 mg), methanol (20 mL) and hydrogen chloride in methanol (4 mL, 5 mol/L) were added into a reaction flask and reacted at room temperature. After the reaction was complete, the system was concentrated under reduced pressure, and the residue was added with methanol (20 mL) and continually concentrated under reduced pressure. ⅕ of the residue was taken and separated by PLC to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 16.7 mg of the product.

ESI-MS Calculated for [M+H]$^+$=411.22; Found: 411.10. The calculated value was consistent with the found value.

Preparation Example 167, Final Product RC71: 2-(3-((1-methyl-9-(1,2,3,6-tetrahydropyridin-4-yl)-6,7-dihydro-5H-benzo[c][1,2,3]triazolo[1,5-a]azepin-7-yl)amino)phenyl)acetonitrile 2,2,2-trifluoroacetate

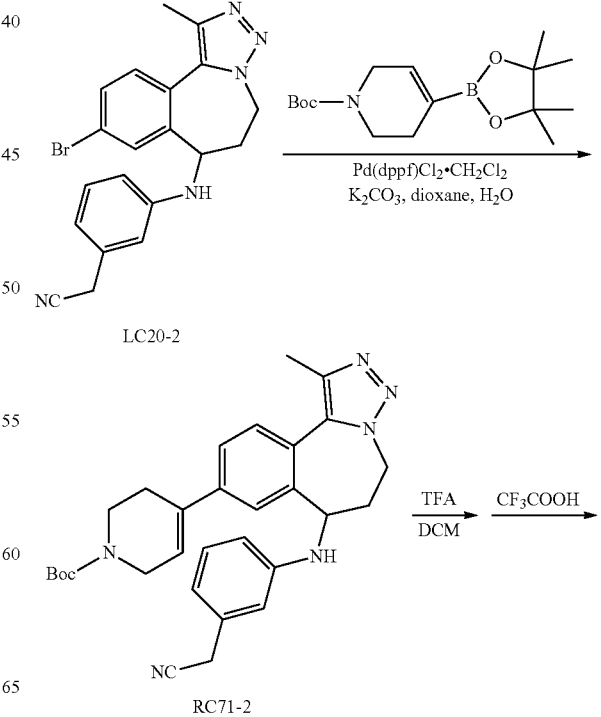

-continued

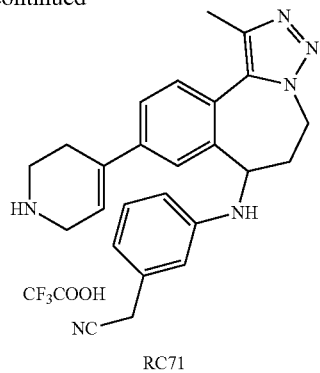

RC71

Step 1: Synthesis of tert-butyl 4-(7-((3-(cyanomethyl)phenyl)amino)-1-methyl-6,7-dihydro-5H-benzo[c][1,2,3]triazolo[1,5-a]azepin-9-yl)-3,6-dihydropyridine-1 (2H)-carboxylate (RC71-2)

LC20-2 (180.3 mg, 0.44 mmol), N-Boc-1,2,5,6-tetrahydropyridine-4-pinacolborate (177.3 mg, 0.57 mmol), potassium carbonate (145.4 mg, 1.05 mmol), [1,1'-bis(diphenylphosphino) ferrocene]dichloropalladium-dichloromethane complex (66.1 mg, 0.081 mmol), 1,4-dioxane (10 mL) and water (0.5 mL) were added into a reaction flask in sequence. The air in the reaction flask was replaced with nitrogen three times, and the system was heated to react under reflux under nitrogen protection. After the reaction was complete, the system was cooled down, added with water (100 mL) and extracted with EA (40 mL, 30 mL). The combined EA phase was washed with saturated brine (50 mL), dried over anhydrous magnesium sulfate and filtered under suction. The filtrate was concentrated under reduced pressure, and the residue was separated by column chromatography to obtain 110.3 mg of the product with a yield of 50.0%.

ESI-MS Calculated for [M+H]$^+$=511.27; Found: 511.10. The calculated value was consistent with the found value.

Step 2: Synthesis of 2-(3-((1-methyl-9-(1,2,3,6-tetrahydropyridin-4-yl)-6,7-dihydro-5H-benzo[c][1,2,3]triazolo[1,5-a]azepin-7-yl)amino)phenyl)acetonitrile 2,2,2-trifluoroacetate (RC71)

RC71-2 (110.3 mg), DCM (10 mL) and trifluoroacetic acid (1 mL) were added into a reaction flask and reacted at room temperature for 1 hour. After the reaction was complete, the system was concentrated under reduced pressure, and the residue was separated by column chromatography to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 19.7 mg of the product.

Product analysis: $^1$HNMR (CDCl$_3$, 400 MHz): δ 7.55 (d, J=5.0 Hz, 1H), 7.48-7.40 (m, 2H), 6.98 (t, J=8.0 Hz, 1H), 6.69-6.63 (m, 1H), 6.35 (q, J=2.2 Hz, 1H), 6.19-6.07 (m, 2H), 4.78 (dd, J=14.2, 7.2 Hz, 1H), 4.39-4.22 (m, 2H), 4.13 (d, J=3.2 Hz, 1H), 4.00-4.08 (m, 2H), 3.77-3.89 (m, 1H), 3.67 (t, J=5.7 Hz, 1H), 2.96-3.05 (m, 1H), 2.54 (s, 3H), 2.36-2.47 (m, 3H), 2.18-2.26 (m, 1H), 1.20 (q, J=7.1 Hz, 3H).

ESI-MS Calculated for [M+H]$^+$=411.22; Found: 411.00. The calculated value was consistent with the found value.

Preparation Example 168, Final Product RC73: 2-(4-((1-methyl-9-(1,2,3,6-tetrahydropyridin-4-yl)-6,7-dihydro-5H-benzo[c][1,2,3]triazolo[1,5-a]azepin-7-yl)amino)phenyl)acetonitrile 2,2,2-trifluoroacetate

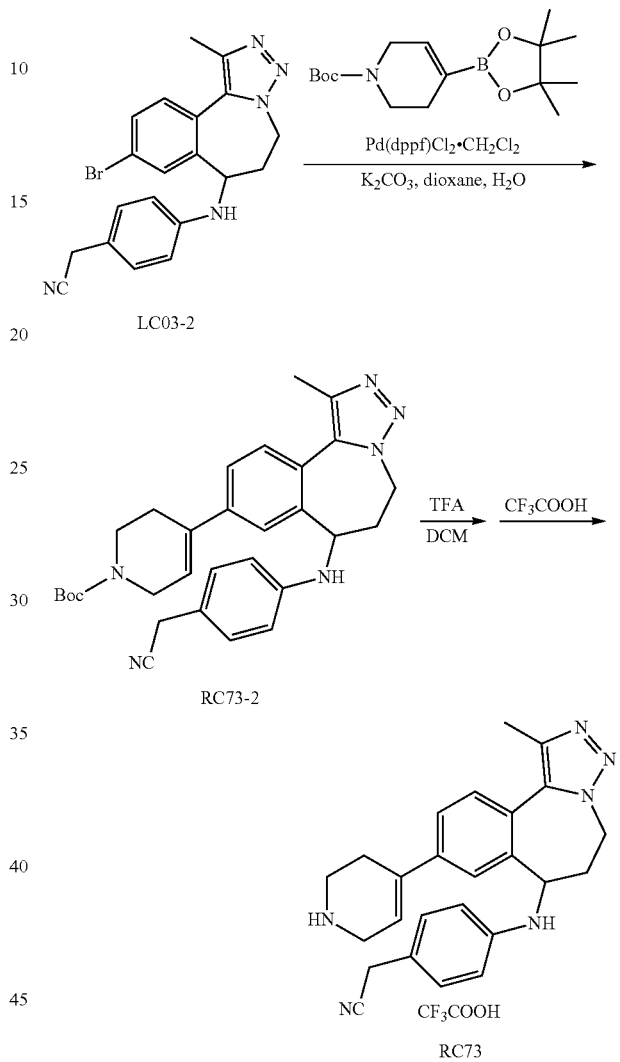

Step 1: Synthesis of tert-butyl 4-(7-((4-(cyanomethyl)phenyl)amino)-1-methyl-6,7-dihydro-5H-benzo[c][1,2,3]triazolo[1,5-a]azepin-9-yl)-3,6-dihydropyridine-1 (2H)-carboxylate (RC73-2)

LC03-2 (116.2 mg, 0.28 mmol), N-Boc-1,2,5,6-tetrahydropyridine-4-pinacolborate (134.3 mg, 0.43 mmol), potassium carbonate (119.7 mg, 0.81 mmol), [1,1'-bis(diphenylphosphino) ferrocene]dichloropalladium-dichloromethane complex (54.8 mg, 0.067 mmol), 1,4-dioxane (10 mL) and water (0.5 mL) were added into a reaction flask in sequence. The air in the reaction flask was replaced with nitrogen three times, and the system was heated to react under reflux under nitrogen protection. After the reaction was complete, the system was cooled down, added with water (100 mL) and extracted with EA (40 mL, 30 mL). The combined EA phase was washed with saturated brine (50 mL), dried over anhydrous magnesium sulfate and filtered under suction. The filtrate was concentrated under reduced pressure, and the residue was separated by column chromatography to obtain 158.5 mg of a crude.

ESI-MS Calculated for [M+H]$^+$=511.27; Found: 511.10. The calculated value was consistent with the found value.

Step 2: Synthesis of 2-(4-((1-methyl-9-(1,2,3,6-tetrahydropyridin-4-yl)-6,7-dihydro-5H-benzo[c][1,2,3]triazolo[1,5-a]azepin-7-yl)amino)phenyl)acetonitrile 2,2,2-trifluoroacetate (RC73)

RC73-2 (158.5 mg), DCM (10 mL) and trifluoroacetic acid (1 mL) were added into a reaction flask and reacted at room temperature for 1 hour. After the reaction was complete, the system was concentrated under reduced pressure, and the residue was separated by column chromatography to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 56.8 mg of the product.

Product analysis: $^1$HNMR(CDCl$_3$, 400 MHz): δ 7.52 (d, J=1.8 Hz, 1H), 7.46-7.38 (m, 2H), 6.99 (d, J=8.2 Hz, 2H), 6.26 (d, J=8.3 Hz, 2H), 5.95 (s, 1H), 4.81 (dd, J=14.0, 7.6 Hz, 1H), 4.27 (dd, J=10.9, 6.8 Hz, 1H), 4.06-3.97 (m, 1H), 3.82 (s, 2H), 3.55 (s, 2H), 3.40 (s, 2H), 2.74 (s, 1H), 2.55 (s, 3H).

ESI-MS Calculated for [M+H]$^+$=411.22; Found: 411.00. The calculated value was consistent with the found value.

Preparation Example 169, Final Product RC82: 2-(2-((1-methyl-9-(1,2,3,6-tetrahydropyridin-4-yl)-6,7-dihydro-5H-benzo[c][1,2,3]triazolo[1,5-a]azepin-7-yl)amino)phenyl) acetonitrile 2,2,2-trifluoroacetate

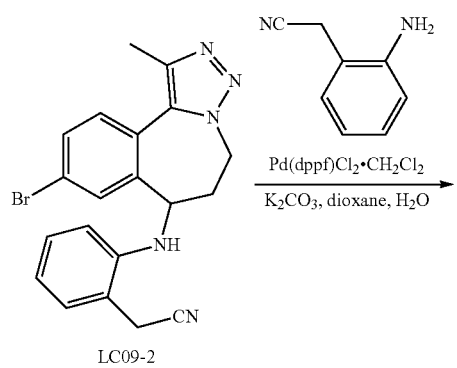

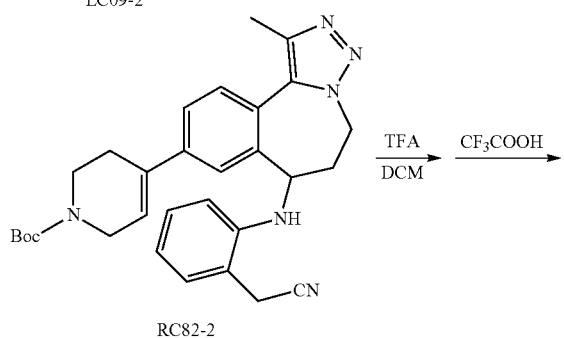

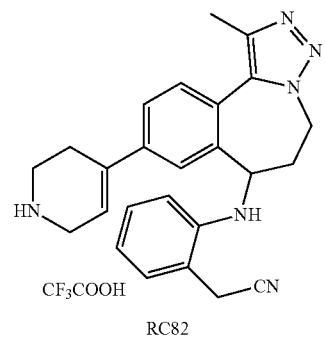

The final product RC82 was prepared by using LC09-2 as a reactant according to the method of Preparation Example 168.

ESI-MS Calculated for [M+H]$^+$=411.22; Found: 411.00. The calculated value was consistent with the found value.

Preparation Example 170, Final Product RC116: 2-((1-methyl-9-(1,2,3,6-tetrahydropyridin-4-yl)-6,7-dihydro-5H-benzo[c][1,2,3]triazolo[1,5-a]azepin-7-yl)amino)benzonitrile 2,2,2-trifluoroacetate

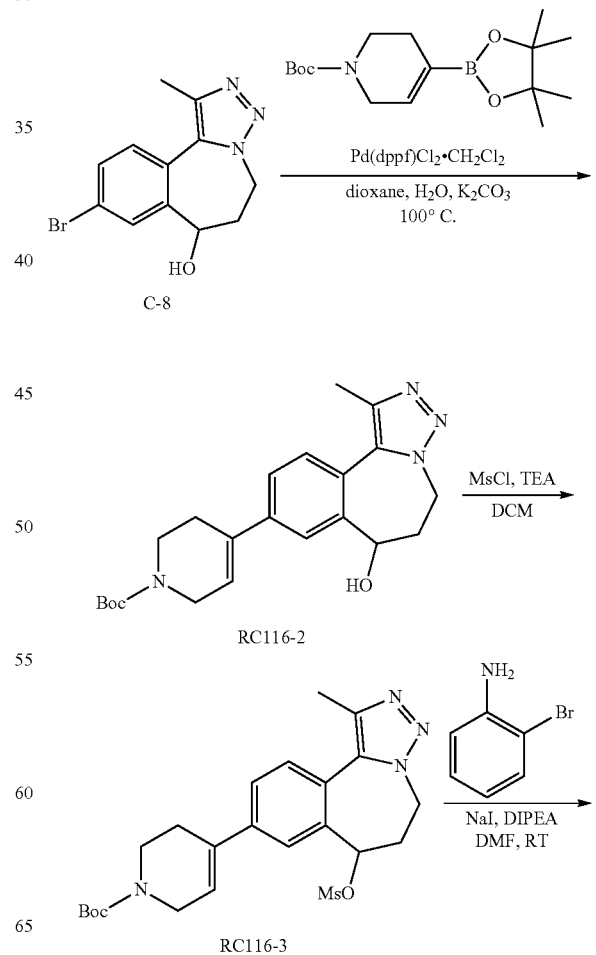

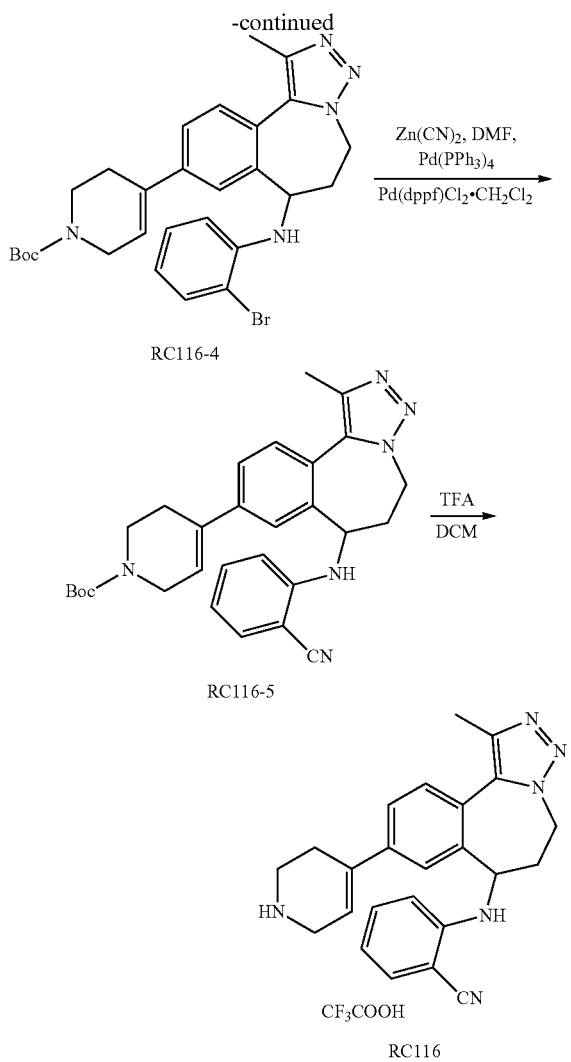

Step 1: Synthesis of tert-butyl 4-(7-hydroxyl-1-methyl-6,7-dihydro-5H-benzo[c][1,2,3]triazolo[1,5-a]azepin-9-yl)-5,6-dihydropyridine-1 (2H)-carboxylate (RC116-2)

C-8 (611.5 mg, 2.06 mmol), 1,4-dioxane (20 mL), N-Boc-1,2,5,6-tetrahydropyridine-4-pinacolborate (761.6 mg, 2.46 mmol), Pd(dppf)Cl$_2$-dichloromethane complex (297.8 mg, 0.36 mmol), potassium carbonate (572.8 mg, 4.14 mmol) and water (1 mL) were added into a reaction flask. The air in the reaction flask was replaced with nitrogen three times, and the system was reacted at 100° C. for 3 hours under nitrogen protection. The system was filtered and the filtrate was concentrated under reduced pressure. The residue was separated by column chromatography to obtain 639.4 mg of the product with a yield of 78.1%.

ESI-MS Calculated for [M+1]$^+$=397.22, Found: 397.00. The calculated value was consistent with the found value.

Step 2: Synthesis of tert-butyl 4-(1-methyl-7-((methylsulfonyl)oxy)-6,7-dihydro-5H-benzo[c][1,2,3]triazolo[1,5-a]azepin-9-yl)-5,6-dihydropyridine-1 (2H)-carboxylate (RC116-3)

RC116-2 (639.4 mg, 1.61 mmol), dry DCM (20 mL) and triethylamine (351.7 mg, 3.48 mmol) were added into a reaction flask in sequence. The system was cooled down in an ice bath, controlled at 0-5° C., added dropwise with a solution of MsCl (276.61 mg, 2.41 mmol) in DCM (10 mL) and stirred for 2 hours at 0-5° C. The system was washed with water (100 mL*2), and the organic layer was dried over anhydrous sodium sulfate, filtered and rotary-evaporated to dryness. The resultant was used directly in the next step.

Step 3: Synthesis of tert-butyl 4-(7-((2-bromophenyl)amino)-1-methyl-6,7-dihydro-5H-benzo[c][1,2,3]triazolo[1,5-a]azepin-9-yl)-5,6-dihydropyridine-1 (2H)-carboxylate (RC116-4)

RC116-3, DMF (10 mL), DIPEA (331.8 mg, 2.57 mmol), o-bromoaniline (342.9 mg, 1.99 mmol) and NaI (1.25 g, 8.33 mmol) were added into a reaction flask in sequence, and stirred at room temperature for 18 hours. The system was added with 100 mL of ethyl acetate and 100 mL of water, shaken and separated. The aqueous layer was extracted with 100 mL of ethyl acetate. The combined organic layer was washed with water (100 mL) and saturated brine (30 mL), dried over anhydrous sodium sulfate and filtered with suction. The filtrate was concentrated under reduced pressure, and the residue was separated by column chromatography to obtain 124.8 mg of a crude with a yield of 14.1%.

ESI-MS Calculated for [M+1]$^+$=552.17, Found: 552.00. The calculated value was consistent with the found value.

Step 4: Synthesis of tert-butyl 4-(7-((2-cyanophenyl)amino)-1-methyl-6,7-dihydro-5H-benzo[c][1,2,3]triazolo[1,5-a]azepin-9-yl)-5,6-dihydropyridine-1 (2H)-carboxylate (RC116-5)

RC116-4 (124.38 mg, 0.23 mmol), DMF (10 mL), Zn(CN)$_2$ (16.6 mg, 0.14 mmol), Pd(dppf)Cl$_2$-dichloromethane complex (37.1 mg, 0.045 mmol), Pd(PPh$_3$)$_4$ (28.1 mg, 0.024 mmol) were added into a reaction flask and heated to 120° C. by microwave to react for 30 minutes. The system was added with 50 mL of ethyl acetate and 50 mL of water, shaken and separated. The aqueous layer was extracted with 50 mL of ethyl acetate. The combined organic layer was washed with water (100 mL) and saturated brine (30 mL), dried over anhydrous sodium sulfate and filtered with suction. The filtrate was concentrated under reduced pressure, and the residue was separated by column chromatography to obtain a crude of 89.6 mg with a yield of 80.1%.

ESI-MS Calculated for [M+1]$^+$=497.26, Found: 497.10. The calculated value was consistent with the found value.

Step 5: Synthesis of 2-((1-methyl-9-(1,2,3,6-tetrahydropyridin-4-yl)-6,7-dihydro-5H-benzo[c][1,2,3]triazolo[1,5-a]azepin-7-yl)amino)benzonitrile 2,2,2-trifluoroacetate (RC116)

RC116-5 (89.6 mg, 0.18 mmol), 10 mL of dichloromethane and 1 mL of trifluoroacetic acid were added into a reaction flask and stirred at room temperature for 2 hours. The system was concentrated under reduced pressure, and the residue was seperated by PLC to obtain a crude, which was separated by medium-pressure preparative chromatography (mobile phase: A: purified water with 0.05% trifluoroacetic acid, B: acetonitrile with 0.05% trifluoroacetic acid) to obtain the target compound RC116, which was lyophilized to give 2.2 mg of a white solid.

ESI-MS Calculated for [M+1]$^+$=397.21, Found: 397.10. The calculated value was consistent with the found value.

427

Preparation Example 171, Final Product RD06:
N-(2-chlorophenyl)-1-methyl-9-(1-methyl-1,2,3,6-tetrahydropyridin-4-yl)-6,7-dihydro-5H-benzo[c][1,2,3]triazolo[1,5-a]azepin-7-amine 2,2,2-trifluoroacetate

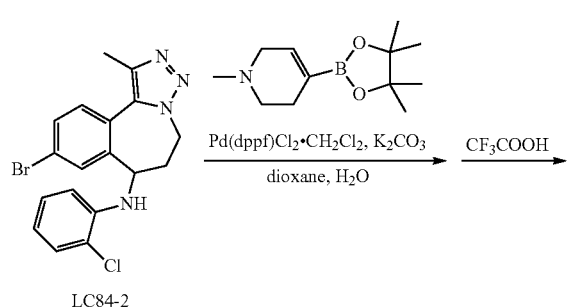

LC84-2

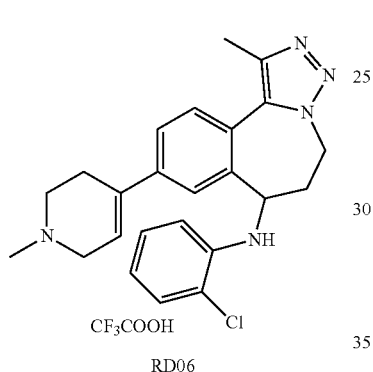

RD06

Synthesis of N-(2-chlorophenyl)-1-methyl-9-(1-methyl-1,2,3,6-tetrahydropyridin-4-yl)-6,7-dihydro-5H-benzo[c][1,2,3]triazolo[1,5-a]azepin-7-amine 2,2,2-trifluoroacetate (RD06)

LC84-2 (234.5 mg, 0.58 mmol), 1-methyl-4-(4,4,5,5-tetramethyl-1,3,2-dioxaborolan-2-yl)-1,2,3,6-tetrahydropyridine (206.5 mg, 0.93 mmol), potassium carbonate (169.4 mg, 1.23 mmol), [1,1′-bis(diphenylphosphino)ferrocene]dichloropalladium-dichloromethane complex (66.9 mg, 0.082 mmol), 1,4-dioxane (10 mL) and water (0.5 mL) were added into a reaction flask in sequence. The air in the reaction flask was replaced with nitrogen three times, and the system was heated to react under reflux under nitrogen protection. After the reaction was complete, the system was added with water (80 mL) and extracted with DCM (30 mL*2). The combined DCM phase was washed with brine (50 mL), dried over anhydrous magnesium sulfate and filtered under suction. The filtrate was concentrated under reduced pressure and the residue was separated by PLC to obtain the crude, which was separated by medium-pressure preparative column chromatography (mobile phase: A: purified water with 0.05% trifluoroacetic acid, B: acetonitrile with 0.05% trifluoroacetic acid) and lyophilized to obtain 34.0 mg of the product.

ESI-MS Calculated for $[M+H]^+$=420.18; Found: 419.90. The calculated value was consistent with the found value.

428

Preparation Example 172, Final Product RD21:
(3-((1-methyl-9-(1,2,3,6-tetrahydropyridin-4-yl)-6,7-dihydro-5H-benzo[c][1,2,3]triazolo azepin-7-yl)amino)phenyl)methanol 2,2,2-trifluoroacetate

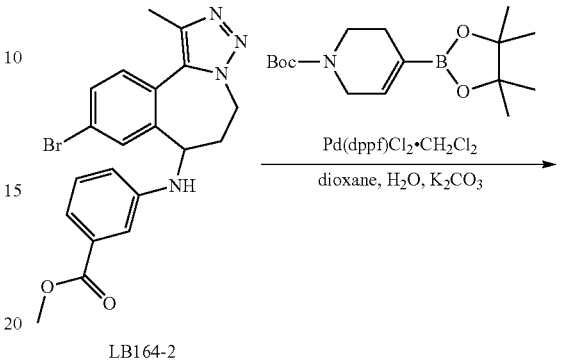

LB164-2

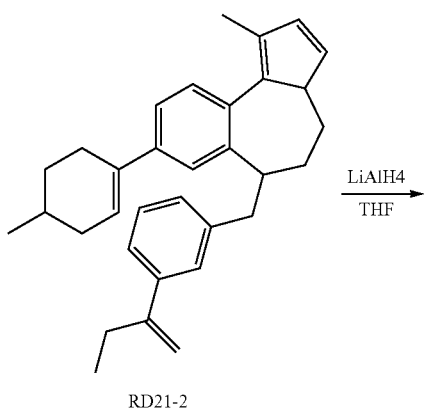

RD21-2

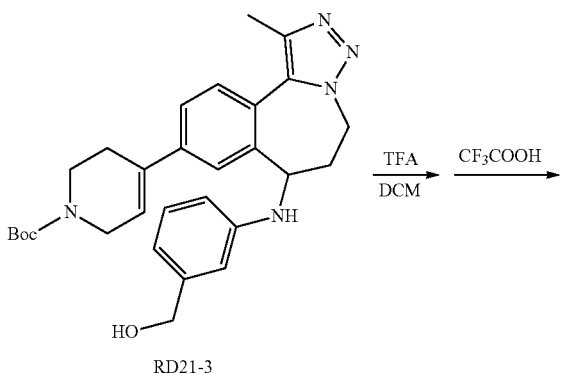

RD21-3

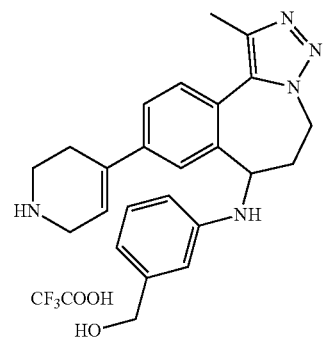

RD21

Step 1: Synthesis of tert-butyl 4-(7-((3-(methoxy-carbonyl)phenyl)amino)-1-methyl-6,7-dihydro-5H-benzo[c][1,2,3]triazolo[1,5-a]azepin-9-yl)-5,6-dihydropyridine-1 (2H)-carboxylate (RD21-2)

LB164-2 (381.5 mg, 0.28 mmol), N-Boc-1,2,5,6-tetrahydropyridine-4-pinacolborate (420.3 mg, 1.36 mmol), potassium carbonate (251.5 mg, 1.82 mmol), dioxane (10 mL) and water (0.5 mL) were added into a reaction flask, and the air in the reaction flask was replaced with $N_2$ three times. The system was added with Pd(dppf)Cl$_2$-dichloromethane complex (66.6 mg, 0.081 mmol), and the air in the reaction flask was replaced with $N_2$ again three times. The system was heated to reflux, and the reaction was monitored by LC-MS. The system was added with water (50 mL) and EA (30 mL), shaken and separated. The aqueous phase was extracted with EA (40 mL*2). The combined organic phase was washed with water (40 mL*2) and brine (40 mL), dried over anhydrous Na2SO$_4$ and filtered under suction. The filtrate was concentrated and the residue was separated by PLC to obtain 329.4 mg of a crude with a yield of 69.6%.

ESI-MS Calculated for [M+H]$^+$=530.27; Found: 530.10.

Step 2: Synthesis of tert-butyl 4-(7-((3-(hydroxymethyl)phenyl)amino)-1-methyl-6,7-dihydro-5H-benzo[c][1,2,3]triazolo[1,5-a]azepin-9-yl)-5,6-dihydropyridine-1 (2H)-carboxylate (RD21-3)

RD21-2 (329.4 mg, 0.62 mmol) and THF (10 mL) were added to a 100 mL single necked flask, and the air in the reaction flask was replaced with $N_2$ three times. The system was cooled to 0-10° C. and added with LiAlH$_4$ (468.5 mg, 12.34 mmol) in batches. After the addition, the system was reacted at 0-10° C. for 1 hour, added with water (0.4 mL), 2M NaOH (0.8 mL) and water (1.2 mL) successively to quench the reaction, and filtered. The filtrate was concentrated and the residue was separated by column chromatography to obtain 298.1 mg of a crude with a yield of 95.8%.

ESI-MS Calculated for [M+H]$^+$=502.27; Found: 502.00. The calculated value was consistent with the found value.

Step 3: (3-((1-methyl-9-(1,2,3,6-tetrahydropyridin-4-yl)-6,7-dihydro-5H-benzo[c][1,2,3]triazolo[1,5-a]azepin-7-yl)amino)phenyl)methanol 2,2,2-trifluoroacetate (RD21)

RD21-3 (298.1 mg, 0.47 mmol), 10 mL of dichloromethane and 1 mL of trifluoroacetic acid were sequentially added into a reaction flask and stirred at room temperature for 2 hours. The system was concentrated under reduced pressure and the residue was separated by PLC to obtain a crude, which was separated by medium-pressure preparative chromatography (mobile phase: A: purified water with 0.05% trifluoroacetic acid, B: acetonitrile with 0.05% trifluoroacetic acid) to obtain the target compound, which was lyophilized to obtain 13.4 mg of a white solid.

ESI-MS Calculated for [M+1]$^+$=402.27, Found: 402.00. The calculated value was consistent with the found value.

Preparation Example 173, Final Product RD41: (4-((1-methyl-9-(1-methyl-1,2,3,6-tetrahydropyridin-4-yl)-6,7-dihydro-5H-benzo[c][1,2,3]triazolo[1,5-a]azepin-7-yl)amino)pheny l)methanol 2,2,2-trifluoroacetate

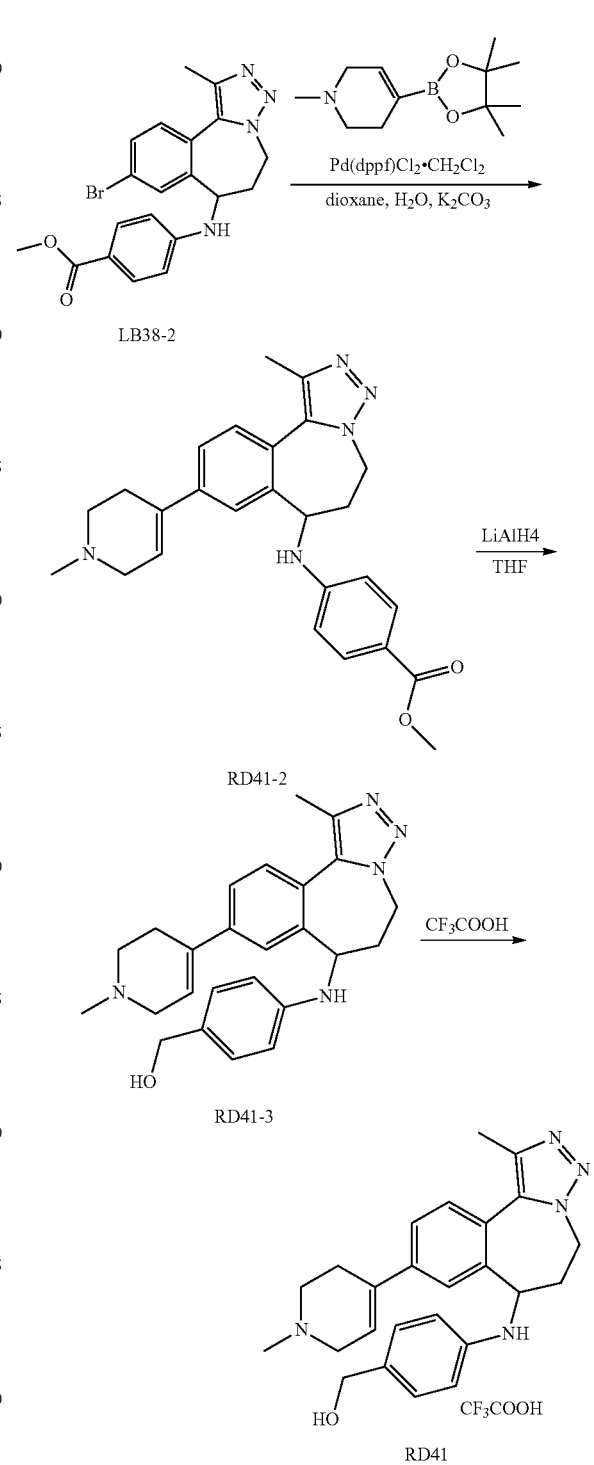

The final product RD41 was prepared according to the method of Preparation Example 172, except that the reactant N-Boc-1,2,5,6-tetrahydropyridine-4-pinacolborate in Preparation Example 172 was replaced with 1-methyl-4-(4,4,5,5-tetramethyl-1,3,2-dioxaborolan-2-yl)-1,2,3,6-tetrahydropyridine.

ESI-MS Calculated for [M+H]$^+$=416.23, Found: 416.10. The calculated value was consistent with the found value.

Preparation Example 174, Final Product RD115:
N-(3-chloro-2-fluorophenyl)-9-(1-ethyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate

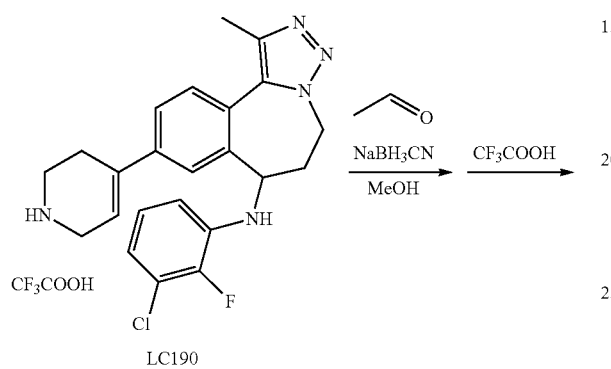

LC190

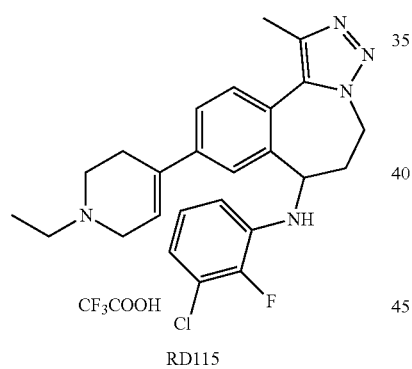

RD115

LC190 (124.7 mg, 0.24 mmol), methanol (10 mL), acetaldehyde (2 mL) and sodium cyanoborohydride (345.50 mg, 5.50 mmol) were added into a reaction flask in sequence, and stirred at room temperature for 3 hours. The system was concentrated under reduced pressure, and the residue was added with dichloromethane (50 mL) and water (50 mL), shaken and separated. The aqueous layer was extracted with dichloromethane (50 mL). The combined organic layer was washed with water (100 mL) and saturated brine (30 mL), dried over anhydrous sodium sulfate and filtered with suction. The filtrate was concentrated under reduced pressure, and the residue was separated by PLC to obtain a crude, which was separated by medium-pressure preparative chromatography (mobile phase: A: purified water with 0.05% trifluoroacetic acid, B: acetonitrile with 0.05% Trifluoroacetic acid) to obtain the target compound, which was lyophilized to obtain 18.7 mg of a white solid.

Product analysis: $^1$HNMR(CD$_3$OD, 400 MHz): δ 7.66-7.54 (m, 3H), 6.76-6.57 (m, 2H), 6.16 (s, 1H), 5.89-5.93 (m, 1H), 4.84-4.79 (m, 1H), 4.33 (dd, J=11.1, 6.8 Hz, 1H), 4.15-3.96 (m, 2H), 3.78 (d, J=17.3 Hz, 2H), 3.27-3.31 (m, 3H), 2.96-3.05 (m, 1H), 2.83 (s, 2H), 2.52 (s, 3H), 2.43-2.48 (m, 1H), 1.40 (t, J=7.3 Hz, 3H).

ESI-MS Calculated for [M+H]$^+$=452.19; Found: 452.10. The calculated value was consistent with the found value.

Preparation Example 175, Final Product RD121:
N-(3-chloro-4-fluorophenyl)-9-(1-ethyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate

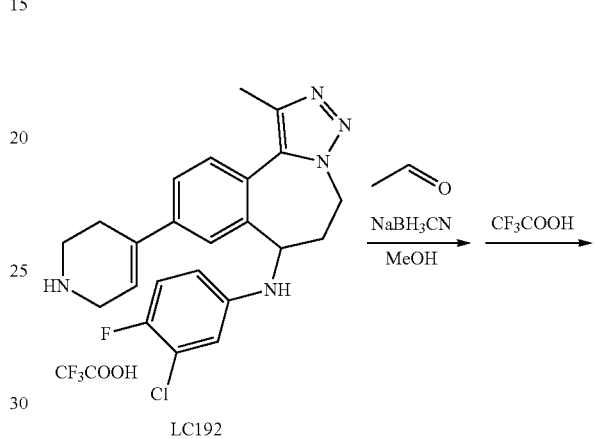

LC192

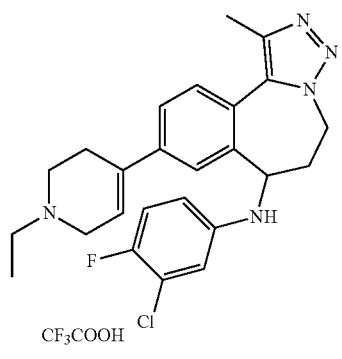

RD121

The final product RD121 was prepared according to the method in Preparation Example 174, except that the reactant was replaced with LC192.

Product analysis: $^1$HNMR (CD$_3$OD, 400 MHz): δ 7.69-7.55 (m, 3H), 6.85 (t, J=9.0 Hz, 1H), 6.36-6.38 (m,1H), 6.13-6.17 (m, 2H), 4.84-4.77 (m, 1H), 4.17 (dd, J=11.2, 6.8 Hz, 1H), 4.12-3.97 (m, 2H), 3.79 (d, J=16.9 Hz, 2H), 3.28-3.32 (m, 3H), 2.93-3.02 (m, 1H), 2.84 (s, 2H), 2.52 (s, 3H), 2.27-2.35(m, 1H), 1.40 (t, J=7.3 Hz, 3H).

ESI-MS Calculated for [M+H]$^+$=452.19; Found: 452.10. The calculated value was consistent with the found value.

Preparation Example 176, Final Product RD123: N-(5-chloro-2-fluorophenyl)-9-(1-ethyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate

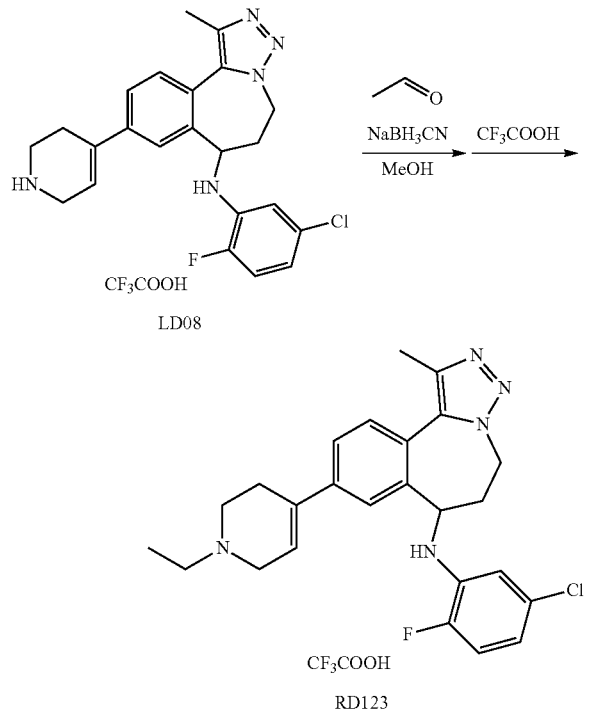

The final product RD123 was prepared according to the method in Preparation Example 174, except that the reactant was replaced with LD08.

Product analysis: ¹HNMR (CD3OD, 400 MHz): δ 7.62 (dd, J=15.1, 7.6 Hz, 3H), 6.94 (dd, J=11.5, 8.5 Hz, 1H), 6.49-6.53 (m, 1H), 6.19 (d, J=8.3 Hz, 1H), 5.94 (dd, J=7.6, 2.5 Hz, 1H), 4.81 (dd, J=14.3, 7.5 Hz, 1H), 4.30 (dd, J=10.7, 6.8 Hz, 1H), 4.06 (s, 2H), 3.80 (d, J=17.3 Hz, 2H), 3.29 (d, J=7.3 Hz, 3H), 2.94-3.03 (m, 1H), 2.86 (s, 2H), 2.52 (s, 3H), 1.41 (t, J=7.3 Hz, 3H).

ESI-MS Calculated for [M+H]⁺=452.19; Found: 452.10. The calculated value was consistent with the found value.

Preparation Example 177, Final Product RD142: N-(3-chlorophenyl)-9-(1-ethylpiperidin-4-yl)-1-methyl-6,7-dihydro-5H-benzo[c][1,2,3]triazolo[1,5-a]azepin-7-amine 2,2,2-trifluoroacetate

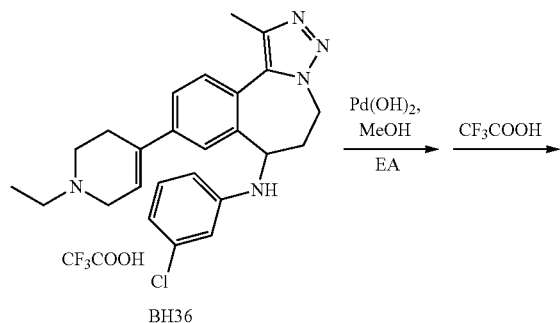

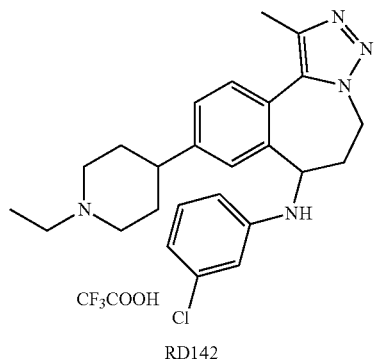

Synthesis of N-(3-chlorophenyl)-9-(1-ethylpiperidin-4-yl)-1-methyl-6,7-dihydro-5H-benzo[c][1,2,3]triazolo[1,5-a]azepin-7-amine 2,2,2-trifluoroacetate (RD142)

BH36 (50.5 mg, 0.12 mmol), 5 mL of methanol, 5 mL of EA and Pd(OH)₂/C (0.51 g, palladium content 10%) were added into a 100 mL single necked flask. The air in the reaction flask was replaced with hydrogen three times, and the system was reacted at room temperature under hydrogen balloon pressure. After the reaction was complete, the system was filtered under suction, and the filter cake was rinsed with methanol (10 mL). The filtrate was concentrated under reduced pressure to obtain a crude, which was separated by medium-pressure preparative column chromatography (mobile phase: A: purified water with 0.05% trifluoroacetic acid, B: acetonitrile with 0.05% trifluoroacetic acid) and lyophilized to obtain 11.2 mg of the product.

ESI-MS Calculated for [M+H]⁺=436.22; Found: 436.20. The calculated value was consistent with the found value.

Preparation Example 178, Final Product RD178: N-(3-chloro-2-fluorophenyl)-9-(1-cyclohexyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate

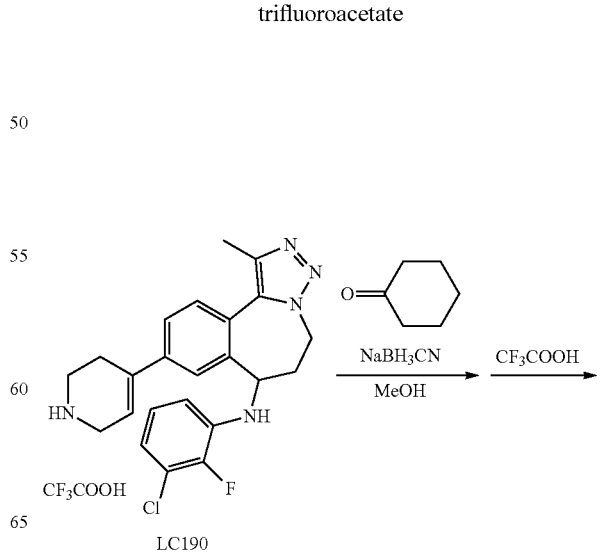

-continued

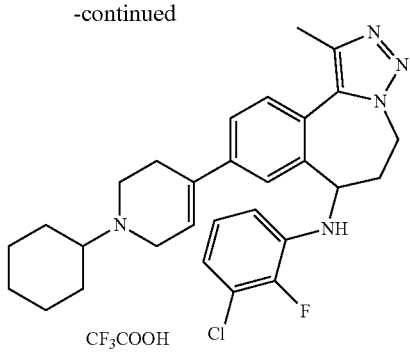

RD178

The final product RD178 was prepared according to the method in Preparation Example 174, except that the reactant acetaldehyde was replaced with cyclohexanone.

ESI-MS Calculated for [M+H]⁺=506.24; Found: 506.40. The calculated value was consistent with the found value.

Preparation Example 179, Final Product RD179: N-(3-chloro-2-fluorophenyl)-9-(1-cyclopentyl-1,2,3,6-tetrahydropyridin-4-yl)-1-methyl-6,7-dihydro-5H-benzo[c][1,2,3]triazolol[1,5-a]azepin-7-amine 2,2,2-trifluoroacetate

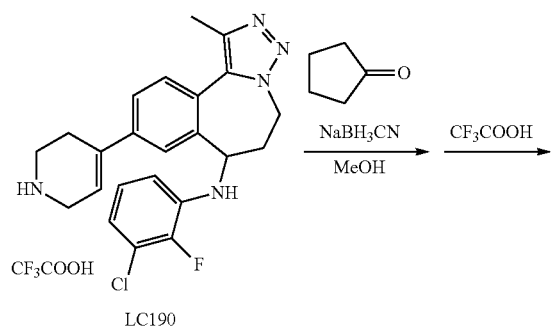

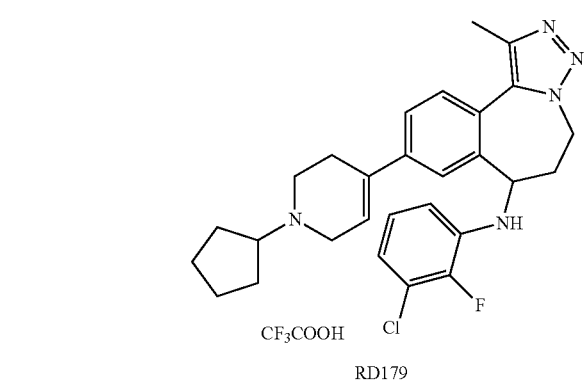

RD179

The final product RD179 was prepared According to the method in Preparation Example 174, except that the reactant acetaldehyde was replaced with cyclopentanone.

ESI-MS Calculated for [M+H]⁺=492.23; Found: 492.40. The calculated value was consistent with the found value.

Preparation Example 180, Final Product RD180: 1-(4-(7-((3-chloro-2-fluoro-phenyl)amino)-1-methyl-6,7-dihydro-5H-benzo[c][1,2,3]triazolo[1,5-a]azepin-9-yl)-3,6-dihydropyridin-1 (2H)-yl)ethan-1-one

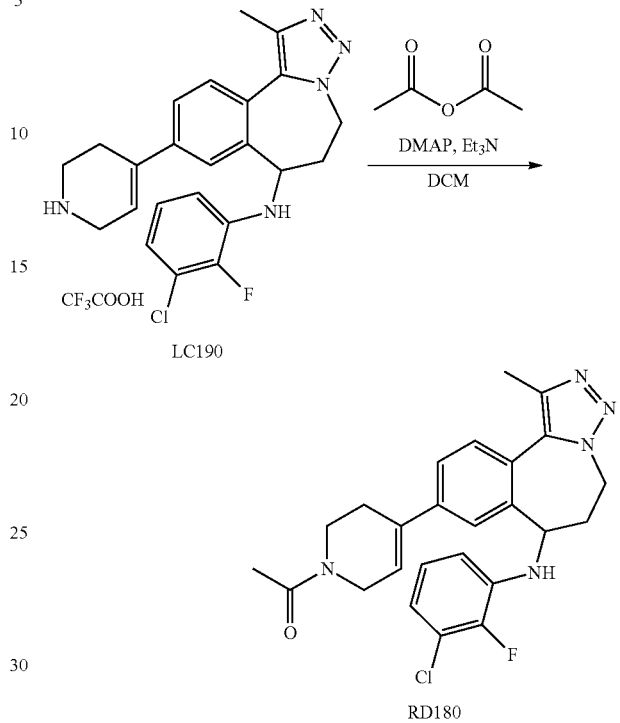

RD180

LC190 (138.1.0 mg, 0.28 mmol), DCM (10 mL), acetic anhydride (117.7 mg, 1.15 mmol), triethylamine (566.9 mg, 5.60 mmol) and DMAP (11.6 mg, 0.095 mmol) were added into a reaction flask and stirred at room temperature overnight under nitrogen protection. The system was concentrated under reduced pressure, and the redisue was added with dichloromethane (50 mL) and water (50 mL), shaken and separated. The aqueous layer was extracted with dichloromethane (50 mL). The combined organic layer was washed with water (100 mL) and saturated brine (30 mL), dried over anhydrous sodium sulfate and filtered with suction. The filtrate was concentrated under reduced pressure and the residue was separated by PLC to obtain a crude, which was separated by medium-pressure preparative column chromatography (mobile phase: A: purified water, B: acetonitrile) and lyophilized to obtain 8.7 mg of the product.

ESI-MS Calculated for [M+H]⁺=466.17; Found: 466.40. The calculated value was consistent with the found value.

Preparation Example 181, Final Product RE10(S): (7S)—N-(3-chlorophenyl)-9-(1-isopropyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate

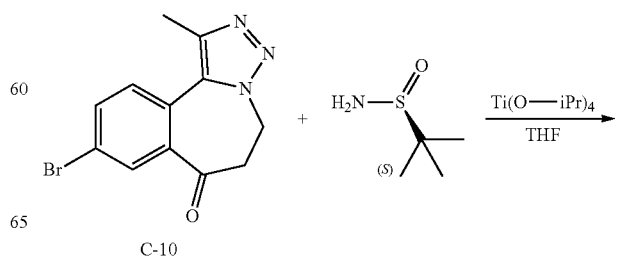

C-10

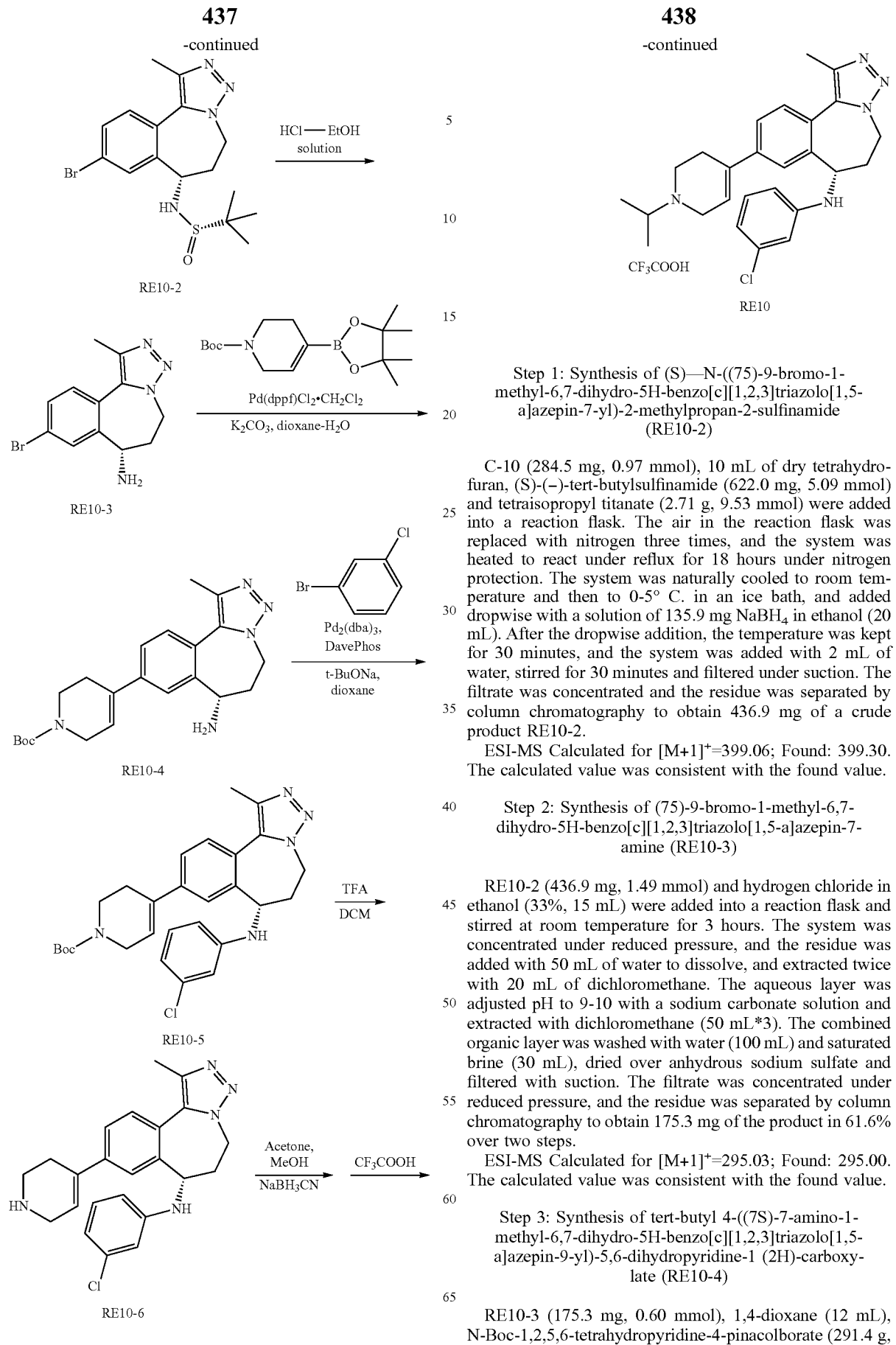

Step 1: Synthesis of (S)—N-((7S)-9-bromo-1-methyl-6,7-dihydro-5H-benzo[c][1,2,3]triazolo[1,5-a]azepin-7-yl)-2-methylpropan-2-sulfinamide (RE10-2)

C-10 (284.5 mg, 0.97 mmol), 10 mL of dry tetrahydrofuran, (S)-(−)-tert-butylsulfinamide (622.0 mg, 5.09 mmol) and tetraisopropyl titanate (2.71 g, 9.53 mmol) were added into a reaction flask. The air in the reaction flask was replaced with nitrogen three times, and the system was heated to react under reflux for 18 hours under nitrogen protection. The system was naturally cooled to room temperature and then to 0-5° C. in an ice bath, and added dropwise with a solution of 135.9 mg NaBH$_4$ in ethanol (20 mL). After the dropwise addition, the temperature was kept for 30 minutes, and the system was added with 2 mL of water, stirred for 30 minutes and filtered under suction. The filtrate was concentrated and the residue was separated by column chromatography to obtain 436.9 mg of a crude product RE10-2.

ESI-MS Calculated for [M+1]$^+$=399.06; Found: 399.30. The calculated value was consistent with the found value.

Step 2: Synthesis of (7S)-9-bromo-1-methyl-6,7-dihydro-5H-benzo[c][1,2,3]triazolo[1,5-a]azepin-7-amine (RE10-3)

RE10-2 (436.9 mg, 1.49 mmol) and hydrogen chloride in ethanol (33%, 15 mL) were added into a reaction flask and stirred at room temperature for 3 hours. The system was concentrated under reduced pressure, and the residue was added with 50 mL of water to dissolve, and extracted twice with 20 mL of dichloromethane. The aqueous layer was adjusted pH to 9-10 with a sodium carbonate solution and extracted with dichloromethane (50 mL*3). The combined organic layer was washed with water (100 mL) and saturated brine (30 mL), dried over anhydrous sodium sulfate and filtered with suction. The filtrate was concentrated under reduced pressure, and the residue was separated by column chromatography to obtain 175.3 mg of the product in 61.6% over two steps.

ESI-MS Calculated for [M+1]$^+$=295.03; Found: 295.00. The calculated value was consistent with the found value.

Step 3: Synthesis of tert-butyl 4-((7S)-7-amino-1-methyl-6,7-dihydro-5H-benzo[c][1,2,3]triazolo[1,5-a]azepin-9-yl)-5,6-dihydropyridine-1 (2H)-carboxylate (RE10-4)

RE10-3 (175.3 mg, 0.60 mmol), 1,4-dioxane (12 mL), N-Boc-1,2,5,6-tetrahydropyridine-4-pinacolborate (291.4 g, 0.94 mmol), Pd(dppf)Cl$_2$-dichloromethane complex (58.9 mg, 0.072 mmol), potassium carbonate (178.0 mg, 1.29 mmol) and 0.5 mL of water were added into a reaction flask in sequence. The air in the reaction flask was replaced with nitrogen three times, and the system was reacted at 100° C. for 3 hours under nitrogen protection. The system was filtered and the filtrate was concentrated under reduced pressure. The residue was separated by column chromatography to obtain 130.9 mg of the product with a yield of 55.1%.

ESI-MS Calculated for [M+1]$^+$=396.50; Found: 396.30. The calculated value was consistent with the found value.

Step 4: Synthesis of tert-butyl 4-((7S)-7-((3-chlorophenyl)amino)-1-methyl-6,7-dihydro-5H-benzo[c][1,2,3]triazolo[1,5-a]azepin-9-yl)-5,6-dihydropyridine-1(2H)-carboxylate (RE10-5)

RE10-4 (130.9 mg, 0.33 mmol), dry 1,4-dioxane (12 mL), m-chlorobromobenzene (185.2 mg, 0.97 mmol), Pd$_2$(dba)$_3$ (78.2 mg, 0.085 mmol), 2-dicyclohexylphosphino-2'-(N,N-dimethylamine)-biphenyl (52.1 mg, 0.13 mmol) and sodium tert-butoxide (70.2 mg, 0.73 mmol) were added into a reaction flask in sequence. The air in the reaction flask was replaced with nitrogen three times, and the system was reacted at 100° C. for 18 hours under nitrogen protection. The system was filtered, and the filtrate was concentrated under reduced pressure. The residue was separated by column chromatography to obtain 79.8 mg of the product with a yield of 47.7%.

ESI-MS Calculated for [M+1]$^+$=506.22; Found: 506.40. The calculated value was consistent with the found value.

Step 5: Synthesis of (7S)—N-(3-chlorophenyl)-1-methyl-9-(1,2,3,6-tetrahydropyridin-4-yl)-6,7-dihydro-5H-benzo[c][1,2,3]triazolo[1,5-a]azepin-7-amine (RE10-6)

RE10-5 (79.8 mg, 0.16 mmol), 10 mL of dichloromethane and 1 mL of trifluoroacetic acid were added into a reaction flask in sequence and stirred for 2 hours at room temperature. The system was concentrated under reduced pressure, and the resultant was used directly in the next step.

Step 6: Synthesis of (7S)-N-(3-chlorophenyl)-9-(1 sopropyl-1,2,3,6-tetrahydropyridin-4-yl)-1-methyl-6,7-dihydro-5H-benzo[c][1,2,3]triazolo[1,5-a]azepin-7-amine (RE10)

RE10-6, methanol (10 mL), acetone (1 mL) and sodium cyanoborohydride (119.0 mg, 1.89 mmol) were added into a reaction flask in sequence and stirred at room temperature for 3 hours. The system was concentrate under reduced pressure, and the residue was added with dichloromethane (50 mL) and water (50 mL), shaken and separated. The aqueous layer was extracted with dichloromethane (50 mL). The combined organic layer was washed with water (100 mL) and saturated brine (30 mL), dried over anhydrous sodium sulfate and filtered with suction. The filtrate was concentrated under reduced pressure, and the residue was separated by PLC to obtain a crude, which was separated by medium-pressure preparative chromatography (mobile phase: A: purified water with 0.05% trifluoroacetic acid, B: acetonitrile with 0.05% trifluoroacetic acid) to obtain the target compound RE10, which was lyophilized to obtain 16.7 mg of a white solid. [α]$_D^{20}$=−94.31 (c=0.001, acetone).

ESI-MS Calculated for [M+1]$^+$=448.22, Found: 448.30. The calculated value was consistent with the found value.

Preparation Example 182, Final Product RE13(R): (7R)—N-(3-chlorophenyl)-9-(1-isopropyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate

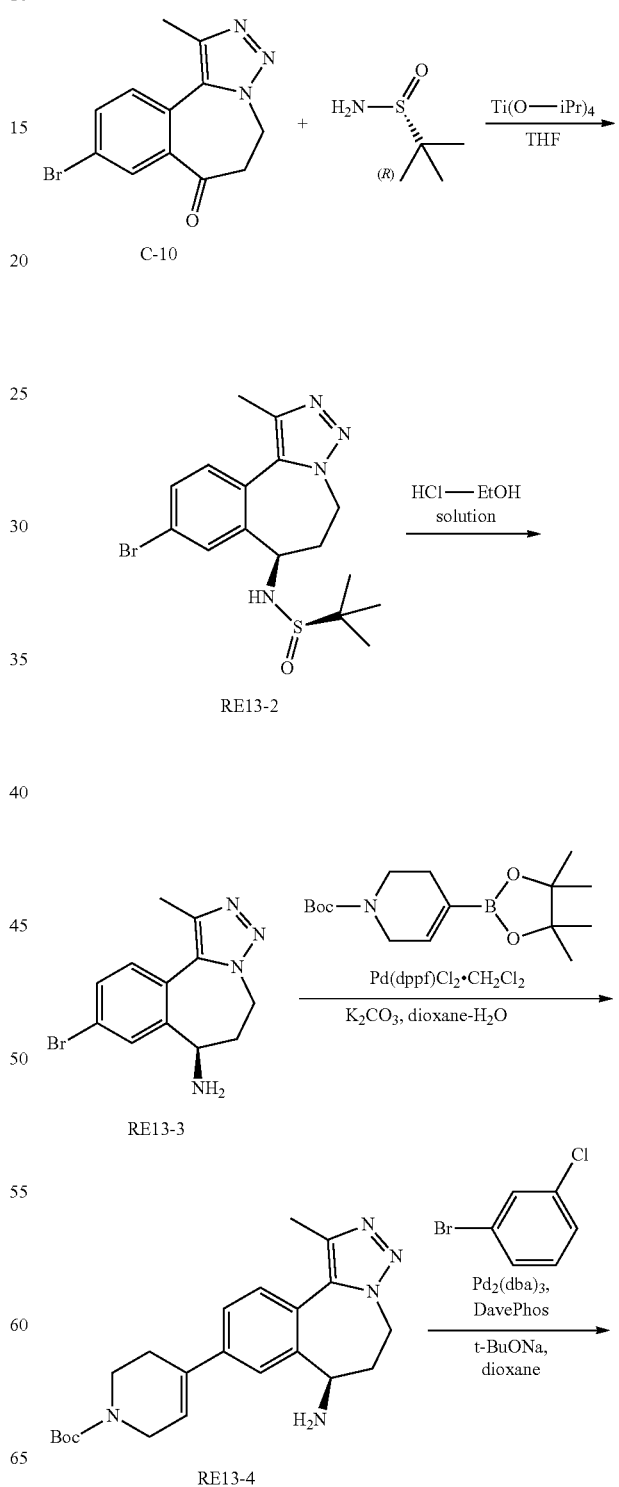

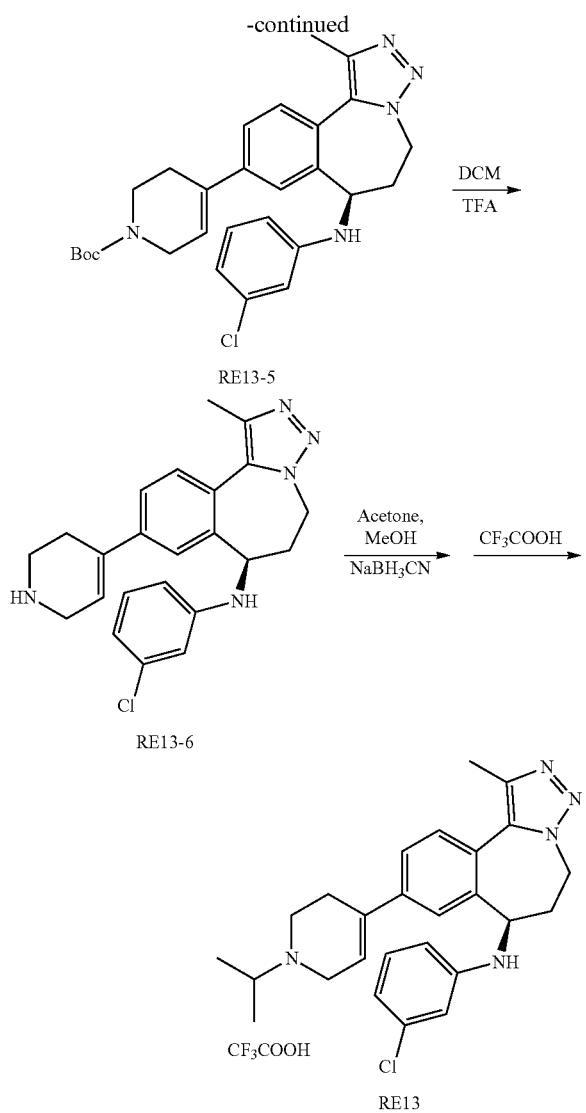

Step 1: Synthesis of (R)—N-((7R)-9-bromo-1-methyl-6,7-dihydro-5H-benzo[c][1,2,3]triazolo[1,5-a]azepin-7-yl)-2-methylpropan-2-sulfinamide (RE13-2)

C-10 (595.5 mg, 2.03 mmol), 12 mL of dry tetrahydrofuran, (R)-(−)-tert-butylsulfinamide (1.07 g, 8.83 mmol) and tetraisopropyl titanate (5.02 g, 17.66 mmol) were adde into a reaction flask in sequence. The air in the reaction flask was replaced with nitrogen three times, and the system was heated to react under reflux for 18 hours under nitrogen protection. The system was naturally cooled to room temperature and then to 0-5° C. in an ice bath, added dropwise with a solution of 375.0 mg NaBH₄ in ethanol (20 mL). After the dropwise addtion, the temperature was kept for 30 minutes, and the system was added with 2 mL of water, stirred for 30 minutes and filtered under suction. The filtrate was concentrated under reduced pressure, and the residue was separated by column chromatography to obtain 578.0 mg of a crude product RE13-2.

ESI-MS Calculated for [M+1]⁺=399.06; Found: 399.30. The calculated value was consistent with the found value.

Step 2: Synthesis of (7R)-9-bromo-1-methyl-6,7-dihydro-5H-benzo[c][1,2,3]triazolo[1,5-a]azepin-7-amine (RE13-3)

RE13-2 (578.0 mg, 1.46 mmol) and 15 mL of hydrogen chloride in ethanol (33%) were added into a reaction flask and stirred at room temperature for 3 hours. The system was concentrated under reduced pressure, and the residue was added with 50 mL of water to dissolve, and extracted twice with 20 mL of dichloromethane. The aqueous layer was adjusted pH to 9-10 with a sodium carbonate solution and extracted with dichloromethane (50 mL*3). The combined organic layer was washed with water (100 mL) and saturated brine (30 mL), dried over anhydrous sodium sulfate and filtered with suction. The filtrate was concentrated under reduced pressure, and the residue was separated by column chromatography to obtain 211.3 mg of the productin 35.4% over a two-step yield. $[\alpha]_D^{20}$=61.93 (c=0.25 g/100 mL in ethanol)

ESI-MS Calculated for [M+1]⁺=295.03, Found: 295.00. The calculated value was consistent with the found value.

Step 3: Synthesis of tert-butyl 4-((7R)-7-amino-1-methyl-6,7-dihydro-5H-benzo[c][1,2,3]triazolo[1,5-a]azepin-9-yl)-5,6-dihydropyridine-1 (2H)-carboxylate (RE13-4)

RE13-3 (211.3 mg, 0.72 mmol), 1,4-dioxane (10 mL), N-Boc-1,2,5,6-tetrahydropyridine-4-pinacolborate (338.3 g, 1.09 mmol), Pd(dppf)Cl₂-dichloromethane complex (114.2 mg, 0.14 mmol), potassium carbonate (225.7 mg, 2.27 mmol) and 0.5 mL of water were added into a reaction flask in sequence. The air in the reaction flask was replaced with nitrogen three times, and the system was reacted at 100° C. for 3 hours under nitrogen protection. The system was filtered, and the filtrate was concentrated under reduced pressure. The residue was separated by column chromatography to obtain 213.2 mg of the product with a yield of 75.0%.

ESI-MS Calculated for [M+1]⁺=396.50; Found: 396.30. The calculated value was consistent with the found value.

Step 4: Synthesis of tert-butyl 4-((7R)-7-((3-chlorophenyl)amino)-1-methyl-6,7-dihydro-5H-benzo[c][1,2,3]triazolo[1,5-a]azepin-9-yl)-5,6-dihydropyridine-1(2H)-carboxylate (RE13-5)

RE13-4 (213.2 mg, 0.54 mmol), dry 1,4-dioxane (12 mL), m-chlorobromobenzene (415.2 mg, 2.17 mmol), Pd₂(dba)₃ (92.2 mg, 0.10 mmol), DavePhos (90.8 mg, 0.23 mmol) and sodium tert-butoxide (113.8 mg, 1.18 mmol) were added into a reaction flask in sequence. The air in the reaction flask was replaced with nitrogen three times, and the system was reacted at 100° C. for 18 hours under nitrogen protection. The system was filtered, and the filtrate was concentrated under reduced pressure. The residue was separated by column chromatography to obtain 77.9 mg of the product with a yield of 28.5%.

ESI-MS Calculated for [M+1]⁺=506.22; Found: 506.40. The calculated value was consistent with the found value.

Step 5: Synthesis of (7R)—N-(3-chlorophenyl)-1-methyl-9-(1,2,3,6-tetrahydropyridin-4-yl)-6,7-dihydro-5H-benzo[c][1,2,3]triazolo[1,5-a]azepin-7-amine (RE13-6)

RE13-5 (77.9 mg, 0.15 mmol), 10 mL of dichloromethane and 1 mL of trifluoroacetic acid were added into a reaction flask and stirred for 2 hours at room temperature. The system was concentrated under reduced pressure, and the resultant was used directly in the next step.

Step 6: Synthesis of (7R)—N-(3-chlorophenyl)-9-(1-isopropyl-1,2,3,6-tetrahydropyridin-4-yl)-1-methyl-6,7-dihydro-5H-benzo[c][1,2,3]triazolo[1,5-a]azepin-7-amine (RE13)

RE13-6, methanol (10 mL), acetone (1 mL) and sodium cyanoborohydride (120.0 mg, 1.89 mmol) were added into a reaction flask in sequence and stirred at room temperature for 3 hours. The system was concentrated under reduced pressure, and the residue was added with dichloromethane (50 mL) and water (50 mL), shaken and separated. The aqueous layer was extracted with dichloromethane (50 mL). The combined organic layer was washed with water (100 mL) and saturated brine (30 mL), dried over anhydrous sodium sulfate and filtered with suction. The filtrate was concentrated under reduced pressure and the residue was separated by PLC to obtain a crude, which was separated by medium-pressure preparative chromatography (mobile phase: A: purified water with 0.05% trifluoroacetic acid, B: acetonitrile with 0.05% Trifluoroacetic acid) to obtain the target compound RE13, which was lyophilized to obtain 5.0 mg of a white solid. $[\alpha]_D^{20}$=95.07. (c=0.001, acetone).

ESI-MS Calculated for $[M+1]^+$=448.22; Found: 448.40. The calculated value was consistent with the found value.

Preparation Example 183, Final Product RE29:
N-(3-chloro-2-fluorophenyl)-9-(1-isopropyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate

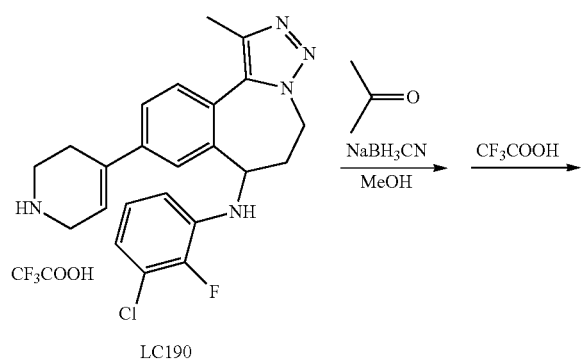

The final product RE29 was prepared according to the method in Preparation Example 174, except that the reactant acetaldehyde was replaced with acetone.

ESI-MS Calculated for $[M+H]^+$=466.21; Found: 466.30. The calculated value was consistent with the found value.

Preparation Example 184, Final Product RE30:
N-(3-chloro-2-fluorophenyl)-9-(1-cyclobutyl-1,2,3,6-tetrahydropyridin-4-yl)-1-methyl-6,7-dihydro-5H-benzo[c][1,2,3]triazolo[1,5-a]azepin-7-amine 2,2,2-trifluoroacetate

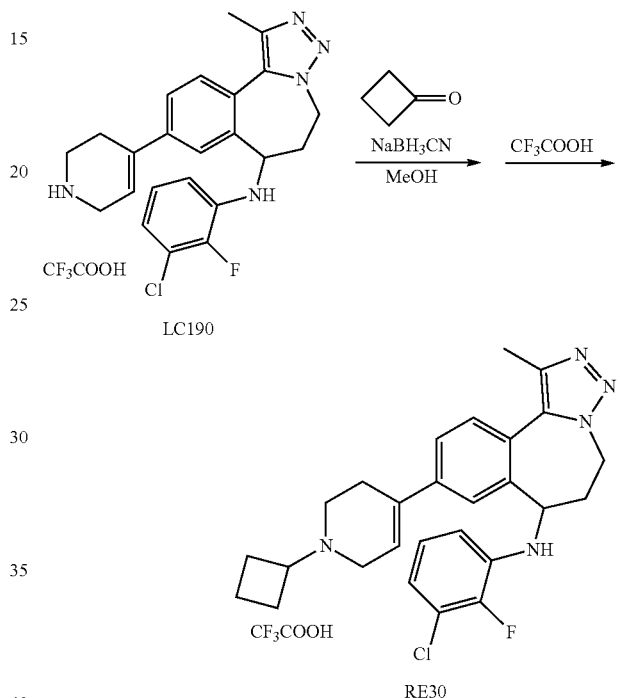

The final product RE30 was prepared according to the method in Preparation Example 174, except that the reactant acetaldehyde was replaced with cyclobutanone.

ESI-MS Calculated for NA-W=478.21; Found: 478.30. The calculated value was consistent with the found value.

Preparation Example 185: (R)—N-(3-chlorophenyl)-1-methyl-9-(1-methyl-1H-pyrazol-4-yl)-6,7-dihydro-5H-benzo[c][1,2,3]triazolo[1,5-a]azepin-7-amine (RE124)

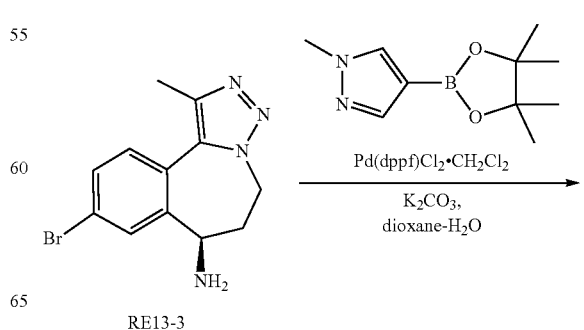

-continued

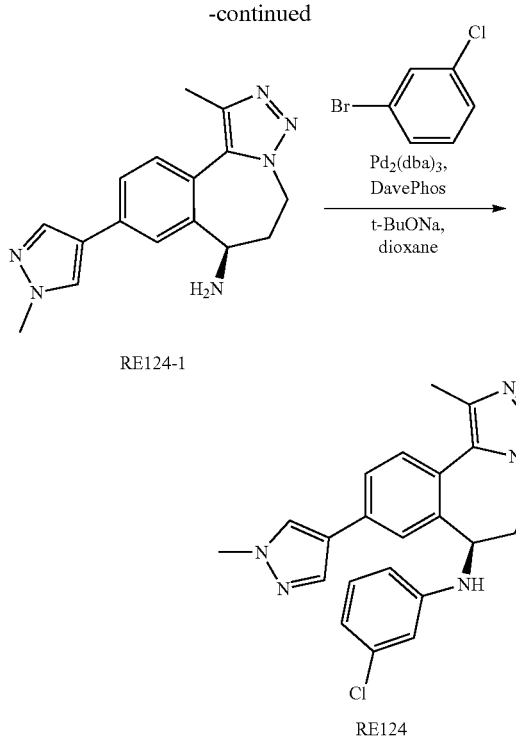

The synthesis of RE124 is similar to that of RE13-5.

Step 1: Synthesis of (R)-1-methyl-9-(1-methyl-1H-pyrazol-4-yl)-6,7-dihydro-5H-benzo[c][1,2,3]triazolo[1,5-a]azepin-7-amine (RE124-1)

To a round bottom flask, RE13-3 (1.13 g, 3.85 mmol), 1,4-dioxane (20 mL), 1-methyl-4-(4,4,5,5-tetramethyl-1,3,2-dioxaborolan-2-yl)-1H-pyrazole (1.35 g, 6.48 mmol), Pd(dppf)Cl$_2$—CH$_2$Cl$_2$ (0.35 g, 0.43 mmol), K$_2$CO$_3$ (1.16 g, 8.39 mmol), and water (1 mL) were added. The reaction system was degassed and refilled with nitrogen. The reaction mixture was heated up at 100° C. for 4 h. The reaction solution was filtered and concentrated and the remaining residue was purified by flash column chromatography to yield the desired product in 1.28 g (94% yield, 84% purity).
ESI-MS [M+H]$^+$ calculated: 295.16, Found: 295.00.

Step 2: Synthesis of (R)—N-(3-chlorophenyl)-1-methyl-9-(1-methyl-1H-pyrazol-4-yl)-6,7-dihydro-5H-benzo[c][1,2,3]triazolo[1,5-a]azepin-7-amine (RE124)

To a round bottom flask, RE124-1 (635.0 mg, 2.16 mmol), anhydrous 1,4-dioxane (20 mL), 3-chloroaniline (884.7 mg, 4.62 mmol), Pd$_2$(dba)$_3$ (441.6 mg, 0.48 mmol), DavePhos (355.8 mg, 0.90 mmol), and tBuONa (310.9 mg, 3.24 mmol) were added. The reaction system was degassed and refilled with nitrogen. The reaction mixture was heated up at 110° C. for 18 h. The reaction solution was filtered and concentrated and the remaining residue was purified by flash column chromatography to yield the desired product, which was further purified by reverse phase HPLC. The desired product was lyophilized and obtained in 337.5 mg.
[α]$_D^{20}$=117.37 (c=0.19 g/100 mL in acetone). ESI-MS [M+H]$^+$ calculated: 405.15, Found: 404.80.

Preparation Example 186: Synthesis of (R)—N-(4-chlorophenyl)-1-methyl-9-(1-methyl-1H-pyrazol-4-yl)-6,7-dihydro-5H-benzo[c][1,2,3]triazolo[1,5-a]azepin-7-amine (RE127)

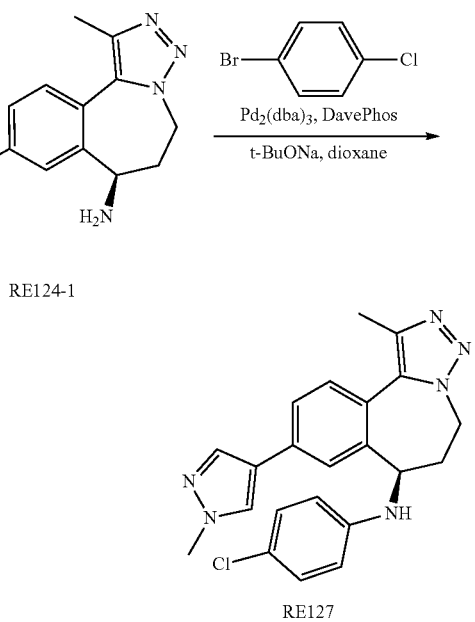

The synthesis of RE127 is similar to that of RE13-5.
To a round bottom flask, RE124-1 (635.0 mg, 2.16 mmol), anhydrous 1,4-dioxane (15 mL), 4-chloroaniline (829.7 mg, 4.33 mmol), Pd$_2$(dba)$_3$ (414.3 mg, 0.45 mmol), DavePhos (351.0 mg, 0.89 mmol), and tBuONa (318.4 mg, 3.31 mmol) were added. The reaction system was degassed and refilled with nitrogen. The reaction mixture was heated up at 110° C. for 18 h. The reaction solution was filtered and concentrated and the remaining residue was purified by flash column chromatography to yield the desired product, which was further purified by reverse phase HPLC. The desired product was lyophilized and obtained in 212.5 mg.
[α]$_D^{20}$=170.20 (c=0.18 g/100 mL in acetone). ESI-MS [M+H]$^+$ calculated: 405.15, Found: 404.80.

Preparation Example 187: Synthesis of (R)—N-(4-chlorophenyl)-9-(1-ethyl-1H-pyrazol-4-yl)-1-methyl-6,7-dihydro-5H-benzo[c][1,2,3]triazolo[1,5-a]azepin-7-amine (RE136)

The synthesis of RE136 is similar to that of RE13-5.

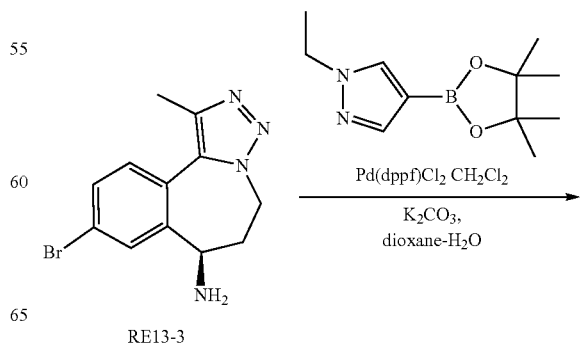

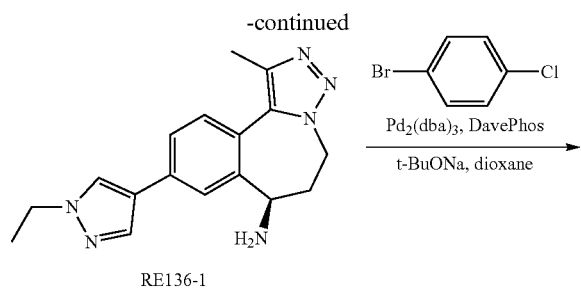

RE136-1

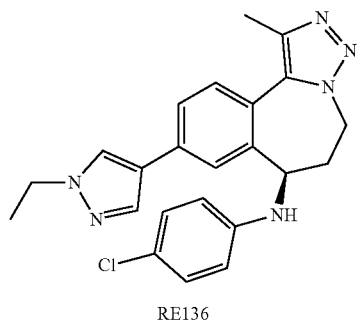

RE136

Step 1: Synthesis of (R)-9-(1-ethyl-1H-pyrazol-4-yl)-1-methyl-6,7-dihydro-5H-benzo[c][1,2,3]triazolo[1,5-a]azepin-7-amine (RE136-1)

To a round bottom flask, RE13-3 (306.3 mg, 1.04 mmol), 1,4-dioxane (12 mL), 1-ethyl-4-(4,4,5,5-tetramethyl-1,3,2-dioxaborolan-2-yl)-1H-pyrazole (462.9 mg, 2.08 mmol), Pd(dppf)Cl$_2$—CH$_2$Cl$_2$ (104.9 mg, 0.13 mmol), K$_2$CO$_3$ (296.8 mg, 2.15 mmol), and water (0.5 mL) were added. The reaction system was degassed and refilled with nitrogen. The reaction mixture was heated up at 100° C. for 4 h. The reaction solution was filtered and concentrated and the remaining residue was purified by flash column chromatography to yield the desired product in 316.7 mg (98% yield).
ESI-MS [M+H]$^+$ calculated: 309.17, Found: 309.00.

Step 2: Synthesis of (R)—N-(4-chlorophenyl)-9-(1-ethyl-1H-pyrazol-4-yl)-1-methyl-6,7-dihydro-5H-benzo[c][1,2,3]triazolo[1,5-a]azepin-7-amine (RE136)

To a round bottom flask, RE136-1 (316.7 mg, 1.02 mmol), anhydrous 1,4-dioxane (16 mL), 4-chloroaniline (391.3 mg, 2.04 mmol), Pd$_2$(dba)$_3$ (183.5 mg, 0.20 mmol), DavePhos (173.8 mg, 0.44 mmol), and tBuONa (189.4 mg, 1.97 mmol) were added. The reaction system was degassed and refilled with nitrogen. The reaction mixture was heated up at 110° C. for 18 h. The reaction solution was filtered and concentrated and the remaining residue was purified by flash column chromatography to yield the desired product, which was further purified by reverse phase HPLC. The desired product was lyophilized and obtained in 232.8 mg.
$[\alpha]_D^{20}$=167.55 (c=0.20 g/100 mL in acetone). ESI-MS [M+H]$^+$ calculated: 419.17, Found: 418.90.

According to the preparation method disclosed above in the present invention, those skilled in the art can use the same principles and methods to prepare the various specific compounds involved in the compound of formula (I) of the present invention.

It should be understood that within the scope of the present invention, the above various technical features of the present invention and the various technical features specifically described in the steps involved in the above preparation method can be combined with each other to form a new or preferred technical solution. All possible combinations are not detailed here.

The present invention also relates to use of the compound of formula (I) in a disease related to the activity or expression of the BET Bromodomain BRD4 protein. The compound of formula (I) was tested for its binding to the BD1 domain and BD2 domain of the BRD4 protein and its binding to active cells.

1. Determination of the value of binding affinity constant (KO between the compound and BRD4 BD1 protein The purity of BRD4 BD1 protein used in the experiment was greater than 95%, and the protein concentration was 43.4 uM. The 96-well plate was purchased from Corning (black, #3694). The multifunctional microplate reader was a product of TECAN, model: SPARK 10M. Buffer: 100 mM potassium phosphate (pH 6.5), 2% ethylene glycol (Sigma) and 0.01% Trition X-100 (Sigma). The experimental water was Millipore-Q pure water.

The specific experimental steps were as follows.

First, the compound to be tested was dissolved in ethylene glycol to prepare into a 10 mM standard stock solution. Subsequently, the standard stock solution of the compound to be tested was diluted into a working sample solution with the buffer in an EP tube and ready for use. The concentration of the prepared working sample solution was 5 times of the highest sample concentration required on the test plate (5×test compound solution).

40 λL of a 5× test compound solution of a sample A was added to wells B1-B3 of a 96-well plate, and 40 μL of a 5× test compound solution of a sample B was added to wells B7-B9 of the 96-well plate, respectively. 20 uL of the buffer was added to the remaining wells, except for wells B1-B3 and B7-B9. Then, 20 uL of a solution was taken from wells B1-B3 to C1-C3, and this 2-fold dilution was repeated from C1-C3 until H$_4$-H6; in the same way, 20 uL of a solution was taken from B7-B9 to C7-C9, this 2-fold dilution was repeated from C7-C9 until H10-H12. Finally, 80 uL of a mixed solution containing 2.5 nM Tracer and 37.5 nM BRD4 BD1 protein was added to each well.

Wells A1-A3 were used as the blank control group, and added with 80 uL of the buffer. Wells A4-A6 were used as the negative signal reference group and added with 80 uL of a buffer containing only 2.5 nM fluorescent-labeled molecular probe. Wells A7-A9 were used as the positive reference group and added with 80 uL of a mixed solution containing 2.5 nM fluorescent-labeled molecular probe and 37.5 nM BRD4 BD1 protein.

The 96-well plate was covered with an aluminum foil, and placed on a 96-well plate shaker and incubated at room temperature for 30 mM. Then the fluorescence polarization value (mP) at Ex485 nm/Em530 nm was read on the microplate reader. The measured mP value was plotted against the compound concentration gradient, and the sample compound concentration corresponding to the median of the maximum and minimum mP values was the IC$_{50}$ value of the binding between the compound and the protein ([I]$_{50}$).

According to this IC$_{50}$ value ([I]$_{50}$, the binding affinity constant (K$_i$) of the compound and the protein was calculated by using the equation below:

$$Ki=[I]_{50}/([L]_{50}/K_d+[P]_0/K_d+1).$$

In the equation, [L]$_{50}$ represents the concentration of the fluorescent-labeled molecular probe in the system when 50% of the protein was bound; [P]$_0$ represents the concentration of BRD4 BD1 protein in the above-mentioned test system, and K$_d$ was the dissociation constant of the protein and the fluorescent-labeled molecular probe.

2. Determination of the binding affinity constant value (K0 of the compound and BRD4 BD2 protein The purity of BRD4 BD2 protein used in the experiment was greater than 95%, and the protein concentration was 46.33 uM. The 96-well plate was purchased from Corning (black, #3694). The multifunctional microplate reader was a product of TECAN, model: SPARK 10M. Buffer: 100 mM potassium phosphate (pH 6.5), 2% ethylene glycol (Sigma) and 0.01% Trition X-100 (Sigma). The experimental water was Millipore-Q pure water.

The K$_i$ value of the compound and BRD4 BD2 protein was measured according to the FP test procedures for detecting the K$_i$ value of the compound and BRD4 BD1 protein except that the BRD4 BD1 protein was replaced with the BRD4 BD2 protein.

Using the above two methods, the protein binding affinity values of the compounds having the structure of formula (I) with BRD4 BD1 and BRD4 BD2 can be determined. The specific values are shown in Table 1.

TABLE 1

The binding affinity values of the compounds with BRD4 BD1 protein and BRD4 BD2 protein

| No. | Code | BRD4 BD1 K$_i$ (nM) | BRD4 BD2 K$_i$ (nM) |
|---|---|---|---|
| 1 | FA01 | 169.42 | 104.83 |
| 2 | FA02 | 58.34 | 37.1 |
| 3 | FA03 | 205.57 | 56.27 |
| 4 | FA05 | 204.5 | 137.5 |
| 5 | FA06 | 83.1 | 55.9 |
| 6 | BB188 | 94.15 | 41.38 |
| 7 | BB189 | 171.83 | 92.12 |
| 8 | BE02 | 128.20 | 42.77 |
| 9 | BE25 | 20.82 | 9.40 |
| 10 | BE44 | 173.36 | 48.10 |
| 11 | BE95 | 577 | 86.9 |
| 12 | LA55 | 53.70 | 25.5 |
| 13 | LA93 | 76.29 | 46.67 |
| 14 | LA108 | 80.55 | 31.70 |
| 15 | LA198 | 44.01 | 21.37 |
| 16 | LB01 | 94.82 | 26.91 |
| 17 | LB17 | 235.61 | 44.04 |
| 18 | LB20 | 1723.41 | 82.81 |
| 19 | LB24 | 64.52 | 22.37 |
| 20 | LB32 | 235.21 | 43.74 |
| 21 | LB35 | 614.40 | 23.89 |
| 22 | LB36 | 97.62 | 42.55 |
| 23 | LB37 | 45.05 | 10.87 |
| 24 | LB38 | 44.75 | 9.29 |
| 25 | RA180 | 33.73 | 7.60 |
| 26 | RA188 | 73.67 | 17.09 |
| 27 | RA193 | 52.00 | 11.12 |
| 28 | RA194 | 29.06 | 24.10 |
| 29 | RB03 | 36.85 | 16.63 |
| 30 | RB05 | 23.20 | 5.73 |
| 31 | RB06 | 128.84 | 15.4 |
| 32 | RB07 | 51.20 | 19.76 |
| 33 | RB11 | 89.94 | 12.87 |
| 34 | RB31 | 33.6 | 24.7 |
| 35 | RB42 | 53 | 25.7 |
| 36 | RB43 | 45.8 | 14 |
| 37 | RB48 | 45.1 | 16.5 |
| 38 | RB66 | 62.9 | 9 |
| 39 | BE114 | 45.4 | 7 |
| 40 | BE118 | 271.8 | 23.6 |
| 41 | BE128 | 176 | 17.1 |
| 42 | BE130 | 138.7 | 29.9 |
| 43 | LB42 | 34.47 | 8.19 |
| 44 | LB62 | 228.6 | 13 |
| 45 | LB63 | 77.8 | 14 |
| 46 | LB68 | 68.5 | 13 |
| 47 | LB71 | 92.2 | 30.5 |
| 48 | LB77 | 99.9 | 6 |
| 49 | LB83 | 180.04 | 38.36 |
| 50 | LB86 | 56.04 | 13.98 |
| 51 | LB88 | 137.20 | 15.07 |
| 52 | LB89 | 426.5 | 50.5 |
| 53 | LB90 | 133.56 | 16.53 |
| 54 | LB91 | 81.41 | 11.56 |
| 55 | LB92 | 132.62 | 17.92 |
| 56 | LB97 | 355.14 | 27.89 |
| 57 | LB98 | 52.4 | 9.1 |
| 58 | LB103 | 607.4 | 95.2 |
| 59 | LB113 | 38 | 7.4 |
| 60 | LB114 | 45.3 | 8.8 |
| 61 | LB128 | 89.30 | 22.76 |
| 62 | LB138 | 1038.97 | 203.39 |
| 63 | LB139 | 123.99 | 48.34 |
| 64 | LB142 | 68.95 | 11.45 |
| 65 | LB143 | 78.27 | 9.61 |
| 66 | RB90 | 103.5 | 35.2 |
| 67 | RB99 | 421.7 | 19.4 |
| 68 | LB152 | 75.51 | 16.72 |
| 69 | LB160 | 96.36 | 12.48 |
| 70 | LB164 | 95.68 | 12.71 |
| 71 | LB170 | 74.85 | 4.78 |
| 72 | LB171 | 26.11 | 7.06 |
| 73 | LB173 | 178.54 | 32.09 |
| 74 | LB175 | 43.51 | 18.61 |
| 75 | LB181 | 132.46 | 14.49 |
| 76 | LB185 | 218.21 | 14.46 |
| 77 | LB186 | 82.23 | 13.69 |
| 78 | LB192 | 94.58 | 16.07 |
| 79 | LC01 | 56.04 | 28.37/9.08 |
| 80 | LC03 | 32.92 | 1.33/4.03 |
| 81 | LC07 | 133.50 | 8.4/18.8 |
| 82 | LC09 | 15.46 | <Kd |
| 83 | LC10 | 69.29 | <Kd |
| 84 | LC11 | 7.80 | <Kd |
| 85 | LC18 | 34.63 | 15.24 |
| 86 | LC20 | 59.58 | 14.99 |
| 87 | LC29 | 19.42 | 7.60 |
| 88 | LC31 | 92.60 | 20.86 |
| 89 | LC56 | 1515.88 | 70.28 |
| 90 | LC75 | 2291 | 116.20 |
| 91 | LC79 | 639.03 | 34.25 |
| 92 | LC84 | 844.60 | 37.77 |
| 93 | LC87 | >20000 | 142.21 |
| 94 | LC97 | 795.49 | 40.62 |
| 95 | LC99 | 38.40 | 12.86 |
| 96 | LC101 | 89.03 | 13.61 |
| 97 | LC117 | 2369.95 | 115.52 |
| 98 | LC127 | 793.48 | 41.53 |
| 99 | LC128 | 466.80 | 56.21 |
| 100 | LC131 | 835.47 | 86.32 |
| 101 | LC132 | 723.73 | 55.85 |
| 102 | LC133 | 2189.64 | 206.52 |
| 103 | LC136 | 49.71 | 8.83 |
| 104 | LC158 | 858.60 | 41.59 |
| 105 | LC159 | 2132.70 | 65.44 |
| 106 | LC160 | 2267.93 | 114.42 |
| 107 | LC174 | 949.46 | 622.75 |
| 108 | LC185 | 162.42 | 16.37 |
| 109 | LC186 | 31.30 | 6.98 |
| 110 | LC190 | 592.42 | 59.99 |
| 111 | LC191 | 51.79 | 11.17 |
| 112 | LC192 | 818.63 | 56.57 |
| 113 | LC193 | >4000 | 698.24 |
| 114 | LC198 | 2982 | 152.63 |
| 115 | LD07 | 770.11 | 33.12 |
| 116 | LD08 | 1265.56 | 62.34 |
| 117 | LD13 | 943.77 | 1736.93 |
| 118 | LD14 | 14.26 | 6.14 |

TABLE 1-continued

The binding affinity values of the compounds
with BRD4 BD1 protein and BRD4 BD2 protein

| No. | Code | BRD4 BD1 $K_i$ (nM) | BRD4 BD2 $K_i$ (nM) |
|---|---|---|---|
| 119 | LD17 | 616.02 | 51 |
| 120 | LD19 | 38.73 | 9.67 |
| 121 | LD23 | 334.42 | 41.49 |
| 122 | LD24 | 292.90 | 21.65 |
| 123 | LD31 | 39.07 | 17.15 |
| 124 | LD76 | 1055.51 | 10.69/36.11 |
| 125 | LD77 | 81.67 | 3.97/3.16 |
| 126 | BF169 | >20000 | 661.47 |
| 127 | BF178 | >20000 | >20000 |
| 128 | BJ28 | 1826 | 250 |
| 129 | BJ122 | 756.94 | 68.64 |
| 130 | BJ123 | 1237.12 | 52.73 |
| 131 | BJ126 | 1106.28 | 60.37 |
| 132 | BJ179 | 435.60 | 25.95 |
| 133 | BJ183 | 939.14 | 44.97 |
| 134 | BJ193 | 28.28 | 8.40 |
| 135 | BH06 | 596.21 | 35.74 |
| 136 | BH23 | 751.49 | 75.32 |
| 137 | BH27 | 70.09 | 2.95 |
| 138 | BH29 | 39.49 | 1.26 |
| 139 | BH32 | 524.68 | 9.75 |
| 140 | BH33 | 1781.59/693.36 | 38.60/27.91 |
| 141 | BH36 | 716.61/1403.19 | 13.84/16.02 |
| 142 | BH37 | 1882.41/1562.14 | 61.85/28.34 |
| 143 | BH43 | >100000 | 316.48 |
| 144 | BH46 | 688.74 | 906.67 |
| 145 | BH57 | 2047.3 | 1630.53 |
| 146 | BH81 | 869.39 | 31.09 |
| 147 | BH86 | 9.51 | 6.43 |
| 148 | BH87 | 1100.11 | 44.45 |
| 149 | BH104 | 710.21 | 13.43 |
| 150 | BH107 | 1742.44 | 17.63 |
| 151 | BH108 | 450.66 | 24.30 |
| 152 | BH120 | 582.93 | 21.91 |
| 153 | BH123 | 46.73 | 7.64 |
| 154 | BH159 | 878.56 | 9.31 |
| 155 | BH187 | 1722.13 | 28.76 |
| 156 | BH190 | 1624.01 | 12.87/27.93 |
| 157 | BH192 | 105.82 | 3.45 |
| 158 | BI23 | 1063.22 | 57.33 |
| 159 | BI24 | 5405.45 | 86.36 |
| 160 | BI26 | 861.33 | 45.44 |
| 161 | BI29 | 2664.12 | 168.22 |
| 162 | BI31 | 2286.91 | 151.44 |
| 163 | BI34 | 4201.45 | 290.62 |
| 164 | BI36 | 1851.57 | 89.77 |
| 165 | BI37 | 2573.97 | 196.41 |
| 166 | BI55 | 3097.91 | 116.33 |
| 167 | BI57 | 3612.04 | 147.09 |
| 168 | BI60 | 4744.32 | 306.93 |
| 169 | BI61 | 3202.89 | 147.95 |
| 170 | BI68 | 1109.06 | 45.08 |
| 171 | WYA10 | 718.98 | 20.73/47.35 |
| 172 | WA78 | 281.16 | 19.79 |
| 173 | WA82 | 435.72 | 53.65 |
| 174 | WA83 | 431.45 | 88.59 |
| 175 | RC71 | 1035.11 | 52.46 |
| 176 | RC73 | 2369.95 | 139.43 |
| 177 | RC82 | 2369.95 | 1522.67 |
| 178 | RC116 | 1000.35 | 115.06 |
| 179 | RD06 | 1034.75 | 56.39 |
| 180 | RD21 | 1525.37 | 90.39 |
| 181 | RD41 | 1549.09 | 55.09 |
| 182 | RD115 | 1131.90 | 59.06 |
| 183 | RD121 | 787.55 | 31.76 |
| 184 | RD123 | 1094.66 | 40.76 |
| 185 | RD142 | 4408.2 | 192.99 |
| 186 | RD178 | 1257.28 | 32.7 |
| 187 | RD179 | 2805.28 | 32.58 |
| 188 | RD180 | 52.02 | 12.11 |
| 189 | RE10 (S) | 883.51 | 176.53 |
| 190 | RE13 (R) | 1415.15 | 14.79 |
| 191 | RE29 | 1545.53 | 65.76 |
| 192 | RE30 | 412.82 | 30.17 |
| 193 | RE124 | 9.92 ± 3.36 | <1.0 |
| 194 | RE127 | 4.15 ± 0.21 | <1.0 |
| 195 | RE136 | 2.66 ± 0.37 | <1.0 |

It can be seen from Table 1 that all compounds having the structure of formula (I) can bind to the BD1 domain and BD2 domain of the BRD4 protein. Therefore, the compounds in the examples of the present invention and their enantiomers, diastereomers, racemates and mixtures thereof, and their chemically acceptable salts, crystalline hydrates and solvent mixtures, as well as a pharmaceutical compositions containing the compound of the present invention as the main active ingredients can be used for treating, preventing and alleviating the diseases related to the activity or expression of BET Bromodomain BRD4 protein.

3. Determination of cell viability of the compound

The sample to be tested was dissolved with 100% dimethyl sulfoxide to prepare a 20 mM stock solution of the compound, which was diluted with 100% dimethyl sulfoxide to the highest compound concentration required for the experiment (2.5 mM).

First, 145 uL of a complete cell culture medium was added to wells B1-G1 of a 96-well flat-bottomed tansparent cell culture plate, and 100 uL of the complete medium was added to wells B2-G12, respectively. Then, 5 uL of the 2.5 mM solution of the compound was added to wells B1-D1 and E1-G1 respectively, and then diluted gradiently by 3-folds to B12-D12 and E12-G12 in sequence. Finally, 50 uL of the solution of the cells to be tested was added to each well, with about 3000-5000 cells per well, and a total volume of 150 uL per well.

In the experiment, in addition to the tested compound, two other control groups were set up: 1) a control group adding the cells and the complete medium, but without adding the compound; 2) a control group adding the complete medium only, without adding the cells and the compound. The 96-well plate was placed in a 37° C. cell culture incubator containing 5% carbon dioxide for 4 days, added with 15 uL of a CCK-8 reagent per well, and then incubated at 37° C. for 2-4 hours. The 96-well plate was read on a TECAN microplate reader, and the absorbance value at 450 nm wavelength was taken.

The effect of different concentrations of the compound on cell viability was calculated by the following equation: [absorption value of the experimental group−absorption value of pure cell culture medium without the cells or the compound]/[absorption value of the control group with the tumor cells but no testing compound−absorption value of pure cell culture medium without the cell or the compound]× 100%.

The above data were precessed by software, and the $IC_{50}$ value was the concentration of the compound corresponding to the 50% inhibition rate of cell growth.

Based on the above test method of the compound on cell viability, a variety of diabetes, cardiovascular disease and cancer cell lines were tested, using multiple myeloma MM.1S, breast cancer MDA-MB-231 and leukemia MV4-11 cell lines as exemples. Using this test method, the $IC_{50}$ values of partial compounds in the examples of the present invention measured in multiple myeloma MM.1S, breast cancer MDA-MB-231 cell lines and leukemia MV4-11 cell lines were shown in Table 2. The blank value in Table 2 indicates that the compound was not tested.

TABLE 2

IC$_{50}$ values of the compounds binded with different cell lines

| No. | Code | MM.1S IC$_{50}$ (nM) | MDA-MB-231 IC$_{50}$ (μM) | MV4-11 IC$_{50}$ (nM) |
|---|---|---|---|---|
| 1 | FA01 | 558.6 | | |
| 2 | FA02 | | | |
| 3 | FA03 | 502.3 | | |
| 4 | FA05 | 25.23 | | |
| 5 | FA06 | 6.05 | 0.089 | |
| 6 | BB188 | 805.2 | | |
| 7 | BB189 | 230.2 | | |
| 8 | BE02 | 137.8 | | |
| 9 | BE25 | 3.47 | | |
| 10 | BE44 | 988.7 | | |
| 11 | BE95 | 3186 | | |
| 12 | LA55 | 26.48 | | |
| 13 | LA93 | | | |
| 14 | LA108 | 30.19 | | |
| 15 | LA198 | 22.91 | | |
| 16 | LB01 | 4.28 | 0.450 | |
| 17 | LB17 | 118.8 | | |
| 18 | LB20 | 2458 | | |
| 19 | LB24 | 51.68 | | |
| 20 | LB32 | 601.9 | | |
| 21 | LB35 | 36.53 | | |
| 22 | LB36 | 411.9 | | |
| 23 | LB37 | 2.03 | 0.043 | |
| 24 | LB38 | 32.87 | | |
| 25 | RA180 | 2.34 | 0.011 | |
| 26 | RA188 | 8.54 | | |
| 27 | RA193 | 50.49 | | |
| 28 | RA194 | 329.1 | | |
| 29 | RB03 | 16.86 | | |
| 30 | RB05 | 2.32 | 0.001 | <0.1 |
| 31 | RB06 | 53.23 | | |
| 32 | RB07 | 13.63 | | |
| 33 | RB11 | 323.2 | | |
| 34 | RB31 | 676.3 | | |
| 35 | RB42 | 324.1 | | |
| 36 | RB43 | 1.1 | 0.105 | |
| 37 | RB48 | 2.5 | 0.065 | |
| 38 | RB66 | 31.3 | | |
| 39 | BE114 | 775 | | |
| 40 | BE118 | 604.1 | | |
| 41 | BE128 | 688.9 | | |
| 42 | BE130 | 171.2 | | |
| 43 | LB42 | 16 | | |
| 44 | LB62 | 14020 | | |
| 45 | LB63 | 160.2 | | |
| 46 | LB68 | 112.4 | | |
| 47 | LB71 | 151.3 | | |
| 48 | LB77 | 71.7 | | |
| 49 | LB83 | 250.2 | | |
| 50 | LB86 | 45.1 | | |
| 51 | LB88 | 24.3 | | |
| 52 | LB89 | 143.1 | | |
| 53 | LB90 | 51.9 | | |
| 54 | LB91 | 13.4 | | |
| 55 | LB92 | 121.2 | | |
| 56 | LB97 | 8156 | | |
| 57 | LB98 | 21.5 | | |
| 58 | LB103 | 388.9 | | |
| 59 | LB113 | 11.2 | | |
| 60 | LB114 | 1.2 | | |
| 61 | LB128 | 153 | | |
| 62 | LB138 | 961 | | |
| 63 | LB139 | 120 | | |
| 64 | LB142 | 114 | | |
| 65 | LB143 | 118 | | |
| 66 | RB90 | 256.8 | | |
| 67 | RB99 | 215.3 | | |
| 68 | LB152 | 26.18 | | |
| 69 | LB164 | 26.02 | | 39.3 |
| 70 | LB170 | 151.8 | | |
| 71 | LB171 | 22.75/20.8 | | |
| 72 | LB173 | 1202 | | |
| 73 | LB181 | 167.8 | | |
| 74 | LB185 | 1618 | | |
| 75 | LB186 | 36.64 | | |
| 76 | LB192 | <1 | | <0.1 |
| 77 | LC01 | 48.83 | | |
| 78 | LC03 | 58.98 | | |
| 79 | LC07 | 164.8 | | |
| 80 | LC09 | 39.26 | | |
| 81 | LC10 | 103.7 | | 12.8 |
| 82 | LC11 | 25.2 | | 15.4 |
| 83 | LC18 | 4.7 | | |
| 84 | LC20 | 25.3 | | |
| 85 | LC29 | 12.2 | | |
| 86 | LC31 | 27.9 | | |
| 87 | LC56 | 2893 | | |
| 88 | LC79 | 935.6 | | |
| 89 | LC97 | 590.8 | | |
| 90 | LD07 | 146.2 | | |
| 91 | LD19 | <1 | | |
| 92 | LD23 | 443.4 | | 7.32 |
| 93 | LD24 | 447.1 | | 19.03 |
| 94 | LD76 | 878.8 | | 105.5 |
| 95 | LD77 | 1.86 | | |
| 96 | BH29 | 1 | | |
| 97 | BH32 | 119 | | |
| 98 | BH33 | 186.9 | | |
| 99 | BH36 | 146.2 | | 57.53 |
| 100 | BH37 | 352.4 | | |
| 101 | BH104 | 118.6 | | 1.32 |
| 102 | BH159 | 284.6 | | 75.17 |
| 103 | BH187 | 1297 | | 105.8 |
| 104 | BH190 | 247.6 | | 62.76 |
| 105 | BH192 | 6.15 | | 0.21 |
| 106 | RE13 | 545.8 | | 125.6 |

It can be seen from Table 2 that the test compounds involved in the examples of the present invention can inhibit the growth of multiple myeloma MM.1S, breast cancer MDA-MB-231 and leukemia MV4-11 cell lines, and the test compounds have high activity in inhibiting the growth of the above-mentioned tumor cells, all the compounds have IC$_{50}$ values of less than 10 uM, and some compounds have IC$_{50}$ values of less than 10 nM. These data indicate that the compound represented by formula (I) had a good medical prospect in treatment of diseases related to the activity or expression of the BET Bromodomain BRD4 protein.

Compared with the prior art, the present invention provides a class of compounds with a novel structure and having a benzo seven-membered ring structure. In the preparation process of this class of compounds, the advantages lie in mild conditions, easy access to raw materials, simple product post-processing, etc., and this class of compounds can effectively inhibit the activity of BRD4 protein, and thus has medical prospects for treatment of various diseases.

Although the present invention has been described in detail with reference to the foregoing embodiments, an ordinary person skilled in the art should understand that the technical solutions described in the respective foregoing embodiments still can be modified, or some of the technical features therein can be equivalently replaced; and this modification or replacement does not cause the essence of the corresponding technical solutions to depart from the spirit and scope of the technical solutions of the embodiments of the present invention.

The invention claimed is:
1. A compound having a benzo seven-membered ring structure, wherein the compound has a structure represented by formula (I):

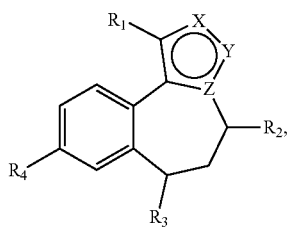

or a chemically acceptable salt thereof,
wherein, X, Y and Z each independently represent CH, N and O, and X, Y and Z form a five-membered heterocyclic ring or a five-membered heteroaromatic ring structure together with the other two carbon atoms;
$R_1$ represents H, C1-C6 alkyl, C3-C6 cycloalkyl, halogen, hydroxyl, cyano, deuterium, C1-C6 alkyl substituted by C1-C4 alkoxyl, or C3-C6 cycloalkyl substituted by halogen, hydroxyl, cyano, deuterium or C1-C4 alkoxyl;
$R_2$ represents H, deuterium, halogen, hydroxyl, amino, cyano, an ester group, trifluoromethyl, aminocarbonyl, aminocarbonylamino, carbamoyloxyl, C1-C6 alkyl, C3-C6 cycloalkyl, C1-C6 alkyl substituted by halogen, hydroxyl, amino, cyano, deuterium, C1-C4 alkoxyl or C1-C4 alkylamino, C3-C6 cycloalkyl substituted by halogen, hydroxyl, amino, cyano, deuterium, C1-C4 alkoxyl or C1-C4 alkylamino, C1-C6 alkyl substituted by (C1-C6 alkoxyl)carbonyl, C1-C6 alkyl substituted by (C1-C6 alkylamino)carbonyl, C1-C6 alkyl substituted by (C1-C6 alkoxyl)carbonylamino, C1-C6 alkyl substituted by carboxyl;
$R_3$ represents —OAr, —$NR_5$Ar or —$NHR_6$;
Ar represents benzene ring, substituted benzene ring, 5-12 membered monocyclic or fused heterocyclic ring containing 1-4 heteroatoms selected from the group consisting of S, O and N, 5-12 membered monocyclic or fused heteroaromatic ring containing 1-4 heteroatoms selected from the group consisting of S, O and N, 5-12 membered monocyclic or fused heterocyclic ring containing 1-4 heteroatoms selected from the group consisting of S, O and N and substituted by 1-3 substituents, 5-12 membered monocyclic or fused heteroaromatic ring containing 1-4 heteroatoms selected from the group consisting of S, O and N and substituted by 1-3 substituents;
the substituents in Ar may each independently represent a substituent selected from the group consisting of deuterium, halogen, hydroxyl, amino, cyano, an ester group, trifluoromethyl, aminocarbonyl, aminocarbonylamino, carbamoyloxyl, C1-C6 alkyl, C3-C6 cycloalkyl, C1-C6 alkyl substituted by halogen, hydroxyl, amino, cyano, deuterium, C1-C4 alkoxyl, C1-C4 alkylamino or di(C1-C4 alkyl)amino, C1-C6 alkyl substituted by 3-7 membered saturated heterocyclic ring, C3-C6 cycloalkyl substituted by halogen, hydroxyl, amino, cyano, deuterium, C1-C4 alkoxyl, C1-C4 alkylamino or di(C1-C4 alkyl)amino, C3-C6 cycloalkyl substituted by 3-7 membered saturated heterocyclic ring, C1-C6 alkyl substituted by (C1-C6 alkoxyl) carbonyl, C1-C6 alkyl substituted by (C1-C6 alkylamino)carbonyl, C1-C6 alkyl substituted by (C1-C6 alkoxyl)carbonylamino, C1-C6 alkyl substituted by (C1-C6 alkylamino)carbonylamino, C1-C6 alkyl substituted by carboxyl, aminocarbonyl substituted by C1-C6 alkyl, aminocarbonylamino substituted by C1-C6 alkyl, carbamoyloxyl substituted by C1-C6 alkyl;
$R_5$ represents H, deuterium, C1-C5 alkyl, C1-C5 alkylcarbonyl or formyl;
$R_6$ represents substituted or unsubstituted C4-C8 aliphatic ring;
$R_4$ represents H, OMe, Cl, Br, benzene ring, benzene ring substituted by 1-3 substituents, 5-12 membered monocyclic or fused heterocyclic ring containing 1-4 heteroatoms selected from the group consisting of S, O and N, 5-12 membered monocyclic or fused heteroaromatic ring containing 1-4 heteroatoms selected from the group consisting of S, O and N, saturated or partially saturated 5-12 membered monocyclic or fused heterocyclic ring containing 1-4 heteroatoms selected from the group consisting of S, O and N, 5-12 membered monocyclic or fused heterocyclic ring containing 1-4 heteroatoms selected from the group consisting of S, O and N and substituted by 1-3 substituents, 5-12 membered monocyclic or fused heteroaromatic ring containing 1-4 heteroatoms selected from the group consisting of S, O and N and substituted by 1-3 substituents, saturated or partially saturated 5-12 membered monocyclic or fused heterocyclic ring containing 1-4 heteroatoms selected from the group consisting of S, O and N and substituted by 1-3 substituents; the above-mentioned substituents may each independently represent a substituent selected from the group consisting of deuterium, halogen, hydroxyl, amino, cyano, an ester group, carboxyl, trifluoromethyl, C1-C6 alkyl, C3-C6 cycloalkyl, C1-C6 alkyl substituted by halogen, hydroxyl, amino, cyano, deuterium, an ester group, carboxyl, C1-C4 alkoxyl, C1-C4 alkylamino, C1-C4 alkylaminocarbonyl, C1-C4 alkylaminocarbonylamino, C1-C4 alkyloxycarbonylamino or C1-C4 alkylcarbamoyloxyl, C1-C6 alkyl substituted by (C1-C6 alkylamino) carbonyl, C3-C6 cycloalkyl substituted by halogen, hydroxyl, amino, cyano, deuterium, an ester group, carboxyl, C1-C4 alkoxyl, C1-C4 alkylamino, C1-C5 acyl, C1-C4 alkylaminocarbonyl, C1-C4 alkylaminocarbonylamino, C1-C4 alkyloxycarbonylamino or C1-C4 alkylcarbamoyloxyl, or C1-C6 alkyl substituted by (C1-C6 alkoxyl) carbonyl.

2. The compound or chemically acceptable salt thereof according to claim 1, wherein the compound has a structure represented by the following formula (I-1) and/or (I-2) and/or (I-3):

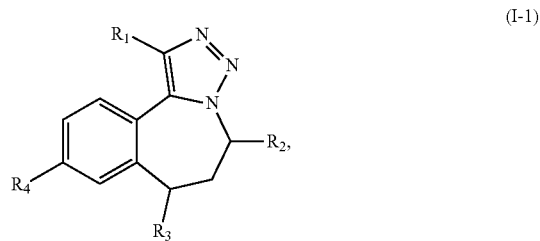

(I-2)

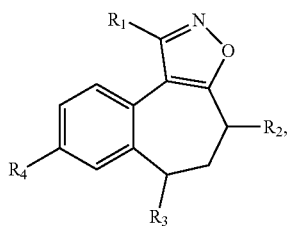

(I-3)

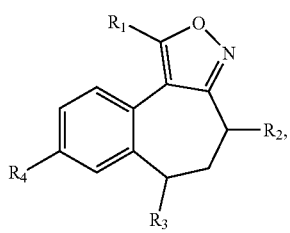

wherein, in each formula, $R_1$, $R_2$, $R_3$, and $R_4$ have the same definition as those in formula (I).

3. The compound or chemically acceptable salt thereof according to claim 1, wherein, the compound has a structure represented by the following formula (I-4) and/or (I-5):

(I-4)

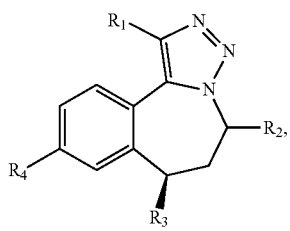

(I-5)

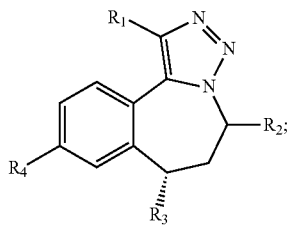

wherein, in each formula, $R_1$, $R_2$, $R_3$, and $R_4$ have the same definition as those in formula (I).

4. The compound or chemically acceptable salt thereof according to claim 1, wherein, the compound has a structure represented by the following formula (I-6) and/or (I-7):

(I-6)

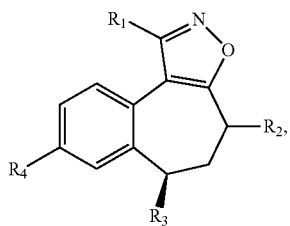

(I-7)

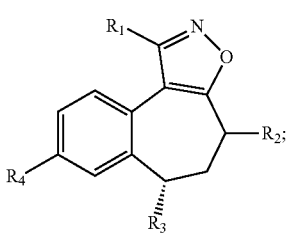

wherein, in each formula, $R_1$, $R_2$, $R_3$, and $R_4$ have the same definition as those in formula (I).

5. The compound or chemically acceptable salt thereof according to claim 1, wherein, the compound has a structure represented by the following formula (I-8) and/or (I-9):

(I-8)

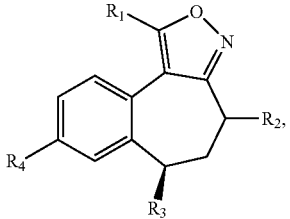

(I-9)

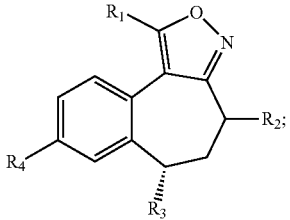

wherein, in each formula, $R_1$, $R_2$, $R_3$, and $R_4$ have the same definition as those in formula (I).

6. The compound or chemically acceptable salt thereof according to claim 1, wherein the compound or the chemically acceptable salt thereof is selected from the group consisting of:

| No. | Code | Structure |
|---|---|---|
| 1 | FA01 |  |

| No. | Code | Structure |
|---|---|---|
| 2 | FA02 | 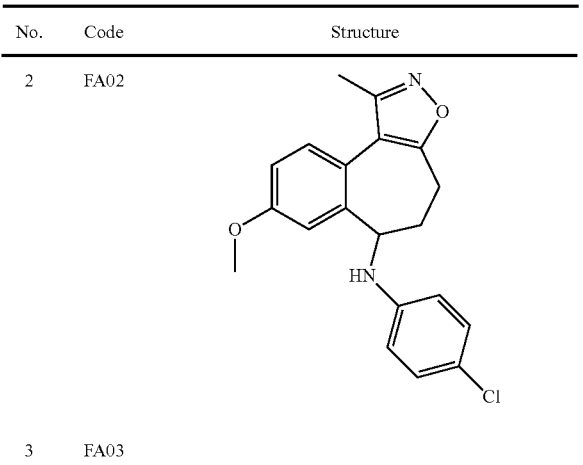 |
| 3 | FA03 | |
| 4 | FA05 | |
| 5 | FA06 | |
| No. | Code | Structure |
|---|---|---|
| 6 | BB188 | 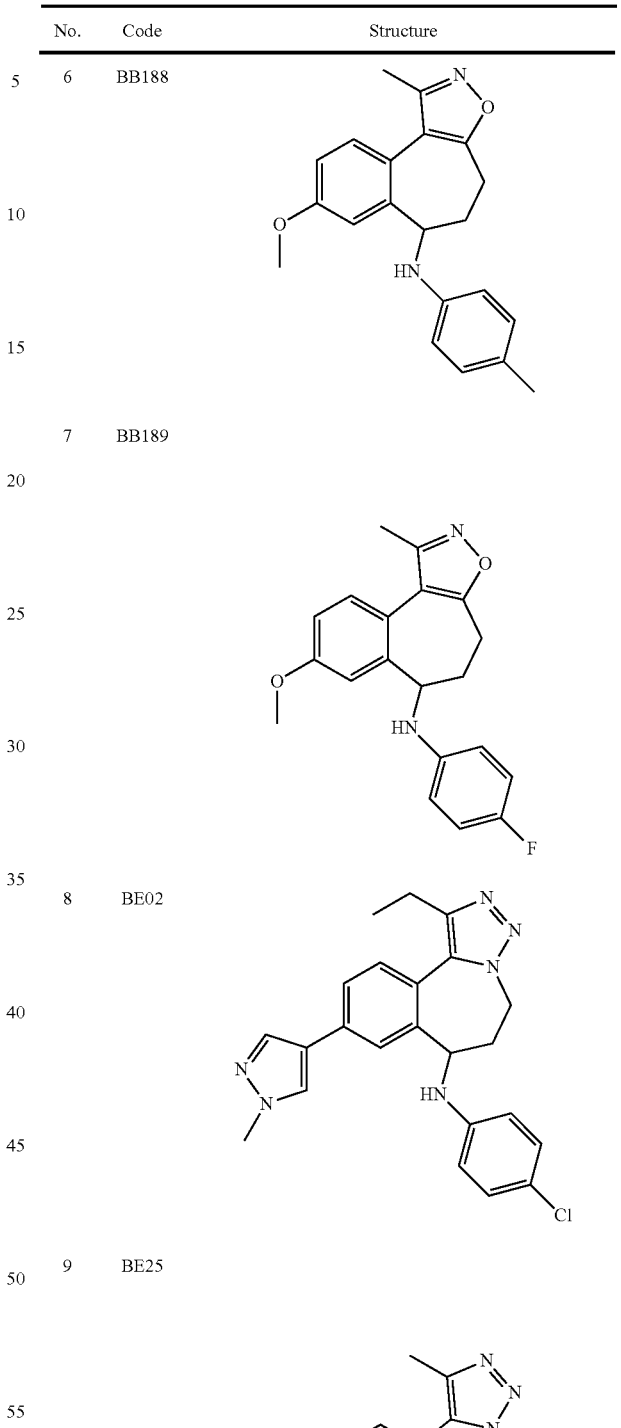 |
| 7 | BB189 | |
| 8 | BE02 | |
| 9 | BE25 | 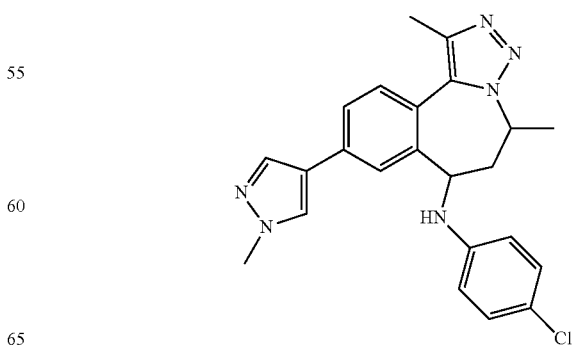 |

-continued

| No. | Code | Structure |
|-----|------|-----------|
| 10 | BE44 | 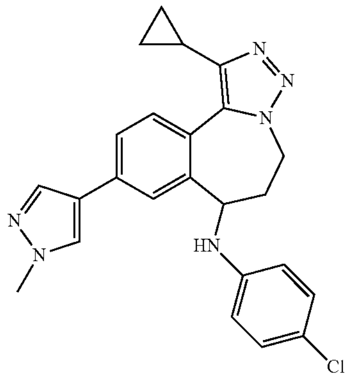 [SMILES: Cn1cc(-c2ccc3c(c2)C(Nc2ccc(Cl)cc2)CCn2nnc(C4CC4)c2-3)cn1] |
| 11 | BE95 | 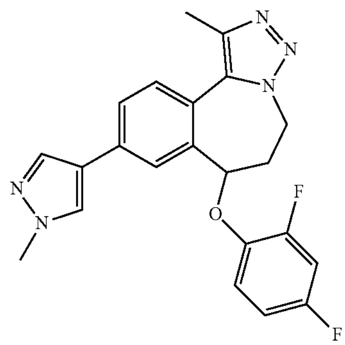 [SMILES: Cc1nnn2c1-c1ccc(-c3cnn(C)c3)cc1C(Oc1ccc(F)cc1F)CC2] |
| 12 | LA55 | 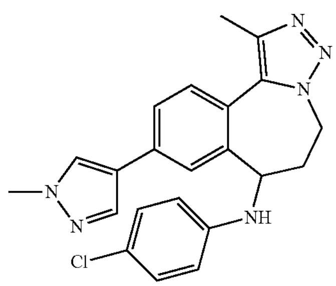 [SMILES: Cc1nnn2c1-c1ccc(-c3cnn(C)c3)cc1C(Nc1ccc(Cl)cc1)CC2] |
| 13 | LA93 | 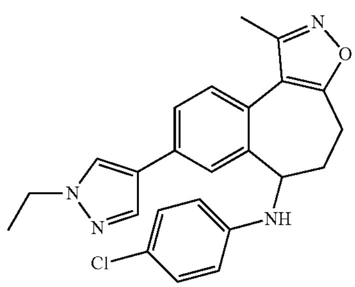 [SMILES: CCn1cc(-c2ccc3c(c2)C(Nc2ccc(Cl)cc2)CCc2onc(C)c2-3)cn1] |
| 14 | LA108 | 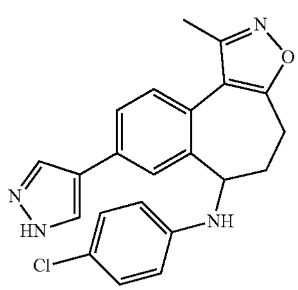 [SMILES: Cc1noc2c1-c1ccc(-c3cn[nH]c3)cc1C(Nc1ccc(Cl)cc1)CC2] |

-continued

| No. | Code | Structure |
|-----|------|-----------|
| 15 | LA198 | 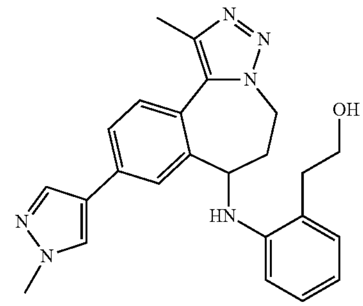 [SMILES: Cc1nnn2c1-c1ccc(-c3cnn(C)c3)cc1C(Nc1ccccc1CCO)CC2] |
| 16 | LB01 | 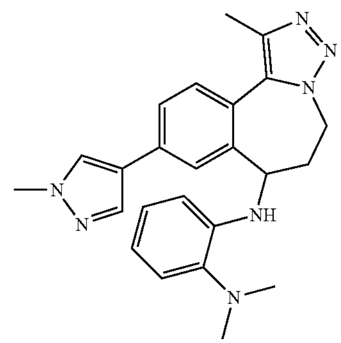 [SMILES: Cc1nnn2c1-c1ccc(-c3cnn(C)c3)cc1C(Nc1ccccc1N(C)C)CC2] |
| 17 | LB17 | 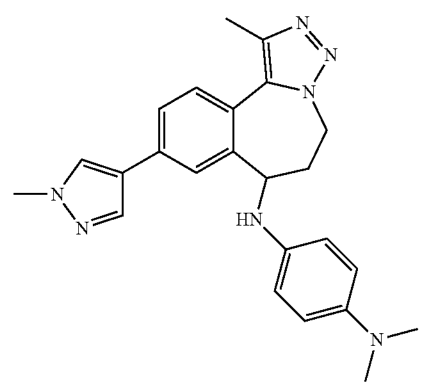 |
| 18 | LB20 | 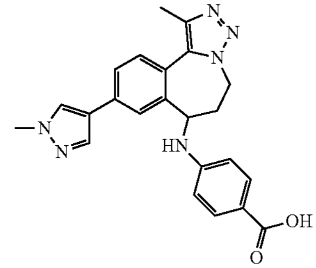 [SMILES: Cc1nnn2c1-c1ccc(-c3cnn(C)c3)cc1C(Nc1ccc(C(=O)O)cc1)CC2] |

-continued

| No. | Code | Structure |
|-----|------|-----------|
| 19 | LB24 | 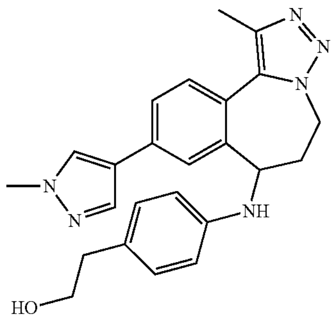 [SMILES: Cc1nnn2c1-c1ccc(-c3cnn(C)c3)cc1C(Nc1ccc(CCO)cc1)CC2] |
| 20 | LB32 | 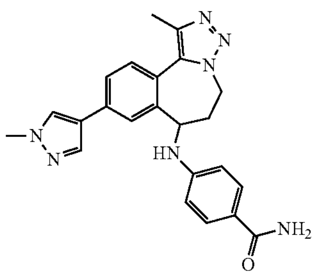 [SMILES: Cc1nnn2c1-c1ccc(-c3cnn(C)c3)cc1C(Nc1ccc(C(N)=O)cc1)CC2] |
| 21 | LB35 | 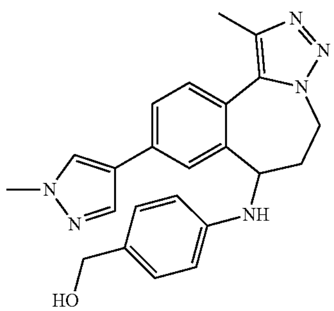 [SMILES: Cc1nnn2c1-c1ccc(-c3cnn(C)c3)cc1C(Nc1ccc(CO)cc1)CC2] |
| 22 | LB36 | 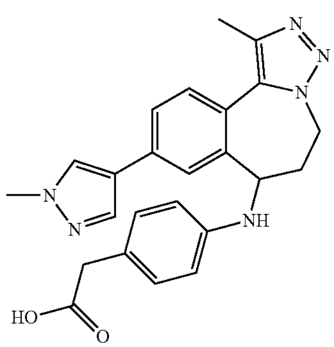 [SMILES: Cc1nnn2c1-c1ccc(-c3cnn(C)c3)cc1C(Nc1ccc(CC(=O)O)cc1)CC2] |
| 23 | LB37 | 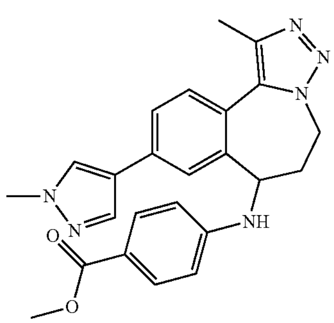 [SMILES: COC(=O)c1ccc(NC2CCn3nnc(C)c3-c3ccc(-c4cnn(C)c4)cc32)cc1] |

-continued

| No. | Code | Structure |
|-----|------|-----------|
| 24 | LB38 | |
| 25 | RA180 | |
| 26 | RA188 | |
| 27 | RA193 | |

-continued
| No. | Code | Structure |
|---|---|---|
| 28 | RA194 | 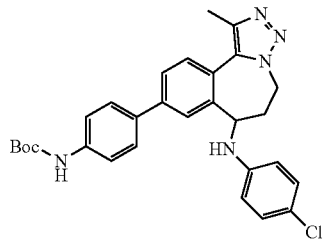 [SMILES: Cc1nnn2c1-c1ccc(-c3ccc(NC(=O)OC(C)(C)C)cc3)cc1C(Nc1ccc(Cl)cc1)CC2] |
| 29 | RB03 | 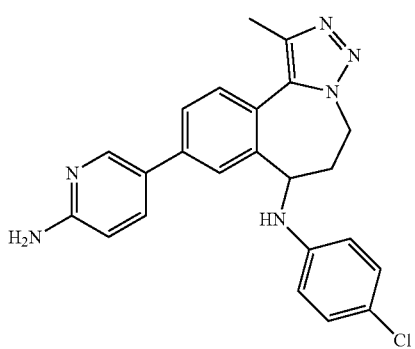 [SMILES: Cc1nnn2c1-c1ccc(-c3ccc(N)nc3)cc1C(Nc1ccc(Cl)cc1)CC2] |
| 30 | RB05 | 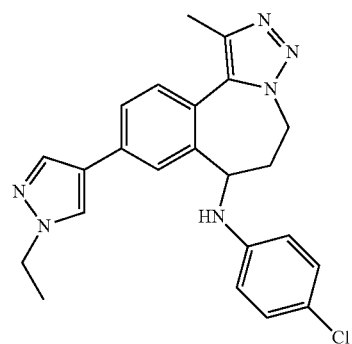 [SMILES: CCn1cc(-c2ccc3c(c2)C(Nc2ccc(Cl)cc2)CCn2nnc(C)c2-3)cn1] |
| 31 | RB06 | 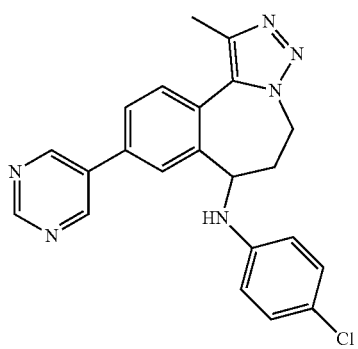 [SMILES: Cc1nnn2c1-c1ccc(-c3cncnc3)cc1C(Nc1ccc(Cl)cc1)CC2] |
-continued
| No. | Code | Structure |
|---|---|---|
| 32 | RB07 | 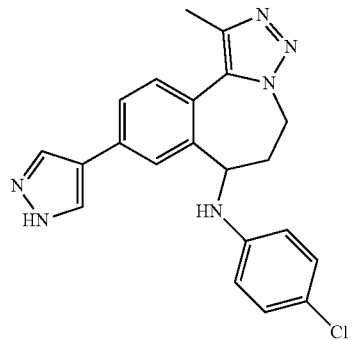 [SMILES: Cc1nnn2c1-c1ccc(-c3cn[nH]c3)cc1C(Nc1ccc(Cl)cc1)CC2] |
| 33 | RB11 | 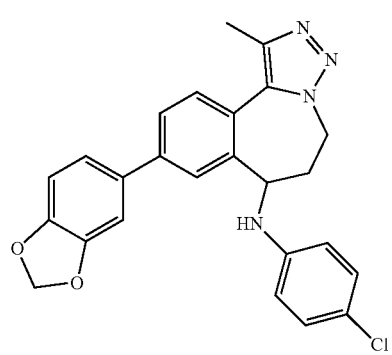 [SMILES: Cc1nnn2c1-c1ccc(-c3ccc4c(c3)OCO4)cc1C(Nc1ccc(Cl)cc1)CC2] |
| 34 | RB31 | 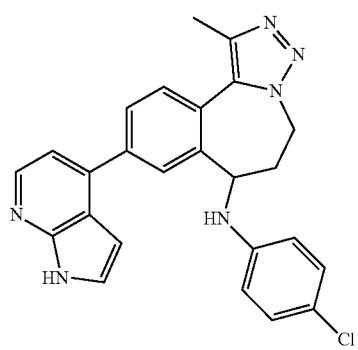 [SMILES: Cc1nnn2c1-c1ccc(-c3ccnc4[nH]ccc34)cc1C(Nc1ccc(Cl)cc1)CC2] |
| 35 | RB42 | 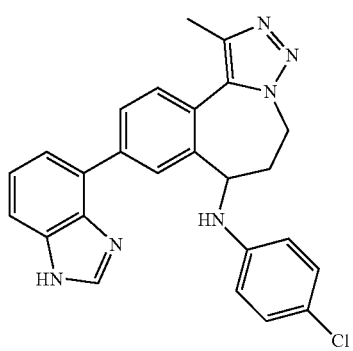 [SMILES: Cc1nnn2c1-c1ccc(-c3cccc4[nH]cnc34)cc1C(Nc1ccc(Cl)cc1)CC2] |

| No. | Code | Structure |
|---|---|---|
| 36 | RB43 | 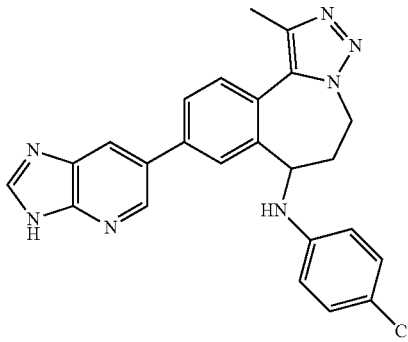 |
| 37 | RB48 | 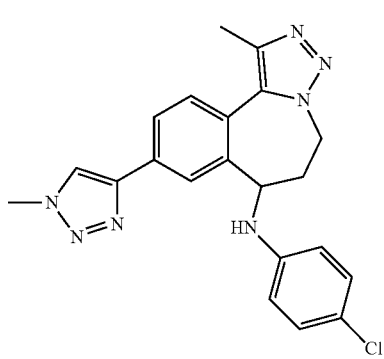 [SMILES: Cc1nnn2c1-c1ccc(-c3cn(C)nn3)cc1C(Nc1ccc(Cl)cc1)CC2] |
| 38 | RB66 | 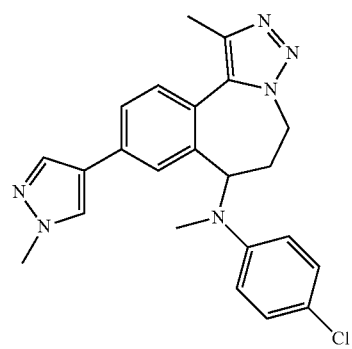 [SMILES: Cc1nnn2c1-c1ccc(-c3cnn(C)c3)cc1C(N(C)c1ccc(Cl)cc1)CC2] |
| 39 | BE114 | 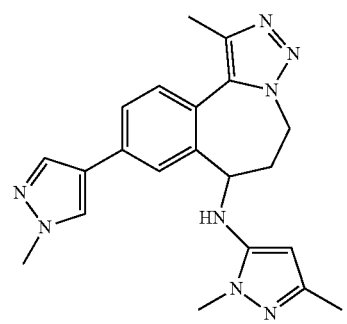 [SMILES: Cc1cc(NC2CCn3nnc(C)c3-c3ccc(-c4cnn(C)c4)cc32)n(C)n1] |
| No. | Code | Structure |
|---|---|---|
| 40 | BE118 | 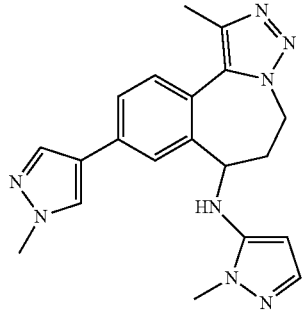 [SMILES: Cc1nnn2c1-c1ccc(-c3cnn(C)c3)cc1C(Nc1ccnn1C)CC2] |
| 41 | BE128 | 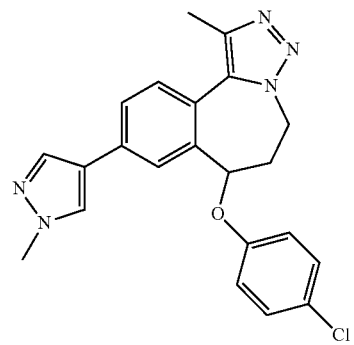 [SMILES: Cc1nnn2c1-c1ccc(-c3cnn(C)c3)cc1C(Oc1ccc(Cl)cc1)CC2] |
| 42 | BE130 | 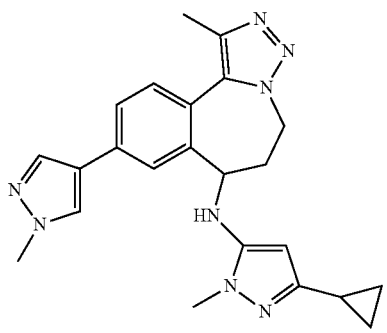 [SMILES: Cc1nnn2c1-c1ccc(-c3cnn(C)c3)cc1C(Nc1cc(C3CC3)nn1C)CC2] |
| 43 | LB42 | 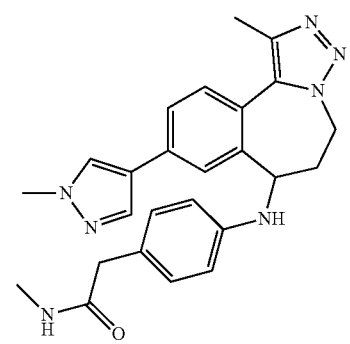 [SMILES: CNC(=O)Cc1ccc(NC2CCn3nnc(C)c3-c3ccc(-c4cnn(C)c4)cc32)cc1] |

-continued
| No. | Code | Structure |
|---|---|---|
| 44 | LB62 | 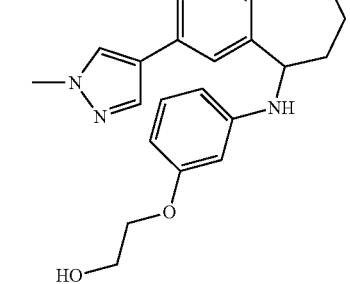 |
| 45 | LB63 | 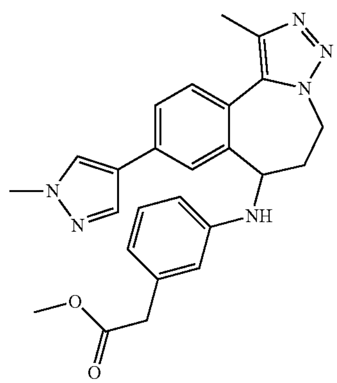 [SMILES: COC(=O)Cc1cccc(NC2CCn3nnc(C)c3-c3ccc(-c4cnn(C)c4)cc32)c1] |
| 46 | LB68 | 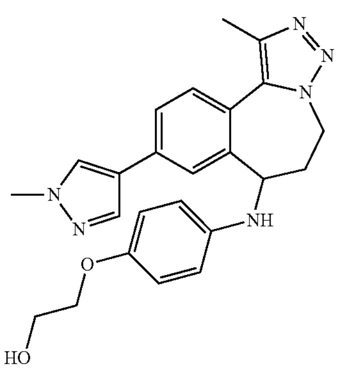 [SMILES: Cc1nnn2c1-c1ccc(-c3cnn(C)c3)cc1C(Nc1ccc(OCCO)cc1)CC2] |
| 47 | LB71 | 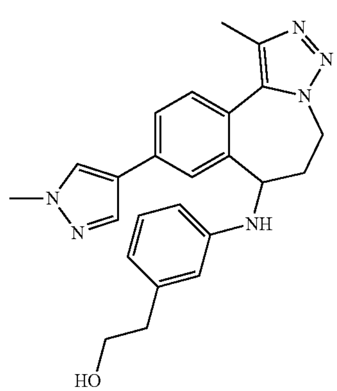 [SMILES: Cc1nnn2c1-c1ccc(-c3cnn(C)c3)cc1C(Nc1cccc(CCO)c1)CC2] |
-continued
| No. | Code | Structure |
|---|---|---|
| 48 | LB77 | 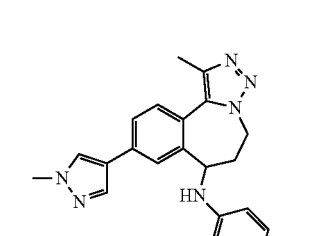 |
| 49 | LB83 | |
| 50 | LB86 | |
| 51 | LB88 | |

| No. | Code | Structure |
|---|---|---|
| 52 | LB89 | 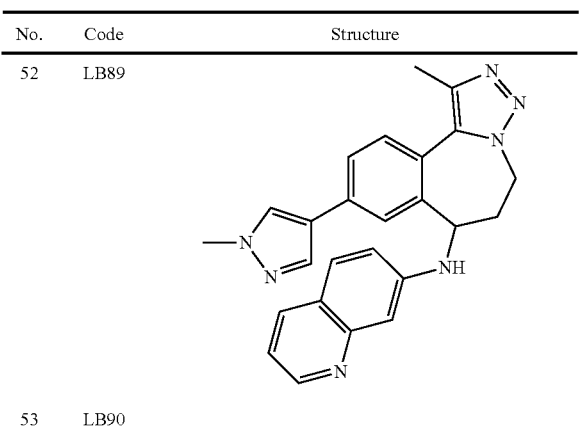 |
| 53 | LB90 |  |
| 54 | LB91 | 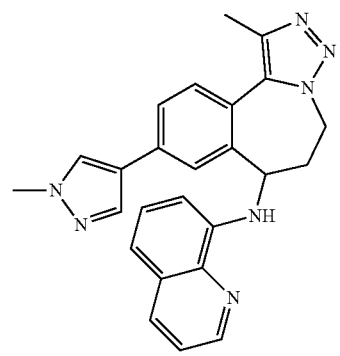 [SMILES: Cc1nnn2c1-c1ccc(-c3cnn(C)c3)cc1C(Nc1cccc3cccnc13)CC2] |
| 55 | LB92 | 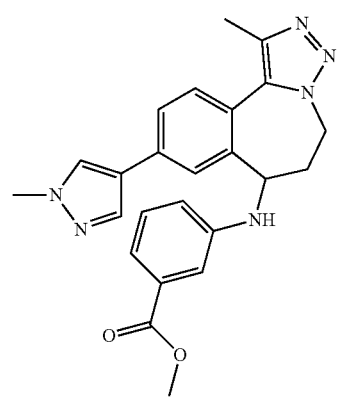 [SMILES: COC(=O)c1cccc(NC2CCn3nnc(C)c3-c3ccc(-c4cnn(C)c4)cc32)c1] |
| No. | Code | Structure |
|---|---|---|
| 56 | LB97 | 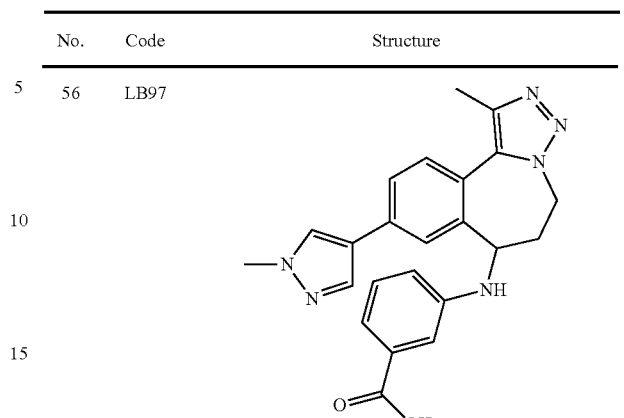 |
| 57 | LB98 |  |
| 58 | LB103 | 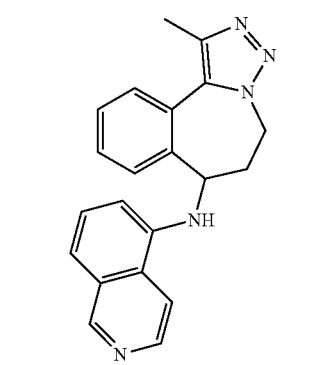 [SMILES: Cc1nnn2c1-c1ccccc1C(Nc1cccc3cnccc13)CC2] |
| 59 | LB113 | 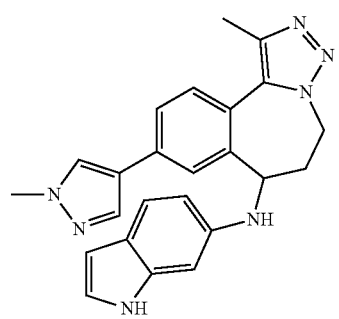 [SMILES: Cc1nnn2c1-c1ccc(-c3cnn(C)c3)cc1C(Nc1ccc3cc[nH]c3c1)CC2] |

-continued

| No. | Code | Structure |
|---|---|---|
| 60 | LB114 | 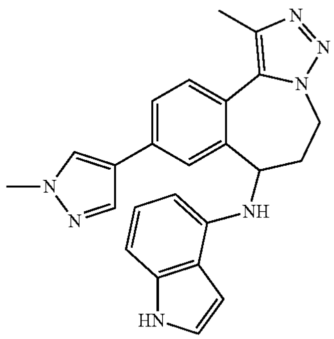 [SMILES: Cc1nnn2c1-c1ccc(-c3cnn(C)c3)cc1C(Nc1cccc3[nH]ccc13)CC2] |
| 61 | LB128 | 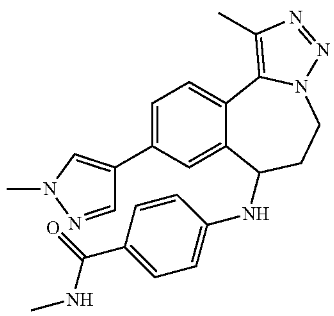 [SMILES: CNC(=O)c1ccc(NC2CCn3nnc(C)c3-c3ccc(-c4cnn(C)c4)cc32)cc1] |
| 62 | LB138 | 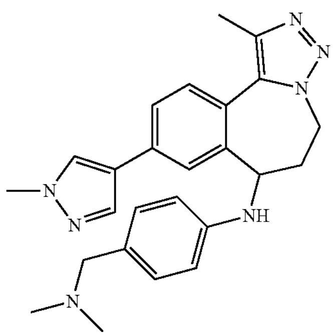 [SMILES: Cc1nnn2c1-c1ccc(-c3cnn(C)c3)cc1C(Nc1ccc(CN(C)C)cc1)CC2] |
| 63 | LB139 | 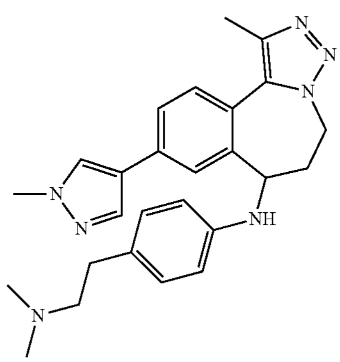 [SMILES: Cc1nnn2c1-c1ccc(-c3cnn(C)c3)cc1C(Nc1ccc(CCN(C)C)cc1)CC2] |

-continued

| No. | Code | Structure |
|---|---|---|
| 64 | LB142 | 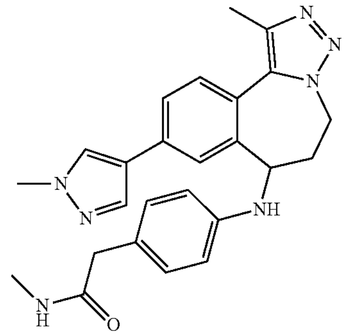 [SMILES: CNC(=O)Cc1ccc(NC2CCn3nnc(C)c3-c3ccc(-c4cnn(C)c4)cc32)cc1] |
| 65 | LB143 | 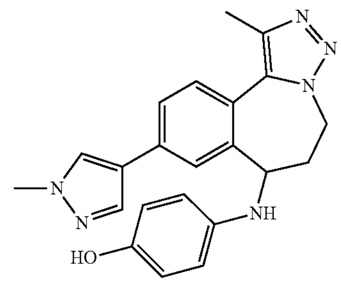 [SMILES: Cc1nnn2c1-c1ccc(-c3cnn(C)c3)cc1C(Nc1ccc(O)cc1)CC2] |
| 66 | RB90 | 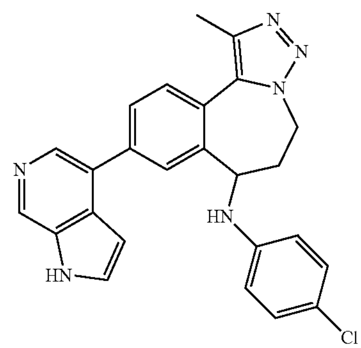 [SMILES: Cc1nnn2c1-c1ccc(-c3cncc4[nH]ccc34)cc1C(Nc1ccc(Cl)cc1)CC2] |
| 67 | RB99 | 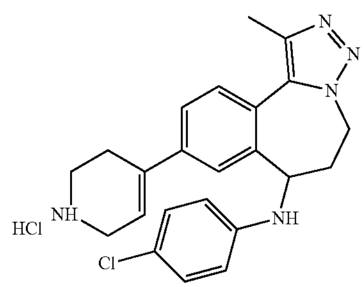 [SMILES: Cl ; Cc1nnn2c1-c1ccc(C3=CCNCC3)cc1C(Nc1ccc(Cl)cc1)CC2] |
| 68 | LB152 | 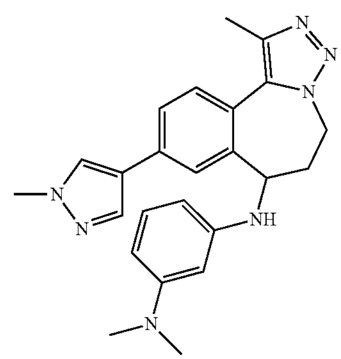 [SMILES: Cc1nnn2c1-c1ccc(-c3cnn(C)c3)cc1C(Nc1cccc(N(C)C)c1)CC2] |

475
-continued
| No. | Code | Structure |
|---|---|---|
| 69 | LB160 | 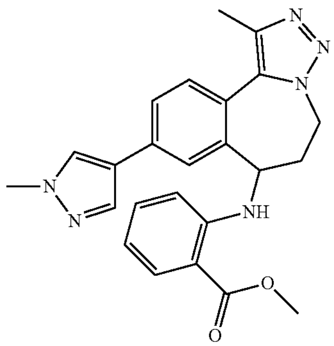 [SMILES: COC(=O)c1ccccc1NC1CCn2nnc(C)c2-c2ccc(-c3cnn(C)c3)cc21] |
| 70 | LB164 | 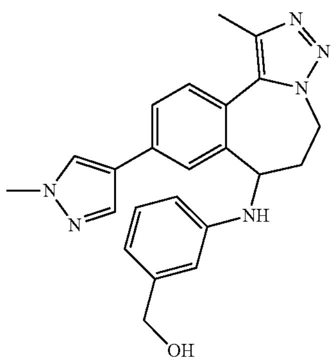 [SMILES: Cc1nnn2c1-c1ccc(-c3cnn(C)c3)cc1C(Nc1cccc(CO)c1)CC2] |
| 71 | LB170 | 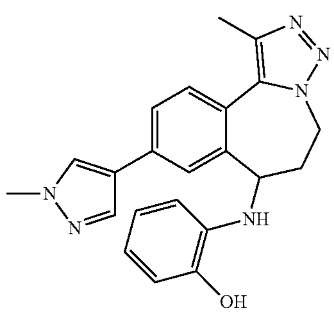 |
| 72 | LB171 | 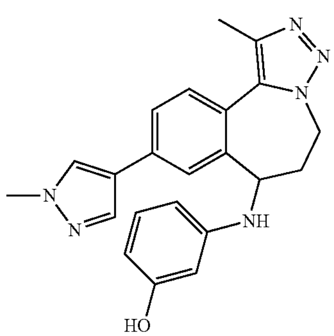 |
476
-continued
| No. | Code | Structure |
|---|---|---|
| 73 | LB173 | |
| 74 | LB175 | |
| 75 | LB181 | |
| 76 | LB185 | |
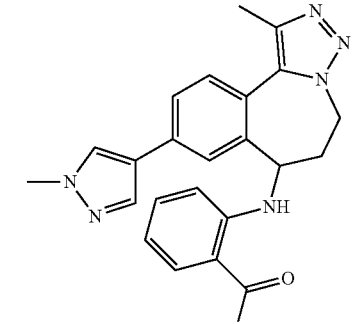
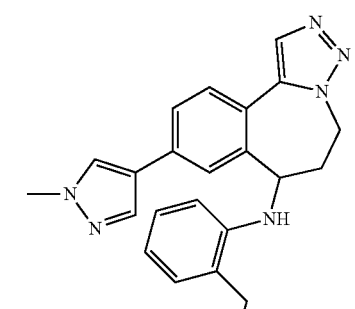
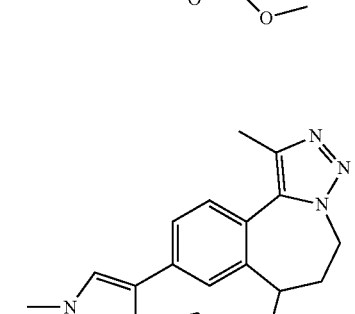
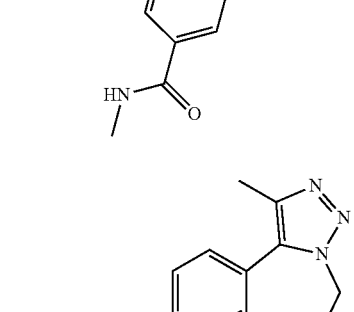

-continued

| No. | Code | Structure |
|---|---|---|
| 77 | LB186 | 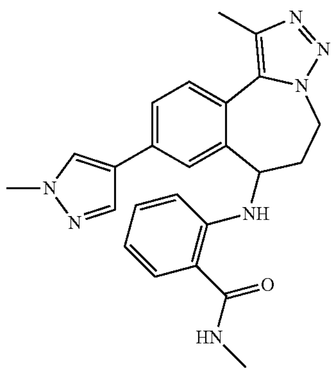 [SMILES: CNC(=O)c1ccccc1NC1CCn2nnc(C)c2-c2ccc(-c3cnn(C)c3)cc21] |
| 78 | LB192 | 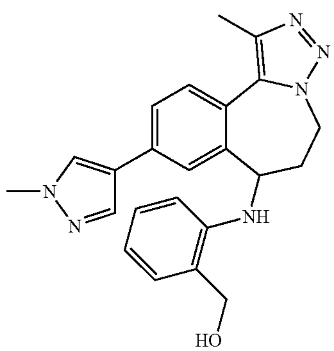 |
| 79 | LCO1 | 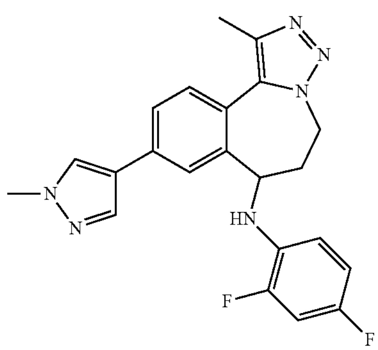 [SMILES: Cc1nnn2c1-c1ccc(-c3cnn(C)c3)cc1C(Nc1ccc(F)cc1F)CC2] |
| 80 | LCO3 | 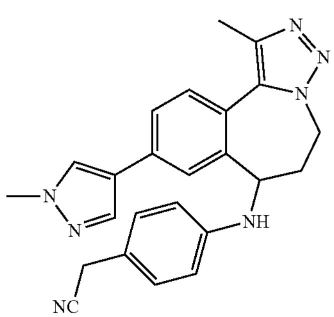 [SMILES: Cc1nnn2c1-c1ccc(-c3cnn(C)c3)cc1C(Nc1ccc(CC#N)cc1)CC2] |

-continued

| No. | Code | Structure |
|---|---|---|
| 81 | LCO7 | 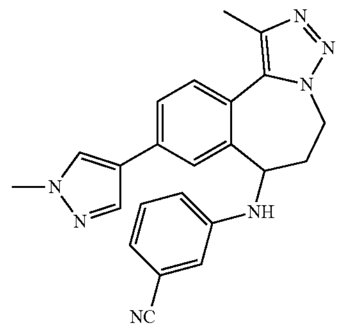 [SMILES: Cc1nnn2c1-c1ccc(-c3cnn(C)c3)cc1C(Nc1cccc(C#N)c1)CC2] |
| 82 | LCO9 | 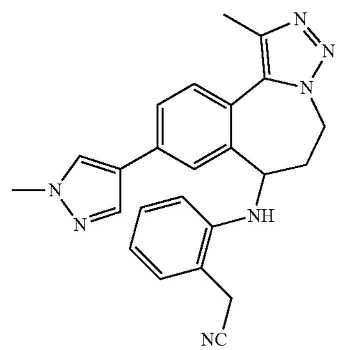 [SMILES: Cc1nnn2c1-c1ccc(-c3cnn(C)c3)cc1C(Nc1ccccc1CC#N)CC2] |
| 83 | LC10 | 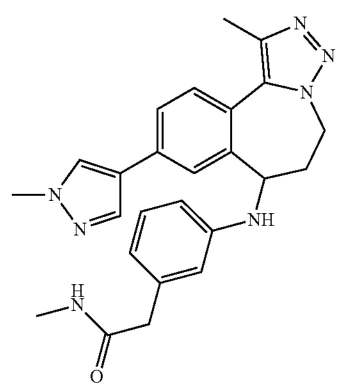 [SMILES: CNC(=O)Cc1cccc(NC2CCn3nnc(C)c3-c3ccc(-c4cnn(C)c4)cc32)c1] |
| 84 | LC11 | 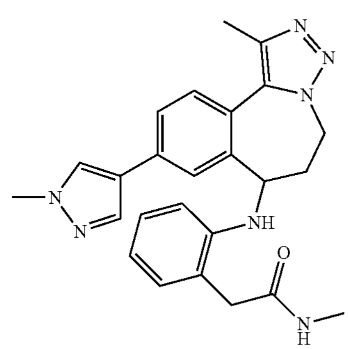 |

-continued

| No. | Code | Structure |
|---|---|---|
| 85 | LC18 | 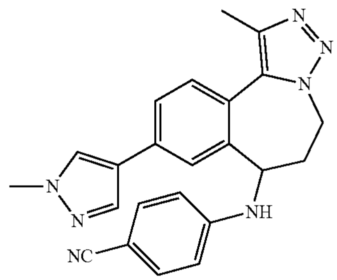 [SMILES: Cc1nnn2c1-c1ccc(-c3cnn(C)c3)cc1C(Nc1ccc(C#N)cc1)CC2] |
| 86 | LC20 | 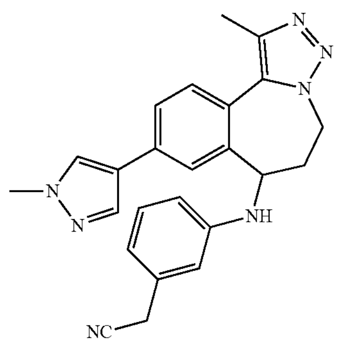 [SMILES: Cc1nnn2c1-c1ccc(-c3cnn(C)c3)cc1C(Nc1cccc(CC#N)c1)CC2] |
| 87 | LC29 | 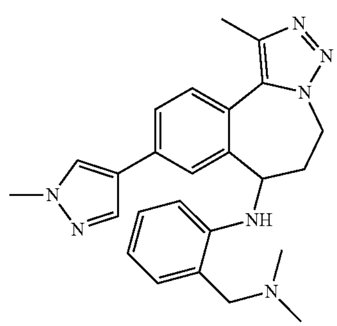 [SMILES: Cc1nnn2c1-c1ccc(-c3cnn(C)c3)cc1C(Nc1ccccc1CN(C)C)CC2] |
| 88 | LC31 | 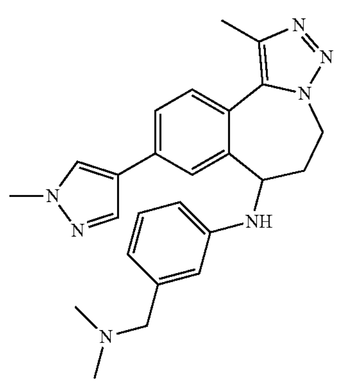 [SMILES: Cc1nnn2c1-c1ccc(-c3cnn(C)c3)cc1C(Nc1cccc(CN(C)C)c1)CC2] |

-continued

| No. | Code | Structure |
|---|---|---|
| 89 | LC56 | |
| 90 | LC75 | |
| 91 | LC79 | |
| 92 | LC84 | |

| No. | Code | Structure |
|---|---|---|
| 93 | LC87 | 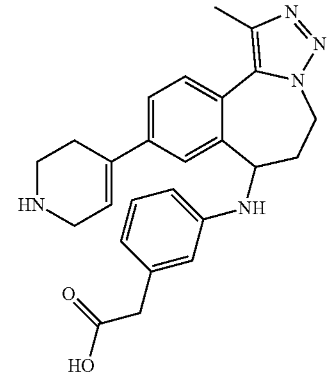 [SMILES: Cc1nnn2c1-c1ccc(C3=CCNCC3)cc1C(Nc1cccc(CC(=O)O)c1)CC2] |
| 94 | LC97 | 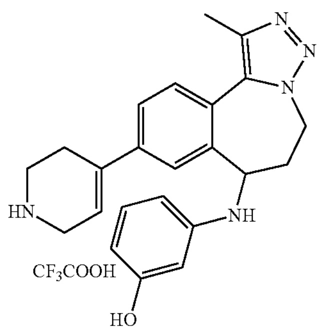 [SMILES: "CF3COOH" ; Cc1nnn2c1-c1ccc(C3=CCNCC3)cc1C(Nc1cccc(O)c1)CC2] |
| 95 | LC99 | 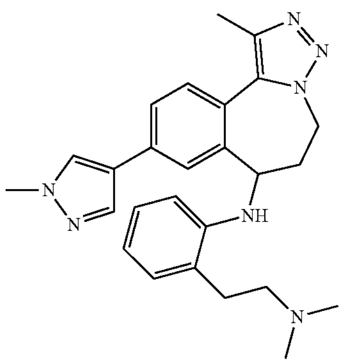 |
| 96 | LC101 | 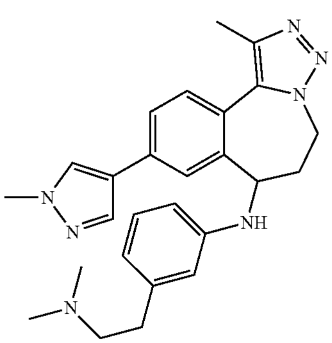 [SMILES: Cc1nnn2c1-c1ccc(-c3cnn(C)c3)cc1C(Nc1cccc(CCN(C)C)c1)CC2] |

| No. | Code | Structure |
|---|---|---|
| 97 | LC117 | |
| 98 | LC127 | |
| 99 | LC128 | |
| 100 | LC131 | |

-continued
| No. | Code | Structure |
|---|---|---|
| 101 | LC132 | 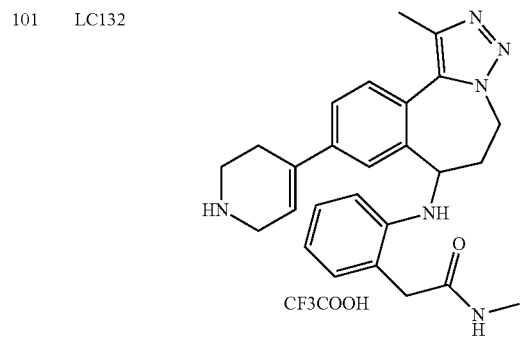 CF3COOH |
| 102 | LC133 | 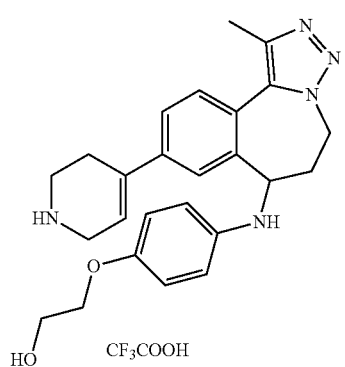 [SMILES: Cc1nnn2c1-c1ccc(C3=CCNCC3)cc1C(Nc1ccc(OCCO)cc1)CC2 ; "CF3COOH"] CF3COOH |
| 103 | LC136 | 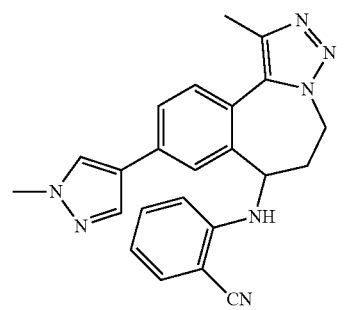 |
| 104 | LC158 | 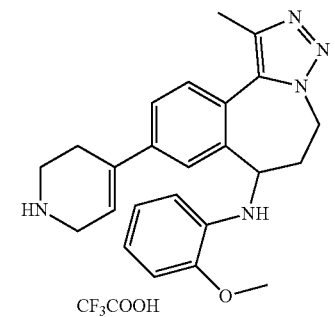 [SMILES: "CF3COOH" ; COc1ccccc1NC1CCn2nnc(C)c2-c2ccc(C3=CCNCC3)cc21] CF3COOH |
-continued
| No. | Code | Structure |
|---|---|---|
| 105 | LC159 | 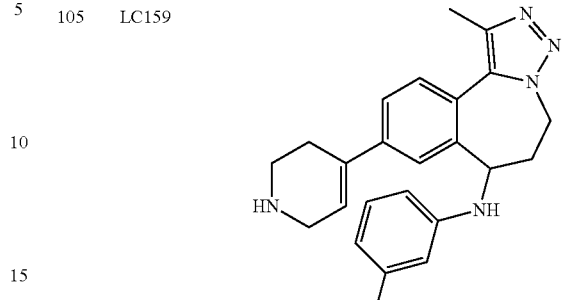 CF3COOH |
| 106 | LC160 | 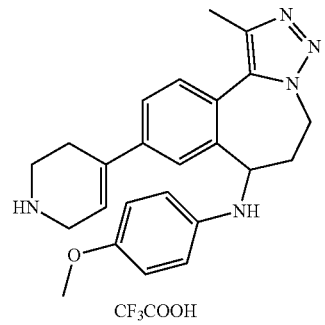 [SMILES: COc1ccc(NC2CCn3nnc(C)c3-c3ccc(C4=CCNCC4)cc32)cc1 ; "CF3COOH"] CF3COOH |
| 107 | LC174 | 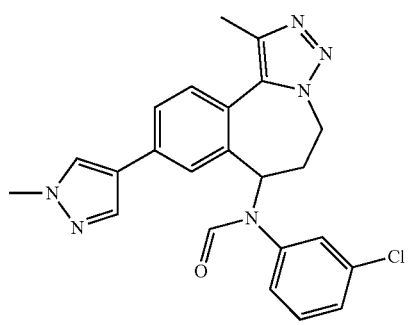 [SMILES: Cc1nnn2c1-c1ccc(-c3cnn(C)c3)cc1C(N(C=O)c1cccc(Cl)c1)CC2] |
| 108 | LC185 | 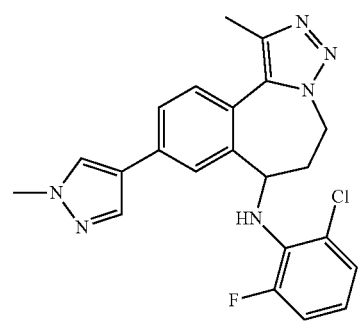 [SMILES: Cc1nnn2c1-c1ccc(-c3cnn(C)c3)cc1C(Nc1c(F)cccc1Cl)CC2] |

| No. | Code | Structure |
|---|---|---|
| 109 | LC186 | 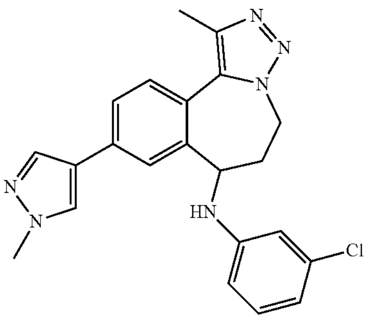 [SMILES: Cc1nnn2c1-c1ccc(-c3cnn(C)c3)cc1C(Nc1cccc(Cl)c1)CC2] |
| 110 | LC190 | 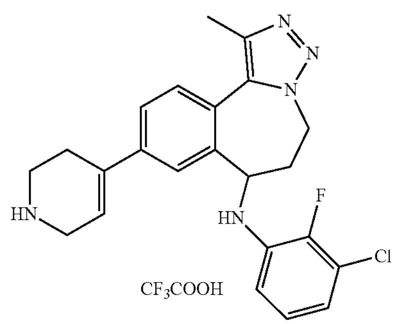 [SMILES: Cc1nnn2c1-c1ccc(C3=CCNCC3)cc1C(Nc1cccc(Cl)c1F)CC2 ; "CF3COOH"] |
| 111 | LC191 | 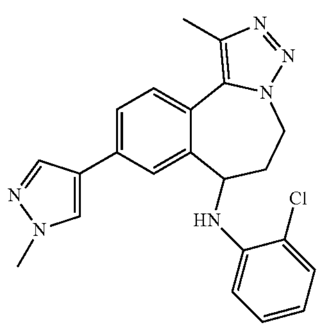 [SMILES: Cc1nnn2c1-c1ccc(-c3cnn(C)c3)cc1C(Nc1ccccc1Cl)CC2] |
| 112 | LC192 | 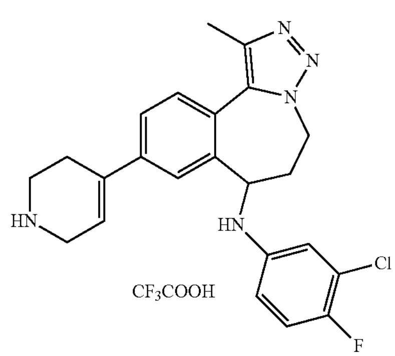 [SMILES: Cc1nnn2c1-c1ccc(C3=CCNCC3)cc1C(Nc1ccc(F)c(Cl)c1)CC2 ; "CF3COOH"] |
| 113 | LC193 | 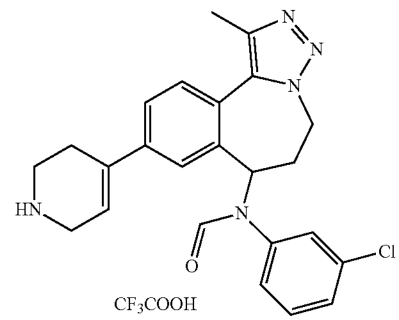 [SMILES: Cc1nnn2c1-c1ccc(C3=CCNCC3)cc1C(N(C=O)c1cccc(Cl)c1)CC2 ; "CF3COOH"] |
| 114 | LC198 | 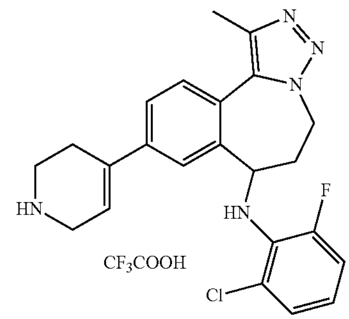 |
| 115 | LD07 | 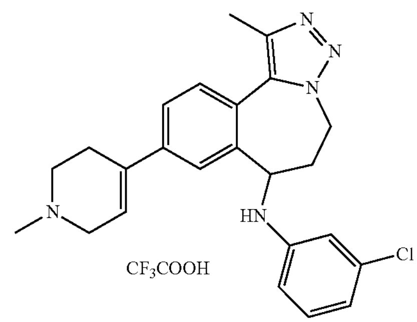 |
| 116 | LD08 | 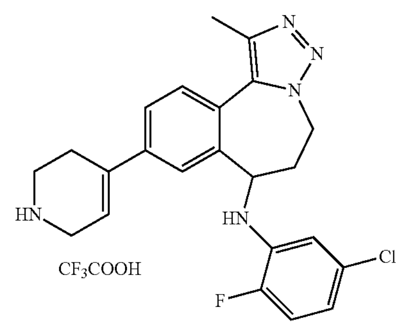 [SMILES: "CF3COOH" ; Cc1nnn2c1-c1ccc(C3=CCNCC3)cc1C(Nc1cc(Cl)ccc1F)CC2] |
| 117 | LD13 | 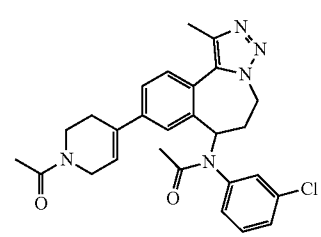 [SMILES: CC(=O)N1CC=C(c2ccc3c(c2)C(N(C(C)=O)c2cccc(Cl)c2)CCn2nnc(C)c2-3)CC1] |

-continued
| No. | Code | Structure |
|---|---|---|
| 118 | LD14 | 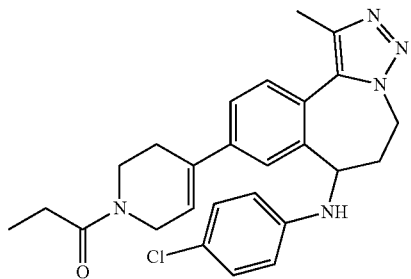 [SMILES: CCC(=O)N1CC=C(c2ccc3c(c2)C(Nc2ccc(Cl)cc2)CCn2nnc(C)c2-3)CC1] |
| 119 | LD17 | 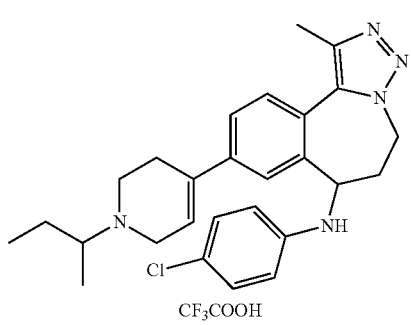 [SMILES: CCC(C)N1CC=C(c2ccc3c(c2)C(Nc2ccc(Cl)cc2)CCn2nnc(C)c2-3)CC1 ; "CF3COOH"] CF₃COOH |
| 120 | LD19 | 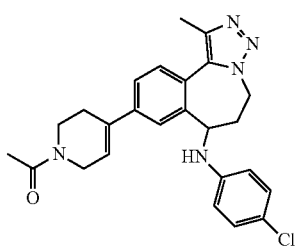 [SMILES: CC(=O)N1CC=C(c2ccc3c(c2)C(Nc2ccc(Cl)cc2)CCn2nnc(C)c2-3)CC1] |
| 121 | LD23 | 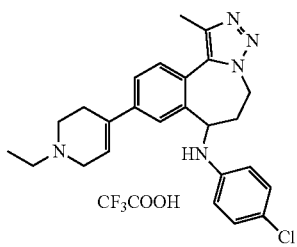 [SMILES: CCN1CC=C(c2ccc3c(c2)C(Nc2ccc(Cl)cc2)CCn2nnc(C)c2-3)CC1 ; "CF3COOH"] CF₃COOH |
| 122 | LD24 | 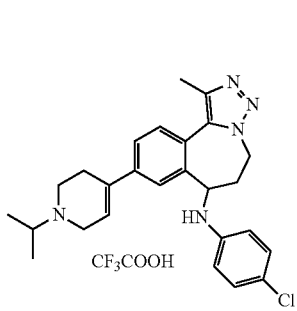 [SMILES: Cc1nnn2c1-c1ccc(C3=CCN(C(C)C)CC3)cc1C(Nc1ccc(Cl)cc1)CC2 ; "CF3COOH"] CF₃COOH |
-continued
| No. | Code | Structure |
|---|---|---|
| 123 | LD31 | |
| 124 | LD76 | CF₃COOH |
| 125 | LD77 | |
| 126 | BF169 | HCl |
| 127 | BF178 | |

| No. | Code | Structure |
|---|---|---|
| 128 | BJ28 | 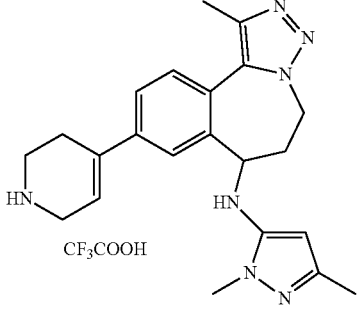 [SMILES: "CF3COOH" ; Cc1cc(NC2CCn3nnc(C)c3-c3ccc(C4=CCNCC4)cc32)n(C)n1] CF₃COOH |
| 129 | BJ122 | 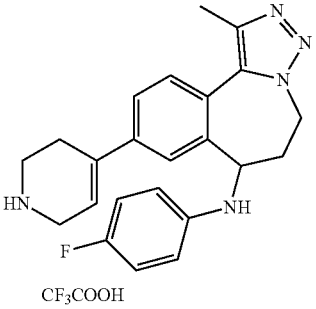 [SMILES: "CF3COOH" ; Cc1nnn2c1-c1ccc(C3=CCNCC3)cc1C(Nc1ccc(F)cc1)CC2] CF₃COOH |
| 130 | BJ123 | 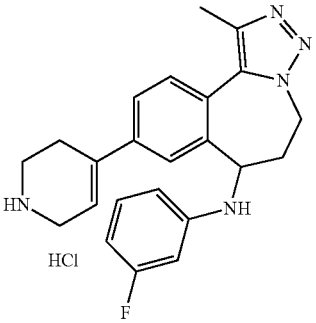 [SMILES: Cc1nnn2c1-c1ccc(C3=CCNCC3)cc1C(Nc1cccc(F)c1)CC2 ; Cl] HCl |
| 131 | BJ126 | 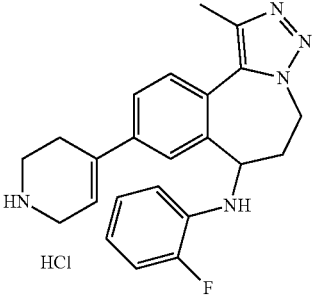 [SMILES: Cc1nnn2c1-c1ccc(C3=CCNCC3)cc1C(Nc1ccccc1F)CC2 ; Cl] HCl |
| 132 | BJ179 | 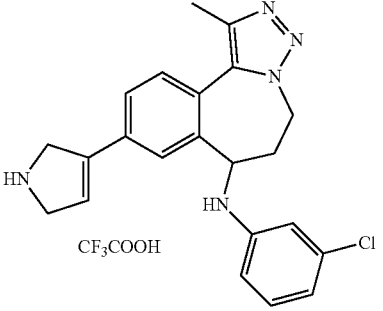 [SMILES: Cc1nnn2c1-c1ccc(C3=CCNC3)cc1C(Nc1cccc(Cl)c1)CC2 ; "CF3COOH"] CF₃COOH |
| No. | Code | Structure |
|---|---|---|
| 133 | BJ183 | 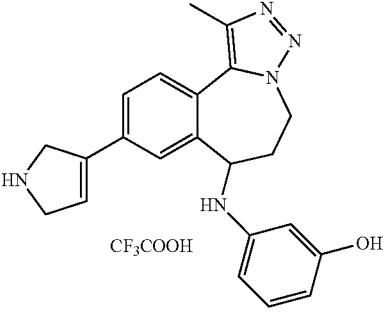 CF₃COOH |
| 134 | BJ193 | 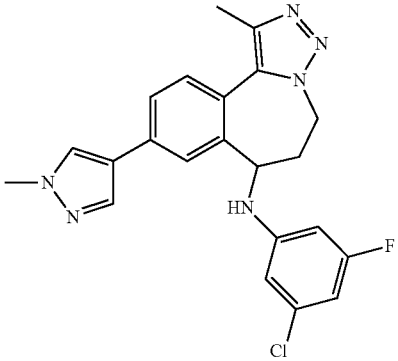 [SMILES: Cc1nnn2c1-c1ccc(-c3cnn(C)c3)cc1C(Nc1cc(F)cc(Cl)c1)CC2] |
| 135 | BH06 | 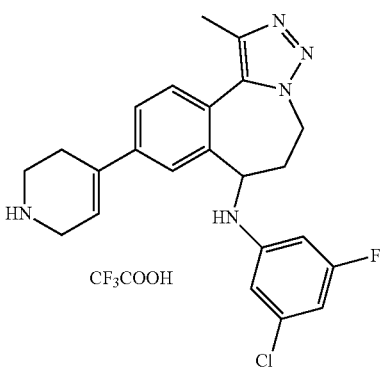 [SMILES: Cc1nnn2c1-c1ccc(C3=CCNCC3)cc1C(Nc1cc(F)cc(Cl)c1)CC2 ; "CF3COOH"] CF₃COOH |
| 136 | BH23 | 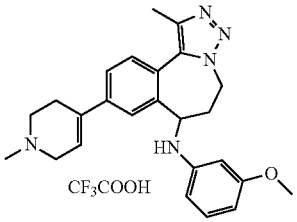 CF₃COOH |
| 137 | BH27 | 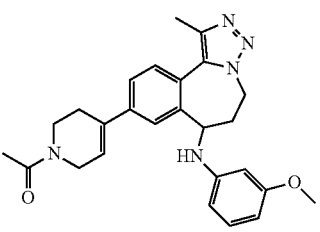 [SMILES: COc1cccc(NC2CCn3nnc(C)c3-c3ccc(C4=CCN(C(C)=O)CC4)cc32)c1] |

-continued

| No. | Code | Structure |
|---|---|---|
| 138 | BH29 | 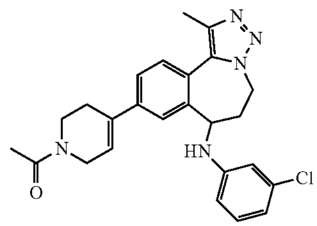 [SMILES: CC(=O)N1CC=C(c2ccc3c(c2)C(Nc2cccc(Cl)c2)CCn2nnc(C)c2-3)CC1] |
| 139 | BH32 | 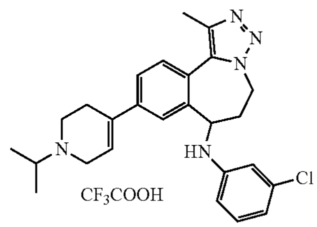 [SMILES: Cc1nnn2c1-c1ccc(C3=CCN(C(C)C)CC3)cc1C(Nc1cccc(Cl)c1)CC2 ; "CF3COOH"] |
| 140 | BH33 | 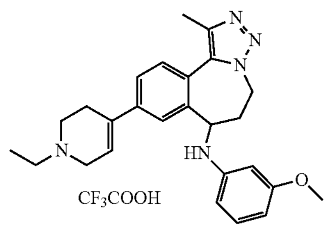 [SMILES: CCN1CC=C(c2ccc3c(c2)C(Nc2cccc(OC)c2)CCn2nnc(C)c2-3)CC1 ; "CF3COOH"] |
| 141 | BH36 | 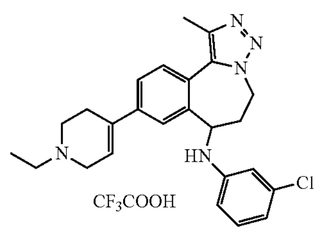 [SMILES: CCN1CC=C(c2ccc3c(c2)C(Nc2cccc(Cl)c2)CCn2nnc(C)c2-3)CC1 ; "CF3COOH"] |
| 142 | BH37 | 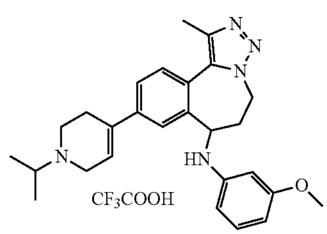 [SMILES: COc1cccc(NC2CCn3nnc(C)c3-c3ccc(C4=CCN(C(C)C)CC4)cc32)c1 ; "CF3COOH"] |
| 143 | BH43 | 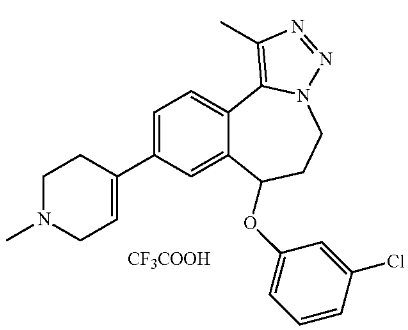 |

-continued

| No. | Code | Structure |
|---|---|---|
| 144 | BH46 | 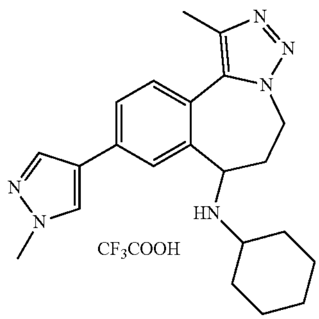 |
| 145 | BH57 | 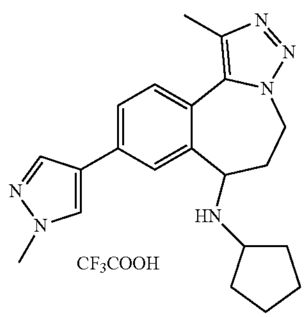 [SMILES: Cc1nnn2c1-c1ccc(-c3cnn(C)c3)cc1C(NC1CCCC1)CC2 ; "CF3COOH"] |
| 146 | BH81 | 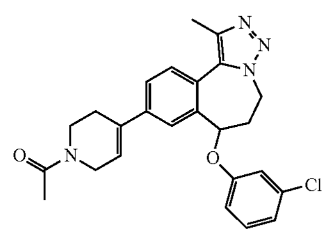 [SMILES: CC(=O)N1CC=C(c2ccc3c(c2)C(Oc2cccc(Cl)c2)CCn2nnc(C)c2-3)CC1] |
| 147 | BH86 | 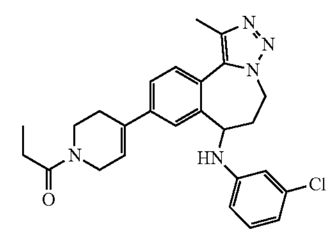 [SMILES: CCC(=O)N1CC=C(c2ccc3c(c2)C(Nc2cccc(Cl)c2)CCn2nnc(C)c2-3)CC1] |
| 148 | BH87 | 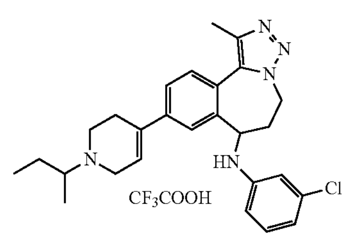 [SMILES: CCC(C)N1CC=C(c2ccc3c(c2)C(Nc2cccc(Cl)c2)CCn2nnc(C)c2-3)CC1 ; "CF3COOH"] |
| 149 | BH104 | 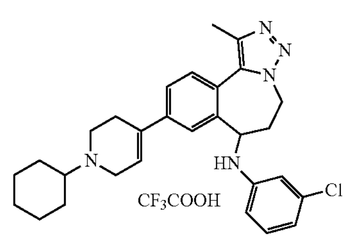 [SMILES: Cc1nnn2c1-c1ccc(C3=CCN(C4CCCCC4)CC3)cc1C(Nc1cccc(Cl)c1)CC2 ; "CF3COOH"] |

| No. | Code | Structure |
|---|---|---|
| 150 | BH107 | 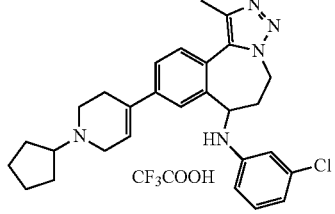 |
| 151 | BH108 | 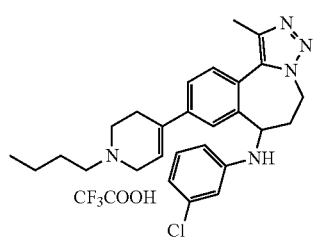 [SMILES: CCCCN1CC=C(c2ccc3c(c2)C(Nc2cccc(Cl)c2)CCn2nnc(C)c2-3)CC1 ; "CF3COOH"] |
| 152 | BH120 | 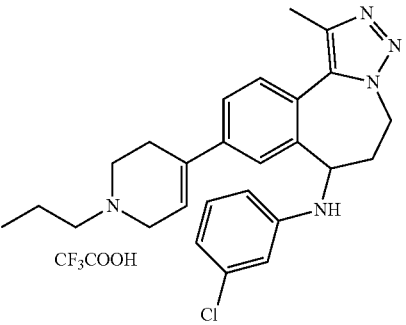 [SMILES: CCCN1CC=C(c2ccc3c(c2)C(Nc2cccc(Cl)c2)CCn2nnc(C)c2-3)CC1 ; "CF3COOH"] |
| 153 | BH123 | 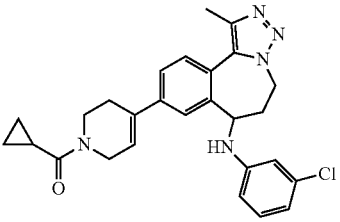 [SMILES: Cc1nnn2c1-c1ccc(C3=CCN(C(=O)C4CC4)CC3)cc1C(Nc1cccc(Cl)c1)CC2] |
| 154 | BH159 | 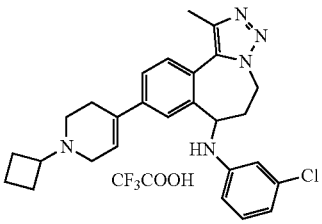 [SMILES: Cc1nnn2c1-c1ccc(C3=CCN(C4CCC4)CC3)cc1C(Nc1cccc(Cl)c1)CC2 ; "CF3COOH"] |
| 155 | BH187 | 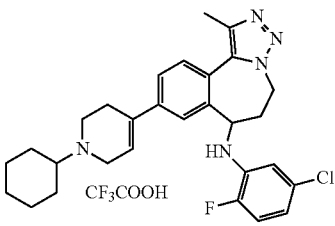 [SMILES: Cc1nnn2c1-c1ccc(C3=CCN(C4CCCCC4)CC3)cc1C(Nc1cc(Cl)ccc1F)CC2 ; "CF3COOH"] |//
| No. | Code | Structure |
|---|---|---|
| 156 | BH190 | 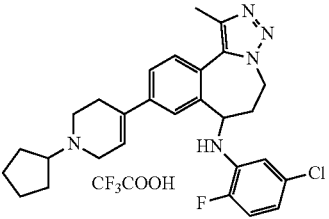 [SMILES: Cc1nnn2c1-c1ccc(C3=CCN(C4CCCC4)CC3)cc1C(Nc1cc(Cl)ccc1F)CC2 ; "CF3COOH"] |
| 157 | BH192 | 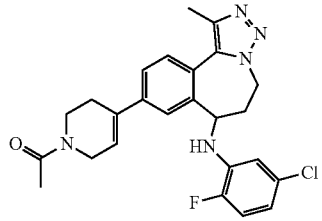 [SMILES: CC(=O)N1CC=C(c2ccc3c(c2)C(Nc2cc(Cl)ccc2F)CCn2nnc(C)c2-3)CC1] |
| 158 | B123 | 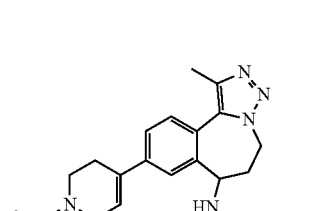 |
| 159 | B124 | 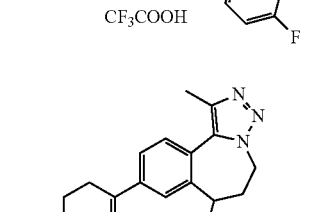 |
| 160 | B126 | 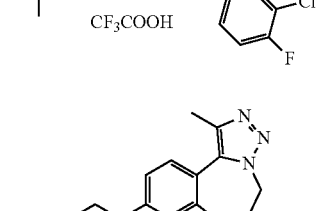 |
| 161 | B129 | 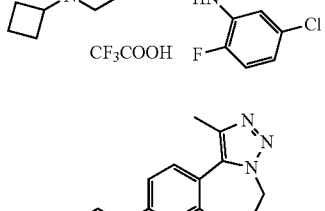 |

| No. | Code | Structure |
|---|---|---|
| 162 | B131 | 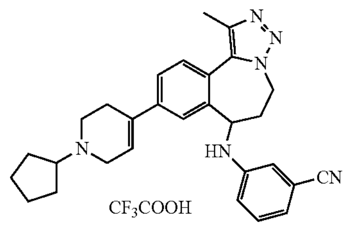 [SMILES: Cc1nnn2c1-c1ccc(C3=CCN(C4CCCC4)CC3)cc1C(Nc1cccc(C#N)c1)CC2 ; "CF3COOH"] |
| 163 | B134 | 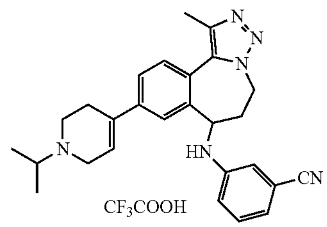 [SMILES: Cc1nnn2c1-c1ccc(C3=CCN(C(C)C)CC3)cc1C(Nc1cccc(C#N)c1)CC2 ; "CF3COOH"] |
| 164 | B136 | 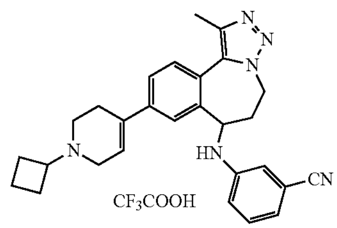 [SMILES: Cc1nnn2c1-c1ccc(C3=CCN(C4CCC4)CC3)cc1C(Nc1cccc(C#N)c1)CC2 ; "CF3COOH"] |
| 165 | B137 | 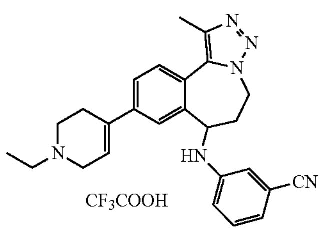 [SMILES: CCN1CC=C(c2ccc3c(c2)C(Nc2cccc(C#N)c2)CCn2nnc(C)c2-3)CC1 ; "CF3COOH"] |
| 166 | B155 | 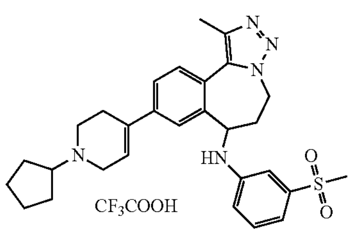 [SMILES: Cc1nnn2c1-c1ccc(C3=CCN(C4CCCC4)CC3)cc1C(Nc1cccc(S(C)(=O)=O)c1)CC2 ; "CF3COOH"] |
| 167 | B157 | 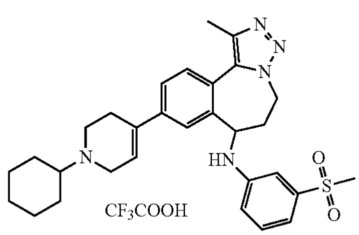 [SMILES: Cc1nnn2c1-c1ccc(C3=CCN(C4CCCCC4)CC3)cc1C(Nc1cccc(S(C)(=O)=O)c1)CC2 ; "CF3COOH"] |

| No. | Code | Structure |
|---|---|---|
| 168 | B160 | 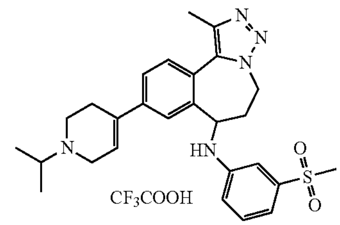 [SMILES: Cc1nnn2c1-c1ccc(C3=CCN(C(C)C)CC3)cc1C(Nc1cccc(S(C)(=O)=O)c1)CC2 ; "CF3COOH"] |
| 169 | B161 | 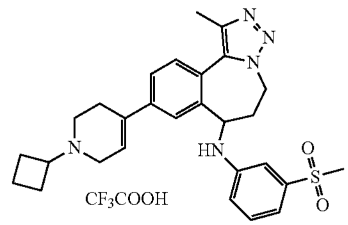 [SMILES: Cc1nnn2c1-c1ccc(C3=CCN(C4CCC4)CC3)cc1C(Nc1cccc(S(C)(=O)=O)c1)CC2 ; "CF3COOH"] |
| 170 | B168 | 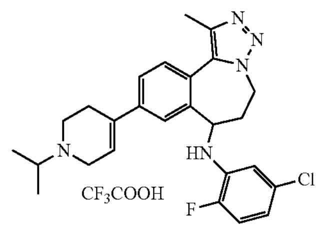 [SMILES: Cc1nnn2c1-c1ccc(C3=CCN(C(C)C)CC3)cc1C(Nc1cc(Cl)ccc1F)CC2 ; "CF3COOH"] |
| 171 | WYA10 | 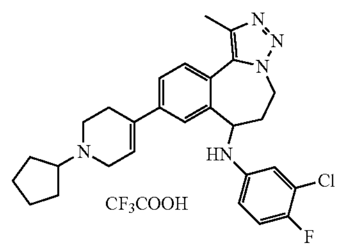 [SMILES: Cc1nnn2c1-c1ccc(C3=CCN(C4CCCC4)CC3)cc1C(Nc1ccc(F)c(Cl)c1)CC2 ; "CF3COOH"] |
| 172 | WA78 | 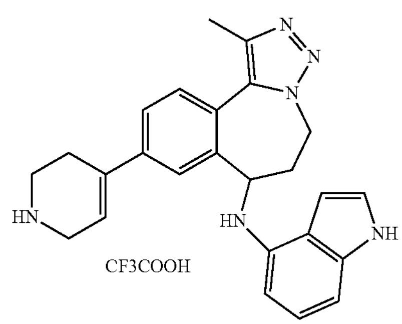 |
| 173 | WA82 | 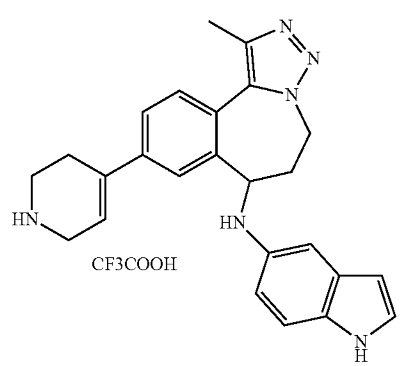 |

| No. | Code | Structure |
|---|---|---|
| 174 | WA83 | 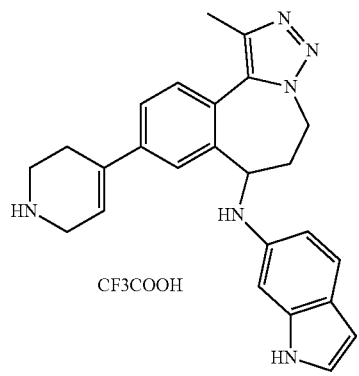 [SMILES: Cc1nnn2c1-c1ccc(C3=CCNCC3)cc1C(Nc1ccc3cc[nH]c3c1)CC2 ; "CF3COOH"] CF3COOH |
| 175 | RC71 | 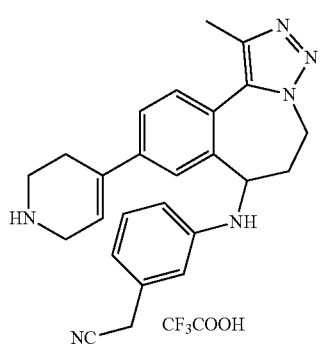 [SMILES: Cc1nnn2c1-c1ccc(C3=CCNCC3)cc1C(Nc1cccc(CC#N)c1)CC2 ; "CF3COOH"] CF3COOH |
| 176 | RC73 | 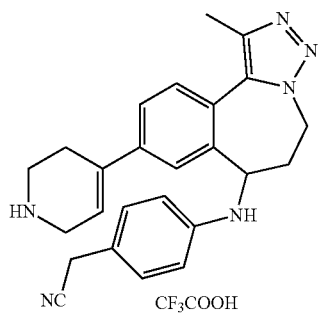 [SMILES: Cc1nnn2c1-c1ccc(C3=CCNCC3)cc1C(Nc1ccc(CC#N)cc1)CC2 ; "CF3COOH"] CF3COOH |
| 177 | RC82 | 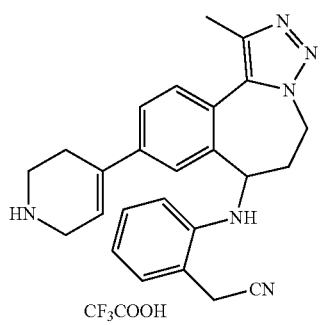 [SMILES: Cc1nnn2c1-c1ccc(C3=CCNCC3)cc1C(Nc1ccccc1CC#N)CC2 ; "CF3COOH"] CF3COOH |
| No. | Code | Structure |
|---|---|---|
| 178 | RC116 | 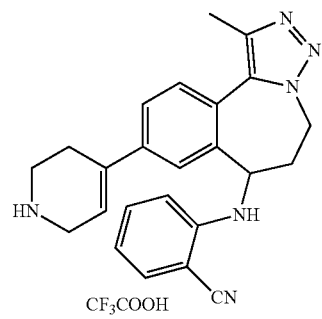 [SMILES: Cc1nnn2c1-c1ccc(C3=CCNCC3)cc1C(Nc1ccccc1C#N)CC2 ; "CF3COOH"] CF3COOH |
| 179 | RD06 | 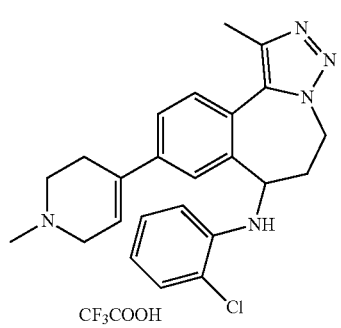 [SMILES: Cc1nnn2c1-c1ccc(C3=CCN(C)CC3)cc1C(Nc1ccccc1Cl)CC2 ; "CF3COOH"] CF3COOH |
| 180 | RD21 | 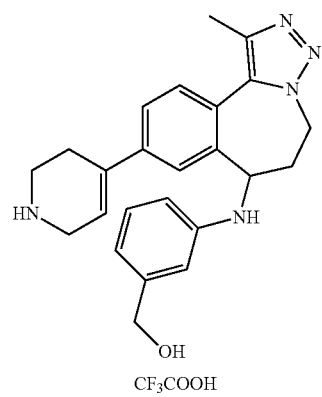 [SMILES: Cc1nnn2c1-c1ccc(C3=CCNCC3)cc1C(Nc1cccc(CO)c1)CC2 ; "CF3COOH"] CF3COOH |
| 181 | RD41 | 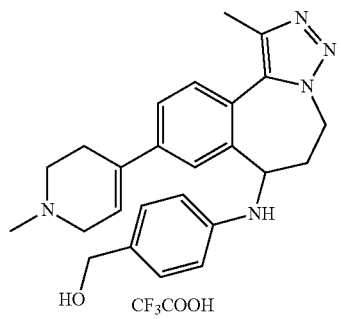 [SMILES: Cc1nnn2c1-c1ccc(C3=CCN(C)CC3)cc1C(Nc1ccc(CO)cc1)CC2 ; "CF3COOH"] CF3COOH |

-continued
| No. | Code | Structure |
|---|---|---|
| 182 | RD115 | 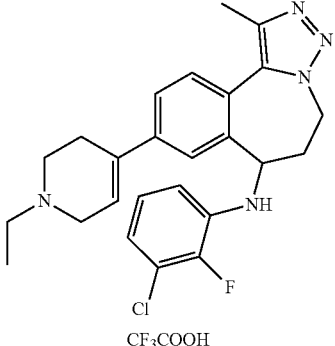 CF₃COOH |
| 183 | RD121 | 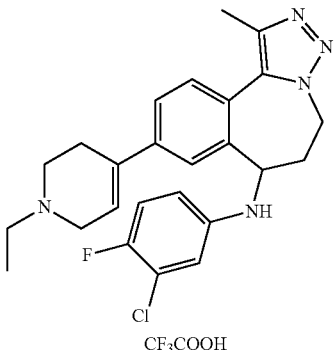 CF₃COOH |
| 184 | RD123 | 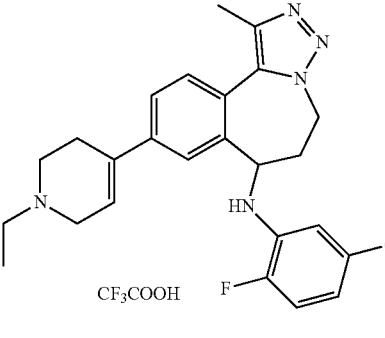 CF₃COOH |
| 185 | RD142 | 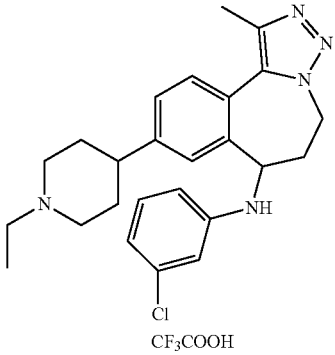 [SMILES: CCN1CCC(c2ccc3c(c2)C(Nc2cccc(Cl)c2)CCn2nnc(C)c2-3)CC1 ; "CF3COOH"] CF₃COOH |
-continued
| No. | Code | Structure |
|---|---|---|
| 186 | RD178 | 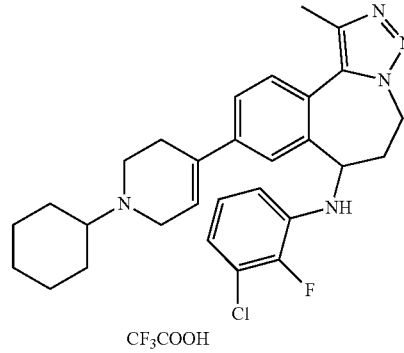 CF₃COOH |
| 187 | RD179 | 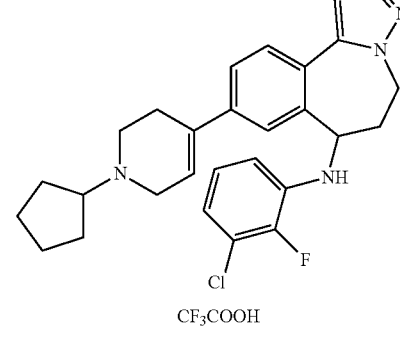 CF₃COOH |
| 188 | RD180 | 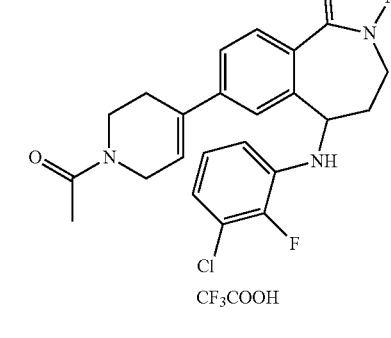 CF₃COOH |
| 189 | RE10 (S) | 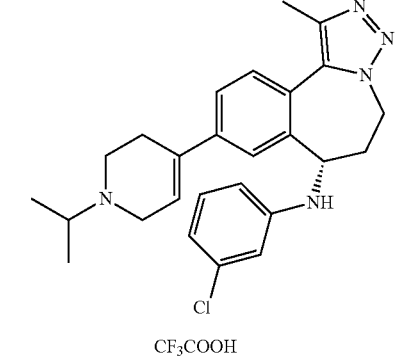 [SMILES: Cc1nnn2c1-c1ccc(C3=CCN(C(C)C)CC3)cc1[C@@H](Nc1cccc(Cl)c1)CC2 ; "CF3COOH"] CF₃COOH |

501
-continued
| No. | Code | Structure |
|---|---|---|
| 190 | RE13 (R) | 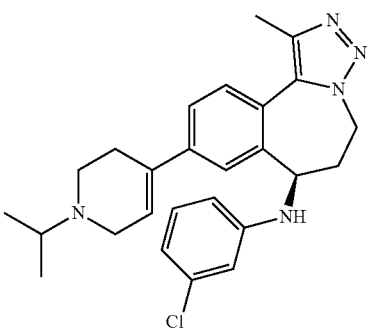 CF₃COOH |
| 191 | RE29 | 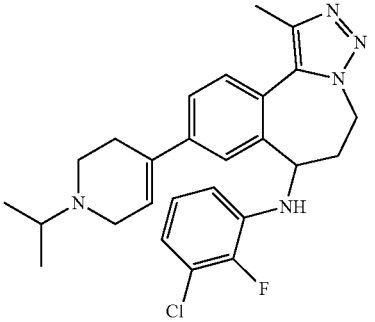 CF₃COOH |
| 192 | RE30 | 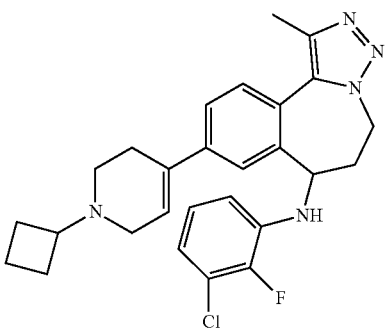 CF₃COOH |
| 193 | RE124 | 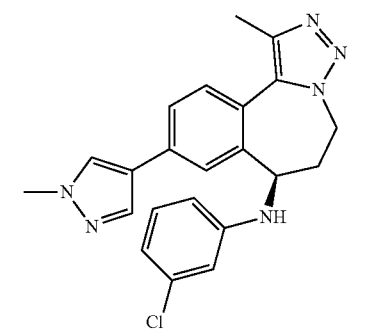 [SMILES: Cc1nnn2c1-c1ccc(-c3cnn(C)c3)cc1[C@H](Nc1cccc(Cl)c1)CC2] |
502
-continued
| No. | Code | Structure |
|---|---|---|
| 194 | RE127 | 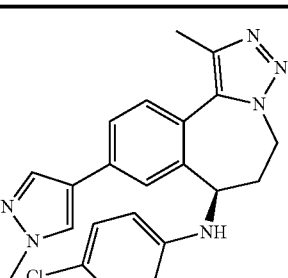 |
| 195 | RE136 | 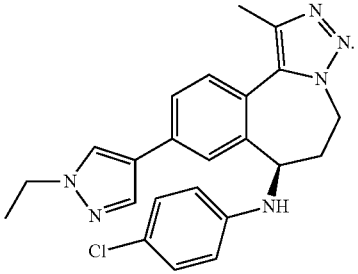 [SMILES: CCn1cc(-c2ccc3c(c2)[C@H](Nc2ccc(Cl)cc2)CCn2nnc(C)c2-3)cn1] |
7. A method for preparing the compounds of claim 1, wherein the method comprises the steps of:
(1) preparing the compound of formula Ib with the compound of formula Ia,
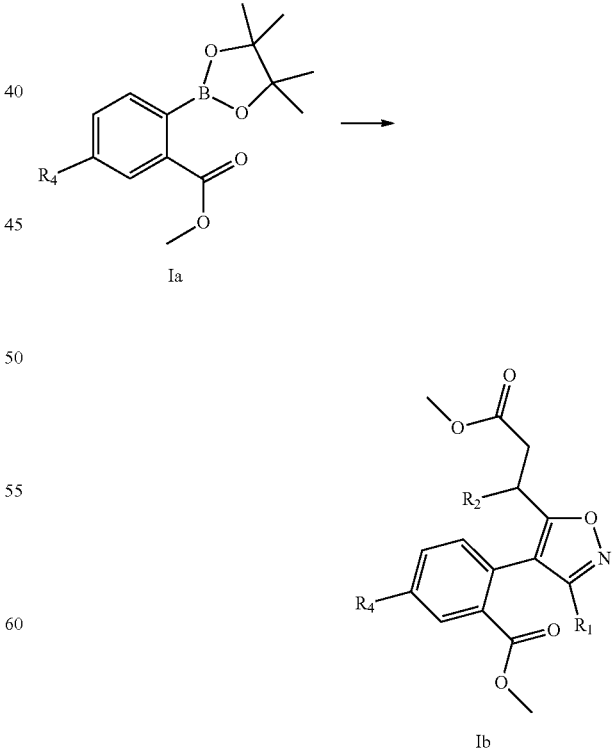

(2) preparing the compound of formula Ic with the compound of formula Ib,
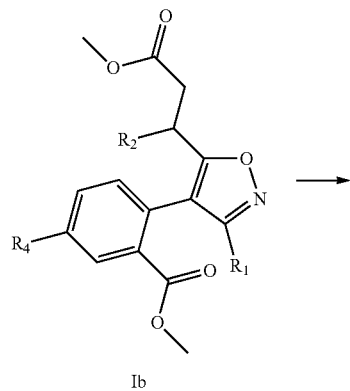
Ib
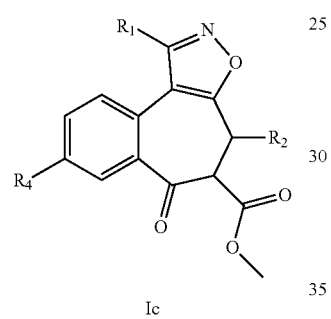
Ic
(3) preparing the compound of formula Id with the compound of formula Ic,
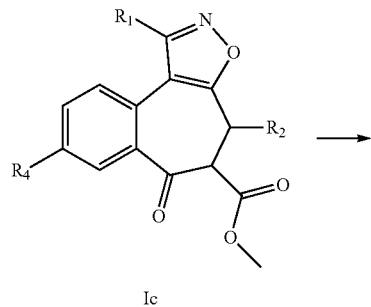
Ic
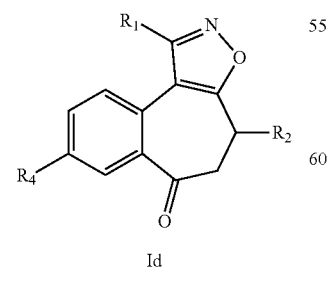
Id
(4) preparing the compound of formula (I-2) with the compound of formula Id,
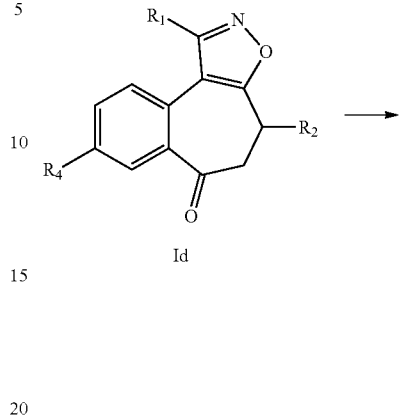
Id
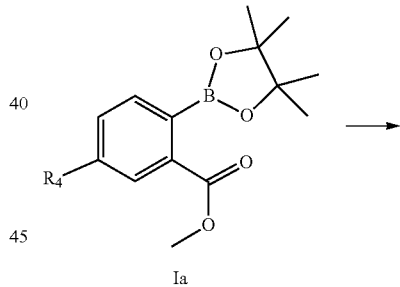
(I-2)
(5) preparing the compound of formula Ie with the compound of formula Ia,
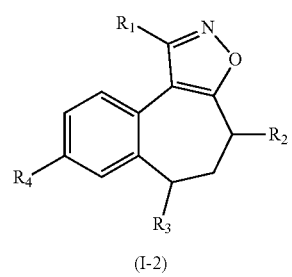
Ia
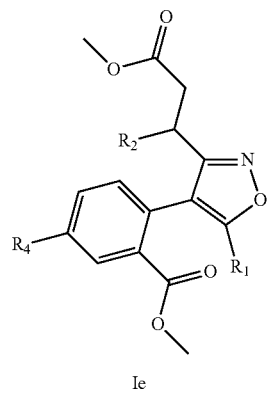
Ie (6) preparing the compound of formula If with the compound of formula Ie,

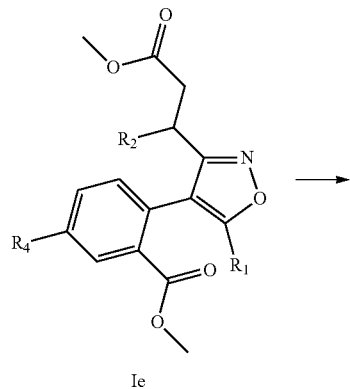

Ie

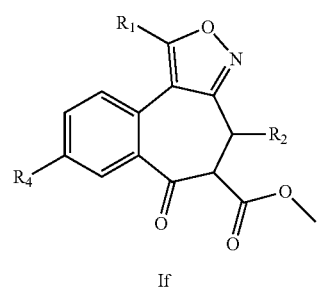

If (7) preparing the compound of formula Ig with the compound of formula If,

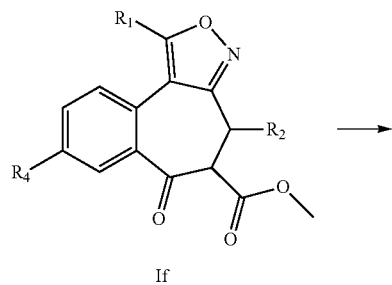

If

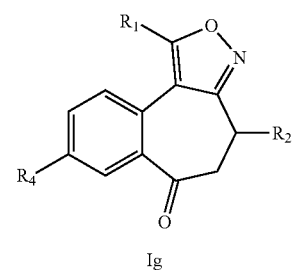

Ig (8) preparing the compound of formula (I-3) with the compound of formula Ig,

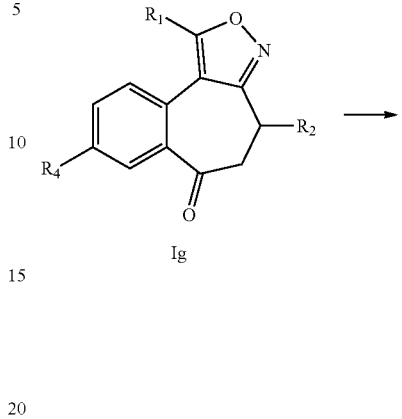

Ig

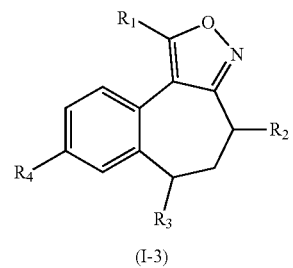

(I-3)

(9) preparing the compound of formula Ii with the compound of formula Ih,

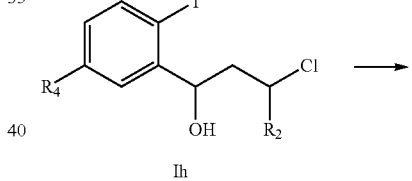

Ih

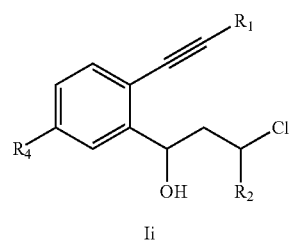

Ii

(10) preparing the compound of formula Ij by reacting the compound of formula Ii with sodium azide,

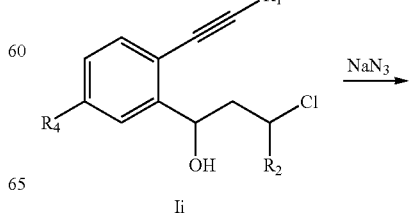

Ii

-continued
(11) preparing the compound of formula Ik with the compound of formula Ij,
(12) preparing the compound of formula II with the compound of formula Ik,
(13) preparing the compound of formula (I-1) with the compound of formula II,
(14) preparing the compound of formula Im with the compound of formula Ik,
(15) preparing the compound of formula (I-1) with the compound of formula Im,
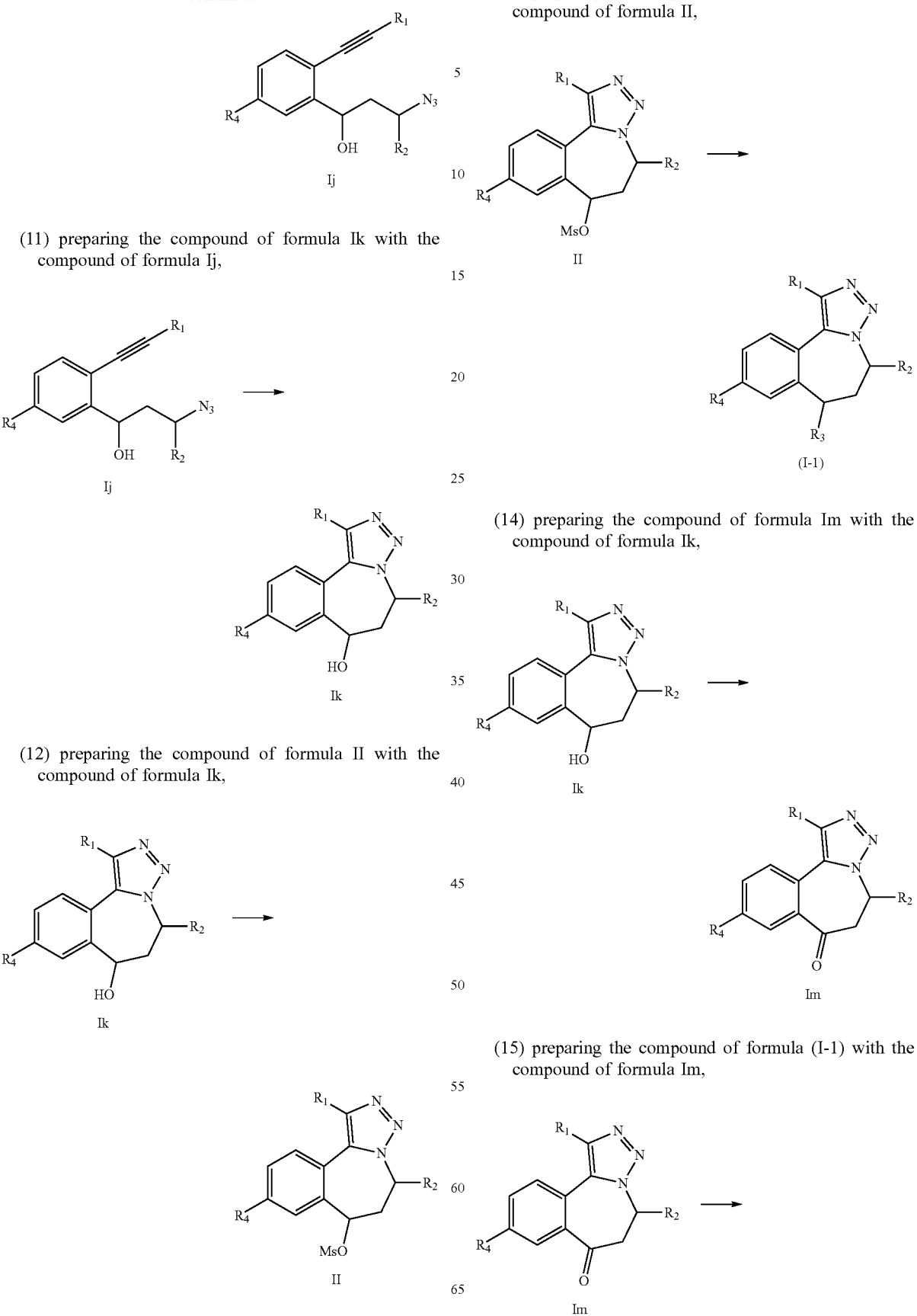

-continued

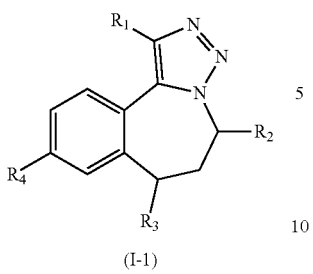
(I-1)

(16) preparing the compound of formula (I-4) and the compound of formula (I-5) by separating and purifying the compound of formula (I-1),

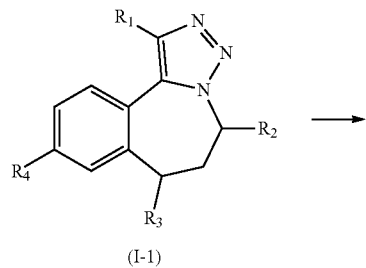
(I-1)

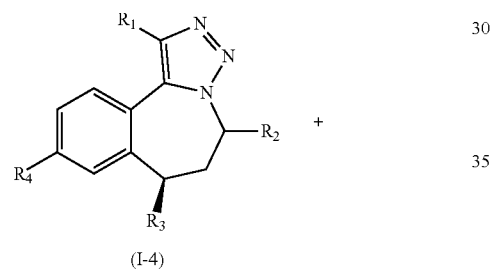
(I-4)

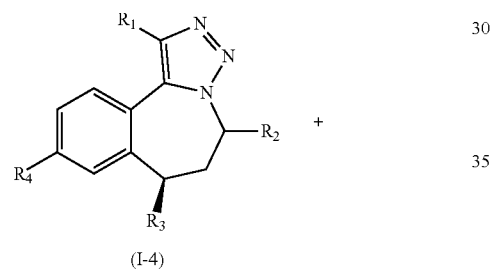
(I-5)

(17) preparing the compound of formula (I-6) and the compound of formula (I-7) by separating and purifying the compound of formula (I-2),

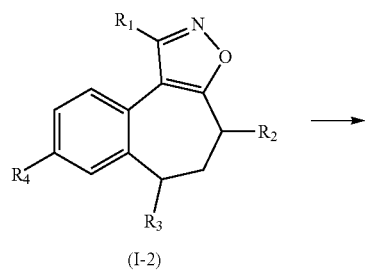
(I-2)

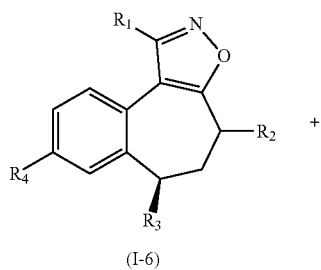
(I-6)

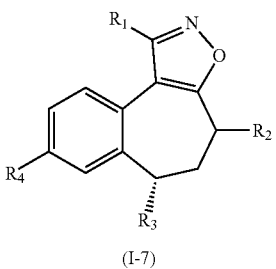
(I-7)

(18) preparing the compound of formula (I-8) and the compound of formula (I-9) by separating and purifying the compound of formula (I-3),

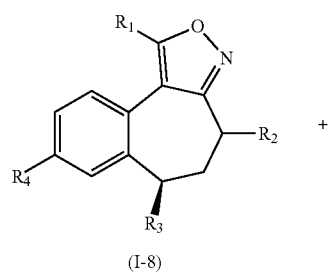
(I-3)

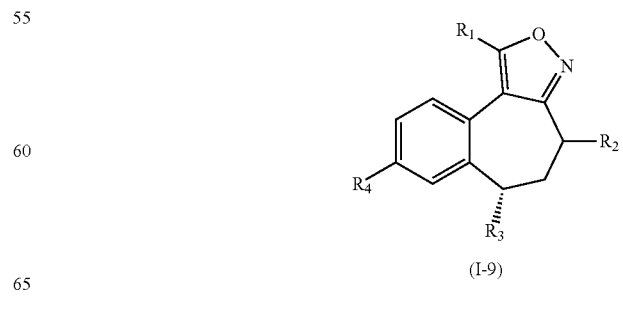
(I-8)

(I-9)

(19) preparing the compound of formula (I-4) by chiral synthesis with the compound of formula Im,

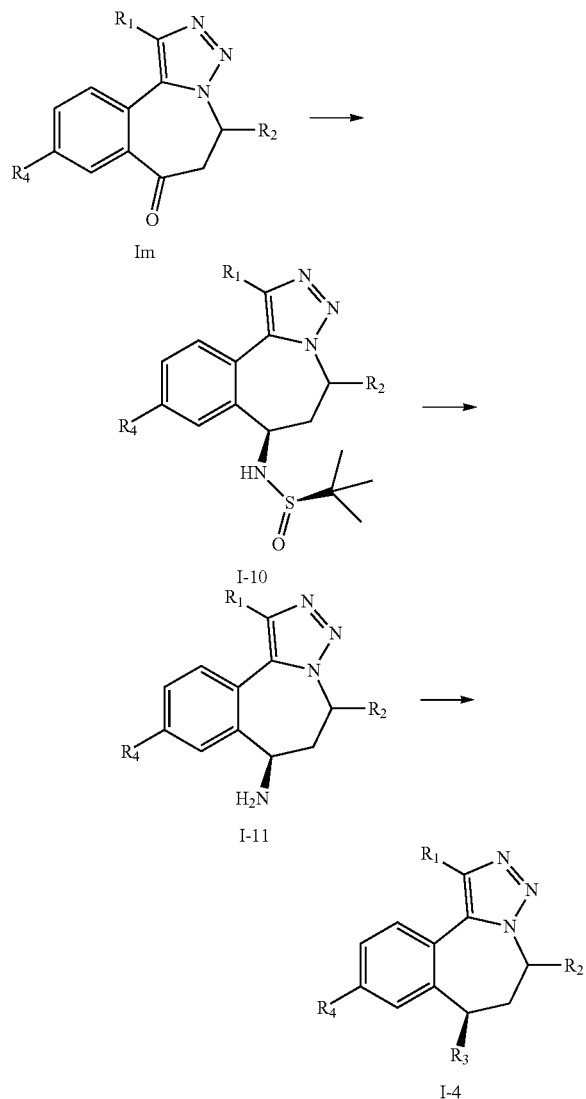

(20) preparing the compound of formula (I-5) by chiral synthesis with the compound of formula Im,

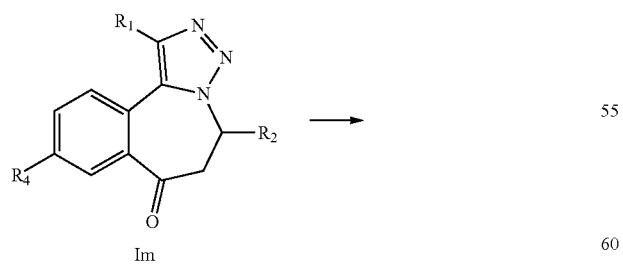

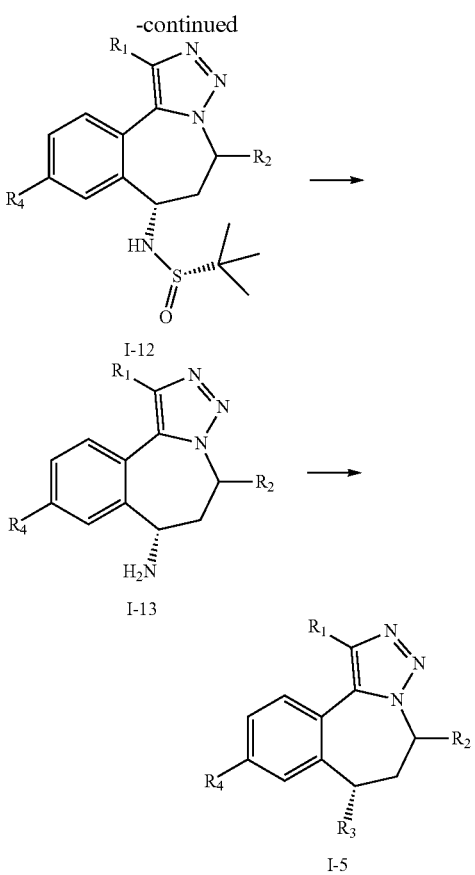

In each of the above schemes, $R_1$, $R_2$, $R_3$, and $R_4$ have the same definitions as those in formula (I).

8. A pharmaceutical composition comprising one or more compounds of claim 1, their enantiomers, diastereomers, racemates or mixtures thereof, and chemically acceptable salts, crystalline hydrates, solvent mixtures of the compounds, their enantiomers, diastereomers, racemates and mixtures thereof.

9. A method of treating a disease related to the activity or expression of BET Bromodomain BRD4 comprising administering a subject in need thereof one or more compounds of claim 1, their enantiomers, diastereomers, racemates or mixtures thereof, and chemically acceptable salts, crystalline hydrates, solvent mixtures of the compounds, their enantiomers, diastereomers, racemates and mixtures thereof.

10. The method according to claim 9, wherein, the disease related to the activity or expression of BET Bromodomain BRD4 includes diabetes, cardiovascular diseases and cancer.

11. The method according to claim 10, wherein,
the diabetes includes type 1 and type 2 diabetes;
the cardiovascular diseases include heart diseases related to heart failure, arrhythmia and coronary artery lesion;
the cancer includes non-Hodgkin's lymphoma, breast cancer, liver cancer, bowel cancer, esophageal cancer, myelofibrosis, pancreatic cancer, lung cancer, and uterine cancer.

* * * * *